United States Patent
Cremonesi et al.

(10) Patent No.: US 10,239,870 B2
(45) Date of Patent: *Mar. 26, 2019

(54) DOPAMINE D3 RECEPTOR ANTAGONISTS

(71) Applicant: Indivior UK Limited, Slough, Berkshire (GB)

(72) Inventors: Susanna Cremonesi, Verona (IT); Fabrizio Micheli, Verona (IT); Teresa Semerano, Verona (IT); Luca Tarsi, Verona (IT)

(73) Assignee: Indivior UK Limited, Slough (GB)

( * ) Notice: Subject to any disclaimer, the term of this patent is extended or adjusted under 35 U.S.C. 154(b) by 0 days.

This patent is subject to a terminal disclaimer.

(21) Appl. No.: 15/975,466

(22) Filed: May 9, 2018

(65) Prior Publication Data

US 2018/0282318 A1 Oct. 4, 2018

Related U.S. Application Data

(63) Continuation of application No. 15/522,863, filed as application No. PCT/GB2015/053272 on Oct. 30, 2015, now Pat. No. 10,000,477.

(30) Foreign Application Priority Data

Oct. 31, 2014 (GB) .................................. 1419430.2
Oct. 31, 2014 (GB) .................................. 1419433.6

(51) Int. Cl.
| C07D 413/14 | (2006.01) |
| C07D 493/08 | (2006.01) |
| C07D 471/04 | (2006.01) |
| C07D 417/14 | (2006.01) |
| C07D 401/14 | (2006.01) |
| C07D 403/12 | (2006.01) |
| C07D 405/14 | (2006.01) |
| C07D 403/14 | (2006.01) |
| C07D 409/14 | (2006.01) |

(52) U.S. Cl.
CPC ......... *C07D 413/14* (2013.01); *C07D 401/14* (2013.01); *C07D 403/12* (2013.01); *C07D 403/14* (2013.01); *C07D 405/14* (2013.01); *C07D 409/14* (2013.01); *C07D 417/14* (2013.01); *C07D 471/04* (2013.01); *C07D 493/08* (2013.01)

(58) Field of Classification Search
None
See application file for complete search history.

(56) References Cited

U.S. PATENT DOCUMENTS

| 3,654,305 A | 4/1972 | German |
| 10,000,477 B2 * | 6/2018 | Cremonesi ........... C07D 403/12 |
| 2013/0109668 A1 | 5/2013 | Ceccarelli et al. |

FOREIGN PATENT DOCUMENTS

| WO | WO-91/09594 A1 | 7/1991 |
| WO | WO-93/00313 A2 | 1/1993 |
| WO | WO-93/00313 A3 | 1/1993 |
| WO | WO-01/21615 A1 | 3/2001 |
| WO | WO-01/44193 A1 | 6/2001 |
| WO | WO-01/81347 A2 | 11/2001 |
| WO | WO-01/81347 A3 | 11/2001 |
| WO | WO-03/091220 A1 | 11/2003 |
| WO | WO-2006/034089 A1 | 3/2006 |
| WO | WO-2006/082511 A1 | 8/2006 |
| WO | WO-2007/084875 A2 | 7/2007 |
| WO | WO-2007/084875 A3 | 7/2007 |
| WO | WO-2007/098953 A1 | 9/2007 |
| WO | WO-2007/133561 A2 | 11/2007 |
| WO | WO-2007/133561 A3 | 11/2007 |
| WO | WO-2008/087512 A1 | 7/2008 |
| WO | WO-01/005763 A2 | 1/2011 |
| WO | WO-01/005763 A3 | 1/2011 |
| WO | WO-2011/114275 A1 | 9/2011 |
| WO | WO-2012/128582 A2 | 9/2012 |
| WO | WO-2012/128582 A3 | 9/2012 |
| WO | WO-2013/071697 A1 | 5/2013 |
| WO | WO-2013/092893 A1 | 6/2013 |

OTHER PUBLICATIONS

Bonanomi, G. et al. (May 3, 2010). "Triazolyl azabicyclo[3.1.0]hexanes: A class of potent and selective dopamine D(3) receptor antagonists," *ChemMedChem* 5(5):705-715.

Cervo, L. et al. (Apr. 2007, e-published Jan. 23, 2006). "Selective antagonism at dopamine D3 receptors attenuates cocaine-seeking behaviour in the rat," *Int J Neuropsychopharmacol* 10(2):167-181.

Feng, Z. et al. (Dec. 2012). "Structure-based drug design for dopamine D3 receptor," *Comb Chem High Throughput Screen* 15(10):775-791.

Hackling, A.E. et al. (Oct. 2002). "Dopamine D3 receptor ligands with antagonist properties," *Chembiochem* 3(10):946-961.

Hedou, G. et al. (May 14, 1999). "Effects of cocaine on dopamine in subregions of the rat prefrontal cortex and their efferents to subterritories of the nucleus accumbens," *Eur J Pharmacol* 372(2):143-155.

Heidbreder, C.A. et al. (Mar. 1999). "Dopamine and serotonin imbalances in the left anterior cingulate and pyriform cortices following the repeated intermittent administration of cocaine," *Neuroscience* 89(3):701-715.

Heidbreder, C.A. et al. (Apr. 2004). "Role of dopamine D3 receptors in the addictive properties of ethanol," *Drugs Today* 40(4):355-365.

Heidbreder, C.A. et al. (Jul. 2005). "The role of central dopamine D3 receptors in drug addiction: a review of pharmacological evidence," *Brain Res Brain Res Rev* 49(1):77-105.

(Continued)

*Primary Examiner* — Brian J Davis
(74) *Attorney, Agent, or Firm* — Edward D. Grieff; Mintz, Levin, Cohn, Ferris, Glovsky and Popeo, P.C.

(57) ABSTRACT

The disclosure is directed to novel dopamine D3 receptor antagonists, processes for their preparation, intermediates used in these processes, pharmaceutical compositions containing them and their use in therapy, including treating drug dependency and psychosis.

40 Claims, No Drawings

(56) References Cited

OTHER PUBLICATIONS

Heidbreder, C.A. et al. (Feb. 2010). "Current perspectives on selective dopamine D(3) receptor antagonists as pharmacotherapeutics for addictions and related disorders," *Ann NY Acad Sci* 1187:4-34.

Heidbreder, C. (Feb. 2013, e-published Oct. 28, 2012). "Rationale in support of the use of selective dopamine $D_3$ receptor antagonists for the pharmacotherapeutic management of substance use disorders," *Naunyn Schmiedebergs Arch Pharmacol* 386(2):167-176.

International Search Report dated Jan. 29, 2016, for PCT Application No. PCT/GB2015/053272, filed Oct. 30, 2015, 3 pages.

Micheli, F. (Jul. 4, 2011, e-published Mar. 18, 2011). "Recent advances in the development of dopamine D3 receptor antagonists: a medicinal chemistry perspective," *ChemMedChem* 6(7):1152-1162.

Micheli, F. et al. (Mar. 2013, e-published Jan. 3, 2013). "Dopamine D3 receptor antagonists: a patent review (2007-2012)," *Expert Opin Ther Pat* 23(3):363-381.

Micheli, F. et al. (Feb. 15, 2016, e-published Jan. 5, 2016). "Novel morpholine scaffolds as selective dopamine (DA) D3 receptor antagonists," *Bioorg Med Chem Lett* 26(4):1329-1332.

Micheli, F. et al. (Sep. 22, 2016, e-published Sep. 9, 2016). "1,2,4-Triazolyl 5-Azaspiro[2.4]heptanes: Lead Identification and Early Lead Optimization of a New Series of Potent and Selective Dopamine D3 Receptor Antagonists," *J Med Chem* 59(18):8549-8576.

Mugnaini, M. et al. (Jan. 2013, e-published Sep. 12, 2012). "Occupancy of brain dopamine D3 receptors and drug craving: a translational approach," *Neuropsychopharmacology* 38(2):302-312.

Schwartz, A. et al. (Oct. 2004). "Selective dopamine D(3) receptor antagonist SB-277011-A potentiates phMRI response to acute amphetamine challenge in the rat brain," *Synapse* 54(1):1-10.

Search Report dated Jul. 29, 2015, for U.K. Application No. GB1419430.2, 9 pages.

Search Report dated Jul. 29, 2015, for U.K. Application No. GB1419433.6, 10 pages.

Search Report dated Aug. 18, 2016, for U.K. Application No. GB1518124.1, 4 pages.

Written Opinion dated Jan. 29, 2016, for PCT Application No. PCT/GB2015/053272, filed Oct. 30, 2015, 6 pages.

Xi, Z.X. et al. (Jun. 2005). "Selective dopamine D3 receptor antagonism by SB-277011A attenuates cocaine reinforcement as assessed by progressive-ratio and variable-cost-variable-payoff fixed-ratio cocaine self-administration in rats," *Eur J Neurosci* 21(12):3427-3438.

Zocchi, A. et al. (Oct. 28, 2005). "Aripiprazole increases dopamine but not noradrenaline and serotonin levels in the mouse prefrontal cortex," *Neurosci Lett* 387(3):151-161.

\* cited by examiner

DOPAMINE D3 RECEPTOR ANTAGONISTS

RELATED APPLICATIONS

This application claims priority to U.S. application Ser. No. 15/522,863 filed Apr. 28, 2017, issued as U.S. Pat. No. 10,000,477, which is a § 371 national stage of PCT Application No. PCT/GB2015/053272 filed Oct. 30, 2015, which claims priority to United Kingdom Application Numbers GB1419430.2 and GB1419433.6 both filed Oct. 31, 2014, the disclosures of which are incorporated by reference herein in their entirety.

FIELD OF THE INVENTION

The present invention relates to novel compounds, processes for their preparation, intermediates used in these processes, pharmaceutical compositions containing them and their use in therapy, as modulators of dopamine $D_3$ receptors.

BACKGROUND OF THE INVENTION

Dopamine is a neurotransmitter that plays an essential role in normal brain functions. As a chemical messenger, dopamine is similar to adrenaline. In the brain, dopamine is synthesized in the pre-synaptic neurons and released into the space between the pre-synaptic and post-synaptic neurons. Dopamine affects brain processes that control movement, emotional response, and ability to experience pleasure and pain. Therefore, the regulation of dopamine plays an important role in mental and physical health. Neurons containing dopamine are clustered in the midbrain area called the substantia nigra. Abnormal dopamine signaling in the brain has been implicated in a substantial number of pathological conditions, including drug abuse, depression, anxiety, schizophrenia, Tourette's syndrome, eating disorders, alcoholism, chronic pain, obsessive compulsive disorders, restless leg syndrome, and Parkinson's Disease.

Dopamine molecules bind to and activate dopamine receptors on the post-synaptic neurons. Dopamine molecules then are transported through the dopamine transporter protein (DAT) back into the pre-synaptic neurons, where they are metabolized by monoamine oxidase (MAO). In conditions such as drug abuse, the drug binds to the dopamine transporter and blocks the normal flow of dopamine molecules. Excess concentrations of dopamine cause overactivation of dopamine receptors. In other conditions, such as Parkinson's Disease, lack of sufficient dopamine receptors in the brain causes insufficient activation of dopamine receptors.

Dopaminergic neurotransmission is mediated by five dopamine receptors, which can be grouped into the D1-like (i.e., D1 and D5) and D2-like (i.e., D2, D3, and D4) receptor subtypes. The dopamine D3 receptor has been implicated as an important target for agents currently used clinically for the treatment of schizophrenia, Parkinson's disease, depression, and other neurological diseases. Studies have also provided evidence that potent and selective D3 receptor antagonists may have a therapeutic potential as pharmacotherapies for the treatment of drug abuse. Therefore, considerable effort has been devoted to the discovery and development of potent and selective D3 receptor antagonists.

SUMMARY OF THE INVENTION

A new class of compounds which have affinity for dopamine receptors, in particular the dopamine $D_3$ receptor has been found. These compounds are useful in the treatment of conditions wherein modulation, especially antagonism/inhibition, of the $D_3$ receptor is beneficial, e.g. to treat drug dependency or as antipsychotic agents.

The disclosure provides compounds of formula (I) or pharmaceutically acceptable salts thereof: The disclosure provides methods of antagonizing the D3 receptor to treat diseases, including psychosis and substance abuse.

DETAILED DESCRIPTION

The present invention provides a compound of formula (I) or a pharmaceutical acceptable salt thereof:

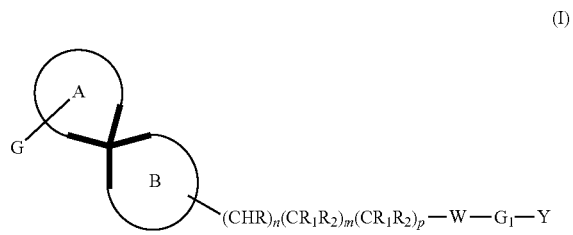

(I)

wherein

A is a saturated 3-6 membered carbocyclic ring and such ring may be substituted by one or more $C_{1-4}$alkyl group;

B is a saturated 4-6 membered heterocyclic ring, in which one or two carbon atoms may be replaced by an heteroatom selected from at least one Nitrogen or an Oxygen and the linking atom is always a Nitrogen atom; such ring may be also substituted at the carbon atoms or, possibly, at a different Nitrogen atom, by one or more $C_{1-4}$alkyl group;

G is aryl or a 5-6 membered heteroaromatic group or 8-11 membered heteroaromatic group, which may be benzofused or optionally substituted by 1, 2, 3 4 or 5 substituents selected from the group consisting of: halogen, cyano, hydroxyl, amino, $C_{1-4}$alkylamino, $C_{1-4}$alkyl, $C_{1-4}$alkoxy, halo$C_{1-4}$ alkyl, halo$C_{1-4}$alkoxy, $SF_5$, $C(=O)NH_2$ and $C(=O)(O)_zR_3$;

W is S, $SO_2$, O, $CHR_2$ or $NR_3$;

n is 0 or 1;

m is 1 or 2;

p is 1 or 2;

z is each independently 0 or 1;

R is hydrogen or $C_{1-4}$alkyl; $C_{1-4}$alkoxy;

$R_1$ is each independently hydrogen or F, $C_{1-4}$alkyl; OH, $C_{1-4}$alkoxy;

$R_2$ is each independently hydrogen or F, $C_{1-4}$alkyl; OH, $C_{1-4}$alkoxy;

$R_3$ is each independently hydrogen or $C_{1-4}$alkyl;

$R_4$ is each independently hydrogen or $C_{1-4}$alkyl; or —C(=O)$C_{1-4}$alkyl; —C(=O)$C_{1-4}$alkoxy$C_{1-4}$alkyl; —C(=O)$C_{3-6}$cycloalkyl;

$R_5$ is each independently hydrogen or $C_{1-4}$alkyl;

$R_6$ is each independently hydrogen or $C_{1-4}$alkyl;

$R_7$ is each independently halogen, $C_{1-4}$alkyl; OH, $C_{1-4}$alkoxy;

$G_1$ is a phenyl or a 5-6-membered heteroaromatic group or a 8-11 membered heteroaromatic group; any of which groups may be optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, halo$C_{1-4}$alkoxy, $C_{1-4}$alkoxy, SF$_5$, C(=O)NH$_2$ and C(=O)(O)$_z$R$_3$;

Y is phenyl or a moiety selected from the group consisting of: 5-6 membered heteroaromatic group, a 8-11 membered heteroaromatic group, a saturated mono 3-7 membered carbocyclic group and a 8-11 membered bicyclic carbocyclic group, and for any of such groups one or more ring carbons may be replaced by N(R$_4$)$_z$, O, S; any of which groups may be optionally substituted by 1, 2 or 3 substituents selected from: halogen, cyano, hydroxyl, $C_{1-4}$alkylamino, $C_{1-4}$alkyl, $C_{1-4}$alkoxy, halo$C_{1-4}$alkyl, halo$C_{1-4}$alkoxy, oxo, —NHC(=O)$C_{1-4}$alkyl, —NR$_5$R$_6$, SF$_5$, —(CH$_2$)$_z$C(=O)NR$_5$R$_6$, —C(=O)(O)$_z$R$_3$, —$C_{1-4}$alkylCN, —SO$_2$NR$_5$R$_6$, Y' or OY';

Y' is phenyl, or a 5-6-membered heteroaromatic group optionally substituted by 1 or 2 R$_7$ groups; provided that Y, Y' and G$_1$ are not simultaneously phenyl.

The term "aryl" refers to an aromatic carbocyclic moiety such as phenyl, biphenyl or naphtyl.

The term "5-6-membered heteroaromatic group" refers to a monocyclic 5- or 6-membered aromatic heterocyclic group containing 1, 2, 3 or 4 heteroatoms, for example from 1 to 3 heteroatoms, selected from O, N and S. When the group contains 2-4 heteroatoms, one may be selected from O, N and S and the remaining heteroatoms may be N. Examples of 5 and 6-membered heteroaromatic groups include pyrrolyl, imidazolyl, pyrazolyl, oxazolyl, isoxazolyl, oxadiazolyl, isothiazolyl, thiazolyl, furyl, thienyl, thiadiazolyl, pyridyl, triazolyl, triazinyl, pyridazinyl, pyrimidinyl and pyrazinyl.

The term "8-11-membered heteroaromatic group" refers to a bicyclic aromatic ring system containing a total of 8, 9, 10 or 11 ring atoms, wherein 1, 2, 3 or 4 or 5 of the ring atoms are a heteroatom independently selected from O, S and N. The term includes bicyclic systems wherein both rings are aromatic, as well as bicyclic ring systems wherein one of the rings is partially or fully saturated and the other ring is aromatic. Examples of 8- to 11-membered bicyclic heteroaromatic groups having 1, 2, 3, 4 or 5 heteroatoms, in which both rings are aromatic, include: 6H-thieno[2,3-b]pyrrolyl, imidazo[2,1-b][1,3]thiazolyl, imidazo[5,1-b][1,3]thiazolyl, [1,3]thiazolo[3,2-b][1,2,4]triazolyl, indolyl, isoindolyl, indazolyl, benzimidazolyl e.g. benzimidazol-2-yl, benzoxazolyl e.g. benzoxazol-2-yl, benzisoxazolyl, benzothiazolyl, benzisothiazolyl, benzothienyl, benzofuranyl, naphthridinyl, quinolyl, quinoxalinyl, quinazolinyl, cinnolinyl, isoquinolyl, 1H-imidazo[4,5-b]pyridin-5-yl and [1,2,4]triazolo[4,3-a]pyridinyl. Examples of 8- to 11-membered bicyclic heteroaromatic groups having 1, 2, 3, 4 or 5 heteroatoms, in which one of the rings is partially or fully saturated include dihydrobenzofuranyl, indanyl, indolinyl, isoindolinyl, tetrahydroisoquinolinyl, tetrahydroquinolyl, benzoxazinyl and benzazepinyl.

The term "$C_{1-4}$alkyl" refers to an alkyl group having from one to four carbon atoms, in all isomeric forms, such as methyl, ethyl, propyl, isopropyl, butyl, isobutyl, sec-butyl and tert-butyl. The term "n-$C_{1-4}$alkyl" refers to the unbranched alkyls as defined above.

The term "$C_{1-4}$alkoxy" refers to a straight chain or branched chain alkoxy (or "alkyloxy") group having from one to four carbon atoms, such as methoxy, ethoxy, propoxy, isopropoxy, butoxy, isobutoxy, sec-butoxy and tert-butoxy.

The term —$C_{1-4}$alkylCN refers to an $C_{1-4}$alkyl group substituted by a cyano group, for example —CH$_2$CN.

The term "—C(=O)$C_{1-4}$alkoxy$C_{1-4}$alkyl" refers to the carbon of the $C_{1-4}$alkoxy being linked to the C(=O) group, to give, for example, a group of the formula —C(O)—(CH$_2$)$_{1-4}$—O—$C_{1-4}$alkyl The term "halogen" and its abbreviation "halo" refer to fluorine (F), chlorine (Cl), bromine (Br) or iodine (I). Where the term "halo" is used before another group, it indicates that the group is substituted by one, two or three halogen atoms. For example, "halo$C_{1-4}$alkyl" refers to groups such as trifluoromethyl, bromoethyl, trifluoropropyl, and other groups derived from $C_{1-4}$alkyl groups as defined above; and the term "halo$C_{1-4}$alkoxy" refers to groups such as trifluoromethoxy, bromoethoxy, trifluoropropoxy, and other groups derived from $C_{1-4}$alkoxy groups as defined above.

The term "saturated mono 3-7 membered carbocyclic group" and the term "8-11 membered bicyclic carbocyclic group" refers to 3 or 4, 5, 6, or 7-membered saturated monocyclic group or 8, 9, 10, 11 membered saturated bicyclic wherein 1, 2, 3, 4 or 5 of the carbon atoms are optionally replaced by a heteroatom independently selected from O, S and N(R$_4$)$_z$ (for example NR$_3$) and which is partially or fully saturated. Examples of 3-7 membered carbocyclic group containing heteroatoms which are fully saturated include pyrrolidinyl, imidazolidinyl, pyrazolidinyl, isothiazolyl, thiazolyl, tetrahydrofuranyl, dioxolanyl, piperidinyl, piperazinyl, morpholinyl, thiomorpholinyl, tetrahydrothienyl, dioxanyl, tetrahydro-2H-pyranyl and dithianyl.

Examples of a saturated 3-7 membered (for example 3-6 membered) carbocyclic groups or rings containing only carbon atoms in the ring which are fully saturated include $C_{3-7}$cycloalkyl, for example cyclopropyl, cyclobutyl, cyclopentyl, cyclohexyl and cycloheptyl. Examples of carbocyclic groups containing only carbon atoms in the ring which are partially saturated include $C_{4-7}$cycloalkenyl, for example cyclopentenyl and cyclohexenyl.

Examples of "3-7 membered carbocyclic group containing heteroatoms" which are partially saturated 5 or 6-membered monocyclic rings include oxazolinyl, isoaxazolinyl, imidazolinyl, pyrazolinyl, 1,2,3,6-tetrahydropyridyl and 3,6-dihydro-2H-pyranyl.

Examples of "8-11 membered bicyclic carbocyclic group" include decahydroquinolinyl, octahydro-2H-1,4-benzoxazinyl, 8-oxabicyclo[3.2.1]octan-3-yl, 8-oxa-3-azabicyclo[3.2.1]octane and octahydro-1H-cyclopenta[b]pyridinyl.

Examples of partially saturated "8-11 membered bicyclic groups" include 2,3-dihydro-1H-indolyl, 1,2,3,4-tetrahydroquinolinyl, 1,2,3,4-tetrahydroisoquinolinyl and 2,3,4,5-tetrahydro-1H-3-benzazepinyl.

As will be recognised B is a saturated 4-6 membered heterocyclic ring which contains at least 1 ring nitrogen and wherein B is linked to the —(CHR)$_n$(CR$_1$R$_2$)$_p$— by the ring nitrogen group in B. In addition to that ring nitrogen B optionally contains one or two further ring hetero atoms selected from O and N. B is unsubstituted or may be substituted at on a ring carbon or an available ring nitrogen atom by one or more $C_{1-4}$alkyl group.

As used herein, the term "salt" refers to any salt of a compound according to the present invention prepared from an inorganic or organic acid or base, quaternary ammonium salts and internally formed salts. Physiologically acceptable salts are particularly suitable for medical applications because of their greater aqueous solubility relative to the parent compounds. Such salts must clearly have a physiologically acceptable anion or cation. Suitably physiologically acceptable salts of the compounds of the present invention include acid addition salts formed with inorganic acids such as hydrochloric, hydrobromic, hydroiodic, phosphoric, metaphosphoric, nitric and sulfuric acids, and with organic acids, such as tartaric, acetic, trifluoroacetic, citric, malic, lactic, fumaric, benzoic, formic, propionic, glycolic, gluconic, maleic, succinic, camphorsulfuric, isothionic, mucic, gentisic, isonicotinic, saccharic, glucuronic, furoic, glutamic, ascorbic, anthranilic, salicylic, phenylacetic, mandelic, embonic (pamoic), methanesulfonic, ethanesulfonic, pantothenic, stearic, sulfinilic, alginic, galacturonic and arylsulfonic, for example benzenesulfonic and p-toluenesulfonic, acids; base addition salts formed with alkali metals and alkaline earth metals and organic bases such as N,N-dibenzylethylenediamine, chloroprocaine, choline, diethanolamine, ethylenediamine, meglumine (N-methylglucamine), lysine and procaine; and internally formed salts. Salts having a non-physiologically acceptable anion or cation are within the scope of the invention as useful intermediates for the preparation of physiologically acceptable salts and/or for use in non-therapeutic, for example, in vitro, situations.

In a preferred embodiment compounds of formula (IA) are provided in which A and B of compounds of formula (I) may be selected from the following:

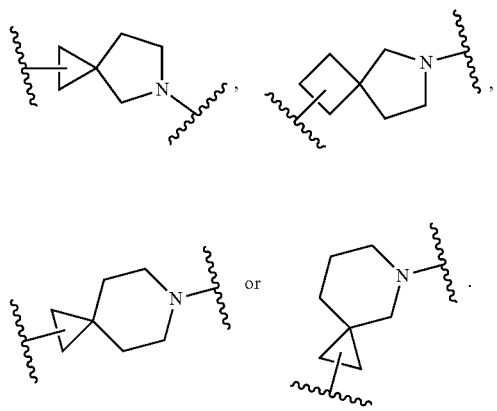

and wherein G, $G_1$, W, Y, n, m, p, z, $R_1$, $R_2$, and $R_3$ are defined as above for compounds of formula (I).

In another embodiment of the present invention compounds of formula (II) are provided in which A and B of compound of formula (I) correspond to a 5-azaspiro[2.4] heptane derivative

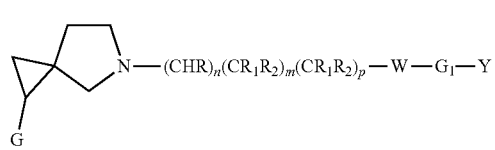

(II)

wherein G, $G_1$, W, Y, n, m, p, z, $R_1$, $R_2$, and $R_3$ are defined as above for compounds of formula (I).

In another embodiment of the present invention compounds of formula (III) are provided in which A and B of compound of formula (I) correspond to a 6-azaspiro[3.4] octane derivative

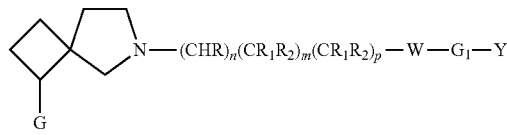

(III)

wherein G, $G_1$, W, Y, n, m, p, z, $R_1$, $R_2$, and $R_3$ are defined as above for compounds of formula (I).

In another embodiment of the present invention compounds of formula (IV) are provided in which A and B of compound of formula (I) correspond to a 6-azaspiro[2.5] octane derivative

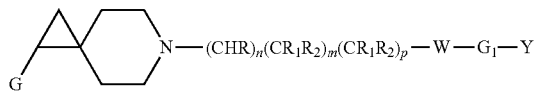

(IV)

wherein G, $G_1$, W, Y, n, m, p, z, R, $R_1$, $R_2$, and $R_3$ are defined as above for compounds of formula (I).

In another embodiment of the present invention compounds of formula (V) are provided in which A and B of compound of formula (I) correspond to a 5-azaspiro[2.5] octane derivative

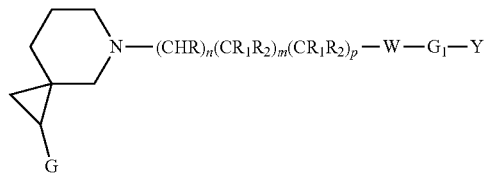

(V)

wherein G, $G_1$, W, Y, n, m, p, z, R, $R_1$, $R_2$, and $R_3$ are defined as above for compounds of formula (I).

The position of the substituent G with respect to the ring B may be in a "cis" or "trans" disposition or not.

Relative stereochemistry "cis" is represented by using the bold highlight of the bonds, while the "trans" relative stereochemistry is represented by using bold and dotted highlight of the bonds.

In a preferred embodiment compounds of formula (IB) are provided in which A and B of compounds of formula (I) may be selected from the following:

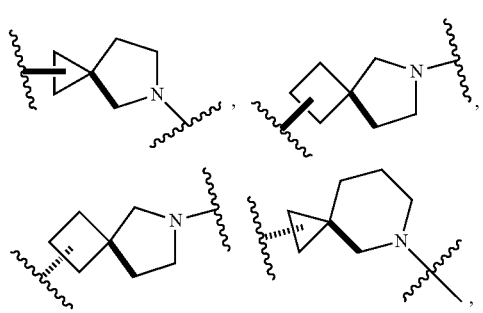

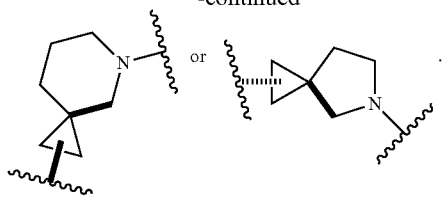 or

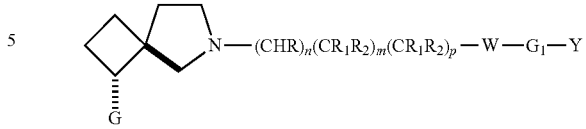

and wherein G, $G_1$, W, Y, n, m, p, z, $R_1$, $R_2$, and $R_3$ are defined as above for compounds of formula (I).

In another embodiment of the present invention compounds of formula (IIA) are provided which correspond to the compounds of formula (II) having "cis" disposition, represented by the bold highlight of the bonds

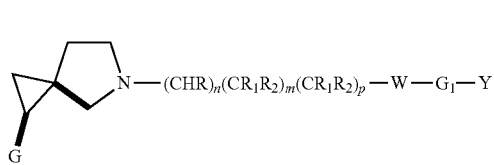

(IIA)

wherein G, $G_1$, W, Y, n, m, p, z, R, $R_1$, $R_2$, and $R_3$ are defined as above for compounds of formula (I).

In another embodiment of the present invention compounds of formula (IIB) are provided which correspond to the compounds of formula (II) having "trans" disposition, represented by the bold and dotted highlight of the bonds

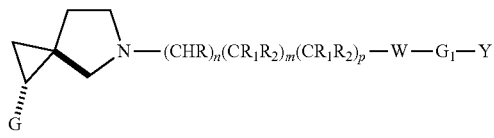

(IIB)

wherein G, $G_1$, W, Y, n, m, p, z, R, $R_1$, $R_2$, and $R_3$ are defined as above for compounds of formula (I).

In another embodiment of the present invention compounds of formula (IIIA) are provided which correspond to the compounds of formula (III) having "cis" disposition, represented by the bold highlight of the bonds (IIIA)

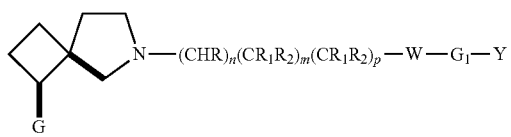

wherein G, $G_1$, W, Y, n, m, p, z, R, $R_1$, $R_2$, and $R_3$ are defined as above for compounds of formula (I).

In another embodiment of the present invention compounds of formula (IIIB) are provided which correspond to the compounds of formula (III) having "trans" disposition, represented by the bold and dotted highlight of the bonds (IIIB)

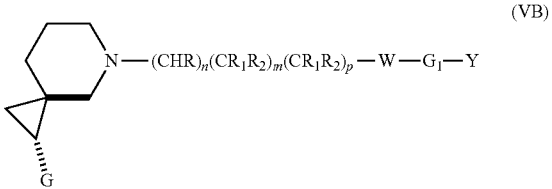

wherein G, $G_1$, W, Y, n, m, p, z, R, $R_1$, $R_2$, and $R_3$ are defined as above for compounds of formula (I).

In another embodiment of the present invention compounds of formula (VA) are provided which correspond to the compounds of formula (V) having "cis" disposition, represented by the bold highlight of the bonds (VA)

wherein G, $G_1$, W, Y, n, m, p, z, R, $R_1$, $R_2$, and $R_3$ are defined as above for compounds of formula (I).

In another embodiment of the present invention compounds of formula (VB) are provided which correspond to the compounds of formula (V) having "trans" disposition, represented by the bold and dotted highlight of the bonds (VB)

wherein G, $G_1$, W, Y, n, m, p, z, R, $R_1$, $R_2$, and $R_3$ are defined as above for compounds of formula (I).

It will be appreciated that compounds of formula (IIA) possess at least two chiral centres, namely at position 1 and 3 in the 5-azaspiro[2.4]heptane portion of the molecule. Because of the fixed cis disposition, the compounds may exist in two stereoisomers which are enantiomers with respect to the chiral centres in the cyclopropane. It will also be appreciated, in common with most biologically active molecules that the level of biological activity may vary between the individual stereoisomers of a given molecule.

In compounds of formula (IIA) there are at least two chiral centres, which are located in the cyclopropane portion, as depicted below (the bold highlight of the bonds means the "cis" configuration):

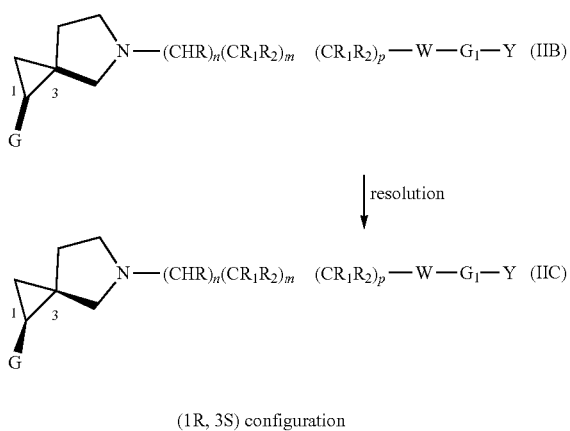

(1R, 3S) configuration

Depending on the substituents on the G group, the configuration may become (1S,3S) due to different Cahn-Ingold-Prelog nomenclature priorities.

In a further embodiment of the present invention compounds of formula (IIC) are provided that correspond to stereochemical isomers of compounds of formula (IIA), enriched in configuration (1R,3S) or (1S,3S)

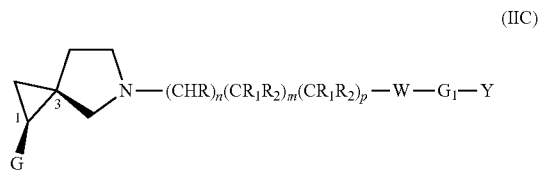

(IIC)

wherein G, $G_1$, W, Y, n, m, p, z, R, $R_1$, $R_2$, and $R_3$ are defined as above for compounds of formula (I).

It is intended in the context of the present invention that stereochemical isomers enriched in configuration (1R,3S) or (1S,3S) of formula (IIC) correspond in one embodiment to at least 90% enantiomeric excess (e.e). In another embodiment the isomers correspond to at least 95% e.e. In another embodiment the isomers correspond to at least 99% e.e.

The strategy for determining the absolute configuration of the compounds of the present invention comprised as a first step the preparation of the chiral intermediate, (1R,3S)-[4-(trifluoromethyl)phenyl]-5-azaspiro[2.4]heptane,

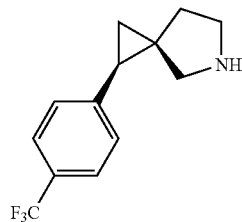 [SMILES: FC(F)(F)c1ccc([C@H]2C[C@]23CCNC3)cc1]

by preparation of (1R,3S/1S,3R)-[4-(trifluoromethyl)phenyl]-5-azaspiro[2.4]heptane (preparation 14) and resolution of the racemic mixture by use of chiral HPLC procedure (preparation 15).

The assignment of the absolute configuration of the title compound was determined by a single crystal X-ray structure obtained from a crystal of 5-(4-methylbenzenesulfonyl)-(1R,3S)-[4-(trifluoromethyl)phenyl]-5-azaspiro[2.4] heptane derived from the desired enantiomer and crystallized in EtOH as solvent (see preparation 290) to obtain a single crystal.

The present molecule exhibits two stereocenters. According to the absolute structure determination, the configuration at the carbon atom corresponding to C1 is R, whereas the configuration at the carbon atom corresponding to C3 is S.

In order to further confirmed the absolute stereochemistry also the opposite enantiomer (1S,3R)-[4-(trifluoromethyl) phenyl]-5-azaspiro[2.4]heptane was analogously derivatized (see preparation 291) and submitted to the same analyses that confirmed that the configuration at the carbon atom corresponding to C1 is S, whereas the configuration at the carbon atom corresponding to C3 is R.

For those compounds synthesised from (1R,3S)-[4-(trifluoromethyl)phenyl]-5-azaspiro[2.4]heptane or (1S,3R)-[4-(trifluoromethyl)phenyl]-5-azaspiro[2.4]heptane (with known absolute stereochemistry based on X-ray structure) a common trend was recognised between absolute configuration of the 5-azaspiro[2.4]heptane moiety and measured binding activity at the dopamine D3 receptor for each pair of enantiomers. For the remainder of the compounds of the present invention, where stereoisomers were evaluated separately, absolute configuration was assigned based on a reasonable assumption by a skilled person in the art, i.e. absolute configuration was then assigned based on measured binding activity at the dopamine D3 receptor for both enantiomers and comparison with the data of those compounds which were subjected to detailed analysis.

Also provided are compounds of the formula (PI), or a pharmaceutically acceptable salt thereof:

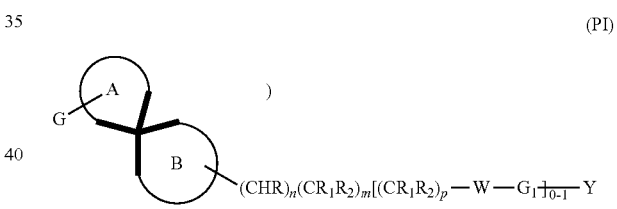

(PI)

wherein:
A is a saturated 3-6 carbocyclic ring and such ring may be substituted by one or more $C_{1-4}$alkyl group;
B is a saturated 4-6 carbocyclic ring, in which one or two carbon atoms may be replaced by an heteroatom selected from at least one Nitrogen or an Oxygen and the linking atom is always a Nitrogen atom; such ring may be also substituted at the carbon atoms or, possibly, at the different Nitrogen atom, by one or more $C_{1-4}$alkyl group;
G is aryl or a 5-6 membered heteroaromatic group or 8-11 membered heteroaromatic group, which may be benzofused or optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, C(=O)$NH_2$, C(=O)$OR_3$;
W is S, $SO_2$, O, $CHR_2$, $NR_3$;
n is 0 or 1;
m is 1 or 2;
p is 1 or 2;
R is hydrogen or $C_{1-4}$alkyl; $C_{1-4}$alkoxy;
$R_1$ is hydrogen or F, $C_{1-4}$alkyl; OH, $C_{1-4}$alkoxy;
$R_2$ is hydrogen or F, $C_{1-4}$alkyl; OH, $C_{1-4}$alkoxy;

$R_3$ is hydrogen or $C_{1-4}$alkyl;

$G_1$ is a phenyl group or a 5-6-membered heteroaromatic group or a 8-11 membered heteroaromatic group, any of which groups may be optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_3$;

Y is H or a moiety selected from the group consisting of: 5-6 membered heteroaromatic group, saturated mono 3-7 membered carbocyclic group or 8-11 membered bicyclic carbocyclic group in which one or more atom carbons may be replaced by $NR_3$, O, S; any of which groups may be optionally substituted by one or two substituents selected from: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_3$; or, when $G_1$ is a phenyl group, $G_1$ and Y may be fused together to form a benzofused aromatic or heteroaromatic system which might be optionally substituted by one or two substituents selected from: halogen, cyano, hydroxy, amide, ester, amino $C_{1-4}$alkyl, halo$C_{1-4}$alkyl, $C_{1-4}$alkoxy, $C_{1-4}$alkanoyl, $SF_5$.

In another embodiment compounds of formula (PII) are provided in which A and B of compound of formula (PI) correspond to a 5-azaspiro[2.4]heptane derivative (PII)

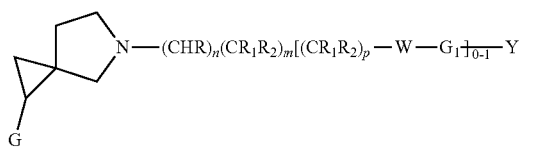

In another embodiment compounds of formula (PIII) are provided in which A and B of compound of formula (PI) correspond to a 6-azaspiro[3.4]octane derivative (PIII)

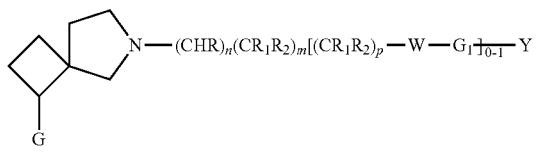

In another embodiment compounds of formula (PIV) are provided in which A and B of compound of formula (PI) correspond to a 6-azaspiro[2.5]octane derivative (PIV)

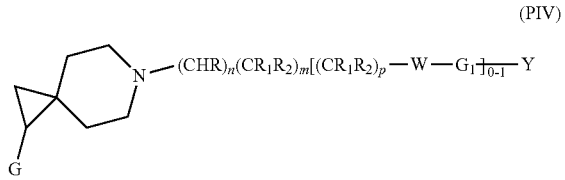

The position of the substituent G with respect to the ring B may be in a "cis" or "trans" disposition or not.

Relative stereochemistry "cis" is represented by using the bold highlight of the bonds, while the "trans" relative stereochemistry is represented by using bold and dotted highlight of the bonds.

In another embodiment compounds of formula (PIIA) are provided which correspond to the compounds of formula (PII) having "cis" disposition, represented by the bold highlight of the bonds (PIIA)

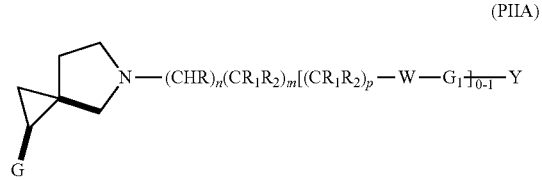

wherein G, $G_1$, W, Y, n, m, p, $R_1$, $R_2$, and $R_3$ are defined as above for compounds of formula (PI).

In another embodiment compounds of formula (PIIB) are provided which correspond to the compounds of formula (PII) having "trans" disposition, represented by the bold highlight of the bonds (PIIB)

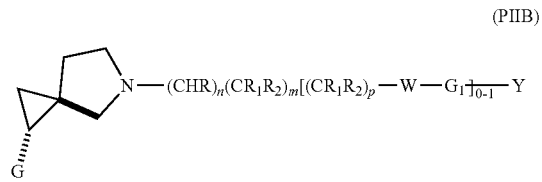

wherein G, p, $R_1$, $R_2$, $R_3$, $R_4$, and $R_5$ are defined as above for compounds of formula (PI).

In another embodiment compounds of formula (PIIIA) are provided which correspond to the compounds of formula (PIII) having "cis" disposition, represented by the bold highlight of the bonds (PIIIA)

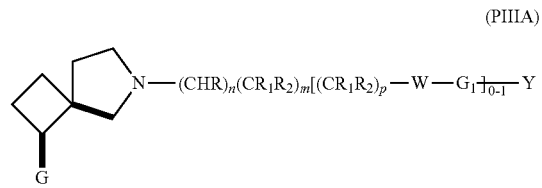

wherein G, $G_1$, W, Y, n, m, p, $R_1$, $R_2$, and $R_3$ are defined as above for compounds of formula (PI).

In another embodiment compounds of formula (PIIIB) are provided which correspond to the compounds of formula (PIII) having "trans" disposition, represented by the bold highlight of the bonds (PIIIB)

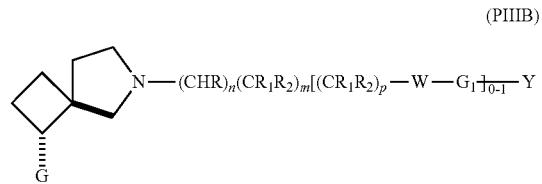

wherein G, p, $R_1$, $R_2$, $R_3$, $R_4$, and $R_5$ are defined as above for compounds of formula (PI).

Also provided are compounds of the formula (PNI), or a pharmaceutically acceptable salt thereof:

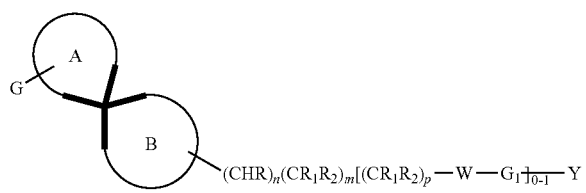

(PN1)

wherein
A and B are selected from:

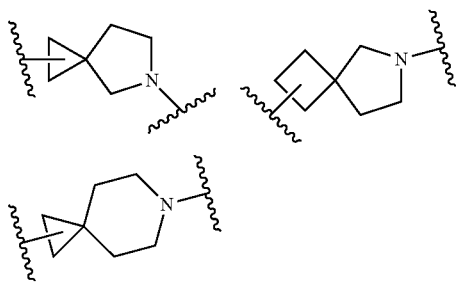

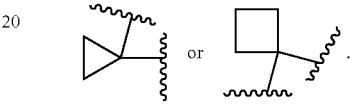

G is phenyl or a 5-6 membered heteroaromatic group or 8-11 membered heteroaromatic group, which may be benzofused or optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_3$;

W is S, $SO_2$, O, $CHR_2$, $NR_3$;

n is 0 or 1;

m is 1 or 2;

p is 1 or 2;

R is hydrogen or $C_{1-4}$alkyl; $C_{1-4}$alkoxy;

$R_1$ is hydrogen or F, $C_{1-4}$alkyl; OH, $C_{1-4}$alkoxy;

$R_2$ is hydrogen or F, $C_{1-4}$alkyl; OH, $C_{1-4}$alkoxy;

$R_3$ is hydrogen or $C_{1-4}$alkyl;

$G_1$ is a phenyl group or a 5-6-membered heteroaromatic group or a 8-11 membered heteroaromatic group, any of which groups may be optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_3$;

Y is H or a moiety selected from the group consisting of: 5-6 membered heteroaromatic group, saturated mono 3-7 membered carbocyclic group or 8-11 membered bicyclic carbocyclic group in which one or more atom carbons may be replaced by $NR_3$, O, S; any of which groups may be optionally substituted by one or two substituents selected from: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_3$; or, when $G_1$ is a phenyl group, $G_1$ and Y may be fused together to form a benzofused aromatic or heteroaromatic system which might be optionally substituted by one or two substituents selected from: halogen, cyano, hydroxy, amide, ester, amino $C_{1-4}$alkyl, halo$C_{1-4}$alkyl, $C_{1-4}$alkoxy, $C_{1-4}$alkanoyl, $SF_5$.

Suitably in the compounds of the formulae (PI) to (PIV), (PIIA), (PIIB), (PIIIA), (PIIIB) and (PN1) Y is not H.

Suitably in the compounds of the formulae (PI) to (PIV), (PIIA), (PIIB), (PIIIA), (PIIIB) and (PN1) the group —$(CR_1R_2)_p$—W—$G_1$- is present in the compound.

Particular compounds of the invention include, for example, compounds of the formulae (I), (IA), (IB), (II), (IIA), (IIB), (III), (IIIA), (IIIB), (IV), (V), (VA) or (VB), or pharmaceutically acceptable salts and pro-drugs thereof, wherein, unless otherwise stated, each of A, B, G, $G^1$, Y, Y', $R^1$, $R^2$, $R^3$, $R^4$, $R^5$, $R^6$, $R^7$, n, m, p and z has any of the meanings defined hereinbefore or in any of paragraphs (1) to (42) hereinafter:—

(1) A in formula (I) is a saturated 3-6 membered carbocyclic ring and such ring may be substituted by one or more $C_{1-4}$alkyl group, wherein the carbocyclic ring contains only carbon atoms in the ring.

(2) A in formula (I) is selected from (3) G is aryl or a 5-6 membered heteroaromatic group or 8-11 membered heteroaromatic group, which may be benzofused or optionally substituted by 1, 2, 3 or 4 substituents selected from the group consisting of: halogen, cyano, hydroxyl, amino, $C_{1-4}$alkylamino, $C_{1-4}$alkyl, halo$C_{1-4}$alkyl, $C_{1-4}$alkoxy, $C_{1-4}$alkanoyl, $SF_5$, $C(=O)NH_2$, $C(=O)OR_3$.

(4) G is phenyl or pyridyl optionally substituted by 1, 2, 3, 4 or 5 (for example 1 or 2) substituents independently selected from the group consisting of: halogen, cyano, hydroxyl, amino, $C_{1-4}$alkylamino, $C_{1-4}$alkyl, halo$C_{1-4}$alkyl, halo$C_{1-4}$alkoxy, $C_{1-4}$alkoxy, —$C(=O)NH_2$ and —$C(=O)(O)_zR_3$.

(5) G is phenyl or pyridyl optionally substituted by 1, 2, 3, 4 or 5 (for example 1 or 2) substituents independently selected from the group consisting of: halogen, cyano, hydroxyl, $C_{1-4}$alkyl, halo$C_{1-4}$alkyl, halo$C_{1-4}$alkoxy and $C_{1-4}$alkoxy.

(6) G is phenyl or pyridyl, optionally substituted by 1, 2 or 3 groups independently selected from halo, $C_{1-4}$alkyl and halo$C_{1-4}$alkyl.

(7) G is phenyl or pyridyl, optionally substituted by 1 or 2 groups independently selected from fluoro, chloro and trifluoromethyl.

(8) G is phenyl optionally substituted by 1, 2, 3, 4 or 5 (for example 1 or 2) substituents independently selected from the group consisting of: halogen, cyano, hydroxyl, $C_{1-4}$alkyl, halo$C_{1-4}$alkyl, halo$C_{1-4}$alkoxy and $C_{1-4}$alkoxy.

(9) G is phenyl, optionally substituted by 1, 2 or 3 groups independently selected from halo, $C_{1-4}$alkyl and halo$C_{1-4}$alkyl.

(10) G is phenyl optionally substituted by 1 or 2 groups independently selected from fluoro, chloro and trifluoromethyl.

(11) G is phenyl.

(12) G is phenyl substituted by 1, 2 or 3 (for example 1 or 2) groups independently selected from halo, $C_{1-4}$alkyl and halo$C_{1-4}$alkyl.

(13) G is pyridyl optionally substituted by halo$C_{1-4}$alkyl, for example trifluoromethyl. For example G is 6-(trifluoromethyl)pyridin-3-yl. For example G is pyridyl.

(14) G is 4-(halo$C_{1-4}$alkyl)phenyl, for example 4-trifluoromethylphenyl.

(15) G is phenyl, 4-trifluoromethyl-phenyl, 2-fluoro-4-trifluoromethyl-phenyl, 2,4-difluorophenyl, 4-fluorophenyl, 2-trifluoromethyl-phenyl, 2-trifluoromethyl-4-fluorophenyl or 3,5-dichlorophenyl.

(16) The group $(CHR)_n(CR_1R_2)_m(CR_1R_2)_p$ is selected from

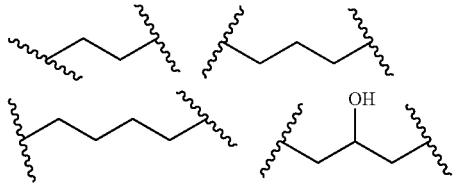

(17) The group $(CHR)_n(CR_1R_2)_m(CR_1R_2)_p$ is

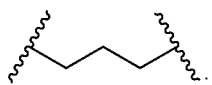 [SMILES: *CCC*]

(18) W is selected from S, O and $CHR_2$.
(19) W is $CHR_2$.
(20) W is S or O.
(21) W is S.
(22) The group $-(CHR)_n(CR_1R_2)_m(CR_1R_2)_pW-$ is

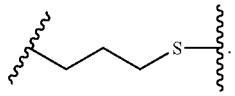

(23) W is S and R, $R_1$ and $R_2$ are hydrogen.
(24) $G_1$ is a phenyl group or a 5-6-membered heteroaromatic group or a 8-11 membered heteroaromatic group, any of which groups may be optionally substituted by 1, 2, 3 or 4 substituents selected from the group consisting of: halogen, cyano, hydroxyl, amino, $C_{1-4}$alkylamino, $C_{1-4}$alkyl, haloC$_{1-4}$alkyl, $C_{1-4}$alkoxy, $C_{1-4}$alkanoyl, SF$_5$, C(=O)NH$_2$, C(=O)OR$_3$.

(25) $G_1$ is phenyl or a 5-6-membered heteroaromatic group any of which groups may be optionally substituted by 1, 2, 3 or 4 substituents independently selected from the group consisting of: halogen, cyano, hydroxyl, amino, $C_{1-4}$alkylamino, $C_{1-4}$alkyl, haloC$_{1-4}$alkyl, haloC$_{1-4}$alkoxy, $C_{1-4}$alkoxy, SF$_5$, $-C(=O)NH_2$ and $-C(=O)(O)_zR_3$.

(26) $G_1$ is a phenyl or a 5-6-membered heteroaromatic group any of which groups may be optionally substituted by 1 or 2 substituents selected from the group consisting of: halogen, hydroxyl, $C_{1-4}$alkyl, haloC$_{1-4}$alkyl, haloC$_{1-4}$alkoxy and $C_{1-4}$alkoxy.

(27) $G_1$ is a 5-6-membered heteroaromatic group optionally substituted by 1, 2, 3 or 4 (for example 1, 2, or 3) substituents independently selected from the group consisting of: halogen, cyano, hydroxyl, amino, $C_{1-4}$alkylamino, $C_{1-4}$alkyl, haloC$_{1-4}$alkyl, haloC$_{1-4}$alkoxy, $C_{1-4}$alkoxy, $-C(=O)NH_2$ and $-C(=O)(O)_zR_3$.

(28) $G_1$ is a 5-6-membered heteroaromatic group containing at least one ring nitrogen and optionally one or two additional ring hetero atoms selected from O and S, wherein the heteroaromatic group is optionally substituted by 1, 2, 3 or 4 (for example 1, 2, or 3) substituents independently selected from the group consisting of: halogen, cyano, hydroxyl, amino, $C_{1-4}$alkylamino, $C_{1-4}$alkyl, haloC$_{1-4}$alkyl, haloC$_{1-4}$alkoxy, $C_{1-4}$alkoxy, $-C(=O)NH_2$ and $-C(=O)(O)_zR_3$.

(29) $G_1$ is a 5-6-membered heteroaromatic group containing at least one ring nitrogen (for example 1, 2 or 3 ring nitrogens) wherein the heteroaromatic group is optionally substituted by 1, 2, 3 or 4 (for example 1, 2, or 3, preferably 1 or 2) substituents independently selected from the group consisting of: halogen, cyano, hydroxyl, amino, $C_{1-4}$alkylamino, $C_{1-4}$alkyl, haloC$_{1-4}$alkyl, haloC$_{1-4}$alkoxy, $C_{1-4}$alkoxy, $-C(=O)NH_2$ and $-C(=O)(O)_zR_3$.

(30) $G_1$ is a 5-6-membered heteroaromatic group any of which groups may be optionally substituted by 1 or 2 substituents selected from the group consisting of: $C_{1-4}$alkyl and haloC$_{1-4}$alkyl.

(31) $G_1$ is a 5-membered heteroaromatic group containing at least one ring nitrogen (for example 1, 2 or 3 ring nitrogens) wherein the heteroaromatic group is optionally substituted by 1 or 2 substituents independently selected from the group consisting of: halogen, cyano, hydroxyl, amino, $C_{1-4}$alkylamino, $C_{1-4}$alkyl, haloC$_{1-4}$alkyl, haloC$_{1-4}$alkoxy and $C_{1-4}$alkoxy; optionally wherein the heteroaromatic group is optionally substituted by 1 or 2 substituents selected from the group consisting of: $C_{1-4}$alkyl and haloC$_{1-4}$alkyl.

(32) $G_1$ is any of the groups set out in paragraphs (24) to (31), wherein $G_1$ is linked to W and Y by carbon atoms in the $G_1$ ring.

(33) $G_1$ is a triazole, for example 1,2,4-triazole optionally substituted by $C_{1-4}$alkyl.

(34) $G_1$ is

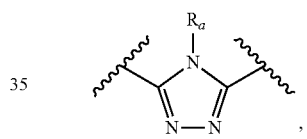

wherein $R_a$ is H or $C_{1-4}$alkyl. Suitably $R_a$ is $C_{1-4}$alkyl.
(35) $G_1$ is

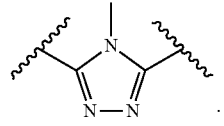 [SMILES: *c1nnc(*)n1C]

(36) Y is a moiety selected from the group consisting of: 5-6 membered heteroaromatic group, saturated mono 3-7 membered carbocyclic group or 8-11 membered bicyclic carbocyclic group in which one or more atom carbons may be replaced by NR$_3$, O, S; any of which groups may be optionally substituted by one or two substituents selected from: halogen, cyano, hydroxyl, amino, $C_{1-4}$alkylamino, $C_{1-4}$alkyl, haloC$_{1-4}$alkyl, $C_{1-4}$alkoxy, $C_{1-4}$alkanoyl, SF$_5$, C(=O)NH$_2$, C(=O)OR$_3$.

(37) Y is selected from phenyl, a 5-6-membered heteroaromatic group, $C_{3-7}$cycloalkyl,

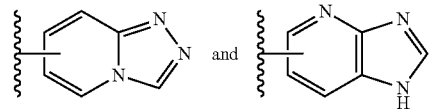

and any of which groups may be optionally substituted by 1, 2 or 3 substituents selected from: halogen, cyano, hydroxyl, $C_{1-4}$alkylamino, $C_{1-4}$alkyl, $C_{1-4}$alkoxy, halo$C_{1-4}$alkyl, halo$C_{1-4}$alkoxy, oxo, —NHC(=O)$C_{1-4}$alkyl, —NR$_5$R$_6$, SF$_5$, —(CH$_2$)$_z$C(=O)NR$_5$R$_6$, —C(=O)(O)$_z$R$_3$, CH$_2$CN, SO$_2$NH$_2$, Y' or OY'; and wherein a ring NH in Y is optionally substituted by R$_4$; and Y' is phenyl, or a 5-6-membered heteroaromatic group optionally substituted by 1 or 2 R$_7$ groups; provided that Y, Y' and G$_1$ are not simultaneously phenyl.

(38) Y is selected from phenyl, oxazolyl, isoxazolyl, furanyl, thiazolyl, isothiazolyl, pyrrolyl, imadazolyl, thiophenyl, thiodiazolyl, pyrazolyl, pyridyl, pyrimidinyl, pyrazinyl, 1,2-dihydropyridinyl, oxanyl, 8-oxabicyclo[3.2.1]octanyl, azetidinyl, pyrrolidinyl, piperidinyl, piperazinyl, morpholinyl, cyclopropyl, cyclobutyl, cyclohexyl,

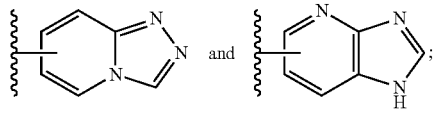

any of which groups may be optionally substituted on a ring carbon atom by 1, 2 or 3 substituents selected from: halogen, cyano, hydroxyl, $C_{1-4}$alkylamino, $C_{1-4}$alkyl, $C_{1-4}$alkoxy, halo$C_{1-4}$alkyl, halo$C_{1-4}$alkoxy, oxo, —NHC(=O)$C_{1-4}$alkyl, —NR$_5$R$_6$, —(CH$_2$)$_z$C(=O)NR$_5$R$_6$, —C(=O)R$_3$, CH$_2$CN, SO$_2$NH$_2$, Y' or OY'; and wherein a ring NH in Y is optionally substituted by R$_4$; and Y' is phenyl, oxadiazolyl, tetrazolyl, pyrazolyl, triazolyl, oxazolyl or pyridyl, optionally substituted by 1 or 2 R$_7$ groups; provided that Y, Y' and G$_1$ are not simultaneously phenyl.

(39) Y is phenyl substituted by 1 or 2 substituents (for example 1 substituent) selected from cyano, CH$_2$CN, —C(=O)R$_3$, —(CH$_2$)$_z$C(=O)NR$_5$R$_6$, —SO$_2$NH$_2$ and Y', wherein Y' is selected from oxadiazolyl, tetrazolyl, triazolyl and oxazolyl, which Y' is optionally substituted by $C_{1-4}$alkyl.

For example Y is phenyl substituted by 1 substituent selected from cyano, CH$_2$CN, acetyl, —CH$_2$C(=O)NH$_2$, —C(=O)NH$_2$, —SO$_2$NH$_2$ and Y', wherein Y' is selected from oxadiazolyl, tetrazolyl, triazolyl and oxazolyl, which Y' is optionally substituted by methyl.

(40) Y is selected from pyridyl, pyrimidinyl, pyrazinyl any of which groups may be optionally substituted by 1 or 2 substituents selected from: fluoro, cyano, $C_{1-4}$alkyl, $C_{1-4}$alkoxy, halo$C_{1-4}$alkyl, and —C(=O)NR$_5$R$_6$. For example Y is pyridyl optionally substituted by 1 or 2 substituents selected from: $C_{1-4}$alkyl and —C(=O)NH$_2$.

(41) Y is selected from the group consisting of:
(i) phenyl optionally substituted by one or two substituents selected from: cyano, C(=O)NH$_2$, sulphonamide, acetyl, CH$_2$CN, CH$_2$C(=O)NH$_2$ or Y'. Preferably Y' is a 5-membered heteroaromatic group (e.g. Y is selected from 4-(1H-1,2,3-tetrazol-5-yl)phenyl, 4-(1,3,4-oxadiazol-2-yl)phenyl, 4-(5-methyl-1,2,4-oxadiazol-3-yl) phenyl, 4-(4H-1,2,4-triazol-4-yl)phenyl, 4-(1,3-oxazol-2-yl)phenyl, and 3-(1,3-oxazol-2-yl)phenyl);
(ii) a saturated mono 3-7 membered carbocyclic group in which 0 or 1 or 2 carbon atoms are replaced by a heteroatom independently selected from O or NR$_3$ (e.g. cyclohexyl, morpholinyl, piperidinyl, tetrahydropyranyl, azetidinyl or piperidin-2-one) optionally substituted by one or more substituents selected from —NHC(=O)$C_{1-4}$alkyl, —NR$_5$R$_6$, $C_{1-4}$alkyl; in a more preferred embodiment R$_3$ is C(=O)$C_{1-4}$alkyl;
(iii) a 8-11 membered bicyclic carbocyclic group (e.g. 3-[(4-methyl-5-{8-oxabicyclo[3.2.1]octan-3-yl}), optionally substituted by one or more (for example 1 or 2) $C_{1-4}$alkyl;
(iv) a 5-6 membered heteroaromatic group (e.g. oxazolyl, thiazolyl, 1-methyl-1H-pyrazol-4-yl, furanyl, thiophenyl, 1-methyl-1H-pyrrolyl, thiadiazolyl, piridinyl, 1,2-dihydropyridin-2-one, pirimidinyl, pirazyl, piridazinyl) optionally substituted by one or two substituents selected from: halogen, cyano, hydroxyl, $C_{1-4}$alkyl, halo$C_{1-4}$alkyl, $C_{1-4}$alkoxy, (CH$_2$)$_z$C(=O)N(R$_4$R$_5$), Y' and OY'.

In a more preferred embodiment $C_{1-4}$alkyl is methyl, halo$C_{1-4}$alkyl is trifluoromethyl, $C_{1-4}$alkoxy is methoxy and Y' is phenyl or pyridine;
(v) a 8-11 membered heteroaromatic group in which 1 or 2 or 3 atom carbons may be replaced by N, optionally substituted by one or more (for example 1 or 2) $C_{1-4}$alkyl (e.g. -{3-[(4-methyl-5-{[1,2,4]triazolo[4,3-a] pyridin-8-yl}).

(42) G$_1$ is a phenyl group, G$_1$ and Y may be fused together to form a benzofused aromatic or heteroaromatic system which might be optionally substituted by one or two substituents selected from: halogen, cyano, hydroxy, amide, ester, amino $C_{1-4}$alkyl, halo$C_{1-4}$alkyl, $C_{1-4}$alkoxy, $C_{1-4}$alkanoyl, SF$_5$.

It is to be understood that any two or more of the features in paragraphs (1) to (42) may be applied to any of the compounds of the formulae (I), (IA), (IB), (II), (IIA), (IIB), (III), (IIIA), (IIIB), (IV), (V), (VA) or (VB), or a pharmaceutically acceptable salt thereof. For example, the features of paragraph (41) for Y may be combined with any one of paragraphs (3) to (15) defining the group G.

As a further representative example paragraph (41) defining Y can be combined with any one of paragraphs (16) to (23). By way of a further example Paragraphs (15), (22) and (41) may be combined. Other combinations of two, three or four of paragraphs (1) to (42) are also contemplated.

Certain of the compounds of the invention may form acid addition salts with one or more equivalents of the acid. The present invention includes within its scope all possible stoichiometric and non-stoichiometric forms.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms.

Pharmaceutical acceptable salts may also be prepared from other salts, including other pharmaceutically acceptable salts, of the compound of formula (I) using conventional methods.

Those skilled in the art of organic chemistry will appreciate that many organic compounds can form complexes with solvents in which they are reacted or from which they are precipitated or crystallized. These complexes are known as "solvates". For example, a complex with water is known as a "hydrate". Solvates of the compound of the invention are within the scope of the invention. The compounds of formula (I) may readily be isolated in association with solvent molecules by crystallisation or evaporation of an appropriate solvent to give the corresponding solvates.

In addition, prodrugs are also included within the context of this invention. As used herein, the term "prodrug" means a compound which is converted within the body, e.g. by hydrolysis in the blood, into its active form that has medical effects. Pharmaceutically acceptable prodrugs are described in T. Higuchi and V. Stella, Prodrugs as Novel Delivery Systems, Vol. 14 of the A.C.S. Symposium Series, Edward B. Roche, ed., Bioreversible Carriers in Drug Design, American Pharmaceutical Association and Pergamon Press, 1987, and in D. Fleisher, S. Ramon and H. Barbra "Improved oral drug delivery: solubility limitations overcome by the use of prodrugs", Advanced Drug Delivery Reviews (1996) 19(2) 115-130, each of which are incorporated herein by reference.

Prodrugs are any covalently bonded carriers that release a compound of structure (I) in vivo when such prodrug is administered to a patient. Prodrugs are generally prepared by modifying functional groups in a way such that the modification is cleaved, either by routine manipulation or in vivo, yielding the parent compound. Prodrugs include, for example, compounds of this invention wherein hydroxy, amine or sulfhydryl groups are bonded to any group that, when administered to a patient, cleaves to form the hydroxy, amine or sulfhydryl groups. Thus, representative examples of prodrugs include (but are not limited to) acetate, formate and benzoate derivatives of alcohol, sulfhydryl and amine functional groups of the compounds of structure (I). Further, in the case of a carboxylic acid (—COOH), esters may be employed, such as methyl esters, ethyl esters, and the like. Esters may be active in their own right and/or be hydrolysable under in vivo conditions in the human body. Suitable pharmaceutically acceptable in vivo hydrolysable ester groups include those which break down readily in the human body to leave the parent acid or its salt.

Furthermore, some of the crystalline forms of the compounds of structure (I) may exist as polymorphs, which are included in the present invention.

Those skilled in the art will appreciate that in the preparation of the compound of the invention or a solvate thereof it may be necessary and/or desirable to protect one or more sensitive groups in the molecule to prevent undesirable side reactions. Suitable protecting groups for use according to the present invention are well known to those skilled in the art and may be used in a conventional manner. See, for example, "Protective groups in organic synthesis" by T. W. Greene and P. G. M. Wuts (John Wiley & sons 1991) or "Protecting Groups" by P. J. Kocienski (Georg Thieme Verlag 1994). Examples of suitable amino protecting groups include acyl type protecting groups (e.g. formyl, trifluoroacetyl, acetyl), aromatic urethane type protecting groups (e.g. benzyloxycarbonyl (Cbz) and substituted Cbz), aliphatic urethane protecting groups (e.g. 9-fluorenylmethoxycarbonyl (Fmoc), t-butyloxycarbonyl (Boc), isopropyloxycarbonyl, cyclohexyloxycarbonyl) and alkyl type protecting groups (e.g. benzyl, trityl, chlorotrityl). Examples of suitable oxygen protecting groups may include for example alkyl silyl groups, such as trimethylsilyl or tert-butyldimethylsilyl; alkyl ethers such as tetrahydropyranyl or tert-butyl; or esters such as acetate.

When a specific enantiomer of a compound of general formula (I) is required, this may be obtained for example by resolution of a corresponding enantiomeric mixture of a compound of formula (I) using conventional methods. Thus the required enantiomer may be obtained from the racemic compound of formula (I) by use of chiral HPLC procedure. Alternatively a specific enantiomer of a compound of general formula (I) may be obtained by reacting the single specific enantiomer of the intermediate.

The subject invention also includes isotopically-labelled compounds, which are identical to those recited in formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^2H$, $^3H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

Compounds of the present invention and pharmaceutically acceptable salts of said compounds that contain the aforementioned isotopes and/or other isotopes of other atoms are within the scope of the present invention. Isotopically-labelled compounds of the present invention, for example those into which radioactive isotopes such as $^3H$, $^{14}C$ are incorporated, are useful in drug and/or substrate tissue distribution assays. Tritiated, i.e., $^3H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^2H$, can afford certain therapeutic advantages resulting from greater metabolic stability, for example increased in vivo half-life or reduced dosage requirements and, hence, may be preferred in some circumstances. Isotopically labelled compounds of formula I and following of this invention can generally be prepared by carrying out the procedures disclosed in the Schemes and/or in the Examples below, by substituting a readily available isotopically labelled reagent for a non-isotopically labelled reagent.

Certain groups/substituents included in the present invention may be present as isomers. The present invention includes within its scope all such isomers, including racemates, enantiomers, tautomers and mixtures thereof. Certain of the substituted heteroaromatic groups included in compounds of formula (I) may exist in one or more tautomeric forms. The present invention includes within its scope all such tautomeric forms, including mixtures.

Generally, and without being limited thereto, such compounds may have higher oral bioavailability, and sometimes higher solubility and/or brain penetrancy. Molecular weight here refers to that of the unsolvated free base compound, excluding any molecular weight contributed by addition salts, solvent (e.g. water) molecules, prodrug molecular parts cleaved off in vivo, etc.

In general, the compounds or salts of the invention should be interpreted as excluding those compounds (if any) which are so chemically unstable, either per se or in water, that they are clearly unsuitable for pharmaceutical use through all administration routes, whether oral, parenteral or otherwise. Such compounds are known to the skilled chemist. Prodrugs or compounds which are stable ex vivo and which are convertable in the mammalian (e.g. human) body to the inventive compounds are however included.

Example compounds of the present invention include a compound selected from:

Ex. 1

(1S,3S/1R,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (TRANS);

Ex. 2

(1R,3R or 1S,3S)-5-(2-{[4-methyl-5-(4-methyl-1,3-oxazol-5-yl)-4H-1,2,4-triazol-3-yl]sulfanyl}-ethyl)-1-[4-(trifluoromethyl)phenyl]-5-azaspiro[2.4]heptane (Enantiomer 1);

Ex. 3

(1S,3S or 1R,3R)-5-(2-{[4-methyl-5-(4-methyl-1,3-oxazol-5-yl)-4H-1,2,4-triazol-3-yl]-sulfanyl}-ethyl)-1-[4-(trifluoromethyl)phenyl]-5-azaspiro[2.4]heptane (Enantiomer 2);

Ex. 4

(1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (CIS);

Ex. 5

(1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (CIS);

Ex. 6

(1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane (CIS);

Ex. 7

(1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane (CIS);

Ex. 8

(1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (TRANS);

Ex. 9

(1R,3R or 1S,3S)-5-(3-{[4-methyl-5-(4-methyl-1,3-oxazol-5-yl)-4H-1,2,4-triazol-3-yl]sulfanyl}-propyl)-1-[4-(trifluoromethyl)phenyl]-5-azaspiro[2.4]heptane (Enantiomer 1);

Ex. 10

(1S,3S or 1R,3R)-5-(3-{[4-methyl-5-(4-methyl-1,3-oxazol-5-yl)-4H-1,2,4-triazol-3-yl]sulfanyl}-propyl)-1-[4-(trifluoromethyl)phenyl]-5-azaspiro[2.4]heptane (Enantiomer 2);

Ex. 11

(1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (CIS);

Ex. 12

(1R,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (Enantiomer 1);

Ex. 13

(1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (Enantiomer 2);

Ex. 14

(1S,3S/1R,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (TRANS);

Ex. 15

(1R,3R or 1S, 3S)-5-(3-{[4-methyl-5-(4-methyl-1,3-oxazol-5-yl)-4H-1,2,4-triazol-3-yl]sulfanyl}-propyl)-1-phenyl-5-azaspiro[2.4]heptane (Enantiomer 1);

Ex. 16

(1S,3S or 1R, 3R)-5-(3-{[4-methyl-5-(4-methyl-1,3-oxazol-5-yl)-4H-1,2,4-triazol-3-yl]sulfanyl}-propyl)-1-phenyl-5-azaspiro[2.4]heptane (Enantiomer 2);

Ex. 17

(1R,3S/1S,3R)-5-(3-{[4-methyl-5-(4-methyl-1,3-oxazol-5-yl)-4H-1,2,4-triazol-3-yl]-sulfanyl}-propyl)-1-phenyl-5-azaspiro[2.4]heptane (CIS);

Ex. 18

(1S,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (Enantiomer 1);

Ex. 19

(1R,3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (Enantiomer 2);

Ex. 20

(1R,3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (Enantiomer 2);

Ex. 21

(1R,3S/1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS);

Ex. 22

(1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 1);

Ex. 23

(1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 2);

Ex. 24

(1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 1);

Ex. 25

(1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 2);

Ex. 26

(1S,3S/1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS);

Ex. 27

(1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 1);

Ex. 28

(1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 2);

Ex. 29

(1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 1);

Ex. 30

(1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 2);

Ex. 31

(1R,3S/1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS);

Ex. 32

(1R,3S or 1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 1);

Ex. 33

(1S,3R or 1R,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 2);

Ex. 34

(1R,3S or 1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 1);

Ex. 35

(1S,3R or 1R,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 2);

Ex. 36

(1S,3S/1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS);

Ex. 37

(1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 1);

Ex. 38

(1S,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 2);

Ex. 39

(1S,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 2);

Ex. 40

(1S,3S/1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS);

Ex. 41

(1R,3R or 1S,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 1);

Ex. 42

(1S,3S or 1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 2);

Ex. 43

(1R,3R or 1S,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 1);

Ex. 44

(1S,3S or 1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 2);

Ex. 45

(1R,3S/1S,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS);

Ex. 46

(1S,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 1);

Ex. 47

(1R,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 2);

Ex. 48

(1R,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 2);

Ex. 49

(1S,3S/1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (TRANS);

Ex. 50

(1R,3R or 1S,3S)-5-(3-{[4-methyl-5-(4-methyl-1,3-oxazol-5-yl)-4H-1,2,4-triazol-3-yl]sulfanyl}-propyl)-1-[2-(trifluoromethyl)phenyl]-5-azaspiro[2.4]heptane (Enantiomer 1);

Ex. 51

(1S,3S or 1R,3R)-5-(3-{[4-methyl-5-(4-methyl-1,3-oxazol-5-yl)-4H-1,2,4-triazol-3-yl]sulfanyl}-propyl)-1-[2-(trifluoromethyl)phenyl]-5-azaspiro[2.4]heptane (Enantiomer 2);

Ex. 52

(1R,3R or 1S,3S)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (Enantiomer 1);

Ex. 53

(1S,3S or 1R,3R)-5-(3-{[4-methyl-5-(4-methyl-1,3-oxazol-5-yl)-4H-1,2,4-triazol-3-yl]sulfanyl}-propyl)-1-[2-(trifluoromethyl)phenyl]-5-azaspiro[2.4]heptane (TRANS, Enantiomer 2);

Ex. 54

(1R,3S/1S,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (CIS);

Ex. 55

(1R,3S or 1S,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 1);

Ex. 56

(1S,3R or 1R,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, Enantiomer 2);

Ex. 57

(1S,3S or 1R,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 1);

Ex. 58

(1R,3R or 1S,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS, Enantiomer 2);

Ex. 59

(1S,3S/1R,3R)-1-(3,5-dichlorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS);

Ex. 60

(1R,3S/1S,3R)-1-(3,5-dichlorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS);

Ex. 61

(1R,3S/1S,3R)-5-(3-{[4-methyl-5-(4-methyl-1,3-oxazol-5-yl)-4H-1,2,4-triazol-3-yl]sulfanyl}propyl)-1-[6-(trifluoromethyl)pyridin-3-yl]-5-azaspiro[2.4]heptane (CIS);

Ex. 62

(1S,3S/1R,3R)-5-(3-{[4-methyl-5-(oxan-4-yl)-4H-1,2,4-triazol-3-yl]-sulfanyl}propyl)-1-[4-(trifluoromethyl)phenyl]-5-azaspiro[2.4]heptane (TRANS);

Ex. 63

(1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (Enantiomer 1);

Ex. 64

(1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (Enantiomer 2);

Ex. 65

(1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (Enantiomer 1);

Ex. 66

(1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (Enantiomer 2);

Ex. 67

(1R,3S/1S,3R)-5-(3-{[4-methyl-5-(oxan-4-yl)-4H-1,2,4-triazol-3-yl]-sulfanyl}propyl)-1-[4-(trifluoromethyl)phenyl]-5-azaspiro[2.4]heptane (CIS);

Ex. 68

(1R,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (Enantiomer 1);

Ex. 69

(1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (Enantiomer 2);

Ex. 70

(1R,3S)-5-(3-{[4-methyl-5-(oxan-4-yl)-4H-1,2,4-triazol-3-yl]-sulfanyl}-propyl)-1-[4-(trifluoromethyl)phenyl]-5-azaspiro[2.4]heptane (Enantiomer 1);

Ex. 71

(1R,3S/1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS);

Ex. 72

(1S,3R or 1R,3S)-1-[2-fluoro-4-(trifluoro-methyl)phenyl]-5-(3-{[4-methyl-5-(oxan-4-yl)-4H-1,2,4-triazol-3-yl]sulfanyl}propyl)-5-azaspiro[2.4]heptane (Enantiomer 1);

Ex. 73

(1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (Enantiomer 2);

Ex. 74

(1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (Enantiomer 1);

Ex. 75

(1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (Enantiomer 2);

Ex. 76

(1S,3S/1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (CIS);

Ex. 77

(1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (Enantiomer 1);

Ex. 78

(1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (Enantiomer 2);

Ex. 79

(1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (Enantiomer 2);

Ex. 80

(1R,3S/1S,3R)-5-(3-{[4-methyl-5-(oxan-4-yl)-4H-1,2,4-triazol-3-yl]-sulfanyl}propyl)-1-phenyl-5-azaspiro[2.4]heptane (CIS);

Ex. 81

(1S,3R)-5-(3-{[4-methyl-5-(oxan-4-yl)-4H-1,2,4-triazol-3-yl]sulfanyl}propyl)-1-phenyl-5-azaspiro[2.4]heptane (Enantiomer 1);

Ex. 82

(1R,3S)-5-(3-{[4-methyl-5-(oxan-4-yl)-4H-1,2,4-triazol-3-yl]sulfanyl}propyl)-1-phenyl-5-azaspiro[2.4]heptane (Enantiomer 2);

Ex. 83

(1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (Enantiomer 2);

Ex. 84

(1R,3S/1S,3R)-5-(3-{[4-methyl-5-(oxan-4-yl)-4H-1,2,4-triazol-3-yl]sulfanyl}propyl)-1-[6-(trifluoromethyl)pyridin-3-yl]-5-azaspiro[2.4]heptane (CIS);

Ex. 85

(1R,3S/1S,3R)-5-{3-[(4-methyl-5-{8-oxabicyclo[3.2.1]octan-3-yl}-4H-1,2,4-triazol-3-yl)sulfanyl]-propyl}-1-[4-(trifluoromethyl)phenyl]-5-azaspiro[2.4]heptane (CIS);

Ex. 86

(1R,3S)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (Enantiomer 1);

Ex. 87

(1S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (Enantiomer 2);

Ex. 88

(1R,3S)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (Enantiomer 1);

Ex. 89

(1S,3S/1R,3R)-5-{3-[(5-cyclohexyl-4-methyl-4H-1,2,4-triazol-3-yl)sulfanyl]propyl}-1-[4-(trifluoro-methyl)phenyl]-5-azaspiro[2.4]heptane (TRANS);

Ex. 90

(1R,3R or 1S,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (Enantiomer 1);

Ex. 91

(1S,3S or 1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (Enantiomer 2);

Ex. 92

(1R,3R or 1S,3S)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane (Enantiomer 1);

Ex. 93

(1S,3S or 1R,3R)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane (Enantiomer 2);

Ex. 94

(1R,3S/1S,3R)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane (CIS);

Ex. 95

(1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (Enantiomer 1);

Ex. 96

(1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (Enantiomer 2);

Ex. 97

(1R,3S)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane (Enantiomer 1);

Ex. 98

(1S,3R)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane (Enantiomer 2);

Ex. 99

1-{4-[4-methyl-5-({3-[(1R,3S/1S,R3)-1-[4-(trifluoromethyl)phenyl]-5-azaspiro[2.4]heptan-5-yl]propyl}sulfanyl)-4H-1,2,4-triazol-3-yl]piperidin-1-yl}ethan-1-one (CIS);

Ex. 100

1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}ethan-1-one (CIS, Enantiomer 1);

Ex. 101

1-{4-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidin-1-yl}ethan-1-one (CIS);

Ex. 102

1-{4-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidin-1-yl}ethan-1-one (CIS);

Ex. 103

3-methoxy-1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}propan-1-one (CIS, Enantiomer 1);

Ex. 104

3-methoxy-1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}propan-1-one (CIS, Enantiomer 1);

Ex. 105

(1R,3S)-5-(3-{[5-(1-cyclopropanecarbonylpiperidin-4-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1);

Ex. 106

(1R,3S)-5-(3-{[5-(1-cyclopropanecarbonylpiperidin-4-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1);

Ex. 107

1-{3-[4-methyl-5-({3-[(1R,3S/1S,3R)-1-[4-(trifluoromethyl)phenyl]-5-azaspiro[2.4]heptan-5-yl]-propyl}sulfanyl)-4H-1,2,4-triazol-3-yl]azetidin-1-yl}ethan-1-one (CIS);

Ex. 108

4-[4-methyl-5-({3-[(1R,3S/1S,3R)-1-[4-(trifluoromethyl)phenyl]-5-azaspiro[2.4]heptan-5-yl]-propyl}sulfanyl)-4H-1,2,4-triazol-3-yl]cyclohexan-1-amine (CIS);

Ex. 109

N-{4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexyl}acetamide (CIS);

Ex. 110

N-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]cyclohexyl)}acetamide (CIS, Enantiomer 1);

Ex. 111

N-{4-[4-methyl-5-({3-[(1S,3R)-1-[4-(trifluoromethyl)phenyl]-5-azaspiro[2.4]heptan-5-yl]propyl}sulfanyl)-4H-1,2,4-triazol-3-yl]cyclohexyl)}acetamide (CIS, Enantiomer 2);

Ex. 112

N-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]cyclohexyl)}acetamide (CIS, Enantiomer 1);

Ex. 113

(1S,3S/1R,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (TRANS);

Ex. 114

(1S,3S/1R,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (TRANS);

Ex. 115

(1R,3S/1S,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS);

Ex. 116

(1R,3S)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 117

(1S,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 118

(1R,3S)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 119

4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one (CIS, Enantiomer 1);

Ex. 120

1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one (CIS, Enantiomer 1);

Ex. 121

5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one (CIS, Enantiomer 1);

Ex. 122

6-[4-methyl-5-({3-[(1R,3S/1S,3R)-1-[4-(trifluoromethyl)phenyl]-5-azaspiro[2.4]heptan-5-yl]-propyl}sulfanyl)-4H-1,2,4-triazol-3-yl]-1,2-dihydropyridin-2-one (CIS);

Ex. 123

6-[5-({3-[(1R,3S/1S,3R)-1-[2-fluoro-4-(trifluoromethyl)phenyl]-5-azaspiro[2.4]heptan-5-yl]-propyl}sulfanyl)-4-methyl-4H-1,2,4-triazol-3-yl]-1,2-dihydropyridin-2-one (TRANS);

Ex. 124

3-[4-methyl-5-({3-[(1R,3S/1S,3R)-1-[4-(trifluoromethyl)phenyl]-5-azaspiro[2.4]heptan-5-yl]-propyl}sulfanyl)-4H-1,2,4-triazol-3-yl]-1,2-dihydropyridin-2-one (CIS);

Ex. 125

3-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]-1,2-dihydropyridin-2-one (CIS, Enantiomer 1);

Ex. 126

5-[4-methyl-5-({3-[(1S,3S/1R,3R)-1-[4-(trifluoromethyl)phenyl]-5-azaspiro[2.4]heptan-5-yl]-propyl}sulfanyl)-4H-1,2,4-triazol-3-yl]-1,2-dihydropyridin-2-one (TRANS);

Ex. 127

5-[4-methyl-5-({3-[(1R,3S/1S,3R)-1-[4-(trifluoromethyl)phenyl]-5-azaspiro[2.4]heptan-5-yl]-propyl}sulfanyl)-4H-1,2,4-triazol-3-yl]-1,2-dihydropyridin-2-one (CIS);

Ex. 128

5-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]-1,2-dihydropyridin-2-one (CIS, Enantiomer 1);

Ex. 129

5-[5-({3-[(1S,3S/1R,3R)-1-[2-fluoro-4-(trifluoromethyl)phenyl]-5-azaspiro[2.4]heptan-5-yl]-propyl}sulfanyl)-4-methyl-4H-1,2,4-triazol-3-yl]-1,2-dihydropyridin-2-one (CIS);

Ex. 130

5-[5-({3-[(1S,3S/1R,3R)-1-(2,4-difluorophenyl)-5-azaspiro[2.4]heptan-5-yl]propyl}sulfanyl)-4-methyl-4H-1,2,4-triazol-3-yl]-1,2-dihydropyridin-2-one (CIS);

Ex. 131

5-[5-({3-[(1R,3S/1S,3R)-1-(4-fluorophenyl)-5-azaspiro[2.4]heptan-5-yl]propyl}sulfanyl)-4-methyl-4H-1,2,4-triazol-3-yl]-1,2-dihydropyridin-2-one (CIS);

Ex. 132

5-[4-methyl-5-({3-[(1S,3S/1R,3R)-1-[2-(trifluoromethyl)phenyl]-5-azaspiro[2.4]heptan-5-yl]-propyl}sulfanyl)-4H-1,2,4-triazol-3-yl]-1,2-dihydropyridin-2-one (TRANS);

Ex. 133

1-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1);

Ex. 134

4-[4-methyl-5-({3-[(1R,3S/1S,3R)-1-[4-(trifluoromethyl)phenyl]-5-azaspiro[2.4]heptan-5-yl]-propyl}sulfanyl)-4H-1,2,4-triazol-3-yl]-1,2-dihydropyridin-2-one (CIS);

Ex. 135

4-[4-methyl-5-({3-[(1S,3S/1R,3R)-1-[2-(trifluoromethyl)phenyl]-5-azaspiro[2.4]heptan-5-yl]-propyl}sulfanyl)-4H-1,2,4-triazol-3-yl]-1,2-dihydropyridin-2-one (TRANS);

Ex. 136

1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1);

Ex. 137

1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1);

Ex. 138

4-[5-({3-[(1S,3S)-1-[2-fluoro-4-(trifluoromethyl)phenyl]-5-azaspiro[2.4]heptan-5-yl]-propyl}sulfanyl)-4-methyl-4H-1,2,4-triazol-3-yl]-1-methyl-1,2-dihydropyridin-2-one (CIS, Enantiomer 1);

Ex. 139

4-[5-({3-[(1S,3S)-1-[2-fluoro-4-(trifluoromethyl)phenyl]-5-azaspiro[2.4]heptan-5-yl]-propyl}sulfanyl)-4-methyl-4H-1,2,4-triazol-3-yl]-1-methyl-1,2-dihydropyridin-2-one (CIS, Enantiomer 1);

Ex. 140

(1S,3S/1R,3S)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane (TRANS);

Ex. 141

(1R,3S/1S,3R)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane (CIS);

Ex. 142

(1S,3S/1R,3S)-5-(3-{[4-methyl-5-(pyridin-3-yl)-4H-1,2,4-triazol-3-yl]sulfanyl}propyl)-1-[4-(trifluoromethyl)phenyl]-5-azaspiro[2.4]heptane (TRANS);

Ex. 143

(1R,3S/1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS);

Ex. 144

(1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, Enantiomer 1);

Ex. 145

(1R,3S)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, Enantiomer 2);

Ex. 146

(1R,3S)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, Enantiomer 2);

Ex. 147

(1S,3S/1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS);

Ex. 148

(1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, Enantiomer 1);

Ex. 149

(1S,3S)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, Enantiomer 2);

Ex. 150

(1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, Enantiomer 1);

Ex. 151

(1S,3S)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, Enantiomer 2);

Ex. 152

(1S,3S/1R,3R)-1-(2,4-difluorophenyl)-5-(3-{[4-methyl-5-(pyridin-3-yl)-4H-1,2,4-triazol-3-yl]-sulfanyl}propyl)-5-azaspiro[2.4]heptane (CIS);

Ex. 153

(1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 1);

Ex. 154

(1S,3S)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 2);

Ex. 155

(1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 1);

Ex. 156

(1S,3S)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 2);

Ex. 157

(1R,3S/1S,3R)-1-(4-fluorophenyl)-5-(3-{[4-methyl-5-(pyridin-3-yl)-4H-1,2,4-triazol-3-yl]sulfanyl}-propyl)-5-azaspiro[2.4]heptane (CIS);

Ex. 158

(1S,3R)-1-(4-fluorophenyl)-5-(3-{[4-methyl-5-(pyridin-3-yl)-4H-1,2,4-triazol-3-yl]-sulfanyl}propyl)-5-azaspiro[2.4]heptane (CIS, Enantiomer 1);

Ex. 159

(1R,3S)-1-(4-fluorophenyl)-5-(3-{[4-methyl-5-(pyridin-3-yl)-4H-1,2,4-triazol-3-yl]-sulfanyl}propyl)-5-azaspiro[2.4]heptane (CIS, Enantiomer 2);

Ex. 160

(1R,3S)-1-(4-fluorophenyl)-5-(3-{[4-methyl-5-(pyridin-3-yl)-4H-1,2,4-triazol-3-yl]-sulfanyl}propyl)-5-azaspiro[2.4]heptane (CIS, Enantiomer 2);

Ex. 161

(1R,3S/1S,3R)-5-(3-{[4-methyl-5-(pyridin-3-yl)-4H-1,2,4-triazol-3-yl]sulfanyl}propyl)-1-phenyl-5-azaspiro[2.4]heptane (CIS);

Ex. 162

(1S,3S/1R,3R)-5-(3-{[4-methyl-5-(pyridin-4-yl)-4H-1,2,4-triazol-3-yl]sulfanyl}propyl)-1-[4-(trifluoromethyl)phenyl]-5-azaspiro[2.4]heptane (TRANS);

Ex. 163

(1R,3S/1S,3R)-5-(3-{[4-methyl-5-(pyridin-4-yl)-4H-1,2,4-triazol-3-yl]sulfanyl}propyl)-1-[4-(trifluoromethyl)phenyl]-5azaspiro[2.4]heptane (CIS);

Ex. 164

(1R,3S/1S,3R)-1-[2-fluoro-4-(trifluoromethyl)phenyl]-5-(3-{[4-methyl-5-(pyridin-4-yl)-4H-1,2,4-triazol-3-yl]sulfanyl}propyl)-5-azaspiro[2.4]heptane (TRANS);

Ex. 165

(1R,3S/1S,3R)-5-(3-{[4-methyl-5-(2-methylpyridin-3-yl)-4H-1,2,4-triazol-3-yl]sulfanyl}propyl)-1-[4-(trifluoromethyl)phenyl]-5-azaspiro[2.4]heptane (CIS);

Ex. 166

(1R,3S)-5-(3-{[4-methyl-5-(2-methylpyridin-3-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 167

(1S,3S/1R,3R)-5-(3-{[4-methyl-5-(2-methylpyridin-3-yl)-4H-1,2,4-triazol-3-yl]sulfanyl}propyl)-1-[2-(trifluoromethyl)phenyl]-5-azaspiro[2.4]heptane (TRANS);

Ex. 168

(1S,3S/1R,3R)-5-(3-{[4-methyl-5-(2-methylpyridin-3-yl)-4H-1,2,4-triazol-3-yl]sulfanyl}propyl)-1-[2-(trifluoromethyl)phenyl]-5-azaspiro[2.4]heptane (TRANS);

Ex. 169

(1R,3S/1S,3R)-5-(3-{[4-methyl-5-(6-methylpyridin-3-yl)-4H-1,2,4-triazol-3-yl]sulfanyl}propyl)-1-[4-(trifluoromethyl)phenyl]-5-azaspiro[2.4]heptane (CIS);

Ex. 170

(1R,3S)-5-(3-{[4-methyl-5-(3-methylpyridin-2-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 171

(1R,3S)-5-(3-{[5-(2,6-dimethylpyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1);

Ex. 172

(1R,3S)-5-(3-{[5-(2,6-dimethylpyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1);

Ex. 173

(1R,3S/1S,3R)-5-(3-{[5-(2-fluoropyridin-3-yl)-4-methyl-4H-1,2,4-triazol-3-yl]sulfanyl}propyl)-1-[4-(trifluoromethyl)phenyl]-5-azaspiro[2.4]heptane (CIS);

Ex. 174

(1R,3S)-5-[3-({4-methyl-5-[2-(trifluoromethyl)pyridin-3-yl]-4H-1,2,4-triazol-3-yl}sulfanyl)propyl]-1-[4-(trifluoromethyl)phenyl]-5-azaspiro[2.4]heptane (CIS, Enantiomer 1);

Ex. 175

(1R,3S)-5-(3-{[5-(2-methoxypyridin-3-yl)-4-methyl-4H-1,2,4-triazol-3-yl]sulfanyl})propyl)-1-[4-(trifluoromethyl)phenyl]-5-azaspiro[2.4]heptane (CIS, Enantiomer 1);

Ex. 176

(1R,3S)-5-(3-{[5-(2-methoxypyridin-3-yl)-4-methyl-4H-1,2,4-triazol-3-yl]sulfanyl)}propyl)-1-[4-(trifluoromethyl)phenyl]-5-azaspiro[2.4]heptane (CIS, Enantiomer 1);

Ex. 177

5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carbonitrile (CIS, Enantiomer 1);

Ex. 178

4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]pyridine-2-carbonitrile (CIS, Enantiomer 1);

Ex. 179

5-[4-methyl-5-({3-[(1S,3S/1R,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS);

Ex. 180

5-[4-methyl-5-({3-[(1S,3S or 1R,3R)-1-[4-(trifluoromethyl)phenyl]-5-azaspiro[2.4]heptan-5-yl]-propyl}sulfanyl)-4H-1,2,4-triazol-3-yl]pyridine-2-carboxamide (TRANS, Enantiomer 1);

Ex. 181

5-[4-methyl-5-({3-[(1R,3R or 1S,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, Enantiomer 2);

Ex. 182

5-[4-methyl-5-({3-[(1R,3S/1S,3R)-1-[4-(trifluoromethyl)phenyl]-5-azaspiro[2.4]heptan-5-yl]-propyl}sulfanyl)-4H-1,2,4-triazol-3-yl]pyridine-2-carboxamide (CIS);

Ex. 183

5-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]pyridine-2-carboxamide (CIS, Enantiomer 1);

Ex. 184

5-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]pyridine-2-carboxamide (CIS, Enantiomer 1);

Ex. 185

5-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-2-carboxamide (CIS, Enantiomer 1);

Ex. 186

5-[5-({3-[(1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-2-carboxamide (CIS, Enantiomer 2);

Ex. 187

6-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1);

Ex. 188

6-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxylic acid formate (CIS, Enantiomer 1);

Ex. 189

6-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]pyridine-3-carboxamide (CIS, Enantiomer 1);

Ex. 190

6-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-3-carboxamide (CIS, Enantiomer 1);

Ex. 191

4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]pyridine-2-carboxamide (CIS, Enantiomer 1);

Ex. 192

5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-3-carboxamide (CIS, Enantiomer 1);

Ex. 193

6-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]pyridine-2-carboxamide (CIS, Enantiomer 1);

Ex. 194

N-methyl-6-[4-methyl-5-({3-[(1R,3S)-1-[4-(trifluoromethyl)phenyl]-5-azaspiro[2.4]heptan-5-yl] propyl}sulfanyl)-4H-1,2,4-triazol-3-yl]pyridine-2-carboxamide (CIS, Enantiomer 1);

Ex. 195

N-methyl-6-[4-methyl-5-({3-[(1R,3S)-1-[4-(trifluoromethyl)phenyl]-5-azaspiro[2.4]heptan-5-yl] propyl}sulfanyl)-4H-1,2,4-triazol-3-yl]pyridine-2-carboxamide (CIS, Enantiomer 1);

Ex. 196

N,N-dimethyl-6-[4-methyl-5-({3-[(1R,3S)-1-[4-(trifluoromethyl)phenyl]-5-azaspiro[2.4]heptan-5-yl] propyl}sulfanyl)-4H-1,2,4-triazol-3-yl]pyridine-2-carboxamide (CIS, Enantiomer 1);

Ex. 197

N,N-dimethyl-6-[4-methyl-5-({3-[(1R,3S)-1-[4-(trifluoromethyl)phenyl]-5-azaspiro[2.4]heptan-5-yl] propyl}sulfanyl)-4H-1,2,4-triazol-3-yl]pyridine-2-carboxamide (CIS, Enantiomer 1);

Ex. 198

5-methyl-6-[4-methyl-5-({3-[(1R,3S)-1-[4-(trifluoromethyl)phenyl]-5-azaspiro[2.4]heptan-5-yl] propyl}sulfanyl)-4H-1,2,4-triazol-3-yl]pyridine-2-carboxamide (CIS, Enantiomer 1);

Ex. 199

5-methyl-6-[4-methyl-5-({3-[(1R,3S)-1-[4-(trifluoromethyl)phenyl]-5-azaspiro[2.4]heptan-5-yl] propyl}sulfanyl)-4H-1,2,4-triazol-3-yl]pyridine-2-carboxamide (CIS, Enantiomer 1);

Ex. 200

(1S,3S/1R,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (TRANS);

Ex. 201

(1R,3S/1S,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS);

Ex. 202

(1R,3S)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 203

(1S,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 204

(1R,3S)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 205

(1S,3S/1R,3R)-5-(3-{[4-methyl-5-(pyridazin-3-yl)-4H-1,2,4-triazol-3-yl]sulfanyl}propyl)-1-[4-(trifluoromethyl)phenyl]-5-azaspiro[2.4]heptane (TRANS);

Ex. 206

(1R,3S/1S,3R)-5-(3-{[4-methyl-5-(pyridazin-3-yl)-4H-1,2,4-triazol-3-yl]sulfanyl}propyl)-1-[4-(trifluoromethyl)phenyl]-5-azaspiro[2.4]heptane (CIS);

Ex. 207

(1S,3S/1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS);

Ex. 208

(1S,3S or 1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, Enantiomer 1);

Ex. 209

(1R,3R or 1S,R3)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, Enantiomer 2);

Ex. 210

(1S,3S or 1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, Enantiomer 1);

Ex. 211

(1R,3R or 1S,R3)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, Enantiomer 2);

Ex. 212

(1R,3S/1S,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (CIS);

Ex. 213

(1S,3S/1R,3R)-1-[2-fluoro-4-(trifluoromethyl)phenyl]-5-(3-{[4-methyl-5-(pyrimidin-4-yl)-4H-1,2,4-triazol-3-yl]sulfanyl}propyl)-5-azaspiro[2.4]heptane (CIS);

Ex. 214

(1S,3S/1R,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS);

Ex. 215

(1S,3S or 1R,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, Enantiomer 1);

Ex. 216

(1R,3R or 1S,R3)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, Enantiomer 2);

Ex. 217

(1R,3S/1S,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS);

Ex. 218

(1S,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 219

(1R,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 220

(1R,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 221

(1S,3S/1R,3R)-1-[2-fluoro-4-(trifluoromethyl)phenyl]-5-(3-{[4-methyl-5-(pyrazin-2-yl)-4H-1,2,4-triazol-3-yl]sulfanyl}propyl)-5-azaspiro[2.4]heptane (CIS);

Ex. 222

(1R,3S/1S,3R)-5-(3-{[4-methyl-5-(6-methylpyrazin-2-yl)-4H-1,2,4-triazol-3-yl]sulfanyl}propyl)-1-[4-(trifluoromethyl)phenyl]-5-azaspiro[2.4]heptane (CIS);

Ex. 223

(1R,3S/1S,3R)-5-(3-{[4-methyl-5-(5-methylpyrazin-2-yl)-4H-1,2,4-triazol-3-yl]sulfanyl}propyl)-1-[4-(trifluoromethyl)phenyl]-5-azaspiro[2.4]heptane (CIS);

Ex. 224

(1R,3S/1S,3R)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS);

Ex. 225

(1S,3R)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 226

(1R,3S)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 227

(1R,3S)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 228

5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyrazine-2-carboxamide (CIS);

Ex. 229

(1R,3S/1S,3R)-5-(3-{[4-methyl-5-(1,2-oxazol-5-yl)-4H-1,2,4-triazol-3-yl]sulfanyl}propyl)-1-[4-(trifluoromethyl)phenyl]-5-azaspiro[2.4]heptane (CIS);

Ex. 230

(1S,3S/1R,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (TRANS);

Ex. 231

(1R,3S/1S,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS);

Ex. 232

(1R,3S)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 233

(1S,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 234

(1R,3S)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 235

(1S,3S/1R,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (TRANS);

Ex. 236

(1R,3S/1S,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS);

Ex. 237

(1R,3S)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 238

(1S,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 239

(1R,3S)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 240

(1S,3S/1R,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (TRANS);

Ex. 241

(1R,3S/1S,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS);

Ex. 242

(1R,3S)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 243

(1S,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 244

(1R,3S)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 245

(1S,3S/1R,3R)-5-(3-{[4-methyl-5-(1-methyl-1H-pyrazol-4-yl)-4H-1,2,4-triazol-3-yl]sulfanyl}-propyl)-1-[4-(trifluoromethyl)phenyl]-5-azaspiro[2.4]heptane (TRANS);

Ex. 246

(1R,3S/1S,3R) 5-(3-{[4-methyl-5-(1-methyl-1H-pyrazol-4-yl)-4H-1,2,4-triazol-3-yl]sulfanyl}-propyl)-1-[4-(trifluoromethyl)phenyl]-5-azaspiro[2.4]heptane (CIS);

Ex. 247

(1S,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 248

(1R,3S)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 249

(1R,3S)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 250

C(1R,3S/1S,3R)-5-(3-{[4-methyl-5-(1-methyl-1H-pyrazol-5-yl)-4H-1,2,4-triazol-3-yl]sulfanyl}-propyl)-1-[4-(trifluoromethyl)phenyl]-5-azaspiro[2.4]heptane (CIS);

Ex. 251

(1S,3R)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 252

(1R,3S)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 253

(1R,3S)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, Enantiomer 2);

Ex. 254

(1R,3S/1S,3R)-5-(3-{[5-(furan-2-yl)-4-methyl-4H-1,2,4-triazol-3-yl]sulfanyl}propyl)-1-[4-(trifluoromethyl)phenyl]-5-azaspiro[2.4]heptane (CIS);

Ex. 255

(1R,3S/1S,3R)-5-(3-{[5-(furan-3-yl)-4-methyl-4H-1,2,4-triazol-3-yl]sulfanyl}propyl)-1-[4-(trifluoromethyl)phenyl]-5-azaspiro[2.4]heptane (CIS);

Ex. 256

(1R,3S/1S,3R)-5-(3-{[4-methyl-5-(thiophen-2-yl)-4H-1,2,4-triazol-3-yl]sulfanyl}propyl)-1-[4-(trifluoromethyl)phenyl]-5-azaspiro[2.4]heptane (CIS);

Ex. 257

(1R,3S/1S,3R)-5-(3-{[4-methyl-5-(thiophen-3-yl)-4H-1,2,4-triazol-3-yl]sulfanyl}propyl)-1-[4-(trifluoromethyl)phenyl]-5-azaspiro[2.4]heptane (CIS);

Ex. 258

(1R,3S/1S,3R)-5-(3-{[4-methyl-5-(1-methyl-1H-pyrrol-2-yl)-4H-1,2,4-triazol-3-yl]sulfanyl}propyl)-1-[4-(trifluoromethyl)phenyl]-5-azaspiro[2.4]heptane (CIS);

Ex. 259

(1S,3S/1R,3R)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane (TRANS);

Ex. 260

(1R,3S/1S,3R)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane (CIS);

Ex. 261

(1R,3S)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 262

(1R,3S)-5-(3-{[4-methyl-5-(4-methyl-1,2,3-thiadiazol-5-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 263

(1R,3S)-5-[3-({4-methyl-5-[2-(pyridin-3-yl)-1,3-oxazol-5-yl]-4H-1,2,4-triazol-3-yl}-sulfanyl)propyl]-1-[4-(trifluoromethyl)phenyl]-5-azaspiro[2.4]heptane (CIS, Enantiomer 1);

Ex. 264

(1R,3S)-5-(3-{[4-methyl-5-(6-phenoxypyridin-3-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 265

(1R,3S)-5-(3-{[4-methyl-5-(6-phenoxypyridin-3-yl)-4H-1,2,4-triazol-3-yl]sulfanyl}propyl)-1-[4-(trifluoromethyl)phenyl]-5-azaspiro[2.4]heptane (CIS, Enantiomer 1);

Ex. 266

(1R,3S)-5-{3-[(4-methyl-5-{[1,2,4]triazolo[4,3-a]pyridin-8-yl}-4H-1,2,4-triazol-3-yl)sulfanyl]propyl}-1-[4-(trifluoromethyl)phenyl]-5-azaspiro[2.4]heptane (CIS, Enantiomer 1);

Ex. 267

(1R,3S)-5-{3-[(4-methyl-5-{[1,2,4]triazolo[4,3-a]pyridin-8-yl}-4H-1,2,4-triazol-3-yl)-sulfanyl]propyl}-1-[4-(trifluoromethyl)phenyl]-5-azaspiro[2.4]heptane (CIS, Enantiomer 1);

Ex. 268

(1R,3S)-5-{3-[(4-methyl-5-{[1,2,4]triazolo[4,3-a]pyridin-6-yl}-4H-1,2,4-triazol-3-yl)-sulfanyl]propyl}-1-[4-(trifluoromethyl)phenyl]-5-azaspiro[2.4]heptane (CIS, Enantiomer 1);

Ex. 269

(1R,3S)-5-{3-[(4-methyl-5-{[1,2,4]triazolo[4,3-a]pyridin-7-yl}-4H-1,2,4-triazol-3-yl)-sulfanyl]propyl}-1-[4-(trifluoromethyl)phenyl]-5-azaspiro[2.4]heptane (CIS, Enantiomer 1);

Ex. 270

(1S,3S)-1-[2-fluoro-4-(trifluoromethyl)phenyl]-5-{3-[(4-methyl-5-{[1,2,4]triazolo[4,3-a]pyridin-7-yl}-4H-1,2,4-triazol-3-yl)sulfanyl]propyl}-5-azaspiro[2.4]heptane (CIS, Enantiomer 1);

Ex. 271

(1R,3S)-5-{3-[(4-methyl-5-{3-methyl-[1,2,4]triazolo[4,3-a]pyridin-6-yl}-4H-1,2,4-triazol-3-yl)sulfanyl]propyl}-1-[4-(trifluoromethyl)phenyl]-5-azaspiro[2.4]heptane (CIS, Enantiomer 1);

Ex. 272

(1R,3S)-5-{3-[(5-{1H-imidazo[4,5-b]pyridin-5-yl}-4-methyl-4H-1,2,4-triazol-3-yl)-sulfanyl]propyl}-1-[4-(trifluoromethyl)phenyl]-5-azaspiro[2.4]heptane (CIS, Enantiomer 1);

Ex. 273

(1R,3S)-5-[3-({4-methyl-5-[4-(1H-1,2,3,4-tetrazol-5-yl)phenyl]-4H-1,2,4-triazol-3-yl}sulfanyl)propyl]-1-[4-(trifluoromethyl)phenyl]-5-azaspiro[2.4]heptane (CIS, Enantiomer 1);

Ex. 274

(1R,3S)-5-[3-({4-methyl-5-[4-(1,3,4-oxadiazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1);

Ex. 275

(1R,3S)-5-[3-({4-methyl-5-[4-(5-methyl-1,2,4-oxadiazol-3-yl)phenyl]-4H-1,2,4-triazol-3-yl}sulfanyl)propyl]-1-[4-(trifluoromethyl)phenyl]-5-azaspiro[2.4]heptane (CIS, Enantiomer 1);

Ex. 276

(1R,3S)-5-[3-({4-methyl-5-[4-(4H-1,2,4-triazol-4-yl)phenyl]-4H-1,2,4-triazol-3-yl}sulfanyl)propyl]-1-[4-(trifluoromethyl)phenyl]-5-azaspiro[2.4]heptane (CIS, Enantiomer 1);

Ex. 277

(1R,3S)-5-[3-({4-methyl-5-[4-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1);

Ex. 278

(1R,3S)-5-[3-({4-methyl-5-[4-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1);

Ex. 279

(1R,3S)-5-[3-({4-methyl-5-[3-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1);

Ex. 280

4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]benzamide (CIS, Enantiomer 1);

Ex. 281

4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]benzamide (CIS, Enantiomer 1);

Ex. 282

4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]benzonitrile (CIS, Enantiomer 1);

Ex. 283

4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]benzonitrile (CIS, Enantiomer 1);

Ex. 284

1-{4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]phenyl}ethan-1-one (CIS, Enantiomer 1);

Ex. 285

4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]benzene-1-sulfonamide (CIS, Enantiomer 1);

Ex. 286

2-{4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]phenyl}acetonitrile (CIS, Enantiomer 1);

Ex. 287

2-{4-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]phenyl}acetamide (CIS, Enantiomer 1);

Ex. 288

3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (CIS, Enantiomer 1);

Ex. 289

3-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]benzamide (CIS, Enantiomer 1);

Ex. 290

2-[4-methyl-5-({3-[(1R,3S)-1-[4-(trifluoromethyl)phenyl]-5-azaspiro[2.4]heptan-5-yl]-propyl}sulfanyl)-4H-1,2,4-triazol-3-yl]benzamide (CIS, Enantiomer 1);

Ex. 291

1-{[4-methyl-5-(4-methyl-1,3-oxazol-5-yl)-4H-1,2,4-triazol-3-yl]sulfanyl}-3-{1-[4-(trifluoro-methyl)phenyl]-5-azaspiro[2.4]-heptan-5-yl}propan-2-ol (CIS) diastereoisomeric mixture;

Ex. 292

(1S,3S/1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS);

Ex. 293

(1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (Enantiomer 1);

Ex. 294

(1S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (Enantiomer 2);

Ex. 295

(1S,3S)-1-[2-fluoro-4-(trifluoromethyl)-phenyl]-5-{4-[4-methyl-5-(oxan-4-yl)-4H-1,2,4-triazol-3-yl]butyl}-5-azaspiro[2.4]-heptane (Enantiomer 2);

Ex. 296

(1S,3S/1R,3R)-5-{4-[4-methyl-5-(oxan-4-yl)-4H-1,2,4-triazol-3-yl]butyl}-1-[4-(trifluoromethyl)-phenyl]-5-azaspiro[2.4]heptane (TRANS);

Ex. 297

(1S,3S or 1R,3R)-5-{4-[4-methyl-5-(oxan-4-yl)-4H-1,2,4-triazol-3-yl]butyl}-1-[4-(trifluoro-methyl)phenyl]-5-azaspiro[2.4]heptane (TRANS, Enantiomer 1);

Ex. 298

(1R,3R or 1S,3S)-5-{4-[4-methyl-5-(oxan-4-yl)-4H-1,2,4-triazol-3-yl]butyl}-1-[4-(trifluoro-methyl)phenyl]-5-azaspiro[2.4]heptane (TRANS, Enantiomer 2);

Ex. 299

(1S,3S or 1R,3R)-5-{4-[4-methyl-5-(oxan-4-yl)-4H-1,2,4-triazol-3-yl]butyl}-1-[4-(trifluoro-methyl)phenyl]-5-azaspiro[2.4]heptane (TRANS, Enantiomer 1);

Ex. 300

(1R,3R or 1S,3S)-5-{4-[4-methyl-5-(oxan-4-yl)-4H-1,2,4-triazol-3-yl]butyl}-1-[4-(trifluoro-methyl)phenyl]-5-azaspiro[2.4]heptane (TRANS, Enantiomer 2);

Ex. 301

(1R,3S/1S,3R)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane (CIS);

Ex. 302

(1R,3S)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane (CIS, Enantiomer 1);

Ex. 303

(1S,3S/1R,3R)-5-(3-{[4-methyl-5-(oxan-4-yl)-4H-1,2,4-triazol-3-yl]oxy}propyl)-1-[4-(trifluoro-methyl)phenyl]-5-azaspiro[2.4]heptane (TRANS);

Ex. 304

(1S,3S or 1R,3R)-5-(3-{[4-methyl-5-(oxan-4-yl)-4H-1,2,4-triazol-3-yl]oxy}propyl)-1-[4-(trifluoromethyl)phenyl]-5-azaspiro[2.4]heptane (TRANS, Enantiomer 1);

Ex. 305

(1R,3R or 1S,3S)-5-(3-{[4-methyl-5-(oxan-4-yl)-4H-1,2,4-triazol-3-yl]oxy}propyl)-1-[4-(trifluoro-methyl)phenyl]-5-azaspiro[2.4]heptane (TRANS, Enantiomer 2);

Ex. 306

(1R/1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane;

Ex. 307

(1S or 1R)-6-(3-{[4-methyl-¬5-(4-methyl-1,3-oxazol-5-yl)-4H-1,2,4-triazol-3-yl]sulfanyl}propyl)-1-phenyl-6-azaspiro[2.5]octane (Enantiomer 1);

Ex. 308

(1R or 1S)-6-(3-{[4-methyl-5-¬(4-methyl-1,3-oxazol-5-yl)-4H-1,2,4-triazol-3-yl]sulfanyl}propyl)-1-phenyl-6-azaspiro[2.5]octane (Enantiomer 2);

Ex. 309

(1S or 1R)-6-(3-{[4-methyl-5-(4-methyl-1,3-oxazol-5-yl)-¬4H-1,2,4-triazol-3-yl]sulfanyl}propyl)-1-phenyl-6-azaspiro[2.5]octane (Enantiomer 1);

Ex. 310

(1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS);

Ex. 311

(1R,3S or 1S,3R)-5-(3-{[4-methyl-5-(4-methyl-1,3-oxazol-5-yl)-4H-1,2,4-triazol-3-yl]sulfanyl}-propyl)-1-[4-(trifluoromethyl)phenyl]-5-azaspiro[2.5]octane (TRANS, Enantiomer 1);

Ex. 312

(1S,3R or 1R,3S)-5-(3-{[4-methyl-5-(4-methyl-1,3-oxazol-5-yl)-4H-1,2,4-triazol-3-yl]sulfanyl}-propyl)-1-[4-(trifluoromethyl)phenyl]-5-azaspiro[2.5]octane (TRANS, Enantiomer 2);

Ex. 313

(1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS);

Ex. 314

(1S,3S or 1R,3R)-5-(3-{[4-methyl-5-(4-methyl-1,3-oxazol-5-yl)-4H-1,2,4-triazol-3-yl]sulfanyl}-propyl)-1-[4-(trifluoromethyl)phenyl]-5-azaspiro[2.5]octane (CIS, Enantiomer 1);

Ex. 315

(1R,3R or 1S,3S)-5-(3-{[4-methyl-5-(4-methyl-1,3-oxazol-5-yl)-4H-1,2,4-triazol-3-yl]sulfanyl}-propyl)-1-[4-(trifluoromethyl)phenyl]-5-azaspiro[2.5]octane (CIS, Enantiomer 2);

Ex. 316

6-(3-{[4-methyl-5-(4-methyl-1,3-oxazol-5-yl)-4H-1,2,4-triazol-3-yl]-sulfanyl}propyl)-1-phenyl-6-azaspiro[3.4]octane;

Ex. 317

(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane: (Diastereomer 1 Enantiomer 1);

Ex. 318

(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane: (Diastereomer 1 Enantiomer 2);

Ex. 320

(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane: (Diastereomer 2 Enantiomer 1);

Ex. 321

(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane: (Diastereomer 2 Enantiomer 2);

or a pharmaceutically acceptable salt thereof.

Also provided is a compound selected from:

(1S,3S/1R,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane, TRANS;

(1R,3R or 1S,3S)-5-(2-{[4-methyl-5-(4-methyl-1,3-oxazol-5-yl)-4H-1,2,4-triazol-3-yl]-sulfanyl)}ethyl)-1-[4-(trifluoromethyl)phenyl]-5-azaspiro[2.4]heptane, Enantiomer 1

(1S,3S or 1R,3R)-5-(2-{[4-methyl-5-(4-methyl-1,3-oxazol-5-yl)-4H-1,2,4-triazol-3-yl]-sulfanyl)}ethyl)-1-[4-(trifluoromethyl)phenyl]-5-azaspiro[2.4]heptane, Enantiomer 2

(1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane, CIS;

(1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane, CIS;

(1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane, CIS;

(1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane, CIS;

(1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane, TRANS;

(1R,3R or 1S,3S)-5-(3-{[4-methyl-5-(4-methyl-1,3-oxazol-5-yl)-4H-1,2,4-triazol-3-yl]-sulfanyl}propyl)-1-[4-(trifluoromethyl)phenyl]-5-azaspiro[2.4]heptane, Enantiomer 1;

(1S,3S or 1R,3R)-5-(3-{[4-methyl-5-(4-methyl-1,3-oxazol-5-yl)-4H-1,2,4-triazol-3-yl]sulfanyl}-propyl)-1-[4-(trifluoromethyl)phenyl]-5-azaspiro[2.4]heptane, Enantiomer 2;

(1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane, CIS;

(1R,3S or 1S,3R)-5-(3-{[4-methyl-5-(4-methyl-1,3-oxazol-5-yl)-4H-1,2,4-triazol-3-yl]-sulfanyl}propyl)-1-[4-(trifluoromethyl)phenyl]-5-azaspiro[2.4]heptane, Enantiomer 1;

(1S,3R or 1R,3S)-5-(3-{[4-methyl-5-(4-methyl-1,3-oxazol-5-yl)-4H-1,2,4-triazol-3-yl]-sulfanyl}propyl)-1-[4-(trifluoromethyl)phenyl]-5-azaspiro[2.4]heptane, Enantiomer 2;

(1S,3S/1R,3R)-5-(3-{[4-methyl-5-(4-methyl-1,3-oxazol-5-yl)-4H-1,2,4-triazol-3-yl]-sulfanyl}propyl)-1-phenyl-5-azaspiro[2.4]heptane, TRANS;

(1R,3R or 1S, 3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane, Enantiomer 1;

(1S,3S or 1R, 3R)-5-(3-{[4-methyl-5-(4-methyl-1,3-oxazol-5-yl)-4H-1,2,4-triazol-3-yl]-sulfanyl}propyl)-1-phenyl-5-azaspiro[2.4]heptane, Enantiomer 2;

(1R,3S/1S,3R)-5-(3-{[4-methyl-5-(4-methyl-1,3-oxazol-5-yl)-4H-1,2,4-triazol-3-yl]-sulfanyl}propyl)-1-phenyl-5-azaspiro[2.4]heptane, CIS;

(1S,3R or 1R, 3S)-5-(3-{[4-methyl-5-(4-methyl-1,3-oxazol-5-yl)-4H-1,2,4-triazol-3-yl]-sulfanyl}propyl)-1-phenyl-5-azaspiro[2.4]heptane, Enantiomer 1;

(1R,3S or 1S, 3R)-5-(3-{[4-methyl-5-(4-methyl-1,3-oxazol-5-yl)-4H-1,2,4-triazol-3-yl]-sulfanyl}propyl)-1-phenyl-5-azaspiro[2.4]heptane, Enantiomer 2;

(1R,3S or 1S, 3R)-5-(3-{[4-methyl-5-(4-methyl-1,3-oxazol-5-yl)-4H-1,2,4-triazol-3-yl]-sulfanyl}propyl)-1-phenyl-5-azaspiro[2.4]heptane hydrochloride, Enantiomer 2;

(1R,3S/1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, TRANS;

(1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 1)

(1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 2;

(1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 1;

(1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 2;

(1S,3S/1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, CIS;

(1S,3S or 1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 1;

(1R,3R or 1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 2;

(1S,3S or 1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 1;

(1R,3R or 1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane, Enantiomer 2;

(1S,3S/1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, TRANS;

(1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, Enantiomer 1;

(1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, Enantiomer 2;

(1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, Enantiomer 1;

(1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, Enantiomer 2;

(1R,3S/1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, CIS;

(1R,3S or 1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, Enantiomer 1;

(1S,3R or 1R,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, Enantiomer 2;

(1R,3S or 1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane, Enantiomer 1;

(1R,3S/1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, TRANS;

(1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 1;

(1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 2;

(1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 1;

(1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 2;

(1S,3S/1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, CIS;

(1S,3S or 1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 1;

(1R,3R or 1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 2;

(1R,3R or 1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 2;

(1R,3S/1S,3R)-5-(3-{[4-methyl-5-(oxan-4-yl)-4H-1,2,4-triazol-3-yl]sulfanyl}propyl)-1-phenyl-5-azaspiro[2.4]heptane, CIS;

(1R,3S or 1S,3R)-5-(3-{[4-methyl-5-(oxan-4-yl)-4H-1,2,4-triazol-3-yl]sulfanyl}propyl)-1-phenyl-5-azaspiro[2.4]heptane, Enantiomer 1;

(1S,3R or 1R,3S)-5-(3-{[4-methyl-5-(oxan-4-yl)-4H-1,2,4-triazol-3-yl]sulfanyl}propyl)-1-phenyl-5-azaspiro[2.4]heptane, Enantiomer 2;

(1R,3R or 1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane, Enantiomer 2;

(1R,3S/1S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane, CIS;

(1R,3S or 1 S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane, Enantiomer 1;

(1S,3R1R,3S)-5-{3-[(4-methyl-5-{8-oxabicyclo[3.2.1]octan-3-yl}-4H-1,2,4-triazol-3-yl)-sulfanyl]propyl}-1-[4-(trifluoromethyl)phenyl]-5-azaspiro[2.4]heptane, Enantiomer 2;

(1R,3S or 1 S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane, Enantiomer 1;

(1S,3S/1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, TRANS;

(1R,3R or 1S,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 1;

(1S,3S or 1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 2;

(1R,3R or 1S,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 1;

(1S,3S or 1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 2;

(1R,3S/1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, CIS;

(1R,3S or 1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 1;

(1S,3R or 1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 2;

(1R,3S or 1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 1;

(1S,3R or 1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane, Enantiomer 2;

1-{[4-methyl-5-(4-methyl-1,3-oxazol-5-yl)-4H-1,2,4-triazol-3-yl]sulfanyl}-3-{1-[4-(trifluoromethyl)phenyl]-5-azaspiro[2.4]heptan-5-yl}propan-2-ol, CIS, diastereoisomeric mixture;

(1S,3S/1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E69);

(1S,3S or 1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane, Enantiomer 1;
(1R,3R or 1 S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane, Enantiomer 2;
(1R,3R or 1 S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane, Enantiomer 2;
(1S,3S/1R,3R)-5-(3-{[4-methyl-5-(oxan-4-yl)-4H-1,2,4-triazol-3-yl]oxy}propyl)-1-[4-(trifluoromethyl)phenyl]-5-azaspiro[2.4]heptane;
(1R/1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane;
(1S or 1R)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane, Enantiomer 1;
(1R or 1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane, Enantiomer 2;
(1S or 1R)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane, Enantiomer 1;
1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane, diastereoisomeric mixture;
(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane, Diastereomer 1 Enantiomer 1;
(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane, Diastereomer 1 Enantiomer 2;
(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane, Diastereomer 2, Enantiomer 1;
(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane, Diastereomer 2 Enantiomer 2;
(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane, Diastereoisomer 1, Enantiomer 2;
or pharmaceutically acceptable salts thereof.

The present invention also provides a process for preparing a compound of formula (I) or a salt thereof as defined above.

The process of the present invention for preparing compounds of formula (I) comprises the steps of: (a) reacting a compound of formula (VI):

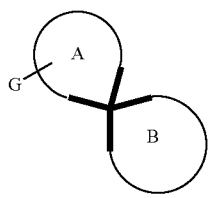

(VI)

wherein G is as defined for formula (I), with a compound of formula (VII):

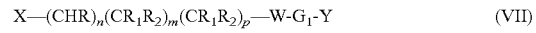

wherein R, $R_1$, $R_2$, n, m, p, W, $G_1$ and Y are as defined for formula (I) and X is a leaving group or an aldehyde, and thereafter optionally for process (a): (i) removing any protecting group(s); and/or (ii) forming a salt; and/or (iii) converting a compound of formula (I) or a salt thereof to another compound of formula (I) or a salt thereof.

Process (a) may be performed using conventional methods for the formation of a tertiary amine. When X is a leaving group, it can be halogen such as chlorine. Alternatively X can be a sulfonyloxy group such $C_{1-4}$alkylsulfonyloxy (e.g. methanesulfonyloxy), $C_{1-4}$alkylsulfonyloxy or halo$C_{1-4}$alkylsulfonyloxy (e.g. trifluoromethanesulfonyloxy); or arylsulfonyloxy wherein aryl is optionally substituted phenyl, an optionally substituted 5- or 6-membered heteroaromatic group, or an optionally substituted bicyclic group, for example optionally substituted phenyl, wherein in each case the optional substituents are one or more $C_{1-2}$alkyl groups; e.g. para-toluenesulfonyloxy. When X is an halogen the reaction may be carried out using a base such as sodium carbonate in the presence of a source of iodide such as sodium iodide in a solvent such as N,N-dimethylformamide at a suitable temperature, e.g. 60° C.

When X is an aldehyde the reaction may be carried out using a reducing agent such as sodium triacetoxyborohydride in a suitable solvent such as dichloromethane or acetonitrile optionally in the presence of acetic acid or a Lewis acid in a catalytic amount and at a suitable temperature such as room temperature.

In one aspect of the present invention there is provided synthetic processes for the preparation of compounds of formula (VI).

Compounds of formula (VI) where A and B form a 5-azaspiro[2.4]heptane system of formula (VIa)

may be synthesised with a process comprising the following Scheme 1:

Scheme 1

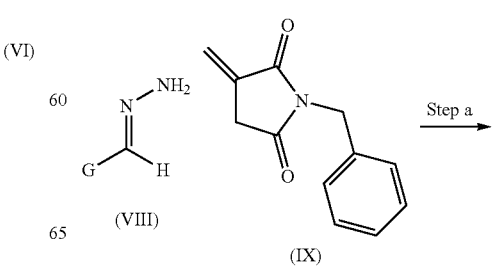

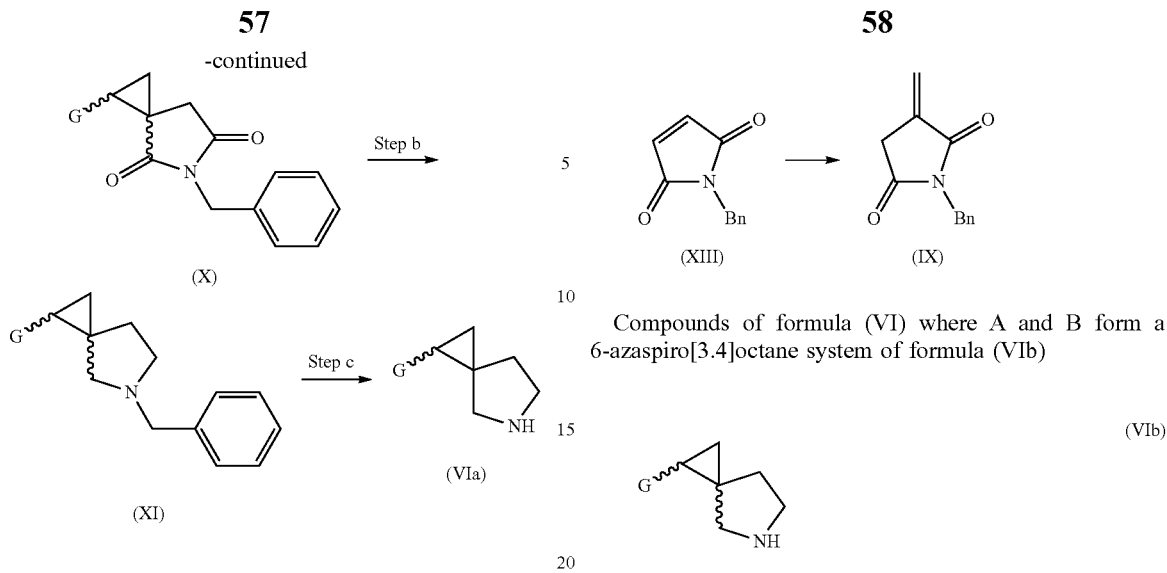

(X)

(XI)

wherein: Step a means the cycloropanation of (IX) to provide the bicyclic spiro imide (X); Step b means the reduction of imide (X) to give the tertiary benzyl amine (XI). Step c means the deprotection of benzyl amine (XI) to give compounds of formula (VIa).

Step a may be effected generating in situ the intermediate diazo compound to be reacted in a 1,3-dipolar cycloaddition with the appropriate double bond. In many cases this step is suitably performed applying a procedure where hydrazone (VIII) is treated with an oxidizing agent, such as manganese dioxide, in a suitable solvent, such as dioxane, and at room temperature to form the diazocompound intermediate that was then added to a solution of imide (IX) in a suitable solvent such as dioxane. This is followed by allowing time to react as appropriate and a suitable workup.

Step b can be performed using a suitable reducing agent in a compatible solvent, such as Lithium aluminium hydride solution in THF, at an appropriate temperature, such as for example 68° C. This is followed by a suitable workup.

Step c consists of the deprotection of benzylamine using well known procedures, for example via hydrogenation refluxing a solution of benzylamine in a suitable solvent such as methanol in the presence of a hydrogen source such as ammonium formate and a hydrogenation catalyst such as palladium on carbon. This is followed by allowing time to react as appropriate and a suitable workup.

Compounds of formula (VIII) may be obtained using well known procedures by reacting the corresponding aldehyde (XII) with hydrazine in a suitable solvent such as ethanol. This is followed by allowing time to react as appropriate and a suitable workup.

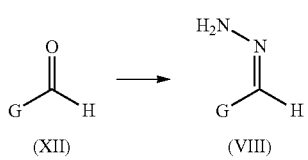

(XII)   (VIII)

Compound of formula (IX) may be obtained via Wittig reaction between the ylide, generated in situ treating benzylmaleimide with triphenylphosphine in acetic acid as solvent, with formaldehyde. This is followed by allowing time to react as appropriate and a suitable workup.

(XIII)   (IX)

Compounds of formula (VI) where A and B form a 6-azaspiro[3.4]octane system of formula (VIb)

(VIb)

may be synthesised with a process comprises the Scheme 2:

Scheme 2

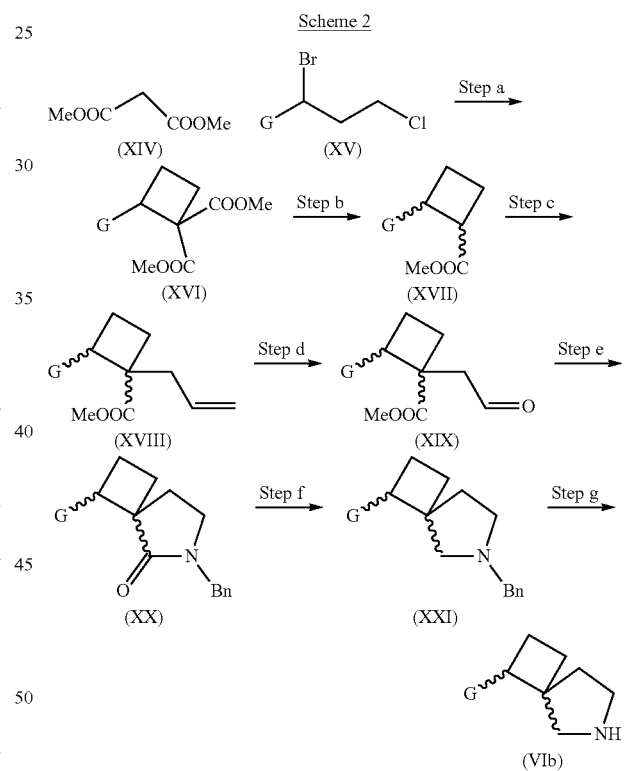

wherein: Step a means double alkylation of malonate to form cyclobutane (XVI); Step b means mono decarboxylation of (XVI) to give the corresponding monoester (XVII); Step c means alkylation of (XVII) to give the corresponding allyl derivative (XVIII); Step d means ozonolysis of allyl derivative (XVIII) to give the corresponding aldehyde (XIX); Step e means ring closure of (XIX) with benzylamine to give the corresponding spiro lactam (XX); Step f means reduction of lactam (XX) to give the corresponding spiro amine (XXI); Step g means deprotection of benzyl amine (XXI) to give compounds of formula (VIb).

Step a may be effected reacting dimethyl malonate with a dihalo compound in the presence of a base such as sodium hydride in a solvent such as dioxane and at a temperature of 90° C. This is followed by allowing time to react as appropriate and a suitable workup.

Step b can be carried out by thermic decarboxylation heating the diester (XVI) in a mixture of DMSO and water to reflux in the presence of salts such as LiCl. This is followed by allowing time to react as appropriate and a suitable workup.

Step c can be performed treating the cyclobutane monoester (XVII) with a strong base such as Lithium bis(trimethylsilyl)amide and adding an allylhalide such as allylbromide in a suitable solvent such as THF at a temperature ranging between −78° C. and room temperature. This is followed by allowing time to react as appropriate and a suitable workup.

Step d may be performed via ozonlysis passing a stream of ozone in oxygen through a solution of allyderivative (XVIII) in a suitable solvent such as dichloromethane at low temperature such as −78° C. This is followed by allowing time to react as appropriate and a suitable workup.

Step e can be performed by first reacting the aldehyde (XIX) with benzylamine in the presence of a reducing agent such as sodium triacetoxyborohydride in a suitable solvent such as THF at a temperature such as room temperature. In a second time, after a suitable workup, the intermediate from reductive amination can be refluxed in a suitable solvent such as THF in order to close the ring forming the spiro lactam (XX). This is followed by allowing time to react as appropriate and a suitable workup.

Step f can be performed using a suitable reducing agent in a compatible solvent, such as Lithium aluminium hydride solution in THF at an appropriate temperature, such as for example 68° C. This is followed by a suitable workup.

Step g consists of deprotection of benzylamine using well known procedures for example via hydrogenation refluxing a solution of benzylamine derivative (XXI) in a suitable solvent such as methanol in the presence of a hydrogen source such as ammonium formate and a hydrogenation catalyst such as palladium on carbon. This is followed by allowing time to react as appropriate and a suitable workup.

Compounds of formula (XV) may be obtained using well known procedures by first reacting the corresponding ketone with a reducing agent such as sodium borohydride in a suitable solvent such as a mixture of ethanol and THF at a temperature ranging from −10° C. to −50° C. This is followed by allowing time to react as appropriate and a suitable workup. In a second step the hydroxyl group may be converted into a bromide using known procedures such as treating it with hydrobromic acid at a temperature such as room temperature. This is followed by allowing time to react as appropriate and a suitable workup.

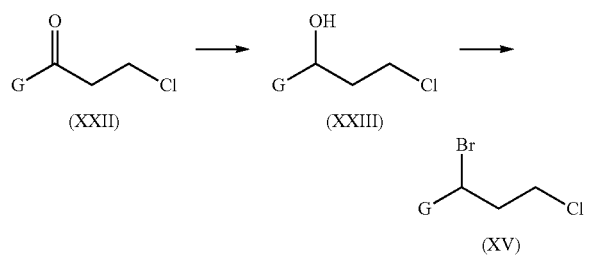

Compounds of formula (VI) where A and B form a 6-azaspiro[2.5]octane system of formula (VIc)

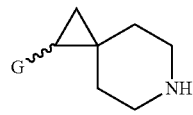

may be synthesised analogously to what described in WO03091220 (A1) with a process comprises the following steps of Scheme 3:

Scheme 3

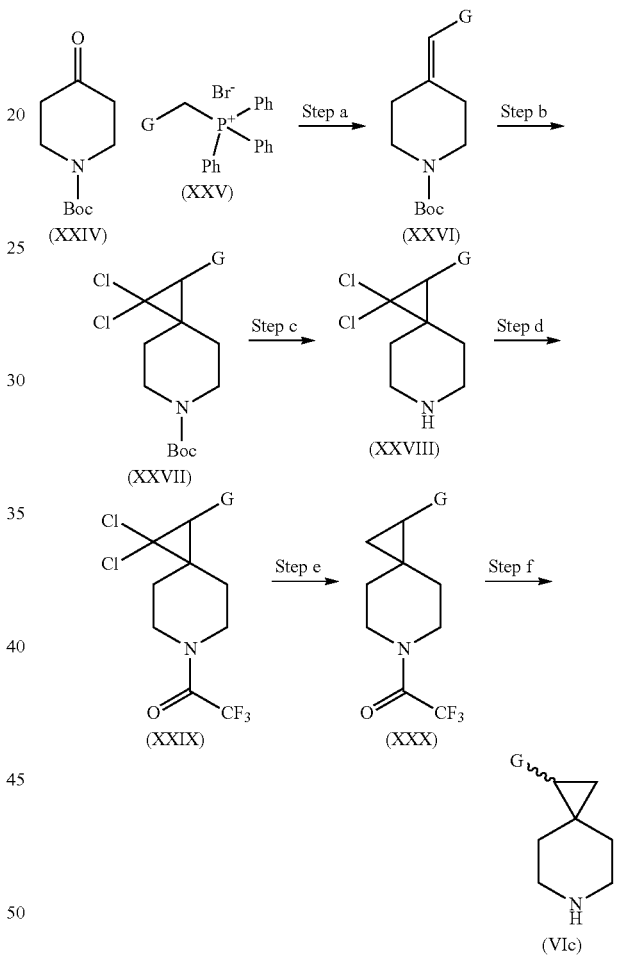

wherein: Step a means Wittig reaction between Boc-piperidinone and a suitable triphenylphosphonium bromide (XXV); Step b means cyclopropanation of the double bond of derivative (XXVI); Step c means deprotection of the amine (XXVII); Step d means protection as trifluoroacetamide of amine (XXVIII); Step e means reduction of dichlorocyclopropane (XXIX); Step f means deprotection of trifluoroacetamide (XXX) to give compounds of formula (VIc).

Step a may be effected treating a suitable triphenylphosphonium bromide with a base such as sodium hydride in a suitable solvent such as THF at a temperature ranging from 0° C. to room temperature in order to form the corresponding ylide to be reacted with N-Boc-piperidinone in a suitable solvent such as THF and at a temperature such as room temperature. This is followed by allowing time to react as appropriate and a suitable workup.

Step b can be carried out by reacting the double bond derivative (XXVI) with chloroform in the presence of a base such as sodium hydroxide and a phase transfer catalyst such as tetrabutylammoniumbromide. This is followed by allowing time to react as appropriate and a suitable workup.

Step c can be performed following well known procedures for the removal of Boc protecting group such as treating the protected compound with an acid such as trifluoroacetic acid in a suitable solvent such as dichloromethane at a temperature such as room temperature.

Step d can be carried out following well known procedures for protection of amines as trifluoroacetic amides such as treating the amine derivative with trifluoroacetic anhydride in a suitable solvent such as dichloromethane. This is followed by allowing time to react as appropriate and a suitable workup.

Step e can be performed treating the dichlorocyclopropane derivative with a reducing agent such as zinc powder in a suitable solvent such as a mixture of ethanol and water at a temperature ranging from 80° C. to 95° C. This is followed by allowing time to react as appropriate and a suitable workup.

Step f consists of deprotection of trifluoroacetamide using well known procedures for example basic conditions such as treating the compound with a suitable base such as potassium carbonate in a suitable solvent such as a mixture of methanol and water and at a temperature such as room temperature. This is followed by allowing time to react as appropriate and a suitable workup.

Compounds of formula (XXV) may be obtained using well known procedures by reacting the corresponding benzylbromides (XXXI) with triphenylphosphine in a suitable solvent such as toluene at reflux temperature. This is followed by allowing time to react as appropriate and a suitable workup.

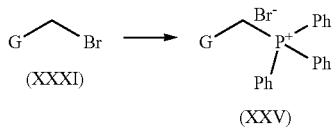

(XXXI)    (XXV)

Compounds of formula (VI) where A and B form a 5-azaspiro[2.5]octane system of formula (VId)

(VId)

may be synthesised analogously to what described in Scheme 1 with a process comprises the following steps of Scheme 4:

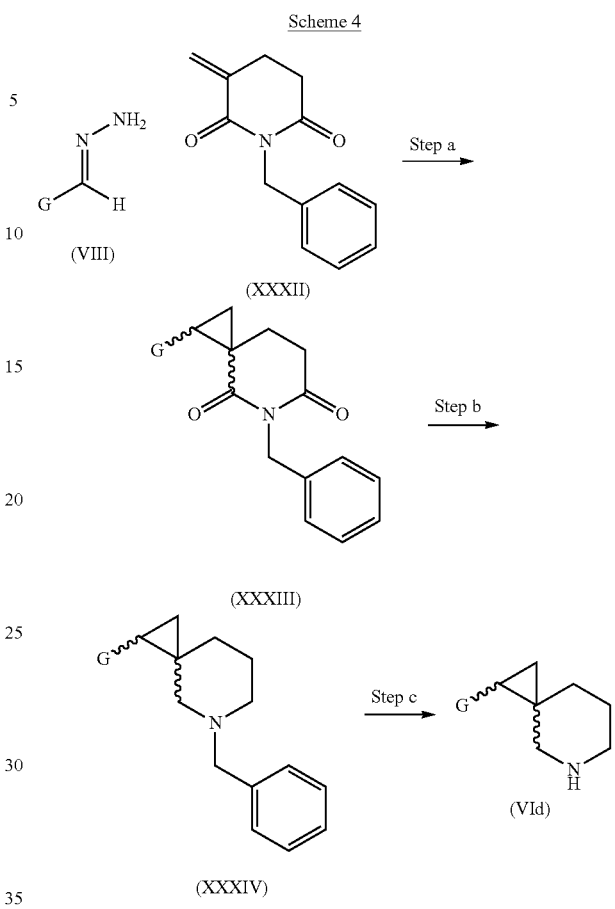

Scheme 4 wherein: Step a means the cycloropanation of (XXXII) to provide the bicyclic spiro imide (XXXIII); Step b means the reduction of imide (XXXIII) to give the tertiary benzyl amine (XXXIV). Step c means the deprotection of benzyl amine (XXXIV) to give compounds of formula (VId).

Step a may be effected generating in situ the intermediate diazocompound to be reacted in a 1,3-dipolar cycloaddition with the appropriate double bond. In many cases this step is suitably performed applying a procedure where hydrazone (VIII) is treated with an oxidizing agent, such as manganese dioxide, in a suitable solvent, such as dioxane, and at room temperature to form the diazocompound intermediate that was then added to a solution of imide (XXXII) in a suitable solvent such as dioxane. This is followed by allowing time to react as appropriate and a suitable workup.

Step b can be performed using a suitable reducing agent in a compatible solvent, such as Lithium aluminium hydride solution in THF, at an appropriate temperature, such as for example 68° C. This is followed by a suitable workup.

Step c consists of the deprotection of benzylamine using well known procedures, for example via hydrogenation refluxing a solution of benzylamine in a suitable solvent such as methanol in the presence of a hydrogen source such as ammonium formate and a hydrogenation catalyst such as palladium on carbon. This is followed by allowing time to react as appropriate and a suitable workup.

Compounds of formula (XXXII) may be obtained by reacting N-Benzyl chloroacetamide (XXXV) with triphenylphosphine in a suitable solvent such as toluene at reflux temperature, then treating the corresponding phosphonium chloride with methyl acrylate in the presence of a base such as sodium methoxide, in a suitable solvent such as MeOH and at 0° C. The phosphanylidene intermediate thus obtained may be reacted with formaldehyde in a suitable solvent, such as Toluene, and at a suitable temperature, such as room temperature. This is followed by allowing time to react as appropriate and a suitable workup.

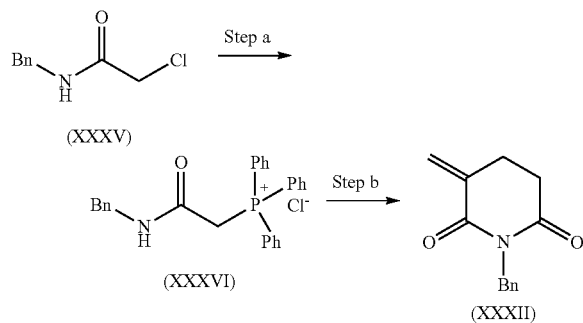

A compound of formula (VII) may itself be prepared by reacting a compound of formula (XXXVII):

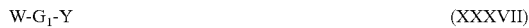

Wherein $G_1$ and Y are as hereinbefore defined with a compound of formula (XXXVIII):

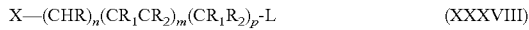

wherein X is defined as for formula (VII) and L is a leaving group, e.g., a bromine atom. For typical reaction conditions, see Preparation 148 hereinafter.

A compound of formula (VII) wherein W is SO or $SO_2$ may itself be prepared by (a) reacting a compound of formula (XXXIX):

wherein $G_1$ and Y are as hereinbefore defined and S is a sulphur atom with a compound of formula (XL):

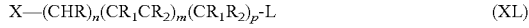

wherein X is defined as for formula (VI) and L is a leaving group, e.g., a bromine atom. For typical reaction conditions, see Preparation 148 hereinafter.

(b) oxidizing the sulphur with an appropriate oxidizing agent such as oxone or m-chloroperbenzoic acid in a suitable solvent such as dichloromethane.

Compounds of formula (I) wherein W is oxygen and G, R, $R_1$, $R_2$, n, m, p, $G_1$ and Y are as defined as above, may be prepared by reacting a compound of formula (XL):

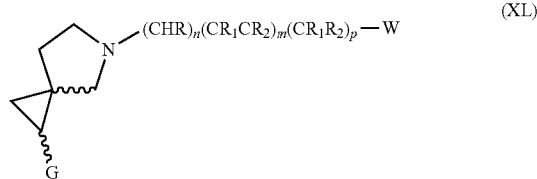

wherein G, R, $R_1$, $R_2$, n, m and p are as defined for formula (I), with a compound of formula (XLI):

wherein $G_1$ and Y are as hereinbefore defined and X is a leaving group such as methyl sulphone. For typical reaction conditions see Example 303.

Interconversion reactions between compounds of formula (I) and salts thereof may be performed using methods well known in the art.

Compounds of formula (I) have been found to exhibit affinity for dopamine receptors, in particular the $D_3$ receptor, and are expected to be useful in the treatment of disease states which require modulation of such receptors, such as psychotic conditions.

Such affinity is typically calculated from the $IC_{50}$ as the concentration of a compound necessary to displace 50% of the radiolabeled ligand from the receptor, and is reported as a "$K_i$" value calculated by the following equation:

$$K_i = \frac{IC_{50}}{1 + L/K_D}$$

where L=radioligand and $K_D$=affinity of radioligand for receptor (Cheng and Prusoff, *Biochem. Pharmacol.* 22:3099, 1973).

In the context of the present invention pKi (corresponding to the antilogarithm of Ki) is used instead of Ki and the compounds of the present invention typically show pKi greater than 7. In one aspect the present invention provides compounds of formula (I) having a pKi comprised between 7 and 8. In another aspect the present invention provides compounds of formula (I) having a pKi comprised between 8 and 9. In a further aspect the present invention provides compounds of formula (I) having a pKi greater than 9.

Many of the compounds of formula (I) have also been found to have greater affinity for dopamine $D_3$ than for $D_2$ receptors. The therapeutic effect of currently available antipsychotic agents (neuroleptics) is generally believed to be exerted via blockade of $D_2$ receptors; however this mechanism is also thought to be responsible for undesirable extrapyramidal side effects (eps) associated with many neuroleptic agents. It has been suggested that blockade of the recently characterised dopamine $D_3$ receptor may give rise to beneficial antipsychotic activity without significant eps. (see for example Sokoloff et al, Nature, 1990; 347: 146-151; and Schwartz et al, Clinical Neuropharmacology, Vol 16, No. 4, 295-314, 1993). In one embodiment compounds of the present invention are provided which have higher (e.g. 210x or 2100x higher) affinity for dopamine $D_3$ than dopamine $D_2$ receptors (such affinity can be measured using standard methodology for example using cloned dopamine receptors—see herein). Said compounds may suitably be used as selective modulators of $D_3$ receptors.

From the localisation of $D_3$ receptors, it could also be envisaged that the compounds could also have utility for the treatment of substance abuse where it has been suggested that $D_3$ receptors are involved (e.g. see Levant, 1997, Pharmacol. Rev., 49, 231-252). Examples of such substance abuse include alcohol, cocaine, heroin and nicotine abuse. Other conditions which may be treated by the compounds include dyskinetic disorders such as Parkinson's disease, neuroleptic-induced parkinsonism and tardive dyskinesias; depression; anxiety, cognitive impairment including memory disorders such as Alzheimers disease, eating disorders, sexual dysfunction, premature ejaculation, sleep disorders, emesis, movement disorders, obsessive-compulsive disorders, amnesia, aggression, autism, vertigo, dementia, circadian rhythm disorders and gastric motility disorders e.g. IBS.

Compounds of formula (I) may be used for treatment of all aspects of drug dependency including withdrawal symptoms from drugs of abuse such as alcohol, cocaine, opiates, nicotine, benzodiazepines and inhibition of tolerance induced by opioids. In addition, compounds of formula (I) and pharmaceutically acceptable salts and solvates thereof may be used to reduce craving and therefore will be useful in the treatment of drug craving. Drug craving can be defined as the incentive motivation to self-administer a psychoactive substance that was previously consumed. Three main factors are involved in the development and maintenance of drug craving: (1) Dysphoric states during drug withdrawal can function as a negative reinforcer leading to craving; (2) Environmental stimuli associated with drug effects can become progressively more powerful (sensitization) in controlling drug seeking or craving, and (3) A cognition (memory) of the ability of drugs to promote pleasurable effects and to alleviate a dysphoric state during withdrawal. Craving may account for the difficulty that individuals have in giving up drugs of abuse and therefore contributes significantly to the development and maintenance of drug dependence.

The compounds of formula (I) are of potential use as antipsychotic agents for example in the treatment of schizophrenia, schizo-affective disorders, psychotic depression, mania, paranoid and delusional disorders. Furthermore, they could have utility as adjunct therapy in Parkinsons Disease, particularly with compounds such as L-DOPA and possibly dopaminergic agonists, to reduce the side effects experienced with these treatments on long term use (e.g. see Schwartz et al., Brain Res. Reviews, 1998, 26, 236-242).

Within the context of the present invention, the terms describing the indications used herein are classified in the Diagnostic and Statistical Manual of Mental Disorders, 4th Edition, published by the American Psychiatric Association (DSM-V). The various subtypes of the disorders mentioned herein are contemplated as part of the present invention.

Within the context of the present invention, the term "schizophrenia spectrum and other psychotic disorder" includes: Schizotypal (personality disorder; Delusional Disorder; Brief Psychotic Disorder; Schizopreniform Disorder; Schizophrenia; Schizoaffective Disorder; Substance/Medication-Induced Psychotic Disorder; Psychotic Disorder due to another Medical Condition.

Within the context of the present invention, the term "catatonia" includes: Catatonia Associated With Another Mental Disorder (Catatonia Specifier); Catatonic Disorder Due to another Medical Condition; Unspecified Catatonia; Other Specified Schizophrenia Spectrum and other Psychotic Disorder; Unspecified Schizophrenia Spectrum and other Psychotic Disorder.

Within the context of the present invention, the term "obsessive-compulsive disorder" includes: Obsessive Compulsive Disorder; Body Dismorphic Disorder; Hoarding Disorder; Trichotillomania (Hair-Pulling Disorder); Excoriation (Skin-Picking) Disorder; Substance/Medication-Induced Obsessive-Compulsive and Related Disorder; Obsessive-Compulsive and Related Disorder due to Another Medical Condition; Other Specified Obsessive-Compulsive and Related Disorders; Unspecified Obsessive-Compulsive and Related Disorders.

Within the context of the present invention, the term "feeding and eating disorders" includes: Pica; Ruminant Disorder; Avoidant/Restrictive Food Intake Disorder; Anorexia Nervosa; Bulimia Nervosa; Binge-Eating Disorder; Other Specified Feeding or eating Disorder; Unspecified Feeding or Eating Disorder.

Within the context of the present invention, the term "sexual disfunctions" includes: Delayed ejaculation; Erectile Disorder; Female Orgasmic Disorder; Female Sexual Interest/Arousal Disorder; Genito-Pelvic Pain/Penetration Disorder; Male Hypoactive Sexual Desire Disorder; Premature (early) Ejaculation; Substance/Medication-Induced Sexual Dysfunction; Unspecified Sexual Dysfunction.

Within the context of the present invention, the term "substance-related disorders and addictive disorders" includes: Substance-Related Disorders such as Substance Use Disorders; Substance-Induced Disorders; Substance Intoxication and Withdrawal; Substance/Medication-Induced Mental Disorders; Alcohol-Related Disorders such as Alcohol Use Disorder; Alcohol Intoxication; Alcohol Withdrawal; Other Alcohol-Induced Disorders; Unspecified Alcohol-Related Disorders; Caffeine-Related Disorders such as Caffeine Intoxication; Caffeine Withdrawal; Other Caffeine-Induced Disorders; Unspecified Caffeine-Related Disorders; *Cannabis*-Related Disorders such as *Cannabis* Use Disorder; *Cannabis* Intoxication; *Cannabis* Withdrawal; Other *Cannabis*-Induced Disorders; Unspecified *Cannabis*-Related Disorders; Hallucinogen-Related Disorders such as Phencyclidine Use Disorder; Other Hallucinogen Use Disorder; Phencyclidine Intoxication; Other Hallucinogen Intoxication; Hallucinogen Persisting Perception Disorder; Other Phencyclidine-Induced Disorders; Other Hallucinogen-Induced Disorders Unspecified Phencyclidine-Related Disorders; Unspecified Hallucinogen-Related Disorders; Inhalant-Related Disorders such as Inhalant Use Disorder; Inhalant Intoxication; Other Inhalant-Induced Disorders; Unspecified Inhalant-Related Disorders; Opioid-Related Disorders such as Opioid Use Disorder; Opioid Intoxication; Opioid Withdrawal; Other Opioid-Induced Disorders; Unspecified Opioid-Related Disorders; Sedative-, Hypnotic-, or Anxiolytic-Related Disorders such as Sedative-, Hypnotic-, or Anxiolytic Use Disorder; Sedative-, Hypnotic-, or Anxiolytic Intoxication; Sedative-, Hypnotic-, or Anxiolytic Withdrawal; Other Sedative-, Hypnotic-, or Anxiolytic-Induced Disorders; Unspecified Sedative-, Hypnotic-, or Anxiolytic-Related Disorders; Stimulant-Related Disorders such as Stimulant Use Disorder; Stimulant Intoxication; Stimulant Withdrawal; Other Stimulant-Induced Disorders; Unspecified Stimulant-Related Disorders; Tobacco-Related Disorders such as Tobacco Use Disorder; Tobacco Intoxication; Tobacco Withdrawal; Other Tobacco-Induced Disorders; Unspecified Tobacco-Related Disorders; Other (or Unknown) Substance-Related Disorders such as Other (or Unknown) Substance Use Disorder; Other (or Unknown) Substance Intoxication; Other (or Unknown) Substance Withdrawal; Other (or Unknown) Substance-Induced Disorders; Unspecified Other (or Unknown) Substance-Related Disorders.

Within the context of the present invention, the term "non-substance-related disorders and addictive disorders" includes: Gambling Disorders.

In a further aspect therefore the present invention provides a method of treating a condition for which modulation (especially antagonism/inhibition) of dopamine receptors (especially dopamine $D_3$ receptors) is beneficial, which comprises administering to a mammal (e.g. human) in need thereof an effective amount of a compound of formula (I) or a pharmaceutically (i.e. physiologically) acceptable salt thereof. Such conditions in particular include psychoses/psychotic conditions such as schizophrenia, and substance abuse.

The invention also provides the use of a compound of formula (I) or a pharmaceutically acceptable salt thereof in the manufacture of a medicament for the treatment of a condition in a mammal for which modulation (especially antagonism/inhibition) of dopamine receptors (especially dopamine $D_3$ receptors) is beneficial.

The invention also provides a compound of formula (I) or a pharmaceutically acceptable salt thereof for use in the treatment of a condition in a mammal for which modulation (especially antagonism/inhibition) of dopamine receptors (especially dopamine $D_3$ receptors) is beneficial.

In one embodiment, $D_3$ antagonists according to the present invention are used in the treatment of psychoses such as schizophrenia or in the treatment of substance abuse.

Thus, a still further aspect the invention provides a method of treating a psychotic condition (e.g. schizophrenia) or substance abuse which comprises administering to a mammal (e.g. human) in need thereof an effective amount of a compound of formula (I) as herein defined or a pharmaceutically acceptable salt thereof.

Also provided is the use of a compound of formula (I) or a pharmaceutically acceptable salt thereof in the manufacture of a medicament for the treatment of a psychotic condition (e.g. schizophrenia) or substance abuse in a mammal.

Also provided is a compound of formula (I) or a pharmaceutically acceptable salt thereof for use in the treatment of a psychotic condition (e.g. schizophrenia) or substance abuse in a mammal.

Also provided is a compound of formula (I) or a pharmaceutically acceptable salt thereof for use as an active therapeutic substance in a mammal, e.g. for use in the treatment of any of the conditions described herein.

"Treatment" includes prophylaxis, where this is appropriate for the relevant condition(s).

For use in medicine, the compounds of the present invention are usually administered as a standard pharmaceutical composition. The present invention therefore provides in a further aspect a pharmaceutical composition comprising a compound of formula (I) or a pharmaceutically (i.e physiologically) acceptable salt thereof and a pharmaceutically (i.e physiologically) acceptable carrier. The pharmaceutical composition can be for use in the treatment of any of the conditions described herein.

The compounds of formula (I) may be administered by any convenient method, for example by oral, parenteral (e.g. intravenous), buccal, sublingual, nasal, rectal or transdermal administration and the pharmaceutical compositions adapted accordingly.

The compounds of formula (I) and their pharmaceutically acceptable salts which are active when given orally can be formulated as liquids or solids, for example syrups, suspensions or emulsions, tablets, capsules and lozenges.

A liquid formulation will generally consist of a suspension or solution of the compound or pharmaceutically acceptable salt in a suitable liquid carrier(s) for example an aqueous solvent such as water, ethanol or glycerine, or a non-aqueous solvent, such as polyethylene glycol or an oil. The formulation may also contain a suspending agent, preservative, flavouring or colouring agent.

A composition in the form of a tablet can be prepared using any suitable pharmaceutical carrier(s) routinely used for preparing solid formulations. Examples of such carriers include magnesium stearate, starch, lactose, sucrose and cellulose.

A composition in the form of a capsule can be prepared using routine encapsulation procedures. For example, pellets containing the active ingredient can be prepared using standard carriers and then filled into a hard gelatin capsule; alternatively, a dispersion or suspension can be prepared using any suitable pharmaceutical carrier(s), for example aqueous gums, celluloses, silicates or oils and the dispersion or suspension then filled into a soft gelatin capsule.

Typical parenteral compositions consist of a solution or suspension of the compound or pharmaceutically acceptable salt in a sterile aqueous carrier or parenterally acceptable oil, for example polyethylene glycol, polyvinyl pyrrolidone, lecithin, *arachis* oil or sesame oil.

Alternatively, the solution can be lyophilised and then reconstituted with a suitable solvent just prior to administration.

Compositions for nasal administration may conveniently be formulated as aerosols, drops, gels and powders. Aerosol formulations typically comprise a solution or fine suspension of the active substance in a pharmaceutically acceptable aqueous or non-aqueous solvent and are usually presented in single or multidose quantities in sterile form in a sealed container, which can take the form of a cartridge or refill for use with an atomising device. Alternatively the sealed container may be a unitary dispensing device such as a single dose nasal inhaler or an aerosol dispenser fitted with a metering valve which is intended for disposal once the contents of the container have been exhausted. Where the dosage form comprises an aerosol dispenser, it will contain a propellant which can be a compressed gas such as compressed air or an organic propellant such as a fluorochlorohydrocarbon. The aerosol dosage forms can also take the form of a pump-atomiser.

Compositions suitable for buccal or sublingual administration include tablets, lozenges and pastilles, wherein the active ingredient is formulated with a carrier such as sugar and acacia, tragacanth, or gelatin and glycerin.

In one embodiment, the composition is in unit dose form such as a tablet, capsule or ampoule.

Each dosage unit for oral administration contains for example from 1 to 250 mg (and for parenteral administration contains for example from 0.1 to 25 mg) of a compound of the formula (I) or a pharmaceutically acceptable salt thereof calculated as the free base.

The pharmaceutically acceptable compounds of the invention will normally be administered in a daily dosage regimen (for an adult patient) of, for example, an oral dose of between 1 mg and 500 mg, for example between 10 mg and 400 mg, e.g. between 10 and 250 mg or an intravenous, subcutaneous, or intramuscular dose of between 0.1 mg and 100 mg, for example between 0.1 mg and 50 mg, e.g. between 1 and 25 mg of the compound of the formula (I) or a pharmaceutically acceptable salt thereof calculated as the free base, the compound being administered 1 to 4 times per day. Suitably the compounds will be administered for a period of continuous therapy, for example for a week or more.

EXAMPLES

The invention is further illustrated by the following non-limiting examples.

In the procedures that follow, after each starting material, reference to a Preparation or Example by number is typically provided. This is provided merely for assistance to the skilled chemist. The starting material may not necessarily have been prepared from the batch referred to.

Were reference is made to the use of a "similar or analogous or as" procedure, as will be appreciated by those skilled in the art, such procedure may involve minor variation, for example reaction temperature, reagent/solvent amount, reaction time, work-up conditions or chromatographic purification conditions.

In the procedures that follow, the absolute stereochemistry "up" or "down" configurations in the structures are to be considered correct if accompanied by a single absolute stereochemistry assignment in the name (for example (1R,3S)-1-[4-(trifluoromethyl)phenyl]-5-azaspiro[2.4]heptane). On the contrary, the absolute stereochemistry "up" or "down" configurations in the structures are to be considered arbitrarily assigned with the only aim to distinguish one enantiomer from the other if not accompanied by a single absolute stereochemistry assignment in the name (for example (1R,3S or 1S,3R)-1-[4-fluoro-2-(trifluoromethyl)phenyl]-5-azaspiro[2.4]heptane).

All temperatures refer to ° C.

Proton Magnetic Resonance (NMR) spectra may be typically recorded either on Varian instruments at 400 or 500 MHz, or on a Bruker instrument at 400 MHz.

Chemical shifts are expressed in parts of million (ppm, δ units). Chemical shifts are reported in ppm downfield (δ) from Me$_4$Si, used as internal standard, and are typically assigned as singlets (s), broad singlets (br.s.), doublets (d), doublets of doublets (dd), doublets of doublets of doublets (ddd), doublets of triplets (dt), triplets (t), triplets of doublets (td), quartets (q), or multiplets (m).

LCMS may be recorded under the following conditions: DAD chromatographic traces, mass chromatograms and mass spectra may be taken on UPLC/PDA/MS Acquity™ system coupled with Micromass ZQ™ or Waters SQD single quadrupole mass spectrometer operated in positive and/or negative ES ionisation mode. The QC methods used were two, one operated under low pH conditions and another one operated under high pH conditions. Details of the method operated under low pH conditions were: column, Acquity BEH C$_{18}$, 1.7 μm, 2.1×50 mm or Acquity CSH C$_{18}$, 1.7 μm, 2.1×50 mm, the temperature column was 40° C.; mobile phase solvent A was milliQ water+0.1% HCOOH, mobile phase solvent B MeCN+0.1% HCOOH. The flow rate was 1 ml/min. The gradient table was t=0 min 97% A-3% B, t=1.5 min 0.1% A-99.9% B, t=1.9 min 0.1% A-99.9% B and t=2 min 97% A-3% B. The UV detection range was 210-350 nm and the ES$^+$/ES$^-$ range was 100-1000 amu.

Details of the method operated under high pH conditions were the same of those listed above for the low pH method apart from: column Acquity BEH C$_{18}$, 1.7 μm, 2.1×50 mm; mobile phase solvent A was 10 mM aqueous solution of NH$_4$HCO$_3$ adjusted to pH=10 with ammonia, mobile phase solvent B MeCN.

Semipreparative mass directed autopurifications (MDAP) were carried out using Waters Fractionlynx™ systems operated under low or high pH chromatographic conditions. The stationary phases used were, XTerra C18, XBridge C18, Sunfire C18, XSelect C18, Gemini AXIA C18. The length of the columns was 5, 10 or 15 cm, while the internal diameter was 19, 21 or 30 mm. The particle size of the stationary phases was 5 or 10 μm. The purifications were carried out using low pH or high pH chromatographic conditions. The mobile phase solvent composition was the same used for QC analysis. The combinations stationary/mobile phases used were: XTerra, XBridge, Sunfire, XSelect—low pH mobile phases and XTerra, XBridge, Gemini AXIA—high pH mobile phases. All the purifications were carried out with the column kept at room T. The flow rate used was 17 or 20 ml/min for columns of internal diameter 19 or 21 mm and 40 or 43 ml/min for columns of internal diameter 30 mm. The trigger for the collection of the target species was the presence of the target m/z ratio value in the TIC MS signal. The gradient timetable was customised on the Rt behaviour of the target species.

Purification may also be performed using Biotage® Isolera or Biotage® SP1 flash chromatography systems, these instruments work with Biotage® KP-SIL cartridges, Biotage® KP-NH cartridges or Biotage® KP-C18 cartridges.

Unless otherwise stated, all reactions are typically performed under inert atmosphere (for example under Nitrogen).

TLC refers to thin layer chromatography on silica plates, and dried refers to a solution dried over anhydrous sodium sulphate, The following abbreviations are used in the text: EtOAc, AcOEt, EA=ethyl acetate; Et$_2$O=diethyl ether; MeOH=methanol; THF=tetrahydrofuran; r.t. (RT) refers to room temperature; DMSO=dimethyl sulfoxide; DMF=N,N'-dimethylformamide; DCM=dichloromethane; EtOH=ethanol; DCE=dichloroethane; DME=1,2-Dimethoxyethane; Cy, cHex=cyclohexane; ACN=Acetonitrile; tBuOH=tert-Butanol; TEA=triethylamine; DIPEA=N,N-Diisopropylethylamine; Boc$_2$O=Di-tert-butyl dicarbonate; TFA=trifluoroacetic acid; Pd$_2$(dba)$_3$=Tris(dibenzylideneacetone)dipalladium(0); TPP=triphenylphosphine; AcOH=acetic acid; LAH=Lithium aluminum hydride; T3P=Propylphosphonic anhydride; SCX Cartridge=Strong Cation Exchange Cartridge; ipa=isopropylamine; FA=formic acid; Py=pyridine; TBAF=Tetrabutylammonium fluoride; TBDMSCl=tert-Butyldimethylsilyl chloride; HOBt*H$_2$O=1-Hydroxybenzotriazole hydrate; EDC*HCl=N-(3-Dimethylaminopropyl)-N'-ethylcarbodiimide hydrochloride; DMAP=4-(Dimethylamino)pyridine; TMSCN=Trimethylsilyl cyanide; mCPBA=3-Chloroperbenzoic acid; mCBA=3-Chlorobenzoic acid; CbzCl=Benzyl chloroformate; ACE-Cl=1-Chloroethyl chloroformate.

Preparation 1: {[4-(trifluoromethyl)phenyl]methylidene}hydrazine

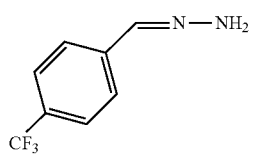

To a solution of hydrazine hydrate (6.4 mL, 86.1 mmol) in EtOH (25 mL) 4-(trifluoromethyl)benzaldehyde (3.92 mL, 28.7 mmol) was added dropwise under nitrogen over 10 min. The resulting solution was stirred at RT for 1 h. The solution was cooled down to RT, then diluted with water and DCM. Phases were separated; organic one was dried and concentrated under reduced pressure affording {[4-(trifluoromethyl)phenyl]methylidene}hydrazine (p1, 5.2 g, y=96%) as pale yellow oil that was used as such in the next step. MS (m/z): 189.2 [MH]$^+$

Preparation 2: (phenylmethylidene)hydrazine

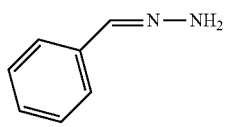

To a solution of hydrazine hydrate (2.5 mL, 30 mmol) in EtOH (10 mL) benzaldehyde (1.04 mL, 10 mmol) was added dropwise under nitrogen over 10 min. The resulting solution was stirred at RT for 1.5 h. After this time, water was added and ethanol was evaporated under vacuum. The aqueous phase was extracted with DCM (×4). Combined organics were dried and concentrated to obtain (phenylmethylidene)hydrazine (p2, 1.2 g, y=quant.) as yellow oil. MS (m/z): 121.1 [MH]$^+$

Preparation 3: [2-fluoro-4-(trifluoromethyl)phenyl]methylidene hydrazine

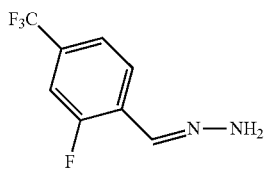 [SMILES: N/N=C/c1ccc(C(F)(F)F)cc1F]

To a solution of hydrazine hydrate (2.5 mL, 30 mmol) in EtOH (10 mL) 2-fluoro-4-(trifluoromethyl)benzaldehyde (1.36 mL, 10 mmol) was added dropwise under nitrogen over 10 min. The resulting solution was stirred at reflux for 1 h, then cooled down to RT in 1 h. After this time, water was added and the aqueous phase was extracted with DCM (×4). Combined organics were dried and concentrated to obtain [2-fluoro-4-(trifluoromethyl)phenyl]methylidene}hydrazine (p3, 2.15 g, y=quant.) as yellow liquid. MS (m/z): 207.3 [MH]$^+$

Preparation 4: [(2,4-difluorophenyl)methylidene]hydrazine

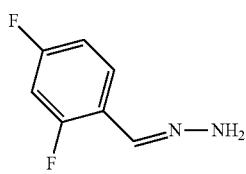 [SMILES: N/N=C/c1ccc(F)cc1F]

To a solution of hydrazine hydrate (2.5 mL, 30 mmol) in EtOH (10 mL) 2,4-difluorobenzaldehyde (1.09 mL, 10 mmol) was added dropwise. The resulting solution was stirred at RT for 1 h, then water was added and the aqueous phase was extracted with DCM (×4). Combined organics were dried and concentrated to obtain [(2,4-difluorophenyl)methylidene]hydrazine (p4, 1.8 g, y=quant.) as white solid. NMR: $^1$H NMR (DMSO-d$_6$) δ: 7.81 (s, 1H), 7.70-7.78 (m, 1H), 7.21 (d, 1H), 7.08 (s, 2H), 7.05 (d, 1H)

Preparation 5: [(4-fluorophenyl)methylidene]hydrazine

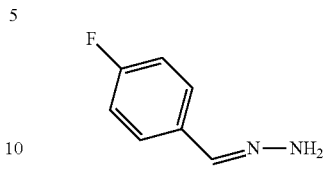

To a solution of hydrazine hydrate (2.5 mL, 30 mmol) in EtOH (10 mL) 4-fluorobenzaldehyde (1.07 mL, 10 mmol) was added dropwise. The resulting solution was stirred at reflux for 1 h, then cooled down to RT. After this time, water was added and the aqueous phase was extracted with DCM (×4). Combined organics were dried and concentrated to obtain [(4-fluorophenyl)methylidene]hydrazine (p5, 1.5 g, y=quant.) as yellow wax. NMR: $^1$H NMR (DMSO-d$_6$) δ: 7.71 (s, 1H), 7.47-7.55 (m, 2H), 7.15 (m, 2H), 6.75 (s, 2H)

Preparation 6: [(3,5-dichlorophenyl)methylidene]hydrazine

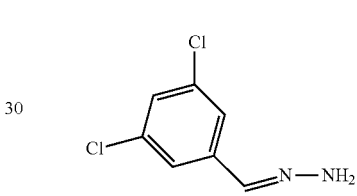

To a solution of hydrazine hydrate (0.72 mL, 8.55 mmol) in EtOH (6 mL) 3,5-dichlorobenzaldehyde (1 g, 5.7 mmol) was added portionwise under nitrogen over 5 min. The resulting solution was stirred at RT for 3 hrs. The solution was evaporated, and the residue was partitioned between DCM and water and extracted several times with DCM. The combined organic phases were washed with brine (15 mL), dried, filtered, and evaporated to yield a yellow solid that was purified by FC on silica gel (eluting from cHex to 30% EtOAc) to afford [(3,5-dichlorophenyl)methylidene]hydrazine (p6, 510 mg, y=47%) as yellow solid. NMR: $^1$H NMR (DMSO-d$_6$) δ:7.62 (s, 1H), 7.48 (d, 2H), 7.38-7.43 (m, 1H), 7.25 (s, 2H)

Preparation 7: {[2-(trifluoromethyl)phenyl]methylidene}hydrazine

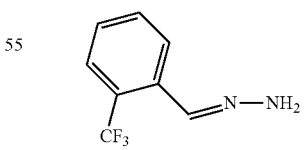

To a solution of hydrazine hydrate 60% in water (2.1 mL, 25.8 mmol) in EtOH (7.5 mL) 2-(trifluoromethyl)benzaldehyde (1.13 mL, 8.6 mmol) was added dropwise, under nitrogen, over 10 min. The resulting solution was stirred at RT for 1.5 h. After this time, water was added and the aqueous phase was extracted with DCM (×3). Combined organics were dried and concentrated to obtain {[2-(trifluoromethyl)phenyl]methylidene}hydrazine (p7, 1.31 g, y=71%) as yellow oil. NMR: $^1$H NMR (DMSO-d$_6$) δ: 8.01 (d, 1H), 7.89-7.96 (m, 1H), 7.65 (d, 1H), 7.59 (m, 1H), 7.34-7.43 (m, 3H)

Preparation 8: {[4-fluoro-2-(trifluoromethyl)phenyl]methylidene}hydrazine

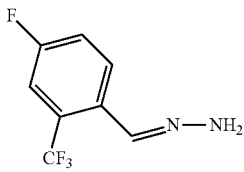

To a solution of hydrazine hydrate (1.9 mL, 23.4 mmol) in EtOH (7.5 mL) 4-fluoro-2-(trifluoromethyl)benzaldehyde (1.07 mL, 7.8 mmol) was added dropwise under nitrogen over 10 min. The resulting solution was stirred at RT for 1 h. After this time, water was added and the aqueous phase was extracted with DCM (×3). Combined organics were dried and concentrated to obtain {[4-fluoro-2-(trifluoromethyl)phenyl]methylidene}hydrazine (p8, 1.81 g, y=98%) as pale yellow solid. NMR: $^1$H NMR (DMSO-d$_6$) δ: 8.03 (m, 1H), 7.89 (m, 1H), 7.54 (m, 1H), 7.48 (d, 1H), 7.39 (s, 2H)

Preparation 9: 5-methanehydrazonoyl-2-(trifluoromethyl)pyridine

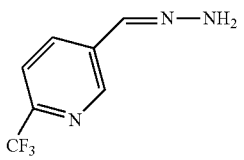 [SMILES: NN=Cc1ccc(C(F)(F)F)nc1]

To a solution of hydrazine hydrate (0.48 mL, 5.7 mmol) in EtOH (5 mL) 6-(trifluoromethyl)-3-pyridinecarboxaldehyde (1 g, 5.7 mmol) was added portionwise under nitrogen over 5 min. The resulting solution was stirred at RT for 3 hrs. The solution was evaporated, and the residue was partitioned between DCM and water and extracted several times with DCM. The combined organic phases were washed with brine (15 mL), dried, filtered, and evaporated to yield 5-methanehydrazonoyl-2-(trifluoromethyl)pyridine (p9, 0.87 g, y=quant.) as a white solid that was used as such in the next step. MS (m/z): 190.4 [MH]$^+$ Preparation 10: 1-benzyl-3-methylidenepyrrolidine-2,5-dione

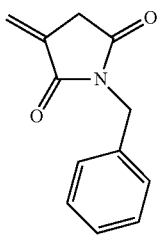

1-benzyl-2,5-dihydro-1H-pyrrole-2,5-dione (25 g, 134 mmol) was dissolved in AcOH (80 mL) and PPh$_3$ (35 g, 134 mmol) was added. The resulting solution was stirred for 1 h at RT then formaldehyde 37% in water (15 mL, 252 mmol) was added. The solution was stirred at RT for 2.5 hrs. Volatiles were removed under reduced pressure. The residue was partitioned between water (300 mL) and DCM (350 mL). The layers were separated and the organic portion was dried over Na$_2$SO$_4$, filtered and concentrated under reduced pressure. The crude material was purified by FC on silica gel (eluent: cyclohexane-EtOAc, 80:20 to 60:40) affording 1-benzyl-3-methylidenepyrrolidine-2,5-dione (p10, 24.44 g, y=90%) as colorless oil. MS (m/z): 202.2 [MH]$^+$.

Preparation 11 and 12: (1S,3S/1R,3R)-5-benzyl-1-[4-(trifluoromethyl)phenyl]-5-azaspiro[2.4]heptane-4,6-dione (TRANS, p11) and (1S,3R/1R,3S)-5-benzyl-1-[4-(trifluoromethyl)phenyl]-5-azaspiro[2.4]heptane-4,6-dione (CIS, p12)

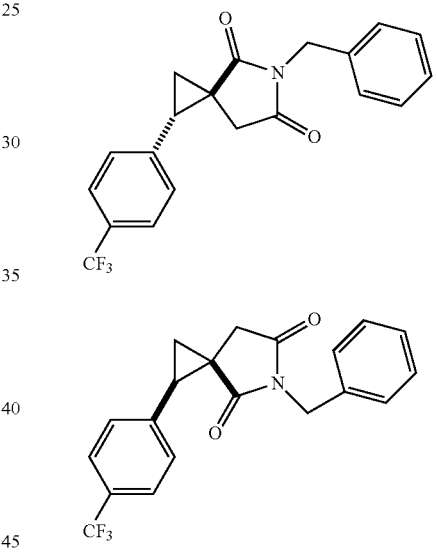

To a solution of {[4-(trifluoromethyl)phenyl]methylidene}hydrazine (p1, 11.29 g, 60 mmol) in dioxane (65 mL) at 10° C., MnO$_2$ (52.16 g, 600 mmol) was added portionwise. The resulting mixture was stirred at RT for 1 h, then it was filtered over a pad of Celite washing with dioxane (70 mL). This pale yellow solution was then added into a solution of 1-benzyl-3-methylidenepyrrolidine-2,5-dione (p10, 12.07 g, 60 mmol) in dioxane (30 mL). The resulting orange/red solution was left stirring at RT for 40 hrs. Solvent was removed and the residue was purified by FC on silica gel (eluent: from cHex to 30% EtOAc) to afford: (1S,3S/1R,3R)-5-benzyl-1-[4-(trifluoromethyl)phenyl]-5-azaspiro[2.4]heptane-4,6-dione (Diastereoisomer 1, TRANS, p11): 7.2 g, y=33%, 96% purity and (1S,3R/1R,3S)-5-benzyl-1-[4-(trifluoromethyl)phenyl]-5-azaspiro[2.4]heptane-4,6-dione (Diastereoisomer 2, CIS, p12): 7.5 g, y=35%, 60% purity, that were used as such in the next step. MS (m/z): 360.3 [MH]$^+$.

Preparation 13: (1S,3S/1R,3R)-1-[4-(trifluoromethyl)phenyl]-5-azaspiro[2.4]heptane (TRANS)

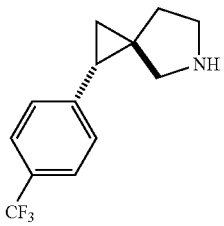

Step a: (1S,3S/1R,3R)-5-benzyl-1-[4-(trifluoromethyl)phenyl]-5-azaspiro[2.4]heptane-4,6-dione (Diastereoisomer 1, TRANS, P11, 0.91 g, 2.53 mmol) was dissolved in THF (15 mL) and LiAlH₄ 1M in THF (5.06 mL, 5.06 mmol) was added dropwise. The resulting orange solution was heated at reflux for 1 h. Then it was cooled with an ice bath and quenched with Na₂SO₄*10 H₂O until gas evolution ceased. The mixture was filtered over a pad of Celite washing with EtOAc, and the solution was concentrated to afford (1S,3S/1R,3R)-5-benzyl-1-[4-(trifluoromethyl)phenyl]-5-azaspiro[2.4]heptane (TRANS, 810 mg) as oil that was used as such in the next step.

Step b: (1S,3S/1R,3R)-5-benzyl-1-[4-(trifluoromethyl)phenyl]-5-azaspiro[2.4]heptane (TRANS, 810 mg from step a) was dissolved in MeOH (20 mL) under N₂ and ammonium formate (1.55 g, 24.4 mmol) was added. After 2 cycles vacuum/N₂ Pd/C (0.25 g) was added. The resulting mixture was stirred at reflux for 1 h. After cooling down to RT, it was filtered over a pad of Celite, the solvent was evaporated and the residue was charged on SCX cartridge (eluting with 1N NH₃ in MeOH) to afford, after evaporation, (1S,3S/1R,3R)-1-[4-(trifluoromethyl)phenyl]-5-azaspiro[2.4]heptane (TRANS, p13, 495 mg, y=81%) as pale yellow oil. MS (m/z): 242.3 [MH]⁺.

Preparation 14: (1R,3S/1S,3R)-1-[4-(trifluoromethyl)phenyl]-5-azaspiro[2.4]heptane (CIS)

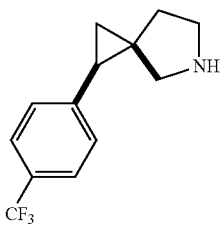

Step a: (1S,3R/1R,3S)-5-benzyl-1-[4-(trifluoromethyl)phenyl]-5-azaspiro[2.4]heptane-4,6-dione (Diastereoisomer 2, CIS, p12, 7.5 g, 20.87 mmol) was dissolved in THF (120 mL) and LiAlH₄ 1M in THF (15.65 mL, 15.65 mmol) was added dropwise at 0° C. The resulting orange solution was heated at reflux for 1 h. Then it was cooled with an ice bath and quenched with Na₂SO₄*10 H₂O until gas evolution ceased. The mixture was filtered over a pad of Celite washing with EtOAc, and the solution was concentrated to afford (1R,3S/1S,3R)-5-benzyl-1-[4-(trifluoromethyl)phenyl]-5-azaspiro[2.4]heptane (CIS, 6.9 g) as oil that was used as such in the next step.

Step b: (1R,3S/1S,3R)-5-benzyl-1-[4-(trifluoromethyl)phenyl]-5-azaspiro[2.4]heptane (CIS, 6.9 g, from step a) was dissolved in MeOH (200 mL) under N₂ and ammonium formate (6.58 g, 104.35 mmol) was added. Then Pd/C (800 mg) was added. The resulting mixture was stirred at reflux for 5 hrs. After cooling it was filtered over a pad of Celite, the solvent was evaporated and 12 mL of HCl~1.25M in MeOH were added. Solvent was eliminated under reduced pressure and the residue was loaded on a SCX cartridge washing with MeOH and eluting with NH₃ 1M in MeOH. Solvent was eliminated under reduced pressure affording (1R,3S/1S,3R)-1-[4-(trifluoromethyl)phenyl]-5-azaspiro[2.4]heptane (CIS, p14, 3.89 g, y=77%). MS (m/z): 242.0 [MH]⁺.

Preparation 15: (1R,3S)-1-[4-(trifluoromethyl)phenyl]-5-azaspiro[2.4]heptane (CIS, Enantiomer 1)

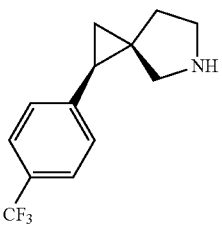 [SMILES: FC(F)(F)c1ccc([C@H]2C[C@]23CCNC3)cc1]

(1R,3S/1S,3R)-1-[4-(trifluoromethyl)phenyl]-5-azaspiro[2.4]heptane (CIS, p14, 3.89 g) was submitted to chiral Prep HPLC (SFC) to separate enantiomers:

Preparative Chromatography:

| | |
|---|---|
| Column | Chiralpak AD-H (25 × 2.1 cm), 5µ |
| Modifier | (Ethanol + 0.1% isopropylamine) 7% |
| Flow rate (ml/min) | 45 ml/min |
| Pressure (bar) | 120 |
| Temperature (° C.) | 38 |
| DAD detection | 220 nm |
| Loop | 900 µL |
| Injection | 53.3 mg/injection | affording: (1R,3S)-1-[4-(trifluoromethyl)phenyl]-5-azaspiro[2.4]heptane (CIS, p15, 1.5 g). Enantiomer 1: Ret. Time 6.4 min, 100% ee. MS (m/z): 242.0 [MH]⁺.

Preparation 16 and 17: (1S,3S/1R,3R)-5-benzyl-1-phenyl-5-azaspiro[2.4]heptane-4,6-dione (TRANS, p16) and (1R,3S/1S,3R)-5-benzyl-1-phenyl-5-azaspiro[2.4]heptane-4,6-dione (CIS, p17)

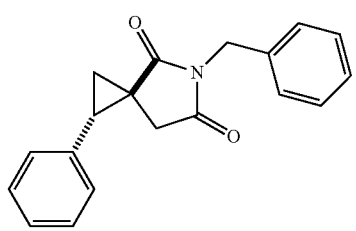

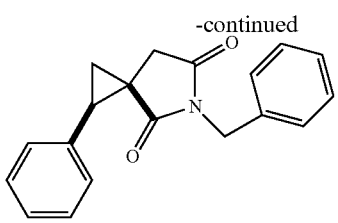

To a solution of (phenylmethylidene)hydrazine (p2, 0.6 g, 5 mmol) in dioxane (10 mL) at 10° C., MnO$_2$ (4.4 g, 50 mmol) was added portionwise. The resulting mixture was stirred at RT for 30 min, then it was filtered over a pad of Celite washing with dioxane and this solution was added to a solution of 1-benzyl-3-methylidenepyrrolidine-2,5-dione (p10, 1 g, 5 mmol) in dioxane (3.5 mL). The resulting orange/red solution was left stirring at RT O/N. Solvent was removed and the residue was purified by FC on silica gel (eluent: from cHex to 30% EtOAc) to afford: (1S,3S/1R,3R)-5-benzyl-1-phenyl-5-azaspiro[2.4]heptane-4,6-dione (Diastereoisomer 1, TRANS, p16): 524 mg, y=36%, 70% purity and 171 mg, y=12%, 90% purity, and (1R,3S/1S,3R)-5-benzyl-1-phenyl-5-azaspiro[2.4]heptane-4,6-dione (Diastereoisomer 2, CIS, p17): 550 mg, y=38%, 76% purity, that were used as such in the next step. MS (m/z): 292.2 [MH]$^+$.

Preparation 18: (1S,3S/1R,3R)-1-phenyl-5-azaspiro[2.4]heptane (TRANS)

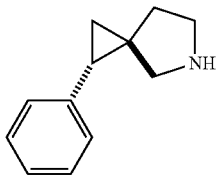

The compound was synthesized in analogy to the method described for Preparation 13 starting from (1S,3S/1R,3R)-5-benzyl-1-phenyl-5-azaspiro[2.4]heptane-4,6-dione (TRANS, p16, 524 mg, 1.8 mmol) and affording (1S,3S/1R,3R)-1-phenyl-5-azaspiro[2.4]heptane (p18, TRANS, 166 mg, 60% purity). MS (m/z): 242.3 [MH]$^+$.

Preparation 19: (1R,3S/1S,3R)-1-phenyl-5-azaspiro[2.4]heptane (CIS)

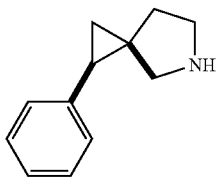

The compound was synthesized in analogy to the method described for Preparation 13 starting from (1R,3S/1S,3R)-5-benzyl-1-phenyl-5-azaspiro[2.4]heptane-4,6-dione (p17, CIS, 1.13 g, 3.88 mmol) and affording (1R,3S/1S,3R)-1-phenyl-5-azaspiro[2.4]heptane (p19, CIS, 42 mg, y=6%). MS (m/z): 174.1 [MH]$^+$.

Preparation 20 and 21: (1R,3S/1S,3R)-5-benzyl-1-[2-fluoro-4-(trifluoromethyl)phenyl]-5-azaspiro[2.4]heptane-4,6-dione (TRANS, p20) and (1S,3S/1R,3R)-5-benzyl-1-[2-fluoro-4-(trifluoromethyl)phenyl]-5-azaspiro[2.4]heptane-4,6-dione (CIS, p21)

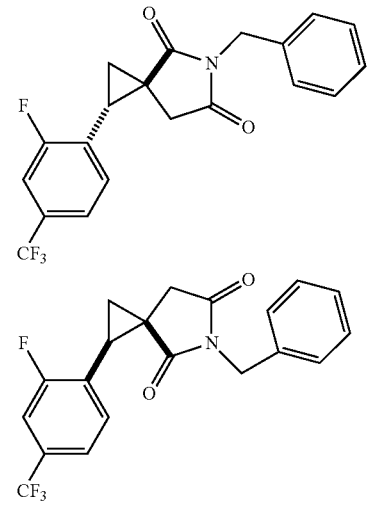

To a solution of {[2-fluoro-4-(trifluoromethyl)phenyl]methylidene}hydrazine (p3, 1.05 g, 5 mmol) in dioxane (10 mL) at 10° C., MnO$_2$ (4.4 g, 50 mmol) was added portionwise. The resulting mixture was stirred at RT for 30 min, then it was filtered over a pad of Celite washing with dioxane (10 mL) directly into a solution of 1-benzyl-3-methylidenepyrrolidine-2,5-dione (p10, 1 g, 5 mmol) in dioxane (10 mL). The resulting orange/red solution was left stirring at RT O/N. Solvent was removed and the residue was purified by FC on Si cartridge (eluent: from cHex to 30% EtOAc) to afford: (1R,3S/1S,3R)-5-benzyl-1-[2-fluoro-4-(trifluoromethyl)phenyl]-5-azaspiro[2.4]heptane-4,6-dione (Diastereoisomer 1, TRANS, p20): 1.12 g, 55% purity and (1S,3S/1R,3R)-5-benzyl-1-[2-fluoro-4-(trifluoromethyl)phenyl]-5-azaspiro[2.4]heptane-4,6-dione (Diastereoisomer 2, CIS, p21): 518 mg, 86% purity, that were used as such in the next step. MS (m/z): 378.3 [MH]$^+$.

Preparation 22: (1R,3S/1S,3R)-1-[2-fluoro-4-(trifluoromethyl)phenyl]-5-azaspiro-[2.4]heptane (TRANS)

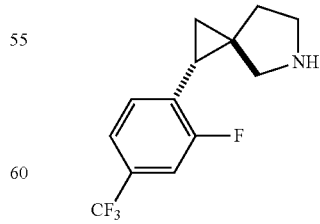

The compound was synthesized in analogy to the method described for Preparation 13 starting from (1R,3S/1S,3R)-5-benzyl-1-[2-fluoro-4-(trifluoromethyl)phenyl]-5-azaspiro[2.4]heptane-4,6-dione (p20, TRANS, 1.2 g, 3.18 mmol)

and affording (1R,3S/1S,3R)-1-[2-fluoro-4-(trifluoromethyl)phenyl]-5-azaspiro[2.4]heptane (p22, TRANS, 308 mg, y=37%). MS (m/z): 260.2 [MH]+.

Preparation 23: (1S,3S/1R,3R)-1-[2-fluoro-4-(trifluoromethyl)phenyl]-5-azaspiro-[2.4]heptane (CIS)

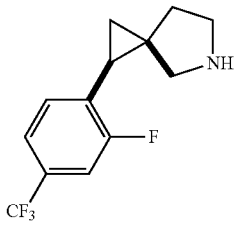

The compound was synthesized in analogy to the method described for Preparation 14 starting from (1S,3S/1R,3R)-5-benzyl-1-[2-fluoro-4-(trifluoromethyl)phenyl]-5-azaspiro[2.4]heptane-4,6-dione (p21, CIS, 0.654 g, 1.73 mmol) and affording (1S,3S/1R,3R)-1-[2-fluoro-4-(trifluoromethyl)phenyl]-5-azaspiro[2.4]heptane (p23, CIS, 234 mg, y=52%). MS (m/z): 260.2 [MH]+.

Preparation 24 and 25: (1S,3S)-1-[2-fluoro-4-(trifluoromethyl)phenyl]-5-azaspiro[2.4]heptane (p24, CIS, Enantiomer 1) and (1R,3R)-1-[2-fluoro-4-(trifluoromethyl)phenyl]-5-azaspiro[2.4]heptane (p25, CIS, Enantiomer 2)

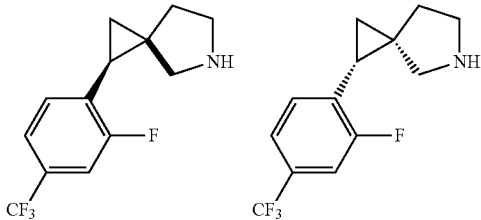 [SMILES: Fc1cc(C(F)(F)F)ccc1[C@H]1C[C@]12CCNC2 ; Fc1cc(C(F)(F)F)ccc1[C@@H]1C[C@@]12CCNC2]

(1S,3S/1R,3R)-1-[2-fluoro-4-(trifluoromethyl)phenyl]-5-azaspiro[2.4]heptane (prepared as in p23, CIS, 1 g) was submitted to chiral Prep HPLC (SFC) to separate enantiomers:
Preparative Chromatography:

| | |
|---|---|
| Column | Chiralpak AD-H (25 × 2.1 cm), 5µ |
| Modifier | (Ethanol + 0.1% isopropylamine) 7% |
| Flow rate (ml/min) | 45 ml/min |
| Pressure (bar) | 120 |
| Temperature (° C.) | 38 |
| DAD detection | 220 nm |
| Loop | 500 µL |
| Injection | 25 mg/injection | affording: (1S,3S)-1-[2-fluoro-4-(trifluoromethyl)phenyl]-5-azaspiro[2.4]heptane (p24, CIS, 351 mg), Enantiomer 1: Ret. Time 4.7 min, 100% ee. MS (m/z): 260.2 [MH]+, and (1R,3R)-1-[2-fluoro-4-(trifluoromethyl)phenyl]-5-azaspiro[2.4]heptane (p25, CIS, 378 mg), Enantiomer 2: Ret. Time 6.2 min, 98.8% ee. MS (m/z): 260.2 [MH]+.

Preparation 26 and 27: (1R,3S/1S,3R)-5-benzyl-1-(2,4-difluorophenyl)-5-azaspiro[2.4]heptane-4,6-dione (TRANS, p26) and (1S,3S/1R,3R)-5-benzyl-1-(2,4-difluorophenyl)-5-azaspiro[2.4]heptane-4,6-dione (CIS, p27)

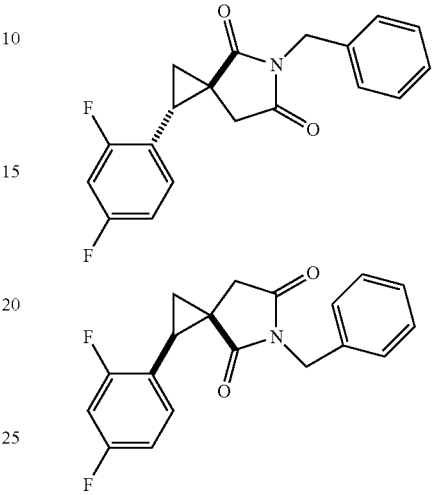

To a solution of [(2,4-difluorophenyl)methylidene]hydrazine (p4, 0.78 g, 5 mmol) in dioxane (10 mL) at 10° C., MnO2 (4.4 g, 50 mmol) was added portionwise. The resulting mixture was stirred at RT for 30 min, then it was filtered over a pad of Celite washing with dioxane (10 mL) directly into a solution of 1-benzyl-3-methylidenepyrrolidine-2,5-dione (p10, 1 g, 5 mmol) in dioxane (10 mL). The resulting orange/red solution was left stirring at RT O/N. Solvent was removed and the residue was purified by FC on silica gel (eluent: from cHex to 30% EtOAc) to afford: (1R,3S/1S,3R)-5-benzyl-1-(2,4-difluorophenyl)-5-azaspiro[2.4]heptane-4,6-dione (Diastereoisomer 1, TRANS, p26): 791 mg, 69% purity, and (1S,3S/1R,3R)-5-benzyl-1-(2,4-difluorophenyl)-5-azaspiro[2.4]heptane-4,6-dione (Diastereoisomer 2, CIS, p27): 653 mg, 87% purity, that were used as such in the next step. MS (m/z): 328.3 [MH]+.

Preparation 34: (1R,3S/1S,3R)-5-benzyl-1-(2,4-difluorophenyl)-5-azaspiro[2.4]heptane (TRANS)

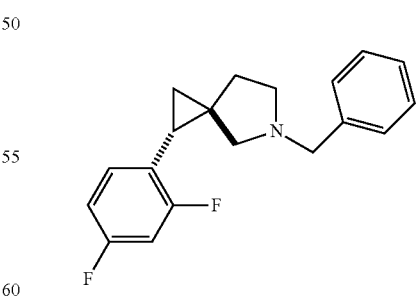

(1R,3S/1S,3R)-5-benzyl-1-(2,4-difluorophenyl)-5-azaspiro[2.4]heptane-4,6-dione (p32, TRANS, 791 mg, 2.42 mmol) was dissolved in THF (15 mL) and LiAlH4 1M in THF (4.83 mL, 4.83 mmol) was added dropwise at 0° C. The reaction was refluxed for 1 h, then cooled down to −20° C. and quenched with Na2SO4*10 H2O. The mixture was Preparation 28: (1R,3S/1S,3R)-1-(2,4-difluorophenyl)-5-azaspiro[2.4]heptane (TRANS)

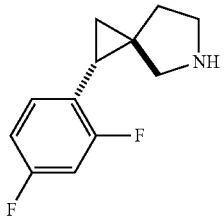

Step a: (1R,3S/1S,3R)-5-benzyl-1-(2,4-difluorophenyl)-5-azaspiro[2.4]heptane-4,6-dione (p26, TRANS, 791 mg, 2.42 mmol) was dissolved in THF (15 mL) and LiAlH$_4$ 1M in THF (4.83 mL, 4.83 mmol) was added dropwise at 0° C. The reaction was refluxed for 1 h, then cooled down to −20° C. and quenched with Na$_2$SO$_4$*10 H$_2$O. The mixture was filtered over a pad of celite washing with EtOAc, and the solution was concentrated to afford (1R,3S/1S,3R)-5-benzyl-1-(2,4-difluorophenyl)-5-azaspiro[2.4]heptane (TRANS, 734 mg) as oil that was used as crude in the next step.

Step b: (1R,3S/1S,3R)-5-benzyl-1-(2,4-difluorophenyl)-5-azaspiro[2.4]heptane (TRANS, 734 mg, from step a) was dissolved in DCM (15 mL) and the mixture was cooled down to 0° C. ACE-Cl (520 uL, 4.82 mmol) was added and the mixture was allowed to reach RT and left stirring at that temperature O/N. The day after solvent was eliminated under reduced pressure and the residue dissolved in MeOH (12 mL). The mixture was refluxed for 30 min and then cooled down to RT and concentrated under reduced pressure. Crude material was purified by FC on silica gel (eluent:DCM to DCM/MeOH 9:1) affording (1R,3S/1S,3R)-1-(2,4-difluorophenyl)-5-azaspiro[2.4]heptane (p28, TRANS, 158 mg, y=31%). MS (m/z): 210.2 [MH]$^+$.

Preparation 29: (1S,3S/1R,3R)-1-(2,4-difluorophenyl)-5-azaspiro[2.4]heptane (CIS)

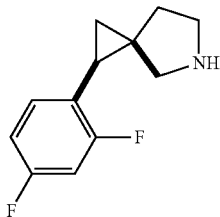

The compound was synthesized in analogy to the method described for Preparation 14 starting from (1S,3S/1R,3R)-5-benzyl-1-(2,4-difluorophenyl)-5-azaspiro[2.4]heptane-4,6-dione (p27, CIS, 0.653 g, 1.99 mmol) and affording (1S,3S/1R,3R)-1-(2,4-difluorophenyl)-5-azaspiro[2.4]heptane (p29, CIS, 326 mg, y=78%). MS (m/z): 210.2 [MH]$^+$.

Preparation 30 and 31: (1S,3S/1R,3R)-5-benzyl-1-(4-fluorophenyl)-5-azaspiro[2.4]heptane-4,6-dione (TRANS, p30) and (1S,3S/1R,3R)-5-benzyl-1-(4-fluorophenyl)-5-azaspiro[2.4]heptane-4,6-dione (CIS, p31)

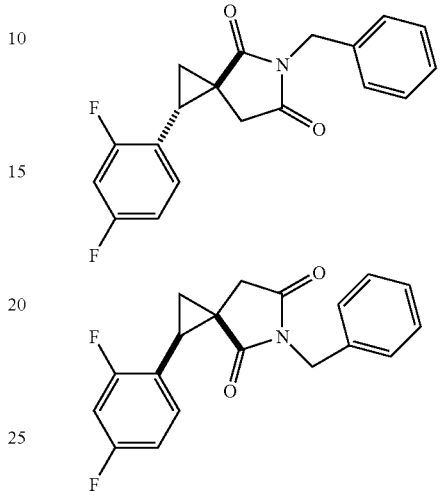

To a solution of [(4-fluorophenyl)methylidene]hydrazine (p5, 0.82 g, 6 mmol) in dioxane (10 mL) at 10° C., MnO$_2$ (4.4 g, 50 mmol) was added portionwise. The resulting mixture was stirred at RT for 30 min, and then it was filtered over a pad of Celite washing with dioxane (10 mL) directly into a solution of 1-benzyl-3-methylidenepyrrolidine-2,5-dione (p10, 1.2 g, 6 mmol) in dioxane (10 mL). The resulting orange/red solution was left stirring at RT O/N. Solvent was removed and the residue was purified by FC on silica gel (eluent: cHex to 30% EtOAc) to afford: (1S,3S/1R,3R)-5-benzyl-1-(4-fluorophenyl)-5-azaspiro[2.4]heptane-4,6-dione (Diastereoisomer 1, TRANS, p30): 951 mg, 82% purity and (1R,3S/1S,3R)-5-benzyl-1-(4-fluorophenyl)-5-azaspiro[2.4]heptane-4,6-dione (Diastereoisomer 2, CIS, p31): 765 mg, 70% purity, that were used as such in the next step. MS (m/z): 310.3 [MH]$^+$.

Preparation 32: (1S,3S/1R,3R)-1-(4-fluorophenyl)-5-azaspiro[2.4]heptane (TRANS)

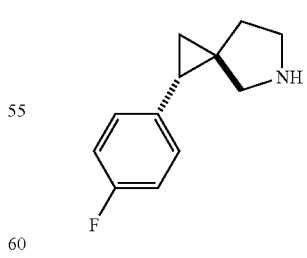

The compound was synthesized in analogy to the method described for Preparation 28 starting from (1S,3S/1R,3R)-5-benzyl-1-(4-fluorophenyl)-5-azaspiro[2.4]heptane-4,6-dione (p30, 951 mg, 3.07 mmol) and affording (1S,3S/1R,3R)-1-(4-fluorophenyl)-5-azaspiro[2.4]heptane (p32, TRANS, 257 mg, y=44%). MS (m/z): 192.2 [MH]$^+$.

Preparation 33: (1R,3S/1S,3R)-1-(4-fluorophenyl)-5-azaspiro[2.4]heptane (CIS)

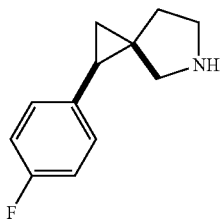

The compound was synthesized in analogy to the method described for Preparation 14 starting from (1R,3S/1S,3R)-5-benzyl-1-(4-fluorophenyl)-5-azaspiro[2.4]heptane-4,6-dione (p31, CIS, 765 mg, 2.47 mmol) and affording (1R,3S/1S,3R)-1-(4-fluorophenyl)-5-azaspiro[2.4]heptane (p33, CIS, 366 mg, y=77%). MS (m/z): 192.2 [MH]$^+$.

Preparation 34 and 35: (1S,3S/1R,3R)-5-benzyl-1-(3,5-dichlorophenyl)-5-azaspiro[2.4]heptane-4,6-dione (TRANS, p34) and (1R,3S/1S,3R)-5-benzyl-1-(3,5-dichlorophenyl)-5-azaspiro[2.4]heptane-4,6-dione (CIS, p35)

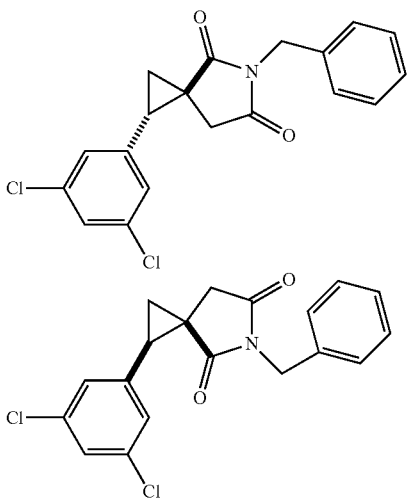

To a solution of [(3,5-dichlorophenyl)methylidene]hydrazine (p6, 0.85 g, 4.49 mmol) in dioxane (10 mL) at 10° C., MnO$_2$ (3.9 g, 45 mmol) was added portionwise. The resulting mixture was stirred at RT for 50 min, and then it was filtered over a pad of Celite washing with dioxane (10 mL) directly into a solution of 1-benzyl-3-methylidenepyrrolidine-2,5-dione (p10, 0.885 g, 4.4 mmol) in dioxane (5 mL). The resulting orange/red solution was left stirring at RT O/N. Solvent was removed and the residue was purified by FC on silica gel (eluent: from cHex to 30% EtOAc) to afford: (1S,3S/1R,3R)-5-benzyl-1-(3,5-dichlorophenyl)-5-azaspiro[2.4]heptane-4,6-dione (Diastereoisomer 1, TRANS, p34): 440 mg, 89% purity and (1R,3S/1S,3R)-5-benzyl-1-(3,5-dichlorophenyl)-5-azaspiro[2.4]heptane-4,6-dione (Diastereoisomer 2, CIS, p35): 440 mg, 40% purity, that were used as such in the next step. MS (m/z): 359.9 [MH]$^+$.

Preparation 36: (1S,3S/1R,3R)-1-(3,5-dichlorophenyl)-5-azaspiro[2.4]heptane (TRANS)

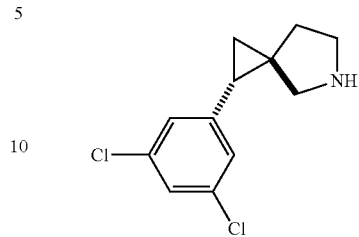

The compound was synthesized in analogy to the method described for Preparation 28 starting from (1S,3S/1R,3R)-5-benzyl-1-(3,5-dichlorophenyl)-5-azaspiro[2.4]heptane-4,6-dione (p34, TRANS, 440 mg, 1.22 mmol) and affording (1S,3S/1R,3R)-1-(3,5-dichlorophenyl)-5-azaspiro[2.4]heptane (p36, TRANS, 164 mg, y=55%). MS (m/z): 241.9 [M]$^+$.

Preparation 37: (1R,3S/1S,3R)-1-(3,5-dichlorophenyl)-5-azaspiro[2.4]heptane (CIS)

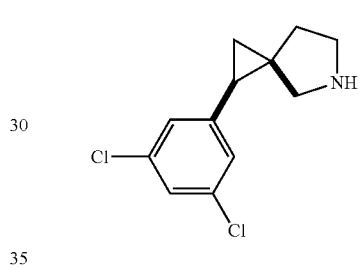

The compound was synthesized in analogy to the method described for Preparation 28 starting from (1R,3S/1S,3R)-5-benzyl-1-(3,5-dichlorophenyl)-5-azaspiro[2.4]heptane-4,6-dione (p35, CIS, 440 mg, 1.22 mmol) and affording (1R,3S/1S,3R)-1-(3,5-dichlorophenyl)-5-azaspiro[2.4]heptane (p37, CIS, 110 mg, y=27%). MS (m/z): 241.9 [M]$^+$.

Preparation 38 and 39: (1R,3S/1S,3R)-5-benzyl-1-[2-(trifluoromethyl)phenyl]-5-azaspiro[2.4]heptane-4,6-dione (CIS, p38) and (1S,3S/1R,3R)-5-benzyl-1-[2-(trifluoromethyl)phenyl]-5-azaspiro[2.4]heptane-4,6-dione (TRANS, p39)

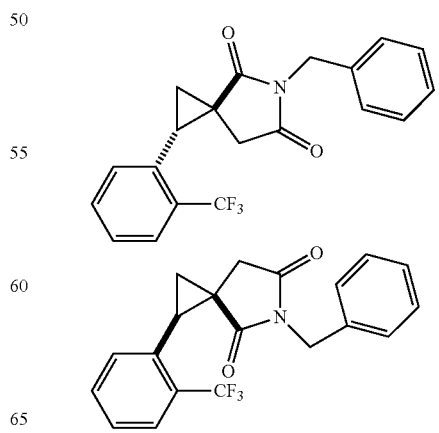

To a solution of {[2-(trifluoromethyl)phenyl]methylidene}hydrazine (p7, 0.935 g, 4.97 mmol) in dioxane (6 mL) at 10° C., MnO₂ (4.32 g, 49.7 mmol) was added portionwise. The resulting mixture was stirred at RT for 30 min, then it was filtered over a pad of Celite washing with dioxane (15 mL) directly into a solution of 1-benzyl-3-methylidenepyrrolidine-2,5-dione (p10, 1 g, 4.97 mmol) in dioxane (3 mL). The resulting orange/red solution was left stirring at RT O/N. Solvent was removed and the residue was purified by FC on silica gel (eluent: cHex to 30% EtOAc, then to EtOAc 100%) affording a mixture of both diastereomers that were separated via chiral Prep HPLC Preparative Chromatography:

| | |
|---|---|
| Column | Chiralpak AD-H (25 × 2.0 cm), 5μ |
| Mobile phase | n-Hexane/(Ethanol/Methanol + 0.1% isopropylamine) 80/20% v/v |
| Flow rate (ml/min) | 18 ml/min |
| DAD detection | 220 nm |
| Loop | 330 μL |
| Injection | 41 mg/injection | affording: (1R,3S/1S,3R)-5-benzyl-1-[2-(trifluoromethyl)phenyl]-5-azaspiro[2.4]heptane-4,6-dione (Diastereoisomer 1, CIS, p38): 531 mg, 100% purity, r.t. 1.17 min, and (1S,3S/1R,3R)-5-benzyl-1-[2-(trifluoromethyl)phenyl]-5-azaspiro[2.4]heptane-4,6-dione (Diastereoisomer 2, TRANS, p39): 425 mg, 100% purity, r.t. 1.20 min. MS (m/z): 360.0 [MH]⁺.

Preparation 40: (1S,3S/1R,3R)-1-[2-(trifluoromethyl)phenyl]-5-azaspiro[2.4]heptane (TRANS)

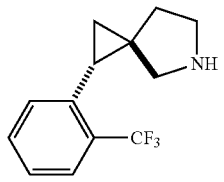

The compound was synthesized in analogy to the method described for Preparation 13 starting from (1S,3S/1R,3R)-5-benzyl-1-[2-(trifluoromethyl)phenyl]-5-azaspiro[2.4]heptane-4,6-dione (p39, TRANS, 128 mg, 0.36 mmol) and affording (1S,3S/1R,3R)-1-[2-(trifluoromethyl)phenyl]-5-azaspiro[2.4]heptane (p40, TRANS, 52 mg, y=60%). MS (m/z): 241.9 [M]⁺.

Preparation 41: (1R,3S/1S,3R)-1-[2-(trifluoromethyl)phenyl]-5-azaspiro[2.4]heptane (CIS)

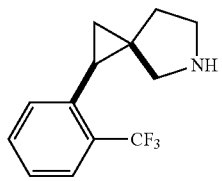

The compound was synthesized in analogy to the method described for Preparation 14 starting from (1S,3R/1R,3S)-5-benzyl-1-[2-(trifluoromethyl)phenyl]-5-azaspiro[2.4]heptane-4,6-dione (p38, CIS, 529 mg, 1.48 mmol) and affording (1R,3S/1S,3R)-1-[2-(trifluoromethyl)phenyl]-5-azaspiro[2.4]heptane (p41, CIS, 181 mg, y=51%). MS (m/z): 241.9 [M]⁺.

Preparation 42, 43, 44 and 45: (1R,3S or 1S,3R)-5-benzyl-1-[4-fluoro-2-(trifluoromethyl)phenyl]-5-azaspiro[2.4]heptane-4,6-dione (CIS, Enantiomer 1, p42), (1S,3R or 1R,3S)-5-benzyl-1-[4-fluoro-2-(trifluoromethyl)phenyl]-5-azaspiro[2.4]heptane-4,6-dione (CIS, Enantiomer 2, p43), (1S,3S or 1R,3R)-5-benzyl-1-[4-fluoro-2-(trifluoromethyl)phenyl]-5-azaspiro[2.4]heptane-4,6-dione (TRANS, Enantiomer 1, p44) and (1R,3R or 1S,3S)-5-benzyl-1-[4-fluoro-2-(trifluoromethyl)phenyl]-5-azaspiro[2.4]heptane-4,6-dione (TRANS, Enantiomer 2, p45)

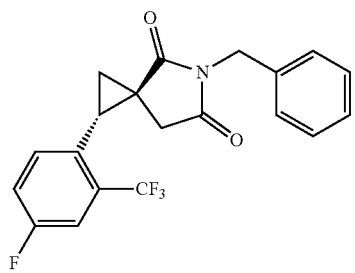

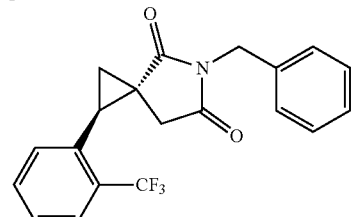

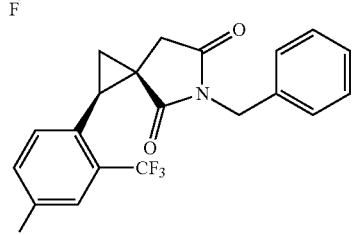

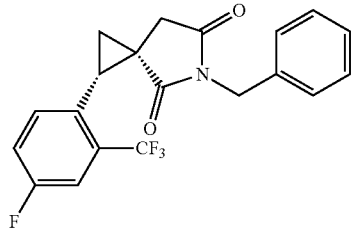

To a solution of {[4-fluoro-2-(trifluoromethyl)phenyl]methylidene}hydrazine (p8, 1.81 g, 8.78 mmol) in dioxane (12 mL) at 10° C., MnO₂ (7.26 g, 83.5 mmol) was added portionwise. The resulting mixture was stirred at RT for 30 min, then it was filtered over a pad of Celite washing with dioxane (30 mL) directly into a solution of 1-benzyl-3-methylidenepyrrolidine-2,5-dione (p10, 1.68 g, 8.35 mmol) in dioxane (6 mL). The resulting orange/red solution was left stirring at RT O/N. Solvent was removed to obtain an orange gum that was purified by FC on silica gel (eluent from Cy to EtOAc 40%) to obtain a mixture of both racemic diastereomers (2.2 g) that was separated into 4 single enantiomers by chiral Prep HPLC.

Preparative Chromatography:

| | |
|---|---|
| Column | Chiralpak AD-H (25 × 2.0 cm), 5μ |
| Mobile phase | n-Hexane/(Ethanol/Methanol 1/1 + 0.1% isopropylamine) 80/20% v/v |
| Flow rate (ml/min) | 16 ml/min |
| DAD detection | 220 nm |
| Loop | 1000 μL |
| Injection | 44 mg/injection | affording: (1R,3S or 1S,3R)-5-benzyl-1-[4-fluoro-2-(trifluoromethyl)phenyl]-5-azaspiro[2.4]heptane-4,6-dione (Diastereoisomer 1, CIS, Enantiomer 1, p42): 500 mg, 98.4% purity, r.t. 5.8 min, (1S,3R or 1R,3S)-5-benzyl-1-[4-fluoro-2-(trifluoromethyl)phenyl]-5-azaspiro[2.4]heptane-4,6-dione (Diastereoisomer 1, CIS, Enantiomer 2, p43): 441 mg, 98% purity, r.t. 6.6 min, (1S,3S or 1R,3R)-5-benzyl-1-[4-fluoro-2-(trifluoromethyl)phenyl]-5-azaspiro[2.4]heptane-4,6-dione (Diastereoisomer 2, TRANS, Enantiomer 1, p44): 361 mg, 99% purity, r.t. 7.3 min, and (1R,3R or 1S,3S)-5-benzyl-1-[4-fluoro-2-(trifluoromethyl)phenyl]-5-azaspiro[2.4]heptane-4,6-dione (Diastereoisomer 2, TRANS, Enantiomer 2, p45): 403 mg, 100% purity, r.t. 9.3 min. MS (m/z): 378.2 [MH]$^+$.

Preparation 46: (1S,3S or 1R,3R)-1-[4-fluoro-2-(trifluoromethyl)phenyl]-5-azaspiro[2.4]heptane (TRANS, Enantiomer 1)

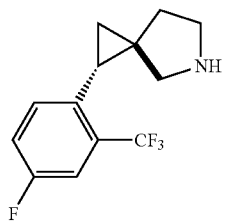 [SMILES: Fc1ccc([C@@H]2C[C@]23CCNC3)c(C(F)(F)F)c1]

Step a: (1S,3S or 1R,3R)-5-benzyl-1-[4-fluoro-2-(trifluoromethyl)phenyl]-5-azaspiro[2.4]heptane-4,6-dione (Diastereoisomer 2, TRANS, Enantiomer 1, p44, 361 mg, 0.96 mmol) was dissolved in THF (5 mL) and LiAlH$_4$ 1M in THF (1.92 mL, 1.92 mmol) was added dropwise at 0° C. The resulting orange solution was heated at reflux for 1 h. Then it was cooled down to 0° C. and quenched with Na$_2$SO$_4$*10 H$_2$O until gas evolution ceased. It was filtered over a pad of Celite washing with EtOAc, the solution was concentrated to afford (1S,3S or 1R,3R)-5-benzyl-1-[4-fluoro-2-(trifluoromethyl)phenyl]-5-azaspiro[2.4]heptane (TRANS, Enantiomer 1, 291 mg) as colourless oil.

Step b: (1S,3S or 1R,3R)-5-benzyl-1-[4-fluoro-2-(trifluoromethyl)phenyl]-5-azaspiro[2.4]heptane (TRANS, Enantiomer 1, 291 mg, from step a) was dissolved in MeOH (10 mL) under N$_2$ and ammonium formate (523 mg, 8.3 mmol) was added. Then Pd/C (33 mg) was added. The resulting mixture was stirred at reflux for 1 h. After cooling it was filtered over a pad of Celite, the solvent was evaporated and MeOH and 1.5 mL of HCl~1.25M in MeOH was added. Solvent was eliminated under reduced pressure and the residue was loaded on a 5 g SCX cartridge washing with MeOH and eluting with NH$_3$ 1M in MeOH. Solvent was eliminated under reduced pressure to obtain a yellow oil that was purified by C18 cartridge (eluent from Water+0.1% HCOOH to 25% ACN+0.1% HCOOH) then loaded on a SCX cartridge (washing with MeOH and eluting with NH$_3$ 1M in MeOH) to obtain (1S,3S or 1R,3R)-1-[4-fluoro-2-(trifluoromethyl)phenyl]-5-azaspiro[2.4]heptane (p46, 42 mg, y=17%) as yellow oil. MS (m/z): 260.2 [M]$^+$.

Preparation 47: (1R,3R or 1S,3S)-1-[4-fluoro-2-(trifluoromethyl)phenyl]-5-azaspiro[2.4]heptane (TRANS, Enantiomer 2)

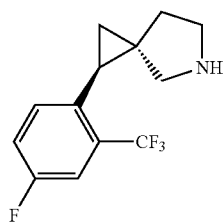

The compound was synthesized in analogy to the method described for Preparation 46 starting from (1R,3R or 1S,3S)-5-benzyl-1-[4-fluoro-2-(trifluoromethyl)phenyl]-5-azaspiro[2.4]heptane-4,6-dione (Diastereoisomer 2, TRANS, Enantiomer 2, p45, 403 mg, 1.07 mmol) and affording (1R,3R or 1S,3S)-1-[4-fluoro-2-(trifluoromethyl)phenyl]-5-azaspiro[2.4]heptane (p47, TRANS, Enantiomer 2, 93 mg, y=33%). MS (m/z): 260.2 [M]$^+$.

Preparation 48: (1R,3S or 1S,3R)-1-[4-fluoro-2-(trifluoromethyl)phenyl]-5-azaspiro[2.4]heptane (CIS, Enantiomer 1)

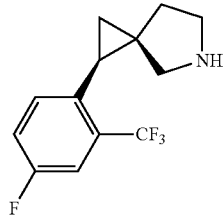

The compound was synthesized in analogy to the method described for Preparation 46 starting from (1R,3S or 1S,3R)-5-benzyl-1-[4-fluoro-2-(trifluoromethyl)phenyl]-5-azaspiro[2.4]heptane-4,6-dione (Diastereoisomer 1, CIS, Enantiomer 1, p42, 500 mg, 1.33 mmol) and affording (1R,3S or 1S,3R)-1-[4-fluoro-2-(trifluoromethyl)phenyl]-5-azaspiro[2.4]heptane (p48, CIS, Enantiomer 1, 126 mg, y=36%). MS (m/z): 260.2 [M]+.

Preparation 49: (1S,3R or 1R,3S)-1-[4-fluoro-2-(trifluoromethyl)phenyl]-5-azaspiro[2.4]heptane (CIS, Enantiomer 2)

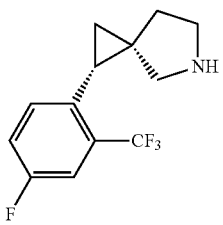

The compound was synthesized in analogy to the method described for Preparation 46 starting from (1S,3R or 1R,3S)-5-benzyl-1-[4-fluoro-2-(trifluoromethyl)phenyl]-5-azaspiro[2.4]heptane-4,6-dione (Diastereoisomer 1, CIS, Enantiomer 2, p43, 441 mg, 1.17 mmol) and affording (1S,3R or 1R,3S)-1-[4-fluoro-2-(trifluoromethyl)phenyl]-5-azaspiro[2.4]heptane (p49, CIS, Enantiomer 2, 76 mg, y=25%). MS (m/z): 260.2 [M]$^+$.

Preparation 50 and 51: (1S,3S/1R,3R)-5-benzyl-1-[6-(trifluoromethyl)pyridin-3-yl]-5-azaspiro[2.4]heptane-4,6-dione (TRANS, p50) and (1R,3S/1S,3R)-5-benzyl-1-[6-(trifluoromethyl)pyridin-3-yl]-5-azaspiro[2.4]heptane-4,6-dione (CIS, p51)

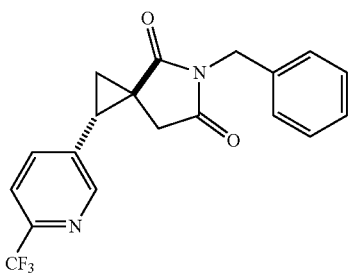

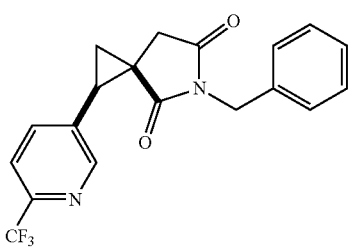

To a solution of 5-methanehydrazonoyl-2-(trifluoromethyl)pyridine (p9, 0.8 g, 4.22 mmol) in dioxane (15 mL) at 10° C., MnO$_2$ (3.6 g, 42.2 mmol) was added portionwise. The resulting mixture was stirred at RT for 45 min, then it was filtered over a pad of Celite washing with dioxane and this solution was added to a solution of 1-benzyl-3-methylidenepyrrolidine-2,5-dione (p10, 0.766 g, 3.8 mmol) in dioxane (5 mL). The resulting orange solution was left stirring at RT O/N. Solvent was removed and the residue was purified by FC on silica gel (eluent: from cHex to 45% EtOAc) to afford: (1S,3S/1R,3R)-5-benzyl-1-[6-(trifluoromethyl)pyridin-3-yl]-5-azaspiro[2.4]heptane-4,6-dione (Diastereoisomer 1, TRANS, p50): 450 mg and (1R,3S/1S,3R)-5-benzyl-1-[6-(trifluoromethyl)pyridin-3-yl]-5-azaspiro[2.4]heptane-4,6-dione (Diastereoisomer 2, CIS, p51): 360 mg, that were used as such in the next step. MS (m/z): 361.0 [MH]$^+$.

Preparation 52: (1R,3S/1S,3R)-1-[6-(trifluoromethyl)pyridin-3-yl]-5-azaspiro[2.4]heptane (CIS)

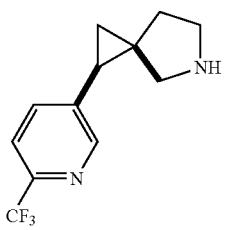

The compound was synthesized in analogy to the method described for Preparation 14 starting from (1R,3S/1S,3R)-5-benzyl-1-[6-(trifluoromethyl)pyridin-3-yl]-5-azaspiro[2.4]heptane-4,6-dione (p51, CIS, 0.36 g, 1 mmol) and affording (1R,3S/1S,3R)-1-[6-(trifluoromethyl)pyridin-3-yl]-5-azaspiro[2.4]heptane (p52, CIS, 100 mg, y=41%). MS (m/z): 243.3 [M]$^+$.

Preparation 53: 4-methyl-1,3-oxazole-5-carboxylic acid

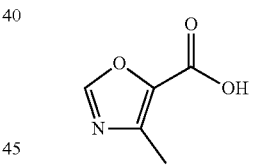

A stirred mixture of ethyl 2-chloro-3-oxobutanoate (16.8 ml, 121.51 mmol) and formamide (13.5 mL, 340.23 mmol) was heated to 120° C. After 6 hrs the mixture was allowed to cool to RT and stirred under nitrogen O/N. The mixture was treated with 3M NaOH (120 mL, reaction moderately exothermic) and stirred at RT for 4 hours. EtOAc (120 mL) was added and the phases allowed separating. The organic layer was discarded while the aqueous was acidified with 37% aqueous HCl to pH 2 (~40 mL). A precipitate started to form. The suspension was treated with EtOAc (160 mL) and, vigorously shaken until the precipitate had dissolved. Phases were separated and the aqueous one was further extracted with EtOAc twice (120 mL). The combined organic layers were concentrated to low volume. Fresh EtOAc (160 mL) was added and the mixture evaporated to dryness under vacuum. The collected solid was placed in the oven at 45° C. O/N under reduced pressure affording 4-methyl-1,3-oxazole-5-carboxylic acid (p53, 8.52 g, y=44%) as rusty brown solid. MS (m/z): 128.0 [MH]$^+$.

Preparation 54: 1-methanesulfonyl-1H-1,2,3-benzotriazole

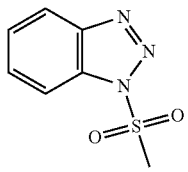

To a solution of benzotriazole (5 g, 42 mmol) and pyridine (5.4 mL, 67.2 mmol) in dry toluene (50 mL), MsCl (3.9 mL, 50.36 mmol) in dry toluene (10 mL) was added dropwise at 0° C. under $N_2$ atmosphere and the mixture was stirred O/N at RT. The mixture was diluted with ethyl acetate (20 mL), washed with water (2×30 mL), brine (30 mL), dried over $MgSO_4$, filtered and evaporated under vacuum affording 1-methanesulfonyl-1H-1,2,3-benzotriazole (p54, 8.44 g, y=quant). NMR: $^1$H NMR (Acetone-$d_6$) δ: 8.21 (dt, 1H), 8.04 (dt, 1H), 7.86-7.75 (m, 1H), 7.67-7.57 (m, 1H), 3.76 (s, 3H)

Preparation 55: methyl 6-(1H-1,2,3-benzotriazole-1-carbonyl)pyridine-2-carboxylate

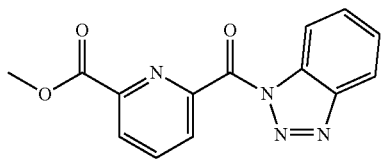 [SMILES: COC(=O)c1cccc(C(=O)n2nnc3ccccc32)n1]

A mixture of 6-(methoxycarbonyl)pyridine-2-carboxylic acid (4 g, 22.08 mmol), 1-methanesulfonyl-1H-1,2,3-benzotriazole (p54, 4.35 g, 22.08 mmol) and triethylamine (6.15 mL, 44.16 mmol) was refluxed in THF (150 mL) 4 hrs. The solvent was evaporated and the residue was dissolved in DCM. The organic layer was washed with water, dried, and evaporated to give methyl 6-(1H-1,2,3-benzotriazole-1-carbonyl)pyridine-2-carboxylate (p55, 5.8 g, y=93%). MS (m/z): 283.2 [MH]$^+$.

Preparation 56: methyl 6-carbamoylpyridine-2-carboxylate

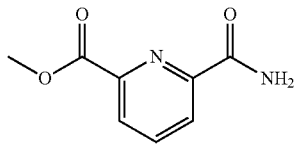

methyl 6-(1H-1,2,3-benzotriazole-1-carbonyl)pyridine-2-carboxylate (p55, 1.9 g, 6.73 mmol) was stirred with ammonium hydroxide (30% aqueous solution, 40 drops, 43 mmol) in MeOH (8 mL) and THF (15 mL) at RT for 2 hrs. After evaporation of solvents in vacuo, 2M NaOH (20 mL) was added to the residue and the mixture then extracted with EtOAc. The combined organic layers were dried. Evaporation of the solvent gave methyl 6-carbamoylpyridine-2-carboxylate (p56, 310 mg, y=crude). MS (m/z): 181.1 [MH]$^+$.

Preparation 57: 6-carbamoylpyridine-2-carboxylic acid

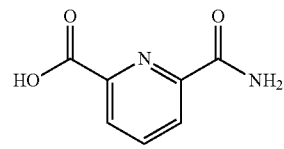 [SMILES: NC(=O)c1cccc(C(=O)O)n1]

A solution of methyl 6-carbamoylpyridine-2-carboxylate (p56, 0.31 g, 1.72 mmol) in THF (5 mL) and water (2 mL) at RT was treated with lithium hydroxide (0.072 g, 1.72 mmol), stirred for 2 hrs, and concentrated. The concentrate was dissolved in water (5 mL) and adjusted to pH 7 with 1N HCl. The aqueous solution was evaporated affording 6-carbamoylpyridine-2-carboxylic acid (p57, 550 mg, y=crude). MS (m/z): 166.0 [M]$^+$.

Preparation 58: methyl 6-(methyl carbamoyl)pyridine-2-carboxylate

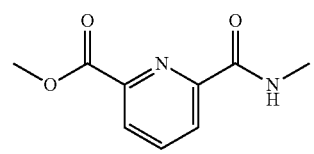

methyl 6-(1H-1,2,3-benzotriazole-1-carbonyl)pyridine-2-carboxylate (p55, 0.75 g, 2.66 mmol) was stirred with Methylamine 2M in THF (1.33 mL, 2.66 mmol) in THF (25 mL) at RT for 4 hrs. After evaporation of solvents in vacuum, 2 M NaOH (20 mL) was added to residue and extracted with EtOAc. The combined organic layers were dried. Evaporation of the solvent gave methyl 6-(methylcarbamoyl)pyridine-2-carboxylate (p58, 350 mg, y=68%). MS (m/z): 195.1 [MH]$^+$.

Preparation 59: 6-(methylcarbamoyl)pyridine-2-carboxylic acid

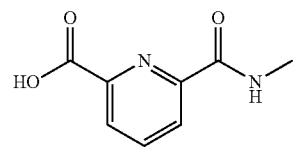

A solution of methyl 6-(methylcarbamoyl)pyridine-2-carboxylate (p58, 0.592 g, 3.05 mmol) in THF (7 mL) and water (3 mL) at RT was treated with LiOH.$H_2O$ (0.128 g, 3.05 mmol), stirred for 1 h, and concentrated. The concentrate was dissolved in water (5 mL) and adjusted to pH 7 with 1N HCl. The aqueous solution was evaporated and the residue was purified by C18 cartridge (eluent: from water to 10% CH₃CN) to afford after evaporation 6-(methylcarbamoyl)pyridine-2-carboxylic acid (p59, 540 mg, y=98%). MS (m/z): 181.1 [MH]⁺.

Preparation 60: methyl 6-(dimethyl carbamoyl)pyridine-2-carboxylate

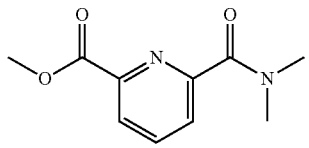

Methyl 6-(1H-1,2,3-benzotriazole-1-carbonyl)pyridine-2-carboxylate (p55, 1.5 g, 5.32 mmol) was stirred with Dimethylamine 2M in THF (2.66 mL, 5.32 mmol) in THF (35 mL) at RT for 4 hrs. After evaporation of solvents in vacuo, 2M NaOH (20 mL) was added to the residue and extracted with EtOAc. The combined organic layers were dried. Evaporation of the solvent gave methyl 6-(dimethylcarbamoyl)pyridine-2-carboxylate (p60, 250 mg, y=22%), MS (m/z): 209.1 [MH]⁺.

Preparation 61: 6-(dimethylcarbamoyl)pyridine-2-carboxylic acid

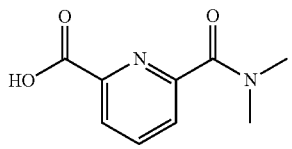

A solution of methyl 6-(dimethylcarbamoyl)pyridine-2-carboxylate (p60, 0.36 g, 1.73 mmol) in THF (6 mL) and water (2 mL) at RT was treated with LiOH.H₂O (0.072 g, 1.73 mmol), stirred for 1 h and then concentrated. The concentrate was dissolved in water (5 mL) and adjusted to pH 7 with 1N HCl. The aqueous solution was evaporated and the residue was purified by FC on C18 cartridge (eluent: water to 10% CH₃CN). After evaporation 6-(dimethylcarbamoyl)pyridine-2-carboxylic acid was obtained (p61, 500 mg, y=crude). MS (m/z): 195.2 [MH]⁺.

Preparation 62: ethyl 2-(pyridin-3-yl)-1,3-oxazole-4-carboxylate

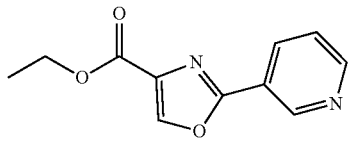 [SMILES: CCOC(=O)c1coc(-c2cccnc2)n1]

Ethyl 2-bromo-1,3-oxazole-4-carboxylate (200 mg, 0.9 mmole), 3-pyridineboronic acid (144 mg, 1.17 mmole), were combined in a screw cap vial, to this was added 1,4-dioxane (5 mL) and 2M Na₂CO₃ (1.13 mL, 2.27 mmol); N₂ was bubbled through the mixture for 1', and then Pd(PPh₃)₄ (100 mg, 0.09 mmol) was added. The vial was capped then heated at 100° C. After 2 hrs the mixture was cooled to RT, diluted with EtOAc, filtered through a pad of Celite washing with EtOAc, and concentrated. The crude material was purified by FC on silica cartridge (eluent: from cHex to EtOAc) to obtain ethyl 2-(pyridin-3-yl)-1,3-oxazole-4-carboxylate (p62, 71 mg, y=35%). MS (m/z): 219.1 [MH]⁺.

Preparation 63: ethyl 2-(pyridin-3-yl)-1,3-oxazole-4-carboxylate

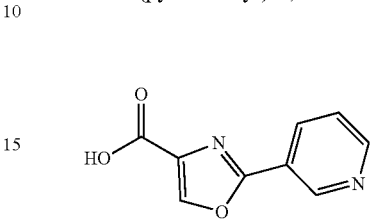

Ethyl 2-(pyridin-3-yl)-1,3-oxazole-4-carboxylate (p62, 380 mg, 1.74 mmol) was dissolved in THF/water (5 mL/2 mL) and LiOH H₂O (72 mg, 1.74 mmol) was added. The mixture was stirred at RT for 2 hrs. Solvent was removed in vacuo, the residue was dissolved with water and acidified with 6N HCl to pH 4. No precipitation was observed, the solution was evaporated affording ethyl 2-(pyridin-3-yl)-1,3-oxazole-4-carboxylate (p63, 330 mg, y=crude). MS (m/z): 191.1 [MH]⁺.

Preparation 64: 4-(1,3-oxazol-2-yl)benzoic acid

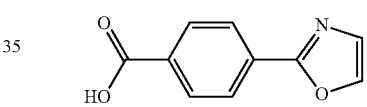

A solution of 4-carbamoylbenzoic (4.8 g, 29 mmol) and 2-bromo-1,1-diethoxyethane (8.7 mL, 58 mmol) in Dioxane (60 mL) was stirred at reflux (101° C.) for 3.5 hrs. The solids were filtered out and the filtrate was concentrated in vacuo. The residue was purified by reverse phase chromatography on C18 cartridge (eluent: Water+0.1% HCOOH to 30% ACN+0.1% HCOOH) to obtain 4-(1,3-oxazol-2-yl)benzoic acid (p64, 232 mg, y=4%). MS (m/z): 190.1 [MH]⁺.

Preparation 65: 4-methyl-5-(4-methyl-1,3-oxazol-5-yl)-4H-1,2,4-triazole-3-thiol

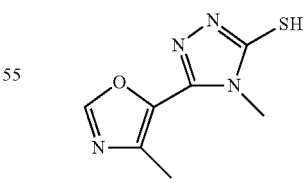

To a solution of 4-methyl-1,3-oxazole-5-carboxylic acid (p53, 2 g, 15.7 mmol) in DMF (9 mL), 4-Methyl-3-thiosemicarbazide (1.82 g, 17.27 mmol) was added. DIPEA (4.8 mL, 28.26 mmol) was added dropwise at RT, then the mixture was cooled with an ice bath before adding T3P (50% w/w in EtOAc) (14 mL, 23.55 mmol). The reaction was stirred at RT O/N. NaOH 4M solution (15 mL) was added (resulting pH=8). The reaction was diluted with EtOAc and the two resulting phases were separated (the upper organic layer eliminated). Additional 4M NaOH was added up to pH 11 and the mixture heated to 70° C. for 40 min. The clear rusty red solution was then cooled down to RT in 3 hours, then 37% HCl was slowly added till pH 5. The clear solution was extracted 3 times with DCM, combined organics were dried and concentrated to obtain a brown solid. Crude material was purified by C18 cartridge (eluting from $H_2O$+ 0.1% HCOOH to 20% MeCN+0.1% HCOOH). Fractions containing the product were collected and concentrated to reduce the volume, then extracted twice with DCM to obtain 4-methyl-5-(4-methyl-1,3-oxazol-5-yl)-4H-1,2,4-triazole-3-thiol (p65, 605 mg, y=17%) as yellow solid. MS (m/z): 197.1 [MH]$^+$.

Preparation 66: 4-methyl-5-(oxan-4-yl)-4H-1,2,4-triazole-3-thiol

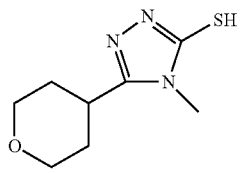

To a solution of oxane-4-carboxylic acid (5 g, 38.42 mmol) in DMF (23 mL), 4-Methyl-3-thiosemicarbazide (4.45 g, 42.26 mmol) was added. DIPEA (11.8 mL, 69.15 mmol) was added dropwise at RT, then the mixture was cooled with an ice bath before adding T3P (50% w/w in EtOAc) (35 mL, 57.63 mmol). The reaction was stirred at RT O/N. NaOH 4M solution was added (resulting pH=8). The reaction was diluted with EtOAc and the two resulting phases were separated (the upper organic layer eliminated). Additional 4M NaOH was added up to pH 11 and the mixture heated to 70° C. for 40 min. The solution was then cooled down to RT, then cooled down to 0° C. and HCl 6N was slowly added till pH-5. The white precipitate was filtered and washed with cHex, then dried at 50° C. overnight to afford 4-methyl-5-(oxan-4-yl)-4H-1,2,4-triazole-3-thiol (3.47 g) as white solid.

The mother liquor was extracted with DCM (2×), the organic layer was dried and evaporated to obtain an oil which was triturated with $Et_2O$ to afford an off-white precipitate which was filtered and dried overnight at 50° C. to afford further 1.8 g of title compound 4-methyl-5-(oxan-4-yl)-4H-1,2,4-triazole-3-thiol (p66, total y=69%) as pale yellow solid. MS (m/z): 200.2 [MH]$^+$.

The following intermediates were prepared in analogy with Preparation 66 starting from the corresponding carboxylic acids either previously described or commercially available.

| Prep num. | Structure | Name | Yield % | MS (m/z) |
|---|---|---|---|---|
| p67 | 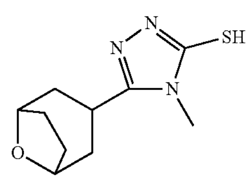 | 4-methyl-5-{8-oxabicyclo[3.2.1]octan-3-yl}-4H-1,2,4-triazole-3-thiol | 93 | 226.2 |
| p68 | 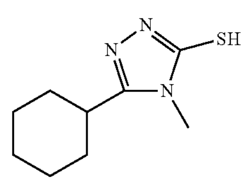 | 5-cyclohexyl-4-methyl-4H-1,2,4-triazole-3-thiol | 70 | 198.0 |
| p69 | 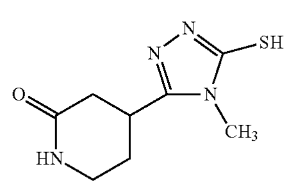 | 4-(4-methyl-5-sulfanyl-4H-1,2,4-triazol-3-yl)piperidin-2-one | 9 | 213.1 |
| p70 | 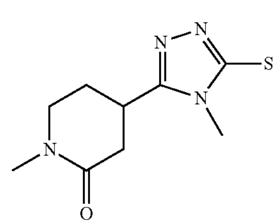 | 1-methyl-4-(4-methyl-5-sulfanyl-4H-1,2,4-triazol-3-yl)piperidin-2-one | 78 | 227.1 |

-continued

| Prep num. | Structure | Name | Yield % | MS (m/z) |
|---|---|---|---|---|
| p71 | 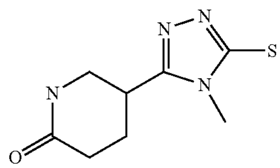 | 5-(4-methyl-5-sulfanyl-4H-1,2,4-triazol-3-yl)piperidin-2-one | 63 | 213.2 |
| p72 | 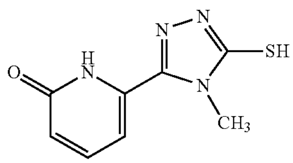 | 6-(4-methyl-5-sulfanyl-4H-1,2,4-triazol-3-yl)-1,2-dihydropyridin-2-one | 24 | 209.2 |
| p73 | 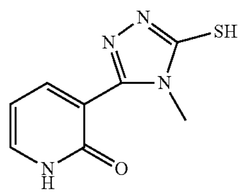 | 3-(4-methyl-5-sulfanyl-4H-1,2,4-triazol-3-yl)-1,2-dihydropyridin-2-one | 33 | 209.1 |
| p74 | 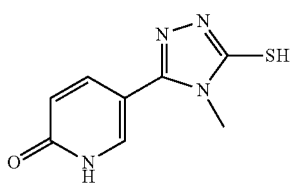 | 5-(4-methyl-5-sulfanyl-4H-1,2,4-triazol-3-yl)-2,3-dihydropyridin-2-one | 60 | 209.1 |
| p75 | 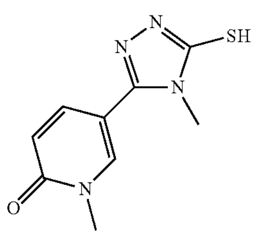 | 1-methyl-5-(4-methyl-5-sulfanyl-4H-1,2,4-triazol-3-yl)-1,2-dihydropyridin-2-one | 65 | 223.1 |
| p76 | 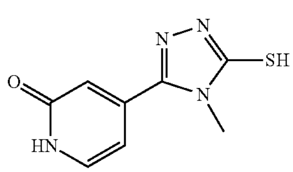 | 4-(4-methyl-5-sulfanyl-4H-1,2,4-triazol-3-yl)-1,2-dihydropyridin-2-one | 45 | 209.1 |
| p77 | 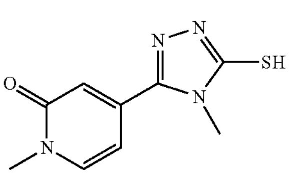 | 1-methyl-4-(4-methyl-5-sulfanyl-4H-1,2,4-triazol-3-yl)-1,2-dihydropyridin-2-one | 51 | 223.1 |
| p78 | 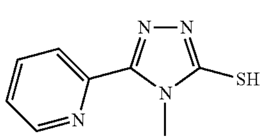 | 4-methyl-5-(pyridin-2-yl)-4H-1,2,4-triazole-3-thiol | 83 | 193.1 |
| p79 | 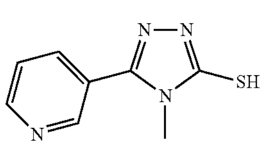 | 4-methyl-5-(pyridin-3-yl)-4H-1,2,4-triazole-3-thiol | 61 | 193.1 |

-continued

| Prep num. | Structure | Name | Yield % | MS (m/z) |
|---|---|---|---|---|
| p80 | 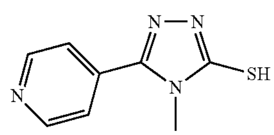 | 4-methyl-5-(pyridin-4-yl)-4H-1,2,4-triazole-3-thiol | 84 | 193.1 |
| p81 | 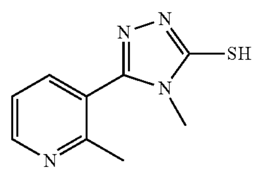 | 4-methyl-5-(2-methylpyridin-3-yl)-4H-1,2,4-triazole-3-thiol | 29 | 207.2 |
| p82 | 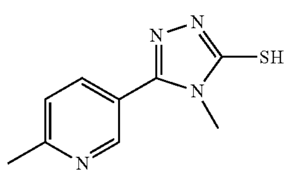 | 4-methyl-5-(6-methylpyridin-3-yl)-4H-1,2,4-triazole-3-thiol | 54 | 207.2 |
| p83 | 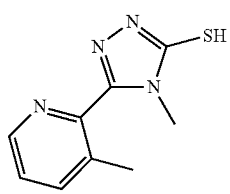 | 4-methyl-5-(3-methylpyridin-2-yl)-4H-1,2,4-triazole-3-thiol | 78 | 207.1 |
| p84 | 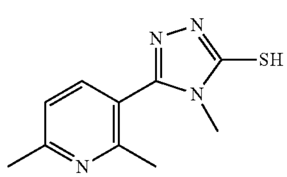 | 5-(2,6-dimethylpyridin-3-yl)-4-methyl-4H-1,2,4-triazole-3-thiol | 49 | 221.2 |
| p85 | 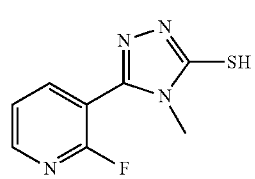 | 5-(2-fluoropyridin-3-yl)-4-methyl-4H-1,2,4-triazole-3-thiol | 56 | 211.1 |
| p86 | 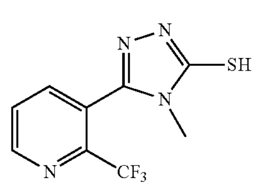 [SMILES: Cn1c(S)nnc1-c1cccnc1C(F)(F)F] | 4-methyl-5-[2-(trifluoromethyl)pyridin-3-yl]-4H-1,2,4-triazole-3-thiol | 35 | 261.1 |
| p87 | 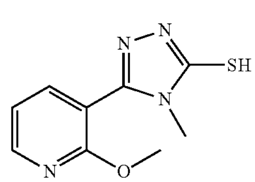 | 5-(2-methoxypyridin-3-yl)-4-methyl-4H-1,2,4-triazole-3-thiol | 77 | 223.2 |

-continued

| Prep num. | Structure | Name | Yield % | MS (m/z) |
|---|---|---|---|---|
| p88 | 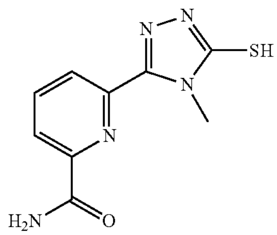 [SMILES: Cn1c(S)nnc1-c1cccc(C(N)=O)n1] | 6-(4-methyl-5-sulfanyl-4H-1,2,4-triazol-3-yl)pyridine-2-carboxamide | 27 | 236.2 |
| p89 | 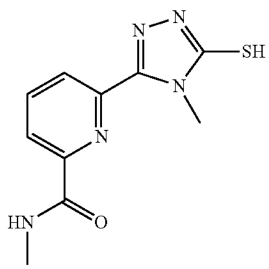 [SMILES: CNC(=O)c1cccc(-c2nnc(S)n2C)n1] | N-methyl-6-(4-methyl-5-sulfanyl-4H-1,2,4-triazol-3-yl)pyridine-2-carboxamide | 40 | 250.1 |
| p90 | 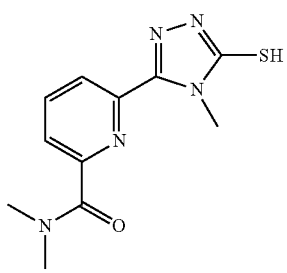 [SMILES: CN(C)C(=O)c1cccc(-c2nnc(S)n2C)n1] | N,N-dimethyl-6-(4-methyl-5-sulfanyl-4H-1,2,4-triazol-3-yl)pyridine-2-carboxamide | 39 | 264.2 |
| p91 | 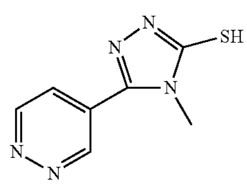 | 4-methyl-5-(pyridazin-4-yl)-4H-1,2,4-triazole-3-thiol | 83 | 194.1 |
| p92 | 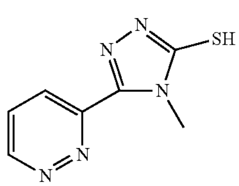 | 4-methyl-5-(pyridazin-3-yl)-4H-1,2,4-triazole-3-thiol | 79 | 194.1 |
| p93 | 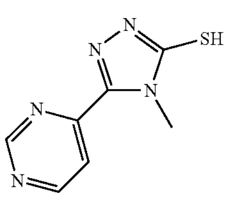 | 4-methyl-5-(pyrimidin-4-yl)-4H-1,2,4-triazole-3-thiol | 93 | 194.1 |
| p94 | 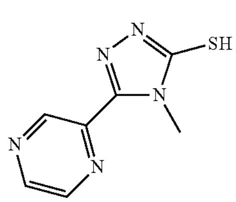 | 4-methyl-5-(pyrazin-2-yl)-4H-1,2,4-triazole-3-thiol | 92 | 194.1 |

-continued

| Prep num. | Name | Yield % | MS (m/z) |
|---|---|---|---|
| p95 | 4-methyl-5-(6-methylpyrazin-2-yl)-4H-1,2,4-triazole-3-thiol | 75 | 208.0 |
| p96 | 4-methyl-5-(5-methylpyrazin-2-yl)-4H-1,2,4-triazole-3-thiol | 72 | 208.0 |
| p97 | 4-methyl-5-(3-methylpyrazin-2-yl)-4H-1,2,4-triazole-3-thiol | 83 | 208.0 |
| p98 | 4-methyl-5-(1,2-oxazol-5-yl)-4H-1,2,4-triazole-3-thiol | 27 | 182.9 |
| p99 | 4-methyl-5-(3-methyl-1,2-oxazol-5-yl)-4H-1,2,4-triazole-3-thiol | 74 | 197.0 |
| p100 | 4-methyl-5-(4-methyl-1,3-thiazol-5-yl)-4H-1,2,4-triazole-3-thiol | 64 | 212.9 |
| p101 | 4-methyl-5-(1,3-thiazol-2-yl)-4H-1,2,4-triazole-3-thiol | 59 | 198.9 |
| p102 | 4-methyl-5-(1-methyl-1H-pyrazol-4-yl)-4H-1,2,4-triazole-3-thiol | 45 | 196.0 |
| p103 | 4-methyl-5-(1-methyl-1H-pyrazol-5-yl)-4H-1,2,4-triazole-3-thiol | 64 | 196.1 |

-continued

| Prep num. | Structure | Name | Yield % | MS (m/z) |
|---|---|---|---|---|
| p104 | 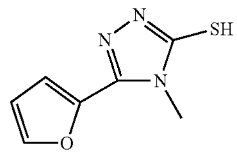 | 5-(furan-2-yl)-4-methyl-4H-1,2,4-triazole-3-thiol | 45 | 181.9 |
| p105 | 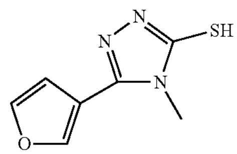 | 5-(furan-3-yl)-4-methyl-4H-1,2,4-triazole-3-thiol | 34 | 181.9 |
| p106 | 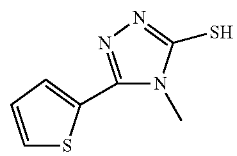 | 4-methyl-5-(thiophen-2-yl)-4H-1,2,4-triazole-3-thiol | 41 | 197.9 |
| p107 | 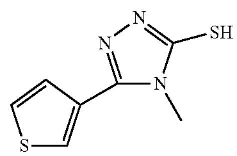 | 4-methyl-5-(thiophen-3-yl)-4H-1,2,4-triazole-3-thiol | 43 | 197.9 |
| p108 | 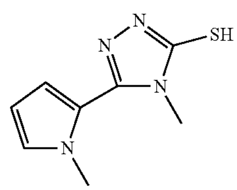 | 4-methyl-5-(1-methyl-1H-pyrrol-2-yl)-4H-1,2,4-triazole-3-thiol | 8 | 195.0 |
| p109 | 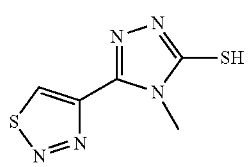 | 4-methyl-5-(1,2,3-thiadiazol-4-yl)-4H-1,2,4-triazole-3-thiol | 55 | 200.1 |
| p110 | 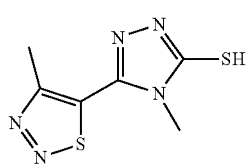 | 4-methyl-5-(4-methyl-1,2,3-thiadiazol-5-yl)-4H-1,2,4-triazole-3-thiol | 89 | 214.1 |
| p111 | 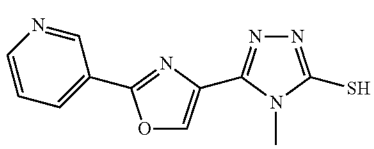 [SMILES: Cn1c(S)nnc1-c1coc(-c2cccnc2)n1] | 4-methyl-5-[2-(pyridin-3-yl)-1,3-oxazol-4-yl]-4H-1,2,4-triazole-3-thiol | 60 | 260.1 |
| p112 | 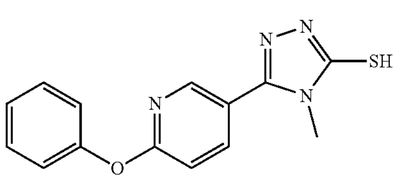 [SMILES: Cn1c(S)nnc1-c1ccc(Oc2ccccc2)nc1] | 4-methyl-5-(6-phenoxypyridin-3-yl)-4H-1,2,4-triazole-3-thiol | 62 | 285.1 |

| Prep num. | Name | Yield % | MS (m/z) |
|---|---|---|---|
| p113 | 4-methyl-5-{[1,2,4]triazolo[4,3-a]pyridin-8-yl}-4H-1,2,4-triazole-3-thiol | 64 | 233.1 |
| p114 | 4-methyl-5-{[1,2,4]triazolo[4,3-a]pyridin-6-yl}-4H-1,2,4-triazole-3-thiol | 83 | 233.1 |
| p115 | 4-methyl-5-{[1,2,4]triazolo[4,3-a]pyridin-7-yl}-4H-1,2,4-triazole-3-thiol | 76 | 232.9 |
| p116 | 4-methyl-5-{3-methyl-[1,2,4]triazolo[4,3-a]pyridin-6-yl}-4H-1,2,4-triazole-3-thiol | 97 | 247.1 |
| p117 | 4-methyl-5-[4-(1H-1,2,3,4-tetrazol-5-yl)phenyl]-4H-1,2,4-triazole-3-thiol | 59 | 260.2 |
| p118 | 4-methyl-5-[4-(1,3,4-oxadiazol-2-yl)phenyl]-4H-1,2,4-triazole-3-thiol | 55 | 260.1 |
| p119 | 4-methyl-5-[4-(5-methyl-1,2,4-oxadiazol-3-yl)phenyl]-4H-1,2,4-triazole-3-thiol | 44 | 274.2 |
| p120 | 4-methyl-5-[4-(4H-1,2,4-triazol-4-yl)phenyl]-4H-1,2,4-triazole-3-thiol | 55 | 259.2 |

-continued

| Prep num. | Structure | Name | Yield % | MS (m/z) |
|---|---|---|---|---|
| p121 | 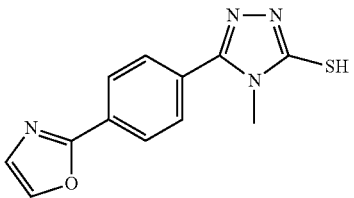 [SMILES: Cn1c(S)nnc1-c1ccc(-c2ncco2)cc1] | 4-methyl-5-[4-(1,3-oxazol-2-yl)phenyl]-4H-1,2,4-triazole-3-thiol | 35 | 258.9 |
| p122 | 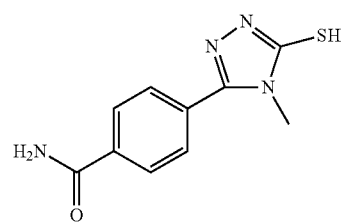 | 4-(4-methyl-5-sulfanyl-4H-1,2,4-triazol-3-yl)benzamide | 77 | 235.1 |
| p123 | 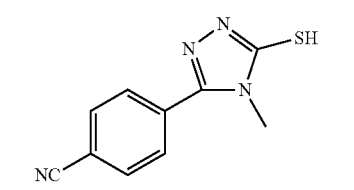 | 4-(4-methyl-5-sulfanyl-4H-1,2,4-triazol-3-yl)benzonitrile | Quant. | 217.1 |
| p124 | 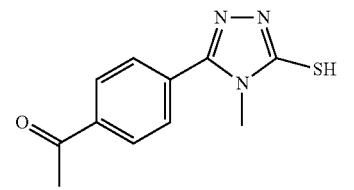 [SMILES: CC(=O)c1ccc(-c2nnc(S)n2C)cc1] | 1-[4-(4-methyl-5-sulfanyl-4H-1,2,4-triazol-3-yl)phenyl]ethan-1-one | 17 | 234.2 |
| p125 | 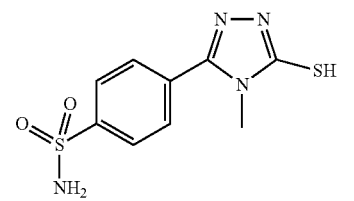 [SMILES: Cn1c(S)nnc1-c1ccc(S(N)(=O)=O)cc1] | 4-(4-methyl-5-sulfanyl-4H-1,2,4-triazol-3-yl)benzene-1-sulfonamide | 37 | 271.1 |
| p126 | 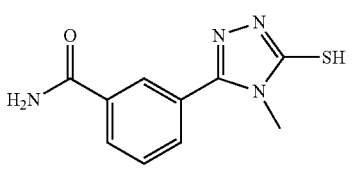 [SMILES: Cn1c(S)nnc1-c1cccc(C(N)=O)c1] | 3-(4-methyl-5-sulfanyl-4H-1,2,4-triazol-3-yl)benzamide | 71 | 235.2 |
| p127 | 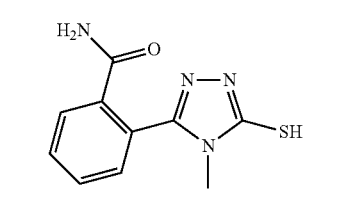 [SMILES: Cn1c(S)nnc1-c1ccccc1C(N)=O] | 2-(4-methyl-5-sulfanyl-4H-1,2,4-triazol-3-yl)benzamide | 21 | 235.1 |

Preparation 128: 5-(4-methyl-5-sulfanyl-4H-1,2,4-triazol-3-yl)pyridine-2-carbonitrile

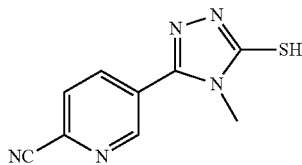

To a stirred solution of 6-cyanopyridine-3-carboxylic acid (230 mg, 1.55 mmol) in DMF (0.9 mL), 4-methyl-3-thiosemicarbazide (180 mg, 1.71 mmol) and DIPEA (0.49 mL, 2.79 mmol) were subsequently added. The mixture was cooled to 0° C. then T3P (50% wt/EA) (1.38 mL, 2.33 mmol) was added portion-wise. The ice-bath was removed and the resulting reaction mixture was stirred O/N at RT. Aqueous 0.5 M NaOH solution was added (resulting pH~8) and the two resulting phases were separated (the upper organic layer was eliminated) then the mixture was heated to 75° C. and stirred for 1.5 h. The solution was cooled to RT and 37% HCl was slowly added until pH~6. The mixture was extracted with DCM, the organic phase was dried by using a phase separator cartridge and concentrated. The residue was treated with water, the mixture was filtered, the white solid was washed with water and dried under vacuum at 45° C. O/N affording 5-(4-methyl-5-sulfanyl-4H-1,2,4-triazol-3-yl)pyridine-2-carbonitrile (p128, 224 mg, y=66%). MS (m/z): 218.1 [MH]$^+$.

Preparation 129: 4-(4-methyl-5-sulfanyl-4H-1,2,4-triazol-3-yl)pyridine-2-carbonitrile

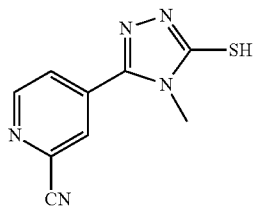

To a stirred solution of 2-cyanopyridine-4-carboxylic acid (1.0 g, 6.75 mmol) in DMF (3.9 mL), 4-methyl-3-thiosemicarbazide (0.78 g, 7.43 mmol) and DIPEA (2.1 mL, 12.15 mmol) were subsequently added. The mixture was cooled to 0° C. then T3P (50% wt/EA) (6.0 mL, 10.13 mmol) was added portion-wise. The ice-bath was removed and the resulting reaction mixture was stirred O/N at RT. Aqueous 0.5 M NaOH solution was added (resulting pH~8) and the two resulting phases were separated (the upper organic layer was eliminated) then the mixture was heated to 75° C. and stirred for 1.5 h. The solution was cooled to RT and 37% HCl was slowly added until pH~5. The mixture was stirred for 5 min then was filtered. The solid was washed with water and dried under vacuum at 45° C. O/N affording a 1:1 mixture of 4-(4-methyl-5-sulfanyl-4H-1,2,4-triazol-3-yl)pyridine-2-carbonitrile and 4-(4-methyl-5-sulfanyl-4H-1,2,4-triazol-3-yl)pyridine-2-carboxamide derivatives (p129, 0.74 g) that was used as crude in the next step. MS (m/z): 218.1 [MH]$^+$.

Preparation 130: 5-(4-methyl-5-sulfanyl-4H-1,2,4-triazol-3-yl)pyridine-2-carboxamide

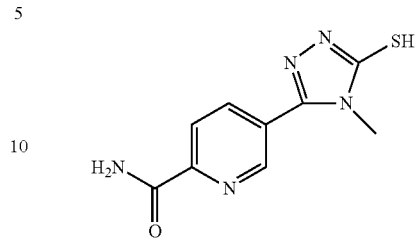

To a solution of 6-cyanopyridine-3-carboxylic acid (0.5 g, 3.35 mmol) in DMF (5 mL), 4-methyl-3-thiosemicarbazide (390 mg, 3.71 mmol) was added; DIPEA (1.1 mL, 6.75 mmol) was added dropwise at RT, then the mixture was cooled in an ice bath before adding T3P (50% w/w in EtOAc) (3 mL, 5.05 mmol). The reaction was stirred at RT O/N NaOH 4M solution was added until the precipitate, formed during the addition, dissolved (resulting pH=8). The reaction was diluted with EtOAc and the two resulting phases were separated (the upper organic layer eliminated). Additional 4M NaOH was added up to pH 11 and the mixture heated to 70° C. for 2.5 hrs. Then pH was increased to 11 by adding NaOH (pellets) and the reaction was stirred at 70° C. for 1 h. The solution was cooled to 0° C., then HCl 6N was slowly added till pH 5. A precipitate formed that was filtered under vacuum to obtain 5-(4-methyl-5-sulfanyl-4H-1,2,4-triazol-3-yl)pyridine-2-carboxamide (p130, 585 mg, y=74%). MS (m/z): 236.1[MH]$^+$.

Preparation 131: 6-(4-methyl-5-sulfanyl-4H-1,2,4-triazol-3-yl)pyridine-3-carbonitrile

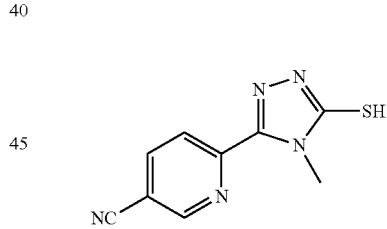

To a stirred solution of 5-cyanopyridine-2-carboxylic acid (1.0 g, 6.75 mmol) in DMF (3.9 mL), 4-methyl-3-thiosemicarbazide (0.78 g, 7.43 mmol) and DIPEA (2.1 mL, 12.15 mmol) were subsequently added. The mixture was cooled to 0° C. then T3P (50% wt/EA) (6.0 mL, 10.13 mmol) was added portion-wise. The ice-bath was removed and the resulting reaction mixture was stirred O/N at RT. Aqueous 0.5 M NaOH solution was added (resulting pH-8) and the two resulting phases were separated (the upper organic layer was eliminated) then the mixture was heated to 70° C. and stirred for 1.5 h. The solution was cooled to RT and 37% HCl was slowly added until pH~6. The mixture was stirred for 5 min then was filtered. The solid was washed with water and dried under vacuum at 45° C. O/N affording 6-(4-methyl-5-sulfanyl-4H-1,2,4-triazol-3-yl)pyridine-3-carbonitrile (p131, 1.47 g y=96%). MS (m/z): 218.1 [MH]$^+$.

Preparation 132: 6-(4-methyl-5-sulfanyl-4H-1,2,4-triazol-3-yl)pyridine-3-carboxamide

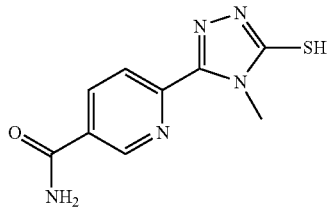 [SMILES: Cn1c(S)nnc1-c1ccc(C(N)=O)cn1]

A mixture of 6-(4-methyl-5-sulfanyl-4H-1,2,4-triazol-3-yl)pyridine-3-carbonitrile (p131, 1.47 g, 6.75 mmol) and crushed KOH (1.14 g, 20.25 mmol) in t-BuOH (90 mL) was heated to 90° C. and stirred for 1.5 h. After allowing the mixture to reach RT it was filtered and the yellow solid washed with t-BuOH then dried under vacuum. The solid was taken up with water, the pH was brought to 4-5 by adding 37% HCl then the mixture was filtered, the solid was washed with water and dried under vacuum at 45° C. O/N affording 6-(4-methyl-5-sulfanyl-4H-1,2,4-triazol-3-yl)pyridine-3-carboxamide (p132, 1.39 g, y=88%). MS (m/z): 236.1 [MH]⁺.

Preparation 133: 4-{5-[(3-chloropropyl)sulfanyl]-4-methyl-4H-1,2,4-triazol-3-yl}pyridine-2-carboxamide

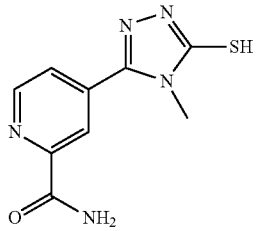 [SMILES: Cn1c(S)nnc1-c1ccnc(C(N)=O)c1]

Step a: Pyridine-2,4-dicarboxylic acid (2.5 g, 14.95 mmol) was dissolved in MeOH (9 mL) and Hydrogen chloride~1.25 M solution in Methanol (6 mL) was added. The suspension was left stirring at 50° C. for 8 hrs. The mixture was concentrated under reduced pressure affording 2-(methoxycarbonyl)pyridine-4-carboxylic acid (2.35 g, crude) as mixture of mainly mono and partly di-ester that was used as such in the next step.

Step b: 2-(methoxycarbonyl)pyridine-4-carboxylic acid (2.35 g from step a) was dissolved in water (5 mL), treated with NH₄OH 28% aqueous solution (15 mL) and the solution was left stirring at RT O/N. Solvent was eliminated under reduced pressure affording 2-carbamoylpyridine-4-carboxylic acid and 4-carbamoylpyridine-2-carboxylic acid (1.27 g) that was used as such in the next step.

Step c: To a stirred solution of 4-carbamoylpyridine-2-carboxylic acid (1.27 g from step b) in DMF (5 mL), 4-methyl-3-thiosemicarbazide (884 mg, 8.4 mmol) and DIPEA (2.4 mL, 13.7 mmol) were subsequently added. The mixture was cooled to 0° C. then T3P (50% wt/EA) (6.82 mL, 11.39 mmol) was added dropwise. The ice-bath was removed and the resulting reaction mixture was stirred at RT O/N.

Aqueous 3M NaOH solution was added (resulting pH 8) followed by AcOEt and the two resulting phases were separated (the upper organic layer was eliminated). Additional 3M NaOH was added up to pH 11 then the mixture was heated to 70° C. and stirred for 40 min. The solution was cooled to RT and 6N HCl was slowly added until pH 5. The precipitate formed was collected by filtration and washed with water and Cy, then dried under high vacuum affording 4-{5-[(3-chloropropyl)sulfanyl]-4-methyl-4H-1,2,4-triazol-3-yl}pyridine-2-carboxamide (p133, 745 mg, y=21%). MS (m/z): 236.1 [MH]⁺.

Preparation 134: 2-(methoxycarbonyl)-3-methylpyridin-N oxide

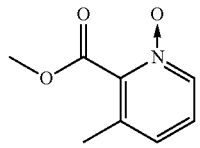

To a solution of ethyl 2-methyl-3-pyridinecarboxylate (1.86 mL, 12.1 mmol) in DCM (50 mL) mCPBA was added (4.18 g, 24.2 mmol) at RT. The solution was stirred at RT for 24 hrs. The solution was filtered and concentrated. The residue was purified by FC on silica (eluent: DCM to 15% MeOH) to a solid still containing mCBA that was dissolved with DCM and washed with NaHCO₃, the organic phase was dried and evaporated to afford 2-(methoxycarbonyl)-3-methylpyridin-N oxide (p134, 1.9 g, y=85%). MS (m/z): 168.1 [M]⁺.

Preparation 135: methyl 6-cyano-3-methylpyridine-2-carboxylate

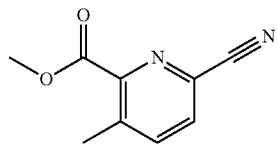

To a solution of 2-(methoxycarbonyl)-3-methylpyridin-N oxide (p134, 1.9 g, 11.29 mmol) in DCM (80 mL) TMSCN was added (2.1 mL, 16.93 mmol) followed, after 5 min, by dimethylcarbamyl chloride (1.56 mL, 16.93 mmol). The solution was stirred at RT for 48 hrs. Then 10% K₂CO₃ was slowly added to make the reaction mixture basic. Organic layer was separated, dried and evaporated to provide the crude, which was purified by FC on silica cartridge (eluent: Cy to 20% EtOAc) to afford methyl 6-cyano-3-methylpyridine-2-carboxylate (p135, 370 mg, y=19%). MS (m/z): 177.1 [MH]⁺.

Preparation 136: 6-cyano-2-methylpyridine-3-carboxylic acid

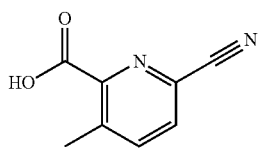

A solution of methyl 6-cyano-3-methylpyridine-2-carboxylate (p135, 0.37 g, 2.1 mmol) in THF (6 mL) and water (2 mL) at RT was treated with LiOH.H₂O (0.097 g, 2.3 mmol), stirred for 1 h, and concentrated. The concentrate was dissolved in water (5 mL) and adjusted to pH 2 with 1N HCl to provide a precipitate. The precipitate was filtered and washed with cold water, then dried to obtain 6-cyano-2-methylpyridine-3-carboxylic acid (p136, 320 mg, y=94%). MS (m/z): 163.0 [MH]⁺.

Preparation 137: 5-methyl-6-(4-methyl-5-sulfanyl-4H-1,2,4-triazol-3-yl)pyridine-2-carbonitrile

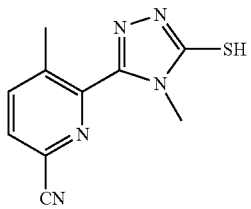 [SMILES: Cc1ccc(C#N)nc1-c1nnc(S)n1C]

To a solution of 6-cyano-2-methylpyridine-3-carboxylic acid (p136, 320 mg, 1.97 mmol) in DMF (2 mL), 4-methyl-3-thiosemicarbazide (228 mg, 2.117 mmol) was added; DIPEA (0.605 mL, 3.54 mmol) was added dropwise at RT, then the mixture was cooled in an ice bath before adding T3P (50% w/w in EtOAc) (1.76 mL, 2.96 mmol). The reaction was stirred at RT O/N. NaOH 4M solution was added until pH=8. The reaction was diluted with EtOAc and the two resulting phases were separated (the upper organic layer eliminated). Additional 4M NaOH solution was added up to pH 9 and the mixture heated to 70° C. for 5 hrs. The solution was then cooled to 0° C. and HCl 6N was slowly added till pH 5. A precipitate formed that was filtered. The mother liquor was extracted several times with DCM, the organic phase was dried and evaporated to afford an oil. After addition of water (~2 mL) a precipitate was obtained. It was filtered and combined with the former precipitate to obtain 5-methyl-6-(4-methyl-5-sulfanyl-4H-1,2,4-triazol-3-yl)pyridine-2-carbonitrile (p137, 160 mg, y=35%). MS (m/z): 232.1 [MH]⁺.

Preparation 138: 1-methyl-4-(4-methyl-5-sulfanyl-4H-1,2,4-triazol-3-yl)-1,2-dihydropyridin-2-one

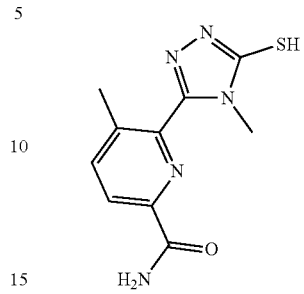

A mixture of 5-methyl-6-(4-methyl-5-sulfanyl-4H-1,2,4-triazol-3-yl)pyridine-2-carbonitrile (p137, 0.16 g, 0.69 mmol) and crushed KOH (0.116 mg, 2.06 mmol) in t-BuOH (5 mL) was heated to 85° C. and stirred for 1 h. After allowing the mixture to reach RT solvent was decanted. The yellow solid was taken up with water, the pH was brought to 4-5 by adding 6 N HCl, and a precipitate was obtained. Then it was filtered, the solid was dried affording 5-methyl-6-(4-methyl-5-sulfanyl-4H-1,2,4-triazol-3-yl)pyridine-2-carboxamide (p138, 120 mg, y=70%). MS (m/z): 250.2 [MH]⁺.

Preparation 139: 2,5-dimethyl pyrazine-2,5-dicarboxylate

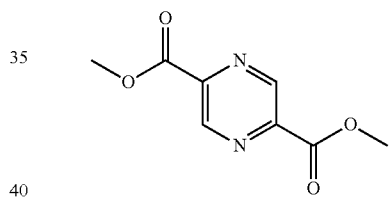

Pyrazine-2,5-dicarboxylic acid (900 mg, 5.35 mmol) was dissolved in MeOH (9 mL) and Hydrogen chloride~1.25M solution in Methanol (9 mL) was added. Then the mixture was heated to 50° C. and stirred at that temperature for 8 hrs. Then it was left stirring at RT overnight. The day after 2 mL more of HCl~1.25 M in MeOH was added and the mixture heated to 50° C. and stirred at that temperature for further 1 h. The mixture was cooled down to RT and concentrated under reduced pressure affording 2,5-dimethyl pyrazine-2,5-dicarboxylate (p139, 949 mg, y=90%). MS (m/z): 197.1 [MH]⁺.

Preparation 140: 5-(4-methyl-5-sulfanyl-4H-1,2,4-triazol-3-yl)pyrazine-2-carboxamide

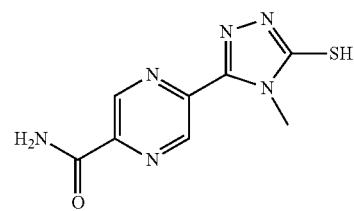 [SMILES: Cn1c(S)nnc1-c1cnc(C(N)=O)cn1]

Step a: 2,5-dimethyl pyrazine-2,5-dicarboxylate (p139, 949 mg, 4.84 mmol) was dissolved in methanol (10 mL) and 1M NaOH (4.84 mL, 4.84 mmol) was slowly added. The resulting suspension was stirred for 1 h at RT, then organic solvent was evaporated and the aqueous residue was acidified to pH 2 and concentrated affording 5-(methoxycarbonyl)pyrazine-2-carboxylic acid (1.23 g) that was used as such in the next step.

Step b: 5-(methoxycarbonyl)pyrazine-2-carboxylic acid (1.23 g from step a) was dissolved in water (5 mL) then NH$_4$OH 28% aqueous solution (10 mL) was added and the solution was left stirring at RT O/N. Solvent was removed under reduced pressure affording 5-carbamoylpyrazine-2-carboxylic acid (845 mg) that was used as such in the next step.

Step c: To a stirred solution of 5-carbamoylpyrazine-2-carboxylic acid (845 mg form step b) in DMF (3 mL), 4-methyl-3-thiosemicarbazide (585 mg, 5.56 mmol) and DIPEA (1.59 mL, 9.1 mmol) were subsequently added. The mixture was cooled to 0° C. then T3P (50% wt/EA) (4.52 mL, 7.55 mmol) was added dropwise. The ice-bath was removed and the resulting reaction mixture was stirred at RT O/N.

Aqueous 3M NaOH solution was added (resulting pH~8) followed by AcOEt and the two resulting phases were separated (the upper organic layer was eliminated). Additional 3M NaOH was added up to pH 11 then the mixture was heated to 70° C. and stirred for 40 min. The solution was cooled to RT and 6N HCl was slowly added until pH 5. The product was collected by filtration washing with water and Cy. Solid was dried under high vacuum affording 5-(4-methyl-5-sulfanyl-4H-1,2,4-triazol-3-yl)pyrazine-2-carboxamide (p140, 218 mg, y=19%). NMR: $^1$H NMR (DMSO-d$_6$) δ: 9.18-9.26 (m, 2H), 8.35-8.44 (m, 1H), 7.92-8.05 (m, 1H), 3.83 (s, 3H)

Preparation 141: 1,5-di-tert-butyl 1H-imidazo[4,5-b]pyridine-1,5-dicarboxylate

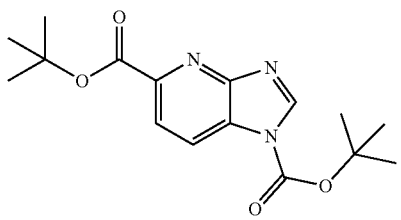 [SMILES: CC(C)(C)OC(=O)c1ccc2c(ncn2C(=O)OC(C)(C)C)n1]

To a stirred solution of 3H-imidazo[4,5-b]pyridine-5-carboxylic acid (1.0 g, 6.13 mmol), TEA (2.4 mL, 15.33 mmol) and DMAP (0.15 g, 1.23 mmol) in DMF (10 mL), Boc$_2$O (2.94 g, 13.49 mmol) was added portion-wise and the resulting reaction mixture was stirred O/N at RT. The mixture was diluted with DCM, washed with saturated ammonium chloride solution, water, dried over sodium sulfate and the solvent removed under reduced pressure. The crude product was purified by FC on silica cartridge (eluting with Cy/EA from 100/0 to 90/10) to give 1,5-di-tert-butyl 1H-imidazo[4,5-b]pyridine-1,5-dicarboxylate (p141, 1.37 g, y=85%) as white foam. MS (m/z): 320.2 [MH]$^+$.

Preparation 142: 1-benzyl 5-tert-butyl 1H-imidazo[4,5-b]pyridine-1,5-dicarboxylate

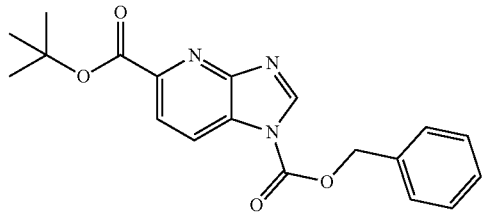 [SMILES: CC(C)(C)OC(=O)c1ccc2c(ncn2C(=O)OCc2ccccc2)n1]

Step a: A stirred solution of 1-[(tert-butoxy)carbonyl]-1H-imidazo[4,5-b]pyridine-5-carboxylic acid (p141, 1.37 g, 5.20 mmol) in MeOH (15 mL) at 0° C. was treated with Cs$_2$CO$_3$ (0.17 g, 0.52 mmol) and stirred at this temperature for 2 hrs. The reaction mixture was concentrated under reduced pressure and the residue was taken up with DCM and saturated NH$_4$Cl solution. The organic phase was dried over sodium sulfate and the solvent removed under vacuum affording 0.89 g of tert-butyl 1H-imidazo[4,5-b]pyridine-5-carboxylate that was used as such.

Step b: To a stirred solution of tert-butyl 1H-imidazo[4,5-b]pyridine-5-carboxylate (0.89 g from step a) and TEA (0.74 mL, 5.28 mmol) in DCM (10 mL), at 0° C. and under a nitrogen atmosphere, CbzCl (0.61 mL, 4.26 mmol) was added drop-wise. The ice-bath was removed and the reaction mixture was stirred O/N at RT. The mixture was diluted with DCM, washed with saturated ammonium chloride solution, water, dried over sodium sulfate and the solvent removed under vacuum. The crude material was purified by FC on silica cartridge (eluting with Cy/EA from 100/0 to 35/65) affording 1-benzyl 5-tert-butyl 1H-imidazo[4,5-b]pyridine-1,5-dicarboxylate (p142, 0.42 g, y=23%) as white foam. MS (m/z): 354.3 [MH]$^+$.

Preparation 143: 5-{1H-imidazo[4,5-b]pyridin-5-yl}-4-methyl-4H-1,2,4-triazole-3-thiol

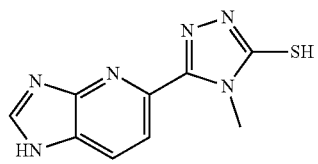 [SMILES: Cn1c(S)nnc1-c1ccc2[nH]cnc2n1]

Step a: To a stirred solution of 1-benzyl 5-tert-butyl 1H-imidazo[4,5-b]pyridine-1,5-dicarboxylate (p142, 0.42 g, 1.19 mmol) in DCM (5 mL), at RT, TFA (1.8 mL) was added and the resulting reaction mixture was stirred at RT for 4 hrs. The mixture was concentrated under reduced pressure and the residue was taken up with DCM. The solution was passed through a phase separator cartridge and the solution was concentrated under vacuum to give 1-[(benzyloxy)carbonyl]-1H-imidazo[4,5-b]pyridine-5-carboxylic acid (225 mg) as crude product that was used as such in the next step.

Step b: To a stirred solution of 1-[(benzyloxy)carbonyl]-1H-imidazo[4,5-b]pyridine-5-carboxylic acid (225 mg, from step a) in DMF (0.8 mL), 4-methyl-3-thiosemicarbazide (88 mg, 0.83 mmol) and DIPEA (0.24 mL, 1.37 mmol) were subsequently added. The mixture was cooled to 0° C.

then T3P (50% wt/EA) (0.68 mL, 1.14 mmol) was added portion-wise. The ice-bath was removed and the resulting reaction mixture was stirred O/N at RT. Aqueous 4M NaOH solution was added (resulting pH~8) and the two resulting phases were separated (the upper organic layer was eliminated). Further 4M NaOH was added up to pH~11 then the mixture was heated to 70° C. and stirred for 1.5 h. The solution was cooled to RT and 37% HCl was slowly added until pH~5. The mixture was stirred for 5 min then was filtered. The solid was washed with water and dried under vacuum at 45° C. O/N affording 5-{1H-imidazo[4,5-b]pyridin-5-yl}-4-methyl-4H-1,2,4-triazole-3-thiol (p143, 125 mg, y=45%) as pale yellow solid. MS (m/z): 233.2 [MH]$^+$.

Preparation 144: 2-[4-(4-methyl-5-sulfanyl-4H-1,2,4-triazol-3-yl)phenyl]acetonitrile

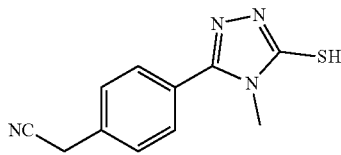 [SMILES: Cn1c(S)nnc1-c1ccc(CC#N)cc1]

To a stirred solution of 4-(cyanomethyl) benzoic acid (1 g, 6.2 mmol) in DMF (4 mL), 4-methyl-3-thiosemicarbazide (0.72 g, 6.82 mmol) and DIPEA (1.95 mL, 11.16 mmol) were subsequently added. The mixture was cooled to 0° C. then T3P (50% wt/EA) (5.36 mL, 9.3 mmol) was added portion-wise. The ice-bath was removed and the resulting reaction mixture was stirred O/N at RT. Aqueous 4M NaOH solution was added (resulting pH~8). The reaction was diluted with EtOAc and the two resulting phases were separated (the upper organic layer was eliminated). Additional 4M NaOH was added up to pH~9 then the mixture was heated to 70° C. and stirred for 6 hrs. Further 4M NaOH was added up to pH~9. The solution was heated to 70° C. for 4 hrs, then it was cooled to RT and 6N HCl was slowly added until pH 4 and a precipitate was obtained. The precipitate was filtered and dried to afford 2-[4-(4-methyl-5-sulfanyl-4H-1,2,4-triazol-3-yl)phenyl]acetonitrile (p144, 900 mg, y=63%). MS (m/z): 231.2 [MH]$^+$.

Preparation 145: 2-[4-(4-methyl-5-sulfanyl-4H-1,2,4-triazol-3-yl)phenyl]acetamide

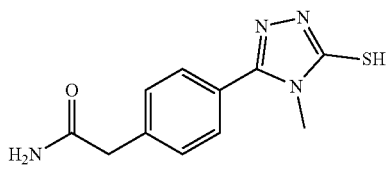 [SMILES: Cn1c(S)nnc1-c1ccc(CC(N)=O)cc1]

A mixture of 2-[4-(4-methyl-5-sulfanyl-4H-1,2,4-triazol-3-yl)phenyl]acetonitrile (p144, 0.75 g, 3.25 mmol) and crushed KOH (0.55 mg, 9.75 mmol) in t-BuOH (10 mL) was heated to 90° C. and stirred for 3 hrs. After allowing the mixture to reach RT solvent was decanted. The yellow solid was taken up with water, the pH was brought to 4-5 by adding 6 N HCl, and a precipitate was obtained. It was filtered and dried affording 2-[4-(4-methyl-5-sulfanyl-4H-1,2,4-triazol-3-yl)phenyl]acetamide (p145, 420 mg, y=80%). MS (m/z): 249.1 [MH]$^+$.

Preparation 146: 3-[(2-chloroethyl)sulfanyl]-4-methyl-5-(4-methyl-1,3-oxazol-5-yl)-4H-1,2,4-triazole

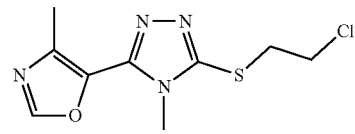 [SMILES: Cc1ncoc1-c1nnc(SCCCl)n1C]

To a suspension of 4-methyl-5-(4-methyl-1,3-oxazol-5-yl)-4H-1,2,4-triazole-3-thiol (p65, 300 mg, 1.53 mmol) in a mixture MeOH/Acetone (0.75 mL/1.6 mL) at RT, 1-Bromo-2-chloroethane (165 µL, 1.99 mmol) was added followed by K$_2$CO$_3$ (296 mg, 2.14 mmol) and the mixture was stirred at RT for 4 hrs. The mixture was then partitioned between water and EtOAc and phases were separated. Organic one was washed with brine then dried and concentrated under reduced pressure. Crude material was purified by FC on silica gel (eluting from cHex to EtOAc) affording 3-[(2-chloroethyl)sulfanyl]-4-methyl-5-(4-methyl-1,3-oxazol-5-yl)-4H-1,2,4-triazole (p146, 237 mg, y=60%). MS (m/z): 259.1 [MH]$^+$.

Preparation 147: (4-chlorobutyl)sulfanyl]-4-methyl-5-(4-methyl-1,3-oxazol-5-yl)-4H-1,2,4-triazole

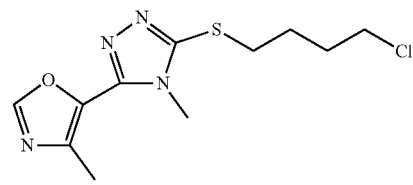 [SMILES: Cc1ncoc1-c1nnc(SCCCCCl)n1C]

To a suspension of 4-methyl-5-(4-methyl-1,3-oxazol-5-yl)-4H-1,2,4-triazole-3-thiol (p65, 300 mg, 1.53 mmol) in a mixture MeOH/Acetone (0.75 mL/1.6 mL) at RT, 1-Bromo-4-chlorobutane (230 µL, 1.99 mmol) was added followed by K$_2$CO$_3$ (296 mg, 2.14 mmol) and the mixture was stirred at RT 4 hrs. Then it was partitioned between water and EtOAc and phases were separated. Organic one was washed with brine then dried and concentrated under reduced pressure. Crude material was purified by FC on silica gel (eluting from cHex to EtOAc) affording (4-chlorobutyl)sulfanyl]-4-methyl-5-(4-methyl-1,3-oxazol-5-yl)-4H-1,2,4-triazole (p147, 270 mg, y=61%). MS (m/z): 287.1 [MH].

Preparation 148: 3-[(3-chloropropyl)sulfanyl]-4-methyl-5-(4-methyl-1,3-oxazol-5-yl)-4H-1,2,4-triazole

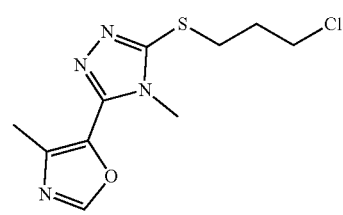 [SMILES: Cc1ncoc1-c1nnc(SCCCCl)n1C]

To a suspension of 4-methyl-5-(4-methyl-1,3-oxazol-5-yl)-4H-1,2,4-triazole-3-thiol (p65, 400 mg, 2.03 mmol) in a mixture MeOH/Acetone (1.3 mL/3.2 mL) at RT, 1-Bromo-3-chloropropane (260 μL, 2.64 mmol) was added, followed by K$_2$CO$_3$ (392 mg, 2.84 mmol) and the mixture was stirred at RT for 4.5 hrs. It was partitioned between water and EtOAc and phases were separated. Organic one was washed with brine then dried and concentrated under reduced pressure. Crude material was purified by FC on silica gel (eluting from cHex to EtOAc) affording 3-[(3-chloropropyl)sulfanyl]-4-methyl-5-(4-methyl-1,3-oxazol-5-yl)-4H-1,2,4-triazole (p148, 400 mg, y=65%), as pale yellow solid. MS (m/z): 273.1 [MH]$^+$.

The following intermediates were prepared in analogy with Preparation 148 reacting the corresponding thiotriazoles, either previously described or commercially available, with 1-Bromo-3-chloropropane.

| Prep. Numb | Structure | Name | Yield % | MS (m/z) |
|---|---|---|---|---|
| p149 | 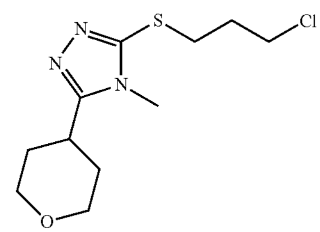 [SMILES: Cn1c(SCCCCl)nnc1C1CCOCC1] | 3-[(3-chloropropyl)sulfanyl]-4-methyl-5-(oxan-4-yl)-4H-1,2,4-triazole | 63 | 276.1 |
| p150 | 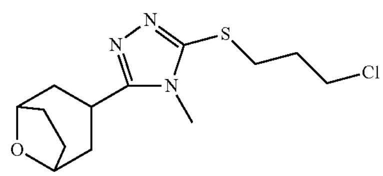 [SMILES: Cn1c(SCCCCl)nnc1C1CC2CCC(C1)O2] | 3-[(3-chloropropyl)sulfanyl]-4-methyl-5-{8-oxabicyclo[3.2.1]octan-3-yl}-4H-1,2,4-triazole | 72 | 302.2 |
| p151 | 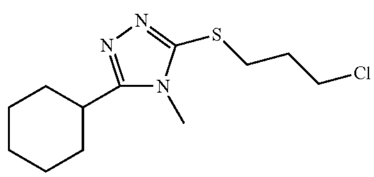 [SMILES: Cn1c(SCCCCl)nnc1C1CCCCC1] | 3-[(3-chloropropyl)sulfanyl]-5-cyclohexyl-4-methyl-4H-1,2,4-triazole | 88 | 274.0 |
| p152 | 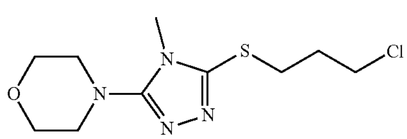 [SMILES: Cn1c(SCCCCl)nnc1N1CCOCC1] | 4-{5-[(3-chloropropyl)sulfanyl]-4-methyl-4H-1,2,4-trizol-3-yl}morpholine | 79 | 277.2 |
| p153 | 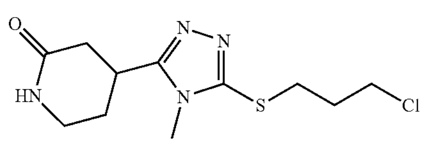 [SMILES: Cn1c(SCCCCl)nnc1C1CCNC(=O)C1] | 4-{5-[(3-chloropropyl)sulfanyl]-4-methyl-4H-1,2,4-triazol-3-yl}piperidin-2-one | 62 | 289.2 |
| p154 | 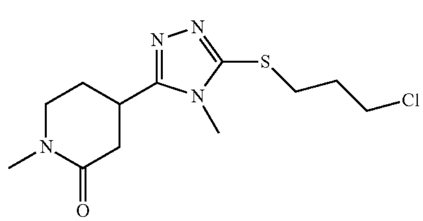 [SMILES: CN1CCC(c2nnc(SCCCCl)n2C)CC1=O] | 4-{5-[(3-chloropropyl)sulfanyl]-4-methyl-4H-1,2,4-triazol-3-yl}-1-methylpiperidin-2-one | 93 | 303.2 |
| p155 | 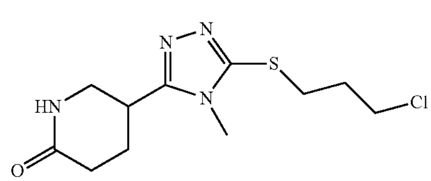 [SMILES: Cn1c(SCCCCl)nnc1C1CCC(=O)NC1] | 5-{5-[(3-chloropropyl)sulfanyl]-4-methyl-4H-1,2,4-triazol-3-yl}piperidin-2-one | 74 | 289.2 |

-continued

| Prep. Numb | Structure | Name | Yield % | MS (m/z) |
|---|---|---|---|---|
| p156 | 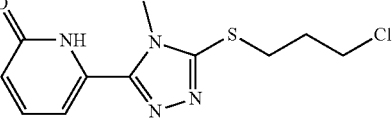 | 6-{5-[(3-chloropropyl)sulfanyl]-4-methyl-4H-1,2,4-triazol-3-yl}-1,2-dihydropyridin-2-one | 80 | 285.2 |
| p157 | 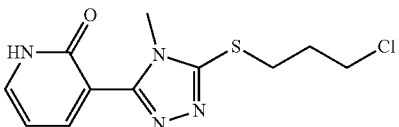 | 3-{5-[(3-chloropropyl)sulfanyl]-4-methyl-4H-1,2,4-triazol-3-yl}-1,2-dihydropyridin-2-one | 18 | 285.2 |
| p158 | 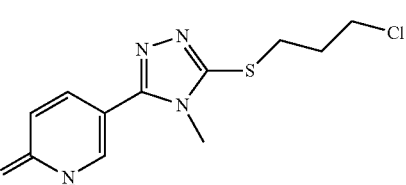 | 5-{5-[(3-chloropropyl)sulfanyl]-4-methyl-4H-1,2,4-triazol-3-yl}-1,2-dihydropyridin-2-one | 39 | 285.2 |
| p159 | 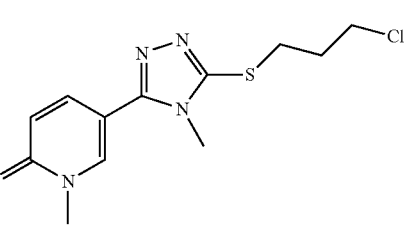 | 5-{5-[(3-chloropropyl)sulfanyl]-4-methyl-4H-1,2,4-triazol-3-yl}-1-methyl-1,2-dihydropyridin-2-one | 80 | 299.2 |
| p160 | 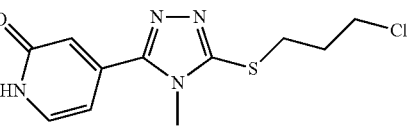 | 4-{5-[(3-chloropropyl)sulfanyl]-4-methyl-4H-1,2,4-triazol-3-yl}-1,2-dihydropyridin-2-one | 36 | 285.2 |
| p161 | 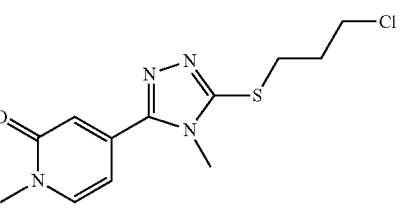 | 4-{5-[(3-chloropropyl)sulfanyl]-4-methyl-4H-1,2,4-triazol-3-yl}-1-methyl-1,2-dihydropyridin-2-one | 80 | 299.2 |
| p162 | 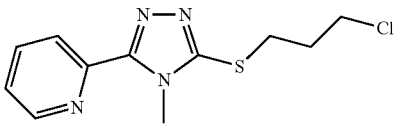 [SMILES: Cn1c(SCCCCl)nnc1-c1ccccn1] | 2-{5-[(3-chloropropyl)sulfanyl]-4-methyl-4H-1,2,4-triazol-3-yl}pyridine | 80 | 269.2 |
| p163 | 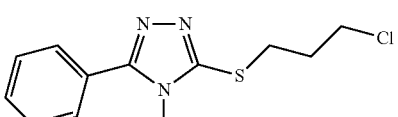 | 3-{5-[(3-chloropropyl)sulfanyl]-4-methyl-4H-1,2,4-triazol-3-yl}pyridine | 88 | 269.2 |
| p164 | 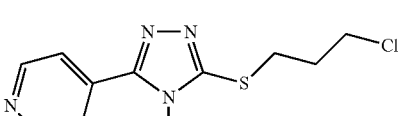 | 4-{5-[(3-chloropropyl)sulfanyl]-4-methyl-4H-1,2,4-triazol-3-yl}pyridine | 83 | 269.2 |

-continued

| Prep. Numb | Structure | Name | Yield % | MS (m/z) |
|---|---|---|---|---|
| p165 | 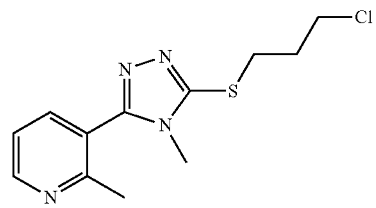 [SMILES: Cc1ncccc1-c1nnc(SCCCCl)n1C] | 3-{5-[(3-chloropropyl)sulfanyl]-4-methyl-4H-1,2,4-triazol-3-yl}-2-methylpyridine | 63 | 283.2 |
| p166 | 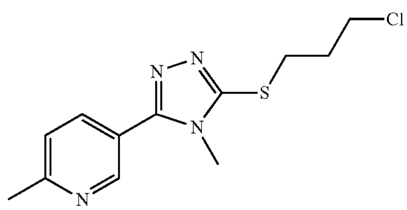 [SMILES: Cc1ccc(-c2nnc(SCCCCl)n2C)cn1] | 5-{5-[(3-chloropropyl)sulfanyl]-4-methyl-4H-1,2,4-triazol-3-yl}-2-methylpyridine | 67 | 283.2 |
| p167 | 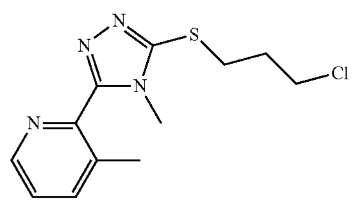 [SMILES: Cc1cccnc1-c1nnc(SCCCCl)n1C] | 2-{5-[(3-chloropropyl)sulfanyl]-4-methyl-4H-1,2,4-triazol-3-yl}-3-methylpyridine | 84 | 282.9 |
| p168 | 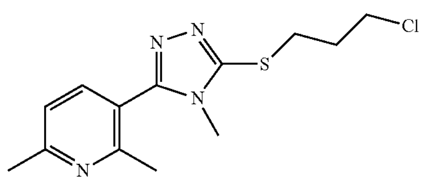 [SMILES: Cc1ccc(-c2nnc(SCCCCl)n2C)c(C)n1] | 3-{5-[(3-chloropropyl)sulfanyl]-4-methyl-4H-1,2,4-triazol-3-yl}-2,6-dimethylpyridine | 50 | 297.2 |
| p169 | 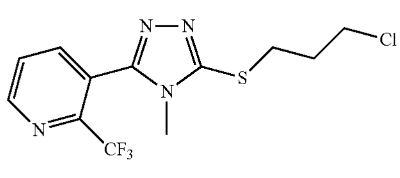 [SMILES: Cn1c(SCCCCl)nnc1-c1cccnc1C(F)(F)F] | 3-{5-[(3-chloropropyl)sulfanyl]-4-methyl-4H-1,2,4-triazol-3-yl}-2-(trifluoromethyl)pyridine | 83 | 337.2 |
| p170 | 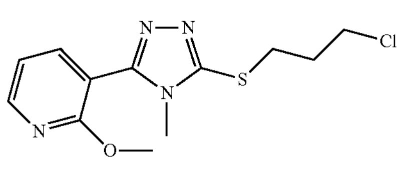 [SMILES: COc1ncccc1-c1nnc(SCCCCl)n1C] | 3-{5-[(3-chloropropyl)sulfanyl]-4-methyl-4H-1,2,4-triazol-3-yl}-2-methoxypyridine | 99 | 299.2 |
| p171 | 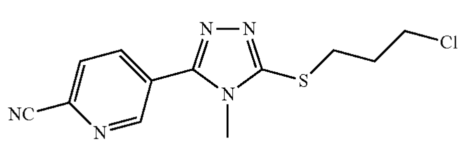 [SMILES: Cn1c(SCCCCl)nnc1-c1ccc(C#N)nc1] | 5-{5-[(3-chloropropyl)sulfanyl]-4-methyl-4H-1,2,4-triazol-3-yl}pyridine-2-carbonitrile | 30 | 294.2 |
| p172 | 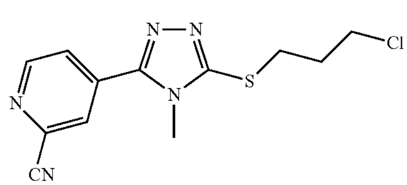 [SMILES: Cn1c(SCCCCl)nnc1-c1ccnc(C#N)c1] | 4-{5-[(3-chloropropyl)sulfanyl]-4-methyl-4H-1,2,4-triazol-3-yl}pyridine-2-carbonitrile | 20 | 294.1 |

| Prep. Numb | Structure | Name | Yield % | MS (m/z) |
|---|---|---|---|---|
| p173 | 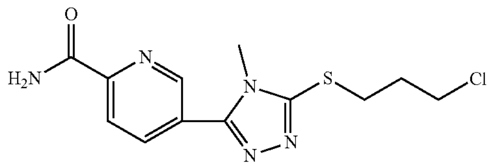 [SMILES: Cn1c(SCCCCl)nnc1-c1ccc(C(N)=O)nc1] | 5-{5-[(3-chloropropyl)sulfanyl]-4-methyl-4H-1,2,4-triazol-3-yl}pyridine-2-carboxamide | 31 | 312.2 |
| p174 | 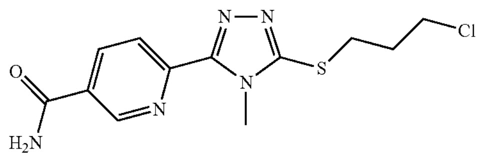 [SMILES: Cn1c(SCCCCl)nnc1-c1ccc(C(N)=O)cn1] | 6-{5-[(3-chloropropyl)sulfanyl]-4-methyl-4H-1,2,4-triazol-3-yl}pyridine-3-carboxamide | 79 | 312.1 |
| p175 | 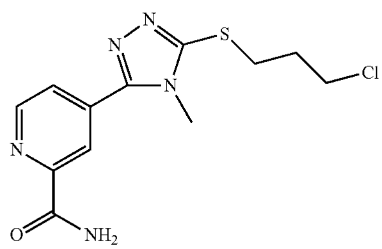 [SMILES: Cn1c(SCCCCl)nnc1-c1ccnc(C(N)=O)c1] | 4-{5-[(3-chloropropyl)sulfanyl]-4-methyl-4H-1,2,4-triazol-3-yl}pyridine-2-carboxamide | 33 | 312.1 |
| p176 | 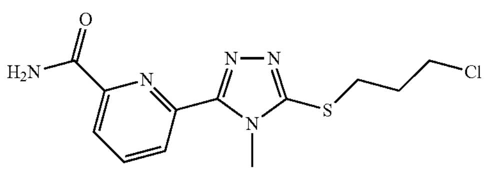 [SMILES: Cn1c(SCCCCl)nnc1-c1cccc(C(N)=O)n1] | 6-{5-[(3-chloropropyl)sulfanyl]-4-methyl-4H-1,2,4-triazol-3-yl}pyridine-2-carboxamide | 41 | 312.1 |
| p177 | 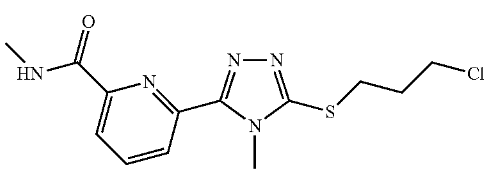 [SMILES: CNC(=O)c1cccc(-c2nnc(SCCCCl)n2C)n1] | 6-{5-[(3-chloropropyl)sulfanyl]-4-methyl-4H-1,2,4-triazol-3-yl}-N-methylpyridine-2-carboxamide | 99 | 326.2 |
| p178 | 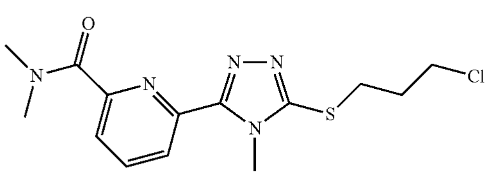 [SMILES: CN(C)C(=O)c1cccc(-c2nnc(SCCCCl)n2C)n1] | 6-{5-[(3-chloropropyl)sulfanyl]-4-methyl-4H-1,2,4-triazol-3-yl}-N,N-dimethylpyridine-2-carboxamide | 52 | 340.2 |
| p179 | 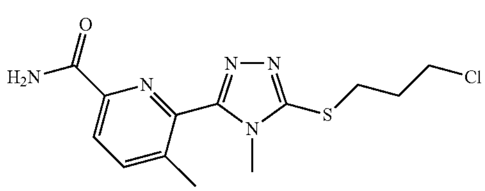 [SMILES: Cc1ccc(C(N)=O)nc1-c1nnc(SCCCCl)n1C] | 6-{5-[(3-chloropropyl)sulfanyl]-4-methyl-4H-1,2,4-triazol-3-yl}-5-methylpyridine-2-carboxamide | 84 | 326.2 |
| p180 | 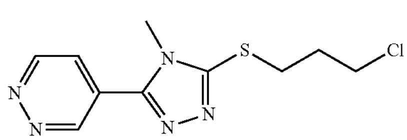 [SMILES: Cn1c(SCCCCl)nnc1-c1ccnnc1] | 4-{5-[(3-chloropropyl)sulfanyl]-4-methyl-4H-1,2,4-triazol-3-yl}pyridazine | 72 | 270.2 |
| p181 | 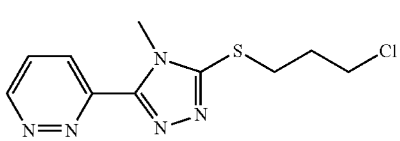 [SMILES: Cn1c(SCCCCl)nnc1-c1cccnn1] | 3-{5-[(3-chloropropyl)sulfanyl]-4-methyl-4H-1,2,4-triazol-3-yl}pyridazine | 76 | 270.2 |

| Prep. Numb | Name | Yield % | MS (m/z) |
|---|---|---|---|
| p182 | 4-{5-[(3-chloropropyl)sulfanyl]-4-methyl-4H-1,2,4-triazol-3-yl}pyrimidine | 71 | 269.9 |
| p183 | 2-{5-[(3-chloropropyl)sulfanyl]-4-methyl-4H-1,2,4-triazol-3-yl}pyrazine | 84 | 270.1 |
| p184 | 2-{5-[(3-chloropropyl)sulfanyl]-4-methyl-4H-1,2,4-triazol-3-yl}-6-methylpyrazine | 73 | 283.9 |
| p185 | 2-{5-[(3-chloropropyl)sulfanyl]-4-methyl-4H-1,2,4-triazol-3-yl}-5-methylpyrazine | 79 | 283.9 |
| p186 | 2-{5-[(3-chloropropyl)sulfanyl]-4-methyl-4H-1,2,4-triazol-3-yl}-3-methylpyrazine | 80 | 283.9 |
| p187 | 5-{5-[(3-chloropropyl)sulfanyl]-4-methyl-4H-1,2,4-triazol-3-yl}pyrazine-2-carboxamide | 7 | 313.1 |
| p188 | 3-[(3-chloropropyl)sulfanyl]-4-methyl-5-(1,2-oxazol-5-yl)-4H-1,2,4-triazole | 62 | 259.0 |
| p189 | 3-[(3-chloropropyl)sulfanyl]-4-methyl-5-(3-methyl-1,2-oxazol-5-yl)-4H-1,2,4-triazole | 80 | 273.0 |
| p190 | 3-[(3-chloropropyl)sulfanyl]-4-methyl-5-(4-methyl-1,3-thiazol-5-yl)-4H-1,2,4-triazole | 70 | 289.0 |
| p191 | 3-[(3-chloropropyl)sulfanyl]-4-methyl-5-(1,3-thiazol-2-yl)-4H-1,2,4-triazole | 84 | 274.9 |

-continued

| Prep. Numb | Structure | Name | Yield % | MS (m/z) |
|---|---|---|---|---|
| p192 | 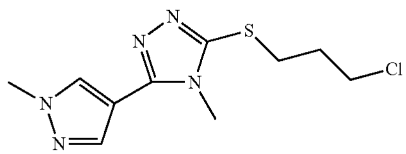 [SMILES: Cn1cc(-c2nnc(SCCCCl)n2C)cn1] | 3-[(3-chloropropyl)sulfanyl]-4-methyl-5-(1-methyl-1H-pyrazol-4-yl)-4H-1,2,4-triazole | 86 | 272.0 |
| p193 | 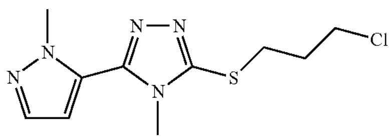 [SMILES: Cn1nccc1-c1nnc(SCCCCl)n1C] | 3-[(3-chloropropyl)sulfanyl]-4-methyl-5-(1-methyl-1H-pyrazol-5-yl)-4H-1,2,4-triazole | 87 | 272.3 |
| p194 | 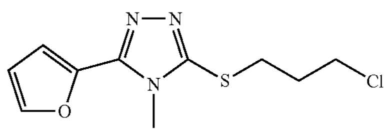 [SMILES: Cn1c(SCCCCl)nnc1-c1ccco1] | 3-[(3-chloropropyl)sulfanyl]-5-(furan-2-yl)-4-methyl-4H-1,2,4-triazole | 74 | 257.9 |
| p195 | 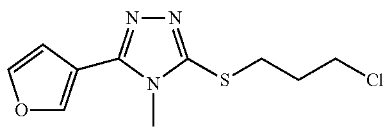 [SMILES: Cn1c(SCCCCl)nnc1-c1ccoc1] | 3-[(3-chloropropyl)sulfanyl]-5-(furan-3-yl)-4-methyl-4H-1,2,4-triazole | 83 | 257.9 |
| p196 | 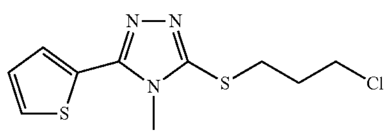 [SMILES: Cn1c(SCCCCl)nnc1-c1cccs1] | 3-[(3-chloropropyl)sulfanyl]-4-methyl-5-(thiophen-2-yl)-4H-1,2,4-triazole | 85 | 273.9 |
| p197 | 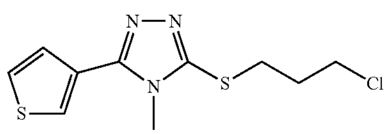 [SMILES: Cn1c(SCCCCl)nnc1-c1ccsc1] | 3-[(3-chloropropyl)sulfanyl]-4-methyl-5-(thiophen-3-yl)-4H-1,2,4-triazole | 77 | 273.9 |
| p198 | 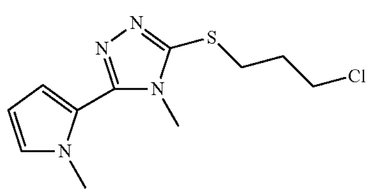 [SMILES: Cn1cccc1-c1nnc(SCCCCl)n1C] | 3-[(3-chloropropyl)sulfanyl]-4-methyl-5-(1-methyl-1H-pyrrol-2-yl)-4H-1,2,4-triazole | 76 | 271.0 |
| p199 | 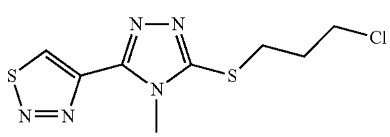 [SMILES: Cn1c(SCCCCl)nnc1-c1csnn1] | 4-{5-[(3-chloropropyl)sulfanyl]-4-methyl-4H-1,2,4-triazol-3-yl}-1,2,3-thiadiazole | 3 | 276.1 |
| p200 | 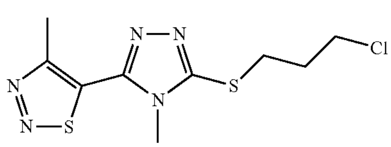 [SMILES: Cc1nnsc1-c1nnc(SCCCCl)n1C] | 5-{5-[(3-chloropropyl)sulfanyl]-4-methyl-4H-1,2,4-triazol-3-yl}-4-methyl-1,2,3-thiadiazole | 93 | 290.16 |
| p201 | 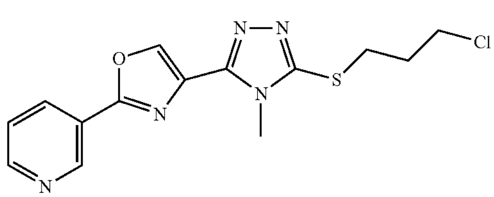 [SMILES: Cn1c(SCCCCl)nnc1-c1coc(-c2cccnc2)n1] | 3-(4-{5-[(3-chloropropyl)sulfanyl]-4-methyl-4H-1,2,4-triazol-3-yl}-1,3-oxazol-2-yl)pyridine | 45 | 336.2 |

| Prep. Numb | Name | Yield % | MS (m/z) |
|---|---|---|---|
| p202 | 5-{5-[(3-chloropropyl)sulfanyl]-4-methyl-4H-1,2,4-triazol-3-yl}-2-phenoxypyridine | 80 | 361.2 |
| p203 | 3-[(3-chloropropyl)sulfanyl]-4-methyl-5-{[1,2,4]triazolo[4,3-a]pyridin-8-yl}-4H-1,2,4-triazole | 28 | 309.2 |
| p204 | 3-[(3-chloropropyl)sulfanyl]-4-methyl-5-{[1,2,4]triazolo[4,3-a]pyridin-6-yl}-4H-1,2,4-triazole | 77 | 309.2 |
| p205 | 3-[(3-chloropropyl)sulfanyl]-4-methyl-5-{[1,2,4]triazolo[4,3-a]pyridin-7-yl}-4H-1,2,4-triazole | 29 | 309.1 |
| p206 | 3-[(3-chloropropyl)sulfanyl]-4-methyl-5-{3-methyl-[1,2,4]trizolo[4,3-a]pyridin-6-yl}-4H-1,2,4-triazole | 71 | 323.2 |
| p207 | 3-[(3-chloropropyl)sulfanyl]-5-{1H-imidazo[4,5-b]pyridin-5-yl}-4-methyl-4H-1,2,4-triazole | 27 | 309.1 |
| p208 | 5-(4-{5-[(3-chloropropyl)sulfanyl]-4-methyl-4H-1,2,4-triazol-3-yl}phenyl)-1H-1,2,3,4-tetrazole | 52 | 336.2 |
| p209 | 2-(4-{5-[(3-chloropropyl)sulfanyl]-4-methyl-4H-1,2,4-triazol-3-yl}phenyl)-1,3,4-oxadiazole | Quant | 336.2 |
| p210 | 3-(4-{5-[(3-chloropropyl)sulfanyl]-4-methyl-4H-1,2,4-triazol-3-yl}phenyl)-5-methyl-1,2,4-oxadiazole | 53 | 350.2 |

-continued

| Prep. Numb | Name | Yield % | MS (m/z) |
|---|---|---|---|
| p211 | 3-[(3-chloropropyl)sulfanyl]-4-methyl-5-[4-(4H-1,2,4-triazol-4-yl)phenyl]-4H-1,2,4-triazole | 49 | 335.2 |
| p212 | 3-[(3-chloropropyl)sulfanyl]-4-methyl-5-[4-(1,3-oxazol-2-yl)phenyl]-4H-1,2,4-triazole | 61 | 335.2 |
| p213 | 4-{5-[(3-chloropropyl)sulfanyl]-4-methyl-4H-1,2,4-triazol-3-yl}benzamide | 55 | 311.1 |
| p214 | 4-{5-[(3-chloropropyl)sulfanyl]-4-methyl-4H-1,2,4-triazol-3-yl}benzonitrile | 93 | 293.2 |
| p215 | 1-(4-{5-[(3-chloropropyl)sulfanyl]-4-methyl-4H-1,2,4-triazol-3-yl}phenyl)ethan-1-one | 59 | 309.9 |
| p216 | 4-{5-[(3-chloropropyl)sulfanyl]-4-methyl-4H-1,2,4-triazol-3-yl}benzene-1-sulfonamide | 48 | 347.1 |
| p217 | 2-(4-{5-[(3-chloropropyl)sulfanyl]-4-methyl-4H-1,2,4-triazol-3-yl}phenyl)acetonitrile | 65 | 307.1 |

| Prep. Numb | Structure | Name | Yield % | MS (m/z) |
|---|---|---|---|---|
| p218 | 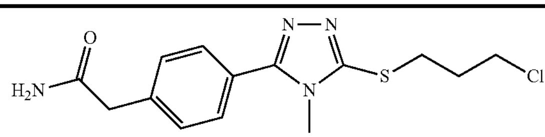 | 2-(4-{5-[(3-chloropropyl)sulfanyl]-4-methyl-4H-1,2,4-triazol-3-yl}phenyl)acetamide | 50 | 325.2 |
| p219 | 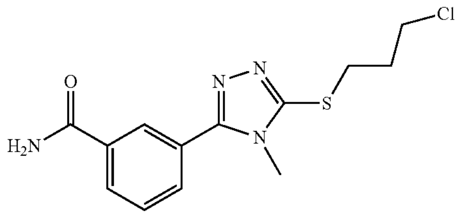 [SMILES: Cn1c(SCCCCl)nnc1-c1cccc(C(N)=O)c1] | 3-{5-[(3-chloropropyl)sulfanyl]-4-methyl-4H-1,2,4-triazol-3-yl}benzamide | 48 | 311.2 |
| p220 | 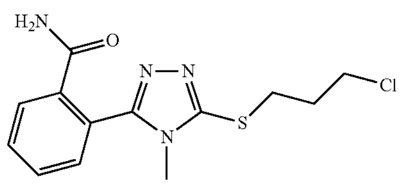 [SMILES: Cn1c(SCCCCl)nnc1-c1ccccc1C(N)=O] | 2-{5-[(3-chloropropyl)sulfanyl]-4-methyl-4H-1,2,4-triazol-3-yl}benzamide | 31 | 311.2 |

Preparation 221: 1-[4-(4-methyl-5-sulfanyl-4H-1,2,4-triazol-3-yl)piperidin-1-yl]ethan-1-one

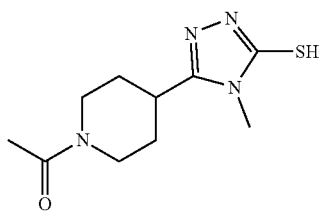 [SMILES: CC(=O)N1CCC(c2nnc(S)n2C)CC1]

To a stirred solution of 1-acetylpiperidine-4-carboxylic acid (1 g, 5.84 mmol) in DMF (3 mL), 4-methyl-3-thiosemicarbazide (676 mg, 6.4 mmol) and DIPEA (1.83 mL, 10.5 mmol) were subsequently added. The mixture was cooled to 0° C. then T3P (50% wt/EA) (5.21 mL, 8.7 mmol) was added dropwise. The ice-bath was removed and the resulting reaction mixture was stirred at RT for 2 hrs.

Aqueous 3M NaOH solution was added (resulting pH~8) followed by AcOEt and the two resulting phases were separated (the upper organic layer was eliminated). Additional 3M NaOH was added up to pH 11 then the mixture was heated to 70° C. and stirred for 40 min. The solution was cooled to RT and 6N HCl was slowly added until pH 5. The mixture was extracted with DCM several times. Aqueous phase was concentrated under reduced pressure and the residue was purified by FC on a C18 cartridge (eluent water+0.1% HCOOH→50% ACN+0.1% HCOOH) affording 1-[4-(4-methyl-5-sulfanyl-4H-1,2,4-triazol-3-yl)piperidin-1-yl]ethan-1-one (p221, 793 mg, y=56%). MS (m/z): 241.2 [MH]+.

Preparation 222: 1-(4-{5-[(3-chloropropyl)sulfanyl]-4-methyl-4H-1,2,4-triazol-3-yl}piperidin-1-yl)ethan-1-one

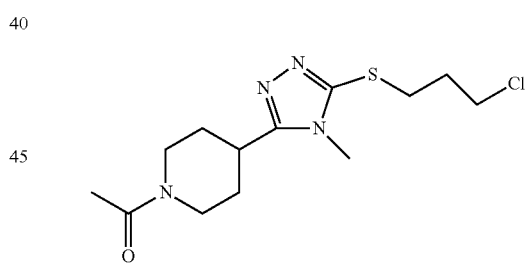

To a suspension of 1-[4-(4-methyl-5-sulfanyl-4H-1,2,4-triazol-3-yl)piperidin-1-yl]ethan-1-one (p221, 793 mg, 3.3 mmol) in a mixture MeOH/Acetone (4 mL/9 mL) at RT 1-Bromo-3-chloropropane (424 uL, 4.3 mmol) was added followed by K₂CO₃ (1.14 g, 8.25 mmol) and the mixture was stirred at RT O/N. Further 1-Bromo-3-chloropropane (230 uL, 2.31 mmol) was added followed by K₂CO₃ (594 mg, 4.3 mmol) and the mixture was stirred at RT for 2 hrs.

The mixture was partitioned between water and DCM and phases were separated. Organic one was washed with brine then dried and concentrated under reduced pressure. Crude material was purified by FC on silica cartridge (eluent: DCM to DCM/MeOH 9:1) affording 1-(4-{5-[(3-chloropropyl)sulfanyl]-4-methyl-4H-1,2,4-triazol-3-yl}piperidin-1-yl)ethan-1-one (p222, 224 mg, y=21%). MS (m/z): 317.3 [MH]+.

Preparation 223: tert-butyl 4-(4-methyl-5-sulfanyl-4H-1,2,4-triazol-3-yl)piperidine-1-carboxylate

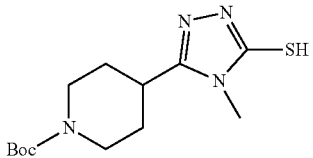 [SMILES: Cn1c(S)nnc1C1CCN(C(=O)OC(C)(C)C)CC1]

To a stirred solution of 1-Boc-piperidine-4-carboxylic acid (1.0 g, 4.36 mmol) in DMF (3 mL), 4-methyl-3-thiosemicarbazide (0.504 g, 4.8 mmol) and DIPEA (1.37 mL, 7.85 mmol) were subsequently added. The mixture was cooled to 0° C. then T3P (50% wt/EA) (3.9 mL, 6.54 mmol) was added dropwise. The ice-bath was removed and the resulting reaction mixture was stirred at RT for 3 hrs.

Aqueous 3M NaOH solution was added (resulting pH~8) followed by AcOEt and the two resulting phases were separated (the upper organic layer was eliminated). Additional 4M NaOH was added up to pH 11 then the mixture was heated to 70° C. and stirred for 40 min. The solution was cooled to RT and 6N HCl was slowly added until pH 5. The product was extracted with DCM several times. The organic phase was washed with brine, filtered and evaporated to afford tert-butyl 4-(4-methyl-5-sulfanyl-4H-1,2,4-triazol-3-yl)piperidine-1-carboxylate (p223, 1.08 g, y=83%) as white solid. MS (m/z): 299.2 [MH]$^+$.

Preparation 224: tert-butyl 4-{5-[(3-chloropropyl)sulfanyl]-4-methyl-4H-1,2,4-triazol-3-yl}piperidine-1-carboxylate

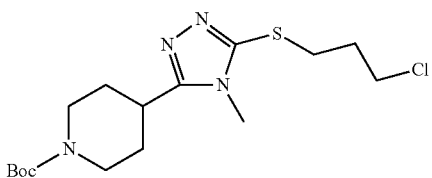 [SMILES: Cn1c(SCCCCl)nnc1C1CCN(C(=O)OC(C)(C)C)CC1]

To a suspension of tert-butyl 4-(4-methyl-5-sulfanyl-4H-1,2,4-triazol-3-yl)piperidine-1-carboxylate (p223, 1.08 g, 3.62 mmol) in a mixture MeOH/Acetone (4 mL/9 mL) at RT 1-Bromo-3-chloropropane (465 uL, 4.7 mmol) was added followed by K$_2$CO$_3$ (700 mg, 5.07 mmol) and the mixture was stirred at RT O/N. Then it was partitioned between water and DCM and phases were separated. Organic one was washed with brine then dried and concentrated under reduced pressure. Crude material was purified by FC on NH column (eluent: Cy to Cy/AcOEt 1:1) affording tert-butyl 4-{5-[(3-chloropropyl)sulfanyl]-4-methyl-4H-1,2,4-triazol-3-yl}piperidine-1-carboxylate (p224, 1.08 g, y=79%). MS (m/z): 375.3 [MH]$^+$.

Preparation 225: tert-butyl 3-(4-methyl-5-sulfanyl-4H-1,2,4-triazol-3-yl)azetidine-1-carboxylate

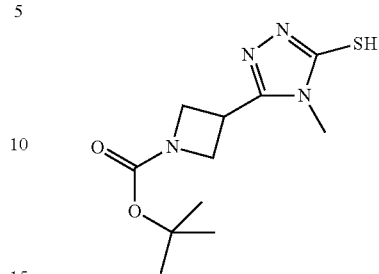

To a solution of 1-[(tert-butoxy)carbonyl]azetidine-3-carboxylic acid (1 g, 4.97 mmol) in DMF (3.5 mL), 4-methyl-3-thiosemicarbazide (0.575 g, 5.47 mmol) was added. DIPEA (1.5 mL, 8.95 mmol) was added at RT, then the mixture was cooled in an ice-bath before adding T3P (50% w/w in EtOAc) (4.1 mL, 6.958 mmol). The reaction was stirred at RT O/N. NaOH 4M solution (3 mL) was added (resulting pH=8). The reaction was diluted with EtOAc. NaOH 4M sol. (1 mL) was added and the mixture was shaken until dissolution. Phases were then separated (the upper organic layer eliminated). Additional 4M NaOH was added up to pH 11 (8 mL) and the clear orange solution was heated to 70° C. for 1.5 h. The clear yellow solution was then cooled to RT, then 37% HCl was slowly added till pH 4.5. The milky suspension was extracted with DCM (×4) and combined organics were dried and concentrated. To the residue (containing DMF) few drops of water were added and a precipitate formed that was filtered and dried under vacuum to obtain tert-butyl 3-(4-methyl-5-sulfanyl-4H-1,2,4-triazol-3-yl)azetidine-1-carboxylate (p225, 1.09 g, y=81%) as white solid. MS (m/z): 271.2 [MH]$^+$.

Preparation 226: tert-butyl 3-{5-[(3-chloropropyl)sulfanyl]-4-methyl-4H-1,2,4-triazol-3-yl}azetidine-1-carboxylate

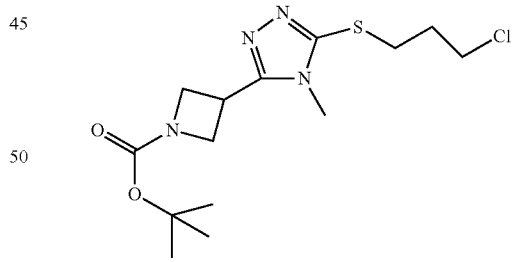

To a suspension of tert-butyl 3-(4-methyl-5-sulfanyl-4H-1,2,4-triazol-3-yl)azetidine-1-carboxylate (p225, 1.09 g, 4.02 mmol) in a mixture MeOH/Acetone (2.2 mL/5.7 mL) at RT, 1-Bromo-3-chloropropane (437 uL, 4.42 mmol) was added, followed by K$_2$CO$_3$ (778 mg, 5.63 mmol) and the mixture was stirred at RT for 5 hrs. The mixture was filtered washing with DCM and the filtrate was concentrated in vacuum. The crude was purified by FC on silica cartridge (eluent from Cy to EtOAc, then AcOEt to 20% MeOH) to obtain tert-butyl 3-{5-[(3-chloropropyl)sulfanyl]-4-methyl-4H-1,2,4-triazol-3-yl}azetidine-1-carboxylate (p226, 1.05 g, y=72%) as yellow oil. MS (m/z): 347.0 [MH]$^+$.

Preparation 227: methyl 4-oxocyclohexane-1-carboxylate

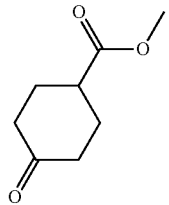

To a solution of 4-oxocyclohexane-1-carboxylic acid (840 mg, 5.91 mmol) in methanol (8 mL) was slowly added thionyl chloride (0.51 mL, 7.09 mmol) at RT. The reaction mixture was stirred for 3 hrs then concentrated under reduced pressure. The residue was taken up with DCM and aqueous saturated sodium bicarbonate, the organic phase was washed with water, dried over sodium sulfate and the solvent removed under vacuum to give methyl 4-oxocyclohexane-1-carboxylate (p227, 840 mg) that was used as crude in the next step. MS (m/z): 157.1 [MH]$^+$.

Preparation 228: methyl 4-(benzylamino)cyclohexane-1-carboxylate

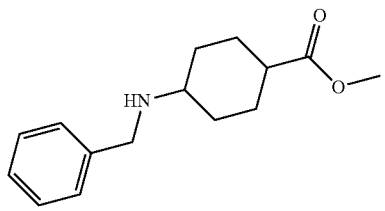 [SMILES: COC(=O)C1CCC(NCc2ccccc2)CC1]

To a solution of methyl 4-oxocyclohexane-1-carboxylate (p227, 0.84 g, 5.38 mmol) in 1,2-DCE (20 mL) was added benzylamine (0.62 mL, 5.65 mmol) followed by sodium triacetoxyborohydride (1.71 g, 8.07 mmol) portion-wise and the resulting reaction mixture was stirred O/N at RT. The mixture was diluted with aqueous saturated sodium bicarbonate solution and DCM. The organic phase was washed with brine, dried over sodium sulfate and the solvent removed under reduced pressure. The crude material so obtained was submitted to SCX cartridge purification (eluting with MeOH and 1N NH$_3$/MeOH) affording methyl 4-(benzylamino)cyclohexane-1-carboxylate (p228, 1.05 g) that was used as crude in the next step. MS (m/z): 248.3 [MH]$^+$.

Preparation 229: methyl 4-{[(tert-butoxy)carbonyl]amino}cyclohexane-1-carboxylate

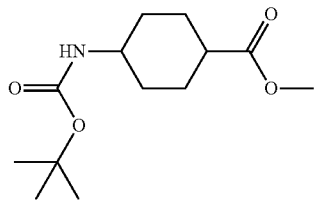 [SMILES: COC(=O)C1CCC(NC(=O)OC(C)(C)C)CC1]

Step a: A mixture of methyl 4-(benzylamino)cyclohexane-1-carboxylate (p228, 1.05 g, 4.25 mmol) and palladium hydroxide on carbon (20 weight %, 0.15 g) in MeOH (25 mL) was hydrogenated at atmospheric pressure for 24 hrs at RT. Additional palladium hydroxide on carbon (20 weight %, 0.15 g) was added and the reaction mixture was placed again under hydrogen atmosphere. After 24 hrs the reaction mixture was filtered through Celite and the filtrate concentrated under reduced pressure to give methyl 4-aminocyclohexane-1-carboxylate (0.61 g).

Step b: To a stirred solution of methyl 4-aminocyclohexane-1-carboxylate (0.61 g from step a) in DCM (5 mL), at RT, a solution of Boc$_2$O (0.14 g, 0.64 mmol) in DCM (0.5 mL) was added portion-wise and the resulting reaction mixture was stirred at RT. The reaction mixture was concentrated under vacuum and the crude product was purified by FC on silica cartridge (eluting with Cy/EA from 100/0 to 90/10) affording methyl 4-{[(tert-butoxy)carbonyl]amino}cyclohexane-1-carboxylate (p229, 0.24 g, y=22%). MS (m/z): 258.3 [MH]$^+$.

Preparation 230: tert-butyl N-(4-{5-[(3-chloropropyl)sulfanyl]-4-methyl-4H-1,2,4-triazol-3-yl}cyclohexyl)carbamate

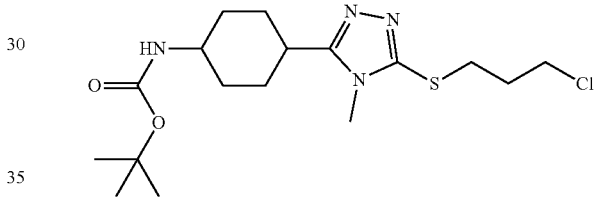

Step a: To a stirred solution of methyl 4-{[(tert-butoxy)carbonyl]amino}cyclohexane-1-carboxylate (p229, 236 mg, 0.92 mmol) in THF/MeOH/water (2 mL/0.5 mL/0.3 mL), at RT, LiOH (58 mg, 1.38 mmol) was added and the reaction mixture was warmed to 50° C. and shaken in a PLS apparatus for 3 hrs. The mixture was concentrated under vacuum, the residue was taken-up with DCM and aqueous 0.1N HCl, the organic phase was dried and the solvent removed under reduced pressure affording 4-{[(tert-butoxy)carbonyl]amino}cyclohexane-1-carboxylic acid (225 mg) that was used as crude in the next step.

Step b: To a stirred solution of 4-{[(tert-butoxy)carbonyl]amino}cyclohexane-1-carboxylic acid (225 mg from step a) in DMF (0.6 mL), 4-methyl-3-thiosemicarbazide (107 mg, 1.02 mmol) and DIPEA (0.29 mL, 1.66 mmol) were subsequently added. The mixture was cooled to 0° C. then T3P (50% wt/EA) (0.83 mL, 1.38 mmol) was added portion-wise. The ice-bath was removed and the resulting reaction mixture was stirred O/N at RT. Aqueous 4M NaOH solution was added (resulting pH~8) and the two resulting phases were separated (the upper organic layer was eliminated). Additional 4M NaOH was added up to pH~11 then the mixture was heated to 70° C. and stirred for 40 min. The solution was cooled to RT and 37% HCl was slowly added until pH~5. The reaction mixture was extracted twice with EA, the organic phase was washed with water, dried over sodium sulfate and concentrated under vacuum to give tert-butyl N-[4-(4-methyl-5-sulfanyl-4H-1,2,4-triazol-3-yl)cyclohexyl]carbamate (275 mg) that was used as such in the next step.

Step c: To a mixture of tert-butyl N-[4-(4-methyl-5-sulfanyl-4H-1,2,4-triazol-3-yl)cyclohexyl]carbamate (275 mg from step b) and potassium carbonate (158 mg, 1.14 mmol) in MeOH/Acetone (0.6 mL/1.6 mL), 1-bromo-3-chloropropane (0.096 mL, 0.97 mmol) was added and the resulting reaction mixture was shaken at RT in a PLS apparatus O/N. The mixture was diluted with EA and filtered, the solid was washed with EA and the filtrate was concentrated under reduced pressure. The crude material was purified by FC on NH column (eluting with Cy/EA from 100/0 to 55/45) affording tert-butyl N-(4-{5-[(3-chloropropyl)sulfanyl]-4-methyl-4H-1,2,4-triazol-3-yl}cyclohexyl)carbamate (p230, 139 mg, y=39%). MS (m/z): 389.3 [MH]$^+$.

Preparation 231:
3-(ethoxycarbonyl)-2-methylpyridin-N oxide

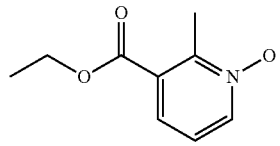

To a solution of ethyl 2-methyl-3-pyridinecarboxylate (1.86 mL, 12.1 mmol) in DCM (50 mL) mCPBA was added (4.18 g, 24.2 mmol) at RT. The solution was stirred at RT for 24 hrs. The solution was filtered and concentrated. The residue was purified by FC on silica cartridge (eluent: from DCM to 10% MeOH) to afford 3-(ethoxycarbonyl)-2-methylpyridin-N oxide (p231, 2.23 g, y=quant). MS (m/z): 183.0 [MH]$^+$.

Preparation 232: ethyl 6-cyano-2-methylpyridine-3-carboxylate

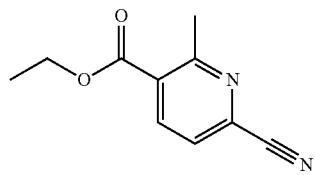

To a solution of 3-(ethoxycarbonyl)-2-methylpyridin-N oxide (p231, 2 g, 10.92 mmol) in DCM (80 mL) TMSCN was added (2.05 mL, 16.37 mmol) followed, after 5 min, by dimethylcarbamyl chloride (1.5 mL, 16.37 mmol). The solution was stirred at RT for 48 hrs. Then 10% K$_2$CO$_3$ was slowly added to make the reaction mixture basic. Organic layer was separated, dried and evaporated to provide the crude material, which was purified by FC on silica cartridge (eluent: Cy to 20% EtOAc) to afford ethyl 6-cyano-2-methylpyridine-3-carboxylate (p232, 1.23 g, y=59%). MS (m/z): 191.1 [MH]$^+$.

Preparation 233:
6-cyano-2-methylpyridine-3-carboxylic acid

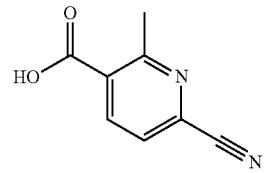

A solution of ethyl 6-cyano-2-methylpyridine-3-carboxylate (p232, 1.37 g, 7.2 mmol) in THF (25 mL) and water (10 mL) at RT was treated with LiOH.H$_2$O (0.453 g, 10.8 mmol), stirred for 2 hrs, and concentrated. The concentrate was dissolved in water (10 mL) and adjusted to pH 2 with 1N HCl to provide a precipitate. The precipitate was filtered and washed with cold water. The mother liquor was extracted several times with EtOAC, the organic solution was dried and evaporated and added to the former solid to obtain 6-cyano-2-methylpyridine-3-carboxylic acid (p233, 1.08 g, y=92%). MS (m/z): 163.0 [MH]$^+$.

Preparation 234 and 235: 5-{5-[(3-chloropropyl)sulfanyl]-4-methyl-4H-1,2,4-triazol-3-yl}-6-methylpyridine-2-carboxamide (p234) and 5-{5-[(3-chloropropyl)sulfanyl]-4-methyl-4H-1,2,4-triazol-3-yl}-6-methylpyridine-2-carboxylic acid (p235)

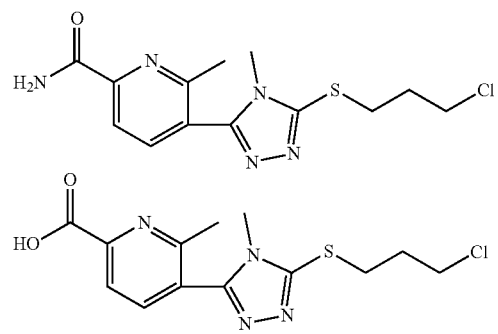

To a solution of 6-cyano-2-methylpyridine-3-carboxylic acid (p234, 1.08 g, 6.66 mmol) in DMF (5 mL), 4-methyl-3-thiosemicarbazide (770 mg, 7.32 mmol) was added DIPEA (2.05 mL, 11.99 mmol) was added dropwise at RT, then the mixture was cooled in an icebath before adding T3P (50% w/w in EtOAc) (5.953 mL, 9.99 mmol). The reaction was stirred at RT O/N NaOH 4M solution was added until pH=8. The reaction was diluted with EtOAc and the two resulting phases were separated (the upper organic layer eliminated). Additional 4M NaOH was added up to pH 11 and the mixture heated to 70° C. for 2.5 hrs. Then pH was increased to 11 by adding NaOH (pellet) and the reaction was stirred at 70° C. for 1 h. The solution was then cooled to 0° C., then HCl 6N was slowly added till pH 5. A precipitate formed that was filtered under vacuum to obtain a solid containing 2 products (87% the carboxylic acid derivative, 12% the primary amide derivative). It was suspended in a mixture MeOH/Acetone (5 mL/10 mL) at RT, 1-Bromo-3-chloropropane (435 uL, 4.4 mmol) was added, followed by K$_2$CO$_3$ (1.32 g, 9.6 mmol) and the mixture was stirred at RT O/N. It was partitioned between water and DCM and phases were separated. The amide derivative was extracted in the organic phase, that was dried and concentrated under reduced pressure, and the crude material was purified by FC on silica cartridge (eluent: from Cy to AcOEt) affording 5-{5-[(3-chloropropyl)sulfanyl]-4-methyl-4H-1,2,4-triazol-3-yl}-6-methylpyridine-2-carboxamide (p234, 37 mg, y=3%). MS (m/z): 326.1 [MH]$^+$.

The aqueous phase containing the carboxylic acid derivative was dried affording 5-{5-[(3-chloropropyl)sulfanyl]-4-methyl-4H-1,2,4-triazol-3-yl}-6-methylpyridine-2-carboxylic acid (p235, 1 g, y=crude). MS (m/z): 327.2 [MH]$^+$.

Preparation 236: 5-{5-[(3-chloropropyl)sulfanyl]-4-methyl-4H-1,2,4-triazol-3-yl}pyridine-3-carboxamide

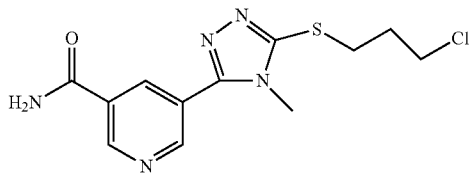 [SMILES: Cn1c(SCCCCl)nnc1-c1cncc(C(N)=O)c1]

Step a: 3,5-dimethyl pyridine-3,5-dicarboxylate (500 mg, 2.56 mmol) was dissolved in methanol (2 mL) and 1M NaOH (2.56 mL, 2.56 mmol) was slowly added. The resulting yellow solution was stirred for 15 mins at RT, then organic solvent was evaporated and the aqueous residue was acidified to pH 2 and extracted with DCM (4×). Material detected in aqueous phase, therefore aqueous and organic phase were combined and concentrated affording 5-(methoxycarbonyl)pyridine-3-carboxylic acid (561 mg) as yellow solid. Presence of ~10% of starting material and 10% dicarboxylic acid detected. Used as such in the next step.

Step b: 5-(methoxycarbonyl)pyridine-3-carboxylic acid (561 mg from step a) was dissolved in 7M NH$_3$ in MeOH (10 mL, 70 mmol). The resulting pale yellow solution turned to a suspension and it was stirred O/N at RT. No traces of desired compound detected, therefore solvent was evaporated under reduced pressure and the residue was treated with NH$_4$OH 28% aqueous solution (10 mL) and the solution was left stirring at RT for 3 hrs. The mixture was then concentrated under reduced pressure affording 5-carbamoylpyridine-3-carboxylic acid (235 mg) that was used as such in the next step.

Step c: To a stirred solution of 5-carbamoylpyridine-3-carboxylic acid (235 mg from step b) in DMF (1.5 mL), 4-methyl-3-thiosemicarbazide (164 mg, 1.56 mmol) and DIPEA (0.444 mL, 2.55 mmol) were subsequently added. The mixture was cooled to 0° C. then T3P (50% wt/EA) (1.26 mL, 2.1 mmol) was added dropwise. The ice-bath was removed and the resulting reaction mixture was stirred at RT O/N.

Aqueous 3M NaOH solution was added (resulting pH~8) followed by AcOEt and the two resulting phases were separated (the upper organic layer was eliminated). Additional 3M NaOH was added up to pH 11 then the mixture was heated to 70° C. and stirred for 40 min. The solution was cooled to RT and 6N HCl was slowly added until pH 5. No precipitate observed. Aqueous solution was therefore concentrated under reduced pressure affording 5-(4-methyl-5-sulfanyl-4H-1,2,4-triazol-3-yl)pyridine-3-carboxamide (705 mg) used as crude in the next step.

Step d: To a suspension of 5-(4-methyl-5-sulfanyl-4H-1,2,4-triazol-3-yl)pyridine-3-carboxamide (705 mg) in a mixture MeOH/Acetone (4 mL/9 mL) at RT 1-Bromo-3-chloropropane (182 uL, 1.84 mmol) was added followed by K$_2$CO$_3$ (488 mg, 3.53 mmol) and the mixture was stirred at RT O/N. Then it was partitioned between water and DCM and phases were separated. Organic one was washed with brine then dried and concentrated under reduced pressure. Crude material was purified by FC on silica cartridge (eluent:DCM to DCM/MeOH 9:1) affording 5-{5-[(3-chloropropyl)sulfanyl]-4-methyl-4H-1,2,4-triazol-3-yl}pyridine-3-carboxamide (p236, 73 mg, y=9%). MS (m/z): 312.2 [MH]$^+$.

Preparation 237: methyl 3-[(2,2-dimethoxyethyl)carbamoyl]benzoate

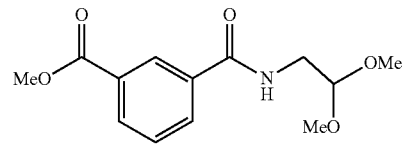 [SMILES: COC(=O)c1cccc(C(=O)NCC(OC)OC)c1]

A mixture of 3-(methoxycarbonyl)benzoic acid (500 mg, 2.77 mmol), 1-Hydroxybenzotriazole hydrate (397 mg, 2.94 mmol), N-(3-Dimethylaminopropyl)-N'-ethylcarbodiimide hydrochloride (564 mg, 2.94 mmol), and TEA (1.16 mL, 8.31 mmol) in DCM (15 mL) was stirred at 0° C. for 10 min, then 2,2-dimethoxyethan-1-amine (0.301 mL, 2.77 mmol) was added and the mixture was left stirring at RT O/N. It was washed with NaHCO$_3$ (×1), NH$_4$Cl (×3) and Brine, organic phase was separated, dried and concentrated under reduced pressure affording methyl 3-[(2,2-dimethoxyethyl)carbamoyl]benzoate (p237, 548 mg, y=74%) that was used as such in the next step. MS (m/z): 268.2 [MH]$^+$.

Preparation 238: methyl 3-(1,3-oxazol-2-yl)benzoate

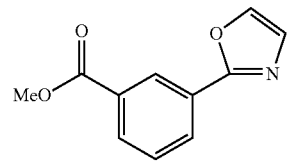 [SMILES: COC(=O)c1cccc(-c2ncco2)c1]

Step a: To a solution of methyl 3-[(2,2-dimethoxyethyl)carbamoyl]benzoate (p237, 548 mg, 2.05 mmol) in THF (4 mL), HCl 6N (1 mL) was added and the mixture was stirred at RT for 1.5 h. Then the mixture was partitioned between brine and AcOEt and the organic layer was dried, filtered and concentrated affording methyl 3-[(2-oxoethyl)carbamoyl]benzoate (426 mg). Used as such in the next step.

Step b: To a solution of PPh₃ (1 g, 3.85 mmol) in DCM (35 mL) at RT, iodine (977 mg, 3.85 mmol) was added followed by a solution of methyl 3-[(2-oxoethyl)carbamoyl] benzoate (426 mg from step a) in DCM (4 mL) and the mixture was stirred at RT for 48 hrs. The mixture was washed with sodium thiosulfate solution and water. Organic layer was then dried and concentrated under reduced pressure. Crude was purified by FC on silica gel (eluent: Cy to AcOEt) affording methyl 3-(1,3-oxazol-2-yl)benzoate (p238, 137.6 mg, y=33%). MS (m/z): 204.1 [MH]⁺.

Preparation 239: 3-[(3-chloropropyl)sulfanyl]-4-methyl-5-[3-(1,3-oxazol-2-yl)phenyl]-4H-1,2,4-triazole

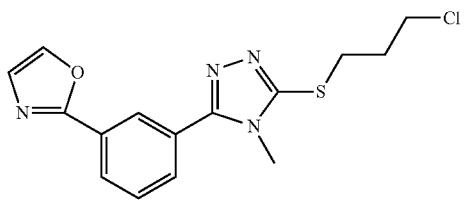 [SMILES: Cn1c(SCCCCl)nnc1-c1cccc(-c2ncco2)c1]

Step a: methyl 3-(1,3-oxazol-2-yl)benzoate (p238, 137.6 mg, 0.68 mmol) was dissolved in MeOH (2 mL) and 1M NaOH (0.68 mL, 1.08 mmol) was slowly added. The resulting yellow solution was stirred for 30 mins at RT, then organic solvent was evaporated and the aqueous residue was acidified to pH 2 and extracted with DCM. Organic phase was dried and concentrated affording 3-(1,3-oxazol-2-yl) benzoic acid (148 mg) that was used as such in the next step.

Step b: To a stirred solution of 3-(1,3-oxazol-2-yl)benzoic acid (148 mg from step a) in DMF (0.5 mL), 4-methyl-3-thiosemicarbazide (79 mg, 0.75 mmol) and DIPEA (0.213 mL, 1.22 mmol) were subsequently added. The mixture was cooled to 0° C. then T3P (50% wt/EA) (0.61 mL, 1.02 mmol) was added dropwise. The ice-bath was removed and the resulting reaction mixture was stirred at RT O/N.

Aqueous 3M NaOH solution was added (resulting pH~8) followed by AcOEt and the two resulting phases were separated (the upper organic layer was eliminated). Additional 3M NaOH was added up to pH 11 then the mixture was heated to 70° C. and stirred for 40 min. The solution was cooled to RT and 6N HCl was slowly added until pH 5. The precipitate was filtered and washed with water and Cy, then collected and dried under high vacuum affording 4-methyl-5-[3-(1,3-oxazol-2-yl)phenyl]-4H-1,2,4-triazole-3-thiol (67.6 mg).

Step c: To a suspension of 4-methyl-5-[3-(1,3-oxazol-2-yl)phenyl]-4H-1,2,4-triazole-3-thiol (67.6 mg from step b) in a mixture MeOH/Acetone (1 mL/2.25 mL) at RT 1-Bromo-3-chloropropane (34 uL, 0.34 mmol) was added followed by K₂CO₃ (90 mg, 0.65 mmol) and the mixture was stirred at RT O/N. Then it was partitioned between water and DCM and phases were separated. Organic one was washed with brine then dried and concentrated under reduced pressure. Crude material was purified by FC on silica gel (eluent: Cy to Cy/AcOEt 100%) affording 3-[(3-chloropropyl)sulfanyl]-4-methyl-5-[3-(1,3-oxazol-2-yl)phenyl]-4H-1,2,4-triazole (p239, 44.3 mg, y=19%). MS (m/z): 259.2 [MH]⁺.

Preparation 240: 1-chloro-3-{[4-methyl-5-(4-methyl-1,3-oxazol-5-yl)-4H-1,2,4-triazol-3-yl]sulfanyl}propan-2-ol

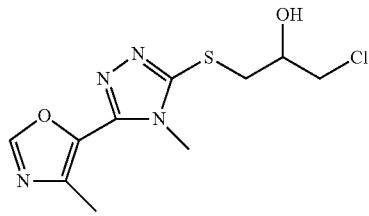 [SMILES: Cc1ncoc1-c1nnc(SCC(O)CCl)n1C]

To a suspension of 4-methyl-5-(4-methyl-1,3-oxazol-5-yl)-4H-1,2,4-triazole-3-thiol (p65, 100 mg, 0.51 mmol) in a mixture MeOH/Acetone (0.33 mL/0.82 mL) at RT, 1-bromo-3-chloropropan-2-ol (64 uL, 0.663 mmol) was added, followed by K₂CO₃ (99 mg, 0.714 mmol) and the mixture was stirred at RT O/N. The mixture was partitioned between water and DCM and phases were separated. Organic one was dried and concentrated under reduced pressure to obtain 1-chloro-3-{[4-methyl-5-(4-methyl-1,3-oxazol-5-yl)-4H-1,2,4-triazol-3-yl]sulfanyl}propan-2-ol (p240, 117 mg, y=69%) as yellow solid that was used as such in the next step. MS (m/z): 289.1 [MH]⁺.

Preparation 241: oxane-4-carbohydrazide

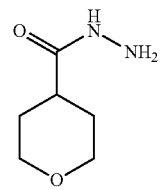

To a stirred solution of methyl tetrahydro-2H-pyran-4-carboxylate (4 g, 27.75 mmol) in MeOH (50 mL) at RT, hydrazine monohydrate (10.8 mL, 222 mmol) was added portion-wise and the resulting reaction mixture was stirred at reflux O/N. The mixture was allowed to reach RT and concentrated under vacuum affording the title compound oxane-4-carbohydrazide (p241, 3.9 g, y=98%) as white solid. MS (m/z): 145.1 [MH]⁺.

Preparation 242: ({[(tert-butoxy)carbonyl]amino}amino)(4-methyl-1,3-oxazol-5-yl)methanone

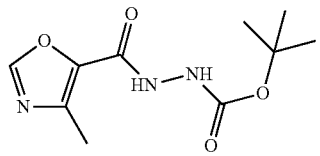 [SMILES: Cc1ncoc1C(=O)NNC(=O)OC(C)(C)C]

To a stirred suspension of 4-methyl-1,3-oxazole-5-carboxylic acid (1.0 g, 7.87 mmol) in DCM (10 mL), at RT, oxalyl chloride (1.5 mL, 11.81 mmol) was added portion-wise followed after 3 min by a catalytic amount of DMF (4 drops) and the resulting reaction mixture was stirred at RT for 2 hrs; then the clear mixture was concentrated under reduced pressure. The residue was dissolved in DCM (5 mL) and this solution was added drop-wise to a stirred solution of tert-butyl carbazate (3.64 g, 27.55 mmol) and TEA (4.1 mL, 11.02 mmol) in DCM (10 mL), at 0° C. and under a nitrogen atmosphere. The resulting reaction mixture was stirred at 0° C. for 3 hrs then it was allowed to reach RT and stirred O/N. The mixture was concentrated under vacuum and the residue was taken up with EA and water. The organic phase was washed with water, saturated ammonium chloride solution, dried over sodium sulfate and the solvent removed under reduced pressure. The crude material was purified by FC on silica cartridge (eluting with Cy/EA from 100/0 to 40/60) to give ({[(tert-butoxy)carbonyl]amino}amino)(4-methyl-1,3-oxazol-5-yl)methanone (p242, 2.45 g, y=quant.) as white waxy solid. MS (m/z): 242.2 [MH]⁺.

Preparation 243:
4-methyl-1,3-oxazole-5-carbohydrazide

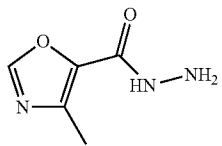

To a stirred solution of ({[(tert-butoxy)carbonyl]amino}amino)(4-methyl-1,3-oxazol-5-yl)methanone (p242, 1.23 g, 5.1 mmol) in dioxane (5 mL), at RT, 4N/dioxane HCl (26 mL, 104 mmol) was added portion-wise and the resulting reaction mixture was stirred at RT for 3 hrs. The mixture was filtered and the solid was dried under vacuum O/N then it was loaded on a SCX cartridge (eluting with MeOH and 2N NH₃/MeOH) affording 4-methyl-1,3-oxazole-5-carbohydrazide (p243, 366 mg, y=51%) as light yellow solid. NMR: ¹H NMR (DMSO-d₆) δ: 9.68 (br. s., 1H), 8.38 (s, 1H), 4.47 (br. s., 2H), 2.37 (s, 3H)

Preparation 244: methyl hex-5-enecarboximidate hydrochloride

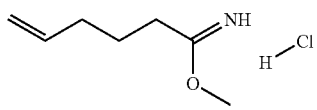

To a stirred solution of 5-hexenenitrile (2 g, 21.02 mmol) and MeOH (0.96 mL) in Et₂O (20 mL), at 0° C., HCl gas was bubbled for 10 min. The reaction mixture was concentrated under vacuum and the brown oil was taken up with Et₂O. The solid was filtered, washed with ether and dried under vacuum affording methyl hex-5-enecarboximidate hydrochloride (p244, 1.20 g, y=42%) as white solid that was used as such in the next step. NMR: ¹H NMR (DMSO-d₆) δ: 11.34-11.86 (m, 1H), 5.68-5.89 (m, 1H), 4.93-5.11 (m, 2H), 3.98-4.14 (m, 3H), 2.56-2.69 (m, 2H), 2.00-2.13 (m, 2H), 1.62-1.78 (m, 2H)

Preparation 245: N,N'-dimethylhexa-5-enimidamide hydrochloride

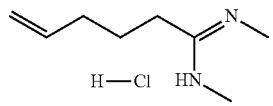

To a stirred solution of methyl hex-5-enecarboximidate hydrochloride (p244, 1.29 g, 7.88 mmol) in MeOH (6 mL), at RT, a 33% wt. solution of MeNH₂ in ethanol (5.9 mL, 47.28 mmol) was added and the resulting reaction mixture was stirred at reflux for 6 hrs and O/N at RT. The mixture was then concentrated under vacuum affording crude N,N'-dimethylhexa-5-enimidamide hydrochloride (p245, 1.47 g) as pale brown oil that was used as such in the next step. MS (m/z): 141.1 [MH]⁺.

Preparation 246: 4-methyl-3-(oxan-4-yl)-5-(pent-4-en-1-yl)-4H-1,2,4-triazole

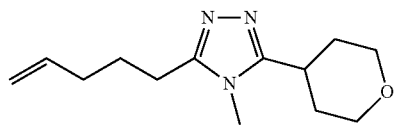 [SMILES: C=CCCCc1nnc(C2CCOCC2)n1C]

A suspension of N,N'-dimethylhexa-5-enimidamide hydrochloride (p245, 1.47 g, 8.32 mmol), oxane-4-carbohydrazide (p241, 1.20 g, 8.32) and K₂CO₃ (1.15 g, 8.32 mmol) in MeOH (50 mL) was heated to reflux and stirred for 24 hrs. The mixture was then filtered and the organic solution was concentrated under vacuum. The crude material was purified by FC on silica cartridge (eluting from DCM to 10% MeOH) to give two batches of the title compound 4-methyl-3-(oxan-4-yl)-5-(pent-4-en-1-yl)-4H-1,2,4-triazole (p246, batch 1: 0.20 g, purity >80% by NMR and batch 2: 0.75 g, purity <70% by NMR). NMR: ¹H NMR (CDCl₃) δ: 5.74-5.91 (m, 1H), 4.94-5.12 (m, 2H), 3.99-4.17 (m, 2H), 3.53-3.61 (m, 2H), 3.52 (s, 3H), 2.87-2.96 (m, 1H), 2.70-2.77 (m, 2H), 2.05-2.25 (m, 4H), 1.83-2.02 (m, 3H)

Preparation 247: 4-[4-methyl-5-(oxan-4-yl)-4H-1,2,4-triazol-3-yl]butanal

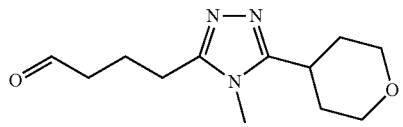 [SMILES: Cn1c(CCCC=O)nnc1C1CCOCC1]

A slow stream of O₃ in O₂ was passed through a −78° C. cooled solution of 4-methyl-3-(oxan-4-yl)-5-(pent-4-en-1-yl)-4H-1,2,4-triazole (p246, 203 mg, 0.86 mmol) in DCM (10 mL) until a pale blue color persisted (40 min). Excess of O₃ was purged by N₂ bubbling, then a solution of PPh₃ (248 mg, 0.946 mmol) in DCM (2 mL) was added. The solution was allowed to reach 25° C. and it was stirred for 2 hrs. The solvent was removed in vacuo and the crude material was purified by FC on silica cartridge (eluting from DCM to MeOH), to obtain 4-[4-methyl-5-(oxan-4-yl)-4H-1,2,4-triazol-3-yl]butanal (p247, 100 mg, 60% pure) as colourless oil that was used as such in the next step. NMR: $^1$H NMR (Acetone-d$_6$) δ: 9.76 (m, 1H), 3.89-4.03 (m, 2H), 3.58-3.65 (m, 3H), 3.44-3.56 (m, 2H), 3.01-3.12 (m, 2H), 2.75 (s, 2H), 2.60-2.66 (m, 1H), 2.29-2.39 (m, 1H), 1.76-1.98 (m, 5H)

Preparation 248: 4-methyl-3-(4-methyl-1,3-oxazol-5-yl)-5-(pent-4-en-1-yl)-4H-1,2,4-triazole

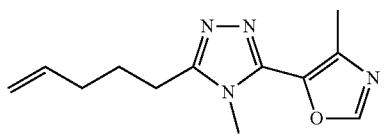 [SMILES: C=CCCCc1nnc(-c2ocnc2C)n1C]

A mixture of N,N'-dimethylhexa-5-enimidamide hydrochloride (p245, 458 mg, 2.59 mmol), 4-methyl-1,3-oxazole-5-carbohydrazide (p243, 366 mg, 2.59 mmol) and K$_2$CO$_3$ (537 mg, 3.89 mmol) in MeOH (20 mL) was refluxed for 32 hrs. The mixture was then allowed to reach RT, concentrated under reduced pressure and the residue was taken-up with DCM and concentrated aqueous sodium bicarbonate solution. The organic phase was washed with water, dried over sodium sulphate and the solvent removed under vacuum. The crude material was purified by FC on silica cartridge (eluting with DCM/MeOH from 100/0 to 96/4) then further purified by FC on NH column (eluting with Cy/EA from 100/0 to 65/35) affording 4-methyl-3-(4-methyl-1,3-oxazol-5-yl)-5-(pent-4-en-1-yl)-4H-1,2,4-triazole (p248, 107 mg, y=18%) as pale yellow waxy solid. MS (m/z): 233.2 [MH]$^+$.

Example 1: (1S,3S/1R,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (TRANS, E1)

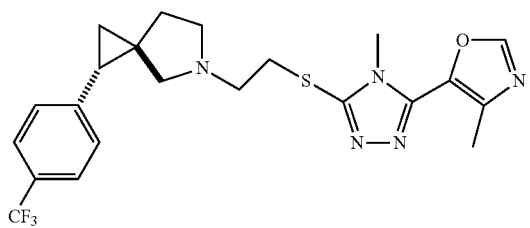

(1S,3S/1R,3R)-1-[4-(trifluoromethyl)phenyl]-5-azaspiro[2.4]heptane (TRANS, p13, 23 mg, 0.096 mmol), 3-[(3-chloropropyl)sulfanyl]-4-methyl-5-(4-methyl-1,3-oxazol-5-yl)-4H-1,2,4-triazole (p146, 25 mg, 0.096 mmol), Na$_2$CO$_3$ (12 mg, 0.115 mmol) and NaI (17 mg, 0.115 mmol) were dissolved in DMF (0.2 mL) and heated at 60° C. O/N. The mixture was diluted with water and EtOAc and extracted several times with EtOAc. The organic phase was washed with brine, dried and evaporated. The residue was purified by FC on silica gel (eluting from DCM to 5% of MeOH) to afford (1S,3S/1R,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (E1, 23 mg, y=51%) as yellow foam. NMR: $^1$H NMR (Acetone-d$_6$) δ: 8.27 (s, 1H), 7.62 (d, 2H), 7.34 (d, 2H), 3.81 (s, 2H), 3.39 (m, 2H), 2.87 (m, 2H), 2.75-2.83 (m, 3H), 2.61-2.73 (m, 3H), 2.43 (s, 2H), 2.21-2.29 (m, 1H), 1.61-1.70 (m, 1H), 1.44 (s, 1H), 1.26 (m, 1H), 1.17-1.23 (m, 1H). MS (m/z): 464.3 [MH]$^+$.

Example 2 and Example 3: (1R,3R or 1S,3S)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane hydrochloride (E2, Enantiomer 1) and (1S,3S or 1R,3R)-5-(2-{[4-methyl-5-(4-methyl-1,3-oxazol-5-yl)-4H-1,2,4-triazol-3-yl]-sulfanyl}ethyl)-1-[4-(trifluoromethyl)phenyl]-5-azaspiro[2.4]heptane hydrochloride (E3, Enantiomer 2)

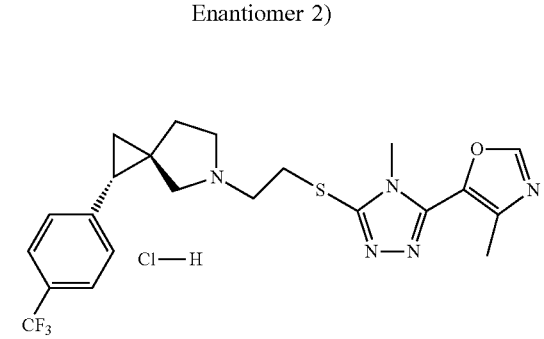

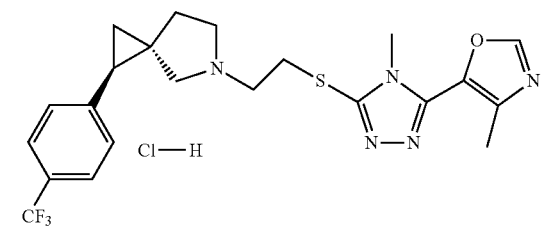

(1S,3S/1R,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (TRANS, E1, 23 mg) was separated into the single enantiomers by preparative chiral HPLC.

Preparative Chromatography:

| Column | Chiralpak AD-H (25 × 2.0 cm), 5 μm |
|---|---|
| Mobile phase | n-Hexane/Ethanol 55/45% v/v |
| Flow rate (ml/min) | 14 ml/min |
| DAD detection | 220 nm |
| Loop | 750 μL |
| Injection | 10 mg/injection |

Each enantiomer was treated with 1N HCl in Et$_2$O (1.1 eq) and evaporated affording (1R,3R or 1S,3S)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane hydrochloride (E2, 5.2 mg), Enantiomer 1: ret. time 11.7 min, 100% ee, MS (m/z): 464.3 [MH]$^+$, and (1S,3S or 1R,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane hydrochloride (E3, 6 mg), Enantiomer 2: ret. time 13.1 min, 97.2% ee, MS (m/z): 464.3 [MH]$^+$.

Example 4: (1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (CIS, E4)

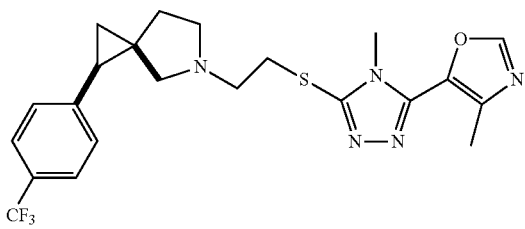

The compound was prepared as in Example 1, reacting (1R,3S/1S,3R)-1-[4-(trifluoromethyl)phenyl]-5-azaspiro[2.4]heptane (CIS, p14, 50 mg, 0.195 mmol), 3-[(3-chloroethyl)sulfanyl]-4-methyl-5-(4-methyl-1,3-oxazol-5-yl)-4H-1,2,4-triazole (p146, 57 mg, 0.22 mmol), Na$_2$CO$_3$ (23 mg, 0.22 mmol) and NaI (33 mg, 0.22 mmol) in DMF (0.2 mL) affording (1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane (E4, 20.5 mg, y=22%) as pale yellow foam. NMR: $^1$H NMR (CDCl$_3$) δ: 7.95 (s, 1H), 7.54 (d, 2H), 7.14-7.23 (m, 2H), 3.68 (s, 3H), 3.28-3.44 (m, 2H), 2.85 (s, 3H), 2.68-2.76 (m, 1H), 2.51-2.57 (m, 3H), 2.43-2.50 (m, 1H), 2.19-2.25 (m, 1H), 2.11-2.18 (m, 1H), 1.94-2.05 (m, 2H), 1.15-1.24 (m, 2H). MS (m/z): 464.3 [MH]$^+$.

Example 5: (1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane hydrochloride (CIS, E5)

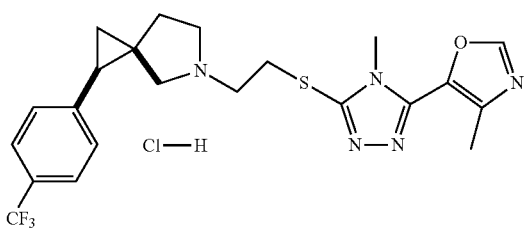

(1R,3S/1S,3R)-5-(2-{[4-methyl-5-(4-methyl-1,3-oxazol-5-yl)-4H-1,2,4-triazol-3-yl]sulfanyl})ethyl)-1-[4-(trifluoromethyl)phenyl]-5-azaspiro[2.4]heptane (E4, 20.5 mg) was dissolved in Et$_2$O and treated with 1.1 eq of 1N HCl in Et$_2$O affording, after evaporation, (1R,3S/1S,3R)-5-(2-{[4-methyl-5-(4-methyl-1,3-oxazol-5-yl)-4H-1,2,4-triazol-3-yl]sulfanyl}ethyl)-1-[4-(trifluoromethyl)phenyl]-5-azaspiro[2.4]heptane hydrochloride (E5, 22.5 mg) as off-white solid. MS (m/z): 464.3 [MH]$^+$.

Example 6: (1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane (CIS, E6)

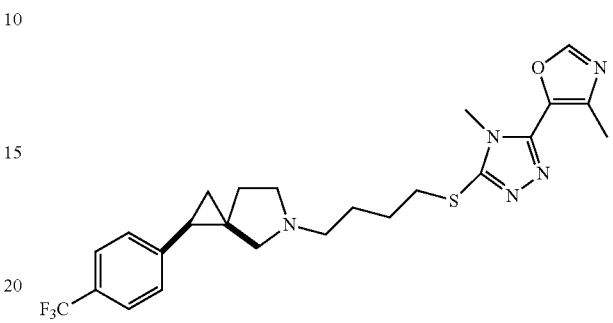

The compound was prepared as in Example 1, reacting (1R,3S/1S,3R)-1-[4-(trifluoromethyl)phenyl]-5-azaspiro[2.4]heptane (CIS, p14, 50 mg, 0.2 mmol), (4-chlorobutyl)sulfanyl]-4-methyl-5-(4-methyl-1,3-oxazol-5-yl)-4H-1,2,4-triazole (p147, 63 mg, 0.22 mmol), Na$_2$CO$_3$ (23 mg, 0.22 mmol) and NaI (33 mg, 0.22 mmol) in DMF (0.2 mL) affording (1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane (E6, 14.5 mg, y=15%) as pale yellow foam. NMR: $^1$H NMR (CDCl$_3$) δ: 7.95 (s, 1H), 7.55 (d, 2H), 7.22 (d, 2H), 3.65-3.74 (m, 3H), 3.20-3.33 (m, 2H), 2.94 (br. s., 1H), 2.70 (br. s., 1H), 2.54 (s, 6H), 2.14-2.27 (m, 2H), 2.05 (d, 2H), 1.82 (m, 3H), 1.19-1.32 (m, 3H). MS (m/z): 492.3 [MH]$^+$.

Example 7: (1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane hydrochloride (CIS, E7)

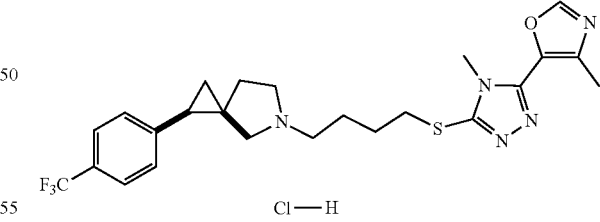

(1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane (E6, 14.5 mg) was dissolved in Et$_2$O and treated with 1.1 eq of 1N HCl in Et$_2$O affording, after evaporation, (1R,3S/1S,3R)-5-(4-{[4-methyl-5-(4-methyl-1,3-oxazol-5-yl)-4H-1,2,4-triazol-3-yl]sulfanyl}butyl)-1-[4-(trifluoromethyl)phenyl]-5-azaspiro[2.4]heptane hydrochloride (E7, 13.5 mg) as white solid. MS (m/z): 492.3 [MH]$^+$.

Example 8: (1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (TRANS, E8)

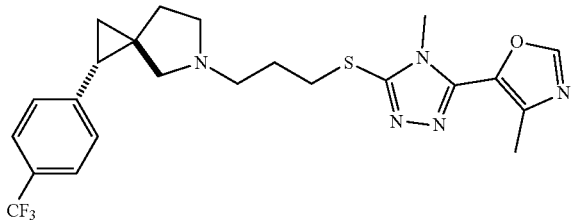

The compound was prepared as in Example 1, reacting (1S,3S/1R,3R)-1-[4-(trifluoromethyl)phenyl]-5-azaspiro[2.4]heptane (TRANS, p13, 47 mg, 0.195 mmol), 3-[(3-chloropropyl)sulfanyl]-4-methyl-5-(4-methyl-1,3-oxazol-5-yl)-4H-1,2,4-triazole (p148, 58 mg, 0.21 mmol), Na$_2$CO$_3$ (22 mg, 0.21 mmol) and NaI (31 mg, 0.21 mmol) in DMF (0.2 mL) affording (1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (TRANS, E8, 35 mg, y=37%) as pale yellow foam. NMR: $^1$H NMR (CDCl$_3$) δ: 7.95 (s, 1H), 7.54 (d, 2H), 7.23 (br. s., 2H), 3.73 (s, 3H), 3.37 (m, 2H), 2.59-2.94 (m, 5H), 2.55 (s, 3H), 1.97-2.31 (m, 3H), 1.63 (br. s., 4H), 1.25-1.36 (m, 1H), 1.11-1.19 (m, 1H) MS (m/z): 478.3 [MH]$^+$.

Example 9 and Example 10: (1R,3R or 1S,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E9, Enantiomer 1) and (1S,3S or 1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E10, Enantiomer 2)

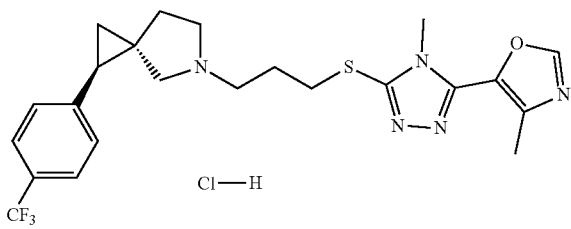

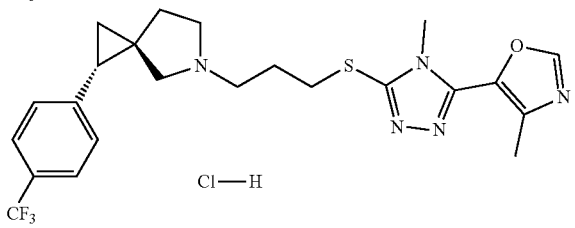

(1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (TRANS) (E8, 31 mg) was separated into the single enantiomers by preparative chiral HPLC.

Preparative Chromatography:

| Column | Chiralpak AD-H (25 × 2.0 cm), 5μ |
|---|---|
| Mobile phase | n-Hexane/Ethanol 50/50% v/v |
| Flow rate (ml/min) | 14 ml/min |
| DAD detection | 220 nm |
| Loop | 875 μL |
| Injection | 15.5 mg/injection |

Each enantiomer was treated with 1N HCl in Et$_2$O (1.2 eq) and evaporated affording (1R,3R or 1S,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E9, 8.3 mg), Enantiomer 1: ret. time 8.5 min, 100% ee, MS (m/z): 478.3 [MH]$^+$, and (1S,3S or 1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E10, 12.9 mg), Enantiomer 2: ret. time 10.9 min, 100% ee, MS (m/z): 478.3 [MH]$^+$.

Example 11: (1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (CIS, E11)

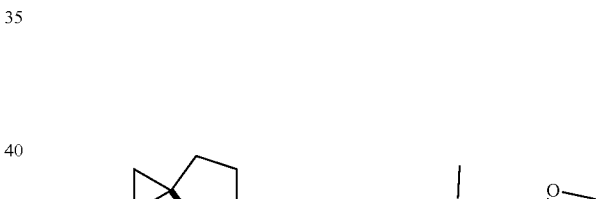

The compound was prepared as in Example 1, reacting (1R,3S/1S,3R)-1-[4-(trifluoromethyl)phenyl]-5-azaspiro[2.4]heptane (CIS, p14, 47 mg, 0.195 mmol), 3-[(3-chloropropyl)sulfanyl]-4-methyl-5-(4-methyl-1,3-oxazol-5-yl)-4H-1,2,4-triazole (p148, 58 mg, 0.21 mmol), Na$_2$CO$_3$ (22 mg, 0.21 mmol) and NaI (31 mg, 0.21 mmol) in DMF (0.2 mL) affording (1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (CIS) (E11, 29 mg, y=31%) as yellow oil. NMR: $^1$H NMR (Acetone-d$_6$) δ: 8.28 (s, 1H), 7.63 (d, 2H), 7.40 (d, 2H), 3.77 (s, 3H), 3.16-3.36 (m, 2H), 2.46-2.69 (m, 5H), 2.44 (s, 3H), 2.22-2.30 (m, 1H), 1.79-2.03 (m, 5H), 1.26-1.35 (m, 1H), 1.19-1.26 (m, 1H), MS (m/z): 478.3 [MH]$^+$.

Example 12 and Example 13: (1R,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E12, Enantiomer 1) and (1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E13, Enantiomer 2)

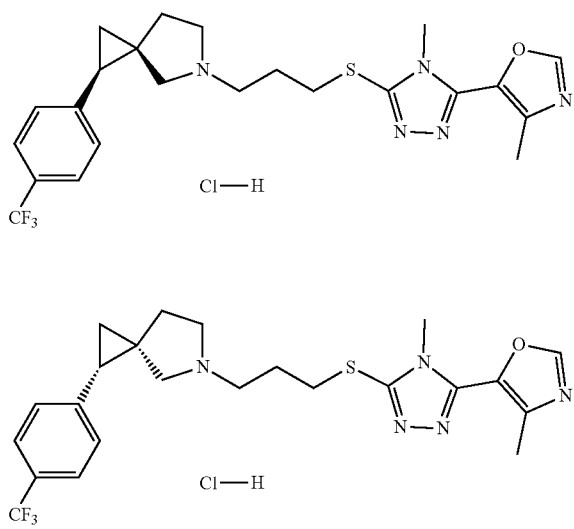 [SMILES: Cc1ncoc1-c1nnc(SCCCN2CC[C@]3(C[C@@H]3c3ccc(C(F)(F)F)cc3)C2)n1C ; Cl ; Cc1ncoc1-c1nnc(SCCCN2CC[C@@]3(C[C@H]3c3ccc(C(F)(F)F)cc3)C2)n1C ; Cl]

(1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane (CIS) (E11, 26 mg) was separated into the single enantiomers by preparative chiral HPLC.

Preparative Chromatography:

| | |
|---|---|
| Column | Chiralcel OJ-H (25 × 2.0 cm), 5μ |
| Mobile phase | n-Hexane/Ethanol 50/50% v/v |
| Flow rate (ml/min) | 14 ml/min |
| DAD detection | 220 nm |
| Loop | 750 μL |
| Injection | 13 mg/injection |

Each enantiomer was treated with 1N HCl in Et$_2$O (1.1 eq) and evaporated affording (1R,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E12, 3.1 mg), Enantiomer 1: ret. time 7.3 min, 100% ee, MS (m/z): 478.3 [MH]$^+$, and (1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.4]heptane hydrochloride (E13, 4.5 mg), Enantiomer 2: ret. time 9.7 min, 100% ee, MS (m/z): 478.3 [MH]$^+$.

Example 14: (1S,3S/1R,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (TRANS, E14)

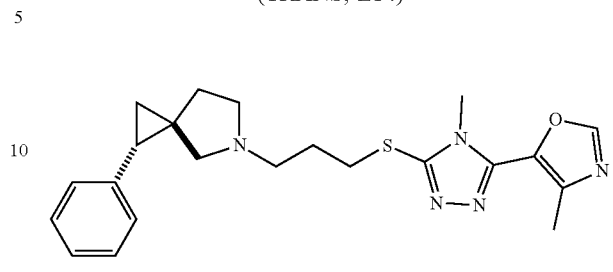

The compound was prepared as in Example 1, reacting (1S,3S/1R,3R)-1-phenyl-5-azaspiro[2.4]heptane (TRANS, p18, 77 mg, 0.44 mmol), 3-[(3-chloropropyl)sulfanyl]-4-methyl-5-(4-methyl-1,3-oxazol-5-yl)-4H-1,2,4-triazole (p148, 120 mg, 0.44 mmol), Na$_2$CO$_3$ (56 mg, 0.53 mmol) and NaI (79 mg, 0.53 mmol) in DMF (0.360 mL) affording (1S,3S/1R,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (TRANS, E14, 20.5 mg, y=11%). NMR: $^1$H NMR (Acetone-d$_6$) δ: 8.26 (s, 1H), 7.09-7.33 (m, 5H), 3.78 (s, 3H), 3.27-3.36 (m, 2H), 2.47-2.76 (m, 6H), 2.41 (s, 3H), 2.09-2.15 (m, 1H), 1.87-2.00 (m, 2H), 1.37-1.65 (m, 2H), 1.04-1.17 (m, 2H), MS (m/z): 410.3 [MH]$^+$.

Example 15 and Example 16: (1R,3R or 1S, 3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (E15, Enantiomer 1) and (1S,3S or 1R, 3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (E16, Enantiomer 2)

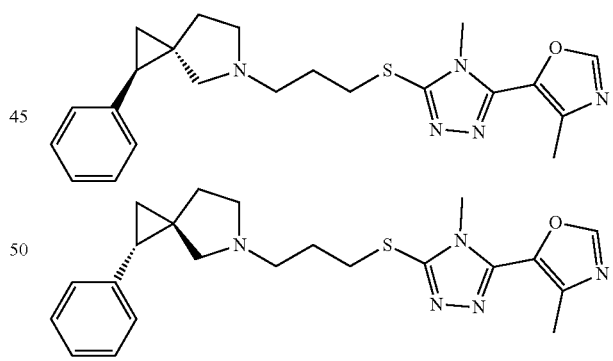

(1S,3S/1R,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (TRANS) (E14, 15 mg) was separated into the single enantiomers by preparative chiral HPLC.

Preparative Chromatography:

| | |
|---|---|
| Column | Chiralcel OJ-H (25 × 2 cm), 5 um |
| Mobile phase | n-Hexane/(Ethanol + 0.1% ipa) 25/75% v/v |
| Flow rate (ml/min) | 14 ml/min |
| DAD detection | 220 nm |

-continued

| Loop | 750 µL |
| Injection | 7 mg/injection | affording (1R,3R or 1S, 3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (E15, 5 mg), Enantiomer 1: ret. time 10.5 min, MS (m/z): 410.4 [MH]+ and (1S,3S or 1R, 3R)-5-(3-{[4-methyl-1,3-oxazol-5-yl)-4H-1,2,4-triazol-3-yl]sulfanyl}propyl)-1-phenyl-5-azaspiro[2.4]heptane (E16, 5 mg), Enantiomer 2: ret. time 12.1 min, MS (m/z): 410.4 [MH]+.

Example 17: (1R,3S/1S,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (CIS, E17)

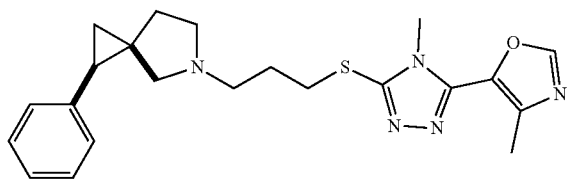

The compound was prepared as in Example 1, reacting (1R,3S/1S,3R)-1-phenyl-5-azaspiro[2.4]heptane (CIS, p19, 42 mg, 0.24 mmol), 3-[(3-chloropropyl)sulfanyl]-4-methyl-5-(4-methyl-1,3-oxazol-5-yl)-4H-1,2,4-triazole (p148, 65 mg, 0.24 mmol), Na$_2$CO$_3$ (31 mg, 0.29 mmol) and NaI (43 mg, 0.29 mmol) in DMF (0.2 mL) affording (1R,3S/1S,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (CIS, E17, 22.5 mg, y=23%). NMR: $^1$H NMR (Acetone-d$_6$) δ: 8.26 (s, 1H) 7.09-7.33 (m, 5H) 3.78 (s, 3H) 3.27-3.36 (m, 2H) 2.47-2.76 (m, 6H) 2.41 (s, 3H) 2.09-2.15 (m, 1H) 1.87-2.00 (m, 2H) 1.37-1.65 (m, 2H) 1.04-1.17 (m, 2H), MS (m/z): 410.3 [MH]+.

Example 18 and Example 19: (1S,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (E18, Enantiomer 1) and (1R,3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (E19, Enantiomer 2)

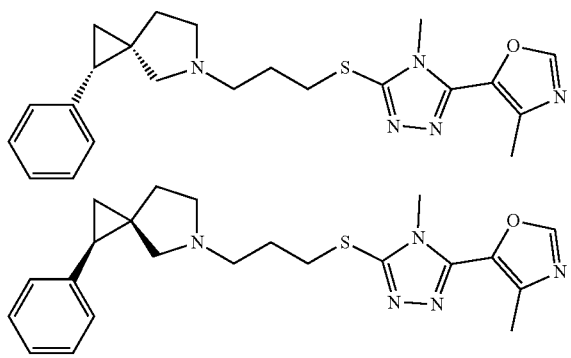

(1R,3S/1S,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (CIS) (E17, 17 mg) was separated into the single enantiomers by preparative chiral HPLC.
Preparative Chromatography:

| Column | Chiralpak AD-H (25 x 2 cm), 5 um |
| Mobile phase | n-Hexane/(Ethanol + 0.1% ipa) 55/45% v/v |
| Flow rate (ml/min) | 14 ml/min |
| DAD detection | 220 nm |
| Loop | 750 µL |
| Injection | 8.5 mg/injection | affording (1S,3R)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (E18, 6.6 mg), Enantiomer 1: ret. time 7.9 min, 100% ee, MS (m/z): 410.3 [MH]+ and (1R,3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (E19, 6.6 mg), Enantiomer 2: ret. time 9.3 min, 95.8% ee, MS (m/z): 410.3 [MH]+.

Example 20: (1R,3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane hydrochloride (E20, Enantiomer 2)

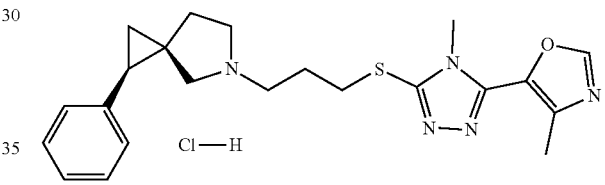

(1R,3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane (Enantiomer 2, E19, 27 mg) was treated with 1.1 eq of HCl in Et$_2$O affording (1R,3S)-5-(3-{[4-methyl-5-(4-methyl-1,3-oxazol-5-yl)-4H-1,2,4-triazol-3-yl]sulfanyl}propyl)-1-phenyl-5-azaspiro[2.4]heptane hydrochloric salt (Enantiomer 2, E20, 29 mg), MS (m/z): 410.4 [MH]+.

Example 21: (1R,3S/1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E21)

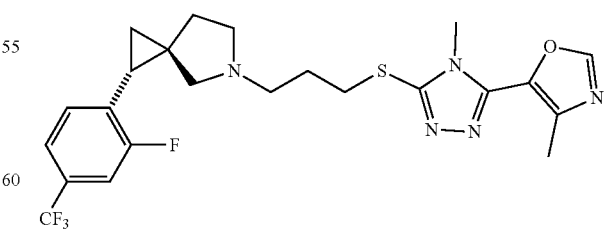

The compound was prepared as in Example 1, reacting (1R,3S/1S,3R)-1-[2-fluoro-4-(trifluoromethyl)phenyl]-5-azaspiro[2.4]heptane (TRANS, p22, 50 mg, 0.193 mmol), 3-[(3-chloropropyl)sulfanyl]-4-methyl-5-(4-methyl-1,3-oxazol-5-yl)-4H-1,2,4-triazole (p148, 58 mg, 0.212 mmol), Na₂CO₃ (25 mg, 0.23 mmol) and NaI (35 mg, 0.23 mmol) in DMF (0.2 mL) affording (1R,3S/1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E21, 59 mg, y=62%). NMR: ¹H NMR (Acetone-d₆) δ: 8.27 (s, 1H), 7.49 (m, 2H), 7.29-7.37 (m, 1H), 3.80 (s, 3H), 3.32-3.38 (m, 2H), 2.47-3.12 (m, 6H), 2.42 (s, 3H), 2.35 (m, 1H), 1.69 (br. s., 1H), 1.42 (br. s., 1H), 1.28-1.39 (m, 3H), MS (m/z): 496.3 [MH]⁺.

Example 22 and Example 23: (1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (E22, TRANS, Enantiomer 1) and (1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (E23, TRANS, Enantiomer 2)

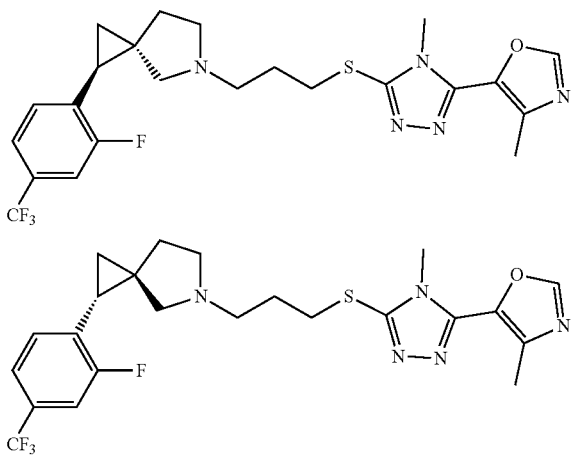

(1R,3S/1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS) (E21, 57 mg) was separated into the single enantiomers by preparative chiral HPLC.

Preparative Chromatography:

| Column | Chiralpak AD-H (25 x 2 cm), 5 um |
|---|---|
| Mobile phase | n-Hexane/(Ethanol + 0.1% ipa) 55/45% v/v |
| Flow rate (ml/min) | 14 ml/min |
| DAD detection | 220 nm |
| Loop | 500 µL |
| Injection | 11 mg/injection | affording (1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (E22, 19.4 mg), Enantiomer 1: ret. time 7.7 min, 100% ee, MS (m/z): 496.3 [MH]⁺ and (1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl] sulfanyl}propyl)-5-azaspiro[2.4]heptane (E23, 19.7 mg) Enantiomer 2: ret. time 9.3 min, 98.6% ee, MS (m/z): 496.3 [MH]⁺.

Example 24: (1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E24, TRANS, Enantiomer 1)

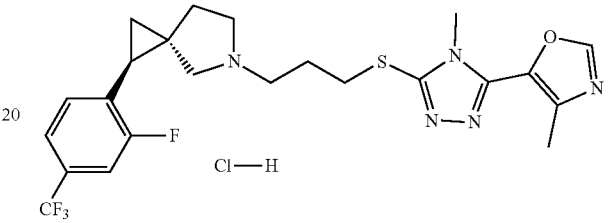

(1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 1, E22, 19.4 mg) was treated with 1.1 eq of HCl in Et₂O affording (1S,3R or 1R,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (Enantiomer 1, E24, 18 mg). MS (m/z): 496.3 [MH]⁺.

Example 25: (1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E25, TRANS, Enantiomer 2)

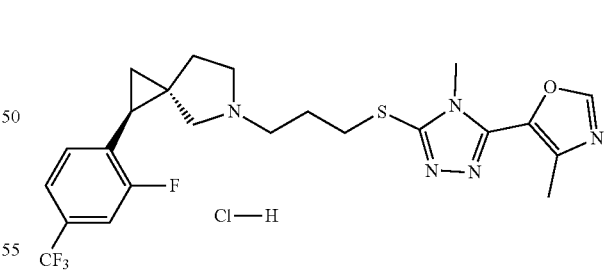

(1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (Enantiomer 2, E23, 19.4 mg) was treated with 1.1 eq of HCl in Et₂O affording (1R,3S or 1S,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (Enantiomer 2, E25, 18 mg). MS (m/z): 496.3 [MH]⁺.

Example 26: (1S,3S/1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E26)

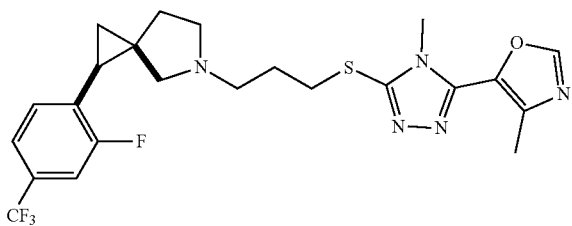

The compound was prepared as in Example 1, reacting (1S,3S/1R,3R)-1-[2-fluoro-4-(trifluoromethyl)phenyl]-5-azaspiro[2.4]heptane (CIS, p23, 50 mg, 0.193 mmol), 3-[(3-chloropropyl)sulfanyl]-4-methyl-5-(4-methyl-1,3-oxazol-5-yl)-4H-1,2,4-triazole (p148, 58 mg, 0.212 mmol), $Na_2CO_3$ (25 mg, 0.23 mmol) and NaI (35 mg, 0.23 mmol) in DMF (0.2 mL) affording (1S,3S/1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E26, 39 mg, y=41%). NMR: $^1$H NMR (Acetone-$d_6$) δ: 8.27 (s, 1H), 7.49 (d, 2H), 7.38 (s, 1H), 3.76 (s, 3H), 3.20-3.35 (m, 2H), 2.87-3.19 (m, 3H), 2.42 (s, 3H), 2.33-2.39 (m, 1H), 2.10-2.19 (m, 1H), 1.92-2.02 (m, 2H), 1.42-1.50 (m, 1H), 1.27-1.36 (m, 2H), MS (m/z): 496.3 $[MH]^+$.

Example 27 and Example 28: (1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (E27, CIS, Enantiomer 1) and (1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (E28, CIS, Enantiomer 2)

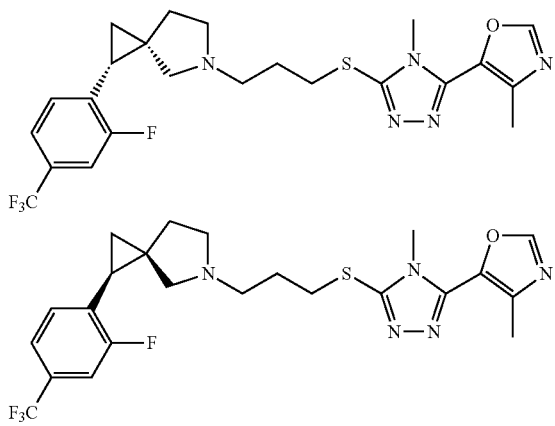

(1S,3S/1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E26, 37 mg) was separated into the single enantiomers by preparative chiral HPLC.

Preparative Chromatography:

| | |
|---|---|
| Column | Chiralpak AD-H (25 x 2 cm), 5 um |
| Mobile phase | n-Hexane/(Ethanol + 0.1% ipa) 70/30% v/v |
| Flow rate (ml/min) | 14 ml/min |
| DAD detection | 220 nm |
| Loop | 500 µL |
| Injection | 9 mg/injection | affording (1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E27, 14 mg) Enantiomer 1: ret. time 7.6 min, 100% ee, MS (m/z): 496.3 $[MH]^+$ and (1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E28, 13.8 mg) Enantiomer 2: ret. time 8.8 min, 94.6% ee, MS (m/z): 496.3 $[MH]^+$.

Example 29: (1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E29, CIS, Enantiomer 1)

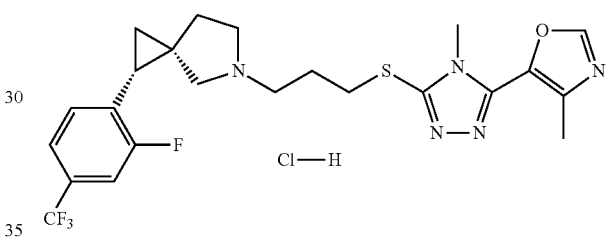

(1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E27, 14 mg) was treated with 1.2 eq of HCl in $Et_2O$ affording (1R,3R)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (Enantiomer 1, CIS, E29, 11 mg). MS (m/z): 496.3 $[MH]^+$.

Example 30: (1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E30, CIS, Enantiomer 2)

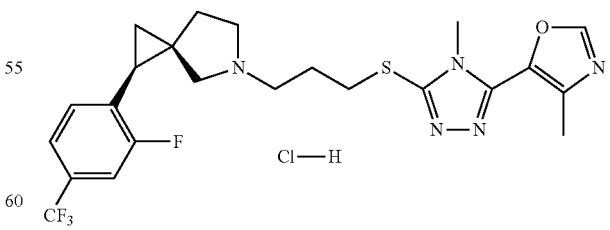

(1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E28, 13.8 mg) was treated with 1.2 eq of HCl in $Et_2O$ affording (1S,3S)-1-[2-fluoro-4-(trifluoromethyl)phenyl]-5-(3-{[4- methyl-5-(4-methyl-1,3-oxazol-5-yl)-4H-1,2,4-triazol-3-yl]sulfanyl}propyl)-5-azaspiro[2.4]heptane hydrochloric salt (Enantiomer 2, CIS, E30, 11 mg). MS (m/z): 496.3 [MH]+.

Example 31: (1R,3S/1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E31)

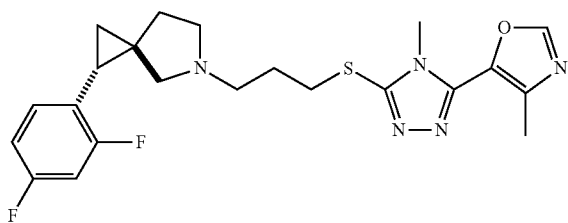

The compound was prepared as in Example 1, reacting (1R,3S/1S,3R)-1-(2,4-difluorophenyl)-5-azaspiro[2.4]heptane (TRANS, p28, 0.24 mmol), 3-[(3-chloropropyl)sulfanyl]-4-methyl-5-(4-methyl-1,3-oxazol-5-yl)-4H-1,2,4-triazole (p148, 71 mg, 0.26 mmol), Na$_2$CO$_3$ (31 mg, 0.29 mmol) and NaI (43 mg, 0.29 mmol) in DMF (0.2 mL) affording (1R,3S/1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E31, 45 mg, y=42%). NMR: $^1$H NMR (Acetone-d$_6$) δ: 8.26-8.29 (m, 1H), 7.06-7.17 (m, 1H), 6.93-7.05 (m, 2H), 3.81 (s, 3H), 3.33 (s, 2H), 2.52-2.74 (m, 6H), 2.44 (s, 3H), 2.12-2.19 (m, 1H), 1.93-2.02 (m, 2H), 1.54 (d, 1H), 1.29-1.40 (m, 1H), 1.17-1.24 (m, 1H), 1.11-1.16 (m, 1H). MS (m/z): 446.4 [MH]+.

Example 32 and Example 33: (1R,3S or 1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E32, TRANS, Enantiomer 1) and (1S,3R or 1R,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E33, TRANS, Enantiomer 2)

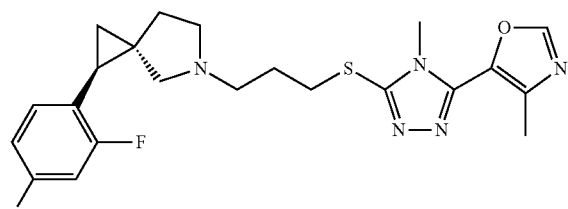

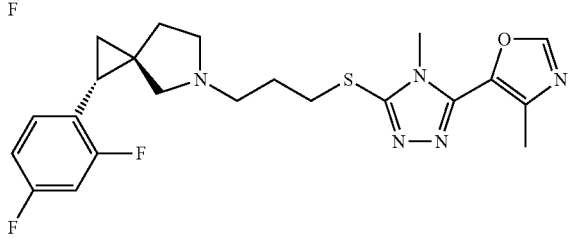

(1R,3S/1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E31, 45 mg) was separated into the single enantiomers by preparative chiral HPLC.

Preparative Chromatography:

| | |
|---|---|
| Column | Chiralpak AD-H (25 x 2.1 cm), 5 µ |
| Mobile phase | (Methanol + 0.1% isopropylamine) 18% |
| Flow rate (ml/min) | 45 ml/min |
| DAD detection | 220 nm |
| Loop | 700 µL |
| Injection | 15.1 mg/injection | affording (1R,3S or 1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E32, 10.8 mg) Enantiomer 1: ret. time 11.5 min, 100% ee, MS (m/z): 446.4 [MH]+ and (1S,3R or 1R,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E33, 14.6 mg) Enantiomer 2: ret. time 15.5 min, 100% ee, MS (m/z): 446.4 [MH]+.

Example 34: (1R,3S or 1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E34, TRANS, Enantiomer 1)

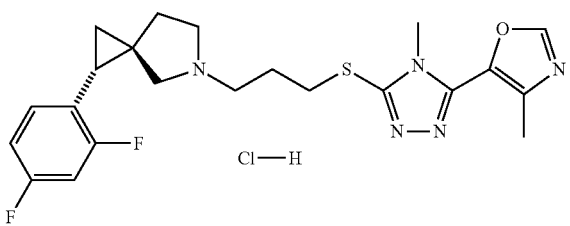

(1R,3S or 1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E32, 10.8 mg) was treated with 1.1 eq of HCl in Et$_2$O affording (1R,3S or 1S,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (TRANS, Enantiomer 1, E34, 11 mg). MS (m/z): 446.5 [MH]+.

Example 35: (1S,3R or 1R,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E35, TRANS, Enantiomer 2)

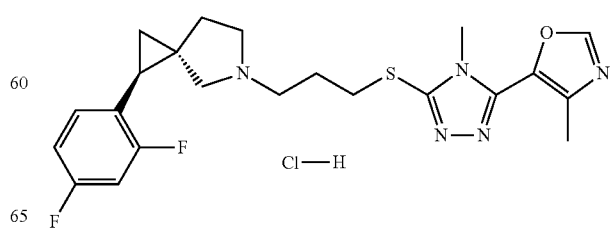

(1S,3R or 1R,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E33, 14.6 mg) was treated with 1.1 eq of HCl in Et$_2$O affording (1S,3R or 1R,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (TRANS, Enantiomer 2, E35, 14.6 mg). MS (m/z): 446.5 [MH]$^+$.

Example 36: (1S,3S/1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E36)

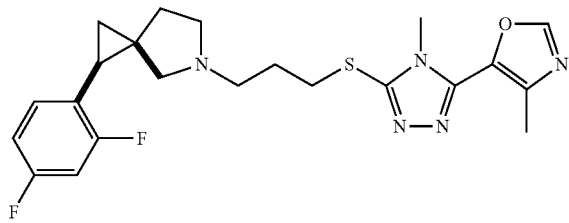

The compound was prepared as in Example 1, reacting (1S,3S/1R,3R)-1-(2,4-difluorophenyl)-5-azaspiro[2.4]heptane (CIS, p29, 50 mg, 0.24 mmol), 3-[(3-chloropropyl)sulfanyl]-4-methyl-5-(4-methyl-1,3-oxazol-5-yl)-4H-1,2,4-triazole (p148, 71 mg, 0.26 mmol), Na$_2$CO$_3$ (31 mg, 0.29 mmol) and NaI (43 mg, 0.29 mmol) in DMF (0.2 mL) affording (1S,3S/1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E36, 52 mg, y=49%). NMR: $^1$H NMR (Acetone-d) δ: 8.28 (s, 1H), 7.09-7.19 (m, 1H), 6.88-7.04 (m, 2H), 3.77 (s, 5H), 3.19-3.31 (m, 2H), 2.73-2.78 (m, 1H), 2.57-2.65 (m, 1H), 2.46-2.55 (m, 2H), 2.43 (s, 3H), 2.34-2.39 (m, 1H), 2.09-2.14 (m, 1H), 1.93-2.01 (m, 3H), 1.84 (m, 2H), 1.18-1.25 (m, 1H), 1.11-1.16 (m, 1H), MS (m/z): 446.4 [MH]$^+$.

Example 37 and Example 38: (1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E37, CIS, Enantiomer 1) and (1S,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E38, CIS, Enantiomer 2)

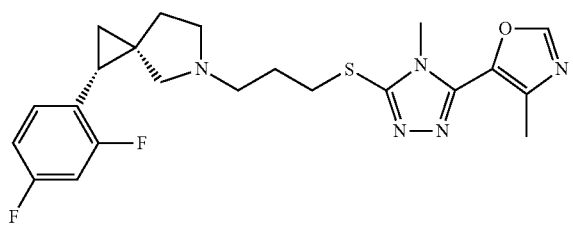

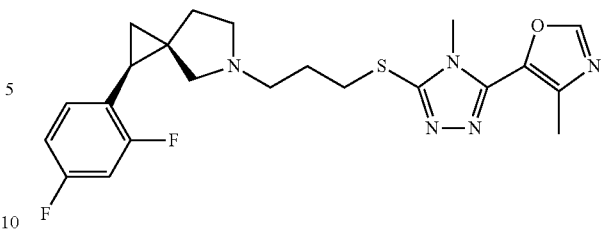

(1S,3S/1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS) (E36, 50 mg) was separated into the single enantiomers by preparative chiral HPLC (SFC).

Preparative Chromatography:

| Column | Chiralpak AD-H (25 x 2.1 cm), 5 µ |
|---|---|
| Mobile phase | (Methanol + 0.1% isopropylamine) 12% |
| Flow rate (ml/min) | 45 ml/min |
| DAD detection | 220 nm |
| Loop | 700 µL |
| Injection | 17.5 mg/injection | affording (1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E37, 14.4 mg), Enantiomer 1: ret. time 14.1 min, 100% ee, MS (m/z): 446.4 [MH]$^+$ and (1S,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E38, 17.1 mg) Enantiomer 2: ret. time 18.5 min, 98.8% ee, MS (m/z): 446.4 [MH]$^+$.

Example 39: (1S,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E39, CIS, Enantiomer 2)

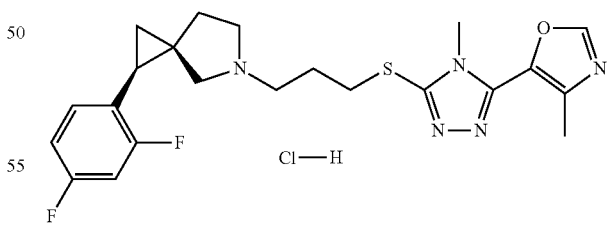

(1S,3S)-1-[2-fluoro-4-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, E38, 17.1 mg) was treated with 1.1 eq of HCl in Et$_2$O affording (1S,3S)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (CIS, Enantiomer 2, E39, 18 mg). MS (m/z): 446.4 [MH]$^+$.

Example 40: (1S,3S/1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E40)

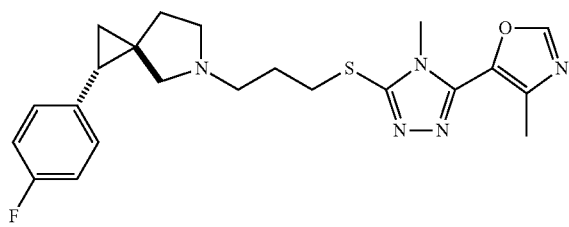

The compound was prepared as in Example 1, reacting (1S,3S/1R,3R)-1-(4-fluorophenyl)-5-azaspiro[2.4]heptane (TRANS, p32, 50 mg, 0.26 mmol), 3-[(3-chloropropyl)sulfanyl]-4-methyl-5-(4-methyl-1,3-oxazol-5-yl)-4H-1,2,4-triazole (p148, 79 mg, 0.29 mmol), Na$_2$CO$_3$ (31 mg, 0.29 mmol) and NaI (43 mg, 0.29 mmol) in DMF (0.2 mL) affording (1S,3S/1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E40, 42 mg, y=38%). NMR: $^1$H NMR (Acetone-d$_6$) δ: 8.25-8.31 (m, 1H), 7.11-7.21 (m, 2H), 7.00-7.11 (m, 2H), 3.80 (s, 3H), 3.29-3.37 (m, 2H), 2.66-2.75 (m, 1H), 2.50-2.66 (m, 5H), 2.44 (s, 3H), 2.10-2.17 (m, 1H), 1.90-2.02 (m, 2H), 1.48-1.63 (m, 1H), 1.35-1.47 (m, 1H), 1.11-1.19 (m, 1H), 1.04-1.08 (m, 1H) MS (m/z): 428.4 [MH]$^+$.

Example 41 and Example 42: (1R,3R or 1S,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E41, TRANS, Enantiomer 1) and (1S,3S or 1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E42, TRANS, Enantiomer 2)

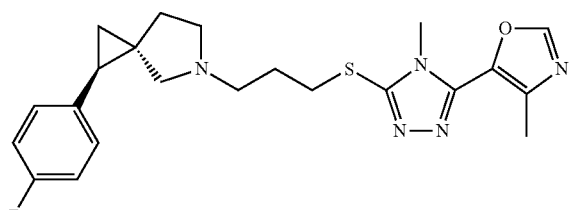

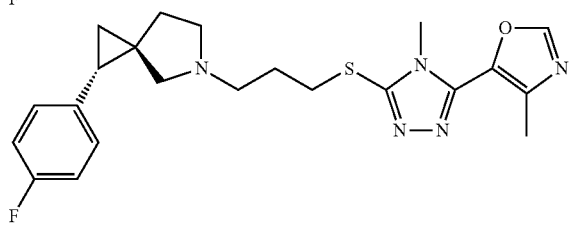

(1S,3S/1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E40, 40 mg) was separated into the single enantiomers by preparative chiral HPLC (SFC).

Preparative Chromatography:

| Column | Chiralpak AD-H (25 x 2.1 cm), 5 μ |
|---|---|
| Modifier | (Methanol + 0.1% isopropylamine) 20% |
| Flow rate (ml/min) | 45 ml/min |
| Pressure (bar) | 120 |
| Temperature (° C.) | 38 |
| DAD detection | 220 nm |
| Loop | 700 μL |
| Injection | 14 mg/injection | affording (1R,3R or 1S,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E41, 14.5 mg), Enantiomer 1: ret. time 11.7 min, 100% ee, MS (m/z): 428.4 [MH]$^+$ and (1S,3S or 1R,3R)-1-(2,4-difluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E42, 14 mg), Enantiomer 2: ret. time 16.3 min, 100% ee, MS (m/z): 428.5 [MH]$^+$.

Example 43: (1R,3R or 1S,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E43, TRANS, Enantiomer 1)

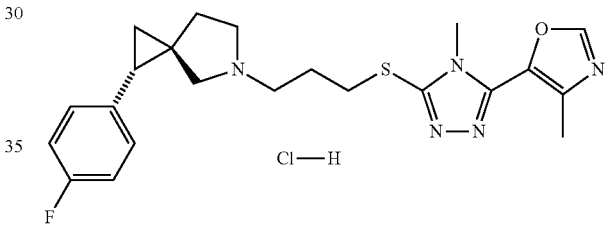

(1R,3R or 1S,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E41, 14.5 mg) was treated with 1.2 eq of HCl in Et$_2$O affording (1R,3R or 1S,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (TRANS, Enantiomer 1, E43, 14.7 mg). MS (m/z): 428.5 [MH]$^+$.

Example 44: (1S,3S or 1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (TRANS, E44, Enantiomer 2)

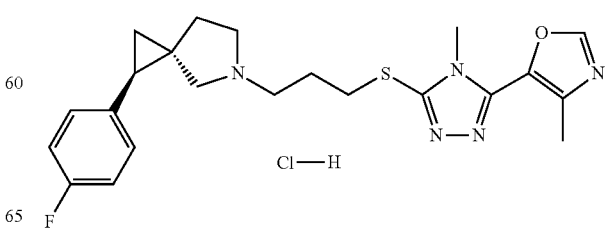

(1S,3S or 1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E42, 14 mg) was treated with 1.2 eq of HCl in Et$_2$O affording (1S,3S or 1R,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (TRANS, Enantiomer 2, E44, 14.3 mg). MS (m/z): 428.5 [MH]$^+$.

Example 45: (1R,3S/1S,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E45)

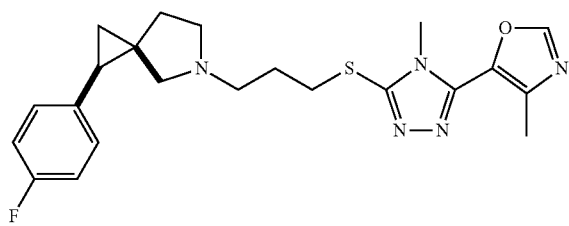

The compound was prepared as in Example 1, reacting (1R,3S/1S,3R)-1-(4-fluorophenyl)-5-azaspiro[2.4]heptane (CIS, p33, 50 mg, 0.26 mmol), 3-[(3-chloropropyl)sulfanyl]-4-methyl-5-(4-methyl-1,3-oxazol-5-yl)-4H-1,2,4-triazole (p148, 79 mg, 0.29 mmol), Na$_2$CO$_3$ (31 mg, 0.29 mmol) and NaI (43 mg, 0.29 mmol) in DMF (0.2 mL) affording (1R,3S/1S,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E45, 52 mg, y=46%). NMR: $^1$H NMR (Acetone-d$_6$) δ: 8.26-8.30 (m, 1H), 7.16-7.21 (m, 2H), 7.00-7.08 (m, 2H), 3.77 (s, 3H), 3.15-3.31 (m, 2H), 2.62-2.75 (m, 2H), 2.50 (m, 2H), 2.43 (s, 3H), 2.37 (d, 1H), 2.09-2.13 (m, 2H), 1.89-1.99 (m, 2H), 1.79-1.88 (m, 2H), 1.06-1.14 (m, 2H), MS (m/z): 428.4 [MH]$^+$.

Example 46 and Example 47: (1S,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E46, CIS, Enantiomer 1) and (1R,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E47, CIS, Enantiomer 2)

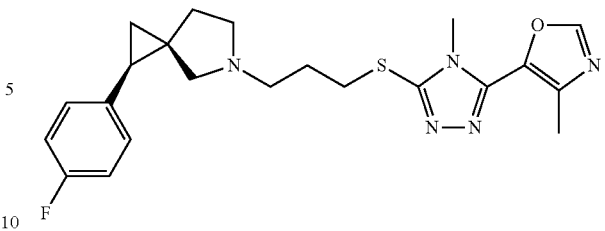

(1R,3S/1S,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E45, 50 mg) was separated into the single enantiomers by preparative chiral HPLC (SFC).

Preparative Chromatography:

| | |
|---|---|
| Column | Chiralpak AD-H (25 x 2.1 cm), 5 μ |
| Modifier | (Methanol + 0.1% isopropylamine) 17% |
| Flow rate (ml/min) | 46 ml/min |
| Pressure (bar) | 120 |
| Temperature (° C.) | 38 |
| DAD detection | 220 nm |
| Loop | 700 μL |
| Injection | 17.5 mg/injection | affording (1S,3R)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E46, 17.9 mg), Enantiomer 1: ret. time 12.1 min, 100% ee, MS (m/z): 428.4 [MH]$^+$ and (1R,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (E47, 18.6 mg) Enantiomer 2: ret. time 15.0 min, 100% ee, MS (m/z): 428.4 [MH]$^+$.

Example 48: (1R,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (E48, CIS, Enantiomer 2)

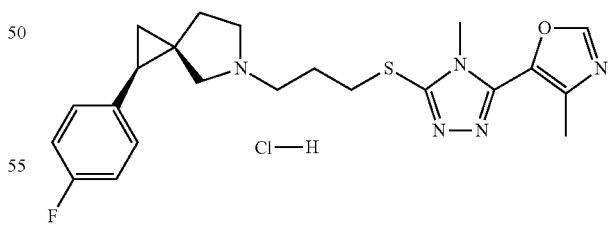

(1R,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E47, 18.6 mg) was treated with 1.1 eq of HCl in Et$_2$O affording (1R,3S)-1-(4-fluorophenyl)-5-(3-{[4-methyl-5-(4-methyl-1,3-oxazol-5-yl)-4H-1,2,4-triazol-3-yl]sulfanyl}propyl)-5-azaspiro[2.4]heptane hydrochloric salt (CIS, Enantiomer 2, E48, 20 mg). MS (m/z): 428.5 [MH]$^+$.

Example 49: (1S,3S/1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane hydrochloride (TRANS, E49)

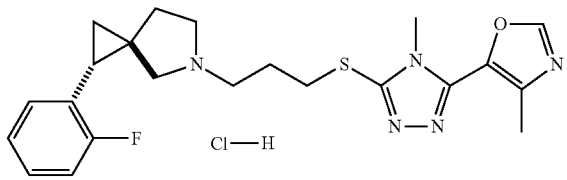

The compound was prepared as in Example 1, reacting (1S,3S/1R,3R)-1-[2-(trifluoromethyl)phenyl]-5-azaspiro[2.4]heptane (TRANS, p40, 30 mg, 0.12 mmol), 3-[(3-chloropropyl)sulfanyl]-4-methyl-5-(4-methyl-1,3-oxazol-5-yl)-4H-1,2,4-triazole (p148, 36 mg, 0.13 mmol), Na$_2$CO$_3$ (15 mg, 0.144 mmol) and NaI (22 mg, 0.144 mmol) in DMF (0.13 mL) affording (1S,3S/1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane that was dissolved in Et$_2$O and DCM and salified with 1.2 eq of HCl 1M in Et$_2$O to obtain (1S,3S/1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane hydrochloride (TRANS, E49, 9 mg, y=13%). NMR: $^1$H NMR (DMSO-d$_6$) δ: 10.13-10.56 (m, 1H), 8.58 (s, 1H), 7.74-7.80 (m, 1H), 7.60-7.68 (m, 1H), 7.43-7.52 (m, 1H), 7.36 (d, 1H), 3.71 (s, 3H), 3.49-3.68 (m, 2H), 3.28 (m, 4H), 3.12-3.22 (m, 1H), 2.93-3.07 (m, 1H), 2.48 (br. s., 2H), 2.39 (s, 3H), 2.10 (br. s., 2H), 1.52-1.72 (m, 2H), 1.32-1.50 (m, 2H). MS (m/z): 478.4 [MH]$^+$.

Example 50 and Example 51: (1R,3R or 1S,3S)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (E50, TRANS, Enantiomer 1) and (1S,3S or 1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (E51, TRANS, Enantiomer 2)

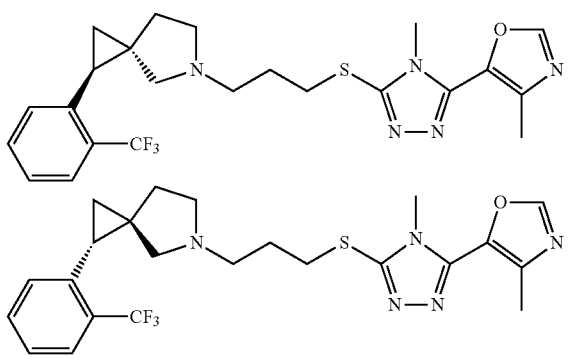

(1S,3S/1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (TRANS, 55 mg) prepared as in Example 1, reacting (1S,3S/1R,3R)-1-[2-(trifluoromethyl)phenyl]-5-azaspiro[2.4]heptane (TRANS, p40, 50 mg, 0.21 mmol), 3-[(3-chloropropyl)sulfanyl]-4-methyl-5-(4-methyl-1,3-oxazol-5-yl)-4H-1,2,4-triazole (p148, 63 mg, 0.23 mmol), Na$_2$CO$_3$ (27 mg, 0.25 mmol) and NaI (38 mg, 0.25 mmol) in DMF (0.2 mL) was separated into the single enantiomers by preparative chiral HPLC.

Preparative Chromatography:

| | |
|---|---|
| Column | Chiralpak AD-H (25 x 2.0 cm), 5 μ |
| Mobile phase | n-Hexane/(Ethanol + 0.1% isopropylamine) 70/30% v/v |
| Flow rate (ml/min) | 16 ml/min |
| DAD detection | 220 nm |
| Loop | 500 μL |
| Injection | 7 mg/injection | affording (1R,3R or 1S,3S)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (TRANS, E50, 17.7 mg) Enantiomer 1: ret. time 7.2 min, 100% ee, MS (m/z): 478.4 [MH]$^+$ and (1S,3S or 1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (TRANS, E51, 19.4 mg) Enantiomer 2: ret. time 8.4 min, 95.5% ee, MS (m/z): 478.5 [MH]$^+$.

Example 52: (1R,3R or 1S,3S)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane hydrochloride (E52, TRANS, Enantiomer 1)

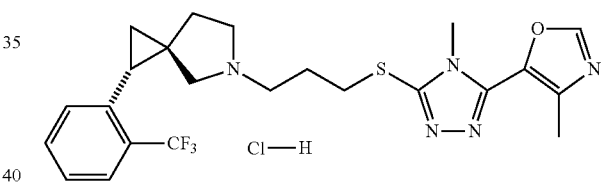

(1R,3R or 1S,3S)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (TRANS, E50, 17.7 mg) was treated with 1.2 eq of HCl in Et$_2$O affording (1R,3R or 1S,3S)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane hydrochloric salt (TRANS, Enantiomer 1, E52, 17.5 mg). MS (m/z): 478.4 [MH]$^+$.

Example 53: (1S,3S or 1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane hydrochloride (TRANS, E53, Enantiomer 2)

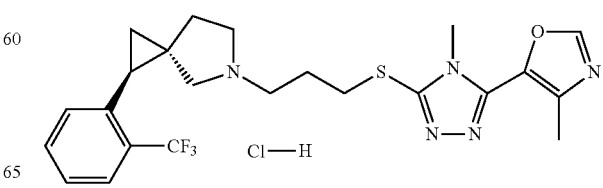

(1S,3S or 1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (TRANS, E51, 19.4 mg) was treated with 1.2 eq of HCl in Et$_2$O affording (1S,3S or 1R,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane hydrochloric salt (TRANS, Enantiomer 2, E53, 13 mg). MS (m/z): 478.4 [MH]$^+$.

Example 54: (1R,3S/1S,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (CIS, E54)

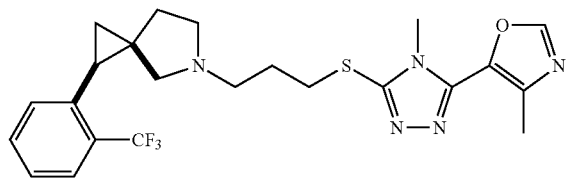

The compound was prepared as in Example 1, reacting (1R,3S/1S,3R)-1-[2-(trifluoromethyl)phenyl]-5-azaspiro[2.4]heptane (CIS, p41, 30 mg, 0.12 mmol), 3-[(3-chloropropyl)sulfanyl]-4-methyl-5-(4-methyl-1,3-oxazol-5-yl)-4H-1,2,4-triazole (p148, 36 mg, 0.13 mmol), Na$_2$CO$_3$ (15 mg, 0.144 mmol) and NaI (22 mg, 0.144 mmol) in DMF (0.13 mL) affording (1R,3S/1S,3R)-5-(3-{[4-methyl-5-(4-methyl-1,3-oxazol-5-yl)-4H-1,2,4-triazol-3-yl]sulfanyl}propyl)-1-[2-(trifluoromethyl)phenyl]-5-azaspiro[2.4]heptane (CIS, E54, 26 mg, y=45%). NMR: $^1$H NMR (Acetone-d$_6$) δ: 8.29 (s, 1H), 7.71-7.78 (m, 1H), 7.54-7.62 (m, 1H), 7.38-7.47 (m, 1H), 7.27-7.33 (m, 1H), 3.77 (s, 3H), 3.17-3.37 (m, 3H), 2.83-3.06 (m, 2H), 2.60 (br. s., 4H), 2.44 (s, 3H), 2.41 (br. s., 1H), 1.80-2.02 (m, 4H), 1.51-1.60 (m, 1H), 1.14-1.25 (m, 1H), MS (m/z): 478.4 [MH]$^+$.

Example 55: (1R,3S or 1S,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (CIS, E55, Enantiomer 1)

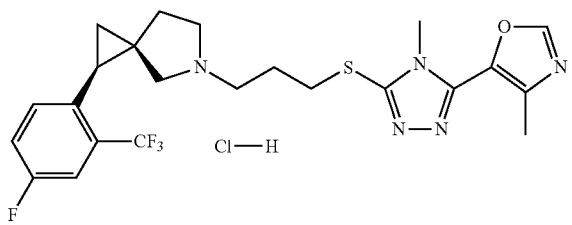

The compound was prepared as in Example 1, reacting (1R,3S or 1S,3R)-1-[4-fluoro-2-(trifluoromethyl)phenyl]-5-azaspiro[2.4]heptane (CIS, Enantiomer 1, p48, 25 mg, 0.096 mmol), 3-[(3-chloropropyl)sulfanyl]-4-methyl-5-(4-methyl-1,3-oxazol-5-yl)-4H-1,2,4-triazole (p148, 29 mg, 0.1 mmol), Na$_2$CO$_3$ (12 mg, 0.115 mmol) and NaI (17 mg, 0.115 mmol) in DMF (0.11 mL) affording (1R,3S or 1S,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, 30 mg, 0.06 mmol) that was dissolved in Et$_2$O and DCM and salified with 1.2 eq of HCl 1M in Et$_2$O to obtain (1R,3S or 1S,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (CIS, Enantiomer 1, E55, 30 mg, y=58%) as yellow solid. NMR: $^1$H NMR (DMSO-d$_6$) δ: 10.12 (br. s., 1H), 8.57 (s, 1H), 7.66 (d, 1H), 7.49 (m., 1H), 7.33-7.42 (m, 1H), 3.72-3.84 (m, 1H), 3.61-3.69 (m, 3H), 3.39-3.25 (m, 6H), 2.84-3.00 (m, 1H), 2.52-2.62 (m, 2H), 2.37 (s, 3H), 1.91-2.27 (m, 4H), 1.61-1.75 (m, 1H), 1.22-1.42 (m, 1H), MS (m/z): 496.4 [MH]$^+$.

Example 56: (1S,3R or 1R,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (CIS, E56, Enantiomer 2)

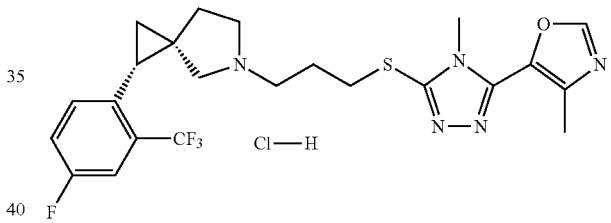

The compound was prepared as in Example 1, reacting (1S,3R or 1R,3S)-1-[4-fluoro-2-(trifluoromethyl)phenyl]-5-azaspiro[2.4]heptane (CIS, Enantiomer 2, p49, 25 mg, 0.096 mmol), 3-[(3-chloropropyl)sulfanyl]-4-methyl-5-(4-methyl-1,3-oxazol-5-yl)-4H-1,2,4-triazole (p148, 29 mg, 0.1 mmol), Na$_2$CO$_3$ (12 mg, 0.115 mmol) and NaI (17 mg, 0.115 mmol) in DMF (0.11 mL) affording (1S,3R or 1R,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (CIS, 29 mg, 0.06 mmol) that was dissolved in Et$_2$O and DCM and salified with 1.2 eq of HCl 1M in Et$_2$O to obtain (1S,3R or 1R,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (CIS, Enantiomer 2, E56, 30 mg, y=58%) as yellow solid. NMR: $^1$H NMR (DMSO-d$_6$) δ: 9.84-10.29 (m, 1H), 8.57 (s, 1H), 7.66 (d, 1H), 7.44-7.54 (m, 1H), 7.32-7.42 (m, 1H), 3.71-3.82 (m, 1H), 3.61-3.70 (m, 3H), 3.04-3.24 (m, 6H), 2.85-2.99 (m, 1H), 2.52-2.62 (m, 2H), 2.37 (s, 3H), 2.11-2.01 (m, 4H), 1.61-1.74 (m, 1H), 1.26 (m, 1H), MS (m/z): 496.4 [MH]$^+$.

Example 57: (1S,3S or 1R,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (TRANS, E57, Enantiomer 1)

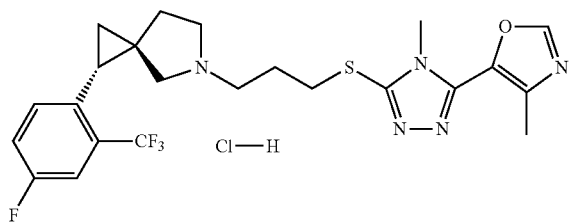

The compound was prepared as in Example 1, reacting (1S,3S or 1R,3R)-1-[4-fluoro-2-(trifluoromethyl)phenyl]-5-azaspiro[2.4]heptane (TRANS, Enantiomer 1, p46, 25 mg, 0.096 mmol), 3-[(3-chloropropyl)sulfanyl]-4-methyl-5-(4-methyl-1,3-oxazol-5-yl)-4H-1,2,4-triazole (p148, 29 mg, 0.1 mmol), $Na_2CO_3$ (12 mg, 0.115 mmol) and NaI (17 mg, 0.115 mmol) in DMF (0.11 mL) affording (1S,3S or 1R,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E1, 24 mg, 0.048 mmol) that was dissolved in $Et_2O$ and DCM and salified with 1.2 eq of HCl 1M in $Et_2O$ to obtain (1S,3S or 1R,3R)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (TRANS, Enantiomer 1, E57, 24 mg, y=47%) as yellow solid. NMR: $^1$H NMR (DMSO-$d_6$) δ: 9.93-10.30 (m, 1H), 8.57 (s, 1H), 7.61-7.70 (m, 1H), 7.46-7.55 (m, 1H), 7.36-7.44 (m, 1H), 3.69 (s, 4H), 3.48-3.62 (m, 2H), 3.34-3.39 (m, 1H), 3.27 (d, 3H), 3.10-3.22 (m, 1H), 2.94-3.08 (m, 1H), 2.41-2.47 (m, 1H), 2.38 (s, 3H), 2.09 (br. s., 2H), 1.51-1.70 (m, 2H), 1.39-1.49 (m, 1H), 1.30-1.39 (m, 1H), MS (m/z): 496.4 [MH]$^+$.

Example 58: (1R,3R or 1S,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (TRANS, E58, Enantiomer 2)

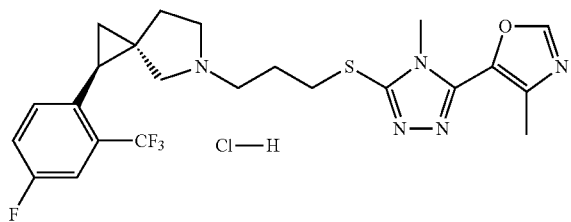

The compound was prepared as in Example 1, reacting (1R,3R or 1S,3S)-1-[4-fluoro-2-(trifluoromethyl)phenyl]-5-azaspiro[2.4]heptane (TRANS, Enantiomer 2, p47, 25 mg, 0.096 mmol), 3-[(3-chloropropyl)sulfanyl]-4-methyl-5-(4-methyl-1,3-oxazol-5-yl)-4H-1,2,4-triazole (p148, 29 mg, 0.1 mmol), $Na_2CO_3$ (12 mg, 0.115 mmol) and NaI (17 mg, 0.115 mmol) in DMF (0.11 mL) affording (1R,3R or 1S,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E2, 29 mg, 0.006 mmol) that was dissolved in $Et_2O$ and DCM and salified with 1.2 eq of HCl 1M in $Et_2O$ to obtain (1R,3R or 1S,3S)-1-[4-fluoro-2-(trifluoromethyl)phenyl]-5-(3-{[4-methyl-5-(4-methyl-1,3-oxazol-5-yl)-4H-1,2,4-triazol-3-yl]sulfanyl}propyl)-5-azaspiro[2.4]heptane hydrochloride (TRANS, Enantiomer 2, E58, 29 mg, y=57%) as yellow solid. NMR: $^1$H NMR (DMSO-$d_6$) δ:10.15 (br. s., 1H), 8.57 (s, 1H), 7.66 (d, 1H), 7.51 (br. s., 1H), 7.38-7.46 (m, 1H), 3.69 (s, 4H), 3.47-3.63 (m, 2H), 3.35-3.46 (m, 1H), 3.11-3.27 (m, 4H), 2.94-3.08 (m, 1H), 2.41-2.47 (m, 1H), 2.38 (s, 3H), 2.02-2.15 (m, 2H), 1.52-1.68 (m, 2H), 1.40-1.50 (m, 1H), 1.28-1.38 (m, 1H), MS (m/z): 496.4 [MH]$^+$.

Example 59: (1S,3S/1R,3R)-1-(3,5-dichlorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E59)

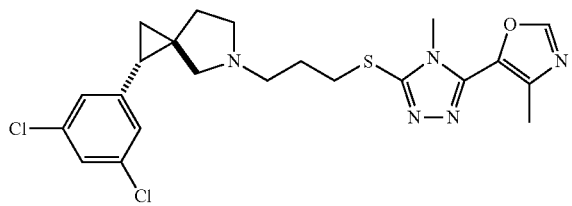

The compound was prepared as in Example 1, reacting (1S,3S/1R,3R)-1-(3,5-dichlorophenyl)-5-azaspiro[2.4]heptane (TRANS, p36, 55 mg, 0.227 mmol), 3-[(3-chloropropyl)sulfanyl]-4-methyl-5-(4-methyl-1,3-oxazol-5-yl)-4H-1,2,4-triazole (p148, 68 mg, 0.25 mmol), $Na_2CO_3$ (29 mg, 0.27 mmol) and NaI (40 mg, 0.27 mmol) in DMF (0.2 mL) affording (1S,3S/1R,3R)-1-(3,5-dichlorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (TRANS, E59, 23 mg, y=21%). NMR: $^1$H NMR (Acetone-$d_6$) δ: 8.30 (s, 1H), 7.32 (s, 3H), 3.82 (s, 3H), 3.37-3.53 (m, 3H), 2.79-2.84 (m, 2H), 2.44 (s, 3H), 2.33-2.41 (m, 1H), 2.13-2.22 (m, 2H), 1.79-1.90 (m, 2H), 1.51-1.72 (m, 3H), 1.28-1.44 (m, 3H). MS (m/z): 478.3 [M]$^+$.

Example 60: (1R,3S/1S,3R)-1-(3,5-dichlorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E60)

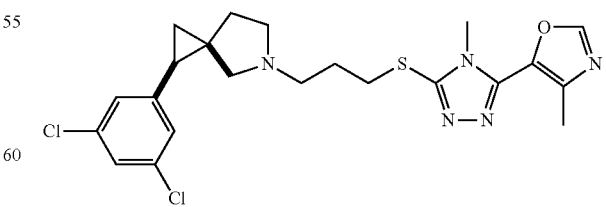

The compound was prepared as in Example 1, reacting (1R,3S/1S,3R)-1-(3,5-dichlorophenyl)-5-azaspiro[2.4]heptane (CIS, p37, 55 mg, 0.227 mmol), 3-[(3-chloropropyl)sulfanyl]-4-methyl-5-(4-methyl-1,3-oxazol-5-yl)-4H-1,2,4- triazole (p148, 68 mg, 0.249 mmol), Na₂CO₃ (29 mg, 0.272 mmol) and NaI (40 mg, 0.272 mmol) in DMF (0.13 mL) affording (1R,3S/1S,3R)-1-(3,5-dichlorophenyl)-5-(3-{[4-methyl-5-(4-methyl-1,3-oxazol-5-yl)-4H-1,2,4-triazol-3-yl]sulfanyl}propyl)-5-azaspiro[2.4]heptane (CIS, E60, 37 mg, y=34%). NMR: ¹H NMR (Acetone-d₆) δ: 8.28 (s, 1H), 7.27-7.31 (m, 1H), 7.22 (s, 2H), 3.78 (s, 3H), 3.25-3.36 (m, 2H), 2.78-2.85 (m, 3H), 2.43 (s, 3H), 2.24-2.39 (m, 2H), 2.08 (br. s., 2H), 1.97 (d, 4H), 1.22-1.52 (m, 3H). MS (m/z): 477.9 [M]⁺.

Example 61: (1R,3S/1S,3R)-5-(3-{[4-methyl-5-(4-methyl-1,3-oxazol-5-yl)-4H-1,2,4-triazol-3-yl]sulfanyl}propyl)-1-[6-(trifluoromethyl)pyridin-3-yl]-5-azaspiro[2.4]heptane (CIS, E61)

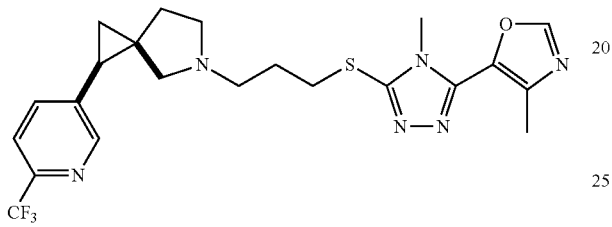

The compound was prepared as in Example 1, reacting (1R,3S/1S,3R)-1-[6-(trifluoromethyl)pyridin-3-yl]-5-azaspiro[2.4]heptane (CIS, p52, 40 mg, 0.165 mmol), 3-[(3-chloropropyl)sulfanyl]-4-methyl-5-(4-methyl-1,3-oxazol-5-yl)-4H-1,2,4-triazole (p148, 50 mg, 0.18 mmol), Na₂CO₃ (21 mg, 0.2 mmol) and NaI (30 mg, 0.2 mmol) in DMF (0.2 mL) affording (1R,3S/1S,3R)-5-(3-{[4-methyl-5-(4-methyl-1,3-oxazol-5-yl)-4H-1,2,4-triazol-3-yl]sulfanyl}propyl)-1-[6-(trifluoromethyl)pyridin-3-yl]-5-azaspiro[2.4]heptane (CIS, E61, 34 mg, y=43%). NMR: ¹H NMR (Acetone-d₆) δ: 8.62 (s, 1H), 8.28 (s, 1H), 7.69-7.85 (m, 2H), 3.77 (s, 3H), 3.16-3.37 (m, 2H), 2.73 (br. s., 1H), 2.47-2.71 (m, 4H), 2.44 (s, 3H), 2.26-2.34 (m, 1H), 2.09-2.15 (m, 2H), 1.94-2.04 (m, 2H), 1.80-1.93 (m, 2H), 1.35-1.43 (m, 1H), 1.27-1.34 (m, 1H). MS (m/z): 479.4 [MH]⁺.

Example 62: (1S,3S/1R,3R)-5-(3-{[4-methyl-5-(oxan-4-yl)-4H-1,2,4-triazol-3-yl]-sulfanyl}propyl)-1-[4-(trifluoromethyl)phenyl]-5-azaspiro[2.4]heptane (TRANS, E62)

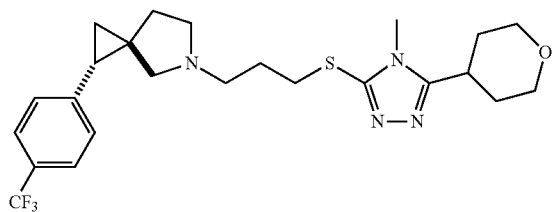

The compound was prepared as in Example 1, reacting (1S,3S/1R,3R)-1-[4-(trifluoromethyl)phenyl]-5-azaspiro[2.4]heptane (TRANS, p13, 50 mg, 0.207 mmol), 3-[(3-chloropropyl)sulfanyl]-4-methyl-5-(oxan-4-yl)-4H-1,2,4-triazole (p149, 63 mg, 0.228 mmol), Na₂CO₃ (26 mg, 0.25 mmol) and NaI (38 mg, 0.25 mmol) in DMF (0.2 mL) affording (1S,3S/1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (TRANS, E62, 49 mg, y=49%). NMR: ¹H NMR (CDCl₃) δ: 7.56 (d, 2H), 7.09-7.26 (d, 2H), 4.06-4.18 (m, 2H), 3.46-3.63 (m, 6H), 3.27 (s, 2H), 2.66-3.05 (m, 6H), 2.00-2.34 (m, 6H), 1.81-1.97 (m, 3H), 1.26-1.38 (m, 1H), 1.12-1.23 (m, 1H). MS (m/z): 481.5 [MH]⁺.

Example 63 and Example 64: (1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (E63, Enantiomer 1) and (1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (E64, Enantiomer 2)

(1S,3S/1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (TRANS, E62, 49 mg) was separated into the single enantiomers by preparative chiral HPLC.

Preparative Chromatography:

| | |
|---|---|
| Column | Chiralcel OJ-H (25 x 2 cm), 5 um |
| Mobile phase | n-Hexane/(Ethanol/Methanol 1/1 + 0.1% isopropylamine) 80/20 v/v |
| Flow rate (ml/min) | 16 ml/min |
| DAD detection | 220 nm |
| Loop | 500 μL |
| Injection | 11.5 mg/injection | affording (1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (E63, 18 mg) Enantiomer 1: ret. time 7.6 min, 100% ee, MS (m/z): 481.5 [MH]⁺ and (1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (E64, 19 mg), Enantiomer 2: ret. time 9.1 min, 100% ee, MS (m/z): 481.5 [MH]⁺.

Example 65: (1R,3R or 1S,3S)-5-(3-{[4-methyl-5-(oxan-4-yl)-4H-1,2,4-triazol-3-yl]-sulfanyl}propyl)-1-[4-(trifluoromethyl)phenyl]-5-azaspiro[2.4]heptane hydrochloride (E65, Enantiomer 1)

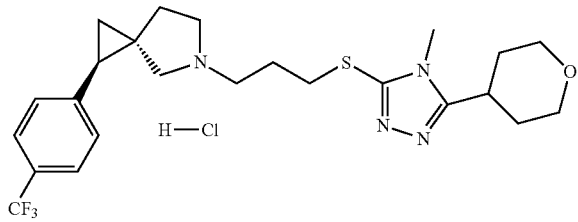

(1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (E63, 18 mg) was treated with 1.2 eq of HCl in Et$_2$O affording (1R,3R or 1S,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane hydrochloric salt (Enantiomer 1, E65, 19 mg). MS (m/z): 481.5 [MH]$^+$.

Example 66: (1S,3S or 1R,3R)-5-(3-{[4-methyl-5-(oxan-4-yl)-4H-1,2,4-triazol-3-yl]-sulfanyl}propyl)-1-[4-(trifluoromethyl)phenyl]-5-azaspiro[2.4]heptane hydrochloride (E66, Enantiomer 2)

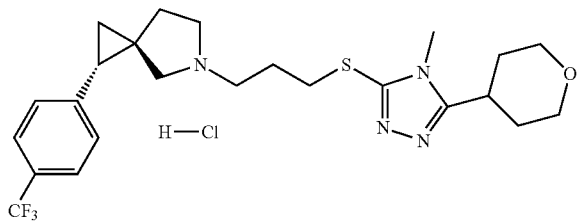

(1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (E64, 19 mg) was treated with 1.2 eq of HCl in Et$_2$O affording (1S,3S or 1R,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane hydrochloric salt (Enantiomer 2, E66, 20 mg). MS (m/z): 481.5 [MH]$^+$.

Example 67: (1R,3S/1S,3R)-5-(3-{[4-methyl-5-(oxan-4-yl)-4H-1,2,4-triazol-3-yl]-sulfanyl}propyl)-1-[4-(trifluoromethyl)phenyl]-5-azaspiro[2.4]heptane (CIS, E67)

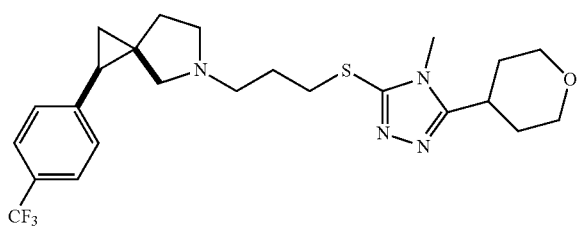

The compound was prepared as in Example 1, reacting (1R,3S/1S,3R)-1-[4-(trifluoromethyl)phenyl]-5-azaspiro[2.4]heptane (CIS, p14, 35 mg, 0.145 mmol), 3-[(3-chloropropyl)sulfanyl]-4-methyl-5-(oxan-4-yl)-4H-1,2,4-triazole (p149, 44 mg, 0.16 mmol), Na$_2$CO$_3$ (19 mg, 0.174 mmol) and NaI (26 mg, 0.174 mmol) in DMF (0.14 mL) affording (1R,3S/1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (CIS, E67, 30 mg, y=43%). NMR: $^1$H NMR (Acetone-d$_6$) δ: 7.63 (d, 2H), 7.41 (s, 2H), 3.93-4.07 (m, 2H), 3.58 (s, 3H), 3.47-3.56 (m, 2H), 3.31-3.35 (m, 1H), 3.05-3.23 (m, 3H), 2.42-2.71 (m, 5H), 2.20-2.30 (m, 1H), 1.76-2.02 (m, 8H), 1.28-1.35 (m, 1H), 1.19-1.26 (m, 1H). MS (m/z): 481.4 [MH]$^+$.

Example 68 and Example 69: (1R,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (CIS, E68, Enantiomer 1) and (1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (CIS, E69, Enantiomer 2)

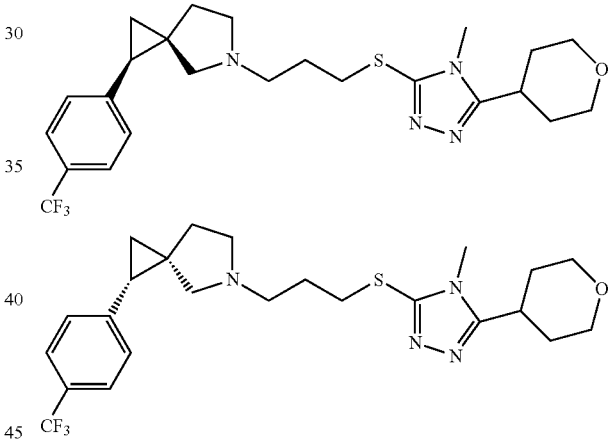

(1R,3S/1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (CIS, E67, 28 mg) was separated into the single enantiomers by preparative chiral HPLC.

Preparative Chromatography:

| | |
|---|---|
| Column | Chiralcel OJ-H (25 x 2 cm), 5 um |
| Mobile phase | n-Hexane/Ethanol 65/35% v/v |
| Flow rate (ml/min) | 14 ml/min |
| DAD detection | 220 nm |
| Loop | 1000 µL |
| Injection | 14 mg/injection | affording (1R,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (CIS, E68, 10.8 mg). Enantiomer 1: ret. time 8.4 min, 100% ee, MS (m/z): 481.3 [MH]$^+$ and (1S,3R)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (CIS, E69, 10.7 mg). Enantiomer 2: ret. time 11.9 min, 100% ee. MS (m/z): 481.3 [MH]⁺.

Example 70: (1R,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane hydrochloride (E70, CIS, Enantiomer 1)

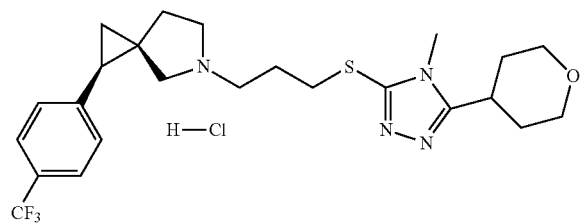

(1R,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane (CIS, E68, 10.8 mg) was treated with 1.2 eq of HCl in Et₂O affording (1R,3S)-5-(3-{[4-methyl-5-(oxan-4-yl)-4H-1,2,4-triazol-3-yl]sulfanyl}propyl)-1-[4-(trifluoromethyl)phenyl]-5-azaspiro[2.4]heptane hydrochloric salt (Enantiomer 1, CIS, E70, 11 mg). MS (m/z): 481.3 [MH]⁺.

Example 71: (1R,3S/1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS, E71)

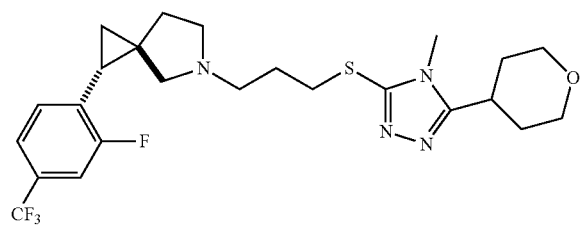

The compound was prepared as in Example 1, reacting (1R,3S/1S,3R)-1-[2-fluoro-4-(trifluoromethyl)phenyl]-5-azaspiro[2.4]heptane (TRANS, p22, 50 mg, 0.193 mmol), 3-[(3-chloropropyl)sulfanyl]-4-methyl-5-(oxan-4-yl)-4H-1,2,4-triazole (p149, 58 mg, 0.212 mmol), Na₂CO₃ (25 mg, 0.23 mmol) and NaI (35 mg, 0.23 mmol) in DMF (0.2 mL) affording (1R,3S/1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS, E71, 40 mg, y=41%). NMR: ¹H NMR (Acetone-d₆) δ: 7.50 (m, 2H), 7.32 (br. s., 1H), 3.99 (d, 2H), 3.62 (s, 3H), 3.48-3.57 (m, 2H), 3.19-3.28 (m, 2H), 3.07-3.17 (m, 1H), 2.53-2.74 (m, 6H), 2.29-2.36 (m, 1H), 1.89 (br. s., 6H), 1.57-1.71 (m, 2H), 1.26-1.43 (m, 4H). MS (m/z): 499.4 [MH]⁺.

Example 72 and Example 73: (1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (E72, TRANS, Enantiomer 1) and (1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (E73, TRANS, Enantiomer 2)

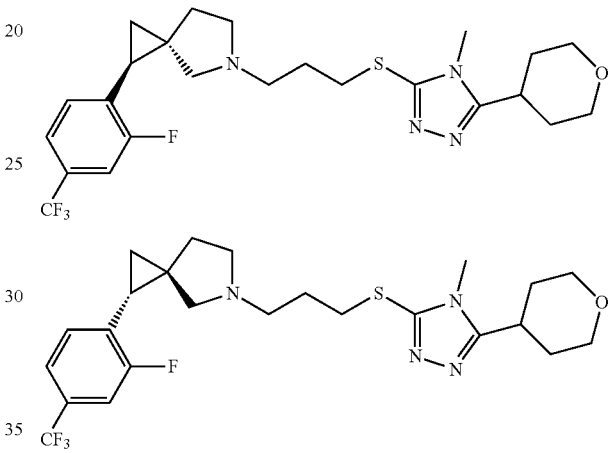

(1R,3S/1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS, E71, 38 mg) was separated into the single enantiomers by preparative chiral HPLC.

Preparative Chromatography:

| Column | Chiralpak AD-H (25 x 2.0 cm), 5 μ |
|---|---|
| Mobile phase | n-Hexane/(Ethanol + 0.1% isopropylamine) 60/40% v/v |
| Flow rate (ml/min) | 14 ml/min |
| DAD detection | 220 nm |
| Loop | 500 μL |
| Injection | 9.5 mg/injection | affording (1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS, E72, 13 mg). Enantiomer 1: ret. time 8.1 min, 100% ee. MS (m/z): 499.4 [MH]⁺ and (1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS, E73, 13 mg). Enantiomer 2: ret. time 9.4 min, 98.8% ee. MS (m/z): 499.4 [MH]⁺.

Example 74: (1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane hydrochloride (E74, TRANS, Enantiomer 1)

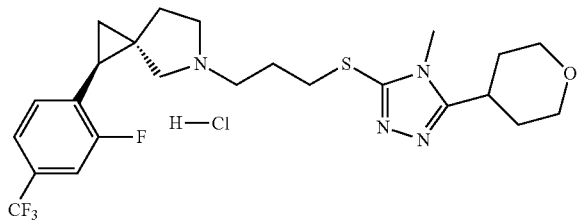

(1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS, E72, 13 mg) was treated with 1.2 eq of HCl in Et$_2$O affording (1S,3R or 1R,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane hydrochloric salt (Enantiomer 1, TRANS, E74, 12 mg). MS (m/z): 499.4 [MH]$^+$.

Example 75: (1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane hydrochloride (E75, TRANS, Enantiomer 2)

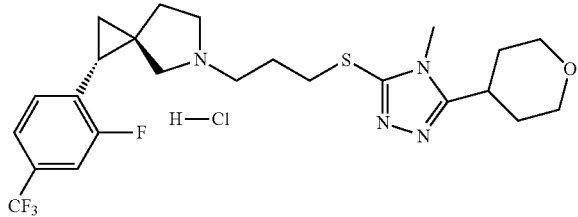

(1R,3S or 1S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (TRANS, E73, 13.8 mg) was treated with 1.2 eq of HCl in Et$_2$O affording (1R,3S or 1 S,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane hydrochloric salt (Enantiomer 2, TRANS, E75, 12 mg). MS (m/z): 499.4 [MH]$^+$.

Example 76: (1S,3S/1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (CIS, E76)

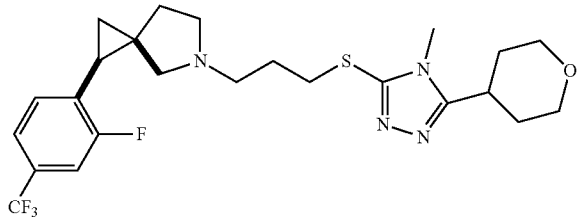

The compound was prepared as in Example 1, reacting (1S,3S/1R,3R)-1-[2-fluoro-4-(trifluoromethyl)phenyl]-5-azaspiro[2.4]heptane (CIS, p23, 50 mg, 0.193 mmol), 3-[(3-chloropropyl)sulfanyl]-4-methyl-5-(oxan-4-yl)-4H-1,2,4-triazole (p149, 58 mg, 0.212 mmol), Na$_2$CO$_3$ (25 mg, 0.23 mmol) and NaI (35 mg, 0.23 mmol) in DMF (0.2 mL) affording the title compound (1S,3S/1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (CIS, E76, 45 mg, y=47%). NMR: $^1$H NMR (Acetone-d$_6$) δ: 7.45-7.52 (m, 2H), 7.35 (m, 1H), 3.98 (m, 2H), 3.46-3.59 (m, 5H), 3.03-3.21 (m, 4H), 2.40-2.70 (m, 5H), 2.24-2.33 (m, 1H), 2.02 (d, 2H), 1.74-1.94 (m, 6H), 1.39 (m, 1H), 1.25 (m, 1H). MS (m/z): 499.4 [MH]$^+$.

Example 77 and Example 78: (1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (E77, CIS, Enantiomer 1) and (1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (E78, CIS, Enantiomer 2)

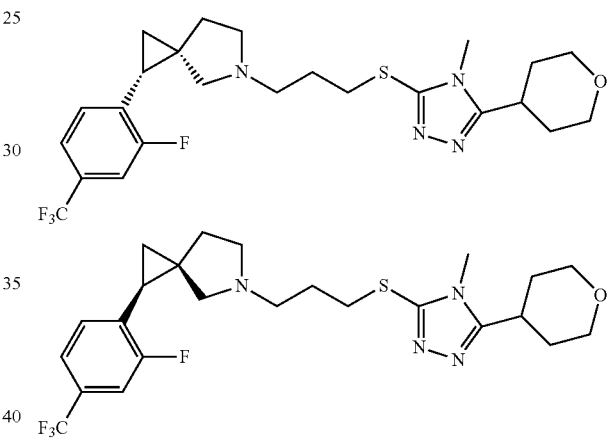

(1S,3S/1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (CIS, E76, 42 mg) was separated into the single enantiomers by preparative chiral HPLC.

Preparative Chromatography:

| | |
|---|---|
| Column | Chiralpak AD-H (25 x 2 cm), 5 um |
| Mobile phase | n-Hexane/(Ethanol + 0.1% isopropylamine) 70/30% v/v |
| Flow rate (ml/min) | 14 ml/min |
| DAD detection | 220 nm |
| Loop | 1000 μL |
| Injection | 14 mg/injection | affording (1R,3R)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (CIS, E77, 15 mg). Enantiomer 1: ret. time 8.2 min, 100% ee. MS (m/z): 499.4 [MH]$^+$ and (1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (CIS, E78, 15 mg). Enantiomer 2: ret. time 9.5 min, 97% ee. MS (m/z): 499.4 [MH]$^+$.

Example 79: (1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane hydrochloride (E79, CIS, Enantiomer 2)

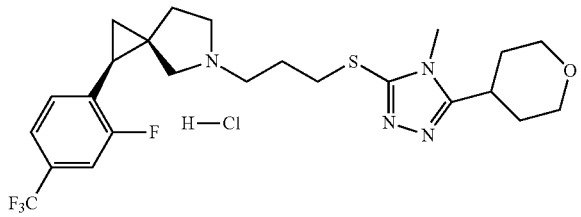

(1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane (CIS, E78, 15 mg) was treated with 1.2 eq of HCl in Et$_2$O affording (1S,3S)-1-[2-fluoro-4-(trifluoromethyl)phenyl]-5-(3-{[4-methyl-5-(oxan-4-yl)-4H-1,2,4-triazol-3-yl]sulfanyl}propyl)-5-azaspiro[2.4]heptane hydrochloric salt (Enantiomer 2, CIS, E79, 16.6 mg). MS (m/z): 499.4 [MH]$^+$.

Example 80: (1R,3S/1S,3R)-5-(3-{[4-methyl-5-(oxan-4-yl)-4H-1,2,4-triazol-3-yl]-sulfanyl}propyl)-1-phenyl-5-azaspiro[2.4]heptane (CIS, E80)

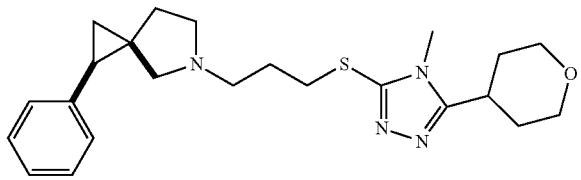

The compound was prepared as in Example 1, reacting (1R,3S/1S,3R)-1-phenyl-5-azaspiro[2.4]heptane (CIS, p19, 50 mg, 0.29 mmol), 3-[(3-chloropropyl)sulfanyl]-4-methyl-5-(oxan-4-yl)-4H-1,2,4-triazole (p149, 80 mg, 0.29 mmol), Na$_2$CO$_3$ (37 mg, 0.348 mmol) and NaI (52 mg, 0.348 mmol) in DMF (0.2 mL) affording the title compound (1R,3S/1S,3R)-5-(3-{[4-methyl-5-(oxan-4-yl)-4H-1,2,4-triazol-3-yl]sulfanyl}propyl)-1-phenyl-5-azaspiro[2.4]heptane (CIS, E80, 23 mg, y=19%). NMR: $^1$H NMR (Acetone-d$_6$) δ: 7.24-7.35 (m, 2H), 7.11-7.19 (m, 3H), 3.99 (m, 2H), 3.59 (s, 3H), 3.48-3.57 (m, 2H), 3.06-3.22 (m, 3H), 2.34-2.71 (m, 5H), 2.14 (br. s., 1H), 2.11 (d, 1H), 1.76-2.01 (m, 8H), 1.08-1.23 (m, 2H). MS (m/z): 413.4 [MH]$^+$.

Example 81 and Example 82: (1S,3R)-5-(3-{[4-methyl-5-(oxan-4-yl)-4H-1,2,4-triazol-3-yl]sulfanyl}propyl)-1-phenyl-5-azaspiro[2.4]heptane (E81, CIS, Enantiomer 1) and (1R,3S)-5-(3-{[4-methyl-5-(oxan-4-yl)-4H-1,2,4-triazol-3-yl]sulfanyl}propyl)-1-phenyl-5-azaspiro[2.4]heptane (E82, CIS, Enantiomer 2)

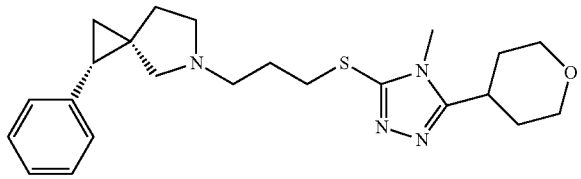

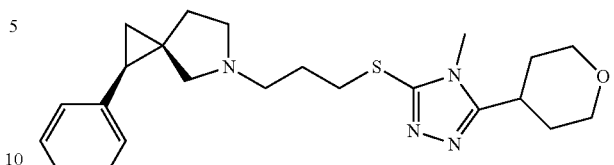

(1R,3S/1S,3R)-5-(3-{[4-methyl-5-(oxan-4-yl)-4H-1,2,4-triazol-3-yl]sulfanyl}propyl)-1-phenyl-5-azaspiro[2.4]heptane (CIS, E80, 22 mg) was separated into the single enantiomers by preparative chiral HPLC.

Preparative Chromatography:

| | |
|---|---|
| Column | Chiralpak AD-H (25 x 2.0 cm), 5 µ |
| Mobile phase | n-Hexane/(Ethanol + 0.1% isopropylamine) 62/38% v/v |
| Flow rate (ml/min) | 14 ml/min |
| DAD detection | 220 nm |
| Loop | 700 µL |
| Injection | 7.4 mg/injection | affording (1S,3R)-5-(3-{[4-methyl-5-(oxan-4-yl)-4H-1,2,4-triazol-3-yl]sulfanyl}propyl)-1-phenyl-5-azaspiro[2.4]heptane (CIS, E81, 8 mg). Enantiomer 1: ret. time 8.4 min, 100% ee. MS (m/z): 413.4 [MH]$^+$ and (1R,3S)-5-(3-{[4-methyl-5-(oxan-4-yl)-4H-1,2,4-triazol-3-yl]sulfanyl}propyl)-1-phenyl-5-azaspiro[2.4]heptane (CIS, E82, 9 mg). Enantiomer 2: ret. time 10.3 min, 100% ee. MS (m/z): 413.4 [MH]$^+$.

Example 83: (1R,3S)-5-(3-{[4-methyl-5-(oxan-4-yl)-4H-1,2,4-triazol-3-yl]sulfanyl}propyl)-1-phenyl-5-azaspiro[2.4]heptane hydrochloride (E83, CIS, Enantiomer 2)

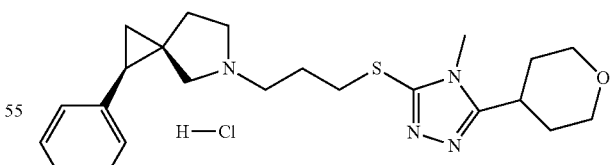

(1R,3S)-5-(3-{[4-methyl-5-(oxan-4-yl)-4H-1,2,4-triazol-3-yl]sulfanyl}propyl)-1-phenyl-5-azaspiro[2.4]heptane (CIS, E82, 9 mg) was treated with 1.2 eq of HCl in Et$_2$O affording (1R,3S)-5-(3-{[4-methyl-5-(oxan-4-yl)-4H-1,2,4-triazol-3-yl]sulfanyl}propyl)-1-phenyl-5-azaspiro[2.4]heptane hydrochloric salt (Enantiomer 2, CIS, E83, 7.8 mg). MS (m/z): 413.4 [MH]$^+$.

Example 84: (1R,3S/1S,3R)-5-(3-{[4-methyl-5-(oxan-4-yl)-4H-1,2,4-triazol-3-yl]sulfanyl}propyl)-1-[6-(trifluoromethyl)pyridin-3-yl]-5-azaspiro[2.4]heptane (CIS, E84)

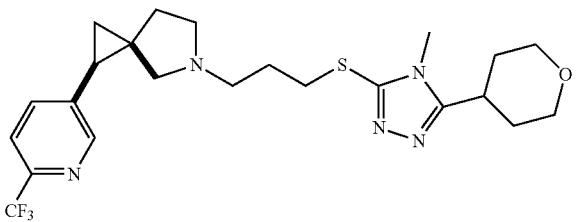

The compound was prepared as in Example 1, reacting (1R,3S/1S,3R)-1-[6-(trifluoromethyl)pyridin-3-yl]-5-azaspiro[2.4]heptane (CIS, p52, 60 mg, 0.247 mmol), 3-[(3-chloropropyl)sulfanyl]-4-methyl-5-(oxan-4-yl)-4H-1,2,4-triazole (p149, 75 mg, 0.272 mmol), $Na_2CO_3$ (31 mg, 0.3 mmol) and NaI (44 mg, 0.3 mmol) in DMF (0.2 mL) affording the title compound (1R,3S/1S,3R)-5-(3-{[4-methyl-5-(oxan-4-yl)-4H-1,2,4-triazol-3-yl]sulfanyl}propyl)-1-[6-(trifluoromethyl)pyridin-3-yl]-5-azaspiro[2.4]heptane (CIS, E84, 25 mg, y=21%). NMR: $^1$H NMR (Acetone-$d_6$) δ: 8.62 (s, 1H), 7.73-7.84 (m, 2H), 3.95-4.04 (m, 2H), 3.58 (s, 3H), 3.49-3.56 (m, 2H), 3.05-3.25 (m, 4H), 2.46-2.74 (m, 5H), 2.28-2.37 (m, 1H), 2.10-2.19 (m, 2H), 1.79-1.97 (m, 7H), 1.37-1.48 (m, 1H), 1.28-1.36 (m, 1H). MS (m/z): 482.5 [MH]$^+$.

Example 85: (1R,3S/1S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (CIS, E85)

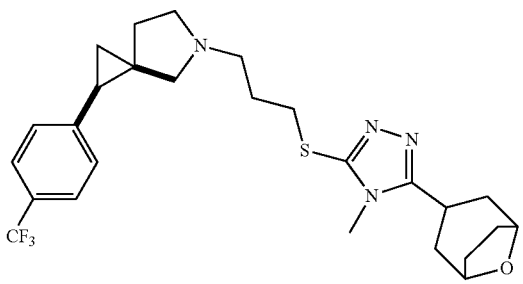

The compound was prepared as in Example 1, reacting (1R,3S/1S,3R)-1-[4-(trifluoromethyl)phenyl]-5-azaspiro[2.4]heptane (CIS, p14, 50 mg, 0.207 mmol), 3-[(3-chloropropyl)sulfanyl]-4-methyl-5-{8-oxabicyclo[3.2.1]octan-3-yl}-4H-1,2,4-triazole (p150, 69 mg, 0.228 mmol), $Na_2CO_3$ (26 mg, 0.248 mmol) and NaI (37 mg, 0.248 mmol) in DMF (0.2 mL) affording the title compound (1R,3S/1S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (CIS, E85, 54 mg, y=52%). NMR: $^1$H NMR (Acetone-$d_6$) δ: 7.62 (d, 2H), 7.40 (s, 2H), 4.33-4.48 (m, 2H), 3.57 (s, 3H), 3.28-3.46 (m, 2H), 3.03-3.22 (m, 2H), 2.38-2.72 (m, 5H), 2.20-2.29 (m, 1H), 1.96 (d, 7H), 1.69-1.86 (m, 5H), 1.27-1.35 (m, 1H), 1.17-1.25 (m, 1H). MS (m/z): 507.1 [MH]$^+$.

Example 86 and Example 87: (1R,3S)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (E86, CIS, Enantiomer 1) and (1S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (E87, CIS, Enantiomer 2)

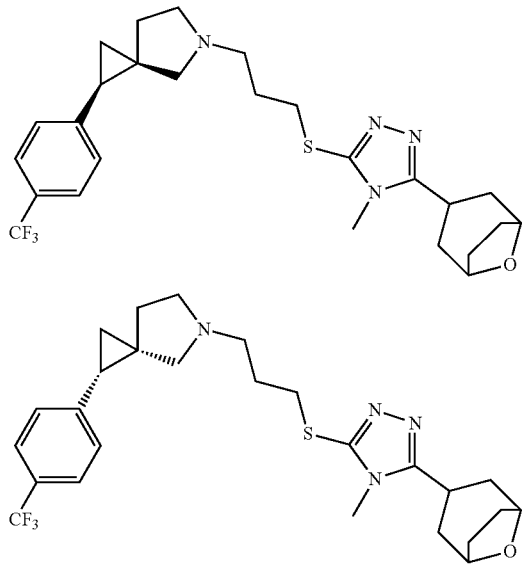

(1R,3S/1S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (CIS, E85, 54 mg) was separated into the single enantiomers by preparative chiral HPLC.

Preparative Chromatography:

| | |
|---|---|
| Column | Chiralcel OJ-H (25 x 2 cm), 5 um |
| Mobile phase | n-Hexane/(Ethanol + 0.1% isopropylamine) 60/40% v/v |
| Flow rate (ml/min) | 14 ml/min |
| DAD detection | 220 nm |
| Loop | 2000 μL |
| Injection | 27 mg/injection | affording (1R,3S)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (CIS, E86, 24 mg). Enantiomer 1: ret. time 6.5 min, 100% ee. MS (m/z): 507.4 [MH]$^+$ and (1S,3R)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (CIS, E87, 23 mg). Enantiomer 2: ret. time 9.6 min, 100% ee. MS (m/z): 507.4 [MH]$^+$.

Example 88: (1R,3S)-5-{3-[(4-methyl-5-{8-oxabi-cyclo[3.2.1]octan-3-yl}-4H-1,2,4-triazol-3-yl)sulfanyl]propyl}-1-[4-(trifluoromethyl)phenyl]-5-azaspiro[2.4]heptane hydrochloride (E88, CIS, Enantiomer 1)

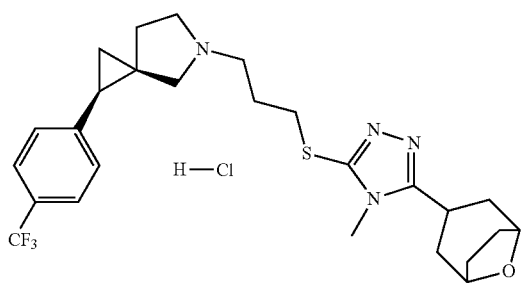 [SMILES: Cn1c(SCCCN2CC[C@]3(C[C@@H]3c3ccc(C(F)(F)F)cc3)C2)nnc1C1CC2CCC(C1)O2 ; Cl]

(1R,3S)-5-{3-[(4-methyl-5-{8-oxabicyclo[3.2.1]octan-3-yl}-4H-1,2,4-triazol-3-yl)sulfanyl]propyl}-1-[4-(trifluoromethyl)phenyl]-5-azaspiro[2.4]heptane (CIS, E86, 24 mg) was treated with 1.2 eq of HCl in Et$_2$O affording (1R,3S)-5-{3-[(4-methyl-5-{8-oxabicyclo[3.2.1]octan-3-yl)}-4H-1,2,4-triazol-3-yl)sulfanyl]propyl}-1-[4-(trifluoromethyl)phenyl]-5-azaspiro[2.4]heptane hydrochloric salt (Enantiomer 1, CIS, E88, 24.3 mg). MS (m/z): 507.4 [MH]$^+$.

Example 89: (1S,3S/1R,3R)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane (TRANS, E89)

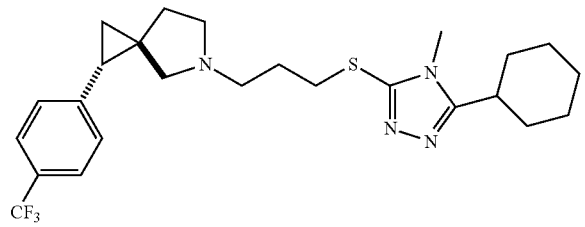

The compound was prepared as in Example 1, reacting (1S,3S/1R,3R)-1-[4-(trifluoromethyl)phenyl]-5-azaspiro[2.4]heptane (TRANS, p13, 50 mg, 0.207 mmol), 3-[(3-chloropropyl)sulfanyl]-5-cyclohexyl-4-methyl-4H-1,2,4-triazole (p151, 63 mg, 0.228 mmol), Na$_2$CO$_3$ (26 mg, 0.25 mmol) and NaI (38 mg, 0.25 mmol) in DMF (0.2 mL) affording the title compound (1S,3S/1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (TRANS, E89, 37 mg, y=37%). NMR: $^1$H NMR (CDCl$_3$) δ: 7.51-7.66 (m, 2H), 7.31-7.42 (m, 2H), 3.53 (s, 3H), 3.24 (m, 2H), 2.74-3.15 (m, 5H), 2.58-2.71 (m, 1H), 2.09-2.41 (m, 3H), 1.95 (m, 4H), 1.68-1.84 (m, 5H), 1.16-1.48 (m, 6H). MS (m/z): 479.5 [MH]$^+$.

Example 90 and Example 91: (1R,3R or 1S,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (E90, TRANS, Enantiomer 1) and (1S,3S or 1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (E91, TRANS, Enantiomer 2)

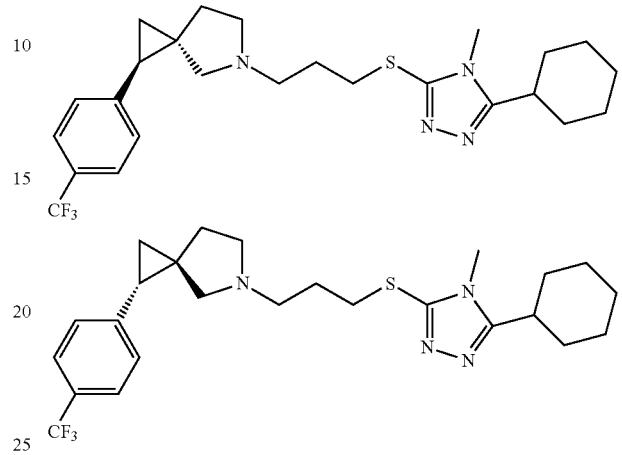

(1S,3S/1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (TRANS, E89, 34 mg) was separated into the single enantiomers by preparative chiral HPLC.

Preparative Chromatography:

| | |
|---|---|
| Column | Chiralcel OJ-H (25 × 2 cm), 5 um |
| Mobile phase | n-Hexane/(Ethanol/Methanol 1/1 + 0.1% isopropylamine) 92/8 v/v |
| Flow rate (ml/min) | 16 ml/min |
| DAD detection | 220 nm |
| Loop | 750 µL |
| Injection | 8.5 mg/injection | affording (1R,3R or 1S,3S)-5-{3-[(5-cyclohexyl-4-methyl-4H-1,2,4-triazol-3-yl)sulfanyl]-propyl}-1-[4-(trifluoromethyl)phenyl]-5-azaspiro[2.4]heptane (TRANS, E90, 14 mg). Enantiomer 1: ret. time 8.8 min, 100% ee. MS (m/z): 479.5 [MH]$^+$ and (1S,3S or 1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (TRANS, E91, 10.5 mg). Enantiomer 2: ret. time 10.5 min, 100% ee. MS (m/z): 479.5 [MH]$^+$.

Example 92: (1R,3R or 1S,3S)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane hydrochloride (E92, TRANS, Enantiomer 1)

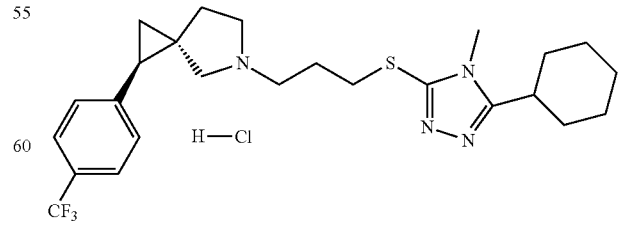

(1R,3R or 1S,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (TRANS, E90, 14 mg) was treated with 1.2 eq of HCl in Et₂O affording (1R,3R or 1S,3S)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane hydrochloric salt (Enantiomer 1, TRANS, E92, 15 mg). MS (m/z): 479.5 [MH]⁺.

Example 93: (1S,3S or 1R,3R)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane hydrochloride (E93, TRANS, Enantiomer 2)

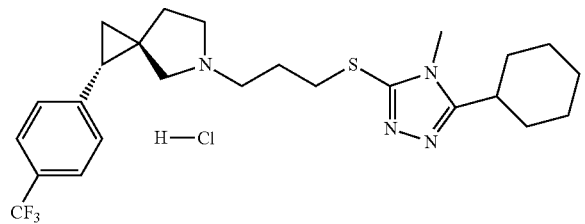

(1S,3S or 1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (TRANS, E91, 10.5 mg) was treated with 1.2 eq of HCl in Et₂O affording (1S,3S or 1R,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane hydrochloric salt (Enantiomer 2, TRANS, E93, 11 mg). MS (m/z): 479.5 [MH]⁺.

Example 94: (1R,3S/1S,3R)-5-{3-[(5-cyclohexyl-4-methyl-4H-1,2,4-triazol-3-yl)-sulfanyl]propyl}-1-[4-(trifluoromethyl)phenyl]-5-azaspiro[2.4]heptane (CIS, E94)

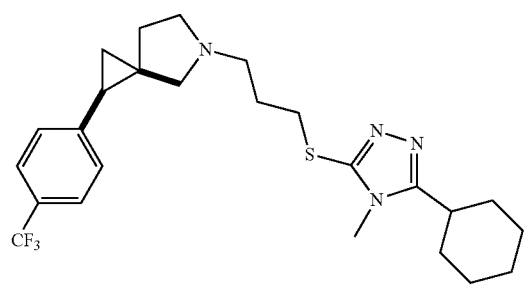

The compound was prepared as in Example 1, reacting (1R,3S/1S,3R)-1-[4-(trifluoromethyl)phenyl]-5-azaspiro[2.4]heptane (CIS, p14, 50 mg, 0.207 mmol), 3-[(3-chloropropyl)sulfanyl]-5-cyclohexyl-4-methyl-4H-1,2,4-triazole (p151, 63 mg, 0.228 mmol), Na₂CO₃ (26 mg, 0.248 mmol) and NaI (37 mg, 0.248 mmol) in DMF (0.2 mL) affording the title compound (1R,3S/1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (CIS, E94, 32 mg, y=32%). NMR: ¹H NMR (Acetone-d₆) δ: 7.63 (d, 2H), 7.39 (d, 2H), 3.54 (s, 3H), 3.42 (m, 1H), 3.02-3.23 (m, 2H), 2.37-2.66 (m, 4H), 2.35-2.67 (m, 1H), 2.18-2.31 (m, 2H), 1.96 (br. s., 4H), 1.83 (br. s., 5H), 1.54-1.67 (m, 2H), 1.27-1.51 (m, 4H), 1.17-1.25 (m, 1H). MS (m/z): 479.5 [MH]⁺.

Example 95 and Example 96: (1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (E95, CIS, Enantiomer 1) and (1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (E96, CIS, Enantiomer 2)

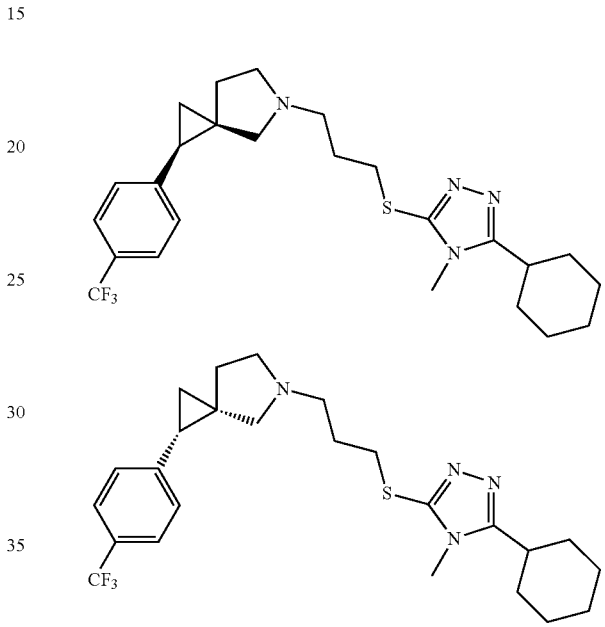

(1R,3S/1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (CIS, E94, 30 mg) was separated into the single enantiomers by preparative chiral HPLC.

Preparative Chromatography:

| | |
|---|---|
| Column | Chiralcel OJ-H (25 × 2.0 cm), 5µ |
| Mobile phase | n-Hexane/(Ethanol/Methanol 1/1 + 0.1% isopropylamine) 85/15% v/v |
| Flow rate (ml/min) | 18 ml/min |
| DAD detection | 220 nm |
| Loop | 1000 µL |
| Injection | 15 mg/injection | affording (1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (CIS, E95, 12 mg). Enantiomer 1: ret. time 6.6 min, 100% ee. MS (m/z): 479.5 [MH]⁺ and (1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (CIS, E96, 11.5 mg). Enantiomer 2: ret. time 8.4 min, 100% ee. MS (m/z): 479.5 [MH]⁺.

Example 97: (1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane hydrochloride (E97, CIS, Enantiomer 1)

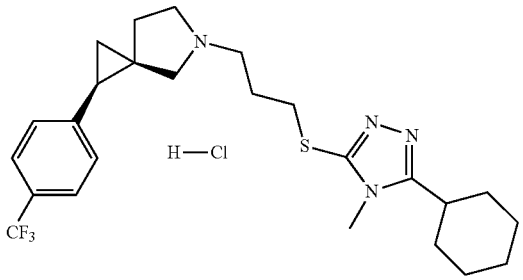 [SMILES: Cn1c(SCCCN2CC[C@]3(C[C@@H]3c3ccc(C(F)(F)F)cc3)C2)nnc1C1CCCCC1 ; Cl]

(1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (CIS, E95, 12 mg) was treated with 1.2 eq of HCl in Et$_2$O affording (1R,3S)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane hydrochloric salt (Enantiomer 1, CIS, E97, 12.5 mg). MS (m/z): 479.5 [MH]$^+$.

Example 98: (1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane hydrochloride (E98, CIS, Enantiomer 2)

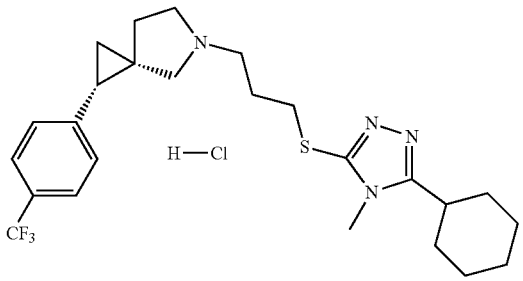 [SMILES: Cn1c(SCCCN2CC[C@@]3(C[C@H]3c3ccc(C(F)(F)F)cc3)C2)nnc1C1CCCCC1 ; Cl]

(1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane (CIS, E96, 11.5 mg) was treated with 1.2 eq of HCl in Et$_2$O affording (1S,3R)-5-{3-[(5-cyclohexyl-4-methyl-4H-1,2,4-triazol-3-yl)sulfanyl]propyl}-1-[4-(trifluoromethyl)phenyl]-5-azaspiro[2.4]heptane hydrochloric salt (Enantiomer 2, CIS, E98, 12.1 mg). MS (m/z): 479.1 [MH]$^+$.

Preparation 249: tert-butyl 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]piperidine-1-carboxylate (CIS, p249)

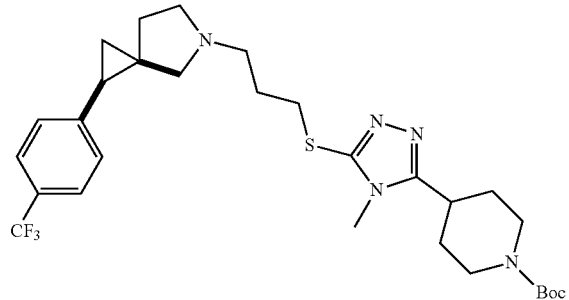

(1R,3S/1S,3R)-1-[4-(trifluoromethyl)phenyl]-5-azaspiro[2.4]heptane (CIS, p14, 50 mg, 0.21 mmol), tert-butyl 4-{5-[(3-chloropropyl)sulfanyl]-4-methyl-4H-1,2,4-triazol-3-yl}piperidine-1-carboxylate (p224, 78 mg, 0.21 mmol), Na$_2$CO$_3$ (27 mg, 0.252 mmol) and NaI (38 mg, 0.252 mmol) were dissolved in DMF (0.2 mL) and heated at 60° C. and shaken in a PLS apparatus at that temperature O/N. The mixture was diluted with water and extracted twice with DCM. The organic phase was dried and evaporated. Crude material was purified by FC on silica cartridge (eluent from DCM to 100% MeOH) affording tert-butyl 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]piperidine-1-carboxylate (CIS, p249, 63 mg, y=35%) that was used as such in the next step. MS (m/z): 580.4 [MH]$^+$.

Preparation 250: (1R,3S/1S,3R)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (CIS, p250)

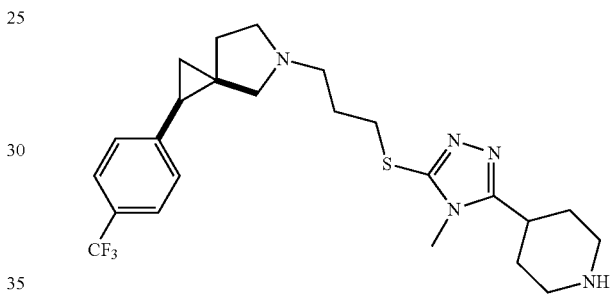

To a solution of tert-butyl 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]piperidine-1-carboxylate (p249, CIS, 63 mg, 0.11 mmol) in DCM (2.5 mL), TFA (0.5 mL) was added and the reaction was stirred at RT for 1.5 h. The reaction mixture was concentrated under vacuum. The residue was loaded on a SCX cartridge and eluted with MeOH/NH$_3$ 1M in MeOH to obtain (1R,3S/1S,3R)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (p250, CIS, 42 mg, y=80%) as pale yellow gum. MS (m/z): 480.4 [MH]$^+$.

Example 99: 1-{4-[4-methyl-5-({3-[(1R,3S/1S,R3)-1-[4-(trifluoromethyl)phenyl]-5-azaspiro[2.4]heptan-5-yl]propyl}sulfanyl)-4H-1,2,4-triazol-3-yl]piperidin-1-yl}ethan-1-one (CIS, E99)

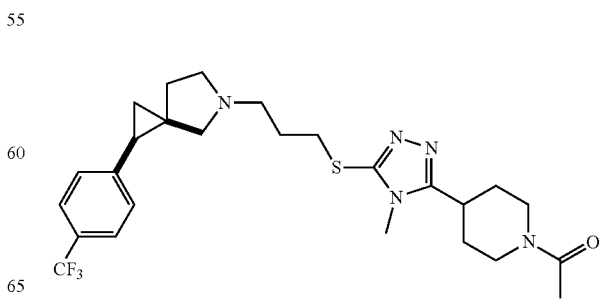

To a solution of (1R,3 S/1S,3R)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (p250, CIS, 42 mg, 0.088 mmol) in DCM (2 mL), Ac$_2$O (11 uL, 0.11 mmol) and Py (16 uL, 0.2 mmol) were added and the mixture was stirred at RT for 1 h. The reaction mixture was diluted with water and extracted with DCM. Organic phase was dried and concentrated under reduced pressure to obtain 1-{4-[4-methyl-5-({3-[(1R,3S/1S,R3)-1-[4-(trifluoromethyl)phenyl]-5-azaspiro[2.4]heptan-5-yl]propyl}sulfanyl)-4H-1,2,4-triazol-3-yl]piperidin-1-yl}ethan-1-one (E99, CIS, 38 mg, y=77%) as colourless oil. NMR: $^1$H NMR (Acetone-d$_6$) δ: 7.62 (d, 2H), 7.32-7.47 (m, 2H), 4.74-4.74 (m, 1H), 4.43-4.58 (m, 1H), 3.93-4.08 (m, 1H), 3.59 (s, 3H), 3.28 (br. s., 5H), 2.82-2.95 (m, 2H), 2.52 (br. s., 4H), 2.27 (br. s., 1H), 2.08-2.18 (m, 2H), 1.92-2.03 (m, 4H), 1.85 (d, 2H), 1.60-1.73 (m, 1H), 1.17-1.39 (m, 3H). MS (m/z): 522.5 [MH]$^+$.

Preparation 251: tert-butyl 4-[4-methyl-5-({3-[(1R, 3S)-1-[4-(trifluoromethyl)phenyl]-5-azaspiro[2.4]heptan-5-yl]propyl}sulfanyl)-4H-1,2,4-triazol-3-yl]piperidine-1-carboxylate (CIS, Enantiomer 1, p251)

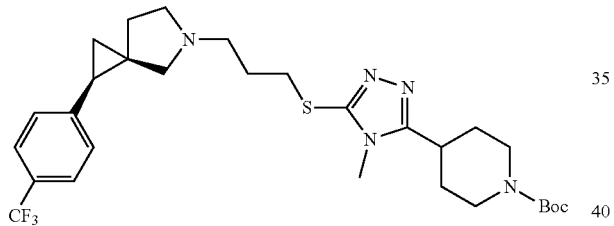

(1R,3S)-1-[4-(trifluoromethyl)phenyl]-5-azaspiro[2.4]heptane (CIS, Enantiomer 1, p15, 300 mg, 1.24 mmol), tert-butyl 4-{5-[(3-chloropropyl)sulfanyl]-4-methyl-4H-1,2,4-triazol-3-yl}piperidine-1-carboxylate (p224, 510 mg, 1.36 mmol), Na$_2$CO$_3$ (159 mg, 1.5 mmol) and NaI (225 mg, 1.5 mmol) were dissolved in DMF (1.4 mL) and heated at 60° C. O/N. Further tert-butyl 4-{5-[(3-chloropropyl)sulfanyl]-4-methyl-4H-1,2,4-triazol-3-yl}piperidine-1-carboxylate (100 mg, 0.27 mmol) was added and the reaction was stirred at 60° C. for 4 hrs. The mixture was diluted with water and extracted three times with DCM. The organic phase was dried and evaporated to obtain an oil that was purified by FC on Silica gel (eluting from DCM to MeOH 10%) to obtain a yellow foam that was dissolved in DCM (3 mL) and treated with MP-isocyanate resin, shaking for 1 h. The resin was filtered and washed with DCM and MeOH. Solvent was evaporated affording tert-butyl 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidine-1-carboxylate (CIS, Enantiomer 1, p251, 550 mg) that was used as crude in the next step. MS (m/z): 580.5 [MH]$^+$.

Preparation 252: (1R,3S)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (CIS, Enantiomer 1, p252)

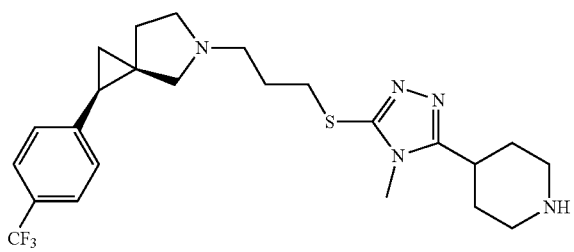 [SMILES: Cn1c(SCCCN2CC[C@]3(C[C@@H]3c3ccc(C(F)(F)F)cc3)C2)nnc1C1CCNCC1]

tert-butyl 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidine-1-carboxylate (p251, CIS, Enantiomer 1, 550 mg, 0.95 mmol), was dissolved in DCM (5 mL) and TFA (1 mL) was added. The resulting solution was stirred at RT for 1 h, then the solvent was evaporated and the residue material was purified by SCX cartridge (eluent MeOH/NH$_3$ 1M in MeOH) to obtain (1R,3S)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (p252, CIS, Enantiomer 1, 232 mg, y=48%) as yellow sticky oil. MS (m/z): 480.4 [MH]$^+$.

Example 100: 1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}ethan-1-one (CIS, Enantiomer 1, E100)

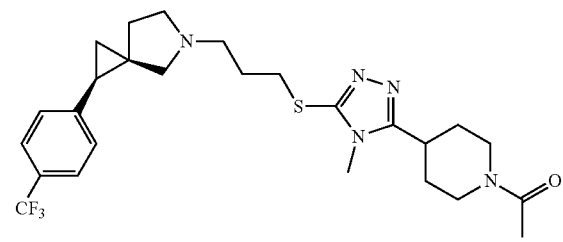 [SMILES: CC(=O)N1CCC(c2nnc(SCCCN3CC[C@]4(C[C@@H]4c4ccc(C(F)(F)F)cc4)C3)n2C)CC1]

To a solution of (1R,3S)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (p252, CIS, Enantiomer 1, 232 mg, 0.48 mmol) in DCM (5 mL), Ac$_2$O (55 uL, 0.576 mmol) and Py (89 uL, 1.1 mmol) were added and the mixture was stirred at RT for 1 h. The reaction mixture was diluted with water and extracted several time with DCM. Organic phase was dried and concentrated under reduced pressure. The crude material was purified by FC on NH cartridge (eluting from cHex to EtOAc 100%, then to MeOH 100%) to obtain 1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}ethan-1-one (E100, CIS, Enantiomer 1, 198 mg, y=79%) as colourless sticky oil. NMR: $^1$H NMR (DMSO-d$_6$) δ: 7.60 (d, 2H), 7.31 (d, 2H), 4.36 (d, 1H), 3.87 (d, 1H), 3.47 (s, 3H), 3.13-3.22 (m, 1H), 2.95-3.11 (m, 3H), 2.74 (td, 1H), 2.62-2.69 (m, 1H), 2.30-2.48 (m, 4H), 2.19 (dd, 1H), 2.02 (s, 3H), 1.80-1.97 (m, 5H), 1.61-1.73 (m, 3H), 1.42-1.53 (m, 1H), 1.22-1.28 (m, 1H), 1.16 (dd, 1H). MS (m/z): 522.4 [MH]+.

Preparation 253: tert-butyl 4-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidine-1-carboxylate (CIS, p253)

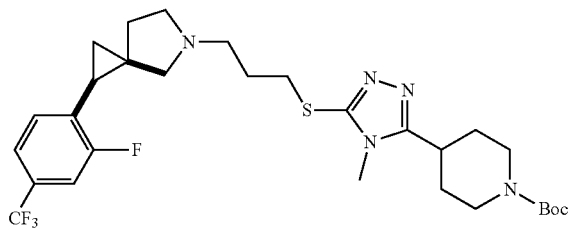 [SMILES: Cn1c(SCCCN2CC[C@]3(C[C@@H]3c3ccc(C(F)(F)F)cc3F)C2)nnc1C1CCN(C(=O)OC(C)(C)C)CC1]

The compound was prepared as in Example 1, reacting (1S,3S/1R,3R)-1-[2-fluoro-4-(trifluoromethyl)phenyl]-5-azaspiro[2.4]heptane (CIS, p23, 50 mg, 0.193 mmol), tert-butyl 4-{5-[(3-chloropropyl)sulfanyl]-4-methyl-4H-1,2,4-triazol-3-yl}piperidine-1-carboxylate (p224, 76 mg, 0.2 mmol), Na$_2$CO$_3$ (25 mg, 0.23 mmol) and NaI (35 mg, 0.23 mmol) in DMF (0.2 mL) affording the title compound tert-butyl 4-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidine-1-carboxylate (CIS, p253, 38 mg, y=33%) that was used as such in the next step. MS (m/z): 598.6 [MH]+.

Preparation 254: (1S,3S/1R,3R)-1-[2-fluoro-4-(trifluoromethyl)phenyl]-5-(3-{[4-methyl-5-(piperidin-4-yl)-4H-1,2,4-triazol-3-yl]sulfanyl}propyl)-5-azaspiro[2.4]heptane (CIS, p254)

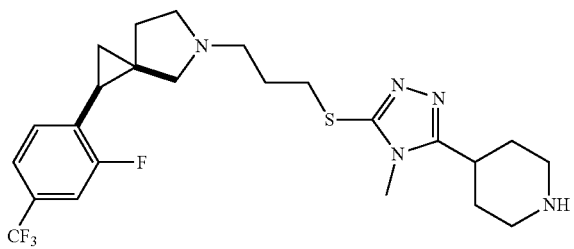 [SMILES: Cn1c(SCCCN2CC[C@]3(C[C@@H]3c3ccc(C(F)(F)F)cc3F)C2)nnc1C1CCNCC1]

To a stirred solution of tert-butyl 4-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidine-1-carboxylate (CIS, p253, 37 mg, 0.062 mmol) in DCM (3 mL) TFA (0.3 mL) was added and the resulting reaction solution was left stirring at RT for 1 h. Solvent was removed in vacuo and the residue was charged on SCX eluting with 1M NH$_3$ in MeOH to afford after evaporation (1S,3S/1R,3R)-1-[2-fluoro-4-(trifluoromethyl)phenyl]-5-(3-{[4-methyl-5-(piperidin-4-yl)-4H-1,2,4-triazol-3-yl]sulfanyl}propyl)-5-azaspiro[2.4]heptane (p254, 28 mg, y=91%). That was used as such in the next step. MS (m/z): 498.5 [MH]+.

Example 101: 1-{4-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidin-1-yl}ethan-1-one (CIS, E101)

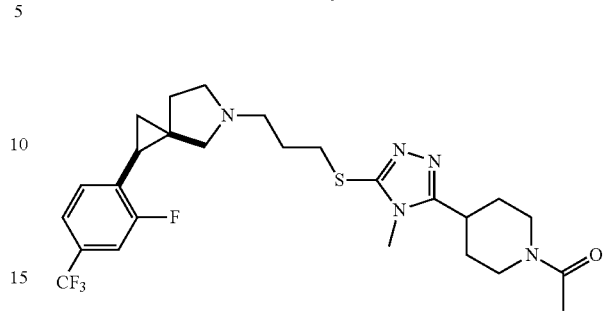

To a solution of (1S,3S/1R,3R)-1-[2-fluoro-4-(trifluoromethyl)phenyl]-5-(3-{[4-methyl-5-(piperidin-4-yl)-4H-1,2,4-triazol-3-yl]sulfanyl}propyl)-5-azaspiro[2.4]heptane (p254, CIS, 28 mg, 0.056 mmol) in DCM (1.25 mL), Ac$_2$O (6 uL, 0.067 mmol) and Py (10 uL, 0.129 mmol) were added and the mixture was stirred at RT O/N. The reaction mixture was diluted with water and extracted with DCM. Organic phase was dried and concentrated under reduced pressure. Crude material was purified by FC on silica gel (eluent: DCM to 100% MeOH) affording 1-{4-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidin-1-yl}ethan-1-one (E101, CIS, 17 mg, y=56%). NMR: $^1$H NMR (Acetone-d$_6$) δ: 7.43-7.54 (m, 2H), 7.35 (s, 1H), 4.44-4.56 (m, 1H), 3.98-4.05 (m, 1H), 3.57-3.65 (m, 3H), 3.05-3.35 (m, 4H), 2.72-2.87 (m, 4H), 2.40-2.68 (m, 4H), 2.24-2.33 (m, 1H), 1.57-2.06 (m, 10H), 1.21-1.40 (m, 2H). MS (m/z): 540.4 [MH]+.

Example 102: 1-{4-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidin-1-yl}ethan-1-one hydrochloride (CIS, E102)

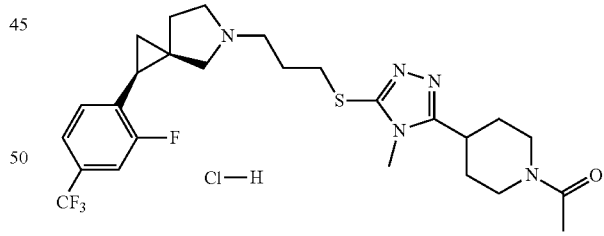

The compound was prepared as in Example 1, reacting (1S,3S)-1-[2-fluoro-4-(trifluoromethyl)phenyl]-5-azaspiro[2.4]heptane (CIS, Enantiomer 1, p24, 25 mg, 0.096 mmol), 1-(4-{5-[(3-chloropropyl)sulfanyl]-4-methyl-4H-1,2,4-triazol-3-yl}piperidin-1-yl)ethan-1-one (p222, 32 mg, 0.1 mmol), Na$_2$CO$_3$ (13 mg, 0.12 mmol) and NaI (18 mg, 0.12 mmol) in DMF (0.1 mL) affording the title compound 1-{4-[5-({3-[(1S,3S or 1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]piperidin-1-yl}ethan-1-one (CIS, Enantiomer 1, 24 mg) that was dissolved in DCM and Et$_2$O and salified by 1.2 eq of HCl 2M in Et$_2$O to obtain 1-{4-[5-({3-[(1S,3S)-1-[2-fluoro-4-(trifluoromethyl)phenyl]-5-azaspiro[2.4]heptan-5-yl]propyl}sulfanyl)-4-methyl- 4H-1,2,4-triazol-3-yl]piperidin-1-yl}ethan-1-one hydrochloric salt (E102, Enantiomer 1, 22.7 mg, y=42%) as yellow solid. NMR: ¹H NMR (DMSO-d₆) δ: 10.16-10.73 (m, 1H), 7.67 (d, 1H), 7.52 (s, 1H), 7.33-7.42 (m, 1H), 4.33-4.44 (m, 1H), 3.82-3.96 (m, 1H), 3.69-3.76 (m, 1H), 3.45-3.51 (m, 3H), 3.03-3.37 (m, 9H), 2.58-2.83 (m, 2H), 2.20-2.31 (m, 1H), 2.05-2.16 (m, 1H), 2.02 (s, 3H), 1.94-2.01 (m, 2H), 1.88 (br. s., 2H), 1.58-1.74 (m, 1H), 1.41-1.57 (m, 2H), 1.20-1.38 (m, 2H). MS (m/z): 540.4 [MH]⁺.

Example 103: 3-methoxy-1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}propan-1-one (CIS, Enantiomer 1, E103)

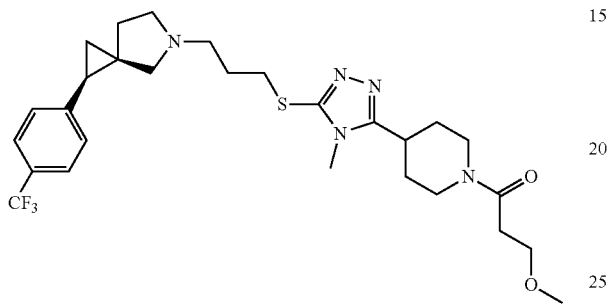

To a solution of (1R,3S)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (p252, CIS, Enantiomer 1, 37 mg, 0.077 mmol) 1-Hydroxybenzotriazole hydrate (11 mg, 0.081 mmol), N-(3-Dimethylaminopropyl)-N'-ethyl carbodiimide hydrochloride (15 mg, 0.078 mmol), 3-Methoxypropionic acid (8 uL, 0.077 mmol) and TEA (32 uL, 0.23 mmol) in DCM (2 mL) was added and the mixture was stirred at RT O/N. Then it was washed with NaHCO₃ (x1), NH₄Cl (×3) and Brine, dried and concentrated under reduced pressure. Crude was purified by FC on NH column (eluent: Cy to 100% AcOEt) affording 3-methoxy-1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}propan-1-one (E103, CIS, Enantiomer 1, 24 mg, y=55%). NMR: ¹H NMR (Acetone-d₆) δ: 7.58-7.68 (m, 2H), 7.33-7.43 (m, 2H), 4.49-4.57 (m, 1H), 4.03-4.14 (m, 1H), 3.65 (s, 2H), 3.60 (s, 3H), 3.23-3.34 (m, 4H), 3.05-3.23 (m, 3H), 2.84-2.90 (m, 1H), 2.69-2.76 (m, 1H), 2.57-2.68 (m, 3H), 2.51 (s, 3H), 2.20-2.26 (m, 1H), 1.98 (s, 5H), 1.63-1.90 (m, 4H), 1.26-1.32 (m, 1H), 1.18-1.24 (m, 1H). MS (m/z): 566.5 [MH]⁺.

Example 104: 3-methoxy-1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}propan-1-one hydrochloride (CIS, Enantiomer 1, E104)

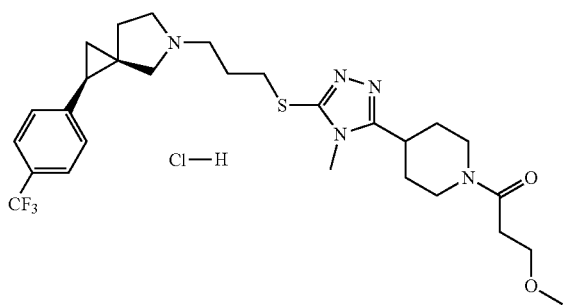 [SMILES: COCCC(=O)N1CCC(c2nnc(SCCCN3CC[C@]4(C[C@@H]4c4ccc(C(F)(F)F)cc4)C3)n2C)CC1 ; Cl]

3-methoxy-1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}propan-1-one (E103, CIS, Enantiomer 1, 24 mg) was dissolved in MeOH/Et₂O and treated with HCl 2M in Et₂O (1.1 eq) to form the corresponding hydrochloride salt. Solvent was eliminated under reduced pressure; the solid was triturated with Et₂O and dried under high vacuum affording 3-methoxy-1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-1-yl}propan-1-one hydrochloride (E104, CIS, Enantiomer 1, 23.4 mg). MS (m/z): 566.5 [MH]⁺.

Example 105: (1R,3S)-5-(3-{[5-(1-cyclopropanecarbonylpiperidin-4-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E105)

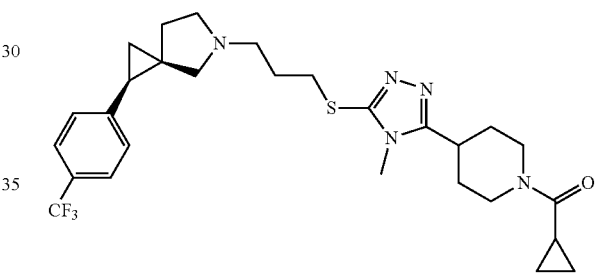

To a solution of (1R,3S)-5-(3-{[4-methyl-5-(piperidin-4-yl)-4H-1,2,4-triazol-3-yl]sulfanyl}propyl)-1-[4-(trifluoromethyl)phenyl]-5-azaspiro[2.4]heptane (p252, CIS, Enantiomer 1, 37 mg, 0.077 mmol) 1-Hydroxybenzotriazole hydrate (11 mg, 0.081 mmol), N-(3-Dimethylaminopropyl)-N'-ethyl carbodiimide hydrochloride (15 mg, 0.078 mmol), cyclopropanecarboxylic acid (7 uL, 0.077 mmol) and TEA (32 uL, 0.23 mmol) in DCM (2 mL) were added and the mixture was stirred at RT O/N. Then it was washed with NaHCO₃ (x1), NH₄Cl (×3) and Brine, dried and concentrated under reduced pressure. Crude was purified by FC on NH column (eluent: Cy to 100% AcOEt) affording (1R,3S)-5-(3-{[5-(1-cyclopropanecarbonylpiperidin-4-yl)-4-methyl-4H-1,2,4-triazol-3-yl]sulfanyl}propyl)-1-[4-(trifluoromethyl)phenyl]-5-azaspiro[2.4]heptane (E105, CIS, Enantiomer 1, 35 mg, y=83%). NMR: ¹H NMR (Acetone-d₆) δ: 7.58-7.68 (m, 2H), 7.36-7.44 (m, 2H), 4.37-4.57 (m, 2H), 3.60 (s, 3H), 3.32-3.45 (m, 1H), 3.05-3.24 (m, 3H), 2.85-2.97 (m, 1H), 2.69-2.76 (m, 1H), 2.57-2.65 (m, 1H), 2.40-2.53 (m, 3H), 2.19-2.27 (m, 1H), 1.89-2.05 (m, 6H), 1.64-1.84 (m, 4H), 1.26-1.31 (m, 1H), 1.18-1.24 (m, 1H), 0.83 (d, 2H), 0.73 (d, 2H). MS (m/z): 548.5 [MH]⁺.

Example 106: (1R,3S)-5-(3-{[5-(1-cyclopropanecarbonylpiperidin-4-yl)-4-methyl-4H-1,2,4-triazol-3-yl]sulfanyl}propyl)-1-[4-(trifluoromethyl)phenyl]-5-azaspiro[2.4]heptane hydrochloride (CIS, Enantiomer 1, E106)

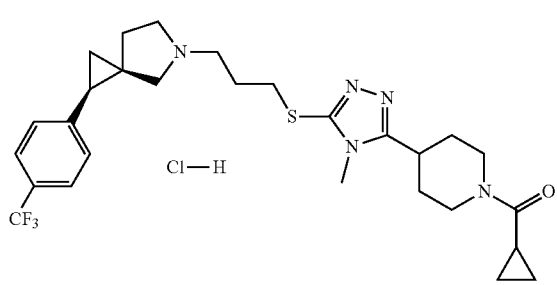 [SMILES: Cn1c(SCCCN2CC[C@]3(C[C@@H]3c3ccc(C(F)(F)F)cc3)C2)nnc1C1CCN(C(=O)C2CC2)CC1 ; Cl]

(1R,3S)-5-(3-{[5-(1-cyclopropanecarbonylpiperidin-4-yl)-4-methyl-4H-1,2,4-triazol-3-yl]sulfanyl}propyl)-1-[4-(trifluoromethyl)phenyl]-5-azaspiro[2.4]heptane (E105, CIS, Enantiomer 1, 35 mg) was dissolved in MeOH/Et$_2$O and treated with HCl 2M in Et$_2$O (1.1 eq) to form the corresponding hydrochloride salt. Solvent was eliminated under reduced pressure; the solid was triturated with Et$_2$O and dried under high vacuum affording (1R,3S)-5-(3-{[5-(1-cyclopropanecarbonylpiperidin-4-yl)-4-methyl-4H-1,2,4-triazol-3-yl]sulfanyl}propyl)-1-[4-(trifluoromethyl)phenyl]-5-azaspiro[2.4]heptane hydrochloride (E106, CIS, Enantiomer 1, 30.8 mg). MS (m/z): 548.4 [MH]$^+$.

Preparation 255: tert-butyl 3-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]azetidine-1-carboxylate (CIS, p255)

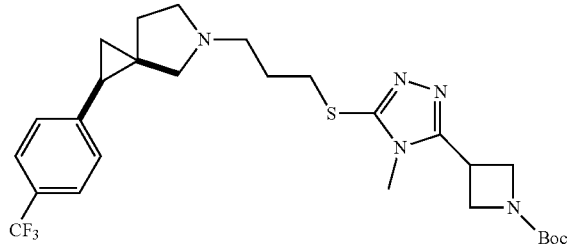 [SMILES: Cn1c(SCCCN2CC[C@]3(C[C@@H]3c3ccc(C(F)(F)F)cc3)C2)nnc1C1CN(C(=O)OC(C)(C)C)C1]

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), tert-butyl 3-{5-[(3-chloropropyl)sulfanyl]-4-methyl-4H-1,2,4-triazol-3-yl}azetidine-1-carboxylate (p226, 46 mg, 0.132 mmol), Na$_2$CO$_3$ (15 mg, 0.144 mmol) and NaI (22 mg, 0.144 mmol) in DMF (0.135 mL) affording the title compound tert-butyl 3-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]azetidine-1-carboxylate (CIS, p255, 37 mg, y=37%) that was used as such in the next step. MS (m/z): 552.5 [MH]$^+$.

Preparation 256: (1R,3S/1S,3R)-5-(3-{[5-(azetidin-3-yl)-4-methyl-4H-1,2,4-triazol-3-yl]sulfanyl}propyl)-1-[4-(trifluoromethyl)phenyl]-5-azaspiro[2.4]heptane (CIS, p256)

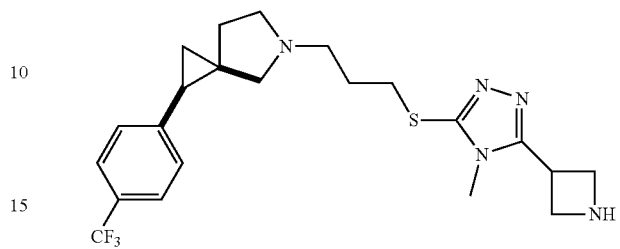

To a solution of tert-butyl 3-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]azetidine-1-carboxylate (p255, 37 mg, 0.11 mmol) in DCM (2 mL), TFA (0.5 mL) was added and the reaction was stirred at RT for 1.5 h. The reaction mixture was concentrated under vacuum. The residue was loaded on a SCX cartridge and eluted with MeOH/NH$_3$ 1M in MeOH to obtain (1R,3S/1S,3R)-5-(3-{[5-(azetidin-3-yl)-4-methyl-4H-1,2,4-triazol-3-yl]sulfanyl}propyl)-1-[4-(trifluoromethyl)phenyl]-5-azaspiro[2.4]heptane (p256, CIS, 25 mg, y=82%) as pale yellow gum. MS (m/z): 452.4 [MH]$^+$.

Example 107: 1-{3-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]azetidin-1-yl}ethan-1-one (CIS, E107)

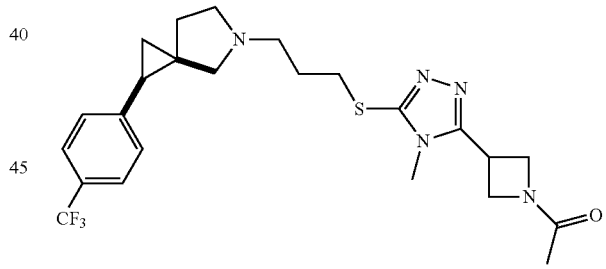

To a solution of (1R,3S/1S,3R)-5-(3-{[5-(azetidin-3-yl)-4-methyl-4H-1,2,4-triazol-3-yl]sulfanyl}propyl)-1-[4-(trifluoromethyl)phenyl]-5-azaspiro[2.4]heptane (p256, CIS, 25 mg, 0.055 mmol) in DCM (1.25 mL), Ac$_2$O (6 uL, 0.066 mmol) and Py (10 uL, 0.127 mmol) were added and the mixture was stirred at RT O/N. The reaction mixture was diluted with water and extracted with DCM. Organic phase was dried and concentrated under reduced pressure. The crude was purified by FC on silica cartridge (eluent from DCM to MeOH) to obtain 1-{3-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]azetidin-1-yl}ethan-1-one (E107, CIS, 7.2 mg, y=27%) as colourless gum. NMR: $^1$H NMR (Acetone-d$_6$) δ: 7.63 (d, 2H), 7.39 (d, 2H), 4.51-4.65 (m, 2H), 4.26-4.35 (m, 1H), 4.15-4.23 (m, 1H), 4.00-4.12 (m, 1H), 3.51 (s, 3H), 3.06-3.26 (m, 3H), 2.68-2.76 (m, 1H), 2.57-2.67 (m, 1H), 2.42-2.56 (m, 3H), 2.20-2.30 (m, 2H), 1.89-2.04 (m, 2H), 1.82 (s, 4H), 1.27-1.37 (m, 2H), 1.17-1.25 (m, 1H). MS (m/z): 494.4 [MH]⁺.

Preparation 257: tert-butyl N-{4-[4-methyl-5-({3-[(1R,3S/1S,R3)-1-[4-(trifluoromethyl)phenyl]-5-azaspiro[2.4]heptan-5-yl]propyl}sulfanyl)-4H-1,2,4-triazol-3-yl]cyclohexyl}carbamate (CIS, p257)

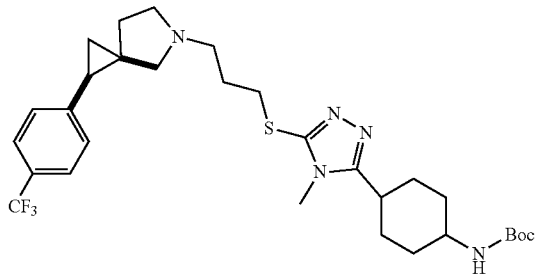

The compound was prepared as in Example 1, reacting (1R,3S/1S,3R)-1-[4-(trifluoromethyl)phenyl]-5-azaspiro[2.4]heptane (CIS, p14, 40 mg, 0.17 mmol), tert-butyl N-(4-{5-[(3-chloropropyl)sulfanyl]-4-methyl-4H-1,2,4-triazol-3-yl}cyclohexyl)carbamate (p230, 66 mg, 0.17 mmol), Na₂CO₃ (22 mg, 0.2 mmol) and NaI (25 mg, 0.17 mmol) in DMF (0.3 mL) affording tert-butyl N-{4-[4-methyl-5-({3-[(1R,3S/1S,R3)-1-[4-(trifluoromethyl)phenyl]-5-azaspiro[2.4]heptan-5-yl]propyl}sulfanyl)-4H-1,2,4-triazol-3-yl]cyclohexyl}carbamate (CIS, p257, 33 mg, y=33%) that was used as such in the next step. MS (m/z): 594.5 [MH]⁺.

Example 108: 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexan-1-amine (CIS, E108)

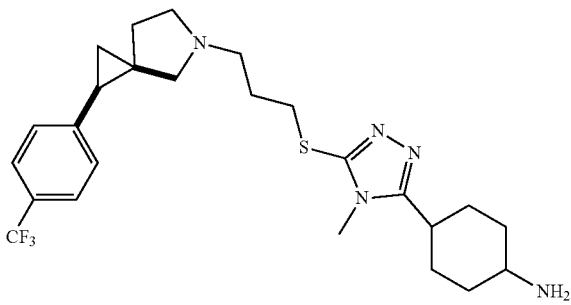

To a solution of tert-butyl N-{4-[4-methyl-5-({3-[(1R,3S/1S,R3)-1-[4-(trifluoromethyl)phenyl]-5-azaspiro[2.4]heptan-5-yl]propyl}sulfanyl)-4H-1,2,4-triazol-3-yl]cyclohexyl}carbamate (CIS, p257, 33 mg, 0.056 mmol) in DCM (0.2 mL), at RT, TFA (0.085 mL) was added and the resulting mixture was left reacting at RT. After 1.5 h the mixture was concentrated under vacuum and the residue was taken up with DCM. The solution was washed with aqueous concentrated sodium bicarbonate solution, water, dried over sodium sulphate and the solvent removed under reduced pressure to give 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexan-1-amine (E108, CIS, 24 mg, y=87%). NMR: ¹H NMR (CDCl₃) δ: 7.53 (d, 2H), 7.20 (d, 2H), 3.44 (s, 3H), 3.19 (d, 2H), 2.99-3.07 (m, 1H), 2.73-2.84 (m, 2H), 2.57-2.66 (m, 1H), 2.50 (s, 2H), 2.39 (s, 1H), 2.11 (d, 2H), 1.93-2.08 (m, 4H), 1.88 (d, 2H), 1.71-1.82 (m, 7H), 1.15-1.23 (m, 2H). MS (m/z): 494.4 [MH]⁺.

Example 109: N-{4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexyl}acetamide hydrochloride (CIS, E109)

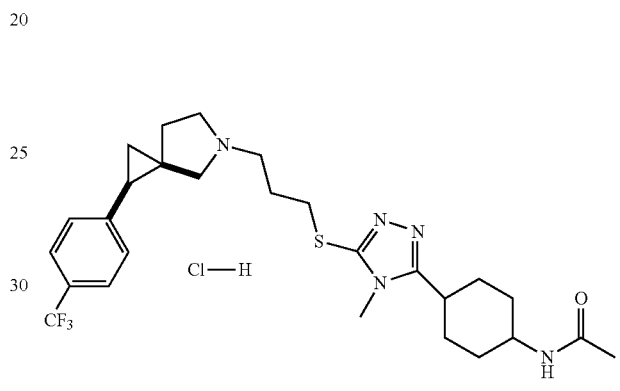

To a solution of 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexan-1-amine (E108, CIS, 24 mg, 0.049 mmol) and DIPEA (0.020 mL, 0.12 mmol) in DCM (0.2 mL), at RT, Ac₂O (0.005 mL, 0.053 mmol) was added and the resulting reaction mixture was left to react for 24 hrs. The mixture was diluted with DCM and washed twice with aqueous saturated sodium carbonate. The organic phase was washed with water, dried over sodium sulfate and the solvent removed under reduced pressure to give N-{4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexyl}acetamide (CIS, 20 mg). The latter was dissolved in DCM (0.2 mL) then 2N HCl/ether (0.021 mL) was added and the reaction mixture was concentrated under vacuum. The solid so obtained was triturated with ether and dried under vacuum at 40° C. O/N, affording N-{4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexyl}acetamide hydrochloride (E109, CIS, 21 mg, y=75%). NMR: ¹H NMR (DMSO-d₆) δ: 10.79-11.23 (m, 1H), 7.83-7.91 (m, 1H), 7.67 (d, 2H), 7.45 (d, 2H), 3.83-3.91 (m, 1H), 3.59-3.72 (m, 1H), 3.55 (s, 3H), 3.34-3.46 (m, 1H), 3.00-3.33 (m, 7H), 2.56-2.66 (m, 1H), 2.35-2.44 (m, 1H), 2.17-2.32 (m, 1H), 1.87-1.98 (m, 3H), 1.85 (s, 3H), 1.68-1.79 (m, 4H), 1.54-1.67 (m, 2H), 1.35-1.53 (m, 2H), 1.22-1.33 (m, 2H). MS (m/z): 536.5 [MH]⁺.

Example 110 and 111: N-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]cyclohexyl}acetamide (CIS, Enantiomer 1, E110) and N-{4-[4-methyl-5-({3-[(1S,3R)-1-[4-(trifluoromethyl)phenyl]-5-azaspiro[2.4]heptan-5-yl]propyl}sulfanyl)-4H-1,2,4-triazol-3-yl]cyclohexyl}acetamide (CIS, Enantiomer 2, E111)

Example 112: N-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]cyclohexyl}acetamide hydrochloride (E112, CIS, Enantiomer 1)

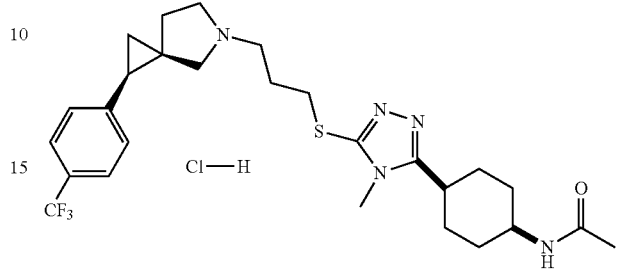

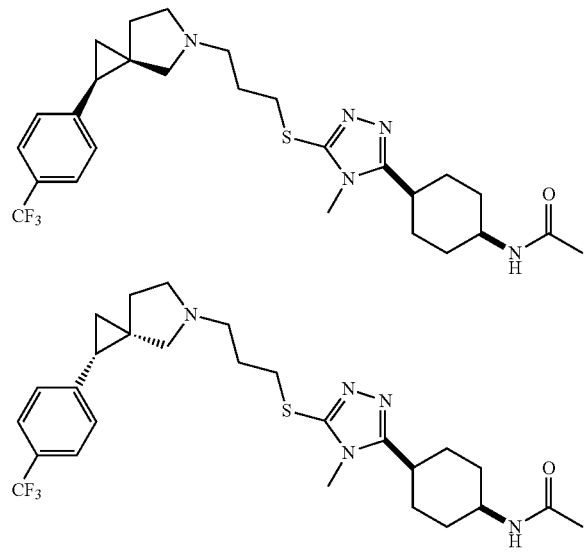

N-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]cyclohexyl}acetamide (E110, CIS, 24 mg) was dissolved in DCM (0.2 mL) then 2N HCl/ether (0.025 mL) was added and the mixture was concentrated under vacuum. The solid so obtained was triturated with ether and dried under vacuum at 40° C. overnight, affording N-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]cyclohexyl}acetamide hydrochloride (E112, Enantiomer 1, 23 mg). MS (m/z): 536.4 [MH]$^+$.

To a solution of 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]cyclohexan-1-amine (E108, 69 mg, 0.14 mmol) and DIPEA (0.061 mL, 0.35 mmol) in DCM (0.5 mL), at RT, Ac$_2$O (0.016 mL, 0.16 mmol) was added and the resulting reaction mixture was left to react for 24 hrs. The mixture was diluted with DCM and washed with aqueous saturated ammonium chloride; the solvent was removed under reduced pressure. The crude material was purified by FC on silica gel (DCM/MeOH from 100/0 to 55/45) to give 73 mg of racemic product that was submitted to chiral prep HPLC Preparative Chromatography:

| | |
|---|---|
| Column | Chiralcel OJ-H (25 × 2.0 cm), 5µ |
| Mobile phase | n-Hexane/(Ethanol/Methanol + 0.1% isopropylamine) 85/15% v/v |
| Flow rate (ml/min) | 16 ml/min |
| DAD detection | 220 nm |
| Loop | 350 µL |
| Injection | 10 mg/injection | affording N-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]cyclohexyl}acetamide (E110, CIS, 24 mg). Enantiomer 1: ret. time 8.7 min, 100% ee. MS (m/z): 536.6 [MH]$^+$ and N-{4-[4-methyl-5-({3-[(1S,3R)-1-[4-(trifluoromethyl)phenyl]-5-azaspiro[2.4]heptan-5-yl]propyl}sulfanyl)-4H-1,2,4-triazol-3-yl]cyclohexyl}acetamide (E111, CIS, 24 mg). Enantiomer 2: ret. time 10.7 min, 98.2% ee. MS (m/z): 536.6 [MH]$^+$.

Example 113: (1S,3S/1R,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (TRANS, E113)

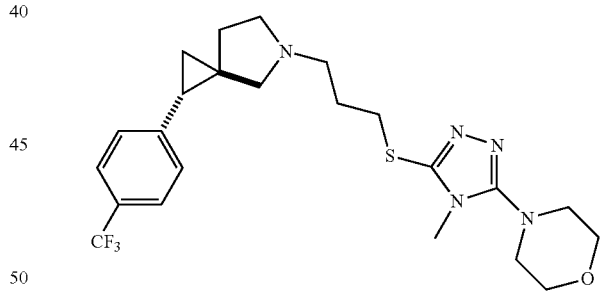

The compound was prepared as in Example 1, reacting (1S,3S or 1R,3R)-1-[4-(trifluoromethyl)phenyl]-5-azaspiro[2.4]heptane (TRANS, p13, 50 mg, 0.207 mmol), 4-{5-[(3-chloropropyl)sulfanyl]-4-methyl-4H-1,2,4-triazol-3-yl}morpholine (p152, 63 mg, 0.228 mmol), Na$_2$CO$_3$ (26 mg, 0.25 mmol) and NaI (37 mg, 0.25 mmol) in DMF (0.2 mL) affording the title compound (1S,3S/1R,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (TRANS, E113, 7.7 mg, y=8%). NMR: $^1$H NMR (Acetone-d$_6$) δ: 7.64 (d, 2H), 7.36 (d, 2H), 3.74-3.84 (m, 4H), 3.49 (s, 3H), 3.09-3.23 (m, 6H), 2.72 (d, 1H), 2.49-2.63 (m, 5H), 2.21-2.31 (m, 1H), 2.09 (br. s., 1H), 1.89 (s, 2H), 1.59-1.70 (m, 1H), 1.37-1.49 (m, 1H), 1.24-1.29 (m, 1H), 1.19-1.24 (m, 1H). MS (m/z): 482.5 [MH]$^+$.

Example 114: (1S,3S/1R,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane hydrochloride (TRANS, E114)

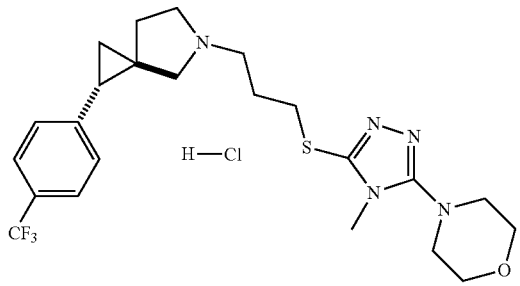

(1S,3S/1R,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (TRANS, E113, 7.7 mg) was treated with 1.2 eq of HCl in Et$_2$O affording (1S,3S/1R,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane hydrochloric salt (TRANS, E114, 8 mg). MS (m/z): 482.5 [MH]$^+$.

Example 115: (1R,3S/1S,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, E115)

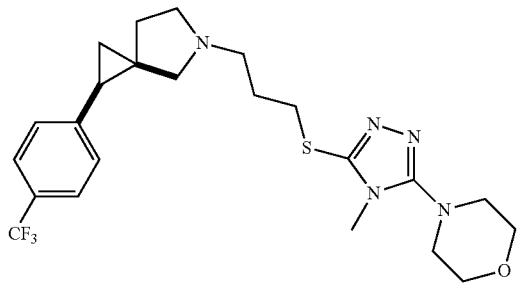

The compound was prepared as in Example 1, reacting (1R,3S/1S,3R)-1-[4-(trifluoromethyl)phenyl]-5-azaspiro[2.4]heptane (CIS, p14, 50 mg, 0.2 mmol), 4-{5-[(3-chloropropyl)sulfanyl]-4-methyl-4H-1,2,4-triazol-3-yl}morpholine (p152, 59 mg, 0.212 mmol), Na$_2$CO$_3$ (25 mg, 0.231 mmol) and NaI (35 mg, 0.231 mmol) in DMF (0.2 mL) affording the title compound (1R,3S/1S,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, E115, 45 mg, y=47%). NMR: $^1$H NMR (CDCl$_3$) δ: 7.55 (d, 2H), 7.23 (d, 2H), 3.82-3.91 (m, 4H), 3.39 (s, 3H), 3.09-3.25 (m, 6H), 2.39-2.96 br. s., 5H), 2.12-2.22 (m, 2H), 1.87-2.08 (m, 4H), 1.18-1.28 (m, 2H). MS (m/z): 482.5 [MH]$^+$.

Example 116 and 117: (1R,3S)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, Enantiomer 1, E116) and (1S,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, Enantiomer 2, E117)

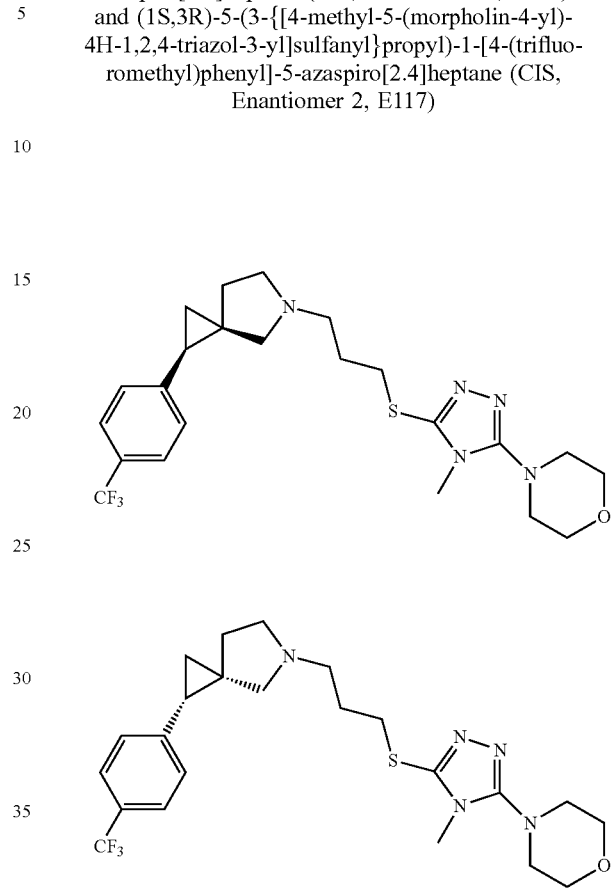

(1R,3S/1S,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, E115, 40 mg) was separated into the single enantiomers by preparative chiral HPLC.

Preparative Chromatography:

| | |
|---|---|
| Column | Chiralcel OJ-H (25 × 2.0 cm), 5μ |
| Mobile phase | n-Hexane/(Ethanol + 0.1% isopropylamine) 60/40% v/v |
| Flow rate (ml/min) | 17 ml/min |
| DAD detection | 220 nm |
| Loop | 1000 μL |
| Injection | 20 mg/injection | affording (1R,3S)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, E116, 10.8 mg). Enantiomer 1: ret. time 6.2 min, 100% ee. MS (m/z): 482.5 [MH]$^+$ and (1S,3R)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, E117, 9.8 mg). Enantiomer 2: ret. time 10.0 min, 100% ee. MS (m/z): 482.5 [MH]$^+$.

Example 118: (1R,3S)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E118)

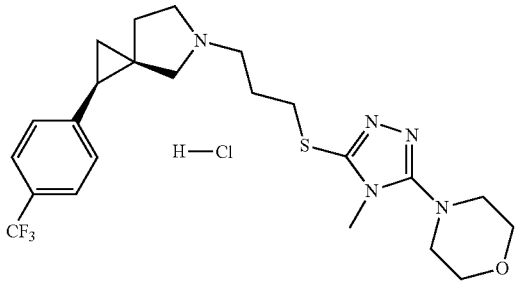 [SMILES: Cn1c(SCCCN2CC[C@]3(C[C@@H]3c3ccc(C(F)(F)F)cc3)C2)nnc1N1CCOCC1 ; Cl]

(1R,3S)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane (CIS, E116, 10.8 mg) was treated with 1.2 eq of HCl in Et$_2$O affording (1R,3S)-5-(3-{[4-methyl-5-(morpholin-4-yl)-4H-1,2,4-triazol-3-yl]sulfanyl}propyl)-1-[4-(trifluoromethyl)phenyl]-5-azaspiro[2.4]heptane hydrochloric salt (CIS, E118, 11 mg). MS (m/z): 482.5 [MH]$^+$.

Example 119: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one hydrochloride (CIS, Enantiomer 1, diastereomeric mixture, E119)

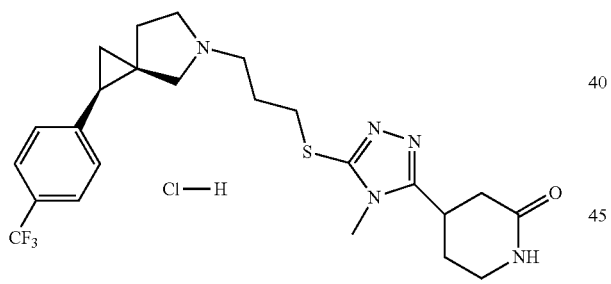

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 4-{5-[(3-chloropropyl)sulfanyl]-4-methyl-4H-1,2,4-triazol-3-yl}piperidin-2-one (p153, 32 mg, 0.11 mmol), Na$_2$CO$_3$ (13 mg, 0.12 mmol) and NaI (18 mg, 0.12 mmol) in DMF (0.1 mL) affording the title compound 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one (CIS, Enantiomer 1, 23.7 mg).

The latter was dissolved with DCM/Et$_2$O and treated with 1.2 eq of HCl in Et$_2$O affording N4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one hydrochloride (E119, CIS, Enantiomer 1, 19 mg, y=36%) as diastereomeric mixture. NMR: $^1$H NMR (DMSO-d$_6$) δ: 9.96-10.25 (m, 1H), 7.68 (d, 2H), 7.60 (br. s., 1H), 7.44 (br. s., 2H), 3.59-3.76 (m, 2H), 3.50 (s, 3H), 3.40 (br. s., 2H), 3.11 (br. s., 5H), 2.40-2.48 (m, 3H), 2.19-2.31 (m, 2H), 1.87-2.16 (m, 4H), 1.71-1.85 (m, 2H), 1.26-1.55 (m, 3H). MS (m/z): 494.5 [MH]$^+$.

Example 120: 1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one (CIS, Enantiomer 1, diastereomeric mixture, E120)

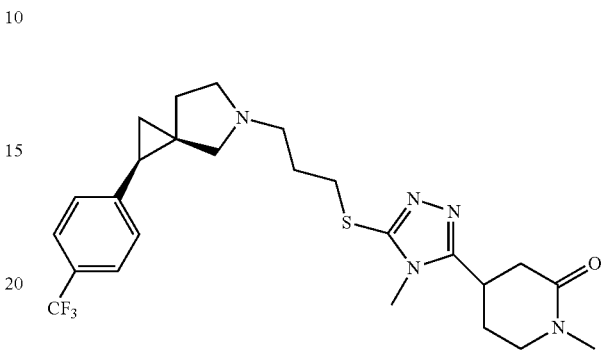

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 4-{5-[(3-chloropropyl)sulfanyl]-4-methyl-4H-1,2,4-triazol-3-yl}-1-methylpiperidin-2-one (p154, 35 mg, 0.113 mmol), Na$_2$CO$_3$ (13 mg, 0.12 mmol) and NaI (18 mg, 0.12 mmol) in DMF (0.1 mL) affording the title compound 1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one (CIS, Enantiomer 1, E120, 28.8 mg, y=55%). NMR: $^1$H NMR (Acetone-d$_6$) δ: 7.63 (s, 2H), 7.33-7.46 (m, 2H), 3.62 (s, 3H), 3.35-3.52 (m, 3H), 3.04-3.25 (m, 2H), 2.91 (s, 3H), 2.33-2.74 (m, 7H), 2.19-2.31 (m, 2H), 1.69-2.06 (m, 6H), 1.20-1.36 (m, 2H). MS (m/z): 508.4 [MH]$^+$.

Example 121: 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one hydrochloride (CIS, Enantiomer 1, diastereomeric mixture, E121)

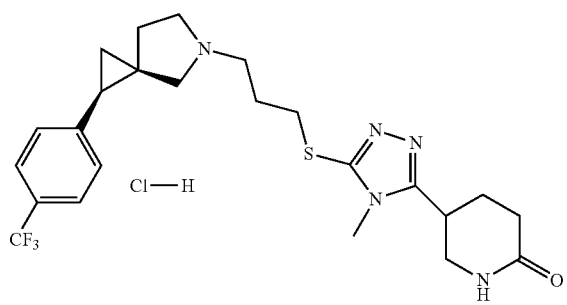

The compound was prepared as in Example 1, reacting (1R,3S)-1-[4-(trifluoromethyl)phenyl]-5-azaspiro[2.4]heptane (CIS, Enantiomer 1, p15, 25 mg, 0.103 mmol), 5-{5-[(3-chloropropyl)sulfanyl]-4-methyl-4H-1,2,4-triazol-3-yl}piperidin-2-one (p155, 33 mg, 0.113 mmol), Na$_2$CO$_3$ (13 mg, 0.12 mmol) and NaI (18 mg, 0.12 mmol) in DMF (0.1 mL) affording 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one (CIS, Enantiomer 1, 12 mg).

The latter was dissolved with DCM/Et₂O and treated with 1.2 eq of HCl in Et₂O affording 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]piperidin-2-one hydrochloride (E121, CIS, Enantiomer 1, 10 mg, y=18%) as diastereomeric mixture. NMR: ¹H NMR (DMSO-d₆) δ: 10.40-10.71 (m, 1H), 7.57-7.74 (m, 3H), 7.44 (d, 2H), 3.61-3.74 (m, 1H), 3.54 (s, 3H), 2.88-3.45 (m, 10H), 2.18-2.67 (m, 4H), 1.84-2.16 (m, 5H), 1.25-1.55 (m, 2H). MS (m/z): 494.3 [MH]⁺.

Preparation 258: (1R,3S/1S,3R)-5-(3-chloropropyl)-1-[4-(trifluoromethyl)phenyl]-5-azaspiro[2.4]heptane (CIS, p258)

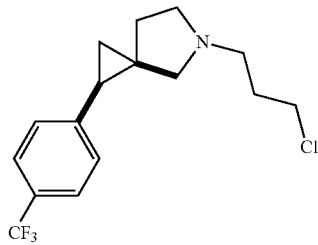

To a solution of (1R,3S/1S,3R)-1-[4-(trifluoromethyl)phenyl]-5-azaspiro[2.4]heptane (p14, 56 mg, 0.23 mmol) in THF (0.4 mL), in a vial, DIPEA (0.12 mL, 0.69 mmol) and 1-bromo-3-chloropropane (0.21 mL, 2.07 mmol) were added, the vial was sealed and the resulting mixture was shaken at 65° C. for 3 hrs. After cooling at RT the reaction mixture was diluted with EA and filtered.

The filtrate was concentrated under reduced pressure and the crude material was purified by FC on silica gel (eluting with DCM/MeOH from 100/0 to 96/4) affording (1R,3S/1S,3R)-5-(3-chloropropyl)-1-[4-(trifluoromethyl)phenyl]-5-azaspiro[2.4]heptane (CIS, p258, 51 mg, y=68%) as pale yellow oil. MS (m/z): 318.3 [MH]⁺.

Example 122: 6-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E122)

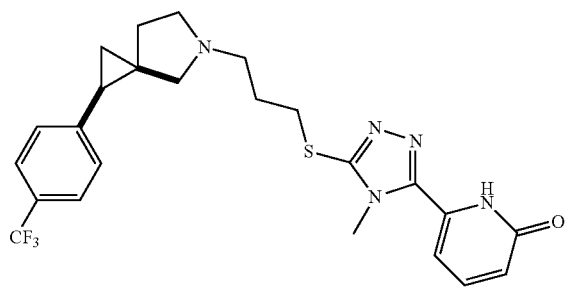

A sealed vial containing a mixture of (1R,3S/1S,3R)-5-(3-chloropropyl)-1-[4-(trifluoromethyl)phenyl]-5-azaspiro[2.4]heptane (p258, CIS, 25 mg, 0.079 mmol), 6-(4-methyl-5-sulfanyl-4H-1,2,4-triazol-3-yl)-1,2-dihydropyridin-2-one (p72, 18 mg, 0.087 mmol), Na₂CO₃ (10 mg, 0.095 mmol) and NaI (12 mg, 0.079 mmol) and DMF (0.2 mL) was shaken O/N at 60° C. in a PLS apparatus. The mixture was diluted with DCM, the organic phase was washed twice with water, dried over sodium sulfate and the solvent removed under reduced pressure. The crude material was purified by FC on silica gel (eluting with DCM/MeOH from 100/0 to 50/50) to give 6-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E122, 26 mg, y=66%). NMR: ¹H NMR (DMSO-d₆) δ: 11.06-11.17 (m, 1H), 7.73-7.81 (m, 1H), 7.56-7.67 (m, 2H), 7.29-7.46 (m, 3H), 6.68-6.76 (m, 1H), 3.86 (s, 3H), 3.14 (d, 2H), 2.64-2.78 (m, 1H), 2.36-2.50 (m, 4H), 2.18-2.26 (m, 1H), 1.83-2.01 (m, 3H), 1.75 (m, 2H), 1.23-1.31 (m, 1H), 1.14-1.23 (m, 1H). MS (m/z): 490.4 [MH]⁺.

Example 123: 6-[5-({3-[(1R,3S/1S,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]-1,2-dihydropyridin-2-one (TRANS, E123)

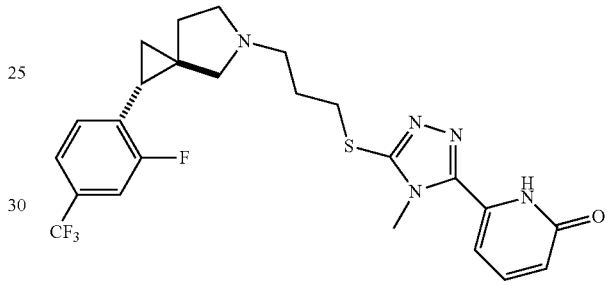

The compound was prepared as in Example 1, reacting (1R,3S/1S,3R)-1-[2-fluoro-4-(trifluoromethyl)phenyl]-5-azaspiro[2.4]heptane (p13, TRANS, 30 mg, 0.12 mmol), 6-{5-[(3-chloropropyl)sulfanyl]-4-methyl-4H-1,2,4-triazol-3-yl}-1,2-dihydropyridin-2-one (p156, 38 mg, 0.132 mmol), Na₂CO₃ (15 mg, 0.144 mmol) and NaI (22 mg, 0.144 mmol) in DMF (0.13 mL) affording 6-[5-({3-[(1R,3S/1S,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]-1,2-dihydropyridin-2-one (TRANS, E123, 30 mg, y=44%). NMR: ¹H NMR (Acetone-d₆) δ: 7.75-7.82 (m, 1H), 7.51-7.57 (m, 1H), 7.45-7.51 (m, 2H), 7.26-7.32 (m, 1H), 6.72-6.77 (m, 1H), 3.97 (s, 3H), 3.33 (m, 2H), 2.75 (d, 1H), 2.63-2.70 (m, 2H), 2.53-2.63 (m, 3H), 2.26-2.33 (m, 1H), 1.93-2.00 (m, 2H), 1.57-1.67 (m, 1H), 1.23-1.39 (m, 3H). MS (m/z): 508.0 [MH]⁺.

Example 124: 3-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E124)

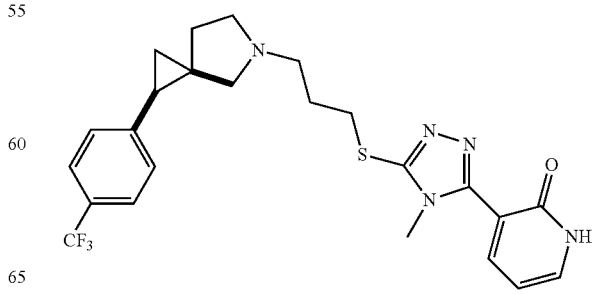

The compound was prepared as in Example 1, reacting (1R,3S/1S,3R)-1-[4-(trifluoromethyl)phenyl]-5-azaspiro[2.4]heptane (p14, CIS, 30 mg, 0.116 mmol), 3-{5-[(3-chloropropyl)sulfanyl]-4-methyl-4H-1,2,4-triazol-3-yl}-1,2-dihydropyridin-2-one (p157, 36 mg, 0.13 mmol), Na$_2$CO$_3$ (15 mg, 0.144 mmol) and NaI (21 mg, 0.144 mmol) in DMF (0.2 mL) affording 3-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E124, 23 mg, y=40%). NMR: $^1$H NMR (CDCl3) δ: 7.64-7.72 (m, 1H), 7.50-7.59 (m, 3H), 7.17-7.25 (m, 2H), 6.32-6.39 (m, 1H), 3.46 (s, 3H), 3.17-3.25 (m, 2H), 2.76-2.85 (m, 1H), 2.57-2.65 (m, 1H), 2.46-2.54 (m, 2H), 2.42 (d, 1H), 2.10-2.16 (m, 2H), 1.81-2.02 (m, 4H), 1.16-1.23 (m, 2H). MS (m/z): 490.4 [MH]$^+$.

Example 125: 3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one hydrochloride (CIS, Enantiomer 1, E125)

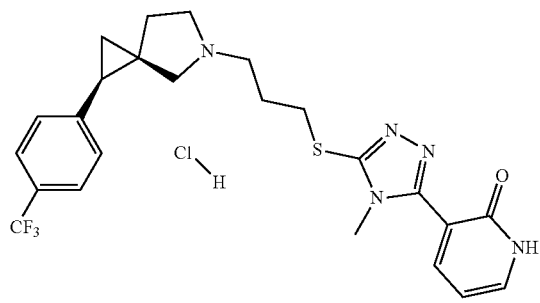 [SMILES: Cn1c(SCCCN2CC[C@]3(C[C@@H]3c3ccc(C(F)(F)F)cc3)C2)nnc1-c1ccc[nH]c1=O ; Cl]

The compound was prepared as in Example 1, reacting (1R,3S)-1-[4-(trifluoromethyl)phenyl]-5-azaspiro[2.4]heptane (p15, CIS, Enantiomer 1, 25 mg, 0.1 mmol), 3-{5-[(3-chloropropyl)sulfanyl]-4-methyl-4H-1,2,4-triazol-3-yl}-1,2-dihydropyridin-2-one (p157, 32 mg, 0.11 mmol), Na$_2$CO$_3$ (13 mg, 0.12 mmol) and NaI (15 mg, 0.1 mmol) in DMF (0.2 mL) affording 3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (25 mg).

The latter was dissolved in DCM (0.2 mL) then 2N HCl/ether (1.1 eq) was added and the reaction mixture was concentrated under vacuum. The solid so obtained was triturated with ether and dried under vacuum at 45° C. overnight affording 3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one hydrochloride (CIS, Enantiomer 1, E125, 26 mg, y=49%) as white solid. NMR: $^1$H NMR (DMSO-d$_6$) δ: 12.22 (br. s., 1H), 10.23-10.66 (m, 1H), 7.74 (m, 1H), 7.61-7.69 (m, 3H), 7.36-7.49 (m, 2H), 6.38 (m, 1H), 2.59-3.79 (m, 11H), 2.25 (m, 5H), 1.23-1.56 (m, 2H). MS (m/z): 490.4 [MH]$^+$.

Example 126: 5-[4-methyl-5-({3-[(1S,3S/1R,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (TRANS, E126)

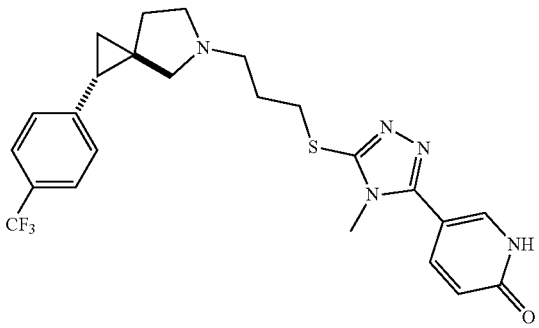

The compound was prepared as in Example 1, reacting (1S,3S/1R,3R)-1-[4-(trifluoromethyl)phenyl]-5-azaspiro[2.4]heptane (p13, TRANS, 50 mg, 0.207 mmol), 5-{5-[(3-chloropropyl)sulfanyl]-4-methyl-4H-1,2,4-triazol-3-yl}-1,2-dihydropyridin-2-one (p158, 65 mg, 0.228 mmol), Na$_2$CO$_3$ (26 mg, 0.248 mmol) and NaI (37 mg, 0.248 mmol) in DMF (0.2 mL) affording 5-[4-methyl-5-({3-[(1S,3S/1R,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (TRANS, E126, 48 mg, y=47%). NMR: $^1$H NMR (Acetone-d$_6$) δ: 7.87 (d, 1H), 7.75-7.83 (m, 1H), 7.64 (d, 2H), 7.35 (d, 2H), 6.52 (d, 1H), 3.71 (s, 3H), 3.29 (m, 2H), 2.75 (d, 2H), 2.53-2.67 (m, 5H), 2.23-2.32 (m, 1H), 1.90-2.00 (m, 2H), 1.61-1.73 (m, 1H), 1.37-1.49 (m, 1H), 1.27 (d, 1H), 1.22 (d, 1H). MS (m/z): 490.4 [MH]$^+$.

Example 127: 5-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E127)

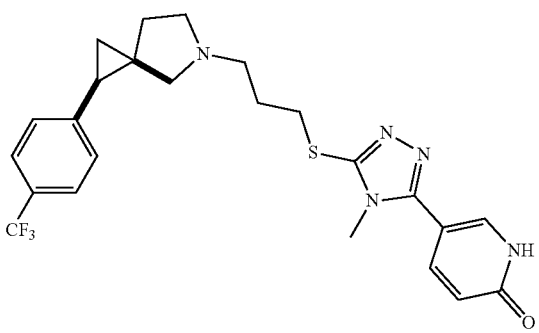

The compound was prepared as in Example 1, reacting (1R,3S/1S,3R)-1-[4-(trifluoromethyl)phenyl]-5-azaspiro[2.4]heptane (p14, CIS, 35 mg, 0.15 mmol), 5-{5-[(3-chloropropyl)sulfanyl]-4-methyl-4H-1,2,4-triazol-3-yl}-1,2-dihydropyridin-2-one (p158, 43 mg, 0.15 mmol), Na$_2$CO$_3$ (19 mg, 0.18 mmol) and NaI (22 mg, 0.15 mmol) in DMF (0.2 mL) affording 5-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E127, 33 mg, y=45%). NMR: $^1$H NMR (DMSO-d$_6$) δ: 11.96-12.10 (m, 1H), 7.68-7.80 (m, 2H), 7.55-7.64 (m, 2H), 7.27-7.36 (m, 2H), 6.44-6.53 (m, 1H), 3.52 (s, 3H), 3.01-3.15 (m, 2H), 2.68 (br. s., 1H), 2.33-2.48 (m, 4H), 2.16-2.26 (m, 1H), 1.81-2.02 (m, 3H), 1.73 (m, 2H), 1.27 (m, 1H), 1.18 (m, 1H). MS (m/z): 490.5 [MH]$^+$.

Example 128: 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1, E128)

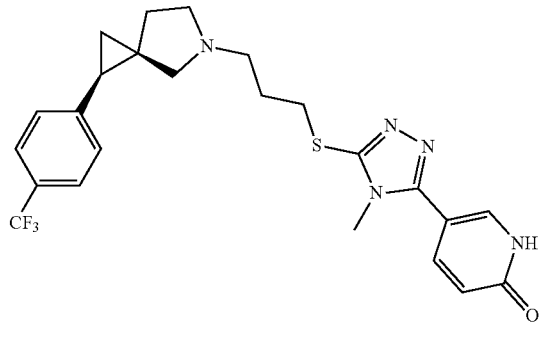 [SMILES: Cn1c(SCCCN2CC[C@]3(C[C@@H]3c3ccc(C(F)(F)F)cc3)C2)nnc1-c1ccc(=O)[nH]c1]

The compound was prepared as in Example 1, reacting (1R,3S)-1-[4-(trifluoromethyl)phenyl]-5-azaspiro[2.4]heptane (p15, CIS, Enantiomer 1, 35 mg, 0.15 mmol), 5-{5-[(3-chloropropyl)sulfanyl]-4-methyl-4H-1,2,4-triazol-3-yl}-1,2-dihydropyridin-2-one (p158, 43 mg, 0.15 mmol), Na$_2$CO$_3$ (19 mg, 0.18 mmol) and NaI (22 mg, 0.15 mmol) in DMF (0.2 mL) affording 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1, E128, 23 mg, y=31%). NMR: $^1$H NMR (Acetone-d$_6$) δ: 7.87-7.91 (m, 1H), 7.73-7.79 (m, 1H), 7.61 (d, 2H), 7.37 (d, 2H), 6.46-6.52 (m, 1H), 3.66 (s, 3H), 3.10-3.27 (m, 3H), 2.68-2.78 (m, 2H), 2.56-2.65 (m, 1H), 2.47 (s, 3H), 2.18-2.27 (m, 1H), 1.92-2.02 (m, 2H), 1.75-1.87 (m, 2H), 1.25-1.30 (m, 1H), 1.17-1.22 (m, 1H). MS (m/z): 490.5 [MH]$^+$.

Example 129: 5-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]-1,2-dihydropyridin-2-one (CIS, E129)

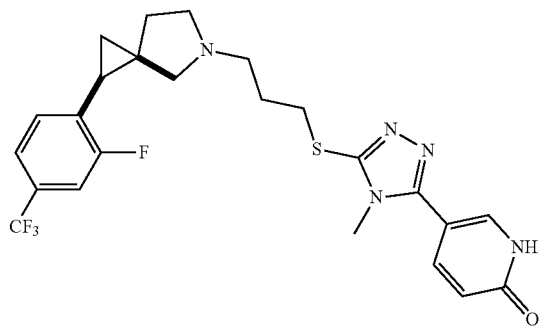

The compound was prepared as in Example 1, reacting (1S,3S/1R,3R)-1-[2-fluoro-4-(trifluoromethyl)phenyl]-5-azaspiro[2.4]heptane (p23, CIS, 50 mg, 0.193 mmol), 5-{5-[(3-chloropropyl)sulfanyl]-4-methyl-4H-1,2,4-triazol-3-yl}-1,2-dihydropyridin-2-one (p158, 60 mg, 0.212 mmol), Na$_2$CO$_3$ (25 mg, 0.23 mmol) and NaI (35 mg, 0.23 mmol) in DMF (0.2 mL) affording 5-[5-({3-[(1S,3S/1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]-1,2-dihydropyridin-2-one (CIS, E129, 17.8 mg, y=18%). NMR: $^1$H NMR (Acetone-d$_6$) δ: 10.73-10.95 (m, 1H), 7.84 (m, 1H), 7.77 (m, 1H), 7.43-7.52 (m, 2H), 7.27-7.39 (m, 1H), 6.51 (m, 1H), 3.66 (s, 3H), 3.10-3.34 (m, 2H), 2.75 (br. s., 1H), 2.38-2.67 (m, 4H), 2.19-2.33 (m, 1H), 1.92-2.03 (m, 3H), 1.73-1.87 (m, 2H), 1.31-1.38 (m, 1H), 1.19-1.28 (m, 1H). MS (m/z): 508.4 [MH]$^+$.

Example 130: 5-[5-({3-[(1S,3S/1R,3R)-1-(2,4-difluorophenyl)-5-azaspiro[2.4]heptan-5-yl]propyl}sulfanyl)-4-methyl-4H-1,2,4-triazol-3-yl]-1,2-dihydropyridin-2-one (CIS, E130)

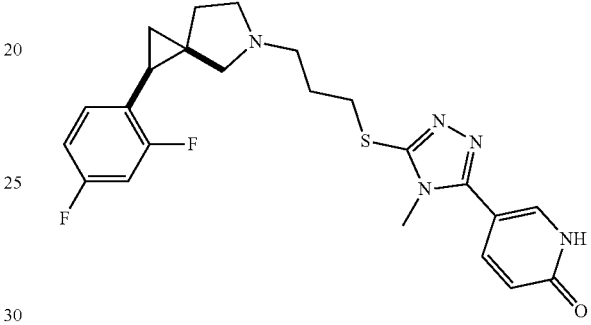

The compound was prepared as in Example 1, reacting (1S,3S/1R,3R)-1-(2,4-difluorophenyl)-5-azaspiro[2.4]heptane (p29, CIS, 50 mg, 0.24 mmol), 5-{5-[(3-chloropropyl)sulfanyl]-4-methyl-4H-1,2,4-triazol-3-yl}-1,2-dihydropyridin-2-one (p158, 74 mg, 0.26 mmol), Na$_2$CO$_3$ (31 mg, 0.28 mmol) and NaI (43 mg, 0.288 mmol) in DMF (0.2 mL) affording 5-[5-({3-[(1S,3S/1R,3R)-1-(2,4-difluorophenyl)-5-azaspiro[2.4]heptan-5-yl]propyl}sulfanyl)-4-methyl-4H-1,2,4-triazol-3-yl]-1,2-dihydropyridin-2-one (CIS, E130, 38 mg, y=34%). NMR: $^1$H NMR (Acetone-d$_6$) δ: 7.83-7.88 (m, 1H), 7.74-7.79 (m, 1H), 7.08-7.18 (m, 1H), 6.88-7.03 (m, 2H), 6.47-6.54 (m, 1H), 3.66 (s, 3H), 3.13-3.27 (m, 2H), 2.60 (d, 1H), 2.48 (m, 2H), 2.35 (d, 1H), 2.08-2.13 (m, 2H), 1.92-2.00 (m, 3H), 1.77-1.86 (m, 2H), 1.17-1.24 (m, 1H), 1.10-1.16 (m, 1H). MS (m/z): 458.3 [MH]$^+$.

Example 131: 5-[5-({3-[(1R,3S/1S,3R)-1-(4-fluorophenyl)-5-azaspiro[2.4]heptan-5-yl]propyl}sulfanyl)-4-methyl-4H-1,2,4-triazol-3-yl]-1,2-dihydropyridin-2-one (CIS, E131)

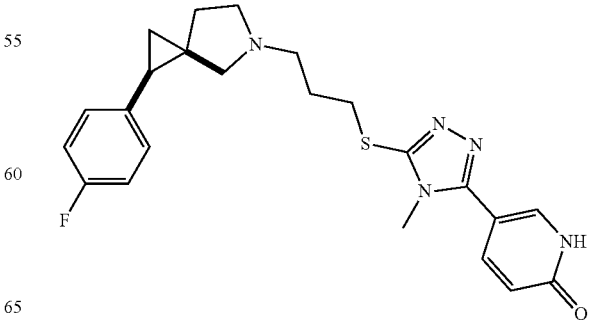

The compound was prepared as in Example 1, reacting (1R,3S/1S,3R)-1-(4-fluorophenyl)-5-azaspiro[2.4]heptane (p33, CIS, 50 mg, 0.26 mmol), 5-{5-[(3-chloropropyl)sulfanyl]-4-methyl-4H-1,2,4-triazol-3-yl}-1,2-dihydropyridin-2-one (p158, 83 mg, 0.29 mmol), Na₂CO₃ (33 mg, 0.31 mmol) and NaI (47 mg, 0.31 mmol) in DMF (0.2 mL) affording 5-[5-({3-[(1R,3S/1S,3R)-1-(4-fluorophenyl)-5-azaspiro[2.4]heptan-5-yl]propyl}sulfanyl)-4-methyl-4H-1,2,4-triazol-3-yl]-1,2-dihydropyridin-2-one (CIS, E131, 30 mg, y=26%). NMR: ¹H NMR (Acetone-d₆) δ: 7.82-7.87 (m, 1H), 7.75-7.81 (m, 1H), 7.16-7.21 (m, 2H), 7.03 (s, 2H), 6.47-6.54 (m, 1H), 3.67 (s, 3H), 3.12-3.26 (m, 2H), 2.59-2.74 (m, 3H), 2.48 (s, 2H), 2.35 (s, 1H), 1.91-2.01 (m, 2H), 1.76-1.87 (m, 2H), 1.11 (s, 2H). MS (m/z): 440.4 [MH]⁺.

Example 132: 5-[4-methyl-5-({3-[(1S,3S/1R,3R)-1-[2-(trifluoromethyl)phenyl]-5-azaspiro[2.4]heptan-5-yl]propyl}sulfanyl)-4H-1,2,4-triazol-3-yl]-1,2-dihydropyridin-2-one (TRANS, E132)

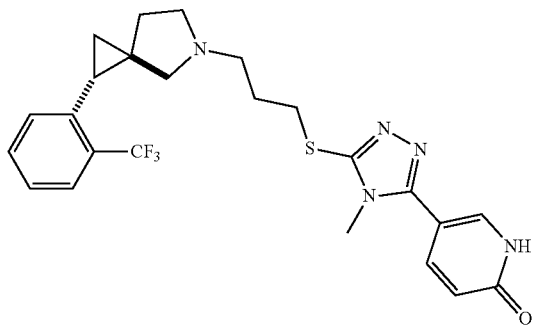

The compound was prepared as in Example 1, reacting (1S,3S/1R,3R)-1-[2-(trifluoromethyl)phenyl]-5-azaspiro[2.4]heptane (p40, TRANS, 30 mg, 0.124 mmol), 5-{5-[(3-chloropropyl)sulfanyl]-4-methyl-4H-1,2,4-triazol-3-yl}-1,2-dihydropyridin-2-one (p158, 35 mg, 0.124 mmol), Na₂CO₃ (16 mg, 0.15 mmol) and NaI (19 mg, 0.124 mmol) in DMF (0.2 mL) affording 5-[4-methyl-5-({3-[(1S,3S/1R,3R)-1-[2-(trifluoromethyl)phenyl]-5-azaspiro[2.4]heptan-5-yl]propyl}sulfanyl)-4H-1,2,4-triazol-3-yl]-1,2-dihydropyridin-2-one (TRANS, E132, 25 mg, y=41%). NMR: ¹H NMR (CDCl₃) δ: 7.71-7.80 (m, 2H), 7.66 (d, 1H), 7.46 (m, 1H), 7.26-7.32 (m, 1H), 7.09 (d, 1H), 6.65-6.80 (m, 1H), 3.59 (s, 3H), 3.35 (m, 2H), 2.48-2.95 (m, 5H), 2.27-2.44 (m, 2H), 1.91-2.09 (m, 2H), 1.45-1.61 (m, 1H), 1.12-1.34 (m, 3H). MS (m/z): 490.4 [MH]⁺.

Example 133: 1-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one hydrochloride (CIS, Enantiomer 1, E133)

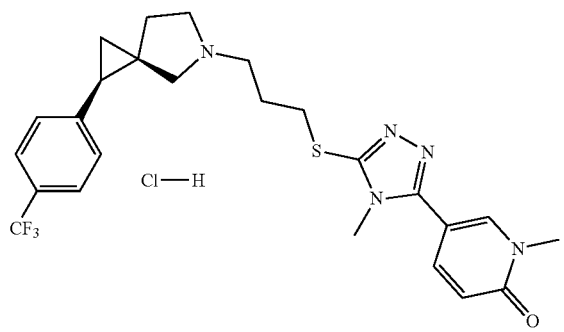 [SMILES: Cn1c(SCCCN2CC[C@]3(C[C@@H]3c3ccc(C(F)(F)F)cc3)C2)nnc1-c1ccc(=O)n(C)c1 ; Cl]

The compound was prepared as in Example 1, reacting (1R,3S)-1-[4-(trifluoromethyl)phenyl]-5-azaspiro[2.4]heptane (p15, CIS, Enantiomer 1, 35 mg, 0.15 mmol), 5-{5-[(3-chloropropyl)sulfanyl]-4-methyl-4H-1,2,4-triazol-3-yl}-1-methyl-1,2-dihydropyridin-2-one (p159, 50 mg, 0.165 mmol), Na₂CO₃ (19 mg, 0.18 mmol) and NaI (22 mg, 0.18 mmol) in DMF (0.2 mL) affording 1-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (45 mg) that was dissolved in Et₂O (0.5 mL) and treated with 1.1 eq of 2N HCl in ether. Solvent was eliminated under vacuum and the solid so obtained was triturated with ether and dried under vacuum affording 1-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one hydrochloride (CIS, Enantiomer 1, E133, 46.8 mg, y=58%). NMR: ¹H NMR (DMSO-d₆) δ: 10.36 (s, 1H), 10.14-10.15 (m, 1H), 8.17 (br. s., 1H), 7.61-7.79 (m, 3H), 7.45 (d, 2H), 6.55 (d, 1H), 3.71 (br. s., 2H), 3.48-3.64 (m, 6H), 3.24-3.47 (m, 2H), 3.18 (d, 4H), 2.99 (br. s., 1H), 2.26 (d, 1H), 1.88-2.18 (m, 3H), 1.25-1.54 (m, 2H). MS (m/z): 504.5 [MH]⁺.

Example 134: 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E134)

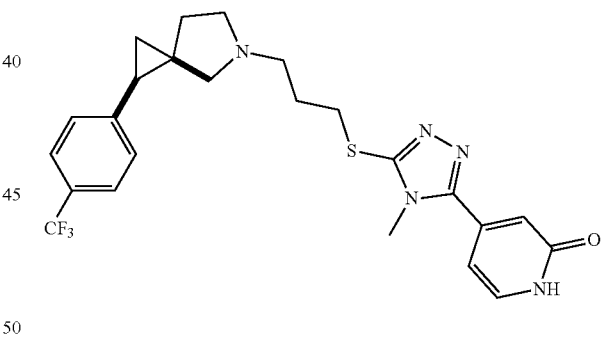

The compound was prepared as in Example 1, reacting (1R,3S/1S,R3)-1-[4-(trifluoromethyl)phenyl]-5-azaspiro[2.4]heptane (p14, CIS, 40 mg, 0.17 mmol), 4-{5-[(3-chloropropyl)sulfanyl]-4-methyl-4H-1,2,4-triazol-3-yl}-1,2-dihydropyridin-2-one (p160, 48 mg, 0.17 mmol), Na₂CO₃ (22 mg, 0.2 mmol) and NaI (25 mg, 0.17 mmol) in DMF (0.25 mL) affording 4-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, E134, 14 mg, y=17%). NMR: ¹H NMR (DMSO-d₆) δ: 7.61 (d, 2H), 7.54 (d, 1H), 7.32 (d, 2H), 6.63 (d, 1H), 6.46-6.53 (m, 1H), 3.61 (s, 3H), 3.07-3.19 (m, 2H), 2.65-2.74 (m, 1H), 2.35-2.49 (m, 5H), 2.17-2.24 (m, 1H), 1.83-1.98 (m, 3H), 1.70-1.79 (m, 2H), 1.24-1.30 (m, 1H), 1.13-1.21 (m, 1H). MS (m/z): 490.4 [MH]⁺.

Example 135: 4-[4-methyl-5-({3-[(1S,3S/1R,3R)-1-[2-(trifluoromethyl)phenyl]-5-azaspiro[2.4]heptan-5-yl]propyl}sulfanyl)-4H-1,2,4-triazol-3-yl]-1,2-dihydropyridin-2-one (TRANS, E135)

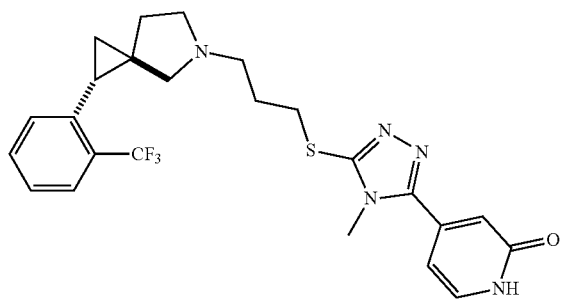

The compound was prepared as in Example 1, reacting (1S,3S/1R,3R)-1-[2-(trifluoromethyl)phenyl]-5-azaspiro[2.4]heptane (p40, TRANS, 30 mg, 0.124 mmol), 4-{5-[(3-chloropropyl)sulfanyl]-4-methyl-4H-1,2,4-triazol-3-yl}-1,2-dihydropyridin-2-one (p160, 35 mg, 0.124 mmol), Na$_2$CO$_3$ (16 mg, 0.15 mmol) and NaI (19 mg, 0.124 mmol) in DMF (0.25 mL) affording 4-[4-methyl-5-({3-[(1S,3S/1R,3R)-1-[2-(trifluoromethyl)phenyl]-5-azaspiro[2.4]heptan-5-yl]propyl}sulfanyl)-4H-1,2,4-triazol-3-yl]-1,2-dihydropyridin-2-one (TRANS, E135, 12 mg, y=20%). NMR: $^1$H NMR (CDCl$_3$) δ: 7.66 (d, 1H), 7.38-7.50 (m, 2H), 7.22-7.33 (m, 1H), 7.09 (d, 1H), 6.76-6.84 (m, 2H), 3.70 (s, 3H), 3.40 (m, 2H), 2.53-2.93 (m, 5H), 2.29-2.40 (m, 2H), 2.02 (m, 2H), 1.48-1.69 (m, 1H), 1.16-1.34 (m, 3H). MS (m/z): 490.4 [MH]$^+$.

Example 136: 1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1, E136)

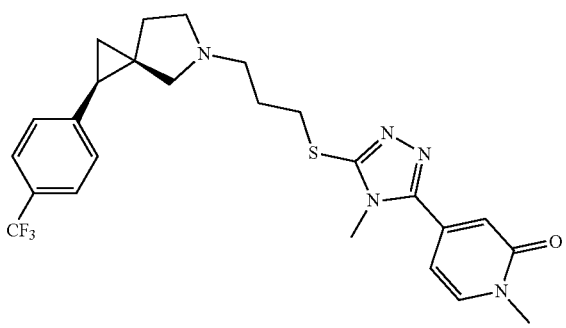 [SMILES: Cn1c(SCCCN2CC[C@]3(C[C@@H]3c3ccc(C(F)(F)F)cc3)C2)nnc1-c1ccn(C)c(=O)c1]

The compound was prepared as in Example 1, reacting (1R,3S)-1-[4-(trifluoromethyl)phenyl]-5-azaspiro[2.4]heptane (p15, CIS, Enantiomer 1, 25 mg, 0.096 mmol), 4-{5-[(3-chloropropyl)sulfanyl]-4-methyl-4H-1,2,4-triazol-3-yl}-1-methyl-1,2-dihydropyridin-2-one (p161, 30 mg, 0.1 mmol), Na$_2$CO$_3$ (12 mg, 0.115 mmol) and NaI (17 mg, 0.115 mmol) in DMF (0.2 mL) affording 1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1, E136, 40 mg, y=82%). NMR: $^1$H NMR (Acetone-d$_6$) δ: 7.72-7.77 (m, 1H), 7.59-7.65 (m, 2H), 7.36-7.43 (m, 2H), 6.68-6.73 (m, 1H), 6.56-6.63 (m, 1H), 3.76 (s, 3H), 3.51-3.58 (m, 3H), 3.15-3.35 (m, 2H), 2.58 (br. s., 4H), 2.23-2.29 (m, 1H), 2.17 (br. s., 1H), 1.81-2.02 (m, 5H), 1.29-1.35 (m, 1H), 1.20-1.26 (m, 1H). MS (m/z): 504.3 [MH]$^+$.

Example 137: 1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one hydrochloride (CIS, Enantiomer 1, E137)

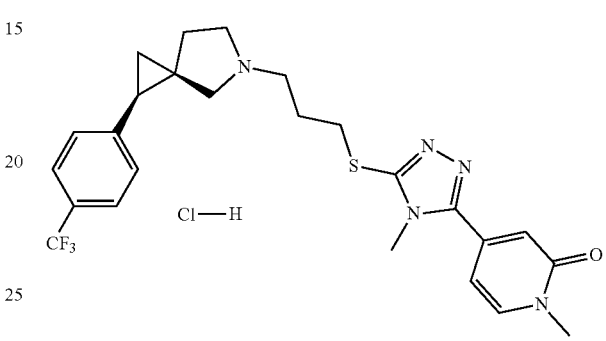

1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one (CIS, Enantiomer 1, E136, 40 mg) was dissolved in MeOH and treated with HCl 2M in Et$_2$O (1.1 eq) to form the corresponding hydrochloride salt. Solvent was eliminated under reduced pressure; the solid was triturated with Et$_2$O and dried under high vacuum affording 1-methyl-4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]-1,2-dihydropyridin-2-one hydrochloride (CIS, Enantiomer 1, E137, 42 mg). MS (m/z): 504.3 [MH]$^+$.

Example 138: 4-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]-1-methyl-1,2-dihydropyridin-2-one (CIS, Enantiomer 1, E138)

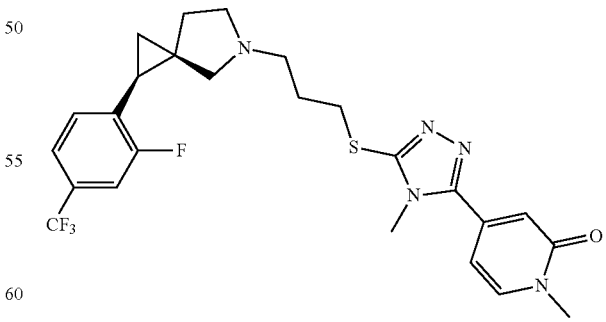

The compound was prepared as in Example 1, reacting (1S,3S)-1-[2-fluoro-4-(trifluoromethyl)phenyl]-5-azaspiro[2.4]heptane (p24, CIS, 26 mg, 0.1 mmol), 4-{5-[(3-chloropropyl)sulfanyl]-4-methyl-4H-1,2,4-triazol-3-yl}-1-methyl-1,2-dihydropyridin-2-one (p161, 33 mg, 0.11 mmol), Na₂CO₃ (13 mg, 0.12 mmol) and NaI (18 mg, 0.12 mmol) in DMF (0.113 mL) affording 4-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]-1-methyl-1,2-dihydropyridin-2-one (CIS, Enantiomer 1, E138, 29 mg, y=55%). NMR: ¹H NMR (Acetone-d₆) δ: 7.72-7.81 (m, 1H), 7.45-7.54 (m, 2H), 7.30-7.45 (m, 1H), 6.68-6.76 (m, 1H), 6.55-6.63 (m, 1H), 3.77 (s, 3H), 3.56 (s, 3H), 3.19-3.37 (m, 2H), 2.26-2.68 (m, 7H), 1.77-2.01 (m, 4H), 1.19-1.48 (m, 2H). MS (m/z): 522.4 [MH]⁺.

Example 139: 4-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]-1-methyl-1,2-dihydropyridin-2-one hydrochloride (CIS, Enantiomer 1, E139)

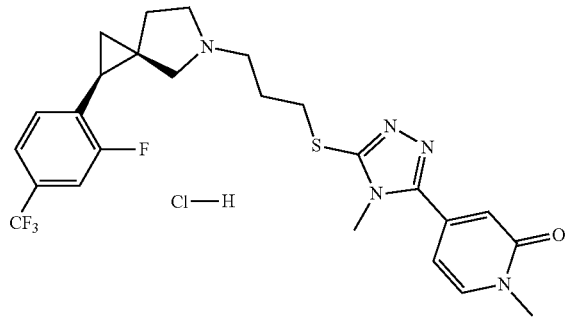 [SMILES: Cn1c(SCCCN2CC[C@]3(C[C@@H]3c3ccc(C(F)(F)F)cc3F)C2)nnc1-c1ccn(C)c(=O)c1 ; Cl]

4-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]-1-methyl-1,2-dihydropyridin-2-one (CIS, Enantiomer 1, E138, 29 mg) was dissolved in MeOH and treated with HCl 2M in Et₂O (1.1 eq) to form the corresponding hydrochloride salt. Solvent was eliminated under reduced pressure; the solid was triturated with Et₂O and dried under high vacuum affording 4-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]-1-methyl-1,2-dihydropyridin-2-one hydrochloride (CIS, Enantiomer 1, E139, 30.7 mg). MS (m/z): 522.3 [MH]⁺.

Example 140: (1S,3S/1R,3R)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane (TRANS, E140)

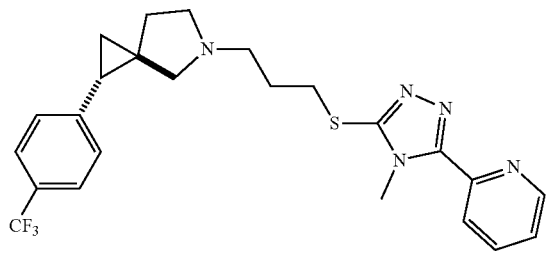

The compound was prepared as in Example 1, reacting (1S,3S/1R,3R)-1-[4-(trifluoromethyl)phenyl]-5-azaspiro[2.4]heptane (p13, TRANS, 50 mg, 0.207 mmol), 2-{5-[(3-chloropropyl)sulfanyl]-4-methyl-4H-1,2,4-triazol-3-yl}pyridine (p162, 62 mg, 0.228 mmol), Na₂CO₃ (26 mg, 0.248 mmol) and NaI (37 mg, 0.248 mmol) in DMF (0.2 mL) affording (1S,3S/1R,3R)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane (TRANS, E140, 57 mg, y=58%). NMR: ¹H NMR (Acetone-d₆) δ: 8.68-8.73 (m, 1H), 8.22 (d, 1H), 7.98 (d, 1H), 7.62 (d, 2H), 7.45-7.51 (m, 1H), 7.35 (d, 2H), 4.05 (s, 3H), 3.30-3.39 (m, 2H), 2.71-2.77 (m, 2H), 2.54-2.68 (m, 5H), 2.23-2.31 (m, 1H), 1.93-2.02 (m, 2H), 1.61-1.71 (m, 1H), 1.37-1.47 (m, 1H), 1.23-1.29 (m, 1H), 1.18-1.23 (m, 1H). MS (m/z): 474.4 [MH]⁺.

Example 141: (1R,3S/1S,3R)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane dihydrochloride (CIS, E141)

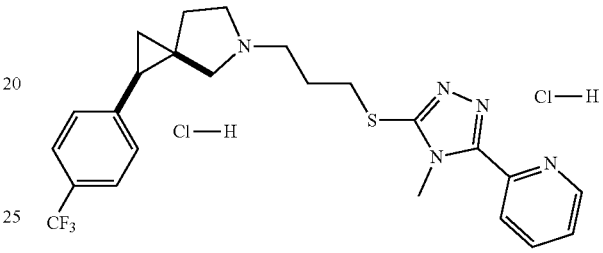

The compound was prepared as in Example 1, reacting (1R,3S/1S,3R)-1-[4-(trifluoromethyl)phenyl]-5-azaspiro[2.4]heptane (CIS, p14, 35 mg, 0.15 mmol), 2-{5-[(3-chloropropyl)sulfanyl]-4-methyl-4H-1,2,4-triazol-3-yl}pyridine (p162, 39 mg, 0.15 mmol), Na₂CO₃ (19 mg, 0.18 mmol) and NaI (22 mg, 0.15 mmol) in DMF (0.2 mL) affording (1R,3S/1S,3R)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane (23 mg).

The latter was dissolved in DCM (0.2 mL) then 2N HCl/ether (0.049 mL) was added and the reaction mixture was concentrated under vacuum. The solid so obtained was triturated with ether and dried under vacuum at 45° C. O/N, affording (1R,3S/1S,3R)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane dihydrochloride (CIS, E141, 25 mg, y=30%). NMR: ¹H NMR (DMSO-d₆) δ: 10.54-10.84 (m, 1H), 8.73 (d, 1H), 8.12 (d, 1H), 8.01 (m, 1H), 7.66 (d, 2H), 7.54 (m, 1H), 7.44 (d, 2H), 3.92 (d, 3H), 3.65-3.75 (m, 1H), 2.92-3.46 (m, 7H), 2.59-2.70 (m, 1H), 2.18-2.43 (m, 2H), 1.92-2.16 (m, 3H), 1.25-1.53 (m, 2H). MS (m/z): 474.5 [MH]⁺.

Example 142: (1S,3S/1R,3R)-5-(3-{[4-methyl-5-(pyridin-3-yl)-4H-1,2,4-triazol-3-yl]sulfanyl}propyl)-1-[4-(trifluoromethyl)phenyl]-5-azaspiro[2.4]heptane (TRANS, E142)

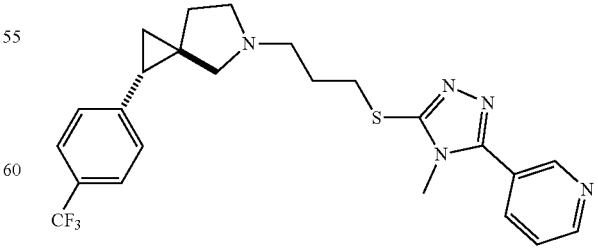

The compound was prepared as in Example 1, reacting (1S,3S/1R,3R)-1-[4-(trifluoromethyl)phenyl]-5-azaspiro[2.4]heptane (p13, TRANS, 50 mg, 0.207 mmol), 3-{5-[(3- chloropropyl)sulfanyl]-4-methyl-4H-1,2,4-triazol-3-yl}pyridine (p163, 62 mg, 0.228 mmol), Na$_2$CO$_3$ (26 mg, 0.248 mmol) and NaI (37 mg, 0.248 mmol) in DMF (0.2 mL) affording (1S,3S/1R,3R)-5-(3-{[4-methyl-5-(pyridin-2-yl)-4H-1,2,4-triazol-3-yl]sulfanyl}propyl)-1-[4-(trifluoromethyl)phenyl]-5-azaspiro[2.4]heptane (TRANS, E142, 58 mg, y=59%). NMR: $^1$H NMR (Acetone-d$_6$) δ: 8.96 (d, 1H), 8.73 (m, 1H), 8.15 (d, 1H), 7.63 (d, 2H), 7.54-7.60 (m, 1H), 7.35 (d, 2H), 3.76 (s, 3H), 3.33 (m, 2H), 2.73-2.77 (m, 1H), 2.54-2.68 (m, 6H), 2.24-2.31 (m, 1H), 1.97 (s, 2H), 1.62-1.72 (m, 1H), 1.38-1.49 (m, 1H), 1.27 (m, 1H), 1.19-1.24 (m, 1H). MS (m/z): 474.4 [MH]$^+$.

Example 143: (1R,3S/1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane dihydrochloride (CIS, E143)

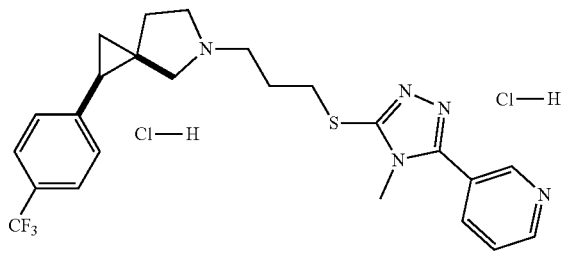

The compound was prepared as in Example 1, reacting (1R,3S/1S,3R)-1-[4-(trifluoromethyl)phenyl]-5-azaspiro[2.4]heptane (CIS, p14, 35 mg, 0.15 mmol), 3-{5-[(3-chloropropyl)sulfanyl]-4-methyl-4H-1,2,4-triazol-3-yl}pyridine (p163, 39 mg, 0.15 mmol), Na$_2$CO$_3$ (19 mg, 0.18 mmol) and NaI (22 mg, 0.15 mmol) in DMF (0.2 mL) affording (1R,3S/1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (25 mg).

The latter was dissolved in DCM (0.2 mL) then 2N HCl/ether (0.049 mL) was added and the reaction mixture was concentrated under vacuum. The solid so obtained was triturated with ether and dried under vacuum at 45° C. O/N, affording (1R,3S/1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane dihydrochloride (CIS, E143, 28 mg, y=34%). NMR: $^1$H NMR (DMSO-d$_6$) δ: 11.12-11.38 (m, 1H), 9.02 (d, 1H), 8.84 (m, 1H), 8.36 (d, 1H), 7.78 (m, 1H), 7.65 (m, 2H), 7.45 (m, 2H), 3.60-3.72 (m, 4H), 2.89-3.46 (m, 7H), 2.56-2.66 (m, 1H), 2.18-2.48 (m, 2H), 1.94-2.16 (m, 3H), 1.48 (s, 2H). MS (m/z): 474.5 [MH]$^+$.

Example 144 and 145: (1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, Enantiomer 1, E144) and (1R,3S)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, Enantiomer 2, E145)

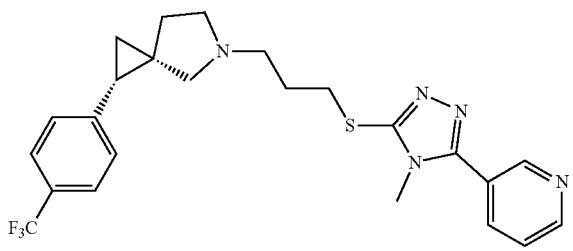

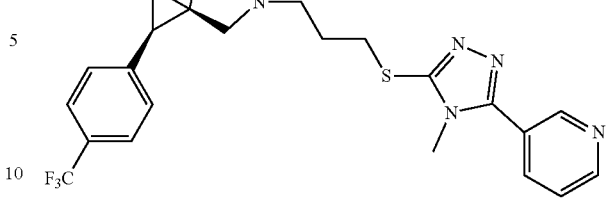

(1R,3S/1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane prepared in analogy with E143 (CIS, 56 mg) was separated into the single enantiomers by preparative chiral HPLC (SFC).

Preparative Chromatography:

| Column | Chiralpak AD-H (25 × 2.1 cm), 5μ |
|---|---|
| Mobile phase | (Methanol + 0.1% isopropylamine) 27% |
| Flow rate (ml/min) | 45 ml/min |
| DAD detection | 220 nm |
| Loop | 500 μL |
| Injection | 14 mg/injection | affording (1S,3R)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, E144, 16.6 mg). Enantiomer 1: ret. time 6.3 min, 100% ee. MS (m/z): 474.4 [MH]$^+$ and (1R,3S)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, E145, 15.8 mg). Enantiomer 2: ret. time 10.0 min, 100% ee. MS (m/z): 474.4 [MH]$^+$.

Example 146: (1R,3S)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane dihydrochloride (CIS, Enantiomer 2, E146)

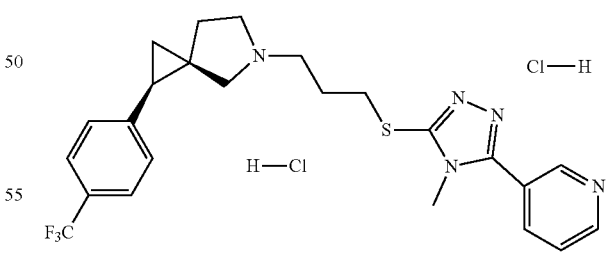

(1R,3S)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane (CIS, E145, 15.8 mg) was treated with 2.2 eq of HCl in Et$_2$O affording (1R,3S)-5-(3-{[4-methyl-5-(pyridin-3-yl)-4H-1,2,4-triazol-3-yl]sulfanyl}propyl)-1-[4-(trifluoromethyl)phenyl]-5azaspiro[2.4]heptane dihydrochloric salt (CIS, Enantiomer 2, E146, 13.8 mg). MS (m/z): 482.5 [MH]$^+$.

Example 147: (1S,3S/1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, E147)

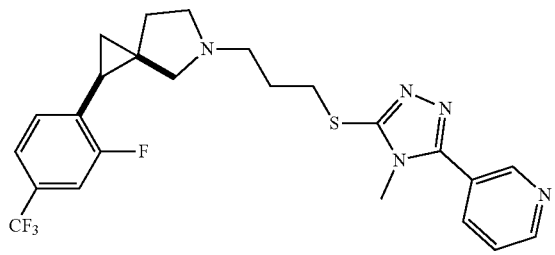

The compound was prepared as in Example 1, reacting (1S,3S/1R,3R)-1-[2-fluoro-4-(trifluoromethyl)phenyl]-5-azaspiro[2.4]heptane (CIS, p23, 50 mg, 0.193 mmol), 3-{5-[(3-chloropropyl)sulfanyl]-4-methyl-4H-1,2,4-triazol-3-yl}pyridine (p163, 57 mg, 0.212 mmol), Na$_2$CO$_3$ (25 mg, 0.23 mmol) and NaI (35 mg, 0.23 mmol) in DMF (0.2 mL) affording (1S,3S/1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, E147, 47 mg, y=49%). NMR: $^1$H NMR (Acetone-d$_6$) δ: 8.96 (d, 1H), 8.72-8.77 (m, 1H), 8.13-8.18 (m, 1H), 7.56-7.60 (m, 1H), 7.49 (d, 2H), 7.32-7.38 (m, 1H), 3.73 (s, 3H), 3.17-3.36 (m, 2H), 2.44-2.71 (m, 5H), 2.26-2.30 (m, 1H), 1.96-2.05 (m, 3H), 1.83-1.90 (m, 2H), 1.22-1.41 (m, 2H). MS (m/z): 492.4 [MH]$^+$.

Example 148 and 149: (1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, Enantiomer 1, E148) and (1S,3S)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, Enantiomer 2, E149)

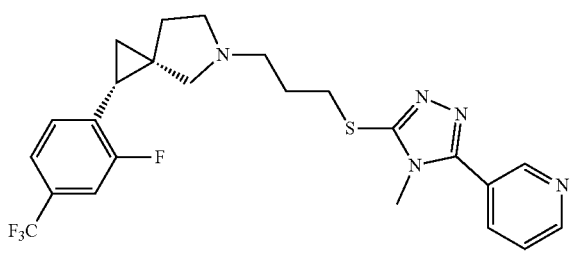

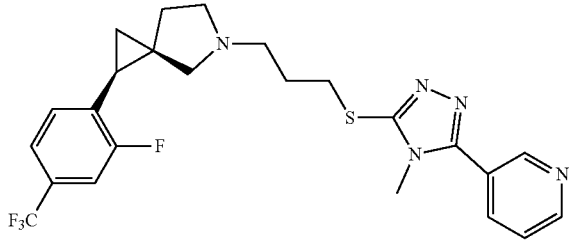

(1S,3S/1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, E147, 56 mg) was separated into the single enantiomers by preparative chiral HPLC (SFC).

Preparative Chromatography:

| | |
|---|---|
| Column | Chiralpak AD-H (25 × 2.0 cm), 5µ |
| Modifier | (Methanol + 0.1% isopropylamine) 22% |
| Flow rate (ml/min) | 45 ml/min |
| Pressure (bar) | 120 |
| Temperature (° C.) | 38 |
| DAD detection | 220 nm |
| Loop | 700 µL |
| Injection | 15.8 mg/injection | affording (1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, E148, 12 mg). Enantiomer 1: ret. time 6.7 min, 100% ee. MS (m/z): 492.4 [MH]$^+$ and (1S,3S)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, E149, 12.4 mg). Enantiomer 2: ret. time 9.1 min, 99.8% ee. MS (m/z): 492.4 [MH]$^+$.

Example 150: (1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane dihydrochloride (CIS, Enantiomer 1, E150)

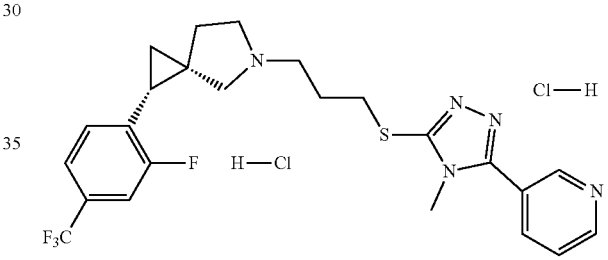

(1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, E148, 12 mg) was treated with 2.2 eq of HCl in Et$_2$O affording (1R,3R)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane dihydrochloric salt (CIS, Enantiomer 1, E150, 13 mg). MS (m/z): 492.4 [MH]$^+$.

Example 151: (1S,3S)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane dihydrochloride (CIS, Enantiomer 2, E151)

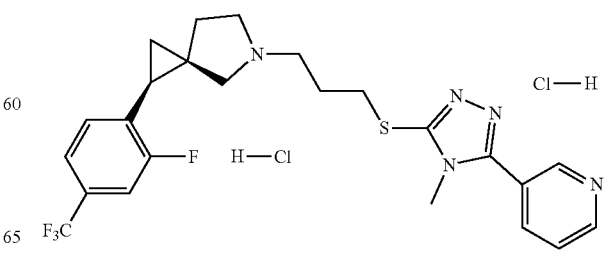

(1S,3S)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane (CIS, E149, 12.4 mg) was treated with 2.2 eq of HCl in Et$_2$O affording (1S,3S)-1-[2-fluoro-4-(trifluoromethyl)phenyl]-5-(3-{[4-methyl-5-(pyridin-3-yl)-4H-1,2,4-triazol-3-yl]sulfanyl}propyl)-5-azaspiro[2.4]heptane dihydrochloric salt (CIS, Enantiomer 2, E151, 13 mg). MS (m/z): 492.4 [MH]$^+$.

Example 152: (1S,3S/1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, E152)

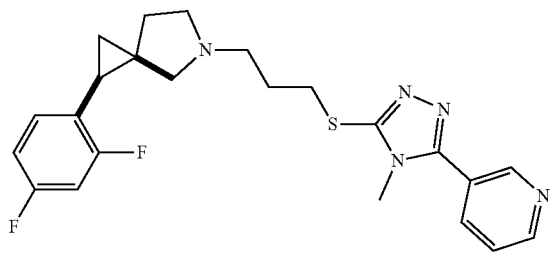

The compound was prepared as in Example 1, reacting (1S,3S/1R,3R)-1-(2,4-difluorophenyl)-5-azaspiro[2.4]heptane (CIS, p29, 50 mg, 0.24 mmol), 3-{5-[(3-chloropropyl)sulfanyl]-4-methyl-4H-1,2,4-triazol-3-yl}pyridine (p163, 71 mg, 0.26 mmol), Na$_2$CO$_3$ (31 mg, 0.28 mmol) and NaI (43 mg, 0.288 mmol) in DMF (0.2 mL) affording (1S,3S/1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, E152, 41 mg, y=39%). NMR: $^1$H NMR (Acetone-d$_6$) δ: 8.94-8.99 (m, 1H), 8.72-8.77 (m, 1H), 8.14-8.19 (m, 1H), 7.55-7.62 (m, 1H), 7.12-7.20 (m, 1H), 6.90-7.04 (m, 2H), 3.74 (s, 3H), 3.26 (d, 2H), 2.74-2.78 (m, 1H), 2.59-2.66 (m, 1H), 2.47-2.56 (m, 2H), 2.38 (d, 1H), 2.09-2.15 (m, 1H), 1.95-2.02 (m, 3H), 1.82-1.92 (m, 2H), 1.20-1.25 (m, 1H), 1.12-1.19 (m, 1H). MS (m/z): 442.4 [MH]$^+$.

Example 153 and 154: (1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 1, E153) and (1S,3S)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 2, E154)

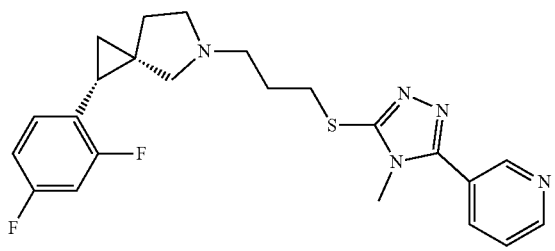

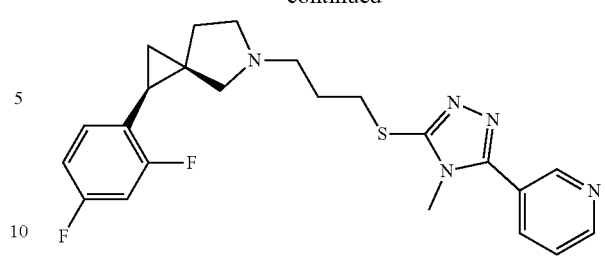

(1S,3S/1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, E152, 41 mg) was separated into the single enantiomers by preparative chiral HPLC (SFC).

Preparative Chromatography:

| Column | Chiralpak AD-H (25 × 2.0 cm), 5μ |
| --- | --- |
| Modifier | (Methanol + 0.1% isopropylamine) 25% |
| Flow rate (ml/min) | 45 ml/min |
| Pressure (bar) | 120 |
| Temperature (° C.) | 38 |
| DAD detection | 220 nm |
| Loop | 700 μL |
| Injection | 14 mg/injection | affording (1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, E153, 13 mg). Enantiomer 1: ret. time 7.8 min, 100% ee. MS (m/z): 442.3 [MH]$^+$ and (1S,3S)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, E154, 12.8 mg). Enantiomer 2: ret. time 11.6 min, 99.8% ee. MS (m/z): 442.4 [MH]$^+$.

Example 155: (1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane dihydrochloride (CIS, Enantiomer 1, E155)

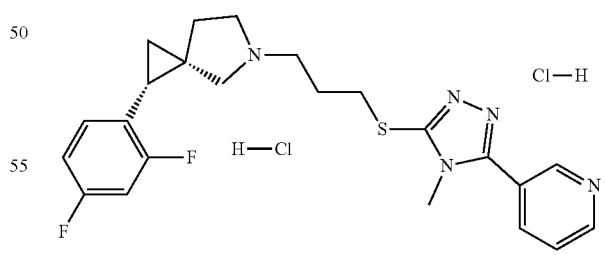

(1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, E153, 13 mg) was treated with 2.2 eq of HCl in Et$_2$O affording (1R,3R)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane dihydrochloric salt (CIS, Enantiomer 1, E155, 15 mg). MS (m/z): 442.4 [MH]$^+$.

Example 156: (1S,3S)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane dihydrochloride (CIS, Enantiomer 2, E156)

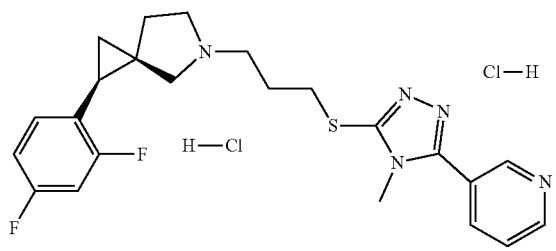

(1S,3S)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane (CIS, E154, 12.8 mg) was treated with 2.2 eq of HCl in Et$_2$O affording (1S,3S)-1-(2,4-difluorophenyl)-5-(3-{[4-methyl-5-(pyridin-3-yl)-4H-1,2,4-triazol-3-yl]sulfanyl}propyl)-5-azaspiro[2.4]heptane dihydrochloric salt (CIS, Enantiomer 2, E156, 14.5 mg). MS (m/z): 442.3 [MH]$^+$.

Example 157: (1R,3S/1S,3R)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, E157)

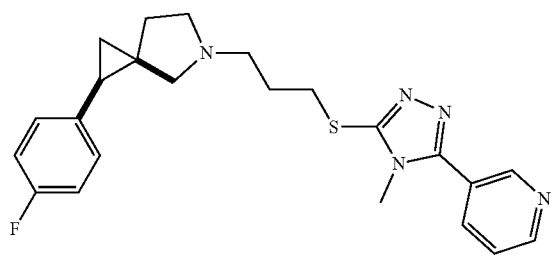

The compound was prepared as in Example 1, reacting (1R,3S/1S,3R)-1-(4-fluorophenyl)-5-azaspiro[2.4]heptane (CIS, p33, 50 mg, 0.26 mmol), 3-{5-[(3-chloropropyl)sulfanyl]-4-methyl-4H-1,2,4-triazol-3-yl}pyridine (p163, 77 mg, 0.29 mmol), Na$_2$CO$_3$ (33 mg, 0.31 mmol) and NaI (47 mg, 0.31 mmol) in DMF (0.2 mL) affording (1R,3S/1S,3R)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, E157, 34 mg, y=31%). NMR: $^1$H NMR (Acetone-d$_6$) δ: 8.97 (d, 1H), 8.74 (m, 1H), 8.16 (m, 1H), 7.58 (m, 1H), 7.17-7.24 (m, 2H), 7.01-7.09 (m, 2H), 3.72-3.76 (m, 3H), 3.18-3.32 (m, 2H), 2.62-2.78 (m, 2H), 2.52 (m, 2H), 2.36-2.44 (m, 1H), 2.09-2.15 (m, 2H), 1.82-2.02 (m, 4H), 1.06-1.16 (m, 2H). MS (m/z): 424.4 [MH]$^+$.

Example 158 and 159: (1S,3R)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 1, E158) and (1R,3S)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 2, E159)

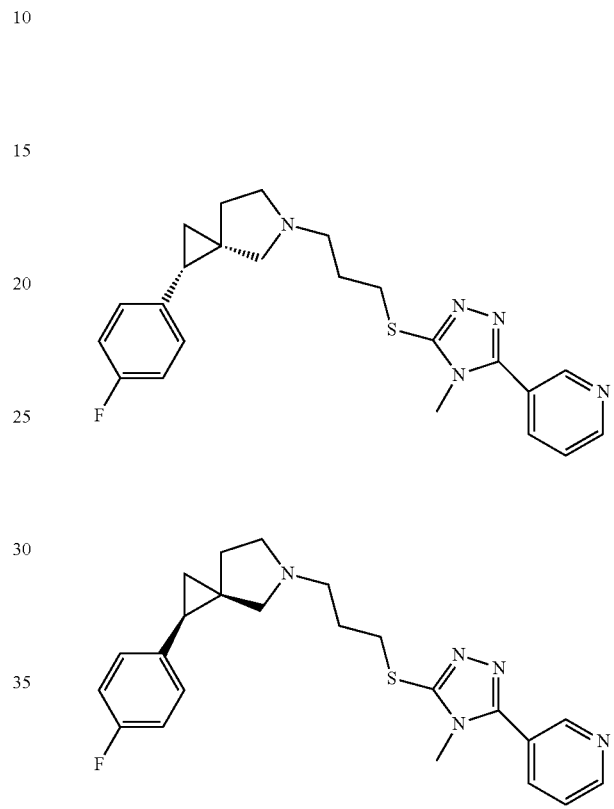

(1R,3S/1S,3R)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, E157, 34 mg) was separated into the single enantiomers by preparative chiral HPLC (SFC).

Preparative Chromatography:

| | |
|---|---|
| Column | Chiralpak AD-H (25 × 2.0 cm), 5µ |
| Mobile phase | (Methanol + 0.1% isopropylamine) 25% |
| Flow rate (ml/min) | 45 ml/min |
| DAD detection | 220 nm |
| Loop | 700 µL |
| Injection | 10.5 mg/injection | affording (1S,3R)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, E158, 10.7 mg). Enantiomer 1: ret. time 10.2 min, 100% ee. MS (m/z): 424.4 [MH]$^+$ and (1R,3S)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, E159, 10.8 mg). Enantiomer 2: ret. time 15.9 min, 99.8% ee. MS (m/z): 424.4 [MH]$^+$.

Example 160: (1R,3S)-1-(4-fluorophenyl)-5-(3-{[4-methyl-5-(pyridin-3-yl)-4H-1,2,4-triazol-3-yl]sulfanyl}propyl)-5-azaspiro[2.4]heptane dihydrochloride (CIS, Enantiomer 2, E160)

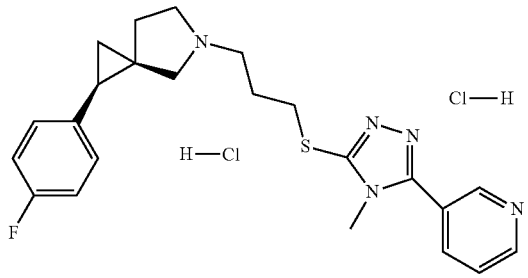 [SMILES: Cn1c(SCCCN2CC[C@]3(C[C@@H]3c3ccc(F)cc3)C2)nnc1-c1cccnc1 ; Cl ; Cl]

(1R,3S)-1-(4-fluorophenyl)-5-(3-{[4-methyl-5-(pyridin-3-yl)-4H-1,2,4-triazol-3-yl]sulfanyl}propyl)-5-azaspiro[2.4]heptane (CIS, Enantiomer 2, E159, 13 mg) was treated with 2.2 eq of HCl in Et$_2$O affording (1R,3S)-1-(4-fluorophenyl)-5-(3-{[4-methyl-5-(pyridin-3-yl)-4H-1,2,4-triazol-3-yl]sulfanyl}propyl)-5-azaspiro[2.4]heptane dihydrochloric salt (CIS, Enantiomer 2, E160, 10 mg). MS (m/z): 424.5 [MH]$^+$.

Example 161: (1R,3S/1S,3R)-5-(3-{[4-methyl-5-(pyridin-3-yl)-4H-1,2,4-triazol-3-yl]sulfanyl}propyl)-1-phenyl-5-azaspiro[2.4]heptane (CIS, E161)

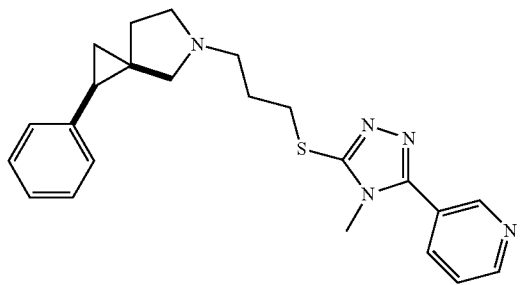

The compound was prepared as in Example 1, reacting (1R,3S/1S,3R)-1-phenyl-5-azaspiro[2.4]heptane (CIS, p19, 50 mg, 0.289 mmol), 3-{5-[(3-chloropropyl)sulfanyl]-4-methyl-4H-1,2,4-triazol-3-yl}pyridine (p163, 85 mg, 0.317 mmol), Na$_2$CO$_3$ (37 mg, 0.35 mmol) and NaI (53 mg, 0.35 mmol) in DMF (0.2 mL) affording (1R,3S/1S,3R)-5-(3-{[4-methyl-5-(pyridin-3-yl)-4H-1,2,4-triazol-3-yl]sulfanyl}propyl)-1-phenyl-5-azaspiro[2.4]heptane (CIS, E161, 55 mg, y=47%). NMR: $^1$H NMR (Acetone-d$_6$) δ: 8.94-9.00 (m, 1H), 8.72-8.79 (m, 1H), 8.13-8.21 (m, 1H), 7.54-7.62 (m, 1H), 7.29 (s, 2H), 7.19 (d, 3H), 3.74 (s, 3H), 3.20-3.36 (m, 3H), 2.52-3.00 (m, 5H), 2.26-2.38 (m, 1H), 2.17 (d, 1H), 1.87-2.04 (m, 4H), 1.22 (d, 1H), 1.12-1.19 (m, 1H). MS (m/z): 406.4 [MH]$^+$.

Example 162: (1S,3S/1R,3R)-5-(3-{[4-methyl-5-(pyridin-4-yl)-4H-1,2,4-triazol-3-yl]sulfanyl}propyl)-1-[4-(trifluoromethyl)phenyl]-5-azaspiro[2.4]heptane (TRANS, E162)

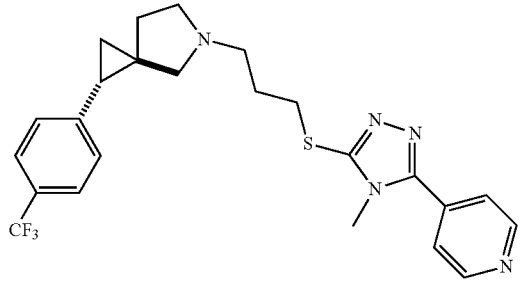

The compound was prepared as in Example 1, reacting (1S,3S/1R,3R)-1-[4-(trifluoromethyl)phenyl]-5-azaspiro[2.4]heptane (TRANS, p13, 50 mg, 0.207 mmol), 4-{5-[(3-chloropropyl)sulfanyl]-4-methyl-4H-1,2,4-triazol-3-yl}pyridine (p164, 62 mg, 0.228 mmol), Na$_2$CO$_3$ (26 mg, 0.248 mmol) and NaI (37 mg, 0.248 mmol) in DMF (0.2 mL) affording (1S,3S/1R,3R)-5-(3-{[4-methyl-5-(pyridin-4-yl)-4H-1,2,4-triazol-3-yl]sulfanyl}propyl)-1-[4-(trifluoromethyl)phenyl]-5-azaspiro[2.4]heptane (TRANS, E162, 61 mg, y=62%). NMR: $^1$H NMR (Acetone-d$_6$) δ: 8.74-8.80 (m, 2H), 7.75-7.80 (m, 2H), 7.63 (d, 2H), 7.36 (d, 2H), 3.81 (s, 3H), 3.35 (m, 2H), 2.64 (br. s., 6H), 2.24-2.32 (m, 1H), 2.09-2.13 (m, 1H), 1.99 (m, 2H), 1.62-1.75 (m, 1H), 1.38-1.50 (m, 1H), 1.27 (d, 1H), 1.22 (s, 1H). MS (m/z): 474.4 [MH]$^+$.

Example 163: (1R,3S/1S,3R)-5-(3-{[4-methyl-5-(pyridin-4-yl)-4H-1,2,4-triazol-3-yl]sulfanyl}propyl)-1-[4-(trifluoromethyl)phenyl]-5azaspiro[2.4]heptane dihydrochloride (CIS, E163)

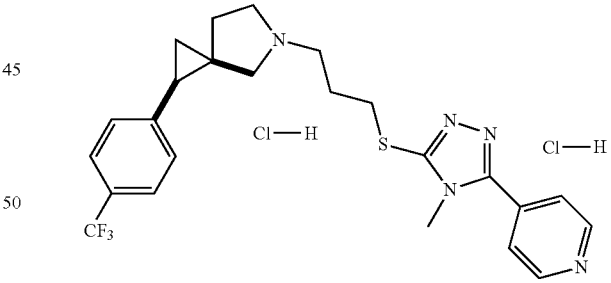

The compound was prepared as in Example 1, reacting (1R,3S/1S,3R)-1-[4-(trifluoromethyl)phenyl]-5-azaspiro[2.4]heptane (CIS, p14, 35 mg, 0.15 mmol), 4-{5-[(3-chloropropyl)sulfanyl]-4-methyl-4H-1,2,4-triazol-3-yl}pyridine (p164, 39 mg, 0.15 mmol), Na$_2$CO$_3$ (19 mg, 0.18 mmol) and NaI (22 mg, 0.15 mmol) in DMF (0.2 mL) affording (1R,3S/1S,3R)-5-(3-{[4-methyl-5-(pyridin-4-yl)-4H-1,2,4-triazol-3-yl]sulfanyl}propyl)-1-[4-(trifluoromethyl)phenyl]-5azaspiro[2.4]heptane (27 mg).

The latter was dissolved in DCM (0.2 mL) then 2N HCl/ether (2 eq) was added and the reaction mixture was concentrated under vacuum. The solid so obtained was triturated with ether and dried under vacuum at 45° C.

overnight, affording (1R,3S/1S,3R)-5-(3-{[4-methyl-5-(pyridin-4-yl)-4H-1,2,4-triazol-3-yl]sulfanyl}propyl)-1-[4-(trifluoromethyl)phenyl]-5azaspiro[2.4]heptane dihydrochloride (CIS, E163, 30 mg, y=30%). NMR: $^1$H NMR (DMSO-$d_6$) δ:11.13-11.35 (m, 1H), 8.92 (d, 2H), 8.07 (d, 2H), 7.61-7.72 (m, 2H), 7.45 (m, 2H), 3.73 (d, 3H), 3.61-3.70 (m, 1H), 3.35-3.45 (m, 1H), 3.23-3.35 (m, 3H), 3.03-3.22 (m, 2H), 2.56-2.65 (m, 1H), 2.56-2.98 (m, 1H), 2.36-2.49 (m, 1H), 1.94-2.34 (m, 4H), 1.25-1.51 (m, 2H). MS (m/z): 474.4 [MH]$^+$.

Example 164: (1R,3S/1S,3R)-1-[2-fluoro-4-(trifluoromethyl)phenyl]-5-(3-{[4-methyl-5-(pyridin-4-yl)-4H-1,2,4-triazol-3-yl]sulfanyl}propyl)-5-azaspiro[2.4]heptane (TRANS, E164)

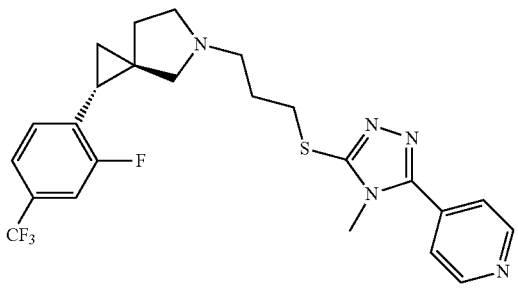 [SMILES: Cn1c(SCCCN2CC[C@]3(C[C@H]3c3ccc(C(F)(F)F)cc3F)C2)nnc1-c1ccncc1]

The compound was prepared as in Example 1, reacting (1R,3S/1S,3R)-1-[2-fluoro-4-(trifluoromethyl)phenyl]-5-azaspiro[2.4]heptane (TRANS, p22, 30 mg, 0.12 mmol), 4-{5-[(3-chloropropyl)sulfanyl]-4-methyl-4H-1,2,4-triazol-3-yl}pyridine (p164, 35 mg, 0.132 mmol), Na$_2$CO$_3$ (15 mg, 0.144 mmol) and NaI (22 mg, 0.144 mmol) in DMF (0.135 mL) affording (1R,3S/1S,3R)-1-[2-fluoro-4-(trifluoromethyl)phenyl]-5-(3-{[4-methyl-5-(pyridin-4-yl)-4H-1,2,4-triazol-3-yl]sulfanyl}propyl)-5-azaspiro[2.4]heptane (TRANS, E164, 35.5 mg, y=56%). NMR: $^1$H NMR (Acetone-$d_6$) δ: 8.77 (d, 2H), 7.73-7.79 (m, 2H), 7.45-7.54 (m, 2H), 7.27-7.34 (m, 1H), 3.82 (s, 3H), 3.36 (m, 2H), 2.59-2.78 (m., 6H), 2.33 (m, 1H), 1.95-2.04 (m, 2H), 1.63-1.72 (m, 1H), 1.23-1.46 (m, 3H). MS (m/z): 492.4 [MH]$^+$.

Example 165: (1R,3S/1S,3R)-5-(3-{[4-methyl-5-(2-methylpyridin-3-yl)-4H-1,2,4-triazol-3-yl]sulfanyl}propyl)-1-[4-(trifluoromethyl)phenyl]-5-azaspiro[2.4]heptane (CIS, E165)

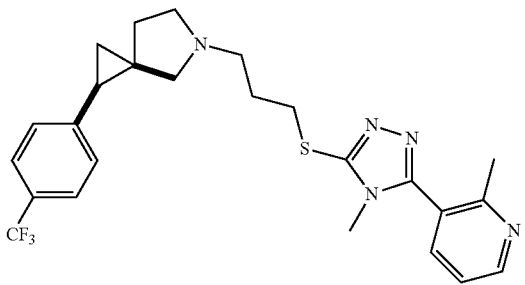

The compound was prepared as in Example 1, reacting (1R,3S/1S,3R)-1-[4-(trifluoromethyl)phenyl]-5-azaspiro[2.4]heptane (CIS, p14, 40 mg, 0.17 mmol), 3-{5-[(3-chloropropyl)sulfanyl]-4-methyl-4H-1,2,4-triazol-3-yl}-2-methylpyridine (p165, 48 mg, 0.17 mmol), Na$_2$CO$_3$ (22 mg, 0.2 mmol) and NaI (25 mg, 0.17 mmol) in DMF (0.25 mL) affording (1R,3S/1S,3R)-5-(3-{[4-methyl-5-(2-methylpyridin-3-yl)-4H-1,2,4-triazol-3-yl]sulfanyl}propyl)-1-[4-(trifluoromethyl)phenyl]-5-azaspiro[2.4]heptane (CIS, E165, 24 mg, y=29%). NMR: $^1$H NMR (CDCl$_3$) δ: 8.68 (m, 1H), 7.66 (m, 1H), 7.54 (d, 2H), 7.26-7.33 (m, 1H), 7.22 (d, 2H), 3.27-3.43 (m, 5H), 2.79-2.88 (m, 1H), 2.63-2.72 (m, 1H), 2.57 (s, 2H), 2.50 (s, 3H), 2.41-2.47 (m, 1H), 2.16 (d, 2H), 1.90-2.07 (m, 4H), 1.74-1.78 (m, 1H), 1.16-1.26 (m, 2H). MS (m/z): 488.5 [MH]$^+$.

Example 166: (1R,3S)-5-(3-{[4-methyl-5-(2-methylpyridin-3-yl)-4H-1,2,4-triazol-3-yl]sulfanyl}propyl)-1-[4-(trifluoromethyl)phenyl]-5-azaspiro[2.4]heptane dihydrochloride (CIS, Enantiomer 1, E166)

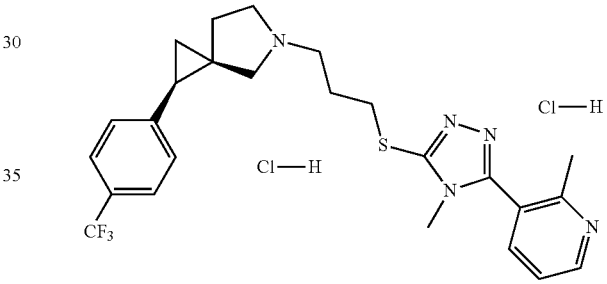

The compound was prepared as in Example 1, reacting (1R,3S)-1-[4-(trifluoromethyl)phenyl]-5-azaspiro[2.4]heptane (CIS, Enantiomer 1, p15, 30 mg, 3-{5-[(3-chloropropyl)sulfanyl]-4-methyl-4H-1,2,4-triazol-3-yl}-2-methylpyridine (p165, 35 mg, 0.12 mmol), Na$_2$CO$_3$ (15 mg, 0.14 mmol) and NaI (18 mg, 0.12 mmol) in DMF (0.2 mL) affording (1R,3S or 1 S,3R)-5-(3-{[4-methyl-5-(2-methylpyridin-3-yl)-4H-1,2,4-triazol-3-yl]sulfanyl}propyl)-1-[4-(trifluoromethyl)phenyl]-5-azaspiro[2.4]heptane (11 mg).

The latter was dissolved in DCM (0.2 mL) then 2N HCl/ether (2.1 eq) was added and the reaction mixture was concentrated under vacuum. The solid so obtained was triturated with ether and dried under vacuum at 45° C. overnight, affording (1R,3S)-5-(3-{[4-methyl-5-(2-methylpyridin-3-yl)-4H-1,2,4-triazol-3-yl]sulfanyl}propyl)-1-[4-(trifluoromethyl)phenyl]-5-azaspiro[2.4]heptane dihydrochloride (CIS, Enantiomer 1, E166, 12 mg, y=18%). NMR: $^1$H NMR (DMSO-$d_6$) δ: 10.72-10.99 (m, 1H), 8.70-8.77 (m, 1H), 8.04-8.14 (m, 1H), 7.66 (d, 2H), 7.56-7.62 (m, 1H), 7.45 (d, 2H), 3.63-3.73 (m, 2H), 3.36-3.48 (m, 4H), 3.07-3.34 (m, 6H), 2.91-3.01 (m, 1H), 2.59-2.71 (m, 1H), 2.17-2.44 (m, 2H), 2.09 (br. s., 3H), 1.36-1.53 (m, 2H), 1.21-1.35 (m, 1H). MS (m/z): 488.4 [MH]$^+$.

Example 167: (1S,3S/1R,3R)-5-(3-{[4-methyl-5-(2-methylpyridin-3-yl)-4H-1,2,4-triazol-3-yl]sulfanyl}propyl)-1-[2-(trifluoromethyl)phenyl]-5-azaspiro[2.4]heptane (TRANS, E167)

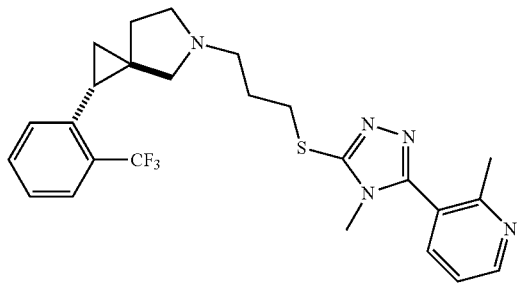

The compound was prepared as in Example 1, reacting (1S,3S/1R,3R)-1-[2-(trifluoromethyl)phenyl]-5-azaspiro[2.4]heptane (TRANS, p40, 30 mg, 0.124 mmol), 3-{5-[(3-chloropropyl)sulfanyl]-4-methyl-4H-1,2,4-triazol-3-yl)}-2-methylpyridine (p165, 35 mg, 0.124 mmol), Na$_2$CO$_3$ (16 mg, 0.15 mmol) and NaI (19 mg, 0.124 mmol) in DMF (0.25 mL) affording (1S,3S/1R,3R)-5-(3-{[4-methyl-5-(2-methylpyridin-3-yl)-4H-1,2,4-triazol-3-yl]sulfanyl}propyl)-1-[2-(trifluoromethyl)phenyl]-5-azaspiro[2.4]heptane (TRANS, E167, 14.5 mg, y=24%). NMR: $^1$H NMR (CDCl$_3$) δ: 8.69 (s, 1H), 7.66-7.72 (m, 2H), 7.45-7.52 (m, 1H), 7.32 (s, 2H), 7.09-7.14 (m, 1H), 3.41 (s, 5H), 2.85-2.93 (m, 1H), 2.62-2.76 (m, 4H), 2.50-2.54 (m, 3H), 2.34-2.43 (m, 2H), 2.03-2.12 (m, 2H), 1.58 (br. s., 1H), 1.23-1.35 (m, 4H). MS (m/z): 488.4 [MH]$^+$.

Example 168: (1S,3S/1R,3R)-5-(3-{[4-methyl-5-(2-methylpyridin-3-yl)-4H-1,2,4-triazol-3-yl]sulfanyl}propyl)-1-[2-(trifluoromethyl)phenyl]-5-azaspiro[2.4]heptane dihydrochloride (TRANS, E168)

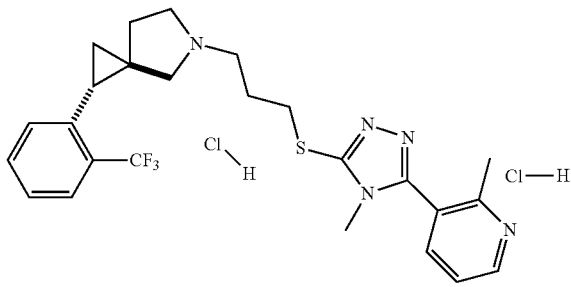

(1S,3S/1R,3R)-5-(3-{[4-methyl-5-(2-methylpyridin-3-yl)-4H-1,2,4-triazol-3-yl]sulfanyl}propyl)-1-[2-(trifluoromethyl)phenyl]-5-azaspiro[2.4]heptane (TRANS, E167, 14.5 mg) was dissolved in Et$_2$O and treated with 2.2 eq of HCl in Et$_2$O affording (1S,3S/1R,3R)-5-(3-{[4-methyl-5-(2-methylpyridin-3-yl)-4H-1,2,4-triazol-3-yl]sulfanyl}propyl)-1-[2-(trifluoromethyl)phenyl]-5-azaspiro[2.4]heptane dihydrochloric salt (TRANS, E168, 13.7 mg). MS (m/z): 488.4 [MH]$^+$.

Example 169: (1R,3S/1S,3R)-5-(3-{[4-methyl-5-(6-methylpyridin-3-yl)-4H-1,2,4-triazol-3-yl]sulfanyl}propyl)-1-[4-(trifluoromethyl)phenyl]-5-azaspiro[2.4]heptane (CIS, E169)

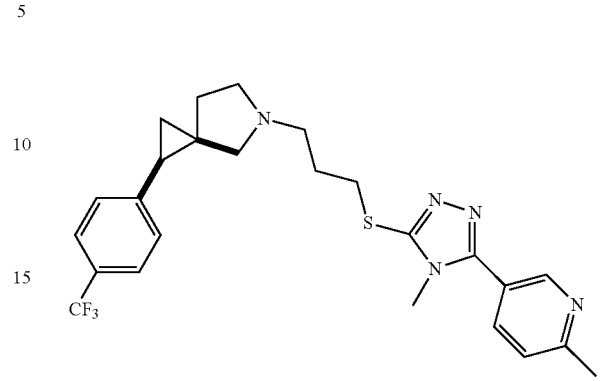

The compound was prepared as in Example 1, reacting (1R,3S/1S,3R)-1-[4-(trifluoromethyl)phenyl]-5-azaspiro[2.4]heptane (CIS, p14, 40 mg, 0.17 mmol), 5-{5-[(3-chloropropyl)sulfanyl]-4-methyl-4H-1,2,4-triazol-3-yl}-2-methylpyridine (p166, 48 mg, 0.17 mmol), Na$_2$CO$_3$ (22 mg, 0.2 mmol) and NaI (25 mg, 0.17 mmol) in DMF (0.25 mL) affording (1R,3S/1S,3R)-5-(3-{[4-methyl-5-(6-methylpyridin-3-yl)-4H-1,2,4-triazol-3-yl]sulfanyl}propyl)-1-[4-(trifluoromethyl)phenyl]-5-azaspiro[2.4]heptane (CIS, E169, 35 mg, y=42%). NMR: $^1$H NMR (CDCl$_3$) δ: 8.77 (d, 1H), 7.91 (m, 1H), 7.54 (d, 2H), 7.33 (d, 1H), 7.21 (d, 2H), 3.59 (s, 3H), 3.23-3.37 (m, 2H), 2.79-2.89 (m, 1H), 2.67 (s, 4H), 2.57 (s, 2H), 2.42-2.48 (m, 1H), 2.11-2.19 (m, 2H), 1.90-2.07 (m, 5H), 1.21 (s, 2H). MS (m/z): 488.5 [MH]$^+$.

Example 170: (1R,3S)-5-(3-{[4-methyl-5-(3-methylpyridin-2-yl)-4H-1,2,4-triazol-3-yl]sulfanyl}propyl)-1-[4-(trifluoromethyl)phenyl]-5-azaspiro[2.4]heptane dihydrochloride (CIS, Enantiomer 1, E170)

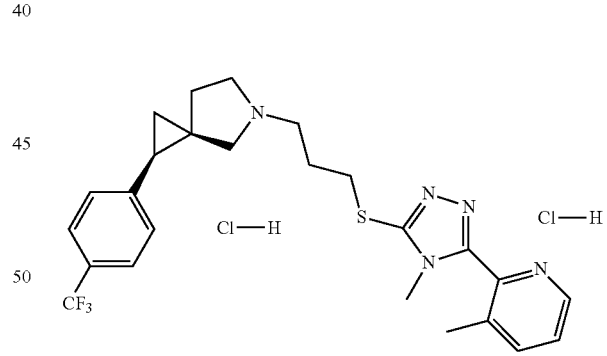

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol) 2-{5-[(3-chloropropyl)sulfanyl]-4-methyl-4H-1,2,4-triazol-3-yl}-3-methylpyridine (p167, 31 mg, 0.11 mmol), Na$_2$CO$_3$ (13 mg, 0.12 mmol) and NaI (18 mg, 0.12 mmol) in DMF (0.113 mL) affording (1R,3S)-5-(3-{[4-methyl-5-(3-methylpyridin-2-yl)-4H-1,2,4-triazol-3-yl]sulfanyl}propyl)-1-[4-(trifluoromethyl)phenyl]-5-azaspiro[2.4]heptane (28.8 mg).

The latter was dissolved in DCM/Et$_2$O then 2N HCl/ether (2.2 eq) was added and the reaction mixture was concentrated under vacuum affording (1R,3S)-5-(3-{[4-methyl-5-(3-methylpyridin-2-yl)-4H-1,2,4-triazol-3-yl]

sulfanyl}propyl)-1-[4-(trifluoromethyl)phenyl]-5-azaspiro[2.4]heptane dihydrochloride (CIS, Enantiomer 1, E170, 30.9 mg, y=55%). NMR: ¹H NMR (DMSO-d₆) δ: 9.84-10.16 (m, 3H), 8.54-8.60 (m, 1H), 7.84-7.91 (m, 1H), 7.66 (d, 2H), 7.45 (d, 3H), 3.67-3.77 (m, 2H), 3.60 (s, 3H), 3.39 (br. s., 2H), 3.22 (d, 3H), 2.45 (s, 3H), 2.36-2.43 (m, 1H), 2.18-2.30 (m, 2H), 1.95-2.15 (m, 3H), 1.26-1.52 (m, 3H). MS (m/z): 488.4 [MH]⁺.

Example 171: (1R,3S)-5-(3-{[5-(2,6-dimethylpyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E171)

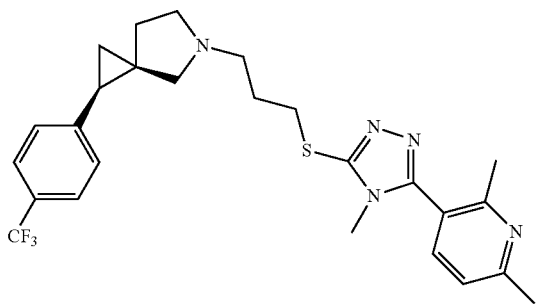 [SMILES: Cc1ccc(-c2nnc(SCCCN3CC[C@]4(C[C@@H]4c4ccc(C(F)(F)F)cc4)C3)n2C)c(C)n1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 3-{5-[(3-chloropropyl)sulfanyl]-4-methyl-4H-1,2,4-triazol-3-yl}-2,6-dimethylpyridine (p168, 34 mg, 0.11 mmol), Na₂CO₃ (13 mg, 0.123 mmol) and NaI (19 mg, 0.123 mmol) in DMF (0.15 mL) affording (1R,3S)-5-(3-{[5-(2,6-dimethylpyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E171, 36 mg, y=71%). NMR: ¹HNMR (Acetone-d₆) δ: 7.66-7.70 (m, 1H), 7.59-7.64 (m, 2H), 7.38-7.44 (m, 2H), 7.21-7.26 (m, 1H), 3.45 (s, 3H), 3.18-3.36 (m, 3H), 2.82-2.90 (m, 1H), 2.57-2.74 (m, 3H), 2.55 (s, 3H), 2.39 (s, 3H), 2.25-2.34 (m, 1H), 2.09-2.15 (m, 1H), 1.98-2.05 (m, 3H), 1.89-1.97 (m, 2H), 1.21-1.38 (m, 2H). MS (m/z): 502.4 [MH]⁺.

Example 172: (1R,3S)-5-(3-{[5-(2,6-dimethylpyridin-3-yl)-4-methyl-4H-1,2,4-triazol-3-yl]sulfanyl}propyl)-1-[4-(trifluoromethyl)phenyl]-5-azaspiro[2.4]heptane dihydrochloride (CIS, Enantiomer 1, E172)

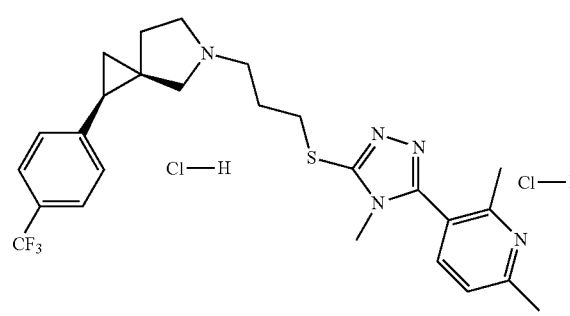

(1R,3S)-5-(3-{[5-(2,6-dimethylpyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E171, 36 mg) was dissolved in Et₂O and treated with 2.2 eq of HCl in Et₂O. The solid so obtained was triturated with ether and dried under vacuum affording (1R,3S)-5-(3-{[5-(2,6-dimethylpyridin-3-yl)-4-methyl-4H-1,2,4-triazol-3-yl]sulfanyl}propyl)-1-[4-(trifluoromethyl)phenyl]-5-azaspiro[2.4]heptane dihydrochloric salt (CIS, E172, 40.8 mg). MS (m/z): 502.4 [MH]⁺.

Example 173: (1R,3S/1S,3R)-5-(3-{[5-(2-fluoropyridin-3-yl)-4-methyl-4H-1,2,4-triazol-3-yl]sulfanyl}propyl)-1-[4-(trifluoromethyl)phenyl]-5-azaspiro[2.4]heptane (CIS, E173)

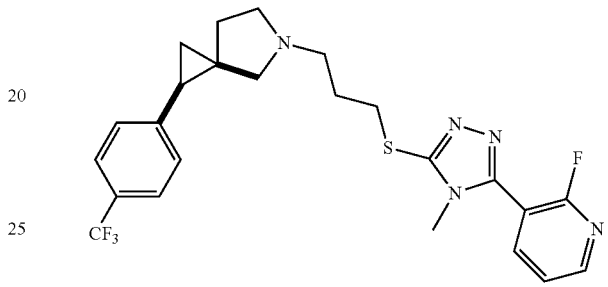

A sealed vial containing a mixture of (1R,3S/1S,3R)-5-(3-chloropropyl)-1-[4-(trifluoromethyl)phenyl]-5-azaspiro[2.4]heptane (p258, 25 mg, 0.079 mmol), 5-(2-fluoropyridin-3-yl)-4-methyl-4H-1,2,4-triazole-3-thiol (p85, 17 mg, 0.083 mmol), Na₂CO₃ (10 mg, 0.095 mmol) and NaI (12 mg, 0.079 mmol) and DMF (0.2 mL) was shaken O/N at 60° C. in a PLS apparatus. The mixture was diluted with DCM, the organic phase was washed twice with water, dried over sodium sulfate and the solvent removed under reduced pressure. The crude material was purified by FC on silica gel (eluting with DCM/MeOH from 100/0 to 90/10) to give (1R,3S/1S,3R)-5-(3-{[5-(2-fluoropyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E173, 24.5 mg, y=63%). NMR: ¹H NMR (DMSO-d₆) δ: 8.47-8.51 (m, 1H), 8.21-8.28 (m, 1H), 7.57-7.64 (m, 3H), 7.34 (d, 2H), 3.46 (d, 3H), 3.10-3.21 (m, 2H), 2.74 (br. s., 1H), 2.38-2.56 (m, 3H), 2.24 (br. s., 1H), 1.72-2.05 (m, 6H), 1.25-1.33 (m, 1H), 1.14-1.25 (m, 1H). MS (m/z): 492.4 [MH]⁺.

Example 174: (1R,3S)-5-[3-({4-methyl-5-[2-(trifluoromethyl)pyridin-3-yl]-4H-1,2,4-triazol-3-yl}sulfanyl)propyl]-1-[4-(trifluoromethyl)phenyl]-5-azaspiro[2.4]heptane dihydrochloride (CIS, Enantiomer 1, E174)

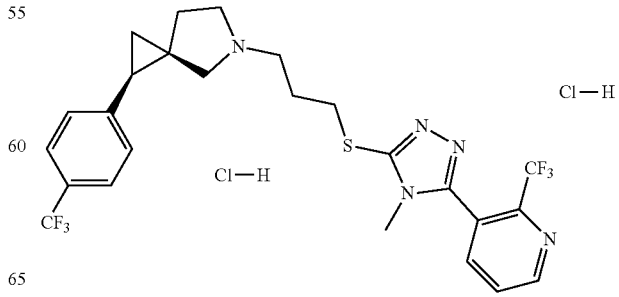

The compound was prepared as in Example 1, reacting (1R,3S)-1-[4-(trifluoromethyl)phenyl]-5-azaspiro[2.4]heptane (CIS, Enantiomer 1, p15, 30 mg, 0.12 mmol) 3-{5-[(3-chloropropyl)sulfanyl]-4-methyl-4H-1,2,4-triazol-3-yl}-2-(trifluoromethyl)pyridine (p169, 44 mg, 0.13 mmol), Na$_2$CO$_3$ (15 mg, 0.14 mmol) and NaI (18 mg, 0.12 mmol) in DMF (0.2 mL) affording (1R,3S)-5-[3-({4-methyl-5-[2-(trifluoromethyl)pyridin-3-yl]-4H-1,2,4-triazol-3-yl}sulfanyl)propyl]-1-[4-(trifluoromethyl)phenyl]-5-azaspiro[2.4]heptane (40 mg).

The latter was dissolved in DCM then 2N HCl/ether (2.2 eq) was added and the reaction mixture was concentrated under vacuum. The solid so obtained was triturated with ether and dried under vacuum at 45° C. O/N affording (1R,3S)-5-[3-({4-methyl-5-[2-(trifluoromethyl)pyridin-3-yl]-4H-1,2,4-triazol-3-yl}sulfanyl)propyl]-1-[4-(trifluoromethyl)phenyl]-5-azaspiro[2.4]heptane dihydrochloride (CIS, Enantiomer 1, E174, 41 mg, y=55%). NMR: $^1$H NMR (DMSO-d$_6$) δ: 10.24-10.57 (m, 1H), 8.98 (d, 1H), 8.25 (d, 1H), 7.95 (m, 1H), 7.66 (d, 2H), 7.44 (m, 2H), 3.65-3.77 (m, 1H), 3.41-3.48 (m, 1H), 3.35 (br. s., 3H), 3.23 (d, 6H), 2.63-3.04 (m, 1H), 2.20-2.45 (m, 2H), 1.92-2.16 (m, 3H), 1.27-1.53 (m, 2H). MS (m/z): 542.4 [MH]$^+$.

Example 175: (1R,3S)-5-(3-{[5-(2-methoxypyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E175)

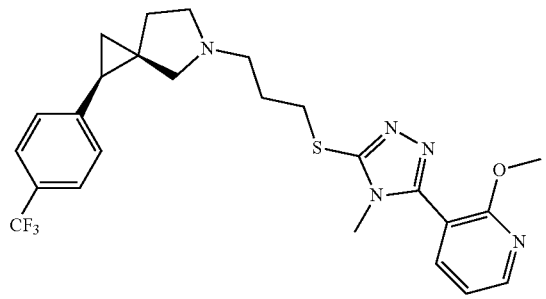 [SMILES: COc1ncccc1-c1nnc(SCCCN2CC[C@]3(C[C@@H]3c3ccc(C(F)(F)F)cc3)C2)n1C]

The compound was prepared as in Example 1, reacting (1R,3S)-1-[4-(trifluoromethyl)phenyl]-5-azaspiro[2.4]heptane (CIS, Enantiomer 1, p15, 30 mg, 0.12 mmol) 3-{5-[(3-chloropropyl)sulfanyl]-4-methyl-4H-1,2,4-triazol-3-yl}-2-methoxypyridine (p170, 39 mg, 0.13 mmol), Na$_2$CO$_3$ (15 mg, 0.14 mmol) and NaI (18 mg, 0.12 mmol) in DMF (0.2 mL) affording (1R,3S)-5-(3-{[5-(2-methoxypyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E175, 33 mg, y=52%). NMR: $^1$H NMR (CDCl3) δ: 8.32-8.39 (m, 1H), 7.84-7.92 (m, 1H), 7.55 (d, 2H), 7.21-7.27 (m, 2H), 7.04-7.10 (m, 1H), 4.00 (s, 3H), 3.43 (s, 3H), 3.29 (m, 2H), 2.98-3.12 (m, 1H), 2.59-2.98 (m, 4H), 2.25-2.38 (m, 1H), 2.18-2.25 (m, 1H), 2.06 (d, 4H), 1.28 (d, 2H). MS (m/z): 504.4 [MH]$^+$.

Example 176: (1R,3S)-5-(3-{[5-(2-methoxypyridin-3-yl)-4-methyl-4H-1,2,4-triazol-3-yl]sulfanyl}propyl)-1-[4-(trifluoromethyl)phenyl]-5-azaspiro[2.4]heptane dihydrochloride (CIS, Enantiomer 1, E176)

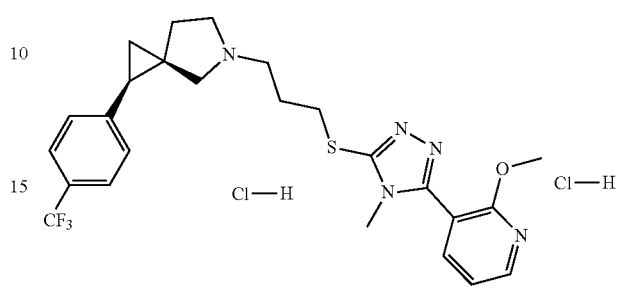

(1R,3S)-5-(3-{[5-(2-methoxypyridin-3-yl)-4-methyl-4H-1,2,4-triazol-3-yl]sulfanyl}propyl)-1-[4-(trifluoromethyl)phenyl]-5-azaspiro[2.4]heptane (CIS, Enantiomer 1, E175, 28 mg) was dissolved in DCM and treated with 2.2 eq of HCl in Et$_2$O. The solid so obtained was triturated with ether and dried under vacuum affording (1R,3S)-5-(3-{[5-(2-methoxypyridin-3-yl)-4-methyl-4H-1,2,4-triazol-3-yl]sulfanyl}propyl)-1-[4-(trifluoromethyl)phenyl]-5-azaspiro[2.4]heptane dihydrochloric salt (CIS, E176, 30 mg). MS (m/z): 504.4 [MH]$^+$.

Example 177: 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carbonitrile dihydrochloride (CIS, Enantiomer 1, E177)

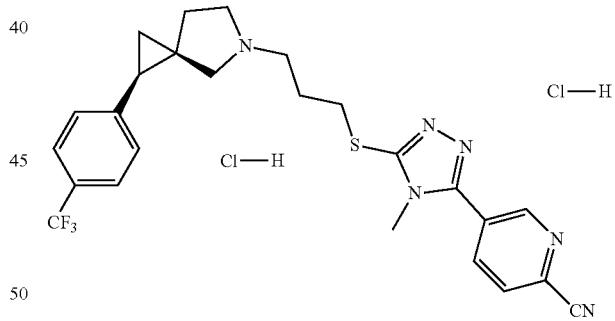

The compound was prepared as in Example 1, reacting (1R,3S)-1-[4-(trifluoromethyl)phenyl]-5-azaspiro[2.4]heptane (CIS, Enantiomer 1, p15, 25 mg, 0.10 mmol) 5-{5-[(3-chloropropyl)sulfanyl]-4-methyl-4H-1,2,4-triazol-3-yl}pyridine-2-carbonitrile (p171, 30 mg, 0.10 mmol), Na$_2$CO$_3$ (13 mg, 0.12 mmol) and NaI (15 mg, 0.10 mmol) in DMF (0.15 mL) affording 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carbonitrile (15 mg).

The latter was dissolved in DCM then 2N HCl/ether (2.1 eq) was added and the reaction mixture was concentrated under vacuum. The solid so obtained was triturated with ether and dried under vacuum at 45° C. O/N affording 5-[4-methyl-5-({3-[(1R,3S)-1-[4-(trifluoromethyl)phenyl]-

5-azaspiro[2.4]heptan-5-yl]propyl}sulfanyl)-4H-1,2,4-triazol-3-yl]pyridine-2-carbonitrile dihydrochloride (CIS, Enantiomer 1, E177, 17 mg, y=30%). NMR: $^1$H NMR (DMSO-d$_6$) δ: 10.41-10.70 (m, 1H), 9.11 (s, 1H), 8.42 (s, 1H), 8.27 (d, 1H), 7.66 (d, 2H), 7.38-7.49 (m, 2H), 3.67 (d, 3H), 3.06-3.47 (m, 7H), 2.61-3.01 (m, 1H), 2.45-2.50 (m, 1H), 2.20-2.44 (m, 2H), 1.92-2.15 (m, 3H), 1.26-1.53 (m, 2H). MS (m/z): 499.5 [MH]$^+$.

Example 178: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carbonitrile (CIS, Enantiomer 1, E178)

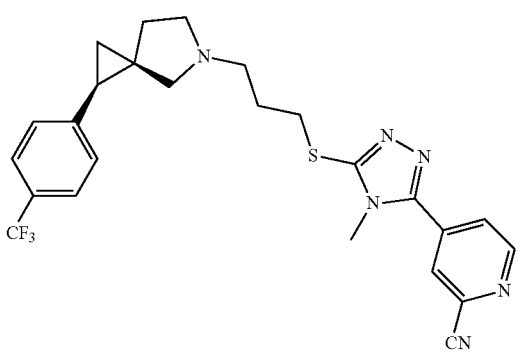 [SMILES: Cn1c(SCCCN2CC[C@]3(C[C@@H]3c3ccc(C(F)(F)F)cc3)C2)nnc1-c1ccnc(C#N)c1]

The compound was prepared as in Example 1, reacting (1R,3S)-1-[4-(trifluoromethyl)phenyl]-5-azaspiro[2.4]heptane (CIS, Enantiomer 1, p15, 80 mg, 0.33 mmol) 4-{5-[(3-chloropropyl)sulfanyl]-4-methyl-4H-1,2,4-triazol-3-yl}pyridine-2-carbonitrile (p172, 98 mg, 0.33 mmol), Na$_2$CO$_3$ (42 mg, 0.4 mmol) and NaI (49 mg, 0.33 mmol) in DMF (0.5 mL) affording 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carbonitrile (CIS, Enantiomer 1, E178, 53 mg, y=32%). NMR: $^1$H NMR (CDCl3) δ: 8.88-8.94 (m, 1H), 8.05-8.08 (m, 1H), 7.88-7.92 (m, 1H), 7.52-7.60 (m, 2H), 7.22-7.27 (m, 2H), 3.73 (s, 3H), 3.31-3.40 (m, 2H), 3.03-3.16 (m, 1H), 2.64-3.01 (m, 4H), 2.30-2.42 (m, 1H), 2.21-2.27 (m, 1H), 2.02-2.20 (m, 4H), 1.30 (d, 2H). MS (m/z): 499.4 [MH]$^+$.

Example 179: 5-[4-methyl-5-({3-[(1S,3S/1R,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, E179)

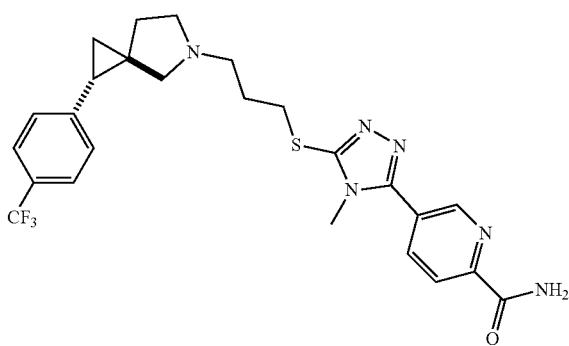

The compound was prepared as in Example 1, reacting (1S,3S/1R,3R)-1-[4-(trifluoromethyl)phenyl]-5-azaspiro[2.4]heptane (TRANS, p13, 50 mg, 0.21 mmol), 5-{5-[(3-chloropropyl)sulfanyl]-4-methyl-4H-1,2,4-triazol-3-yl}pyridine-2-carboxamide (p173, 72 mg, 0.231 mmol), Na$_2$CO$_3$ (38 mg, 0.252 mmol) and NaI (38 mg, 0.252 mmol) in DMF (0.236 mL) affording 5-[4-methyl-5-({3-[(1S,3S/1R,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, E179, 47.6 mg, y=43%). NMR: $^1$H NMR (Acetone-d$_6$) δ: 8.99-9.01 (m, 1H), 8.36 (d, 1H), 8.29 (d, 1H), 7.95-8.04 (m, 1H), 7.62 (d, 2H), 7.32-7.39 (m, 2H), 6.87-6.95 (m, 1H), 3.81 (s, 3H), 3.30-3.38 (m, 2H), 2.72-2.75 (m, 1H), 2.54-2.66 (m, 5H), 2.23-2.30 (m, 1H), 1.92-2.02 (m, 2H), 1.61-1.70 (m, 1H), 1.40-1.48 (m, 1H), 1.23-1.29 (m, 1H), 1.17-1.23 (m, 1H). MS (m/z): 517.4 [MH]$^+$.

Example 180 and 181: 5-[4-methyl-5-({3-[(1S,3S or 1R,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, Enantiomer 1, E180) and 5-[4-methyl-5-({3-[(1R,3R or 1S,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, Enantiomer 2, E181)

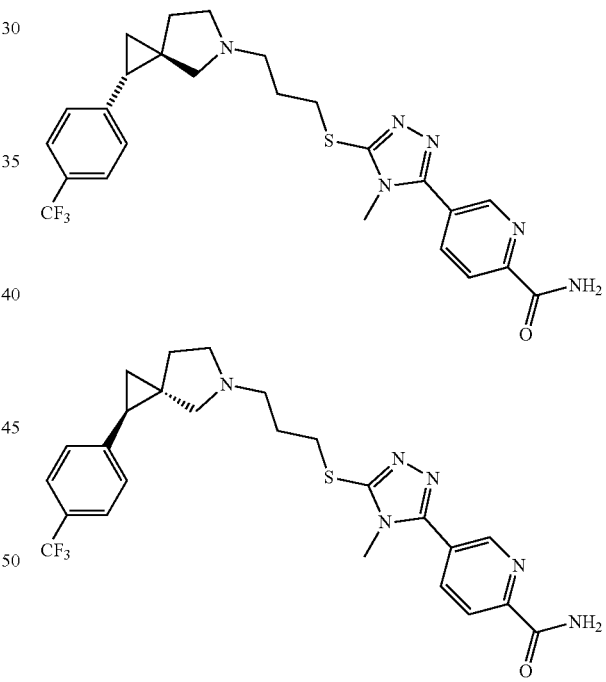

5-[4-methyl-5-({3-[(1S,3S/1R,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, E179, 47.6 mg) was separated into the single enantiomers by preparative chiral HPLC.
Preparative Chromatography:

| Column | Chiralcel OJ-H (25 × 2.0 cm), 5μ |
|---|---|
| Mobile phase | n-Hexane/(Ethanol/Methanol 1/1 + 0.1% isopropylamine) 10/90% v/v |

| | |
|---|---|
| Flow rate (ml/min) | 15 ml/min |
| DAD detection | 220 nm |
| Loop | 1000 μL |
| Injection | 11 mg/injection | affording 5-[4-methyl-5-({3-[(1S,3S or 1R,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, E180, 15.6 mg). Enantiomer 1: ret. time 4.8 min, 100% ee. MS (m/z): 517.3 [MH]+ and 5-[4-methyl-5-({3-[(1R,3R or 1S,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (TRANS, E181, 14.4 mg). Enantiomer 2: ret. time 5.6 min, 99.8% ee. MS (m/z): 517.3 [MH]+.

Example 182: 5-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, E182)

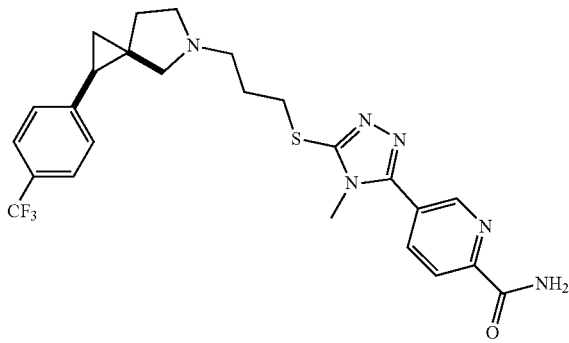

The compound was prepared as in Example 1, reacting (1R,3S/1S,3R)-1-[4-(trifluoromethyl)phenyl]-5-azaspiro[2.4]heptane (CIS, p14, 30 mg, 0.116 mmol), 5-{5-[(3-chloropropyl)sulfanyl]-4-methyl-4H-1,2,4-triazol-3-yl}pyridine-2-carboxamide (p173, 41 mg, 0.13 mmol), Na$_2$CO$_3$ (15 mg, 0.14 mmol) and NaI (21 mg, 0.14 mmol) in DMF (0.2 mL) affording 5-[4-methyl-5-({3-[(1R,3S/1S,3R)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, E182, 23 mg, y=38%). NMR: $^1$H NMR (CDCl3) δ: 8.90-8.96 (m, 1H), 8.36-8.41 (m, 1H), 8.15-8.20 (m, 1H), 7.81-7.91 (m, 1H), 7.52-7.59 (m, 2H), 7.20-7.26 (m, 2H), 5.64-5.74 (m, 1H), 3.66 (s, 3H), 3.26-3.41 (m, 2H), 2.84-2.95 (m, 1H), 2.74 (d, 1H), 2.63 (m, 2H), 2.50 (d, 1H), 2.14-2.26 (m, 2H), 1.92-2.11 (m, 4H), 1.19-1.33 (m, 2H). MS (m/z): 517.5 [MH]+.

Example 183: 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E183)

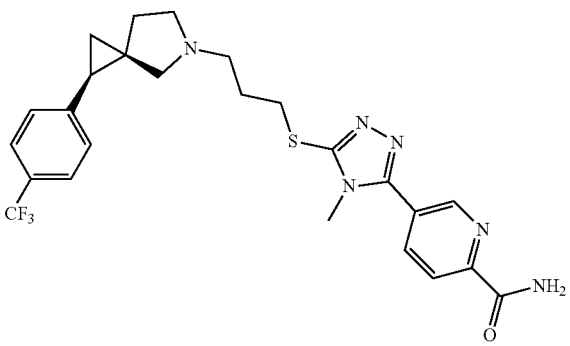 [SMILES: Cn1c(SCCCN2CC[C@]3(C[C@@H]3c3ccc(C(F)(F)F)cc3)C2)nnc1-c1ccc(C(N)=O)nc1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol), 5-{5-[(3-chloropropyl)sulfanyl]-4-methyl-4H-1,2,4-triazol-3-yl}pyridine-2-carboxamide (p173, 33 mg, 0.106 mmol), Na$_2$CO$_3$ (12 mg, 0.115 mmol) and NaI (17 mg, 0.115 mmol) in DMF (0.1 mL) affording 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E183, 13 mg, y=26%). NMR: $^1$H NMR (Acetone-d$_6$) δ: 8.97-9.02 (m, 1H), 8.36 (d, 1H), 8.25-8.31 (m, 1H), 7.95-8.07 (m, 1H), 7.62 (d, 2H), 7.39 (d, 2H), 6.85-6.98 (m, 1H), 3.73-3.81 (m, 3H), 3.18-3.36 (m, 2H), 2.39-2.71 (m, 5H), 2.24 (d, 1H), 2.10-2.17 (m, 1H), 1.79-2.04 (m, 4H), 1.30 (br. s., 1H), 1.23 (d, 1H). MS (m/z): 517.5 [MH]+.

Example 184: 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide dihydrochloride (CIS, Enantiomer 1, E184)

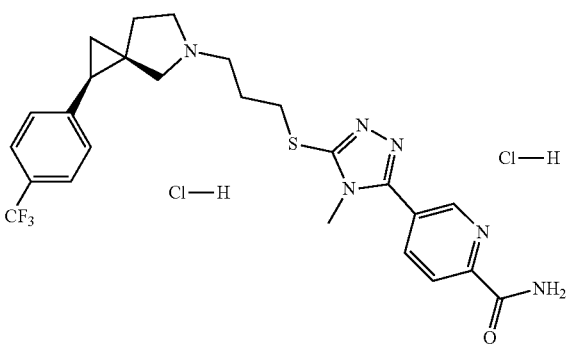 [SMILES: Cn1c(SCCCN2CC[C@]3(C[C@@H]3c3ccc(C(F)(F)F)cc3)C2)nnc1-c1ccc(C(N)=O)nc1 ; Cl ; Cl]

5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E183, 13 mg) was dissolved in DCM and treated with 2.2 eq of HCl in Et$_2$O. The solid so obtained was triturated with ether and dried under vacuum affording 5-[4-methyl-5-({3-

[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide dihydrochloric salt (CIS, Enantiomer 1, E184, 14 mg). MS (m/z): 517.4 [MH]⁺.

Example 185: 5-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-2-carboxamide (CIS, Enantiomer 1, E185)

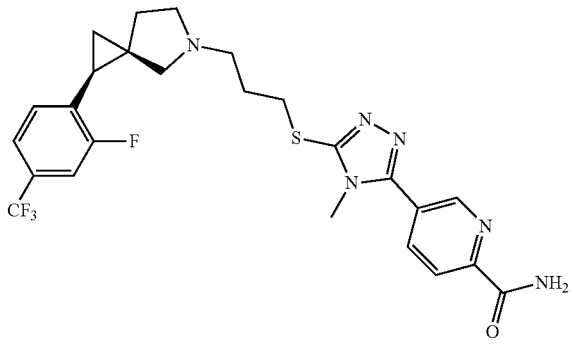 [SMILES: Cn1c(SCCCN2CC[C@]3(C[C@@H]3c3ccc(C(F)(F)F)cc3F)C2)nnc1-c1ccc(C(N)=O)nc1]

The compound was prepared as in Example 1, reacting (1S,3S)-1-[2-fluoro-4-(trifluoromethyl)phenyl]-5-azaspiro[2.4]heptane (CIS, Enantiomer 1, p24, 25 mg, 0.096 mmol), 5-{5-[(3-chloropropyl)sulfanyl]-4-methyl-4H-1,2,4-triazol-3-yl}pyridine-2-carboxamide (p173, 34 mg, 0.11 mmol), Na₂CO₃ (12 mg, 0.115 mmol) and NaI (17 mg, 0.115 mmol) in DMF (0.108 mL) affording 5-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-2-carboxamide (CIS, Enantiomer 1, E185, 26.5 mg, y=52%). NMR: ¹H NMR (Acetone-d₆) δ: 8.96-9.02 (m, 1H), 8.33-8.39 (m, 1H), 8.26-8.31 (m, 1H), 7.97-8.06 (m, 1H), 7.45-7.51 (m, 2H), 7.32-7.39 (m, 1H), 6.84-6.97 (m, 1H), 3.78 (s, 3H), 3.19-3.33 (m, 2H), 2.77 (br. s., 6H), 2.24-2.33 (m, 1H), 2.03 (br. s., 2H), 1.82-1.94 (m, 2H), 1.35-1.42 (m, 1H), 1.22-1.29 (m, 1H). MS (m/z): 535.4 [MH]⁺.

Example 186: 5-[5-({3-[(1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-2-carboxamide (CIS, Enantiomer 2, E186)

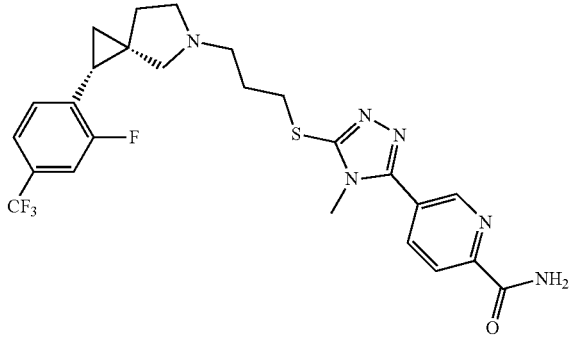 [SMILES: Cn1c(SCCCN2CC[C@@]3(C[C@H]3c3ccc(C(F)(F)F)cc3F)C2)nnc1-c1ccc(C(N)=O)nc1]

The compound was prepared as in Example 1, reacting (1R,3R)-1-[2-fluoro-4-(trifluoromethyl)phenyl]-5-azaspiro[2.4]heptane (CIS, Enantiomer 2, p25, 25 mg, 0.096 mmol), 5-{5-[(3-chloropropyl)sulfanyl]-4-methyl-4H-1,2,4-triazol-3-yl}pyridine-2-carboxamide (p173, 34 mg, 0.11 mmol), Na₂CO₃ (12 mg, 0.115 mmol) and NaI (17 mg, 0.115 mmol) in DMF (0.108 mL) affording 5-[5-({3-[(1R,3R)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-2-carboxamide (CIS, Enantiomer 2, E186, 19.9 mg, y=38%). NMR: ¹H NMR (Acetone-d₆) δ: 8.96-9.02 (m, 1H), 8.33-8.39 (m, 1H), 8.26-8.31 (m, 1H), 7.97-8.06 (m, 1H), 7.45-7.51 (m, 2H), 7.32-7.39 (m, 1H), 6.84-6.97 (m, 1H), 3.78 (s, 3H), 3.19-3.33 (m, 2H), 2.77 (br. s., 6H), 2.24-2.33 (m, 1H), 2.03 (br. s., 2H), 1.82-1.94 (m, 2H), 1.35-1.42 (m, 1H), 1.22-1.29 (m, 1H). MS (m/z): 535.4 [MH]⁺.

Example 187: 6-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E187)

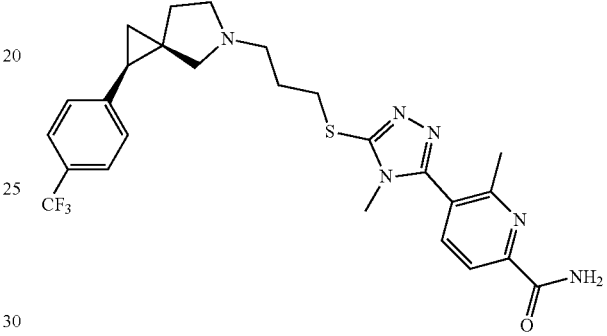

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 5-{5-[(3-chloropropyl)sulfanyl]-4-methyl-4H-1,2,4-triazol-3-yl}-6-methylpyridine-2-carboxamide (p234, 37 mg, 0.11 mmol), Na₂CO₃ (12 mg, 0.115 mmol) and NaI (17 mg, 0.115 mmol) in DMF (0.108 mL) affording 6-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E187, 27 mg, y=51%). NMR: ¹H NMR (DMSO-d₆) δ: 8.10-8.16 (m, 1H), 8.01 (d, 2H), 7.73-7.78 (m, 1H), 7.59 (s, 2H), 7.29-7.36 (m, 2H), 3.37 (s, 3H), 3.10-3.20 (m, 2H), 2.69-2.74 (m, 1H), 2.36-2.54 (m, 7H), 2.17-2.24 (br. s., 1H), 1.82-1.98 (m, 3H), 1.71-1.81 (m, 2H), 1.23-1.31 (m, 1H), 1.16 (d, 1H). MS (m/z): 531.4 [MH]⁺.

Example 188: 6-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxylic acid formate (CIS, Enantiomer 1, E188)

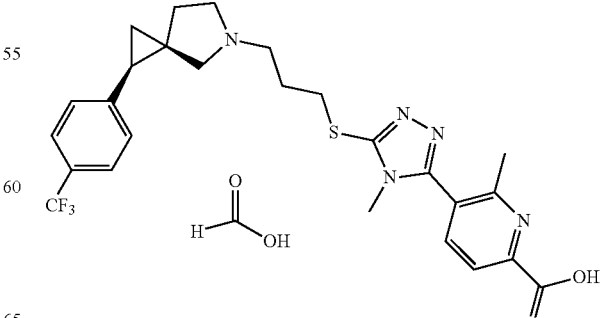

(1R,3S)-1-[4-(trifluoromethyl)phenyl]-5-azaspiro[2.4]heptane (CIS, Enantiomer 1, p15, 30 mg, 0.096 mmol), 5-{5-[(3-chloropropyl)sulfanyl]-4-methyl-4H-1,2,4-triazol-3-yl}-6-methylpyridine-2-carboxylic acid (p235, 300 mg, assumed 0.9 mmol), Na$_2$CO$_3$ (120 mg, 1.15 mmol) and NaI (17 mg, 0.115 mmol) were dissolved in DMF (0.4 mL) and heated at 60° C. O/N.

The mixture was charged on C18 and it was purified by FC on C18 cartridge (eluent water+0.1% FA to 60% water+ 0.1% FA 40% MeOH+0.1%) affording 6-methyl-5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxylic acid formate (CIS, Enantiomer 1, E188, 12 mg, y=18%) as white solid. NMR: $^1$H NMR (Acetone-d$_6$) δ: 8.15 (s, 1H), 8.10-8.13 (m, 1H), 7.61 (s, 2H), 7.36-7.43 (m, 2H), 3.54 (s, 3H), 3.18-3.37 (m, 4H), 2.72 (br. s., 1H), 2.51-2.64 (m, 6H), 2.25-2.31 (m, 1H), 2.09 (br. s., 2H), 1.93-2.02 (m, 2H), 1.86-1.90 (m, 1H), 1.28-1.35 (m, 1H), 1.21-1.26 (m, 1H). MS (m/z): 532.4 [MH]$^+$.

Example 189: 6-[4-methyl-5-({3-[(1R,3S)-1-[4-(trifluoromethyl)phenyl]-5-azaspiro[2.4]heptan-5-yl]propyl}sulfanyl)-4H-1,2,4-triazol 3-yl]pyridine-3-carboxamide dihydrochloride (CIS, Enantiomer 1, E189)

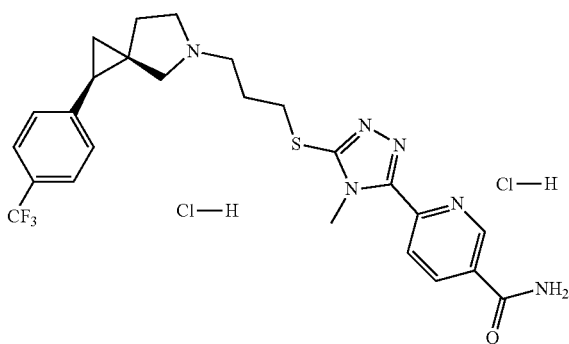

The compound was prepared as in Example 1, reacting (1R,3S)-1-[4-(trifluoromethyl)phenyl]-5-azaspiro[2.4]heptane (CIS, Enantiomer 1, p15, 30 mg, 0.12 mmol) 6-{5-[(3-chloropropyl)sulfanyl]-4-methyl-4H-1,2,4-triazol-3-yl}pyridine-3-carboxamide (p174, 43 mg, 0.14 mmol), Na$_2$CO$_3$ (15 mg, 0.14 mmol) and NaI (18 mg, 0.12 mmol) in DMF (0.2 mL) affording 6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-3-carboxamide (27.5 mg).

The latter was dissolved in DCM then 2N HCl/ether (2.2 eq) was added and the reaction mixture was concentrated under vacuum. The solid so obtained was triturated with ether and dried under vacuum at 45° C. overnight affording 6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-3-carboxamide dihydrochloride (CIS, Enantiomer 1, E189, 31 mg, y=44%). NMR: $^1$H NMR (DMSO-d$_6$) δ: 10.66-10.87 (m, 1H), 9.15 (d, 1H), 8.38-8.44 (m, 1H), 8.30 (br. s., 1H), 8.22 (d, 1H), 7.72 (br. s., 1H), 7.67 (d, 2H), 7.45 (d, 2H), 3.95 (d, 3H), 3.66-3.75 (m, 1H), 2.94-3.46 (m, 7H), 1.96-2.69 (m, 5H), 1.28-1.53 (m, 2H). MS (m/z): 517.4 [MH]$^+$.

Example 190: 6-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-3-carboxamide (CIS, Enantiomer 1, E190)

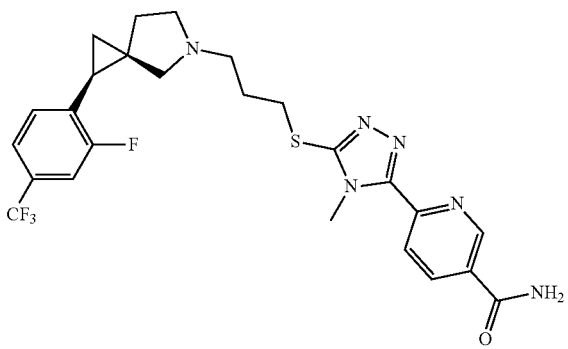 [SMILES: Cn1c(SCCCN2CC[C@]3(C[C@@H]3c3ccc(C(F)(F)F)cc3F)C2)nnc1-c1ccc(C(N)=O)cn1]

The compound was prepared as in Example 1, reacting (1S,3S)-1-[2-fluoro-4-(trifluoromethyl)phenyl]-5-azaspiro[2.4]heptane (CIS, Enantiomer 1, p24, 26 mg, 0.1 mmol) 6-{5-[(3-chloropropyl)sulfanyl]-4-methyl-4H-1,2,4-triazol-3-yl}pyridine-3-carboxamide (p174, 34 mg, 0.11 mmol), Na$_2$CO$_3$ (13 mg, 0.12 mmol) and NaI (18 mg, 0.12 mmol) in DMF (0.113 mL) affording 6-[5-({3-[(1S,3S)-1-[2-fluoro-4-(trifluoromethyl)phenyl]-5-azaspiro[2.4]heptan-5-yl]propyl}sulfanyl)-4-methyl-4H-1,2,4-triazol-3-yl]pyridine-3-carboxamide (CIS, Enantiomer 1, E190, 20.5 mg, y=38%). NMR: $^1$H NMR (DMSO-d$_6$) δ: 9.08-9.18 (m, 1H), 8.35-8.44 (m, 1H), 8.24-8.29 (m, 1H), 8.19-8.24 (m, 1H), 7.68-7.74 (m, 1H), 7.58-7.64 (m, 1H), 7.45-7.50 (m, 1H), 7.25-7.32 (m, 1H), 3.92 (s, 3H), 3.10-3.22 (m, 2H), 2.69-2.78 (m, 1H), 2.35-2.43 (m, 4H), 2.21 (m, 1H), 1.93 (m, 2H), 1.84 (d, 1H), 1.75 (m, 2H), 1.35 (m, 1H), 1.20 (m, 1H). MS (m/z): 535.3 [MH]$^+$.

Example 191: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E191)

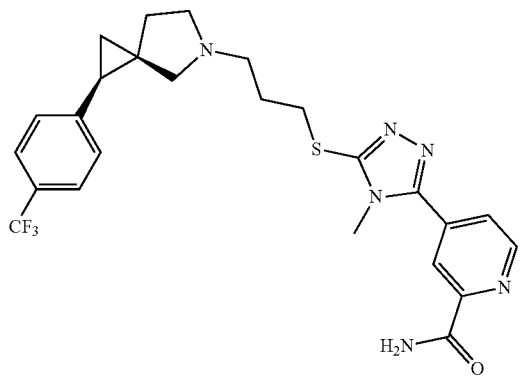 [SMILES: Cn1c(SCCCN2CC[C@]3(C[C@@H]3c3ccc(C(F)(F)F)cc3)C2)nnc1-c1ccnc(C(N)=O)c1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol) 4-{5-[(3-chloropropyl)sulfanyl]-4-methyl-4H-1,2,4-triazol-3-yl}pyridine-2-carboxamide (p175, 34 mg, 0.11 mmol), Na₂CO₃ (13 mg, 0.12 mmol) and NaI (18 mg, 0.12 mmol) in DMF (0.1 mL) affording 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E191, 34.7 mg, y=67%). NMR: ¹H NMR (Acetone-d₆) δ: 8.80 (m, 1H), 8.49 (m, 1H), 7.99-8.04 (m, 1H), 7.97 (m, 1H), 7.61 (d, 2H), 7.38 (d, 2H), 6.82-6.96 (m, 1H), 3.82 (s, 3H), 3.18-3.34 (m, 2H), 2.70-2.75 (m, 1H), 2.58-2.66 (m, 1H), 2.43-2.57 (m, 3H), 2.20-2.27 (m, 1H), 1.81-2.03 (m, 5H), 1.26-1.31 (m, 1H), 1.21 (m, 1H). MS (m/z): 517.4 [MH]⁺.

Example 192: 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-3-carboxamide (CIS, Enantiomer 1, E192)

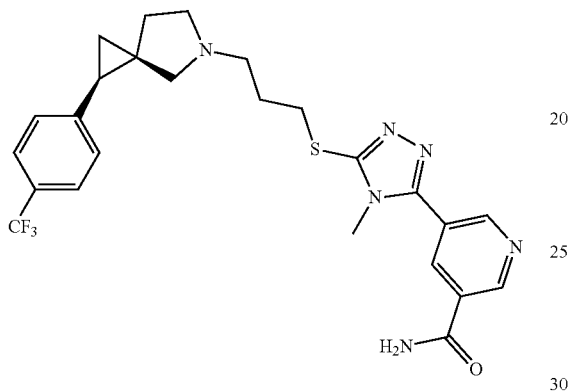

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol) 5-{5-[(3-chloropropyl)sulfanyl]-4-methyl-4H-1,2,4-triazol-3-yl}pyridine-3-carboxamide (p236, 36 mg, 0.11 mmol), Na₂CO₃ (13 mg, 0.12 mmol) and NaI (18 mg, 0.12 mmol) in DMF (0.1 mL) affording 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-3-carboxamide (CIS, Enantiomer 1, E192, 31 mg, y=60%). NMR: ¹H NMR (Acetone-d₆) δ: 9.22 (d, 1H), 9.07 (d, 1H), 8.56 (s, 1H), 7.74-7.88 (m, 1H), 7.60 (s, 2H), 7.39 (s, 2H), 6.93-7.06 (m, 1H), 3.76 (s, 3H), 3.16-3.34 (m, 2H), 2.70-2.76 (m, 1H), 2.58-2.67 (m, 1H), 2.43-2.56 (m, 3H), 2.18-2.27 (m, 1H), 2.08-2.11 (m, 1H), 1.92-2.03 (m, 2H), 1.81-1.92 (m, 2H), 1.25-1.32 (m, 1H), 1.17-1.24 (m, 1H). MS (m/z): 517.3 [MH]⁺.

Example 193: 6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E193)

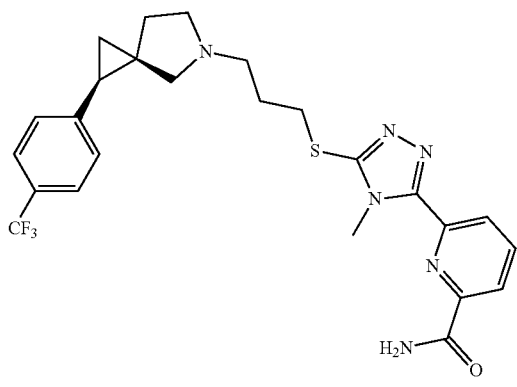 [SMILES: Cn1c(SCCCN2CC[C@]3(C[C@@H]3c3ccc(C(F)(F)F)cc3)C2)nnc1-c1cccc(C(N)=O)n1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol) 6-{5-[(3-chloropropyl)sulfanyl]-4-methyl-4H-1,2,4-triazol-3-yl}pyridine-2-carboxamide (p176, 32 mg, 0.1 mmol), Na₂CO₃ (13 mg, 0.115 mmol) and NaI (18 mg, 0.115 mmol) in DMF (0.1 mL) affording 6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E193, 25.5 mg, y=51%). NMR: ¹H NMR (DMSO-d₆) δ: 8.23-8.29 (m, 1H), 8.11-8.22 (m, 2H), 7.96-8.01 (m, 1H), 7.80-7.88 (m, 1H), 7.58-7.64 (m, 2H), 7.30-7.35 (m, 2H), 3.93 (s, 3H), 3.11-3.23 (m, 2H), 2.66-2.76 (m, 1H), 2.37-2.49 (m, 4H), 2.21 (m, 1H), 1.83-2.01 (m, 3H), 1.77 (m, 2H), 1.27 (m, 1H), 1.18 (m, 1H). MS (m/z): 517.4 [MH]⁺.

Example 194: N-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E194)

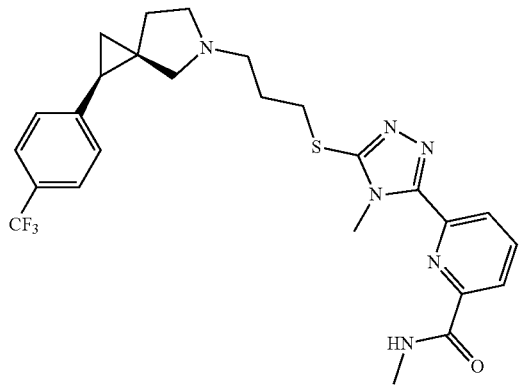 [SMILES: CNC(=O)c1cccc(-c2nnc(SCCCN3CC[C@]4(C[C@@H]4c4ccc(C(F)(F)F)cc4)C3)n2C)n1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol) 6-{5-[(3-chloropropyl)sulfanyl]-4-methyl-4H-1,2,4-triazol-3-yl}-N-methylpyridine-2-carboxamide (p177, 33 mg, 0.1 mmol), Na₂CO₃ (13 mg, 0.115 mmol) and NaI (18 mg, 0.115 mmol) in DMF (0.2 mL) affording N-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E194, 33 mg, y=64%). NMR: ¹H NMR (Acetone-d₆) δ: 8.30-8.36 (m, 1H), 8.16-8.29 (m, 3H), 7.60-7.65 (m, 2H), 7.37-7.43 (m, 2H), 4.02 (s, 3H), 3.24-3.38 (m, 2H), 3 (d, 3H), 2.51-2.71 (m, 4H), 2.13-2.33 (m, 2H), 1.85-2.03 (m, 5H), 1.28-1.36 (m, 1H), 1.20-1.28 (m, 1H). MS (m/z): 531.4 [MH]⁺.

Example 195: N-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide hydrochloride (CIS, Enantiomer 1, E195)

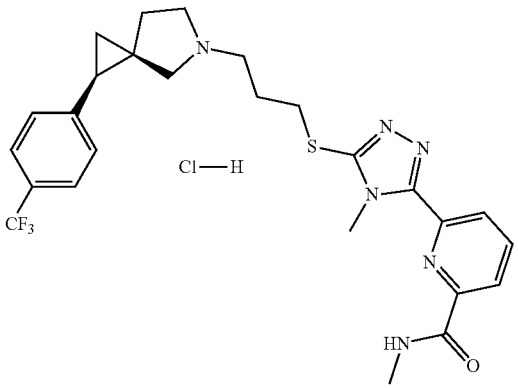 [SMILES: CNC(=O)c1cccc(-c2nnc(SCCCN3CC[C@]4(C[C@@H]4c4ccc(C(F)(F)F)cc4)C3)n2C)n1 ; Cl]

N-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E194, 33 mg) was dissolved in MeOH and treated with 1.1 eq of HCl in Et$_2$O. The solid so obtained was triturated with ether and dried under vacuum affording N-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide hydrochloric salt (CIS, Enantiomer 1, E195, 34.6 mg). MS (m/z): 531.4 [MH]$^+$.

Example 196: N,N-dimethyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E196)

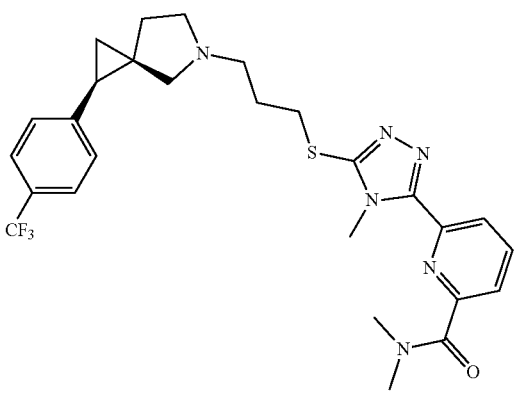 [SMILES: CN(C)C(=O)c1cccc(-c2nnc(SCCCN3CC[C@]4(C[C@@H]4c4ccc(C(F)(F)F)cc4)C3)n2C)n1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol) 6-{5-[(3-chloropropyl)sulfanyl]-4-methyl-4H-1,2,4-triazol-3-yl}-N,N-dimethylpyridine-2-carboxamide (p178, 34 mg, 0.1 mmol), Na$_2$CO$_3$ (13 mg, 0.115 mmol) and NaI (18 mg, 0.115 mmol) in DMF (0.2 mL) affording N,N-dimethyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E196, 33 mg, y=63%). NMR: $^1$H NMR (Acetone-d) δ: 8.27-8.32 (m, 1H), 8.07-8.13 (m, 1H), 7.65-7.70 (m, 1H), 7.60-7.65 (m, 2H), 7.36-7.42 (m, 2H), 4.03 (s, 3H), 3.20-3.36 (m, 2H), 3.12 (d, 6H), 2.72-2.75 (m, 1H), 2.64 (d, 1H), 2.52 (br. s., 3H), 2.21-2.28 (m, 1H), 1.94-2.04 (m, 3H), 1.82-1.94 (m, 2H), 1.30 (m, 1H), 1.22 (m, 1H). MS (m/z): 545.3 [MH]$^+$.

Example 197: N,N-dimethyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide hydrochloride (CIS, Enantiomer 1, E197)

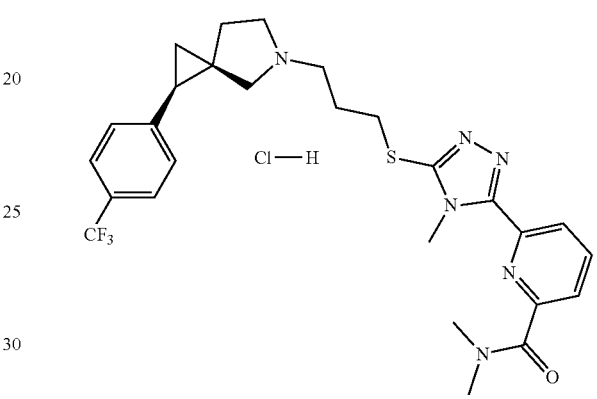

N,N-dimethyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E196, 33 mg) was dissolved in MeOH and treated with 1.1 eq of HCl in Et$_2$O. The solid so obtained was triturated with ether and dried under vacuum affording N,N-dimethyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide hydrochloric salt (CIS, Enantiomer 1, E197, 35.5 mg). MS (m/z): 545.4 [MH]$^+$.

Example 198: 5-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E198)

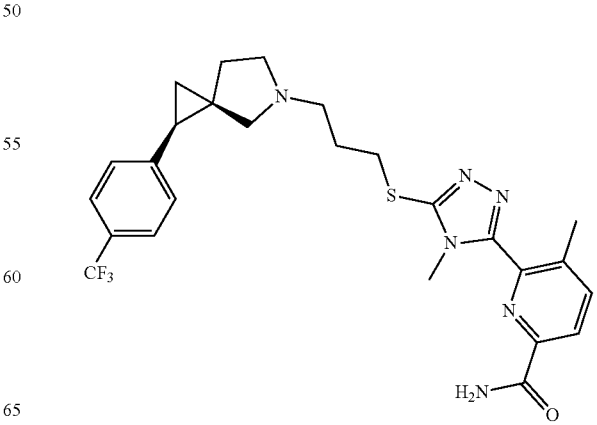

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol) 6-{5-[(3-chloropropyl)sulfanyl]-4-methyl-4H-1,2,4-triazol-3-yl}-5-methylpyridine-2-carboxamide (p179, 33 mg, 0.1 mmol), Na$_2$CO$_3$ (13 mg, 0.115 mmol) and NaI (18 mg, 0.115 mmol) in DMF (0.2 mL) affording 5-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E198, 40 mg, y=78%). NMR: $^1$H NMR (DMSO-d$_6$) δ: 8.00-8.11 (m, 3H), 7.58-7.72 (m, 3H), 7.30-7.40 (m, 2H), 3.65 (s, 3H), 3.15-3.26 (m, 3H), 2.54 (s, 3H), 2.41-2.49 (m, 2H), 1.75-2.29 (m, 8H), 1.15-1.38 (m, 2H). MS (m/z): 531.3 [MH]$^+$.

Example 199: 5-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide hydrochloride (CIS, Enantiomer 1, E199)

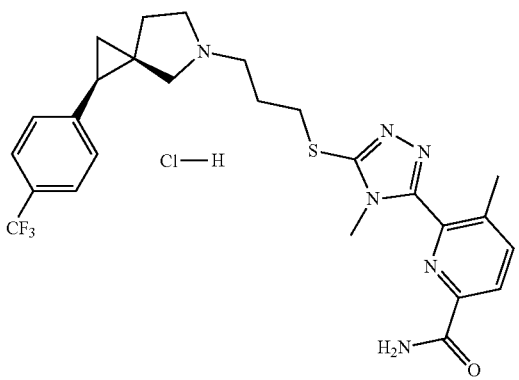 [SMILES: Cc1ccc(C(N)=O)nc1-c1nnc(SCCCN2CC[C@]3(C[C@@H]3c3ccc(C(F)(F)F)cc3)C2)n1C ; Cl]

5-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide (CIS, Enantiomer 1, E198, 40 mg) was dissolved in MeOH and treated with 1.1 eq of HCl in Et$_2$O. The solid so obtained was triturated with ether and dried under vacuum affording 5-methyl-6-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyridine-2-carboxamide hydrochloric salt (CIS, Enantiomer 1, E199, 38 mg). MS (m/z): 531.3 [MH]$^+$.

Example 200: (1S,3S/1R,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (TRANS, E200)

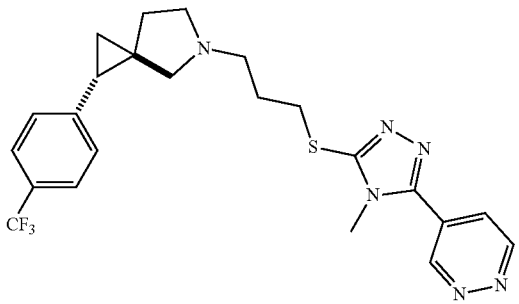

The compound was prepared as in Example 1, reacting (1S,3S/1R,3R)-1-[4-(trifluoromethyl)phenyl]-5-azaspiro[2.4]heptane (TRANS, p13, 50 mg, 0.21 mmol), 4-{5-[(3-chloropropyl)sulfanyl]-4-methyl-4H-1,2,4-triazol-3-yl}pyridazine (p180, 62 mg, 0.228 mmol), Na$_2$CO$_3$ (26 mg, 0.25 mmol) and NaI (37 mg, 0.25 mmol) in DMF (0.2 mL) affording (1S,3S/1R,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (TRANS, E200, 46 mg, y=47%). NMR: $^1$H NMR (Acetone-d$_6$) δ: 9.65 (m, 1H), 9.40 (m, 1H), 8.05 (m, 1H), 7.64 (d, 2H), 7.36 (d, 2H), 3.90 (s, 3H), 3.38 (m, 2H), 2.56-2.67 (m, 5H), 2.25-2.31 (m, 1H), 2.09-2.13 (m, 1H), 1.94-2.03 (m, 2H), 1.63-1.72 (m, 1H), 1.39-1.48 (m, 1H), 1.25-1.30 (m, 1H), 1.20-1.24 (m, 1H). MS (m/z): 475.4 [MH]$^+$.

Example 201: (1R,3S/1S,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, E201)

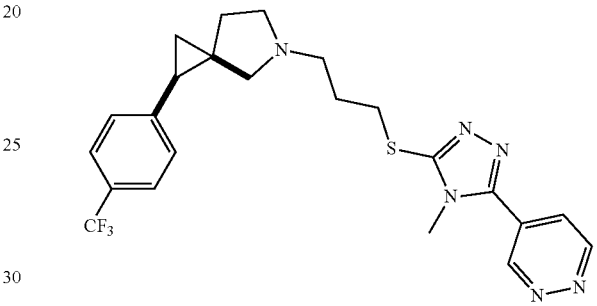

The compound was prepared as in Example 1, reacting (1R,3S/1S,3R)-1-[4-(trifluoromethyl)phenyl]-5-azaspiro[2.4]heptane (CIS, p14, 30 mg, 0.124 mmol), 4-{5-[(3-chloropropyl)sulfanyl]-4-methyl-4H-1,2,4-triazol-3-yl}pyridazine (p180, 33 mg, 0.12 mmol), Na$_2$CO$_3$ (15 mg, 0.14 mmol) and NaI (21 mg, 0.14 mmol) in DMF (0.1 mL) affording (1R,3S/1S,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, E201, 37 mg, y=63%). NMR: $^1$H NMR (Acetone-d$_6$) δ: 9.60-9.66 (m, 1H), 9.37-9.42 (m, 1H), 8.02-8.08 (m, 1H), 7.60-7.66 (m, 2H), 7.36-7.43 (m, 2H), 3.86 (s, 3H), 3.21-3.36 (m, 2H), 2.45-2.73 (m, 4H), 2.21-2.27 (m, 1H), 2.08-2.15 (m, 1H), 1.83-2.03 (m, 5H), 1.19-1.33 (m, 2H). MS (m/z): 475.4 [MH]$^+$.

Example 202 and 203: (1R,3S)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, Enantiomer 1, E202) and (1S,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, Enantiomer 2, E203)

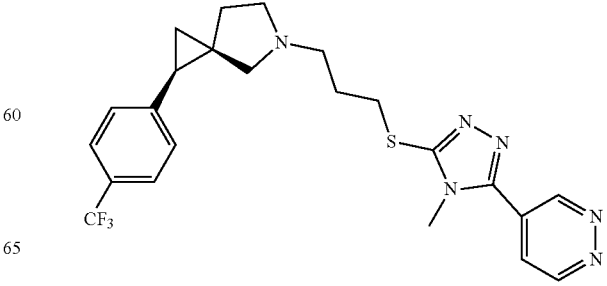

-continued

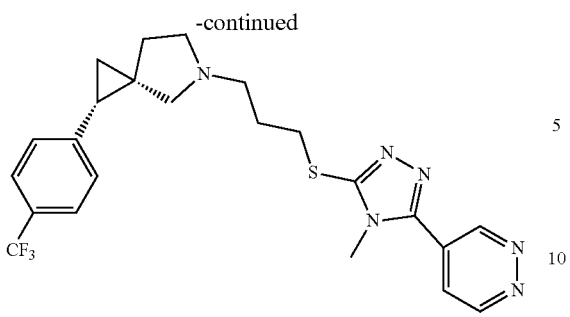

(1R,3S/1S,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, E201, 37 mg) was separated into the single enantiomers by preparative chiral HPLC.

Preparative Chromatography:

| | |
|---|---|
| Column | Chiralcel OJ-H (25 × 2.0 cm), 5μ |
| Mobile phase | n-Hexane/(Ethanol + 0.1% isopropylamine) 60/40% v/v |
| Flow rate (ml/min) | 17 ml/min |
| DAD detection | 220 nm |
| Loop | 1000 μL |
| Injection | 25 mg/injection | affording (1R,3S)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, E202, 11 mg). Enantiomer 1: ret. time 8.5 min, 100% ee. MS (m/z): 475.3 [MH]$^+$ and (1S,3R)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, E203, 11.8 mg). Enantiomer 2: ret. time 10.3 min, 100% ee. MS (m/z): 475.5 [MH]$^+$.

Example 204: (1R,3S)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E204)

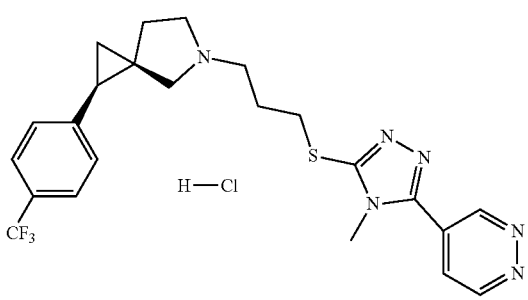 [SMILES: Cn1c(SCCCN2CC[C@]3(C[C@@H]3c3ccc(C(F)(F)F)cc3)C2)nnc1-c1ccnnc1 ; Cl]

(1R,3S)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane (CIS, E202, 11 mg) was treated with 1.1 eq of HCl in Et$_2$O affording (1R,3S)-5-(3-{[4-methyl-5-(pyridazin-4-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 1, E204, 11.9 mg). MS (m/z): 475.4 [MH]$^+$.

Example 205: (1S,3S/1R,3R)-5-(3-{[4-methyl-5-(pyridazin-3-yl)-4H-1,2,4-triazol-3-yl]sulfanyl}propyl)-1-[4-(trifluoromethyl)phenyl]-5-azaspiro[2.4]heptane (TRANS, E205)

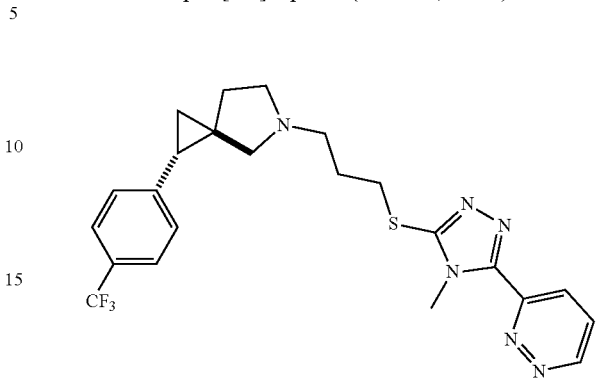

The compound was prepared as in Example 1, reacting (1S,3S/1R,3R)-1-[4-(trifluoromethyl)phenyl]-5-azaspiro[2.4]heptane (TRANS, p13, 50 mg, 0.21 mmol), 3-{5-[(3-chloropropyl)sulfanyl]-4-methyl-4H-1,2,4-triazol-3-yl}pyridazine (p181, 62 mg, 0.228 mmol), Na$_2$CO$_3$ (26 mg, 0.25 mmol) and NaI (37 mg, 0.25 mmol) in DMF (0.2 mL) affording (1S,3S/1R,3R)-5-(3-{[4-methyl-5-(pyridazin-3-yl)-4H-1,2,4-triazol-3-yl]sulfanyl}propyl)-1-[4-(trifluoromethyl)phenyl]-5-azaspiro[2.4]heptane (TRANS, E205, 38 mg, y=39%). NMR: $^1$H NMR (Acetone-d$_6$) δ: 9.27-9.36 (m, 1H), 8.40 (d, 1H), 7.89 (d, 1H), 7.63 (d, 2H), 7.36 (d, 2H), 4.13 (s, 3H), 3.33-3.49 (m, 2H), 2.74-2.79 (m, 2H), 2.56-2.68 (m, 4H), 2.24-2.31 (m, 1H), 2.10-2.13 (m, 1H), 2.09-2.13 (m, 2H), 1.95-2.04 (m, 2H), 1.62-1.71 (m, 1H), 1.39-1.49 (m, 1H), 1.25-1.30 (m, 1H), 1.18-1.24 (m, 1H). MS (m/z): 475.4 [MH]$^+$.

Example 206: (1R,3S/1S,3R)-5-(3-{[4-methyl-5-(pyridazin-3-yl)-4H-1,2,4-triazol-3-yl]sulfanyl}propyl)-1-[4-(trifluoromethyl)phenyl]-5-azaspiro[2.4]heptane (CIS, E206)

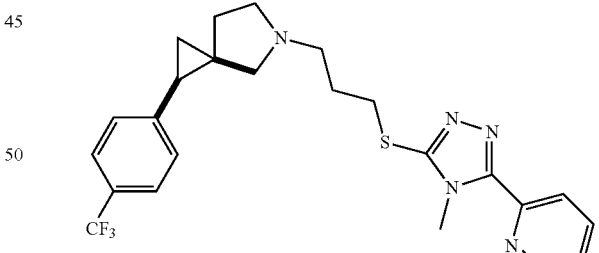

The compound was prepared as in Example 1, reacting (1R,3S/1S,3R)-1-[4-(trifluoromethyl)phenyl]-5-azaspiro[2.4]heptane (CIS, p14, 30 mg, 0.124 mmol), 3-{5-[(3-chloropropyl)sulfanyl]-4-methyl-4H-1,2,4-triazol-3-yl}pyridazine (p181, 33 mg, 0.12 mmol), Na$_2$CO$_3$ (15 mg, 0.14 mmol) and NaI (21 mg, 0.14 mmol) in DMF (0.1 mL) affording (1R,3S/1S,3R)-5-(3-{[4-methyl-5-(pyridazin-3-yl)-4H-1,2,4-triazol-3-yl]sulfanyl}propyl)-1-[4-(trifluoromethyl)phenyl]-5-azaspiro[2.4]heptane (CIS, E206, 34 mg, y=62%). NMR: $^1$H NMR (Acetone-d$_6$) δ: 9.28-9.34 (m, 1H), 8.37-8.44 (m, 1H), 7.84-7.91 (m, 1H), 7.59-7.66 (m, 2H), 7.37-7.45 (m, 2H), 4.09 (s, 3H), 3.25-3.41 (m, 2H), 2.52-2.95 (m., 6H), 2.24-2.32 (m, 1H), 1.87-2.04 (m, 4H), 1.20-1.38 (m, 2H). MS (m/z): 475.4 [MH]+.

Example 207: (1S,3S/1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, E207)

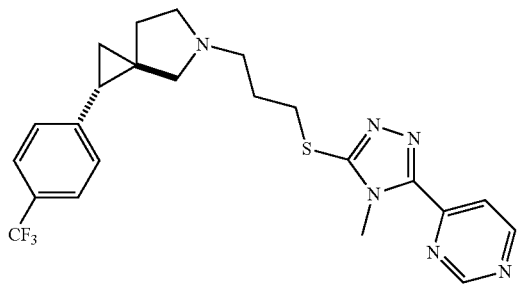

The compound was prepared as in Example 1, reacting (1S,3S/1R,3R)-1-[4-(trifluoromethyl)phenyl]-5-azaspiro[2.4]heptane (TRANS, p13, 50 mg, 0.21 mmol), 4-{5-[(3-chloropropyl)sulfanyl]-4-methyl-4H-1,2,4-triazol-3-yl}pyrimidine (p182, 62.3 mg, 0.231 mmol), Na$_2$CO$_3$ (27 mg, 0.252 mmol) and NaI (38 mg, 0.252 mmol) in DMF (0.22 mL) affording (1S,3S/1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, E207, 21 mg, y=19%). NMR: $^1$H NMR (Acetone-d$_6$) δ: 9.28 (d, 1H), 8.95 (d, 1H), 8.23 (m, 1H), 7.63 (d, 2H), 7.31-7.45 (m, 2H), 4.09 (s, 3H), 3.34-3.47 (m, 2H), 2.56-2.75 (m, 4H), 2.26-2.39 (m, 1H), 1.97-2.05 (m, 3H), 1.63-1.80 (m, 1H), 1.40-1.55 (m, 1H), 1.19-1.37 (m, 3H). MS (m/z): 475.5 [MH]+.

Example 208 and 209: (1S,3S or 1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, Enantiomer 1, E208) and (1R,3R or 1S,R3)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, Enantiomer 2, E209)

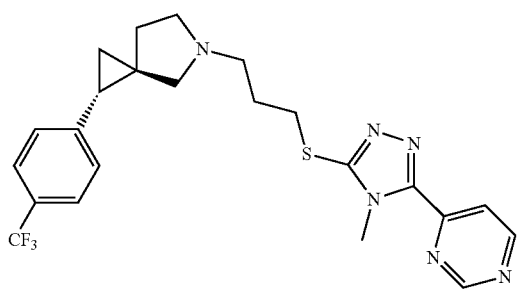

-continued

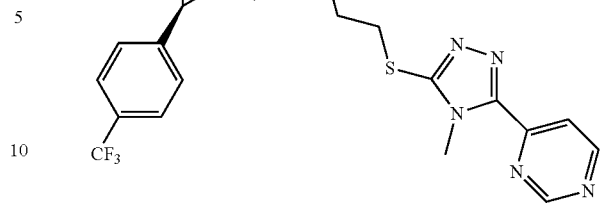

(1S,3S/1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, E207, 21 mg) was separated into the single enantiomers by preparative chiral HPLC.

Preparative Chromatography:

| | |
|---|---|
| Column | Chiralpak AD-H (25 × 2.0 cm), 5µ |
| Mobile phase | n-Hexane/(Ethanol + 0.1% isopropylamine) 35/65% v/v |
| Flow rate (ml/min) | 14 ml/min |
| DAD detection | 220 nm |
| Loop | 1000 µL |
| Injection | 18 mg/injection | affording (1S,3S or 1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, E208, 5.4 mg). Enantiomer 1: ret. time 12.3 min, 100% ee. MS (m/z): 475.0 [MH]+ and (1R,3R or 1S,R3)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, E209, 8.3 mg). Enantiomer 2: ret. time 16.3 min, 100% ee. MS (m/z): 475.0 [MH]+.

Example 210: (1S,3S or 1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane hydrochloride (TRANS, Enantiomer 1, E210)

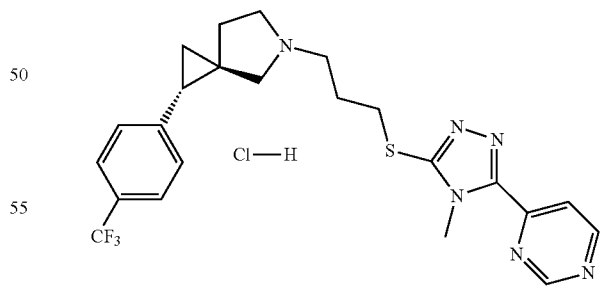

(1S,3S or 1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, E208, 5.4 mg) was treated with 1.2 eq of HCl in Et$_2$O affording (1S,3S or 1R,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane hydrochloric salt (TRANS, Enantiomer 1, E210, 5 mg). MS (m/z): 475.0 [MH]+.

Example 211: (1R,3R or 1S,R3)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane hydrochloride (TRANS, Enantiomer 2, E211)

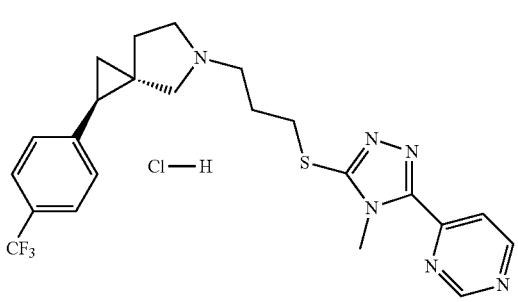 [SMILES: Cn1c(SCCCN2CC[C@@]3(C[C@@H]3c3ccc(C(F)(F)F)cc3)C2)nnc1-c1ccncn1 ; Cl]

(1R,3R or 1S,R3)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (TRANS, E209, 8.3 mg) was treated with 1.2 eq of HCl in Et$_2$O affording (1R,3R or 1S,R3)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane hydrochloric salt (TRANS, Enantiomer 1, E211, 2.5 mg). MS (m/z): 475.0 [MH]$^+$.

Example 212: (1R,3S/1S,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (CIS, E212)

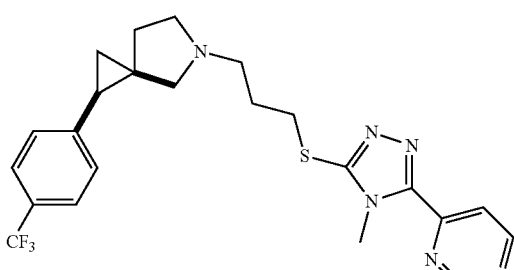

The compound was prepared as in Example 1, reacting (1R,3S/1S,3R)-1-[4-(trifluoromethyl)phenyl]-5-azaspiro[2.4]heptane (CIS, p14, 50 mg, 0.21 mmol), 4-{5-[(3-chloropropyl)sulfanyl]-4-methyl-4H-1,2,4-triazol-3-yl}pyrimidine (p182, 62.3 mg, 0.231 mmol), Na$_2$CO$_3$ (27 mg, 0.252 mmol) and NaI (38 mg, 0.252 mmol) in DMF (0.22 mL) affording (1R,3S/1S,3R)-5-(3-{[4-methyl-5-(pyrimidin-4-yl)-4H-1,2,4-triazol-3-yl]sulfanyl}propyl)-1-[4-(trifluoromethyl)phenyl]-5-azaspiro[2.4]heptane (CIS, E212, 57.2 mg, y=55%). NMR: $^1$H NMR (Acetone-d$_6$) δ: 9.27-9.31 (m, 1H), 8.92-8.99 (m, 1H), 8.22-8.26 (m, 1H), 7.59-7.65 (m, 2H), 7.36-7.42 (m, 2H), 4.07 (s, 3H), 3.22-3.39 (m, 2H), 2.71-2.76 (m, 2H), 2.59-2.68 (m, 1H), 2.46-2.56 (m, 3H), 2.21-2.27 (m, 1H), 1.83-2.03 (m, 4H), 1.26-1.32 (m, 1H), 1.22 (m, 1H). MS (m/z): 475.1 [MH]$^+$.

Example 213: (1S,3S/1R,3R)-1-[2-fluoro-4-(trifluoromethyl)phenyl]-5-(3-{[4-methyl-5-(pyrimidin-4-yl)-4H-1,2,4-triazol-3-yl]sulfanyl}propyl)-5-azaspiro[2.4]heptane (CIS, E213)

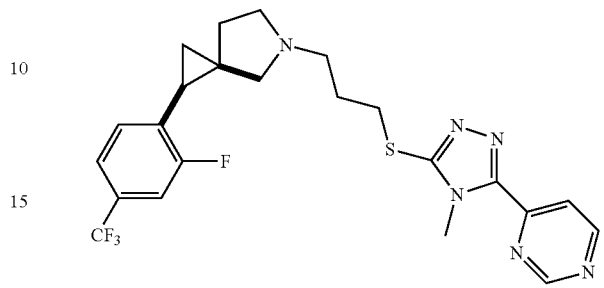

The compound was prepared as in Example 1, reacting (1S,3S/1R,3R)-1-[2-fluoro-4-(trifluoromethyl)phenyl]-5-azaspiro[2.4]heptane (CIS, p23, 50 mg, 0.19 mmol), 4-{5-[(3-chloropropyl)sulfanyl]-4-methyl-4H-1,2,4-triazol-3-yl}pyrimidine (p182, 56.4 mg, 0.209 mmol), Na$_2$CO$_3$ (24 mg, 0.228 mmol) and NaI (34 mg, 0.228 mmol) in DMF (0.22 mL) affording (1S,3S/1R,3R)-1-[2-fluoro-4-(trifluoromethyl)phenyl]-5-(3-{[4-methyl-5-(pyrimidin-4-yl)-4H-1,2,4-triazol-3-yl]sulfanyl}propyl)-5-azaspiro[2.4]heptane (CIS, E213, 11.8 mg, y=12%). NMR: $^1$H NMR (Acetone-d$_6$) δ: 9.27-9.32 (m, 1H), 8.93-8.98 (m, 1H), 8.20-8.26 (m, 1H), 7.45-7.53 (m, 2H), 7.29-7.38 (m, 1H), 4.07 (s, 3H), 3.24-3.45 (m, 2H), 2.44-2.67 (m, 5H), 2.25-2.35 (m, 1H), 1.98-2.05 (m, 3H), 1.83-1.95 (m, 2H), 1.35-1.41 (m, 1H), 1.23-1.29 (m, 1H). MS (m/z): 475.1 [MH]$^+$.

Example 214: (1S,3S/1R,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, E214)

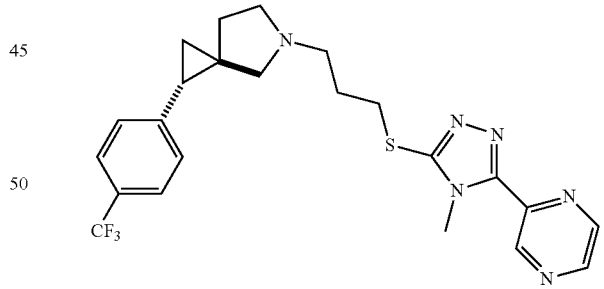

The compound was prepared as in Example 1, reacting (1S,3S/1R,3R)-1-[4-(trifluoromethyl)phenyl]-5-azaspiro[2.4]heptane (TRANS, p13, 50 mg, 0.21 mmol), 2-{5-[(3-chloropropyl)sulfanyl]-4-methyl-4H-1,2,4-triazol-3-yl}pyrazine (p183, 62.3 mg, 0.231 mmol), Na$_2$CO$_3$ (27 mg, 0.252 mmol) and NaI (38 mg, 0.252 mmol) in DMF (0.22 mL) affording (1S,3S/1R,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, E214, 24.5 mg, y=25%). NMR: $^1$H NMR (Acetone-d$_6$) δ: 9.38 (d, 1H), 8.72 (m, 2H), 7.63 (d, 2H), 7.33-7.52 (m, 2H), 4.02 (s, 3H), 3.40-3.50 (m, 2H), 2.89-3.15 (m, 3H), 2.31-2.47 (m, 1H), 2.11-2.19 (m, 1H), 2.02 (br. s., 1H), 1.72-1.86 (m, 2H), 1.43-1.65 (m, 2H), 1.25-1.41 (m, 3H). MS (m/z): 475.1 [MH]+.

Example 215 and 216: (1S,3S or 1R,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, Enantiomer 1, E215) and (1R,3R or 1S,R3)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, Enantiomer 2, E216)

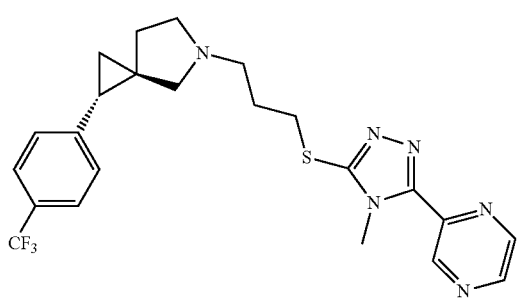

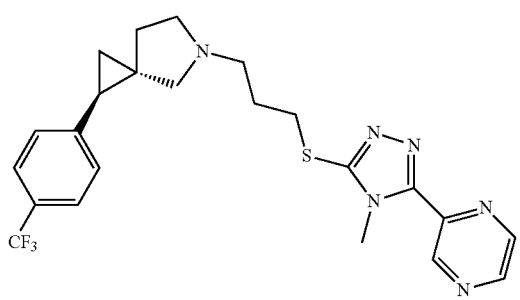

(1S,3S/1R,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, E214, 24.5 mg) was separated into the single enantiomers by preparative chiral HPLC.

Preparative Chromatography:

| Column | Chiralpak AD-H (25 × 2.0 cm), 5µ |
|---|---|
| Mobile phase | n-Hexane/(Ethanol + 0.1% isopropylamine) 40/60% v/v |
| Flow rate (ml/min) | 14 ml/min |
| DAD detection | 220 nm |
| Loop | 1000 µL |
| Injection | 11.5 mg/injection | affording (1S,3S or 1R,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, E215, 8.5 mg). Enantiomer 1: ret. time 11.7 min, 100% ee. MS (m/z): 475.1 [MH]+ and (1R,3R or 1S,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (TRANS, E216, 8.5 mg). Enantiomer 2: ret. time 16.0 min, 100% ee. MS (m/z): 475.1 [MH]+.

Example 217: (1R,3S/1S,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, E217)

The compound was prepared as in Example 1, reacting (1R,3S/1S,3R)-1-[4-(trifluoromethyl)phenyl]-5-azaspiro[2.4]heptane (CIS, p14, 50 mg, 0.21 mmol), 2-{5-[(3-chloropropyl)sulfanyl]-4-methyl-4H-1,2,4-triazol-3-yl}pyrazine (p183, 62.3 mg, 0.231 mmol), Na$_2$CO$_3$ (27 mg, 0.252 mmol) and NaI (38 mg, 0.252 mmol) in DMF (0.22 mL) affording (1R,3S/1S,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, E217, 56.3 mg, y=54%). NMR: $^1$H NMR (Acetone-d$_6$) δ: 9.39 (d, 1H), 8.69-8.76 (m, 2H), 7.62 (d, 2H), 7.39 (d, 2H), 4.00 (s, 3H), 3.21-3.38 (m, 2H), 2.72-2.77 (m, 2H), 2.60-2.68 (m, 1H), 2.47-2.57 (m, 3H), 2.21-2.28 (m, 1H), 1.93-2.03 (m, 2H), 1.83-1.93 (m, 2H), 1.25-1.32 (m, 1H), 1.19-1.24 (m, 1H). MS (m/z): 475.1 [MH]+.

Example 218 and 219: (1S,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, Enantiomer 1, E218) and (1R,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, Enantiomer 2, E219)

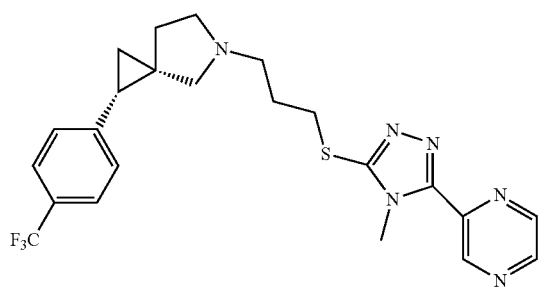

-continued

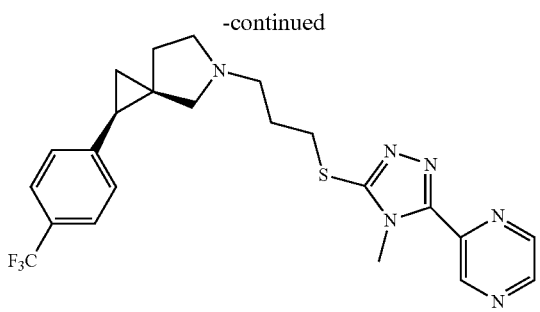

(1R,3S/1S,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, E217, 56.3 mg) was separated into the single enantiomers by preparative chiral HPLC (SFC).

Preparative Chromatography:

| | |
|---|---|
| Column | Chiralpak AD-H (25 × 2.1 cm), 5μ |
| Modifier | (Methanol + 0.1% isopropylamine) 30% |
| Flow rate (ml/min) | 45 ml/min |
| Pressure (bar) | 120 |
| Temperature (° C.) | 38 |
| DAD detection | 220 nm |
| Loop | 500 μL |
| Injection | 17 mg/injection | affording (1S,3R)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, E218, 21.8 mg). Enantiomer 1: ret. time 6.3 min, 100% ee. MS (m/z): 475.5 [MH]+ and (1R,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, E219, 11.4 mg). Enantiomer 2: ret. time 10.5 min, 89.2% ee. MS (m/z): 475.5 [MH]+.

Example 220: (1R,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane hydrochloride (CIS, Enantiomer 2, E220)

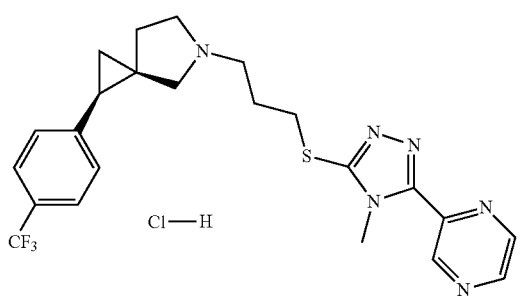 [SMILES: Cn1c(SCCCN2CC[C@]3(C[C@@H]3c3ccc(C(F)(F)F)cc3)C2)nnc1-c1cnccn1 ; Cl]

(1R,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane (CIS, Enantiomer 2, E219, 11.4 mg) was dissolved in Et$_2$O/DCM and treated with 1.2 eq of HCl 2N in Et$_2$O affording (1R,3S)-5-(3-{[4-methyl-5-(pyrazin-2-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 2, E220, 10.8 mg). MS (m/z): 475.1 [MH]+.

Example 221: (1S,3S/1R,3R)-1-[2-fluoro-4-(trifluoromethyl)phenyl]-5-(3-{[4-methyl-5-(pyrazin-2-yl)-4H-1,2,4-triazol-3-yl]sulfanyl}propyl)-5-azaspiro[2.4]heptane (CIS, E221)

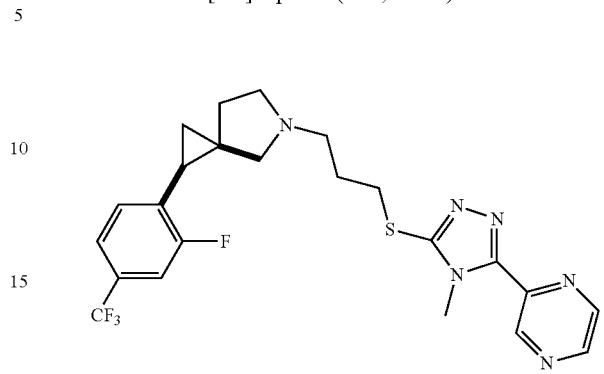

The compound was prepared as in Example 1, reacting (1S,3S/1R,3R)-1-[2-fluoro-4-(trifluoromethyl)phenyl]-5-azaspiro[2.4]heptane (CIS, p23, 50 mg, 0.19 mmol), 2-{5-[(3-chloropropyl)sulfanyl]-4-methyl-4H-1,2,4-triazol-3-yl}pyrazine (p183, 56.4 mg, 0.209 mmol), Na$_2$CO$_3$ (24 mg, 0.228 mmol) and NaI (34 mg, 0.228 mmol) in DMF (0.22 mL) affording (1S,3S/1R,3R)-1-[2-fluoro-4-(trifluoromethyl)phenyl]-5-(3-{[4-methyl-5-(pyrazin-2-yl)-4H-1,2,4-triazol-3-yl]sulfanyl}propyl)-5-azaspiro[2.4]heptane (CIS, E221, 52.7 mg, y=51%). NMR: $^1$H NMR (Acetone-d$_6$) δ: 9.39 (d, 1H), 8.70-8.77 (m, 2H), 7.47-7.52 (m, 2H), 7.34 (m, 1H), 4.00 (s, 3H), 3.22-3.41 (m, 3H), 2.76 (br. s., 1H), 2.58-2.65 (m, 1H), 2.44-2.56 (m, 2H), 2.24-2.30 (m, 1H), 1.96-2.05 (m, 3H), 1.83-1.94 (m, 2H), 1.35-1.41 (m, 1H), 1.22-1.29 (m, 1H). MS (m/z): 493.1 [MH]+.

Example 222: (1R,3S/1S,3R)-5-(3-{[4-methyl-5-(6-methylpyrazin-2-yl)-4H-1,2,4-triazol-3-yl]sulfanyl}propyl)-1-[4-(trifluoromethyl)phenyl]-5-azaspiro[2.4]heptane (CIS, E222)

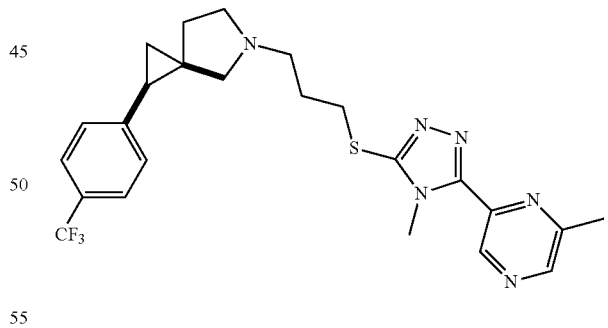

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 2-{5-[(3-chloropropyl)sulfanyl]-4-methyl-4H-1,2,4-triazol-3-yl}-6-methylpyrazine (p184, 37 mg, 0.132 mmol), Na$_2$CO$_3$ (15 mg, 0.144 mmol) and NaI (22 mg, 0.144 mmol) in DMF (0.135 mL) affording (1R,3S/1S,3R)-5-(3-{[4-methyl-5-(6-methylpyrazin-2-yl)-4H-1,2,4-triazol-3-yl]sulfanyl}propyl)-1-[4-(trifluoromethyl)phenyl]-5-azaspiro[2.4]heptane (CIS, E222, 24.8 mg, y=41%). NMR: $^1$H NMR (Acetone-d$_6$) δ: 9.17 (s, 1H), 8.61 (s, 1H), 7.63 (d, 2H), 7.39-7.46 (m, 2H), 4.01 (s, 3H), 3.23-3.40 (m, 2H), 2.57-2.94 (m, 9H), 2.30 (m, 1H), 1.90-2.04 (m, 4H), 1.29-1.37 (m, 1H), 1.23-1.29 (m, 1H). MS (m/z): 489.5 [MH]⁺.

Example 223: (1R,3S/1S,3R)-5-(3-{[4-methyl-5-(5-methylpyrazin-2-yl)-4H-1,2,4-triazol-3-yl]sulfanyl}propyl)-1-[4-(trifluoromethyl)phenyl]-5-azaspiro[2.4]heptane (CIS, E223)

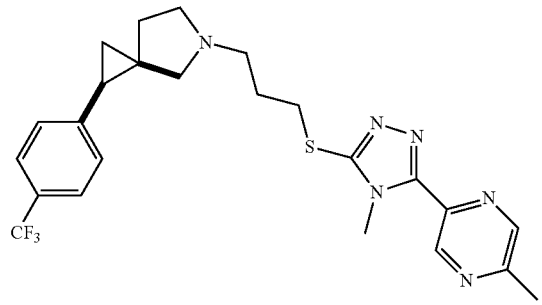

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 2-{5-[(3-chloropropyl)sulfanyl]-4-methyl-4H-1,2,4-triazol-3-yl}-5-methylpyrazine (p185, 37 mg, 0.132 mmol), Na₂CO₃ (15 mg, 0.144 mmol) and NaI (22 mg, 0.144 mmol) in DMF (0.135 mL) affording (1R,3S/1S,3R)-5-(3-{[4-methyl-5-(5-methylpyrazin-2-yl)-4H-1,2,4-triazol-3-yl]sulfanyl}propyl)-1-[4-(trifluoromethyl)phenyl]-5-azaspiro[2.4]heptane (CIS, E223, 37.7 mg, y=63%). NMR: ¹H NMR (Acetone-d₆) δ: 9.24 (d, 1H), 8.64 (s, 1H), 7.63 (d, 2H), 7.42 (d, 2H), 3.97 (s, 3H), 3.22-3.40 (m, 2H), 2.63 (s, 3H), 2.59-2.96 (m, 6H), 2.25-2.34 (m, 1H), 1.89-2.04 (m, 4H), 1.21-1.39 (m, 2H). MS (m/z): 489.4 [MH]⁺.

Example 224: (1R,3S/1S,3R)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, E224)

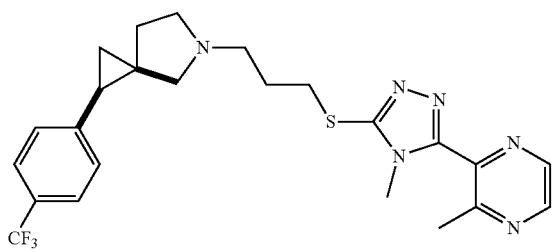 [SMILES: Cc1nccnc1-c1nnc(SCCCN2CC[C@]3(C[C@@H]3c3ccc(C(F)(F)F)cc3)C2)n1C]

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 2-{5-[(3-chloropropyl)sulfanyl]-4-methyl-4H-1,2,4-triazol-3-yl}-3-methylpyrazine (p186, 37 mg, 0.132 mmol), Na₂CO₃ (15 mg, 0.144 mmol) and NaI (22 mg, 0.144 mmol) in DMF (0.135 mL) affording (1R,3S/1S,3R)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, E224, 37.8 mg, y=63%). NMR: ¹H NMR (Acetone-d₆) δ: 8.62 (s, 2H), 7.60-7.68 (m, 2H), 7.39-7.46 (m, 2H), 3.77 (s, 3H), 3.33 (m, 2H), 2.82 (s, 3H), 2.62-2.83 (m, 6H), 2.25-2.34 (m, 1H), 1.92-2.05 (m, 4H), 1.32-1.38 (m, 1H), 1.22-1.31 (m, 1H). MS (m/z): 489.5 [MH]⁺.

Example 225 and 226: (1S,3R)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, Enantiomer 1, E225) and (1R,3S)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, Enantiomer 2, E226)

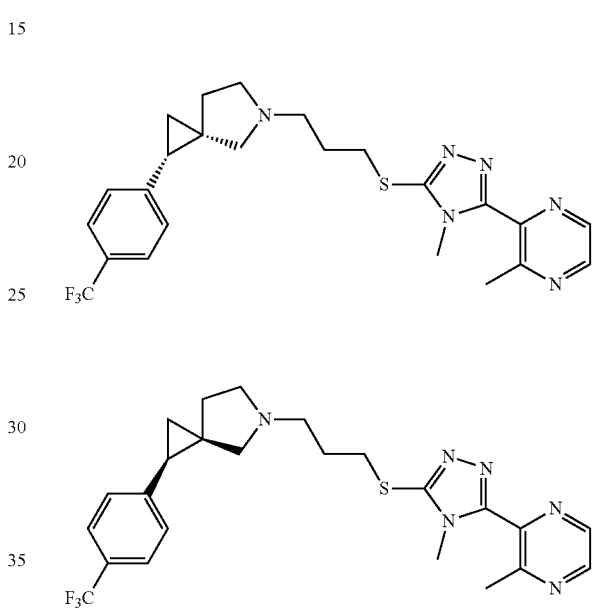

(1R,3S/1S,3R)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, E224, 37.8 mg) was separated into the single enantiomers by preparative chiral HPLC (SFC).

Preparative Chromatography:

| | |
|---|---|
| Column | Chiralpak AD-H (25 × 2.0 cm), 5μ |
| Modifier | (Methanol + 0.1% isopropylamine) 30% |
| Flow rate (ml/min) | 45 ml/min |
| Pressure (bar) | 120 |
| Temperature (° C.) | 38 |
| DAD detection | 220 nm |
| Loop | 500 μL |
| Injection | 12 mg/injection | affording (1S,3R)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, E225, 10.2 mg). Enantiomer 1: ret. time 3.8 min, 100% ee. MS (m/z): 489.5 [MH]⁺ and (1R,3S)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, E226, 11.3 mg). Enantiomer 2: ret. time 5.1 min, 99.8% ee. MS (m/z): 489.5 [MH]⁺.

Example 227: (1R,3S)-5-(3-{[4-methyl-5-(3-methyl-pyrazin-2-yl)-4H-1,2,4-triazol-3-yl]sulfanyl}propyl)-1-[4-(trifluoromethyl)phenyl]-5-azaspiro[2.4]heptane hydrochloride (CIS, Enantiomer 2, E227)

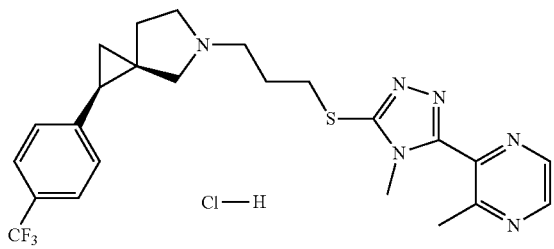 [SMILES: Cc1nccnc1-c1nnc(SCCCN2CC[C@]3(C[C@@H]3c3ccc(C(F)(F)F)cc3)C2)n1C ; Cl]

(1R,3S)-5-(3-{[4-methyl-5-(3-methylpyrazin-2-yl)-4H-1,2,4-triazol-3-yl]sulfanyl}propyl)-1-[4-(trifluoromethyl)phenyl]-5-azaspiro[2.4]heptane (CIS, E226, 11.3 mg) was dissolved in Et$_2$O/DCM and treated with 1.2 eq of HCl 2N in Et$_2$O affording (1R,3S)-5-(3-{[4-methyl-5-(3-methyl-pyrazin-2-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 2, E227, 11.7 mg). MS (m/z): 489.4 [MH]$^+$.

Example 228: 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyrazine-2-carboxamide (CIS, E228)

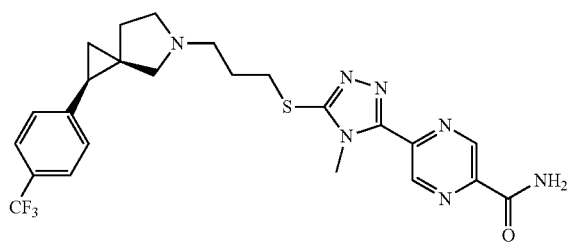 [SMILES: Cn1c(SCCCN2CC[C@]3(C[C@@H]3c3ccc(C(F)(F)F)cc3)C2)nnc1-c1cnc(C(N)=O)cn1]

The compound was prepared as in Example 1, reacting (1R,3S)-1-[4-(trifluoromethyl)phenyl]-5-azaspiro[2.4]heptane (CIS, Enantiomer 1, p15, 15 mg, 0.064 mmol), 5-{5-[(3-chloropropyl)sulfanyl]-4-methyl-4H-1,2,4-triazol-3-yl}pyrazine-2-carboxamide (p187, 20 mg, 0.064 mmol), Na$_2$CO$_3$ (8 mg, 0.077 mmol) and NaI (12 mg, 0.077 mmol) in DMF (0.1 mL) affording 5-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]pyrazine-2-carboxamide (CIS, E228, 14.4 mg, y=43%). NMR: $^1$H NMR (Acetone-d$_6$) δ: 9.28-9.42 (m, 2H), 7.93-8.07 (m, 1H), 7.59-7.68 (m, 2H), 7.38-7.45 (m, 2H), 7.02-7.15 (m, 1H), 4.04 (s, 3H), 3.35 (d, 2H), 2.57-2.93 (m, 8H), 2.30 (br. s., 1H), 1.98 (br. s., 2H), 1.22-1.39 (m, 2H). MS (m/z): 518.4 [MH]$^+$.

Example 229: (1R,3S/1S,3R)-5-(3-{[4-methyl-5-(1,2-oxazol-5-yl)-4H-1,2,4-triazol-3-yl]sulfanyl}propyl)-1-[4-(trifluoromethyl)phenyl]-5-azaspiro[2.4]heptane (CIS, E229)

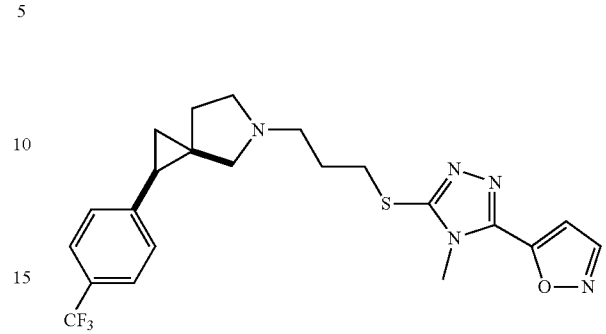

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-4-methyl-5-(1,2-oxazol-5-yl)-4H-1,2,4-triazole (p188, 34 mg, 0.132 mmol), Na$_2$CO$_3$ (15 mg, 0.144 mmol) and NaI (22 mg, 0.144 mmol) in DMF (0.135 mL) affording (1R,3S/1S,3R)-5-(3-{[4-methyl-5-(1,2-oxazol-5-yl)-4H-1,2,4-triazol-3-yl]sulfanyl}propyl)-1-[4-(trifluoromethyl)phenyl]-5-azaspiro[2.4]heptane (CIS, E229, 13 mg, y=20%). NMR: $^1$H NMR (Acetone-d$_6$) δ: 7.62 (d, 3H), 7.36-7.45 (m, 3H), 3.82 (s, 3H), 3.28-3.45 (m, 3H), 2.40-2.71 (m, 6H), 2.23-2.34 (m, 2H), 1.97 (br. s., 2H), 1.31 (br. s., 2H), 1.22-1.26 (m, 1H). MS (m/z): 464.4 [MH]$^+$.

Example 230: (1S,3S/1R,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (TRANS, E230)

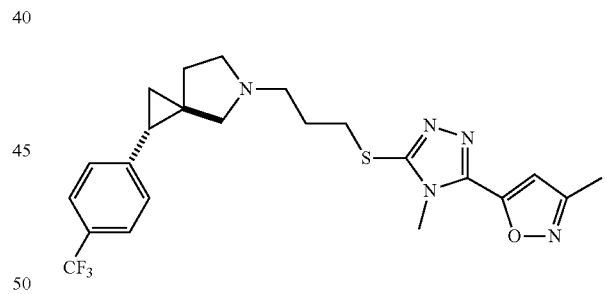

The compound was prepared as in Example 1, reacting (1S,3S/1R,3R)-1-[4-(trifluoromethyl)phenyl]-5-azaspiro[2.4]heptane (TRANS, p13, 50 mg, 0.207 mmol), 3-[(3-chloropropyl)sulfanyl]-4-methyl-5-(3-methyl-1,2-oxazol-5-yl)-4H-1,2,4-triazole (p189, 62 mg, 0.228 mmol), Na$_2$CO$_3$ (26 mg, 0.248 mmol) and NaI (37 mg, 0.248 mmol) in DMF (0.2 mL) affording (1S,3S/1R,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (TRANS, E230, 54 mg, y=55%). NMR: $^1$H NMR (Acetone-d$_6$) δ: 7.64 (d, 2H), 7.35 (d, 2H), 6.90 (s, 1H), 3.89 (s, 3H), 3.36 (m, 3H), 2.75 (d, 1H), 2.55-2.66 (m, 5H), 2.39 (s, 3H), 2.24-2.30 (m, 1H), 1.93-2.02 (m, 2H), 1.61-1.72 (m, 1H), 1.37-1.48 (m, 1H), 1.24-1.29 (m, 1H), 1.21 (s, 1H). MS (m/z): 478.4 [MH]$^+$.

Example 231: (1R,3S/1S,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, E231)

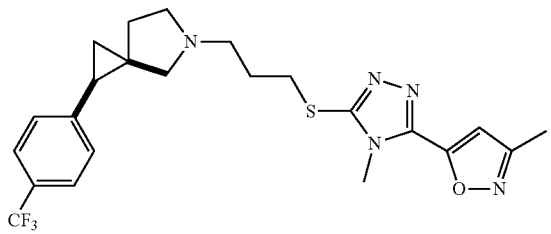

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-4-methyl-5-(3-methyl-1,2-oxazol-5-yl)-4H-1,2,4-triazole (p189, 36 mg, 0.132 mmol), Na$_2$CO$_3$ (15 mg, 0.144 mmol) and NaI (22 mg, 0.144 mmol) in DMF (0.135 mL) affording (1R,3S/1S,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, E231, 38 mg, y=64%). NMR: $^1$H NMR (Acetone-d$_6$) δ: 7.58-7.65 (m, 2H), 7.37-7.41 (m, 2H), 6.88-6.91 (m, 1H), 3.84 (s, 3H), 3.28 (m, 2H), 2.81-2.90 (m, 2H), 2.60 (br. s., 3H), 2.38 (s, 3H), 2.23-2.30 (m, 1H), 1.84-2.03 (m, 5H), 1.29-1.34 (m, 1H), 1.23 (m, 1H). MS (m/z): 478.1 [MH]$^+$.

Example 232 and 233: (1R,3S)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, Enantiomer 1, E232) and (1S,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, Enantiomer 2, E233)

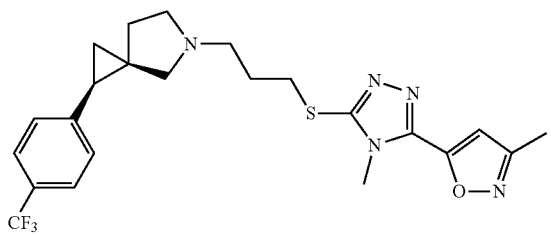 [SMILES: Cc1cc(-c2nnc(SCCCN3CC[C@]4(C[C@@H]4c4ccc(C(F)(F)F)cc4)C3)n2C)on1]

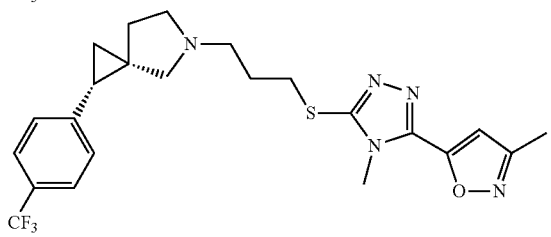

(1R,3S/1S,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, E231, 38 mg) was separated into the single enantiomers by preparative chiral HPLC.

Preparative Chromatography:

| | |
|---|---|
| Column | Chiralcel OJ-H (25 × 2.0 cm), 5µ |
| Mobile phase | n-Hexane/(Ethanol + 0.1% isopropylamine) 50/50% v/v |
| Flow rate (ml/min) | 17 ml/min |
| DAD detection | 220 nm |
| Loop | 1000 µL |
| Injection | 17 mg/injection | affording (1R,3S)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, E232, 13 mg). Enantiomer 1: ret. time 10.1 min, 100% ee, MS (m/z): 478.5 [MH]$^+$ and (1S,3R)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, E233, 10.8 mg), Enantiomer 2: ret. time 14.7 min, 100% ee, MS (m/z): 478.5 [MH]$^+$.

Example 234: (1R,3S)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E234)

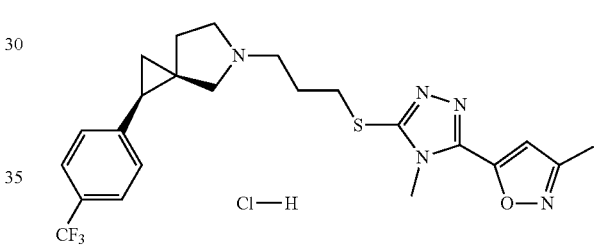

(1R,3S)-5-(3-{[4-methyl-5-(3-methyl-1,2-oxazol-5-yl)-4H-1,2,4-triazol-3-yl]sulfanyl}propyl)-1-[4-(trifluoromethyl)phenyl]-5-azaspiro[2.4]heptane (CIS, E232, 13 mg) was dissolved in Et$_2$O/DCM and treated with 1.2 eq of HCl 2N in Et$_2$O affording (1R,3S)-5-(3-{[4-methyl-1,2-oxazol-5-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 1, E234, 10.8 mg). MS (m/z): 478.5 [MH]$^+$.

Example 235: (1S,3S/1R,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (TRANS, E235)

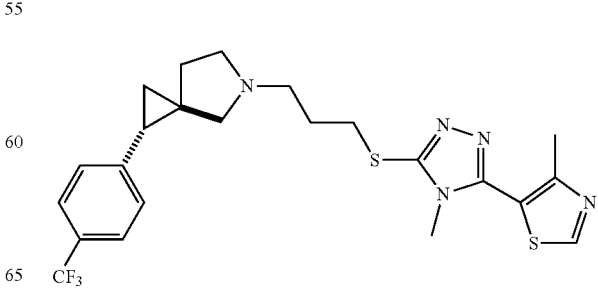

The compound was prepared as in Example 1, reacting (1S,3S/1R,3R)-1-[4-(trifluoromethyl)phenyl]-5-azaspiro[2.4]heptane (TRANS, p13, 50 mg, 0.207 mmol), 3-[(3-chloropropyl)sulfanyl]-4-methyl-5-(4-methyl-1,3-thiazol-5-yl)-4H-1,2,4-triazole (p190, 62 mg, 0.228 mmol), Na$_2$CO$_3$ (26 mg, 0.248 mmol) and NaI (37 mg, 0.248 mmol) in DMF (0.2 mL) affording (1S,3S/1R,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (TRANS, E235, 56 mg, y=55%). NMR: $^1$H NMR (Acetone-d$_6$) δ: 9.15 (s, 1H), 7.64 (d, 2H), 7.39 (d, 2H), 3.62 (s, 3H), 3.36 (s, 2H), 2.72 (br. s., 5H), 2.50 (s, 3H), 2.28-2.36 (m, 1H), 1.97-2.06 (m, 3H), 1.67-1.79 (m, 1H), 1.41-1.53 (m, 1H), 1.23-1.35 (m, 3H). MS (m/z): 494.4 [MH]$^+$.

Example 236: (1R,3S/1S,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, E236)

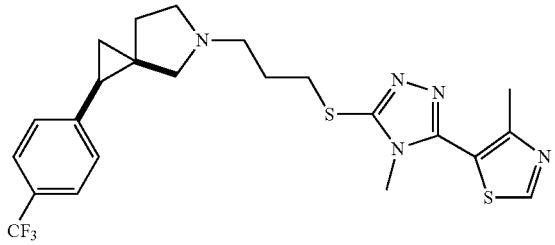 [SMILES: Cc1ncsc1-c1nnc(SCCCN2CC[C@]3(C[C@@H]3c3ccc(C(F)(F)F)cc3)C2)n1C]

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-4-methyl-5-(4-methyl-1,3-thiazol-5-yl)-4H-1,2,4-triazole (p190, 38 mg, 0.132 mmol), Na$_2$CO$_3$ (15 mg, 0.144 mmol) and NaI (22 mg, 0.144 mmol) in DMF (0.135 mL) affording (1R,3S/1S,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, E236, 25 mg, y=40%). NMR: $^1$H NMR (Acetone) δ: 9.15 (s, 1H), 7.60-7.67 (m, 2H), 7.37-7.42 (m, 2H), 3.58 (s, 3H), 3.25 (m, 2H), 2.72-2.77 (m, 2H), 2.60-2.67 (m, 1H), 2.46-2.56 (m, 6H), 2.21-2.26 (m, 1H), 1.95-2.03 (m, 2H), 1.82-1.92 (m, 2H), 1.30 (m, 1H), 1.22 (m, 1H). MS (m/z): 494.5 [MH]$^+$.

Example 237 and 238: (1R,3S)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, Enantiomer 1, E237) and (1S,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, Enantiomer 2, E238)

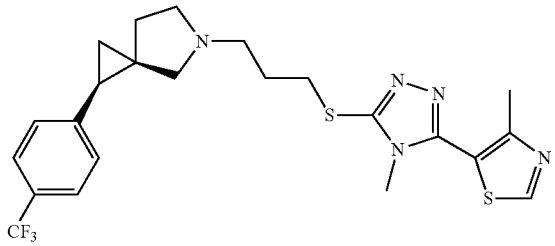 [SMILES: Cc1ncsc1-c1nnc(SCCCN2CC[C@]3(C[C@@H]3c3ccc(C(F)(F)F)cc3)C2)n1C ; Cl]

-continued

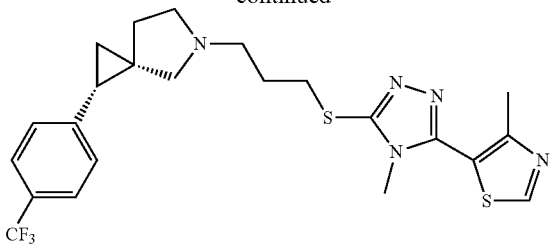

(1R,3S/1S,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, E236, 25 mg) was separated into the single enantiomers by preparative chiral HPLC.

Preparative Chromatography:

| | |
|---|---|
| Column | Chiralcel OJ-H (25 × 2.0 cm), 5μ |
| Mobile phase | n-Hexane/(Ethanol + 0.1% isopropylamine) 65/35% v/v |
| Flow rate (ml/min) | 18 ml/min |
| DAD detection | 220 nm |
| Loop | 500 μL |
| Injection | 12 mg/injection | affording (1R,3S)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, E237, 7 mg). Enantiomer 1: ret. time 6.2 min, 100% ee. MS (m/z): 494.0 [MH]$^+$ and (1S,3R)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, E238, 7 mg). Enantiomer 2: ret. time 8.0 min, 100% ee. MS (m/z): 494.0 [MH]$^+$.

Example 239: (1R,3S)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E239)

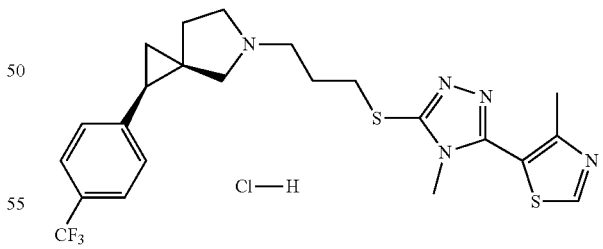

(1R,3S)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane (CIS, E237, 7 mg) was dissolved in Et$_2$O/DCM and treated with 1.2 eq of HCl 2N in Et$_2$O affording (1R,3S)-5-(3-{[4-methyl-5-(4-methyl-1,3-thiazol-5-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 1, E239, 7.6 mg). MS (m/z): 494.0 [MH]$^+$.

Example 240: (1S,3S/1R,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (TRANS, E240)

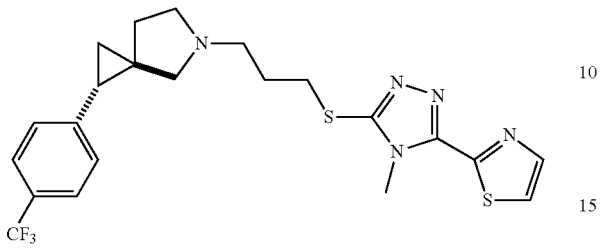

The compound was prepared as in Example 1, reacting (1S,3S/1R,3R)-1-[4-(trifluoromethyl)phenyl]-5-azaspiro[2.4]heptane (TRANS, p13, 50 mg, 0.207 mmol), 3-[(3-chloropropyl)sulfanyl]-4-methyl-5-(1,3-thiazol-2-yl)-4H-1,2,4-triazole (p191, 63 mg, 0.228 mmol), Na₂CO₃ (26 mg, 0.248 mmol) and NaI (37 mg, 0.248 mmol) in DMF (0.2 mL) affording (1S,3S/1R,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (TRANS, E240, 61 mg, y=61%). NMR: $^1$H NMR (Acetone-d$_6$) δ: 8.04 (d, 1H), 7.81 (d, 1H), 7.63 (d, 2H), 7.36-7.44 (m, 2H), 4.06 (s, 3H), 3.39 (m, 2H), 2.96 (br. s., 5H), 2.26-2.39 (m, 1H), 2.01-2.05 (m, 3H), 1.66-1.79 (m, 1H), 1.42-1.53 (m, 1H), 1.21-1.37 (m, 3H). MS (m/z): 480.4 [MH]$^+$.

Example 241: (1R,3S/1S,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, E241)

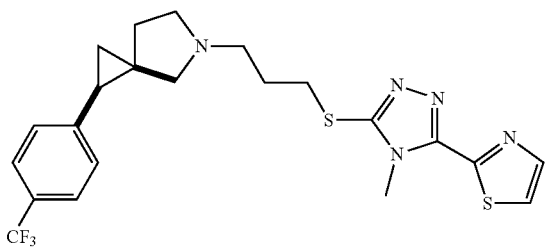 [SMILES: Cn1c(SCCCN2CC[C@]3(C[C@@H]3c3ccc(C(F)(F)F)cc3)C2)nnc1-c1nccs1]

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-4-methyl-5-(1,3-thiazol-2-yl)-4H-1,2,4-triazole (p191, 40 mg, 0.132 mmol), Na₂CO₃ (15 mg, 0.144 mmol) and NaI (22 mg, 0.144 mmol) in DMF (0.135 mL) affording (1R,3S/1S,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, E241, 28 mg, y=48%). NMR: $^1$H NMR (Acetone-d$_6$) δ: 8.03 (d, 1H), 7.79 (d, 1H), 7.61 (d, 2H), 7.37 (d, 2H), 4.02 (s, 3H), 3.19-3.37 (m, 2H), 2.70-2.76 (m, 2H), 2.61 (d, 1H), 2.44-2.57 (m, 3H), 2.19-2.26 (m, 1H), 1.92-2.02 (m, 2H), 1.82-1.91 (m, 2H), 1.28 (m, 1H), 1.20 (m, 1H). MS (m/z): 480.0 [MH]$^+$.

Example 242 and 243: (1R,3S)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, Enantiomer 1, E242) and (1S,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, Enantiomer 2, E243)

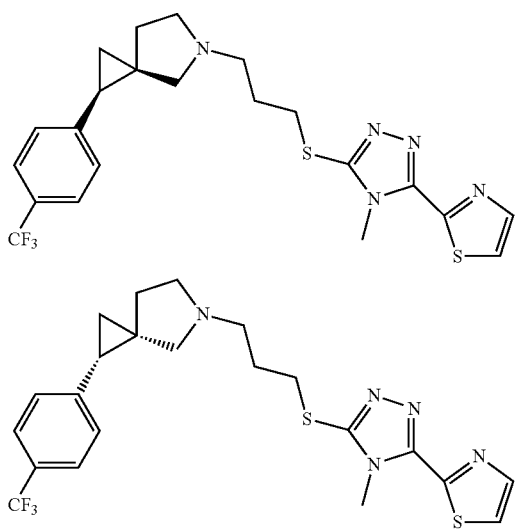

(1R,3S/1S,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, E241, 28 mg) was separated into the single enantiomers by preparative chiral HPLC.

Preparative Chromatography:

| | |
|---|---|
| Column | Chiralcel OJ-H (25 × 2.0 cm), 5μ |
| Mobile phase | n-Hexane/(Ethanol + 0.1% isopropylamine) 65/35% v/v |
| Flow rate (ml/min) | 18 ml/min |
| DAD detection | 220 nm |
| Loop | 1000 μL |
| Injection | 13 mg/injection | affording (1R,3S)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, E242, 9 mg). Enantiomer 1: ret. time 10.6 min, 100% ee. MS (m/z): 480.0 [MH]$^+$ and (1S,3R)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, E243, 8 mg). Enantiomer 2: ret. time 17.7 min, 100% ee, MS (m/z): 480.0 [MH]$^+$.

Example 244: (1R,3S)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E244)

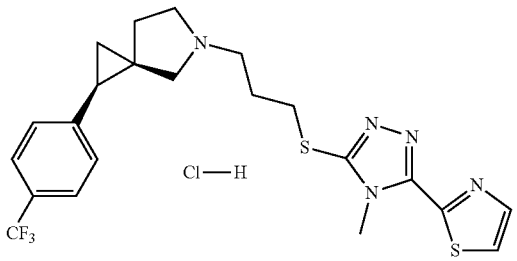 [SMILES: Cn1c(SCCCN2CC[C@]3(C[C@@H]3c3ccc(C(F)(F)F)cc3)C2)nnc1-c1nccs1 ; Cl]

(1R,3S)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane (CIS, E242, 9 mg) was dissolved in Et$_2$O/DCM and treated with 1.2 eq of HCl 2N in Et$_2$O affording (1R,3S)-5-(3-{[4-methyl-5-(1,3-thiazol-2-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 1, E244, 10 mg). MS (m/z): 480.0 [MH]$^+$.

Example 245: (1S,3S/1R,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (TRANS, E245)

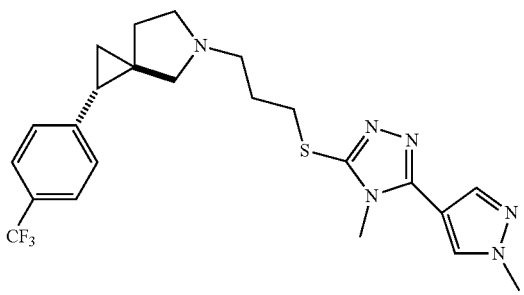

The compound was prepared as in Example 1, reacting (1S,3S/1R,3R)-1-[4-(trifluoromethyl)phenyl]-5-azaspiro[2.4]heptane (TRANS, p13, 50 mg, 0.207 mmol), 3-[(3-chloropropyl)sulfanyl]-4-methyl-5-(1-methyl-1H-pyrazol-4-yl)-4H-1,2,4-triazole (p192, 62 mg, 0.228 mmol), Na$_2$CO$_3$ (26 mg, 0.248 mmol) and NaI (37 mg, 0.248 mmol) in DMF (0.2 mL) affording (1S,3S/1R,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (TRANS, E245, 46.7 mg, y=47%). NMR: $^1$H NMR (Acetone-d$_6$) δ: 8.15 (s, 1H), 7.87 (s, 1H), 7.63 (d, 2H), 7.39 (br. s., 2H), 3.99 (s, 3H), 3.74 (s, 3H), 3.26 (br. s., 2H), 2.48-2.76 (m, 5H), 2.28-2.38 (m, 1H), 1.94-2.03 (m, 2H), 1.65-1.82 (m, 1H), 1.39-1.52 (m, 1H), 1.31 (br. s., 3H). MS (m/z): 477.4 [MH]$^+$.

Example 246: (1R,3S/1S,3R) 5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, E246)

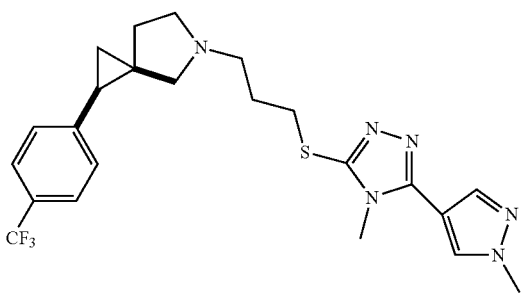

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-4-methyl-5-(1-methyl-1H-pyrazol-4-yl)-4H-1,2,4-triazole (p192, 36 mg, 0.132 mmol), Na$_2$CO$_3$ (15 mg, 0.144 mmol) and NaI (22 mg, 0.144 mmol) in DMF (0.135 mL) affording (1R,3S/1S,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, E246, 31 mg, y=54%). NMR: $^1$H NMR (Acetone-d$_6$) δ: 8.13-8.17 (m, 1H), 7.86-7.89 (m, 1H), 7.60-7.65 (m, 2H), 7.36-7.41 (m, 2H), 4.00 (s, 3H), 3.71 (s, 3H), 3.08-3.24 (m, 2H), 2.71-2.76 (m, 1H), 2.57-2.65 (m, 1H), 2.43-2.54 (m, 3H), 2.20-2.26 (m, 2H), 1.95-2.04 (m, 3H), 1.78-1.87 (m, 2H), 1.26-1.32 (m, 1H), 1.19-124 (m, 1H). MS (m/z): 477.5 [MH]$^+$.

Example 247 and 248: (1S,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, Enantiomer 1, E247) and (1R,3S)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, Enantiomer 2, E248)

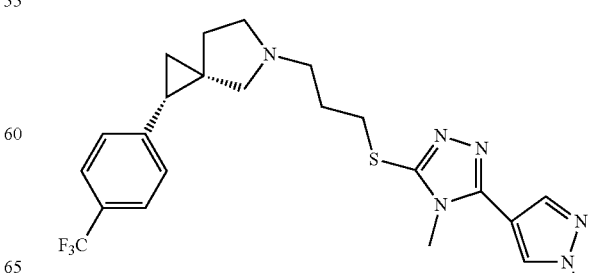

-continued

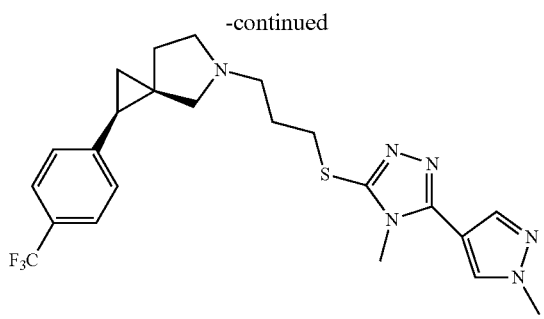

(1R,3S/1S,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, E246, 31 mg) was separated into the single enantiomers by preparative chiral HPLC (SFC).

Preparative Chromatography:

| | |
|---|---|
| Column | Chiralpak AD-H (25 × 2.1 cm), 5µ |
| Modifier | (Methanol + 0.1% isopropylamine) 24% |
| Flow rate (ml/min) | 45 ml/min |
| Pressure (bar) | 120 |
| Temperature (° C.) | 38 |
| DAD detection | 220 nm |
| Loop | 750 µL |
| Injection | 15 mg/injection | affording (1S,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, E247, 9.7 mg). Enantiomer 1: ret. time 5.6 min, 96.2% ee. MS (m/z): 477.0 [MH]+ and (1R,3S)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, E248, 10 mg). Enantiomer 2: ret. time 7.3 min, 100% ee. MS (m/z): 477.0 [MH]+.

Example 249: (1R,3S)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane hydrochloride (CIS, Enantiomer 2, E249)

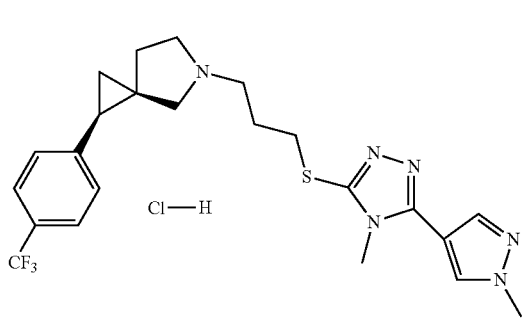 [SMILES: Cn1cc(-c2nnc(SCCCN3CC[C@]4(C[C@@H]4c4ccc(C(F)(F)F)cc4)C3)n2C)cn1 ; Cl]

(1R,3S)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (CIS, E248, 10 mg) was dissolved in Et₂O/DCM and treated with 1.2 eq of HCl 2N in Et₂O affording (1R,3S)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 2, E249, 8.8 mg). MS (m/z): 477.0 [MH]+.

Example 250: (1R,3S/1S,3R)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, E250)

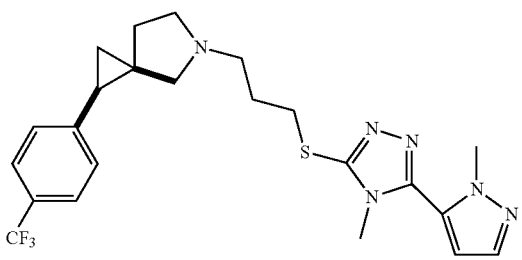

The compound was prepared as in Example 1, reacting (1R,3S/1S,3R)-1-[4-(trifluoromethyl)phenyl]-5-azaspiro[2.4]heptane (CIS, p14, 35 mg, 0.15 mmol), 3-[(3-chloropropyl)sulfanyl]-4-methyl-5-(1-methyl-1H-pyrazol-5-yl)-4H-1,2,4-triazole (p193, 30 mg, 0.15 mmol), Na₂CO₃ (19 mg, 0.18 mmol) and NaI (22 mg, 0.15 mmol) in DMF (0.2 mL) affording (1R,3S/1S,3R)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, E250, 31 mg, y=43%). NMR: ¹H NMR (Acetone-d₆) δ: 7.61 (d, 1H), 7.54 (d, 2H), 7.22 (d, 2H), 6.51 (d, 1H), 4.15 (s, 3H), 3.56-3.60 (m, 3H), 3.25-3.39 (m, 2H), 2.89 (d, 1H), 2.73 (br. s., 1H), 2.62 (br. s., 2H), 2.50 (d, 1H), 2.13-2.25 (m, 2H), 1.91-2.12 (m, 4H), 1.18-1.27 (m, 2H). MS (m/z): 477.4 [MH]+.

Example 251 and 252: (1S,3R)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, Enantiomer 1, E251) and (1R,3S)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, Enantiomer 2, E252)

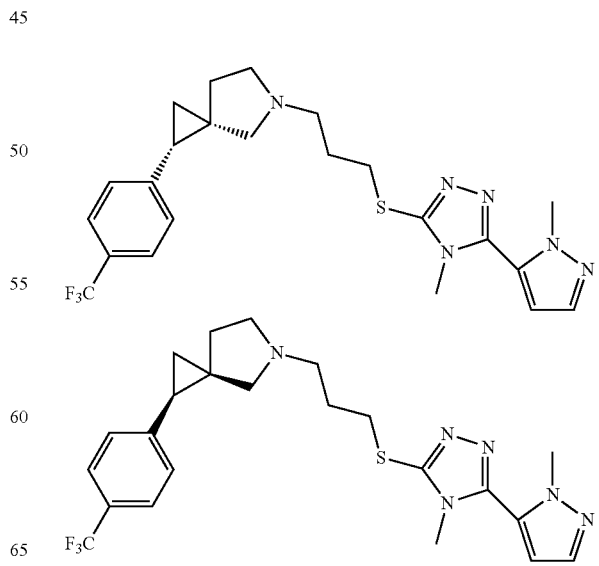

(1R,3S/1S,3R)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, E250, 31 mg) was separated into the single enantiomers by preparative chiral HPLC (SFC).

Preparative Chromatography:

| | |
|---|---|
| Column | Chiralpak AD-H (25 × 2.0 cm), 5μ |
| Modifier | (Methanol + 0.1% isopropylamine) 20% |
| Flow rate (ml/min) | 45 ml/min |
| Pressure (bar) | 120 |
| Temperature (° C.) | 38 |
| DAD detection | 220 nm |
| Loop | 700 μL |
| Injection | 10.2 mg/injection | affording (1S,3R)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, E251, 8.6 mg). Enantiomer 1: ret. time 6.6 min. MS (m/z): 477.4 [MH]+ and (1R,3S)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, E252, 8.6 mg), Enantiomer 2: ret. time 9.0 min. MS (m/z): 477.4 [MH]+.

Example 253: (1R,3S)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane hydrochloride (CIS, Enantiomer 2, E253)

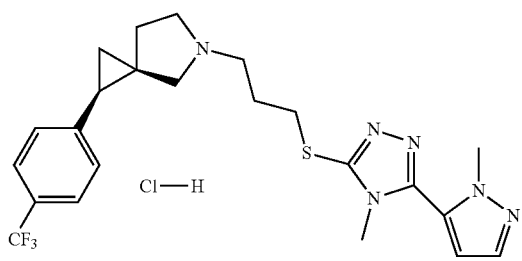

(1R,3S)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane (CIS, E252, 8.6 mg) was dissolved in DCM and treated with 1.1 eq of HCl 2N in Et2O affording (1R,3S)-5-(3-{[4-methyl-5-(1-methyl-1H-pyrazol-5-yl)-4H-1,2,4-triazol-3-yl]sulfanyl}propyl)-1-[4-(trifluoromethyl)phenyl]-5-azaspiro[2.4]heptane hydrochloric salt (CIS, Enantiomer 2, E253, 9 mg). MS (m/z): 477.4 [MH]+.

Example 254: (1R,3S/1S,3R)-5-(3-{[5-(furan-2-yl)-4-methyl-4H-1,2,4-triazol-3-yl]sulfanyl}propyl)-1-[4-(trifluoromethyl)phenyl]-5-azaspiro[2.4]heptane (CIS, E254)

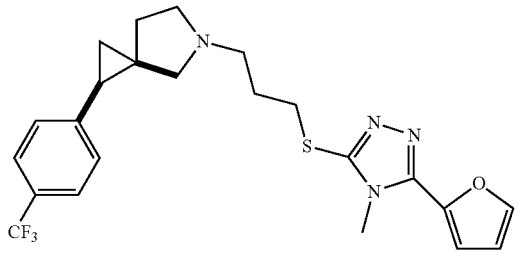

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-5-(furan-2-yl)-4-methyl-4H-1,2,4-triazole (p194, 34 mg, 0.132 mmol), Na2CO3 (15 mg, 0.144 mmol) and NaI (22 mg, 0.144 mmol) in DMF (0.135 mL) affording (1R,3S/1S,3R)-5-(3-{[5-(furan-2-yl)-4-methyl-4H-1,2,4-triazol-3-yl]sulfanyl}propyl)-1-[4-(trifluoromethyl)phenyl]-5-azaspiro[2.4]heptane (CIS, E254, 19.4 mg, y=32%). NMR: 1H NMR (Acetone-d6) δ: 7.80-7.83 (m, 1H), 7.61 (d, 2H), 7.37 (d, 2H), 7.03 (m, 1H), 6.67-6.70 (m, 1H), 3.79 (s, 3H), 3.11-3.28 (m, 2H), 2.70-2.76 (m, 1H), 2.57-2.67 (m, 1H), 2.44-2.56 (m, 3H), 2.20-2.25 (m, 1H), 1.89-2.02 (m, 2H), 1.79-1.87 (m, 2H), 1.46-1.55 (m, 1H), 1.25-1.31 (m, 1H), 1.17-1.24 (m, 1H). MS (m/z): 463.0 [MH]+.

Example 255: (1R,3S/1S,3R)-5-(3-{[5-(furan-3-yl)-4-methyl-4H-1,2,4-triazol-3-yl]sulfanyl}propyl)-1-[4-(trifluoromethyl)phenyl]-5-azaspiro[2.4]heptane (CIS, E255)

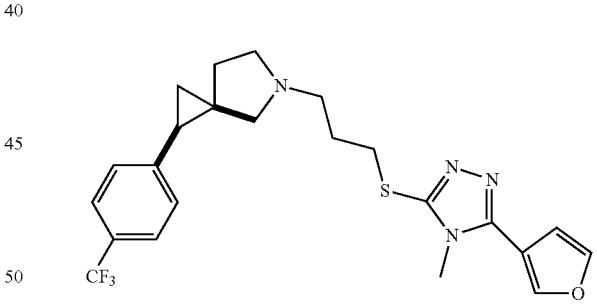

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-5-(furan-3-yl)-4-methyl-4H-1,2,4-triazole (p195, 34 mg, 0.132 mmol), Na2CO3 (15 mg, 0.144 mmol) and NaI (22 mg, 0.144 mmol) in DMF (0.135 mL) affording (1R,3S/1S,3R)-5-(3-{[5-(furan-3-yl)-4-methyl-4H-1,2,4-triazol-3-yl]sulfanyl}propyl)-1-[4-(trifluoromethyl)phenyl]-5-azaspiro[2.4]heptane (CIS, E255, 27 mg, y=45%). NMR: 1H NMR (Acetone-d6) δ: 8.15-8.18 (m, 1H), 7.74-7.78 (m, 1H), 7.61 (d, 2H), 7.37 (d, 2H), 6.94-6.97 (m, 1H), 3.72 (s, 3H), 3.06-3.27 (m, 2H), 2.70-2.76 (m, 2H), 2.56-2.65 (m, 1H), 2.42-2.55 (m, 3H), 2.19-2.24 (m, 1H), 1.92-2.00 (m, 2H), 1.81 (m, 2H), 1.24-1.30 (m, 1H), 1.17-1.24 (m, 1H). MS (m/z): 463.0 [MH]+.

Example 256: (1R,3S/1S,3R)-5-(3-{[4-methyl-5-(thiophen-2-yl)-4H-1,2,4-triazol-3-yl]sulfanyl}propyl)-1-[4-(trifluoromethyl)phenyl]-5-azaspiro[2.4]heptane (CIS, E256)

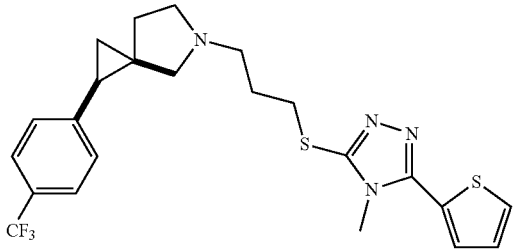

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-4-methyl-5-(thiophen-2-yl)-4H-1,2,4-triazole (p196, 36 mg, 0.132 mmol), Na$_2$CO$_3$ (15 mg, 0.144 mmol) and NaI (22 mg, 0.144 mmol) in DMF (0.135 mL) affording (1R,3S/1S,3R)-5-(3-{[4-methyl-5-(thiophen-2-yl)-4H-1,2,4-triazol-3-yl]sulfanyl}propyl)-1-[4-(trifluoromethyl)phenyl]-5-azaspiro[2.4]heptane (CIS, E256, 29.7 mg, y=50%). NMR: $^1$H NMR (Acetone-d$_6$) δ: 7.66-7.71 (m, 1H), 7.60 (d, 3H), 7.33-7.41 (m, 2H), 7.22-7.27 (m, 1H), 3.79 (s, 3H), 3.10-3.29 (m, 2H), 2.69-2.76 (m, 2H), 2.57-2.65 (m, 1H), 2.43-2.57 (m, 3H), 2.19-2.25 (m, 1H), 1.92-2.03 (m, 2H), 1.77-1.87 (m, 2H), 1.25-1.30 (m, 1H), 1.17-1.23 (m, 1H). MS (m/z): 479.0 [MH]$^+$.

Example 257: (1R,3S/1S,3R)-5-(3-{[4-methyl-5-(thiophen-3-yl)-4H-1,2,4-triazol-3-yl]sulfanyl}propyl)-1-[4-(trifluoromethyl)phenyl]-5-azaspiro[2.4]heptane (CIS, E257)

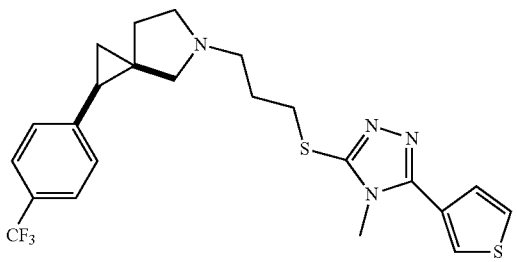

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 3-[(3-chloropropyl)sulfanyl]-4-methyl-5-(thiophen-3-yl)-4H-1,2,4-triazole (p197, 36 mg, 0.132 mmol), Na$_2$CO$_3$ (15 mg, 0.144 mmol) and NaI (22 mg, 0.144 mmol) in DMF (0.135 mL) affording (1R,3S/1S,3R)-5-(3-{[4-methyl-5-(thiophen-3-yl)-4H-1,2,4-triazol-3-yl]sulfanyl}propyl)-1-[4-(trifluoromethyl)phenyl]-5-azaspiro[2.4]heptane (CIS, E257, 27.3 mg, y=45%). NMR: $^1$H NMR (Acetone-d$_6$) δ: 7.95-7.98 (m, 1H), 7.66-7.71 (m, 1H), 7.57-7.64 (m, 3H), 7.37 (d, 2H), 3.76 (s, 3H), 3.10-3.28 (m, 2H), 2.69-2.76 (m, 2H), 2.56-2.65 (m, 1H), 2.42-2.55 (m, 3H), 2.19-2.26 (m, 1H), 1.92-2.02 (m, 2H), 1.77-1.87 (m, 2H), 1.28 (m, 1H), 1.20 (m, 1H). MS (m/z): 479.0 [MH]$^+$.

Example 258: (1R,3S/1S,3R)-5-(3-{[4-methyl-5-(1-methyl-1H-pyrrol-2-yl)-4H-1,2,4-triazol-3-yl]sulfanyl}propyl)-1-[4-(trifluoromethyl)phenyl]-5-azaspiro[2.4]heptane (CIS, E258)

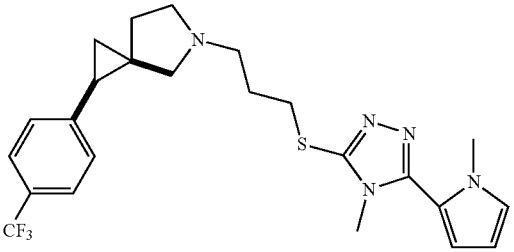

The compound was prepared as in Example 1, reacting (1R,3S/1S,3R)-1-[4-(trifluoromethyl)phenyl]-5-azaspiro[2.4]heptane (CIS, p14, 38 mg, 0.16 mmol), 3-[(3-chloropropyl)sulfanyl]-4-methyl-5-(1-methyl-1H-pyrrol-2-yl)-4H-1,2,4-triazole (p198, 48 mg, 0.176 mmol), Na$_2$CO$_3$ (20 mg, 0.192 mmol) and NaI (29 mg, 0.192 mmol) in DMF (0.17 mL) affording (1R,3S/1S,3R)-5-(3-{[4-methyl-5-(1-methyl-1H-pyrrol-2-yl)-4H-1,2,4-triazol-3-yl]sulfanyl}propyl)-1-[4-(trifluoromethyl)phenyl]-5-azaspiro[2.4]heptane (CIS, E258, 33.2 mg, y=42%). NMR: $^1$H NMR (Acetone-d$_6$) δ: 7.55-7.65 (m, 2H), 7.34-7.40 (m, 2H), 6.91-6.97 (m, 1H), 6.47-6.53 (m, 1H), 6.17-6.23 (m, 1H), 3.84 (s, 3H), 3.62 (s, 3H), 3.11-3.29 (m, 2H), 2.68-2.76 (m, 2H), 2.61 (d, 1H), 2.43-2.57 (m, 3H), 2.20-2.25 (m, 1H), 1.78-2.01 (m, 4H), 1.26-1.31 (m, 1H), 1.17-1.23 (m, 1H). MS (m/z): 476.02 [MH]$^+$.

Preparation 259: (1S,3S/1R,3R)-5-(3-chloropropyl)-1-[4-(trifluoromethyl)phenyl]-5-azaspiro[2.4]heptane (TRANS, p259)

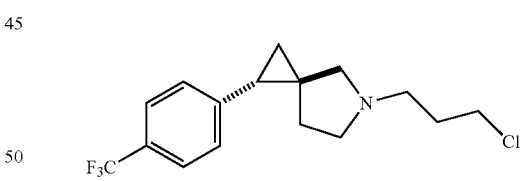

To a solution of (1S,3S/1R,3R)-1-[4-(trifluoromethyl)phenyl]-5-azaspiro[2.4]heptane (TRANS, p13, 100 mg, 0.41 mmol) in THF (0.8 mL), in a vial, DIPEA (0.21 mL, 1.23 mmol) and 1-bromo-3-chloropropane (0.37 mL, 3.73 mmol) were added, the vial was sealed and the resulting mixture was shaken at 65° C. for 3 hrs. After cooling at RT the reaction mixture was diluted with EA and filtered. The filtrate was concentrated under reduced pressure and the crude material was purified by FC on silica gel (eluting with DCM/MeOH from 100/0 to 96/4) affording (1S,3S/1R,3R)-5-(3-chloropropyl)-1-[4-(trifluoromethyl)phenyl]-5-azaspiro[2.4]heptane (p259, TRANS, 75 mg, y=58%) as pale yellow oil. MS (m/z): 318.2 [MH]$^+$.

Example 259: (1S,3S/1R,3R)-5-(3-{[4-methyl-5-(1,2,3-thiadiazol-4-yl)4H-1,2,4-triazol-3-yl]sulfanyl}propyl)-1-[4-(trifluoromethyl)phenyl]-5-azaspiro[2.4]heptane hydrochloride (TRANS, E259)

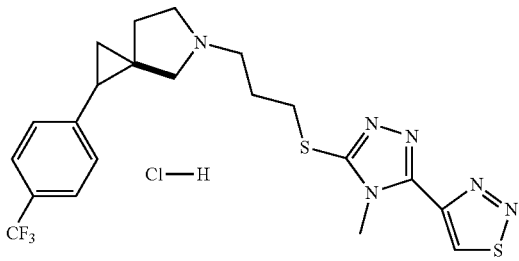 [SMILES: Cn1c(SCCCN2CC[C@]3(CC3c3ccc(C(F)(F)F)cc3)C2)nnc1-c1csnn1 ; Cl]

A sealed vial containing a mixture of (1S,3S/1R,3R)-5-(3-chloropropyl)-1-[4-(trifluoromethyl)phenyl]-5-azaspiro[2.4]heptane (TRANS, p259, 40 mg, 0.13 mmol), 4-methyl-5-(1,2,3-thiadiazol-4-yl)-4H-1,2,4-triazole-3-thiol (p109, 31 mg, 0.16 mmol), Na$_2$CO$_3$ (17 mg, 0.16 mmol) and NaI (15 mg, 0.13 mmol) and DMF (0.2 mL) was shaken O/N at 60° C. in a PLS apparatus. The mixture was diluted with EA, the organic phase was washed with water, dried over sodium sulfate and the solvent removed under reduced pressure. The crude material was purified by FC on silica gel (eluting with DCM/MeOH from 100/0 to 96/6) affording (1S,3S/1R,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane (TRANS, 15 mg).

The latter was dissolved in DCM (0.1 mL) then 2N HCl/ether (1.1 eq) was added and the reaction mixture was concentrated under vacuum. The solid so obtained was triturated with ether and dried under vacuum at 45° C. O/N, affording (1S,3S/1R,3R)-5-(3-{[4-methyl-5-(1-methyl-1H-pyrazol-4-yl)-4H-1,2,4-triazol-3-yl]sulfanyl}propyl)-1-[4-(trifluoromethyl)phenyl]-5-azaspiro[2.4]heptane hydrochloride (TRANS, E259, 15 mg, y=22%). NMR: $^1$H NMR (DMSO-d$_6$) δ:10.58 (br. s., 1H), 9.79 (s, 1H), 7.67 (m, 2H), 7.46 (m, 2H), 3.90 (s, 3H), 3.50-3.70 (m, 4H), 3.16-3.40 (m, 6H), 3.00-3.12 (m, 1H), 2.37-2.48 (m, 1H), 1.80-1.97 (m, 1H), 1.29-1.56 (m, 3H). MS (m/z): 481.4 [MH]$^+$.

Example 260: (1R,3S/1S,3R)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane (CIS, E260)

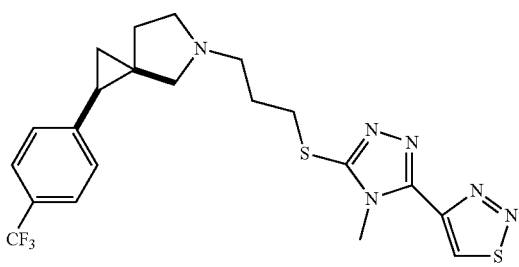

The compound was prepared as in Example 1, reacting (1R,3S/1S,3R)-1-[4-(trifluoromethyl)phenyl]-5-azaspiro[2.4]heptane (CIS, p14, 30 mg, 0.12 mmol), 4-{5-[(3-chloropropyl)sulfanyl]-4-methyl-4H-1,2,4-triazol-3-yl}-1,2,3-thiadiazole (p199, 34 mg, 0.12 mmol), Na$_2$CO$_3$ (15 mg, 0.14 mmol) and NaI (18 mg, 0.12 mmol) in DMF (0.2 mL) affording (1R,3S/1S,3R)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane (CIS, E260, 6 mg, y=9%). NMR: $^1$H NMR (CDCl$_3$) δ: 9.34 (s, 1H), 7.54 (d, 2H), 7.22 (d, 2H), 4.04 (s, 3H), 3.33 (d, 2H), 2.80-2.90 (m, 1H), 2.63-2.74 (m, 1H), 2.58 (br. s., 2H), 2.42-2.49 (m, 1H), 2.16 (d, 2H), 2.01 (br. s., 5H), 1.21 (s, 2H). MS (m/z): 481.4 [MH]$^+$.

Preparation 260: (1R,3S)-5-(3-chloropropyl)-1-[4-(trifluoromethyl)phenyl]-5-azaspiro[2.4]heptane (CIS, Enantiomer 1, p260)

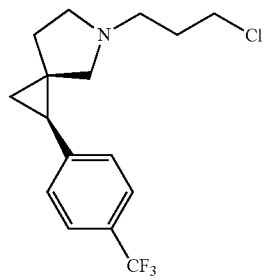 [SMILES: FC(F)(F)c1ccc([C@H]2C[C@]23CCN(CCCCl)C3)cc1]

To a solution of (1R,3S)-1-[4-(trifluoromethyl)phenyl]-5-azaspiro[2.4]heptane (CIS, Enantiomer 1, p15, 48 mg, 0.2 mmol) in THF (0.4 mL), in a vial, DIPEA (0.10 mL, 0.6 mmol) and 1-bromo-3-chloropropane (0.18 mL, 1.79 mmol) were added, the vial was sealed and the resulting mixture was shaken at 65° C. for 3 hrs. After cooling at RT the reaction mixture was diluted with EA and filtered. The filtrate was concentrated under reduced pressure and the crude material was purified by FC on silica gel (eluting with DCM/MeOH from 100/0 to 97/3) affording (1R,3S)-5-(3-chloropropyl)-1-[4-(trifluoromethyl)phenyl]-5-azaspiro[2.4]heptane (CIS, Enantiomer 1, p260, 40 mg, y=62%) as pale yellow oil. MS (m/z): 318.2 [MH]$^+$.

Example 261: (1R,3S)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E261)

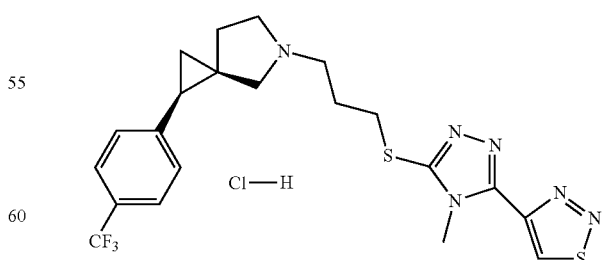

A sealed vial containing a mixture of (1R,3S)-5-(3-chloropropyl)-1-[4-(trifluoromethyl)phenyl]-5-azaspiro[2.4]heptane (CIS, Enantiomer 1, p260, 30 mg, 0.13 mmol), 4-methyl-5-(1,2,3-thiadiazol-4-yl)-4H-1,2,4-triazole-3-thiol (p109, 28 mg, 0.14 mmol), Na$_2$CO$_3$ (17 mg, 0.16 mmol) and NaI (15 mg, 0.13 mmol) and DMF (0.2 mL) was shaken O/N at 60° C. in a PLS apparatus. The mixture was diluted with EA, the organic phase was washed with water, dried over sodium sulfate and the solvent removed under reduced pressure. The crude material was purified by FC on silica gel (eluting with DCM/MeOH from 100/0 to 94/6) then purified again by FC on NH column (eluting with Cy/EA from 100/0 to 30/70) to give (1R,3S)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane (18 mg).

The latter was dissolved in DCM (0.2 mL) then 2N HCl/ether (1.1 eq) was added and the reaction mixture was concentrated under vacuum. The solid so obtained was triturated with ether and dried under vacuum at 45° C. O/N, affording (1R,3S)-5-(3-{[4-methyl-5-(1,2,3-thiadiazol-4-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E261, 19 mg, y=28%). as pale yellow solid. NMR: $^1$H NMR (DMSO-d$_6$) δ: 10.37-10.66 (m, 1H), 9.78 (d, 1H), 7.61-7.71 (m, 2H), 7.39-7.48 (m, 2H), 3.87 (d, 3H), 3.65-3.76 (m, 1H), 3.39-3.47 (m, 1H), 2.94-3.32 (m, 6H), 2.62-2.71 (m, 1H), 2.19-2.44 (m, 2H), 1.94-2.15 (m, 3H), 1.27-1.52 (m, 2H). MS (m/z): 481.3 [MH]$^+$.

Example 262: (1R,3S)-5-(3-{[4-methyl-5-(4-methyl-1,2,3-thiadiazol-5-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E262)

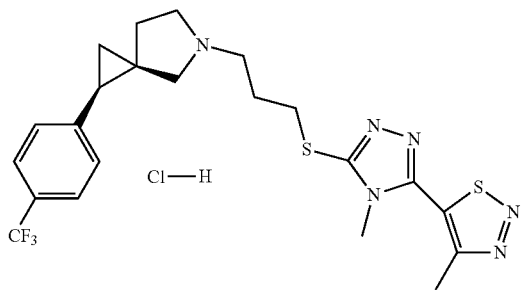 [SMILES: Cc1nnsc1-c1nnc(SCCCN2CC[C@]3(C[C@@H]3c3ccc(C(F)(F)F)cc3)C2)n1C ; Cl]

The compound was prepared as in Example 1, reacting (1R,3S)-1-[4-(trifluoromethyl)phenyl]-5-azaspiro[2.4]heptane (CIS, Enantiomer 1, p15, 30 mg, 0.12 mmol), 5-{5-[(3-chloropropyl)sulfanyl]-4-methyl-4H-1,2,4-triazol-3-yl)}-4-methyl-1,2,3-thiadiazole (p200, 34 mg, 0.12 mmol), Na$_2$CO$_3$ (15 mg, 0.14 mmol) and NaI (18 mg, 0.12 mmol) in DMF (0.2 mL) affording (1R,3S)-5-(3-{[4-methyl-5-(4-methyl-1,2,3-thiadiazol-5-yl)-4H-1,2,4-triazol-3-yl]sulfanyl}propyl)-1-[4-(trifluoromethyl)phenyl]-5-azaspiro[2.4]heptane (29 mg).

The latter was dissolved in DCM (0.2 mL) then 2N HCl/ether (1.1 eq) was added and the reaction mixture was concentrated under vacuum. The solid so obtained was triturated with ether and dried under vacuum at 45° C. O/N, affording (1R,3S)-5-(3-{[4-methyl-5-(4-methyl-1,2,3-thiadiazol-5-yl)-4H-1,2,4-triazol-3-yl]sulfanyl}propyl)-1-[4-(trifluoromethyl)phenyl]-5-azaspiro[2.4]heptane hydrochloride (CIS, Enantiomer 1, E262, 31 mg, y=49%). NMR: $^1$H NMR (DMSO-d$_6$) δ: 10.39-10.67 (m, 1H), 7.66 (d, 2H), 7.44 (d, 2H), 3.69 (br. s., 1H), 3.51-3.59 (m, 3H), 3.37-3.47 (m, 1H), 2.93-3.29 (m, 5H), 2.80 (s, 3H), 2.61-2.72 (m, 1H), 2.19-2.45 (m, 2H), 1.93-2.15 (m, 3H), 1.27-1.52 (m, 2H). MS (m/z): 495.3 [MH]$^+$.

Example 263: (1R,3S)-5-[3-({4-methyl-5-[2-(pyridin-3-yl)-1,3-oxazol-5-yl]-4H-1,2,4-triazol-3-yl}sulfanyl)propyl]-1-[4-(trifluoromethyl)phenyl]-5-azaspiro[2.4]heptane (CIS, Enantiomer 1, E263)

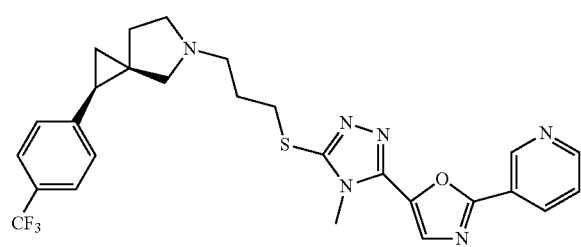 [SMILES: Cn1c(SCCCN2CC[C@]3(C[C@@H]3c3ccc(C(F)(F)F)cc3)C2)nnc1-c1cnc(-c2cccnc2)o1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol), 3-(4-{5-[(3-chloropropyl)sulfanyl]-4-methyl-4H-1,2,4-triazol-3-yl}-1,3-oxazol-2-yl)pyridine (p201, 34 mg, 0.1 mmol), Na$_2$CO$_3$ (12 mg, 0.115 mmol) and NaI (17 mg, 0.115 mmol) in DMF (0.2 mL) affording (1R,3S)-5-[3-({4-methyl-5-[2-(pyridin-3-yl)-1,3-oxazol-5-yl]-4H-1,2,4-triazol-3-yl}sulfanyl)propyl]-1-[4-(trifluoromethyl)phenyl]-5-azaspiro[2.4]heptane (CIS, Enantiomer 1, E263, 34.2 mg, y=66%). NMR: $^1$H NMR (Acetone-d$_6$) δ: 9.29-9.36 (m, 1H), 8.77-8.80 (m, 1H), 8.67-8.69 (m, 1H), 8.44-8.49 (m, 1H), 7.60-7.67 (m, 3H), 7.37-7.45 (m, 2H), 3.97 (s, 3H), 3.20-3.35 (m, 2H), 2.61-2.98 (m, 5H), 2.27-2.34 (m, 1H), 2.09-2.15 (m, 1H), 1.89-2.03 (m, 4H), 1.33-1.40 (m, 1H), 1.23-1.29 (m, 1H). MS (m/z): 541.4 [MH]$^+$.

Example 264: (1R,3S)-5-(3-{[4-methyl-5-(6-phenoxypyridin-3-yl)-4H-1,2,4-triazol-3-yl]sulfanyl}propyl)-1-[4-(trifluoromethyl)phenyl]-5-azaspiro[2.4]heptane (CIS, Enantiomer 1, E264)

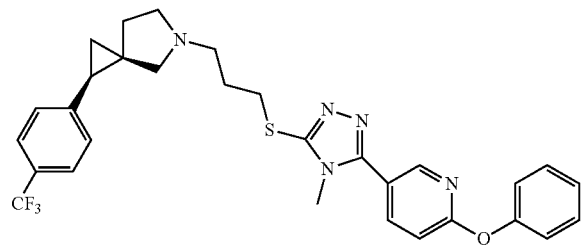 [SMILES: Cn1c(SCCCN2CC[C@]3(C[C@@H]3c3ccc(C(F)(F)F)cc3)C2)nnc1-c1ccc(Oc2ccccc2)nc1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol), 5-{5-[(3-chloropropyl)sulfanyl]-4-methyl-4H-1,2,4-triazol-3-yl}-2-phenoxypyridine (p202, 37 mg, 0.1 mmol), Na$_2$CO$_3$ (12 mg, 0.115 mmol) and NaI (17 mg, 0.115 mmol) in DMF (0.2 mL) affording (1R,3S)-5-(3-{[4-methyl-5-(6-phenoxypyridin-3-yl)-4H-1,2,4-triazol-3-yl]sulfanyl}propyl)-1-[4-(trifluoromethyl)phenyl]-5-azaspiro[2.4]heptane (CIS, Enantiomer 1, E264, 27 mg, y=49%). NMR: $^1$HNMR (Acetone-d$_6$) δ: 8.45-8.50 (m, 1H), 8.16-8.22 (m, 1H), 7.60-7.66

(m, 2H), 7.44-7.52 (m, 2H), 7.34-7.42 (m, 2H), 7.20-7.32 (m, 3H), 7.14-7.20 (m, 1H), 3.70 (s, 3H), 3.11-3.32 (m, 2H), 2.71-2.77 (m, 1H), 2.59-2.66 (m, 1H), 2.44-2.58 (m, 3H), 2.20-2.27 (m, 2H), 1.79-2.02 (m, 4H), 1.26-1.33 (m, 1H), 1.21 (m, 1H). MS (m/z): 566.4 [MH]+.

Example 265: (1R,3S)-5-(3-{[4-methyl-5-(6-phenoxypyridin-3-yl)-4H-1,2,4-triazol-3-yl] sulfanyl}propyl)-1-[4-(trifluoromethyl)phenyl]-5-azaspiro[2.4]heptane dihydrochloride (CIS, Enantiomer 1, E265)

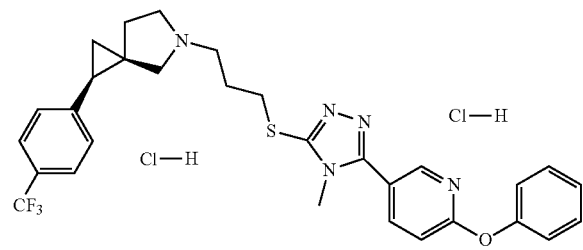 [SMILES: Cn1c(SCCCN2CC[C@]3(C[C@@H]3c3ccc(C(F)(F)F)cc3)C2)nnc1-c1ccc(Oc2ccccc2)nc1 ; Cl ; Cl]

(1R,3S)-5-(3-{[4-methyl-5-(6-phenoxypyridin-3-yl)-4H-1,2,4-triazol-3-yl]sulfanyl}propyl)-1-[4-(trifluoromethyl) phenyl]-5-azaspiro[2.4]heptane (CIS, Enantiomer 1, E264, 27 mg) was dissolved in MeOH and treated with 2.2 eq of HCl 1N in Et₂O affording (1R,3S)-5-(3-{[4-methyl-5-(6-phenoxypyridin-3-yl)-4H-1,2,4-triazol-3-yl] sulfanyl}propyl)-1-[4-(trifluoromethyl)phenyl]-5-azaspiro[2.4]heptane dihydrochloric salt (CIS, Enantiomer 1, E265, 30.3 mg). MS (m/z): 566.4 [MH]+.

Example 266: (1R,3S)-5-{3-[(4-methyl-5-{[1,2,4] triazolo[4,3-a]pyridin-8-yl}-4H-1,2,4-triazol-3-yl) sulfanyl]propyl}-1-[4-(trifluoromethyl)phenyl]-5-azaspiro[2.4]heptane (CIS, Enantiomer 1, E266)

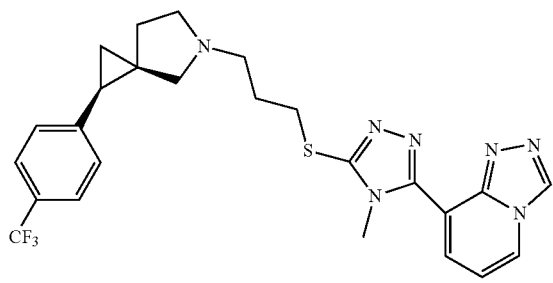 [SMILES: Cn1c(SCCCN2CC[C@]3(C[C@@H]3c3ccc(C(F)(F)F)cc3)C2)nnc1-c1cccn2cnnc12]

The compound was prepared as in Example 1, reacting (1R,3S)-1-[4-(trifluoromethyl)phenyl]-5-azaspiro[2.4]heptane (CIS, Enantiomer 1, p15, 20 mg, 0.083 mmol), 3-[(3-chloropropyl)sulfanyl]-4-methyl-5-{[1,2,4]triazolo[4,3-a] pyridin-8-yl}-4H-1,2,4-triazole (p203, 28 mg, 0.091 mmol), Na₂CO₃ (11 mg, 0.1 mmol) and NaI (15 mg, 0.1 mmol) in DMF (0.1 mL) affording (1R,3S)-5-{3-[(4-methyl-5-{[1,2, 4]triazolo[4,3-a]pyridin-8-yl}-4H-1,2,4-triazol-3-yl)sulfanyl]propyl}-1-[4-(trifluoromethyl)phenyl]-5-azaspiro[2.4] heptane (CIS, Enantiomer 1, E266, 18.7 mg, y=44%). NMR: ¹H NMR (Acetone-d₆) δ: 9.27-9.30 (m, 1H), 8.77-8.80 (m, 1H), 7.70-7.73 (m, 1H), 7.62 (d, 2H), 7.41 (d, 2H), 7.19 (t, 1H), 3.68-3.71 (m, 3H), 3.30 (m, 2H), 2.52-2.76 (m, 5H), 2.13-2.32 (m, 2H), 1.88-2.04 (m, 4H), 1.30-1.36 (m, 1H), 1.24 (m, 1H). MS (m/z): 514.3 [MH]+.

Example 267: (1R,3S)-5-{3-[(4-methyl-5-{[1,2,4] triazolo[4,3-a]pyridin-8-yl}-4H-1,2,4-triazol-3-yl) sulfanyl]propyl}-1-[4-(trifluoromethyl)phenyl]-5-azaspiro[2.4]heptane hydrochloride (CIS, Enantiomer 1, E267)

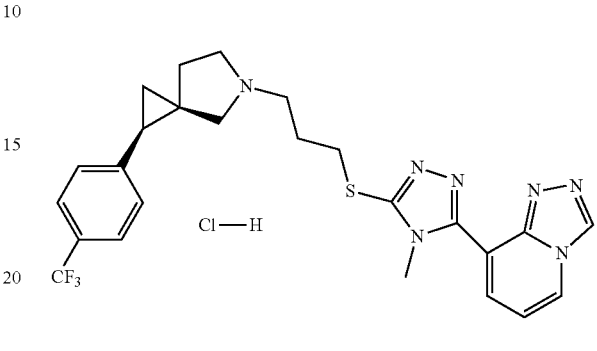

(1R,3S)-5-{3-[(4-methyl-5-{[1,2,4]triazolo[4,3-a]pyridin-8-yl}-4H-1,2,4-triazol-3-yl)sulfanyl]propyl}-1-[4-(trifluoromethyl)phenyl]-5-azaspiro[2.4]heptane (CIS, Enantiomer 1, E266, 18.7 mg) was dissolved in DCM and treated with 1.1 eq of HCl 2N in Et₂O affording (1R,3S)-5-{3-[(4-methyl-5-{[1,2,4]triazolo[4,3-a]pyridin-8-yl)}-4H-1,2,4-triazol-3-yl)sulfanyl]propyl}-1-[4-(trifluoromethyl)phenyl]-5-azaspiro[2.4]heptane hydrochloric salt (CIS, Enantiomer 1, E267, 17 mg). MS (m/z): 514.3 [MH]+.

Example 268: (1R,3S)-5-{3-[(4-methyl-5-{[1,2,4] triazolo[4,3-a]pyridin-6-yl}-4H-1,2,4-triazol-3-yl) sulfanyl]propyl}-1-[4-(trifluoromethyl)phenyl]-5-azaspiro[2.4]heptane hydrochloride (CIS, Enantiomer 1, E268)

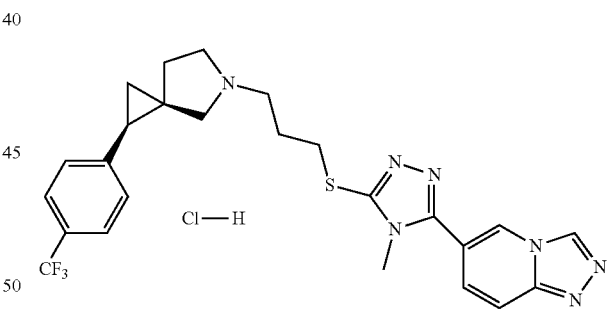

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 3-[(3-chloropropyl)sulfanyl]-4-methyl-5-{[1,2,4]triazolo[4,3-a] pyridin-6-yl}-4H-1,2,4-triazole (p204, 35 mg, 0.113 mmol), Na₂CO₃ (13 mg, 0.123 mmol) and NaI (18 mg, 0.123 mmol) in DMF (0.1 mL) affording (1R,3S)-5-{3-[(4-methyl-5-{[1, 2,4]triazolo[4,3-a]pyridin-6-yl}-4H-1,2,4-triazol-3-yl)sulfanyl]propyl}-1-[4-(trifluoromethyl)phenyl]-5-azaspiro[2.4] heptane (6.5 mg).

The latter was dissolved in DCM and treated with 1.1 eq of HCl 2M in Et₂O, then concentrated under reduced pressure, triturated with Et₂O and dried under high vacuum affording (1R,3S)-5-{3-[(4-methyl-5-{[1,2,4]triazolo[4,3-a] pyridin-6-yl}-4H-1,2,4-triazol-3-yl)sulfanyl]propyl}-1-[4-

(trifluoromethyl)phenyl]-5-azaspiro[2.4]heptane hydrochloride (CIS, Enantiomer 1, E268, 5.5 mg, y=10%). NMR: ¹H NMR (DMSO-d₆) δ:10.39-10.67 (m, 1H), 9.40 (s, 1H), 9.07 (s, 1H), 7.98 (d, 1H), 7.75 (d, 1H), 7.67 (d, 2H), 7.46 (d, 2H), 3.65-3.77 (m, 4H), 2.94-3.48 (m, 7H), 1.95-2.46 (m, 5H), 1.28-1.54 (m, 2H). MS (m/z): 514.3 [MH]⁺.

Example 269: (1R,3S)-5-{3-[(4-methyl-5-{[1,2,4] triazolo[4,3-a]pyridin-7-yl}-4H-1,2,4-triazol-3-yl) sulfanyl]propyl}-1-[4-(trifluoromethyl)phenyl]-5-azaspiro[2.4]heptane (CIS, Enantiomer 1, E269)

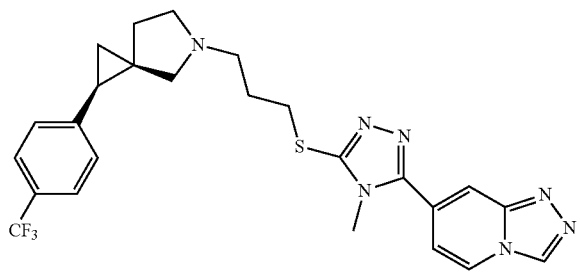 [SMILES: Cn1c(SCCCN2CC[C@]3(C[C@@H]3c3ccc(C(F)(F)F)cc3)C2)nnc1-c1ccn2cnnc2c1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 3-[(3-chloropropyl)sulfanyl]-4-methyl-5-{[1,2,4]triazolo[4,3-a] pyridin-7-yl}-4H-1,2,4-triazole (p205, 34 mg, 0.11 mmol), Na₂CO₃ (13 mg, 0.12 mmol) and NaI (18 mg, 0.12 mmol) in DMF (0.113 mL) affording (1R,3S)-5-{3-[(4-methyl-5-{ [1,2,4]triazolo[4,3-a]pyridin-7-yl}-4H-1,2,4-triazol-3-yl) sulfanyl]propyl}-1-[4-(trifluoromethyl)phenyl]-5-azaspiro [2.4]heptane (CIS, Enantiomer 1, E269, 25.4 mg, y=49%). NMR: ¹H NMR (Acetone-d₆) δ: 9.16-9.25 (m, 1H), 8.67-8.72 (m, 1H), 8.07-8.12 (m, 1H), 7.60-7.66 (m, 2H), 7.42-7.48 (m, 1H), 7.36-7.42 (m, 2H), 3.90 (s, 3H), 3.21-3.37 (m, 2H), 2.72-2.76 (m, 1H), 2.61-2.68 (m, 1H), 2.46-2.58 (m, 3H), 2.21-2.28 (m, 1H), 2.10-2.13 (m, 1H), 1.94-2.05 (m, 2H), 1.83-1.94 (m, 2H), 1.27-1.32 (m, 1H), 1.22 (m, 1H). MS (m/z): 514.3 [MH]⁺.

Example 270: (1S,3S)-1-[2-fluoro-4-(trifluoromethyl)phenyl]-5-{3-[(4-methyl-5-{[1,2,4]triazolo[4, 3-a]pyridin-7-yl}-4H-1,2,4-triazol-3-yl)sulfanyl] propyl}-5-azaspiro[2.4]heptane (CIS, Enantiomer 1, E270)

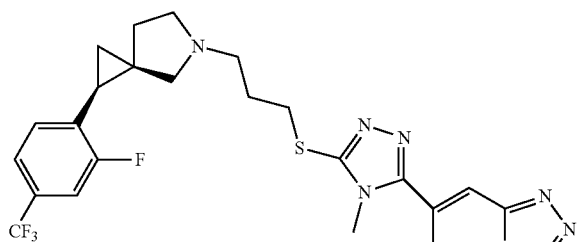

The compound was prepared as in Example 1, reacting (1S,3S)-1-[2-fluoro-4-(trifluoromethyl)phenyl]-5-azaspiro [2.4]heptane (CIS, Enantiomer 1, p24, 26 mg, 0.1 mmol), 3-[(3-chloropropyl)sulfanyl]-4-methyl-5-{[1,2,4]triazolo[4, 3-a]pyridin-7-yl}-4H-1,2,4-triazole (p205, 34 mg, 0.11 mmol), Na₂CO₃ (13 mg, 0.12 mmol) and NaI (18 mg, 0.12 mmol) in DMF (0.113 mL) affording (1S,3S)-1-[2-fluoro-4-(trifluoromethyl)phenyl]-5-{3-[(4-methyl-5-{[1,2,4]triazolo[4,3-a]pyridin-7-yl}-4H-1,2,4-triazol-3-yl)sulfanyl] propyl}-5-azaspiro[2.4]heptane (CIS, Enantiomer 1, E270, 24 mg, y=45%). NMR: ¹H NMR (DMSO-d₆) δ: 9.38 (s, 1H), 8.68-8.74 (m, 1H), 8.15-8.20 (m, 1H), 7.60-7.66 (m, 1H), 7.47-7.53 (m, 1H), 7.34-7.39 (m, 1H), 7.27-7.34 (m, 1H), 3.73 (s, 3H), 3.17 (m, 2H), 2.75 (d, 1H), 2.36-2.48 (m, 4H), 2.23 (s, 1H), 1.91-1.98 (m, 2H), 1.87 (d, 1H), 1.71-1.82 (m, 2H), 1.37 (m, 1H), 1.21 (m, 1H). MS (m/z): 532.3 [MH]⁺.

Example 271: (1R,3S)-5-{3-[(4-methyl-5-{3-methyl-[1,2,4]triazolo[4,3-a]pyridin-6-yl}-4H-1,2,4-triazol-3-yl)sulfanyl]propyl}-1-[4-(trifluoromethyl) phenyl]-5-azaspiro[2.4]heptane (CIS, Enantiomer 1, E271)

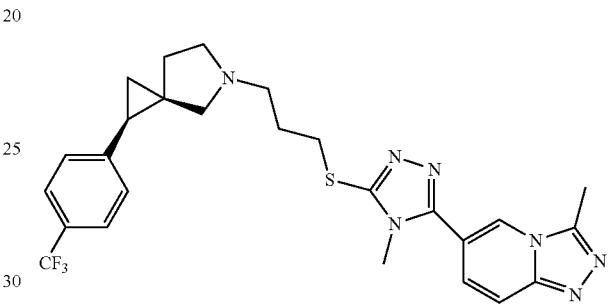

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol), 3-[(3-chloropropyl)sulfanyl]-4-methyl-5-{3-methyl-[1,2,4]triazolo[4,3-a]pyridin-6-yl}-4H-1,2,4-triazole (p206, 32 mg, 0.1 mmol), Na₂CO₃ (13 mg, 0.115 mmol) and NaI (17 mg, 0.115 mmol) in DMF (0.2 mL) affording (1R,3S)-5-{3-[(4-methyl-5-{3-methyl-[1,2,4]triazolo[4,3-a]pyridin-6-yl}-4H-1,2,4-triazol-3-yl)sulfanyl]propyl}-1-[4-(trifluoromethyl) phenyl]-5-azaspiro[2.4]heptane (CIS, Enantiomer 1, E271, 29.7 mg, y=58%). NMR: ¹H NMR (Acetone-d₆) δ: 8.53-8.63 (m, 1H), 7.76-7.85 (m, 1H), 7.63 (s, 3H), 7.36-7.44 (m, 2H), 3.77 (s, 3H), 3.16-3.35 (m, 2H), 2.81 (s, 3H), 2.72-2.77 (m, 1H), 2.59-2.68 (m, 1H), 2.46-2.56 (m, 3H), 2.21-2.28 (m, 2H), 1.83-2.03 (m, 4H), 1.27-1.32 (m, 1H), 1.19-1.25 (m, 1H). MS (m/z): 528.4 [MH]⁺.

Example 272: (1R,3S)-5-{3-[(5-{1H-imidazo[4,5-b] pyridin-5-yl)}-4-methyl-4H-1,2,4-triazol-3-yl)sulfanyl]propyl}-1-[4-(trifluoromethyl)phenyl]-5-azaspiro[2.4]heptane (CIS, Enantiomer 1, E272)

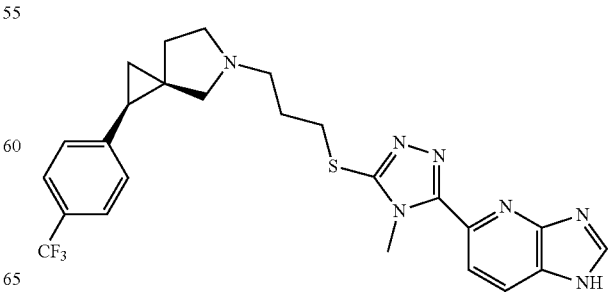

The compound was prepared as in Example 1, reacting (1R,3S)-1-[4-(trifluoromethyl)phenyl]-5-azaspiro[2.4]heptane (CIS, Enantiomer 1, p15, 34 mg, 0.14 mmol), 3-[(3-chloropropyl)sulfanyl]-5-{1H-imidazo[4,5-b]pyridin-5-yl}-4-methyl-4H-1,2,4-triazole (p207, 22 mg, 0.071 mmol), Na₂CO₃ (9 mg, 0.009 mmol) and NaI (10 mg, 0.007 mmol) in DMF (0.2 mL) affording (1R,3S)-5-{3-[(5-{1H-imidazo[4,5-b]pyridin-5-yl}-4-methyl-4H-1,2,4-triazol-3-yl)sulfanyl]propyl}-1-[4-(trifluoromethyl)phenyl]-5-azaspiro[2.4]heptane (CIS, Enantiomer 1, E272, 16 mg, y=44%). NMR: $^1$H NMR (DMSO-d₆) δ: 13.01-13.19 (m, 1H), 8.57 (s, 1H), 8.15-8.21 (m, 1H), 8.05 (s, 1H), 7.57-7.63 (m, 2H), 7.29-7.34 (m, 2H), 3.94-4.01 (m, 3H), 3.08-3.22 (m, 2H), 2.66-2.76 (m, 1H), 2.36-2.50 (m, 4H), 2.21 (m, 1H), 1.82-1.98 (m, 3H), 1.72-1.81 (m, 2H), 1.23-1.29 (m, 1H), 1.15-1.20 (m, 1H). MS (m/z): 514.4 [MH]⁺.

Example 273: (1R,3S)-5-[3-({4-methyl-5-[4-(1H-1,2,3,4-tetrazol-5-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E273)

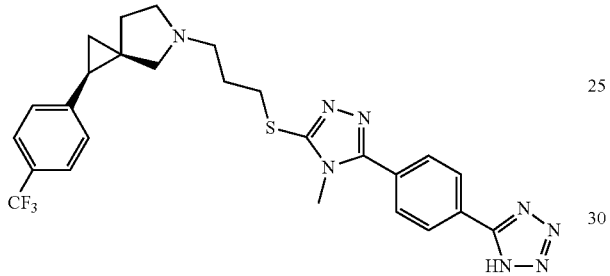

The compound was prepared as in Example 1, reacting (1R,3S)-1-[4-(trifluoromethyl)phenyl]-5-azaspiro[2.4]heptane (CIS, Enantiomer 1, p15, 27 mg, 0.11 mmol), 5-(4-{5-[(3-chloropropyl)sulfanyl]-4-methyl-4H-1,2,4-triazol-3-yl}phenyl)-1H-1,2,3,4-tetrazole (p208, 34 mg, 0.10 mmol), Na₂CO₃ (13 mg, 0.12 mmol) and NaI (15 mg, 0.1 mmol) in DMF (0.2 mL) affording (1R,3S)-5-[3-({4-methyl-5-[4-(1H-1,2,3,4-tetrazol-5-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E273, 9.7 mg, y=16%). NMR: $^1$H NMR (DMSO-d₆) δ: 8.14 (d, 2H), 7.73 (d, 2H), 7.60-7.66 (m, 2H), 7.33-7.38 (m, 2H), 3.63 (s, 3H), 3.09-3.19 (m, 2H), 2.88-3.01 (m, 1H), 2.56-2.85 (m, 4H), 2.28 (m, 1H), 2.19 (br. s., 1H), 2.00-2.07 (m, 1H), 1.89-1.98 (m, 1H), 1.78-1.87 (m, 2H), 1.30-1.36 (m, 1H), 1.19-1.25 (m, 1H). MS (m/z): 541.4 [MH]⁺.

Example 274: (1R,3S)-5-[3-({4-methyl-5-[4-(1,3,4-oxadiazol-2-yl)phenyl]-4H-1,2,4-triazol-3-yl}sulfanyl)propyl]-1-[4-(trifluoromethyl)phenyl]-5-azaspiro[2.4]heptane hydrochloride (CIS, Enantiomer 1, E274)

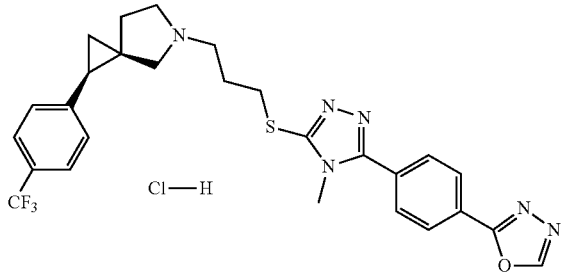 [SMILES: Cn1c(SCCCN2CC[C@]3(C[C@@H]3c3ccc(C(F)(F)F)cc3)C2)nnc1-c1ccc(-c2nnco2)cc1 ; Cl]

The compound was prepared as in Example 1, reacting (1R,3S)-1-[4-(trifluoromethyl)phenyl]-5-azaspiro[2.4]heptane (CIS, Enantiomer 1, p15, 30 mg, 0.12 mmol), 2-(4-{5-[(3-chloropropyl)sulfanyl]-4-methyl-4H-1,2,4-triazol-3-yl}phenyl)-1,3,4-oxadiazole (p209, 47 mg, 0.14 mmol), Na₂CO₃ (15 mg, 0.14 mmol) and NaI (18 mg, 0.12 mmol) in DMF (0.2 mL) affording (1R,3S)-5-[3-({4-methyl-5-[4-(1,3,4-oxadiazol-2-yl)phenyl]-4H-1,2,4-triazol-3-yl}sulfanyl)propyl]-1-[4-(trifluoromethyl)phenyl]-5-azaspiro[2.4]heptane (15 mg).

The latter was dissolved in DCM (0.2 mL) then 2N HCl/ether (1.1 eq) was added and the reaction mixture was concentrated under vacuum. The solid so obtained was triturated with ether and dried under vacuum at 45° C. O/N affording (1R,3S)-5-[3-({4-methyl-5-[4-(1,3,4-oxadiazol-2-yl)phenyl]-4H-1,2,4-triazol-3-yl}sulfanyl)propyl]-1-[4-(trifluoromethyl)phenyl]-5-azaspiro[2.4]heptane hydrochloride (CIS, Enantiomer 1, E274, 15 mg, y=22%). NMR: $^1$H NMR (DMSO-d₆) δ: 10.41-10.75 (m, 1H), 9.44 (s, 1H), 8.16-8.26 (m, 2H), 7.93-8.02 (m, 2H), 7.61-7.71 (m, 2H), 7.38-7.50 (m, 2H), 3.63-3.77 (m, 4H), 2.92-3.51 (m, 7H), 1.94-2.70 (m, 5H), 1.26-1.53 (m, 2H). MS (m/z): 541.4 [MH]⁺.

Example 275: (1R,3S)-5-[3-({4-methyl-5-[4-(5-methyl-1,2,4-oxadiazol-3-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E275)

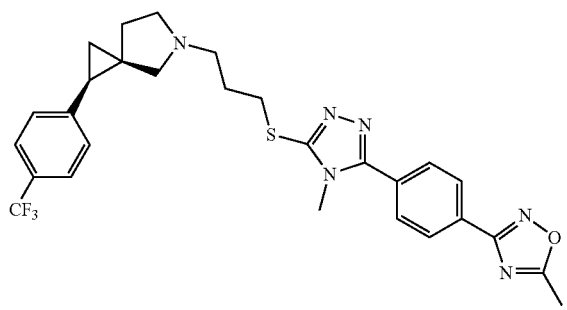 [SMILES: Cc1nc(-c2ccc(-c3nnc(SCCCN4CC[C@]5(C[C@@H]5c5ccc(C(F)(F)F)cc5)C4)n3C)cc2)no1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 3-(4-{5-[(3-chloropropyl)sulfanyl]-4-methyl-4H-1,2,4-triazol-3-yl}phenyl)-5-methyl-1,2,4-oxadiazole (p210, 39 mg, 0.11 mmol), Na₂CO₃ (13 mg, 0.12 mmol) and NaI (18 mg, 0.12 mmol) in DMF (0.2 mL) affording (1R,3S)-5-[3-({4-methyl-5-[4-(5-methyl-1,2,4-oxadiazol-3-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E275, 33 mg, y=60%). NMR: $^1$H NMR (Acetone-d₆) δ: 8.24 (d, 2H), 7.97 (d, 2H), 7.63 (d, 2H), 7.40 (d, 2H), 3.77 (s, 3H), 3.17-3.34 (m, 2H), 2.72 (s, 3H), 2.60-2.70 (m, 1H), 2.48-2.60 (m, 3H), 2.23 (s, 1H), 2.11 (br. s., 1H), 1.95-2.03 (m, 2H), 1.84-1.95 (m, 3H), 1.30 (m, 1H), 1.23 (m, 1H). MS (m/z): 555.4 [MH]⁺.

Example 276: (1R,3S)-5-[3-({4-methyl-5-[4-(4H-1,2,4-triazol-4-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E276)

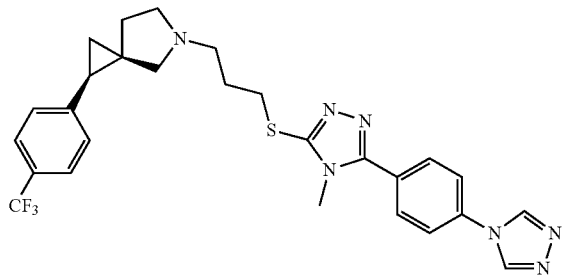 [SMILES: Cn1c(SCCCN2CC[C@]3(C[C@@H]3c3ccc(C(F)(F)F)cc3)C2)nnc1-c1ccc(-n2cnnc2)cc1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 3-[(3-chloropropyl)sulfanyl]-4-methyl-5-[4-(4H-1,2,4-triazol-4-yl)phenyl]-4H-1,2,4-triazole (p211, 37 mg, 0.11 mmol), Na$_2$CO$_3$ (13 mg, 0.12 mmol) and NaI (18 mg, 0.12 mmol) in DMF (0.2 mL) affording (1R,3S)-5-[3-({4-methyl-5-[4-(4H-1,2,4-triazol-4-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E276, 36 mg, y=67%). NMR: $^1$H NMR (Acetone-d$_6$) δ: 8.96 (s, 2H), 7.95-8.01 (m, 2H), 7.87-7.94 (m, 2H), 7.58-7.64 (m, 2H), 7.35-7.41 (m, 2H), 3.74 (s, 3H), 3.16-3.34 (m, 2H), 2.70-2.76 (m, 1H), 2.59-2.66 (m, 1H), 2.42-2.57 (m, 3H), 2.19-2.26 (m, 1H), 2.07-2.11 (m, 1H), 1.80-2.03 (m, 4H), 1.26-1.31 (m, 1H), 1.21 (m, 1H). MS (m/z): 540.4 [MH]$^+$.

Example 277: (1R,3S)-5-[3-({4-methyl-5-[4-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E277)

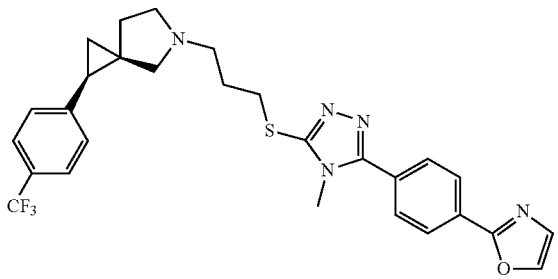 [SMILES: Cn1c(SCCCN2CC[C@]3(C[C@@H]3c3ccc(C(F)(F)F)cc3)C2)nnc1-c1ccc(-c2ncco2)cc1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.096 mmol), 3-[(3-chloropropyl)sulfanyl]-4-methyl-5-[4-(1,3-oxazol-2-yl)phenyl]-4H-1,2,4-triazole (p212, 35 mg, 0.1 mmol), Na$_2$CO$_3$ (12 mg, 0.115 mmol) and NaI (17 mg, 0.115 mmol) in DMF (0.15 mL) affording (1R,3S)-5-[3-({4-methyl-5-[4-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E277, 31 mg, y=60%). NMR: $^1$H NMR (Acetone-d$_6$) δ: 8.19-8.25 (m, 2H), 8.11 (d, 1H), 7.92-7.97 (m, 2H), 7.62 (d, 2H), 7.37-7.44 (m, 3H), 3.76 (s, 3H), 3.20-3.34 (m, 2H), 2.47-2.72 (m, 6H), 2.28 (br. s., 1H), 1.86-2.02 (m, 4H), 1.33 (br. s., 1H), 1.24 (br. s., 1H). MS (m/z): 540.4 [MH]$^+$.

Example 278: (1R,3S)-5-[3-({4-methyl-5-[4-(1,3-oxazol-2-yl)phenyl]-4H-1,2,4-triazol-3-yl}sulfanyl)propyl]-1-[4-(trifluoromethyl)phenyl]-5-azaspiro[2.4]heptane hydrochloride (CIS, Enantiomer 1, E278)

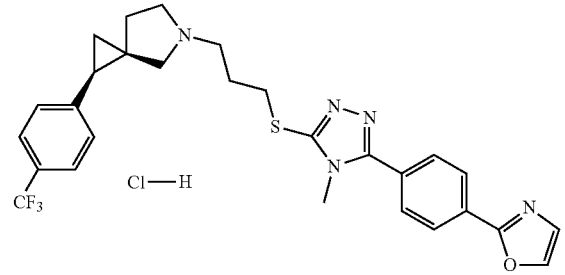 [SMILES: Cn1c(SCCCN2CC[C@]3(C[C@@H]3c3ccc(C(F)(F)F)cc3)C2)nnc1-c1ccc(-c2ncco2)cc1 ; Cl]

(1R,3S)-5-[3-({4-methyl-5-[4-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E277, 31 mg) was dissolved in MeOH and treated with 1.1 eq of HCl 2N in Et$_2$O affording (1R,3S)-5-[3-({4-methyl-5-[4-(1,3-oxazol-2-yl)phenyl]-4H-1,2,4-triazol-3-yl}sulfanyl)propyl]-1-[4-(trifluoromethyl)phenyl]-5-azaspiro[2.4]heptane hydrochloric salt (CIS, Enantiomer 1, E278, 30 mg). MS (m/z): 540.4 [MH]$^+$.

Example 279: (1R,3S)-5-[3-({4-methyl-5-[3-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E279)

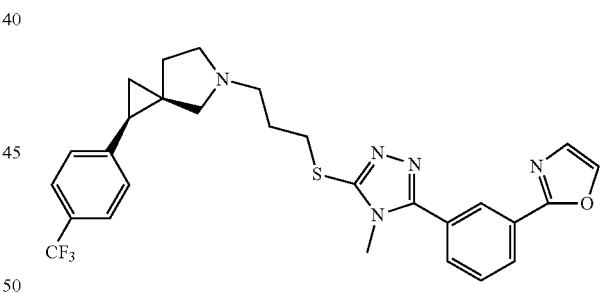

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 3-[(3-chloropropyl)sulfanyl]-4-methyl-5-[3-(1,3-oxazol-2-yl)phenyl]-4H-1,2,4-triazole (p239, 37 mg, 0.11 mmol), Na$_2$CO$_3$ (13 mg, 0.12 mmol) and NaI (18 mg, 0.12 mmol) in DMF (0.1 mL) affording (1R,3S)-5-[3-({4-methyl-5-[3-(1,3-oxazol-2-yl)phenyl]-4H-1,2,4-triazol-3-yl}sulfanyl)propyl]-1-[4-(trifluoromethyl)phenyl]-5-azaspiro[2.4]heptane (CIS, Enantiomer 1, E279, 31 mg, y=57%). NMR: $^1$H NMR (Acetone-d$_6$) δ: 8.42-8.44 (m, 1H), 8.19-8.25 (m, 1H), 8.11 (d, 1H), 7.89-7.94 (m, 1H), 7.70-7.79 (m, 1H), 7.63 (d, 2H), 7.43 (d, 2H), 7.38 (d, 1H), 3.77 (s, 3H), 3.19-3.38 (m, 2H), 2.64-3.04 (m, 6H), 2.28-2.37 (m, 2H), 1.93-2.05 (m, 3H), 1.35-1.41 (m, 1H), 1.25-1.30 (m, 1H). MS (m/z): 540.4 [MH]$^+$.

Example 280: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (CIS, Enantiomer 1, E280)

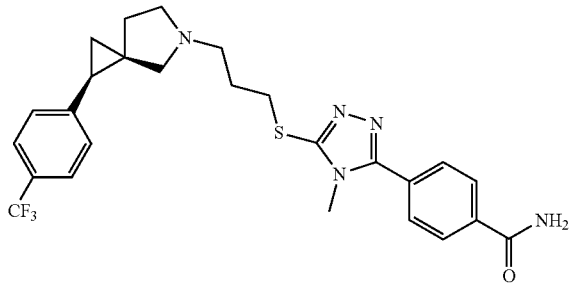 [SMILES: Cn1c(SCCCN2CC[C@]3(C[C@@H]3c3ccc(C(F)(F)F)cc3)C2)nnc1-c1ccc(C(N)=O)cc1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 4-{5-[(3-chloropropyl)sulfanyl]-4-methyl-4H-1,2,4-triazol-3-yl}benzamide (p213, 35 mg, 0.11 mmol), $Na_2CO_3$ (13 mg, 0.12 mmol) and NaI (18 mg, 0.12 mmol) in DMF (0.1 mL) affording 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (CIS, Enantiomer 1, E280, 38.5 mg, y=72%). NMR: $^1$H NMR (Acetone-$d_6$) δ: 8.12 (d, 2H), 7.87 (d, 2H), 7.55-7.65 (m, 2H), 7.39 (d, 2H), 6.68-6.79 (m, 1H), 3.73 (s, 3H), 3.17-3.32 (m, 2H), 2.71-2.76 (m, 1H), 2.59-2.68 (m, 1H), 2.44-2.58 (m, 3H), 2.20-2.29 (m, 1H), 2.08-2.12 (m, 1H), 1.82-2.04 (m, 4H), 1.30 (m, 1H), 1.22 (m, 1H). MS (m/z): 516.4 $[MH]^+$.

Example 281: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide hydrochloride (CIS, Enantiomer 1, E281)

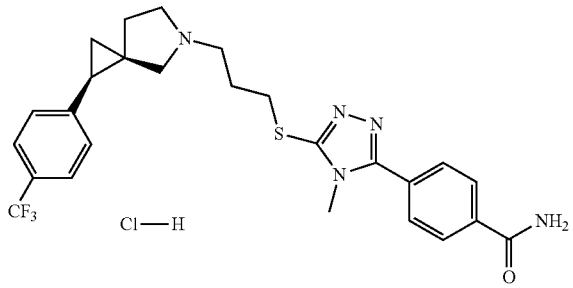 [SMILES: Cn1c(SCCCN2CC[C@]3(C[C@@H]3c3ccc(C(F)(F)F)cc3)C2)nnc1-c1ccc(C(N)=O)cc1 ; Cl]

4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (CIS, Enantiomer 1, E280, 38.5 mg) was dissolved in DCM/$Et_2O$ and treated with 1.1 eq of HCl 2N in $Et_2O$ affording 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide hydrochloric salt (CIS, Enantiomer 1, E281, 40.7 mg). MS (m/z): 516.4 $[MH]^+$.

Example 282: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzonitrile (CIS, Enantiomer 1, E282)

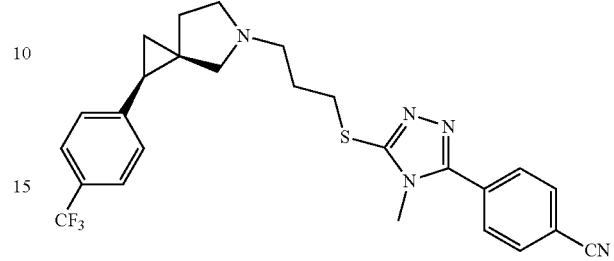

The compound was prepared as in Example 1, reacting (1R,3S)-1-[4-(trifluoromethyl)phenyl]-5-azaspiro[2.4]heptane (CIS, Enantiomer 1, p15, 25 mg, 0.103 mmol), 4-{5-[(3-chloropropyl)sulfanyl]-4-methyl-4H-1,2,4-triazol-3-yl}benzonitrile (p214, 50 mg, 0.113 mmol, considered 60% purity), $Na_2CO_3$ (13 mg, 0.123 mmol) and NaI (18 mg, 0.123 mmol) in DMF (0.1 mL) affording 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzonitrile (CIS, Enantiomer 1, E282, 40 mg, y=78%). NMR: $^1$H NMR (Acetone-$d_6$) δ: 7.93-8.05 (m, 4H), 7.54-7.68 (m, 2H), 7.33-7.44 (m, 2H), 3.76 (s, 3H), 3.19-3.34 (m, 2H), 2.72-2.77 (m, 1H), 2.60-2.68 (m, 1H), 2.45-2.57 (m, 3H), 2.20-2.28 (m, 1H), 2.08-2.13 (m, 1H), 1.81-2.04 (m, 4H), 1.26-1.32 (m, 1H), 1.22 (m, 1H). MS (m/z): 498.4 $[MH]^+$.

Example 283: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzonitrile hydrochloride (CIS, Enantiomer 1, E283)

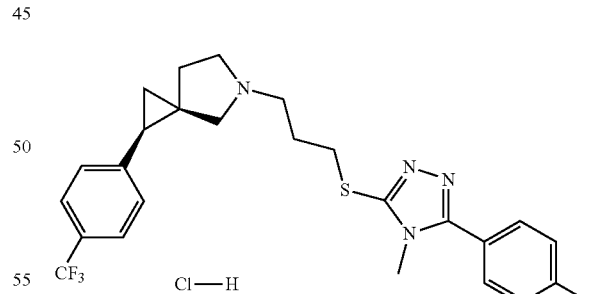

4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzonitrile (CIS, Enantiomer 1, E282, 40 mg) was dissolved in MeOH/$Et_2O$ and treated with 1.1 eq of HCl 2N in $Et_2O$ affording 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzonitrile hydrochloric salt (CIS, Enantiomer 1, E283, 36.1 mg). MS (m/z): 498.4 $[MH]^+$.

Example 284: 1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]phenyl}ethan-1-one hydrochloride (CIS, Enantiomer 1, E284)

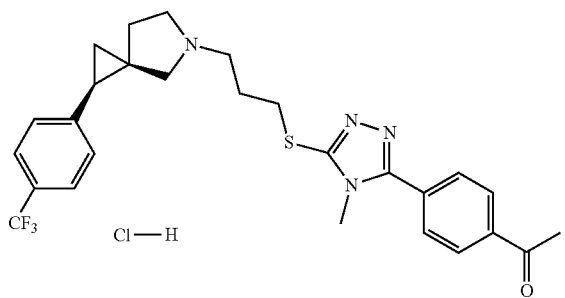 [SMILES: CC(=O)c1ccc(-c2nnc(SCCCN3CC[C@]4(C[C@@H]4c4ccc(C(F)(F)F)cc4)C3)n2C)cc1 ; Cl]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 1-(4-{5-[(3-chloropropyl)sulfanyl]-4-methyl-4H-1,2,4-triazol-3-yl}phenyl)ethan-1-one (p215, 34 mg, 0.11 mmol), Na$_2$CO$_3$ (13 mg, 0.12 mmol) and NaI (18 mg, 0.12 mmol) in DMF (0.113 mL) affording 1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]phenyl}ethan-1-one (34.4 mg).

The latter was dissolved in DCM/Et$_2$O and treated with 2N HCl/ether (1.2 eq) affording 1-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]phenyl}ethan-1-one hydrochloride (CIS, Enantiomer 1, E284, 34.5 mg, y=62%). NMR: $^1$H NMR (DMSO-d$_6$) δ: 10.14-10.44 (m, 1H), 8.12 (d, 2H), 7.88 (d, 2H), 7.65 (d, 2H), 7.38-7.48 (m, 2H), 3.68-3.74 (m, 1H), 3.64 (d, 3H), 3.38-3.47 (m, 1H), 3.21 (d, 6H), 2.65 (s, 3H), 2.20-2.45 (m, 2H), 1.92-2.14 (m, 3H), 1.26-1.53 (m, 2H). MS (m/z): 515.4 [MH]$^+$.

Example 285: 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzene-1-sulfonamide (CIS, Enantiomer 1, E285)

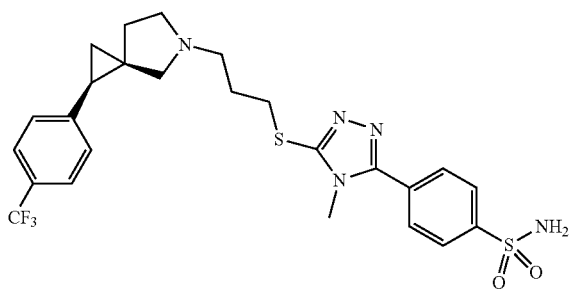 [SMILES: Cn1c(SCCCN2CC[C@]3(C[C@@H]3c3ccc(C(F)(F)F)cc3)C2)nnc1-c1ccc(S(N)(=O)=O)cc1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 4-{5-[(3-chloropropyl)sulfanyl]-4-methyl-4H-1,2,4-triazol-3-yl}benzene-1-sulfonamide (p216, 38 mg, 0.11 mmol), Na$_2$CO$_3$ (13 mg, 0.12 mmol) and NaI (18 mg, 0.12 mmol) in DMF (0.1 mL) affording 4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzene-1-sulfonamide (CIS, Enantiomer 1, E285, 32.9 mg, y=60%). NMR: $^1$H NMR (Acetone) δ: 8.05 (s, 2H), 7.97 (s, 2H), 7.58-7.66 (m, 2H), 7.32-7.42 (m, 2H), 6.70-6.76 (m, 1H), 3.74 (s, 3H), 3.26 (m, 2H), 2.79 (br. s., 2H), 2.45-2.70 (m, 4H), 2.21-2.26 (m, 1H), 1.81-2.02 (m, 4H), 1.29 (m, 1H), 1.21 (m, 1H). MS (m/z): 552.3 [MH]$^+$.

Example 286: 2-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]phenyl}acetonitrile (CIS, Enantiomer 1, E286)

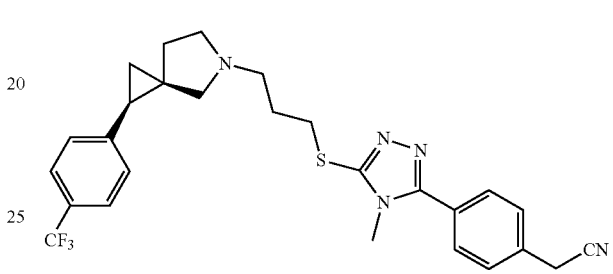

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 2-(4-{5-[(3-chloropropyl)sulfanyl]-4-methyl-4H-1,2,4-triazol-3-yl}phenyl)acetonitrile (p217, 31 mg, 0.11 mmol), Na$_2$CO$_3$ (13 mg, 0.12 mmol) and NaI (18 mg, 0.12 mmol) in DMF (0.1 mL) affording 2-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]phenyl}acetonitrile (CIS, Enantiomer 1, E286, 27 mg, y=55%). NMR: $^1$H NMR (Acetone-d$_6$) δ: 7.79-7.85 (m, 2H), 7.60-7.66 (m, 4H), 7.36-7.43 (m, 2H), 4.11 (s, 2H), 3.71 (s, 3H), 3.15-3.34 (m, 2H), 2.72-2.76 (m, 2H), 2.59-2.68 (m, 1H), 2.47-2.58 (m, 3H), 2.22-2.28 (m, 1H), 1.81-2.04 (m, 4H), 1.27-1.34 (m, 1H), 1.22 (m, 1H). MS (m/z): 512.3 [MH]$^+$.

Example 287: 2-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]phenyl}acetamide (CIS, Enantiomer 1, E287)

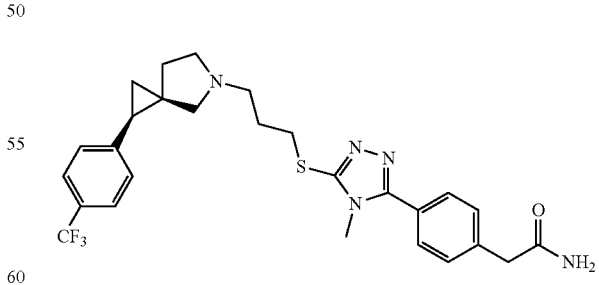

The compound was prepared as in Example 1, reacting (1R,3S)-1-[4-(trifluoromethyl)phenyl]-5-azaspiro[2.4]heptane (CIS, Enantiomer 1, p15, 25 mg, 0.1 mmol), 2-(4-{5-[(3-chloropropyl)sulfanyl]-4-methyl-4H-1,2,4-triazol-3-yl}phenyl)acetamide (p218, 35 mg, 0.11 mmol), Na$_2$CO$_3$ (13 mg, 0.12 mmol) and NaI (18 mg, 0.12 mmol) in DMF (0.1 mL) affording 2-{4-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]phenyl}acetamide (CIS, Enantiomer 1, E287, 31 mg, y=61%). NMR: ¹H NMR (DMSO-d₆) δ: 7.58-7.68 (m, 4H), 7.50-7.56 (m, 1H), 7.41-7.47 (m, 2H), 7.29-7.36 (m, 2H), 6.90-6.98 (m, 1H), 3.58 (s, 3H), 3.48 (s, 2H), 3.12 (d, 2H), 2.64-2.74 (m, 1H), 2.37-2.48 (m, 4H), 2.17-2.25 (m, 1H), 1.96 (d, 3H), 1.76 (s, 2H), 1.28 (m, 1H), 1.18 (m, 1H). MS (m/z): 530.4 [MH]⁺.

Example 288: 3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (CIS, Enantiomer 1, E288)

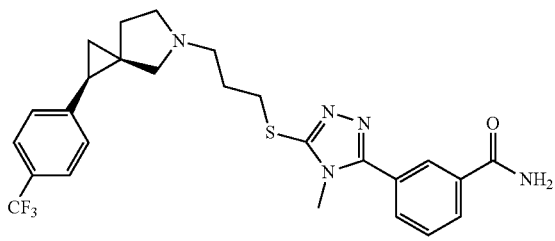 [SMILES: Cn1c(SCCCN2CC[C@]3(C[C@@H]3c3ccc(C(F)(F)F)cc3)C2)nnc1-c1cccc(C(N)=O)c1]

The compound was prepared as in Example 1, reacting (1R,3S)-1-[4-(trifluoromethyl)phenyl]-5-azaspiro[2.4]heptane (CIS, Enantiomer 1, p15, 25 mg, 0.103 mmol), 3-{5-[(3-chloropropyl)sulfanyl]-4-methyl-4H-1,2,4-triazol-3-yl}benzamide (p219, 35 mg, 0.113 mmol), Na₂CO₃ (13 mg, 0.123 mmol) and NaI (18 mg, 0.123 mmol) in DMF (0.1 mL) affording 3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (CIS, Enantiomer 1, E288, 35 mg, y=66%). NMR: ¹H NMR (Acetone-d₆) δ: 8.27 (s, 1H), 8.08-8.15 (m, 1H), 7.88-7.95 (m, 1H), 7.59-7.72 (m, 4H), 7.39 (d, 2H), 6.68-6.83 (m, 1H), 3.72 (s, 3H), 3.16-3.32 (m, 2H), 2.70-2.77 (m, 1H), 2.59-2.68 (m, 1H), 2.42-2.58 (m, 3H), 2.21-2.29 (m, 1H), 1.93-2.07 (m, 3H), 1.81-1.91 (m, 2H), 1.26-1.34 (m, 1H), 1.19-1.25 (m, 1H). MS (m/z): 516.4 [MH]⁺.

Example 289: 3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide hydrochloride (CIS, Enantiomer 1, E289)

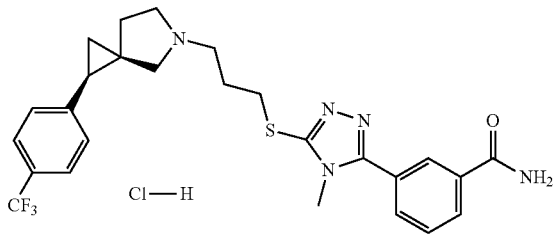 [SMILES: Cn1c(SCCCN2CC[C@]3(C[C@@H]3c3ccc(C(F)(F)F)cc3)C2)nnc1-c1cccc(C(N)=O)c1 ; Cl]

3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (CIS, Enantiomer 1, E288, 35 mg) was dissolved in Et₂O and treated with 1.1 eq of HCl 2N in Et₂O affording 3-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide hydrochloric salt (CIS, Enantiomer 1, E289, 31.5 mg). MS (m/z): 516.4 [MH]⁺.

Example 290: 2-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide hydrochloride (CIS, Enantiomer 1, E290)

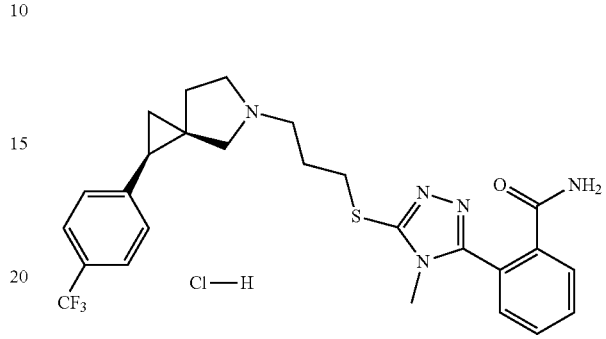

The compound was prepared as in Example 1, reacting (1R,3S)-1-[4-(trifluoromethyl)phenyl]-5-azaspiro[2.4]heptane (CIS, Enantiomer 1, p15, 30 mg, 0.12 mmol), 2-{5-[(3-chloropropyl)sulfanyl]-4-methyl-4H-1,2,4-triazol-3-yl}benzamide (p220, 43 mg, 0.14 mmol), Na₂CO₃ (15 mg, 0.14 mmol) and NaI (18 mg, 0.12 mmol) in DMF (0.2 mL) affording 2-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide (9 mg).

The latter was dissolved in DCM (0.2 mL) then 2N HCl/ether (1.2 eq) was added and the reaction mixture was concentrated under vacuum. The solid so obtained was triturated with ether and dried under vacuum at 45° C. O/N affording 2-[4-methyl-5-({3-[(1R,3S)-1-[4-(trifluoromethyl)phenyl]-5-azaspiro[2.4]heptan-5-yl]propyl}sulfanyl)-4H-1,2,4-triazol-3-yl]benzamide hydrochloride (CIS, Enantiomer 1, E290, 9.7 mg, y=22%). NMR: ¹H NMR (DMSO-d₆) δ: 10.40-11.03 (m, 2H), 7.30-8.02 (m, 7H), 6.87 (br. s., 1H), 3.60-3.82 (m, 3H), 3.05-3.47 (m, 5H), 2.61-3.05 (m, 4H), 1.82-2.48 (m, 4H), 1.22-1.56 (m, 2H). MS (m/z): 516.4 [MH]⁺.

Example 291: 1-{[4-methyl-5-(4-methyl-1,3-oxazol-5-yl)-4H-1,2,4-triazol-3-yl]sulfanyl}-3-{1-[4-(trifluoromethyl)phenyl]-5-azaspiro[2.4]heptan-5-yl}propan-2-ol (CIS, E291) diastereoisomeric mixture

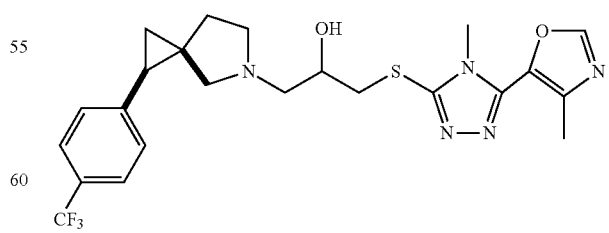

The compound was prepared as in Example 1, reacting (1R,3S/1S,3R)-1-[4-(trifluoromethyl)phenyl]-5-azaspiro[2.4]heptane (CIS, p14, 70 mg, 0.29 mmol), 1-chloro-3-{[4-methyl-5-(4-methyl-1,3-oxazol-5-yl)-4H-1,2,4-triazol-3- yl]sulfanyl}propan-2-ol (p240, 117 mg, 0.41 mmol), Na₂CO₃ (47 mg, 0.444 mmol) and NaI (67 mg, 0.444 mmol) in DMF (0.28 mL) affording 1-{[4-methyl-5-(4-methyl-1,3-oxazol-5-yl)-4H-1,2,4-triazol-3-yl]sulfanyl}-3-{1-[4-(trifluoromethyl)phenyl]-5-azaspiro[2.4]heptan-5-yl}propan-2-ol (CIS, E291, 13 mg, y=9%) as diastereomeric mixture. NMR: ¹H NMR (Acetone-d₆) δ: 8.28 (s, 1H), 7.61 (d, 2H), 7.31-7.43 (m, 2H), 3.77 (d, 3H), 3.52-3.59 (m, 1H), 3.41-3.49 (m, 1H), 3.11-3.24 (m, 2H), 2.57 (br. s., 2H), 2.43 (s, 3H), 2.20-2.28 (m, 2H), 1.92-2.00 (m, 2H), 1.88-1.92 (m, 1H), 1.26-1.35 (m, 2H), 1.17-1.24 (m, 1H). MS (m/z): 494.4 [MH]⁺.

Example 292: (1S,3S/1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E292)

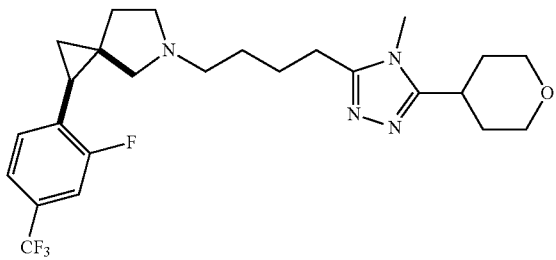

(1S,3S/1R,3R)-1-[2-fluoro-4-(trifluoromethyl)phenyl]-5-azaspiro[2.4]heptane (CIS, p23, 50 mg, 0.19 mmol) and 4-[4-methyl-5-(oxan-4-yl)-4H-1,2,4-triazol-3-yl]butanal (p247, 100 mg, 0.25 mmol), were dissolved in DCM (5 mL) and stirred for 15 min before adding NaBH(OAc)₃ (80 mg, 0.38 mmol). The reaction mixture was stirred at RT O/N. Then it was diluted with water and DCM and extracted several times with DCM. Organic phase was evaporated and the residue was purified by FC on silica gel (eluent from DCM to MeOH) to obtain the title compound (1S,3S/1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E292, 45 mg, y=49%). NMR: ¹H NMR (Acetone-d₆) δ: 7.43-7.54 (m, 2H), 7.32 (m, 1H), 3.97 (m, 2H), 3.57 (s, 3H), 3.51 (d, 2H), 3.00-3.10 (m, 1H), 2.70-2.78 (m, 1H), 2.65 (d, 2H), 2.53-2.60 (m, 1H), 2.32-2.43 (m, 3H), 2.22-2.29 (m, 1H), 1.95-2.02 (m, 3H), 1.78-1.92 (m, 4H), 1.67-1.77 (m, 2H), 1.44-1.53 (m, 2H), 1.32-1.38 (m, 1H), 1.20-1.26 (m, 1H). MS (m/z): 481.1 [MH]⁺.

Example 293 and Example 294: (1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E293, Enantiomer 1) and (1S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E294, Enantiomer 2)

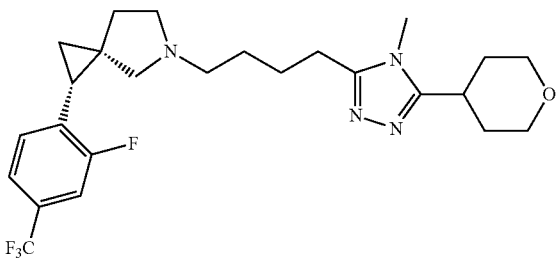

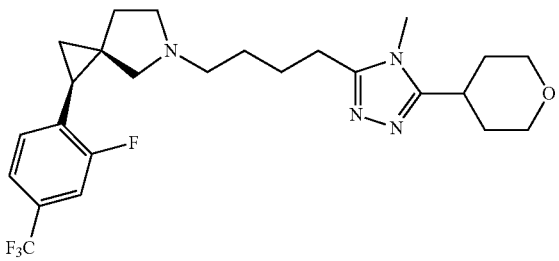

(1S,3S/1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E292, 40 mg) was separated into the single enantiomers by preparative chiral HPLC.

Preparative Chromatography:

| | |
|---|---|
| Column | Chiralpak AD-H (25 × 2 cm), 5 um |
| Mobile phase | n-Hexane/(Ethanol/Methanol 1/1 + 0.1% isopropylamine) 80/20% v/v |
| Flow rate (ml/min) | 17 ml/min |
| DAD detection | 220 nm |
| Loop | 1000 µL |
| Injection | 21 mg/injection | affording (1R,3R)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E293, 11 mg). Enantiomer 1: ret. time 6.4 min, 100% ee. MS (m/z): 481.5 [MH]⁺ and (1S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E294, 11 mg). Enantiomer 2: ret. time 8.5 min, 100% ee. MS (m/z): 481.5 [MH]⁺.

Example 295: (1S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane hydrochloride (CIS, E295, Enantiomer 2)

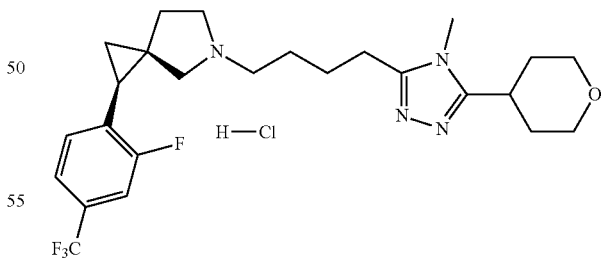

(1S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane (CIS, E294, 11.5 mg) was treated with 1.1 eq of HCl in Et₂O affording (1S,3S)-1-[2-fluoro-4-(trifluoromethyl)phenyl]-5-{4-[4-methyl-5-(oxan-4-yl)-4H-1,2,4-triazol-3-yl]butyl}-5-azaspiro[2.4]heptane hydrochloric salt (CIS, Enantiomer 2, E295, 11.8 mg). MS (m/z): 481.1 [MH]⁺.

Example 296: (1S,3S/1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E296)

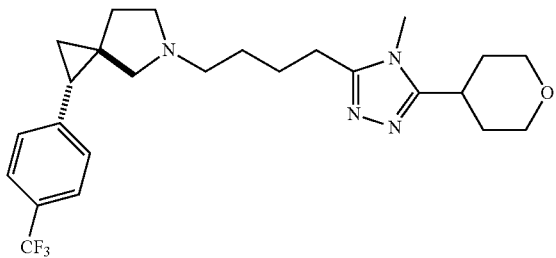

To a solution of 4-[4-methyl-5-(oxan-4-yl)-4H-1,2,4-triazol-3-yl]butanal (p247, 135 mg, 0.57 mmol) and (1S,3S/1R,3R)-1-[4-(trifluoromethyl)phenyl]-5-azaspiro[2.4]heptane (TRANS, p13, 137 mg, 0.57 mmol) in DCM (4 mL), at RT and under a nitrogen atmosphere, sodium triacetoxyborohydride (181 mg, 0.86 mmol) was added portion-wise and the resulting reaction mixture was stirred overnight. A solution of concentrated ammonium chloride was added, the mixture was diluted with DCM, and the organic phase was washed with water, dried over sodium sulfate and the solvent removed under vacuum. The crude material was purified by aminic FC (eluting with DCM/MeOH from 100/0 to 95/5) to give (1S,3S/1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E296, 85 mg, y=32%). NMR: $^1$H NMR (CDCl$_3$) δ: 7.53 (d, 2H), 7.15-7.21 (m, 2H), 4.07-4.17 (m, 2H), 3.52-3.59 (m, 2H), 3.51 (s, 3H), 2.84-2.96 (m, 1H), 2.75 (d, 4H), 2.55-2.66 (m, 2H), 2.47-2.55 (m, 2H), 2.05-2.17 (m, 4H), 1.84 (br. s., 4H), 1.59-1.74 (m, 3H), 1.45-1.56 (m, 1H), 1.22-1.29 (m, 1H), 1.08-1.15 (m, 1H). MS (m/z): 463.5 [MH]$^+$.

Example 297 and Example 298: (1S,3S or 1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E297, Enantiomer 1) and (1R,3R or 1S,3S)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E298, Enantiomer 2)

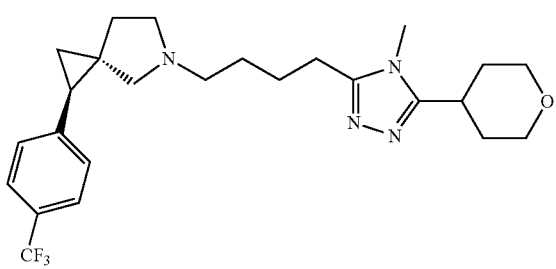

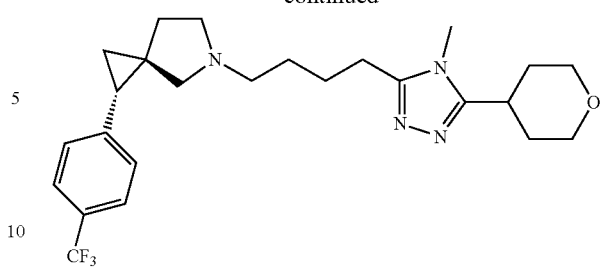

(1S,3S/1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E296, 85 mg) was separated into the single enantiomers by preparative chiral HPLC.

Preparative Chromatography:

| | |
|---|---|
| Column | Chiralpak AD-H (25 × 2.0 cm), 5 um |
| Mobile phase | n-Hexane/(2-Propanol/Methanol 1/1 + 0.1% isopropylamine) 80/20 v/v |
| Flow rate (ml/min) | 18 ml/min |
| DAD detection | 220 nm |
| Loop | 1000 µL |
| Injection | 10 mg/injection | affording (1S,3S or 1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E297, 24 mg), Enantiomer 1: ret. time 9.5 min. MS (m/z): 463.5 [MH]$^+$ and (1R,3R or 1S,3S)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E298, 23 mg), Enantiomer 2: ret. time 12.1 min. MS (m/z): 463.5 [MH]$^+$.

Example 299: (1S,3S or 1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane hydrochloride (TRANS, E299, Enantiomer 1)

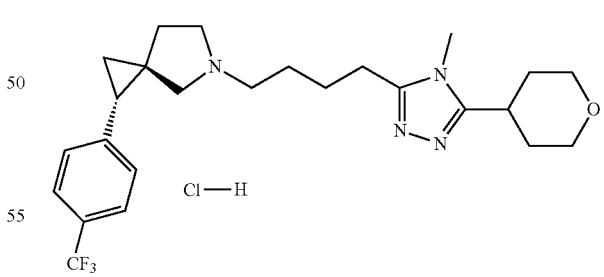

(1S,3S or 1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E297, 24 mg) was dissolved in DCM and treated with 1.1 eq of HCl 2N in Et$_2$O affording (1S,3S or 1R,3R)-5-{4-[4-methyl-5-(oxan-4-yl)-4H-1,2,4-triazol-3-yl]butyl}-1-[4-(trifluoromethyl)phenyl]-5-azaspiro[2.4]heptane hydrochloric salt (TRANS, Enantiomer 1, E299, 25 mg). MS (m/z): 463.5 [MH]$^+$.

Example 300: (1R,3R or 1S,3S)-5-{4-[4-methyl-5-(oxan-4-yl)-4H-1,2,4-triazol-3-yl]butyl}-1-[4-(trifluoromethyl)phenyl]-5-azaspiro[2.4]heptane hydrochloride (TRANS, E300, Enantiomer 2)

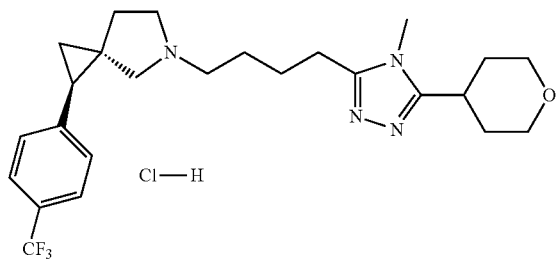 [SMILES: Cn1c(CCCCN2CC[C@@]3(C[C@@H]3c3ccc(C(F)(F)F)cc3)C2)nnc1C1CCOCC1 ; Cl]

(1R,3R or 1S,3S)-5-{4-[4-methyl-5-(oxan-4-yl)-4H-1,2,4-triazol-3-yl]butyl}-1-[4-(trifluoromethyl)phenyl]-5-azaspiro[2.4]heptane (TRANS, E298, 23 mg) was dissolved in DCM and treated with 1.1 eq of HCl 2N in Et₂O affording (1R,3R or 1S,3S)-5-{4-[4-methyl-5-(oxan-4-yl)-4H-1,2,4-triazol-3-yl]butyl}-1-[4-(trifluoromethyl)phenyl]-5-azaspiro[2.4]heptane hydrochloric salt (TRANS, Enantiomer 2, E300, 24 mg). MS (m/z): 463.5 [MH]⁺.

Example 301: (1R,3S/1S,3R)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane hydrochloride (CIS, E301)

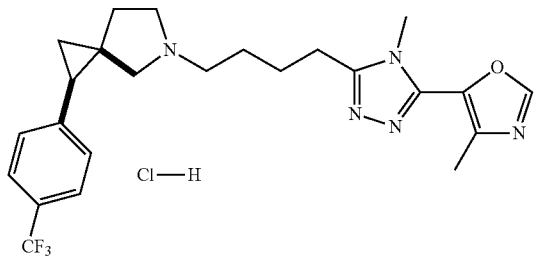

Step a: To a solution of 4-methyl-3-(4-methyl-1,3-oxazol-5-yl)-5-(pent-4-en-1-yl)-4H-1,2,4-triazole (p248, 62 mg, 0.27 mmol) in THF/H₂O (2.3/0.5 mL) were subsequently added OsO₄ (0.10 mL, 4% solution in water, 0.014 mmol) and NaIO₄ (173 mg, 0.81 mmol). The reaction mixture was stirred overnight at RT. Water was added and the mixture was extracted with DCM. The organic phase was dried over sodium sulfate and the solvent removed under vacuum affording 4-[4-methyl-5-(4-methyl-1,3-oxazol-5-yl)-4H-1,2,4-triazol-3-yl]butanal (35 mg) as colorless oil that was used as such in the next step.

Step b: In a vial a solution of 4-[4-methyl-5-(4-methyl-1,3-oxazol-5-yl)-4H-1,2,4-triazol-3-yl]butanal (33 mg, from step a) and (1R,3S/1S,3R)-1-[4-(trifluoromethyl)phenyl]-5-azaspiro[2.4]heptane (CIS, p14, 44 mg, 0.18 mmol) in DCM (0.5 mL) was shaken for 10 min at RT.

Na(AcO)₃BH (45 mg, 0.21 mmol) was added portionwise and the resulting reaction mixture was shaken overnight at RT in a PLS apparatus. The mixture was diluted with DCM and washed with concentrated sodium bicarbonate solution. The organic phase was dried over sodium sulfate and the solvent removed under vacuum. The residue was purified by FC on silica (eluting with DCM/MeOH from 100/0 to 90/10) then further purified by aminic FC (eluting with EA/MeOH from 100/0 to 97/3) affording (1R,3S/1S,3R)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane (16 mg).

Step c: (1R,3S/1S,3R)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane (16 mg) was dissolved in DCM (0.2 mL) then 2N HCl/ether (0.019 mL, 0.038 mmol) was added and the reaction mixture was concentrated under vacuum. The solid so obtained was triturated with ether and dried under vacuum at 45° C. overnight affording (1R,3S/1S,3R)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane hydrochloride (CIS, E301, 17 mg, y=19%) as pale yellow foam. NMR: ¹H NMR (DMSO-d₆) δ: 10.11-10.46 (m, 1H), 8.54 (s, 1H), 7.68 (d, 2H), 7.45 (d, 2H), 3.61-3.71 (m, 4H), 3.20 (br. s., 5H), 2.55-2.87 (m, 4H), 2.31-2.44 (m, 3H), 2.24 (m, 1H), 2.03-2.15 (m, 1H), 1.71 (d, 4H), 1.26-1.54 (m, 2H). MS (m/z): 460.5 [MH]⁺.

Example 302: (1R,3S)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane hydrochloride (CIS, Enantiomer 1, E302)

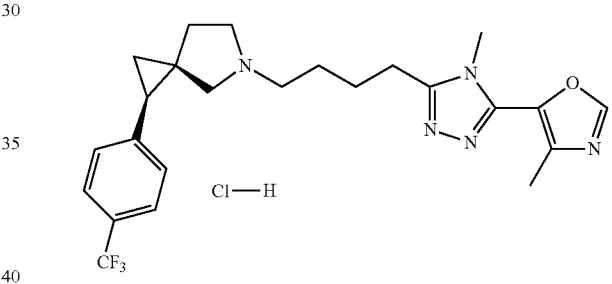

Step a: To a solution of 4-methyl-3-(4-methyl-1,3-oxazol-5-yl)-5-(pent-4-en-1-yl)-4H-1,2,4-triazole (p248, 107 mg, 0.46 mmol) in THF/H₂O (4 mL/00.8 mL) were subsequently added OsO₄ (0.15 mL, 4% solution in water, 0.023 mmol) and NaIO₄ (295 mg, 1.38 mmol). The reaction mixture was stirred overnight at RT. Water was added and the mixture was extracted with DCM. The organic phase was dried over sodium sulfate and the solvent removed under vacuum affording 4-[4-methyl-5-(4-methyl-1,3-oxazol-5-yl)-4H-1,2,4-triazol-3-yl]butanal (107 mg) that was used as crude in the next step.

Step b: In a vial a solution of 4-[4-methyl-5-(4-methyl-1,3-oxazol-5-yl)-4H-1,2,4-triazol-3-yl]butanal (53 mg, from step a) and (1R,3S)-1-[4-(trifluoromethyl)phenyl]-5-azaspiro[2.4]heptane (CIS, Enantiomer 1, p15, 40 mg, 0.17 mmol) in DCM (0.6 mL) was shaken for 10 min at RT.

Na(AcO)₃BH (73 mg, 0.35 mmol) was added portionwise and the resulting reaction mixture was shaken O/N at RT in a PLS apparatus. The mixture was diluted with DCM and washed with concentrated sodium bicarbonate solution. The organic phase was dried over sodium sulfate and the solvent removed under vacuum. The residue was purified by FC on NH column (eluting with EA/MeOH from 100/0 to 97/3) to give (1R,3S)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane (29 mg).

Step c: (1R,3S)-5-{4-[4-methyl-5-(4-methyl-1,3-oxazyl,-oxazol-5-yl)-4H-1,2,4-triazol-3-yl]butyl}-1-[4-(trifluoromethyl)phenyl]-5-azaspiro[2.4]heptane (29 mg) was dissolved in DCM (0.2 mL) then 2N HCl/ether (0.035 mL) was added and the reaction mixture was concentrated under vacuum. The solid so obtained was triturated with ether and dried under vacuum at 45° C. overnight affording (1R,3S)-5-{4-[4-methyl-5-(4-methyl-1,3-oxazol-5-yl)-4H-1,2,4-triazol-3-yl]butyl}-1-[4-(trifluoromethyl)phenyl]-5-azaspiro[2.4]heptane hydrochloride (CIS, Enantiomer 1, E302, 31 mg, y=37%) as white solid. NMR: $^1$H NMR (DMSO-d$_6$) δ: 10.26-10.57 (m, 1H), 8.55 (s, 1H), 7.68 (d, 2H), 7.45 (d, 2H), 3.64 (s, 3H), 2.88-3.42 (m, 6H), 2.37-2.86 (m, 4H), 2.35 (s, 3H), 2.03-2.30 (m, 2H), 1.71 (d, 4H), 1.27-1.53 (m, 2H). MS (m/z): 460.4 [MH]$^+$.

Preparation 261: (1S,3S/1R,3R)-5-{(3-[(tert-butyldimethylsilyl)oxy]propyl}-1-[4-(trifluoromethyl)phenyl]-5-azaspiro[2.4]heptane (TRANS)

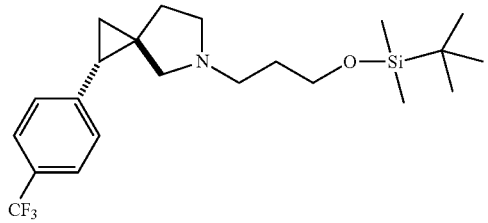

A mixture of (1S,3S/1R,3R)-1-[4-(trifluoromethyl)phenyl]-5-azaspiro[2.4]heptane (TRANS, p13, 100 mg, 0.41 mmol), (3-bromopropoxy)(tert-butyl)dimethylsilane (0.143 mL, 0.615 mmol), TEA (0.171 mL, 1.23 mmol), NaI (12 mg, 0.082 mmol) in DMF (2 mL) was stirred at 50° C. O/N.

The mixture was then diluted with brine and DCM, phases were separated and the aqueous one was extracted twice with DCM. Combined organics were dried and concentrated under reduced pressure. Crude material was purified by FC on NH column (eluent: Cy to EtoAC 20%) affording (1S,3S/1R,3R)-5-{3-[(tert-butyldimethylsilyl)oxy]propyl}-1-[4-(trifluoromethyl)phenyl]-5-azaspiro[2.4]heptane (TRANS, p261, 73 mg, y=44%) as colourless oil. MS (m/z): 414.6 [MH]$^+$ Preparation 262: 3-[(1S,3S/1R,3R)-1-[4-(trifluoromethyl)phenyl]-5-azaspiro[2.4]heptan-5-yl]propan-1-ol (TRANS)

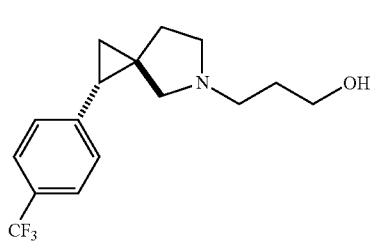

(1S,3S/1R,3R)-5-{3-[(tert-butyldimethylsilyl)oxy]propyl}-1-[4-(trifluoromethyl)phenyl]-5-azaspiro[2.4]heptane (TRANS, p261, 73 mg, 0.18 mmol) was dissolved in THF (1 mL) and treated with HCl 1M (1 mL). The mixture was left stirring at RT for 1 h. NaOH 1M was then added to bring pH to 8 and the mixture was extracted with EtOAc. NaOH 1M was added till pH 10 and the acqueous phase was extracted again with DCM. Combined organics were dried and concentrated to obtain 3-[(1S,3S/1R,3R)-1-[4-(trifluoromethyl)phenyl]-5-azaspiro[2.4]heptan-5-yl]propan-1-ol (TRANS, p262, 49 mg, y=84%) as colourless oil. MS (m/z): 300.3 [MH]$^+$.

Preparation 263: 4-methyl-3-(methylsulfanyl)-5-(oxan-4-yl)-4H-1,2,4-triazole

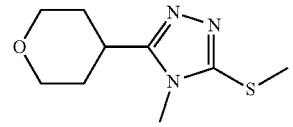

To a solution of 4-methyl-5-(oxan-4-yl)-4H-1,2,4-triazole-3-thiol (p66, 500 mg, 2.5 mmol) in EtOH (3.75 mL) iodomethane (187 uL, 3 mmol) was added dropwise. The resulting mixture was stirred at 80° C. for 30'. Solvent was evaporated in vacuum; the residue was dissolved in NaOH 1M and extracted three times with DCM. Combined organics were dried and concentrated to obtain 4-methyl-3-(methylsulfanyl)-5-(oxan-4-yl)-4H-1,2,4-triazole (p263, 482 mg, y=90%) as white solid. MS (m/z): 214.2 [MH]$^+$ Preparation 264: 3-methanesulfonyl-4-methyl-5-(oxan-4-yl)-4H-1,2,4-triazole

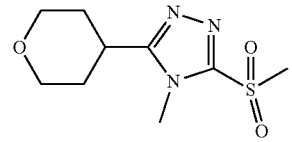 [SMILES: Cn1c(C2CCOCC2)nnc1S(C)(=O)=O]

To a solution of 4-methyl-3-(methylsulfanyl)-5-(oxan-4-yl)-4H-1,2,4-triazole (p263, 482 mg, 2.26 mmol) in DCM (6 mL) 3-chloro perbenzoic acid (1.17 g, 6.78 mmol) was added portionwise. The resulting mixture was stirred at RT for 3 hrs. EtOAc was then added till complete dissolution, followed by NaHCO$_3$ ss. Phases were separated and the aqueous one was backextracted once with EtOAc, then several times with DCM. Combined organics were dried and concentrated to give 3-methanesulfonyl-4-methyl-5-(oxan-4-yl)-4H-1,2,4-triazole (p264, 412 mg, y=71%) as white solid. MS (m/z): 246.2 [MH]$^+$.

Example 303: (1S,3S/1R,3R)-5-(3-{[4-methyl-5-(oxan-4-yl)-4H-1,2,4-triazol-3-yl]oxy}-propyl)-1-[4-(trifluoromethyl)phenyl]-5-azaspiro[2.4]heptane (TRANS, E303)

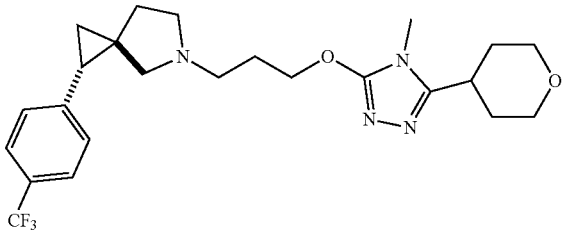 [SMILES: Cn1c(OCCCN2CC[C@]3(C[C@H]3c3ccc(C(F)(F)F)cc3)C2)nnc1C1CCOCC1]

To a solution of 3-[(1S,3S/1R,3R)-1-[4-(trifluoromethyl)phenyl]-5-azaspiro[2.4]heptan-5-yl]propan-1-ol (TRANS, p262, 49 mg, 0.16 mmol) in DMF (1.5 mL), 3-methanesulfonyl-4-methyl-5-(oxan-4-yl)-4H-1,2,4-triazole (p264, 39 mg, 0.16 mmol) was added followed by NaH 60% in mineral oil (9.6 mg, 0.24 mmol) and the mixture was shaken in a PLS apparatus at 60° C. for 4 hrs.

Further NaH was added (52 mg in 5 subsequent additions) and the mixture was shaken for overall 26 hrs. The reaction was cooled down to 0° C. with an ice bath and water was slowly added. The mixture was extracted three times with DCM, then twice with EtOAc. Combined organics were dried and concentrated; crude material was purified by FC on silica gel (eluent: DCM to DCM/MeOH 0:10) to obtain (1S,3S/1R,3R)-5-(3-{[4-methyl-5-(oxan-4-yl)-4H-1,2,4-triazol-3-yl]oxy}propyl)-1-[4-(trifluoromethyl)phenyl]-5-azaspiro[2.4]heptane (TRANS, E303, 49 mg, y=58%) as colourless gum. NMR: $^1$H NMR (Acetone-$d_6$) δ: 7.62 (d, 2H), 7.34 (d, 2H), 4.40-4.49 (m, 2H), 3.91-4.02 (m, 2H), 3.44-3.54 (m, 2H), 3.40 (s, 3H), 2.90-3.01 (m, 1H), 2.72-2.76 (m, 2H), 2.53-2.66 (m, 5H), 2.18-2.30 (m, 1H), 1.94-2.02 (m, 2H), 1.81-1.86 (m, 3H), 1.61-1.70 (m, 1H), 1.37-1.46 (m, 1H), 1.25 (d, 1H), 1.20 (s, 1H). MS (m/z): 481.1 [MH]$^+$.

Example 304 and Example 305: (1S,3S or 1R,3R)-5-(3-{[4-methyl-5-(oxan-4-yl)-4H-1,2,4-triazol-3-yl]oxy}propyl)-1-[4-(trifluoromethyl)phenyl]-5-azaspiro[2.4]heptane (TRANS, E304, Enantiomer 1) and (1R,3R or 1S,3S)-5-(3-{[4-methyl-5-(oxan-4-yl)-4H-1,2,4-triazol-3-yl]oxy}-propyl)-1-[4-(trifluoromethyl)phenyl]-5-azaspiro[2.4]heptane (TRANS, E305, Enantiomer 2)

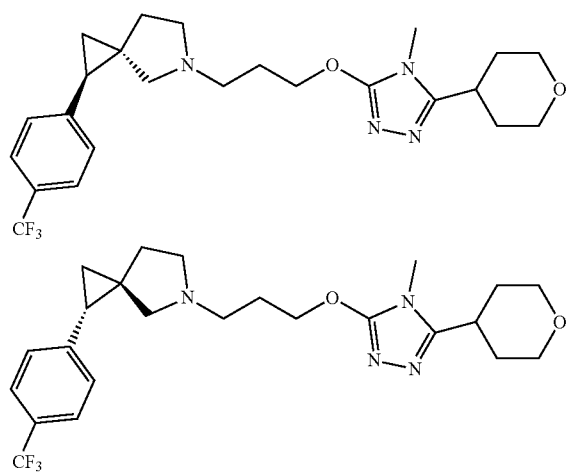

(1S,3S/1R,3R)-5-(3-{[4-methyl-5-(oxan-4-yl)-4H-1,2,4-triazol-3-yl]oxy}propyl)-1-[4-(trifluoromethyl)phenyl]-5-azaspiro[2.4]heptane (TRANS, E303, 49 mg) was separated into the single enantiomers by preparative chiral HPLC.

Preparative Chromatography:

| Column | Chiralcel OJ-H (25 × 2.0 cm), 5µ |
|---|---|
| Mobile phase | n-Hexane/(Ethanol/Methanol 1/1 + 0.1% isopropylamine) 90/10% v/v |
| Flow rate (ml/min) | 18 ml/min |
| DAD detection | 220 nm |
| Loop | 600 µL |
| Injection | 13.3 mg/injection | affording (1S,3S or 1R,3R)-5-(3-{[4-methyl-5-(oxan-4-yl)-4H-1,2,4-triazol-3-yl]oxy}-propyl)-1-[4-(trifluoromethyl)phenyl]-5-azaspiro[2.4]heptane (TRANS, E304, 14 mg). Enantiomer 1: ret. time 16.1 min, 100% ee. MS (m/z): 465.5 [MH]$^+$ and (1R,3R or 1S,3S)-5-(3-{[4-methyl-5-(oxan-4-yl)-4H-1,2,4-triazol-3-yl]oxy}propyl)-1-[4-(trifluoromethyl)phenyl]-5-azaspiro[2.4]heptane (TRANS, E305, 11 mg). Enantiomer 2: ret. time 19.4 min, 100% ee. MS (m/z): 465.5 [MH]$^+$.

Preparation 265: benzyl-triphenyl-phosphonium bromide

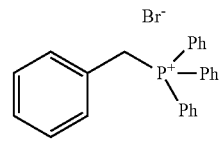 [SMILES: [Br-] ; c1ccc(C[P+](c2ccccc2)(c2ccccc2)c2ccccc2)cc1]

A solution of PPh$_3$ (7.66 g, 29.23 mmol) and benzyl bromide (3.48 mL, 29.23 mmol) in toluene (70 mL) was refluxed O/N; the mixture was then allowed to cool down to RT and the resulting precipitate was collected by filtration, washed with pentane and dried in vacuo to afford benzyl-triphenyl-phosphonium bromide (p265, 12 g, y=95%) as white solid. MS (m/z): 353.2 [M-Br]$^+$ Preparation 266: tert-butyl 4-(phenylmethylidene)piperidine-1-carboxylate

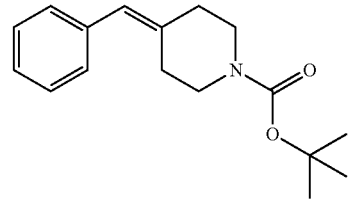 [SMILES: CC(C)(C)OC(=O)N1CCC(=Cc2ccccc2)CC1]

A suspension of benzyl-triphenyl-phosphonium bromide (p265, 10.87 g, 25.09 mmol) in THF (70 mL) was cooled with ice bath, then NaH 60% dispersion in mineral oil (1.1 g, 27.6 mmol) was added. The suspension was stirred at 0° C. for 10 min then at RT for 45 min, the suspension became orange-yellow.

Tert-butyl 4-oxo-1-piperidinecarboxylate (5 g, 25.09 mmol) dissolved in THF (30 mL) was added dropwise and the resulting reaction mixture was stirred at RT O/N. The mixture was then cooled down to 0° C. and diluted with water and EtOAc. The organic phase was separated and washed with NaHCO$_3$ ss, then dried and evaporated. The reasidual oil was treated with Et$_2$O in order to precipitate the triphenylphosphoxide that was filtered off. The solution was evaporated and the residue was purified by FC on silica gel (eluent from cHex to 10% EtOAc) to afford the title compound tert-butyl 4-(phenylmethylidene)piperidine-1-carboxylate (p266, 5.46 g, y=79%) as white solid. MS (m/z): 274.2 [MH]$^+$.

Preparation 267: tert-butyl (2R/2S)-1,1-dichloro-2-phenyl-6-azaspiro[2.5]octane-6-carboxylate

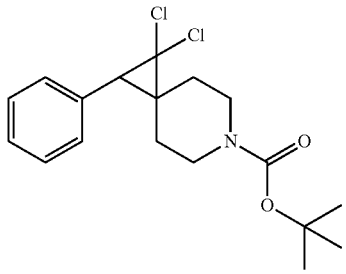 [SMILES: CC(C)(C)OC(=O)N1CCC2(CC1)C(c1ccccc1)C2(Cl)Cl]

Tetrabutylammonium bromide (150 mg, 0.46 mmol) was added to a mixture of tert-butyl 4-(phenylmethylidene)piperidine-1-carboxylate (p266, 3 g, 10.97 mmol) in CHCl₃ (50 mL) and 50% aqueous NaOH (10 mL). The reaction mixture was stirred at RT for 3 hrs, then further 30 mL of 50% aqueous NaOH were added. After 48 hrs the reaction mixture was diluted with DCM and washed with water. The aqueous layer was extracted with DCM and the combined organics were dried and concentrated. The residue was purified by FC on silica gel (eluting from cHex to 10% EtOAc) to afford tert-butyl (2R/2S)-1,1-dichloro-2-phenyl-6-azaspiro[2.5]octane-6-carboxylate (p267, 4 g, y=quant) as colourless oil. MS (m/z): 356.2 [MH]⁺

Preparation 268: (2S/2R)-1,1-dichloro-2-phenyl-azaspiro[2.5]octane

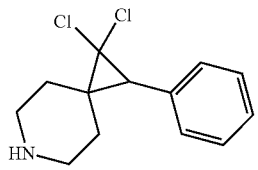 [SMILES: ClC1(Cl)C(c2ccccc2)C12CCNCC2]

To a stirred solution of tert-butyl (2S/2R)-1,1-dichloro-2-phenyl-6-azaspiro[2.5]octane-6-carboxylate (p267, 2 g, 5.6 mmol) in DCM (20 mL), TFA (4 mL) was added and the resulting solution was left stirring at RT for 1 h. Solvent was removed in vacuum and the residue was loaded on a SCX cartridge eluting with 1M NH₃ in MeOH to afford the title compound (2S/2R)-1,1-dichloro-2-phenyl-6-azaspiro[2.5]octane (p268, 1.3 g) as pale yellow oil that was used as such in the next step. MS (m/z): 256.2 [M]⁺.

Preparation 269: 1-[(2S/2R)-1,1-dichloro-2-phenyl-6-azaspiro[2.5]octan-6-yl]-2,2,2-trifluoroethan-1-one

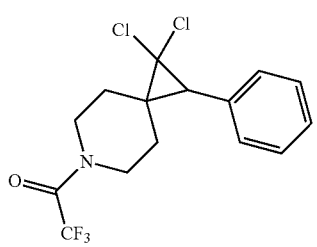 [SMILES: O=C(N1CCC2(CC1)C(c1ccccc1)C2(Cl)Cl)C(F)(F)F]

To a stirred solution of (2S/2R)-1,1-dichloro-2-phenyl-6-azaspiro[2.5]octane (p268, 450 mg, 1.75 mmol) in DCM (10 mL) Trifluoroacetic acid anhydride (0.364 mL) was added and the resulting solution was left stirring at RT O/N. It was then diluted with further DCM and washed with 1N NaOH. The organic solvent was dried and evaporated. The residue was purified by FC on silica gel (eluting from cHex to 10% EtOAc) to afford 1-[(2S/2R)-1,1-dichloro-2-phenyl-6-azaspiro[2.5]octan-6-yl]-2,2,2-trifluoroethan-1-one (p269, 550 mg, y=89%) as white solid. MS (m/z): 352.1 [M]⁺.

Preparation 270: 2,2,2-trifluoro-1-[(1R/1S)-1-phenyl-6-azaspiro[2.5]octan-6-yl]ethan-1-one

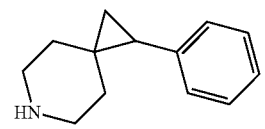 [SMILES: c1ccc(C2CC23CCNCC3)cc1]

To a stirred solution of 1-[(2S/2R)-1,1-dichloro-2-phenyl-6-azaspiro[2.5]octan-6-yl]-2,2,2-trifluoroethan-1-one (p269, 550 mg, 1.56 mmol) in EtOH/H₂O (10 mL/1 mL), Zn powder (560 mg, 8.58 mmol) was added. The resulting mixture was left stirring at reflux O/N. Solid was filtered off and washed with MeOH. The solution was concentrated and the residue was purified by FC on silica gel (eluting from cHex to 10% EtOAc) to afford the title compound 2,2,2-trifluoro-1-[(1R/1S)-1-phenyl-6-azaspiro[2.5]octan-6-yl]ethan-1-one (p270, 130 mg, y=29%) as colourless oil. MS (m/z): 284.2 [MH]⁺.

Preparation 271: (1R/1S)-1-phenyl-6-azaspiro[2.5]octane

To a stirred solution of 2,2,2-trifluoro-1-{1-phenyl-6-azaspiro[2.5]octan-6-yl}ethan-1-one (p270, 130 mg, 0.46 mmol) in MeOH/H₂O (4 mL/2 mL), K₂CO₃ (127 mg, 0.92 mmol) was added. The resulting solution was left stirring at RT for 1 h. MeOH was evaporated, then DCM and 1N NaOH were added and the product was extracted several times with DCM. The organic phase was dried and evaporated to afford (1R/1S)-1-phenyl-6-azaspiro[2.5]octane (p271, 100 mg, 70% pure) as colourless oil that was used as such in the next step. MS (m/z): 188.2 [MH]⁺.

Example 306: (1R/1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane (E306)

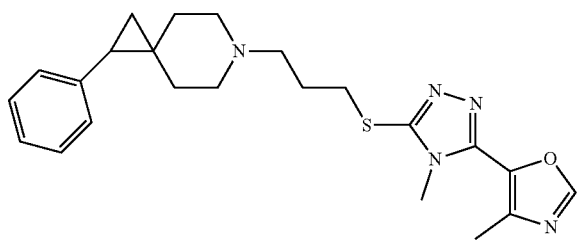 [SMILES: Cc1ncoc1-c1nnc(SCCCN2CCC3(CC2)CC3c2ccccc2)n1C]

The compound was prepared as in Example 1, reacting (1R/1S)-1-phenyl-6-azaspiro[2.5]octane (p271, 50 mg, 0.267 mmol), 3-[(3-chloropropyl)sulfanyl]-4-methyl-5-(4-methyl-1,3-oxazol-5-yl)-4H-1,2,4-triazole (p148, 80 mg, 0.29 mmol), Na$_2$CO$_3$ (34 mg, 0.32 mmol) and NaI (48 mg, 0.32 mmol) in DMF (0.2 mL) affording the title compound (1R/1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane (E306, 53 mg, y=48%). NMR: $^1$H NMR (Acetone-d$_6$) δ: 8.28 (s, 1H), 7.12-7.34 (m, 5H), 3.75-3.86 (m, 3H), 3.30 (m, 2H), 2.45-2.70 (m, 4H), 2.43 (s, 3H), 2.18-2.39 (m, 2H), 1.93-2.04 (m, 3H), 1.49-1.73 (m, 2H), 1.18-1.36 (m, 2H), 0.96-1.03 (m, 1H), 0.78-0.86 (m, 1H). MS (m/z): 424.1 [MH]$^+$.

Example 307 and Example 308: (1S or 1R)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane (E307, Enantiomer 1) and (1R or 1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane (E308, Enantiomer 2)

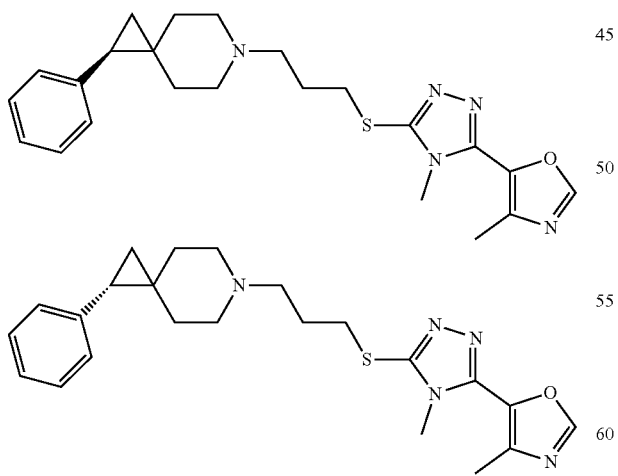

(1R/1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane (E306, 44 mg) was separated into the single enantiomers by preparative chiral HPLC.

Preparative Chromatography:

| | |
|---|---|
| Column | Chiralcel OJ-H (25 × 2 cm), 5 um |
| Mobile phase | n-Hexane/(Ethanol/Methanol 1/1 + 0.1% isopropylamine) 20/80 v/v |
| Flow rate (ml/min) | 20 ml/min |
| DAD detection | 220 nm |
| Loop | 2000 µL |
| Injection | 44 mg/injection | affording (1S or 1R)-6-(3-{[4-methyl-5-(4-methyl-1,3-oxazol-5-yl)-4H-1,2,4-triazol-3-yl]-sulfanyl}propyl)-1-phenyl-6-azaspiro[2.5]octane (E307, 18 mg), Enantiomer 1: ret. time 9.0 min, 100% ee, MS (m/z): 424.5 [MH]$^+$ and (1R or 1S)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane (E308, 19 mg), Enantiomer 2: ret. time 14.9 min, 100% ee. MS (m/z): 424.5 [MH]$^+$.

Example 309: (1S or 1R)-6-(3-{[4-methyl-5-(4-methyl-1,3-oxazol-5-yl)-4H-1,2,4-triazol-3-yl]sulfanyl}propyl)-1-phenyl-6-azaspiro[2.5]octane hydrochloride (E309, Enantiomer 1)

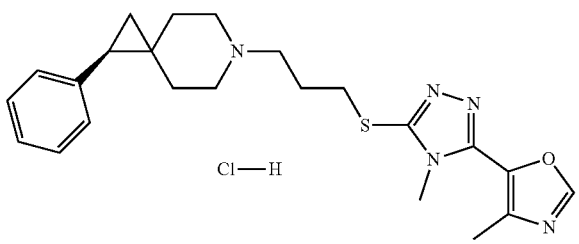 [SMILES: Cc1ncoc1-c1nnc(SCCCN2CCC3(CC2)C[C@@H]3c2ccccc2)n1C ; Cl]

(1S or 1R)-6-(3-{[4-methyl-5-(4-methyl-1,3-oxazol-5-yl)-4H-1,2,4-triazol-3-yl]sulfanyl}-propyl)-1-phenyl-6-azaspiro[2.5]octane (E307, 18 mg) was treated with 1.1 eq of HCl in Et$_2$O affording (1S or 1R)-6-(3-{[4-methyl-5-(4-methyl-1,3-oxazol-5-yl)-4H-1,2,4-triazol-3-yl]-sulfanyl}propyl)-1-phenyl-6-azaspiro[2.5]octane hydrochloric salt (Enantiomer 1, E309, 18.6 mg). MS (m/z): 424.1 [MH]$^+$.

Preparation 272: N-benzyl-2-chloroacetamide

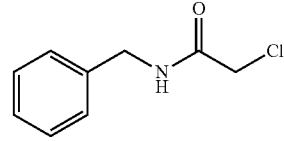 [SMILES: O=C(CCl)NCc1ccccc1]

2-chloroacetyl chloride (0.796 mL, 10 mmol) was slowly added dropwise to a mixture of benzylamine (0.906 mL, 8.3 mmol) and TEA (1.4 mL, 10 mmol) in anhydrous DCM (8 mL) at 0° C. The reaction mixture was warmed to room temperature and stirred for 4 hrs. The reaction mixture was washed with NaHCO$_3$, NH$_4$Cl and Brine. Organic phase was separated, dried over Na$_2$SO$_4$ and concentrated to obtain N-benzyl-2-chloroacetamide (p272, 1.58 g, y=98%) as grey solid. MS (m/z): 184.1 [MH]$^+$.

Preparation 273: [(benzyl carbamoyl)methyl]triphenylphosphonium chloride

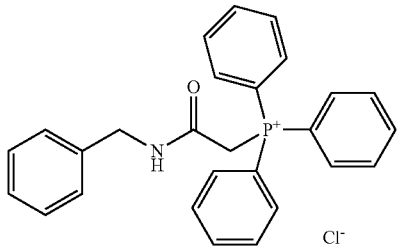 [SMILES: O=C(C[P+](c1ccccc1)(c1ccccc1)c1ccccc1)NCc1ccccc1 ; [Cl-]]

To a solution of N-benzyl-2-chloroacetamide (p272, 1.58 g, 8.17 mmol) in Toluene (10 mL) Triphenylphosphine (2.25 g, 8.58 mmol) was added and the reaction was stirred at reflux (110° C.) O/N. A precipitate formed. The reaction was cooled to RT, Et$_2$O was added and the suspension was filtered. The brown solid was washed with Et$_2$O and dried under high vacuum to obtain [(benzylcarbamoyl)methyl] triphenylphosphonium chloride (p273, 3.26 g, y=83%). MS (m/z): 410.4 [MH]$^+$.

Preparation 274: 1-benzyl-3-methylidenepiperidine-2,6-dione

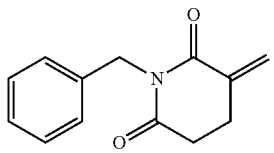 [SMILES: C=C1CCC(=O)N(Cc2ccccc2)C1=O]

Step a: To a solution of [(benzylcarbamoyl)methyl]triphenylphosphonium chloride (p273, 2.76 g, 6.15 mmol) in MeOH (44 mL) at 0° C. methoxysodium (831 mg, 15.38 mmol) was added and the reaction was stirred at 0° C. for 10'. Then the ice bath was removed and methyl acrylate (0.553 mL, 6.15 mmol) was added and the reaction was stirred at RT O/N. The day after the reaction was concentrated and the residue was dissolved in DCM and washed with water. Organic phase was dried over Na$_2$SO$_4$ and concentrated to obtain 1-benzyl-3-(triphenyl-λ$^5$-phosphanylidene)piperidine-2,6-dione (2.91 g) as brown oil that was used as crude in the next step.

Step b: To a solution of 1-benzyl-3-(triphenyl-λ$^5$-phosphanylidene)piperidine-2,6-dione (2.91 g, 6.28 mmol) in Toluene (60 mL), formaldehyde 37% in water (0.374 mL, 5.02 mmol) was added and the reaction was stirred at RT for 2 hrs. EtOAc and water were added, phases were separated, aqueous one was extracted twice with EtOAc. Combined organics were dried over Na$_2$SO$_4$ and concentrated. Crude material was purified by FC on silica gel (eluent from Cy to EtOAc 30%) to obtain 1-benzyl-3-methylidenepiperidine-2,6-dione (p274, 400 mg, y=30%) as yellow oil. MS (m/z): 216.2 [MH]$^+$.

Preparation 275 and 276: (1R,3S/1S,3R)-5-benzyl-1-[4-(trifluoromethyl)phenyl]-5-azaspiro[2.5]octane-4,6-dione (TRANS, p275) and (1S,3S/1R,3R)-5-benzyl-1-[4-(trifluoromethyl)phenyl]-5-azaspiro[2.5]octane-4,6-dione (CIS, p276)

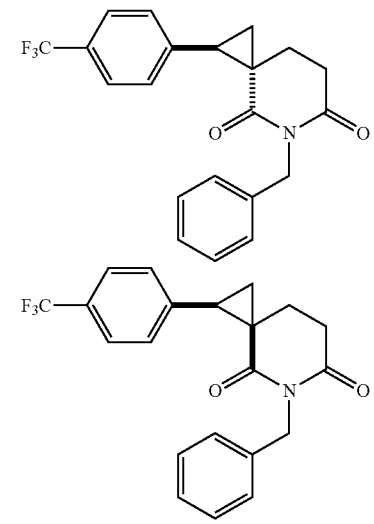

To a solution of {[4-(trifluoromethyl)phenyl] methylidene}hydrazine (p1, 350 mg, 1.86 mmol) in dioxane (4 mL) at 10° C., MnO$_2$ (1.62 g, 50 mmol) was added portionwise. The resulting mixture was stirred at RT for 30 min, then it was filtered over a pad of Celite washing with dioxane and this solution was added to a solution of 1-benzyl-3-methylidenepiperidine-2,6-dione (p274, 400 mg, 1.86 mmol) in dioxane (1.4 mL). The resulting orange solution was left stirring at RT O/N. Solvent was removed and crude material was purified by FC on silica cartridge (eluting from cHex to 30% EtOAc) to afford:

(1R,3S/1S,3R)-5-benzyl-1-[4-(trifluoromethyl)phenyl]-5-azaspiro[2.5]octane-4,6-dione (TRANS, p275, 347 mg, y=45%) as colourless gum and (1S,3S/1R,3R)-5-benzyl-1-[4-(trifluoromethyl)phenyl]-5-azaspiro[2.5]octane-4,6-dione (CIS, p276, 186 mg, y=21%) as wax. MS (m/z): 374.3 [MH]$^+$.

Preparation 277: (1R,3S/1S,3R)-5-benzyl-1-[4-(trifluoromethyl)phenyl]-5-azaspiro[2.5]octane (TRANS)

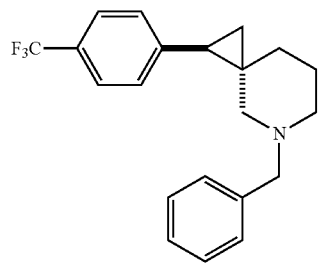

(1R,3S/1S,3R)-5-benzyl-1-[4-(trifluoromethyl)phenyl]-5-azaspiro[2.5]octane-4,6-dione (TRANS, p275, 347 mg, 0.93 mmol) was dissolved in THF (5 mL) and LiAlH$_4$ 1M in THF (1.86 mL, 1.86 mmol) was added dropwise. The resulting orange solution was heated at reflux (70° C.) for 1 h. Then it was cooled with an ice bath and quenched with Na₂SO₄ 10*H₂O until gas evolution ceased. It was filtered over a pad of celite washing with EtOAc, the solution was concentrated to afford (1R,3S/1S,3R)-5-benzyl-1-[4-(trifluoromethyl)phenyl]-5-azaspiro[2.5]octane (TRANS, p277, 260 mg, y=60%) as yellow oil that was used as such in the next step. MS (m/z): 346.4 [MH]⁺.

Preparation 278: (1R,3S/1S,3R)-1-[4-(trifluoromethyl)phenyl]-5-azaspiro[2.5]octane (TRANS)

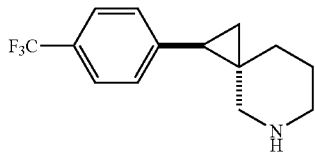

(1R,3S/1S,3R)-5-benzyl-1-[4-(trifluoromethyl)phenyl]-5-azaspiro[2.5]octane (TRANS, p277, 260 mg, 0.75 mmol) was dissolved in MeOH (3 mL) under N₂ and Ammonium formate (236 mg, 3.75 mmol) was added followed by Pd/C (25 mg). The resulting mixture was stirred at reflux for 1.5 h.

After cooling, it was filtered over a pad of Celite, the solvent was evaporated and the residue was partitioned between DCM and NaHCO₃ (aqueous phase with pH~8) and washed three times with DCM. Organic layers were combined, dried over a Phase Separator and concentrated. Crude material was purified with C18 cartridge (eluent from Water to ACN 30%). Fractions containing the product were combined and volatiles were evaporated. The remaining water was basified and extracted several times with DCM. Combined organics were dried over Na₂SO₄ and concentrated to obtain (1R,3S/1S,3R)-1-[4-(trifluoromethyl)phenyl]-5-azaspiro[2.5]octane (TRANS, p278, 50 mg, y=26%) as yellow oil. MS (m/z): 256.1 [MH]⁺.

Preparation 279: (1S,3S/1R,3R)-5-benzyl-1-[4-(trifluoromethyl)phenyl]-5-azaspiro[2.5]octane (CIS)

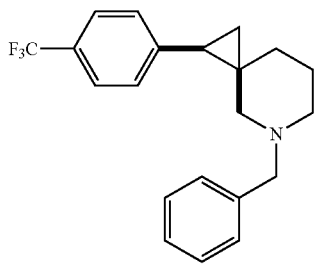

(1S,3S/1R,3R)-5-benzyl-1-[4-(trifluoromethyl)phenyl]-5-azaspiro[2.5]octane-4,6-dione (CIS, p276, 186 mg, 0.5 mmol) was dissolved in THF (3 mL) and LiAlH₄ 1M in THF (1 mL, 1 mmol) was added dropwise. The resulting orange solution was heated at reflux (70° C.) for 1 h. Then it was cooled with an ice bath and quenched with Na₂SO₄ 10*H₂O until gas evolution ceased. It was filtered over a pad of celite washing with EtOAc, the solution was concentrated to afford (1S,3S/1R,3R)-5-benzyl-1-[4-(trifluoromethyl)phenyl]-5-azaspiro[2.5]octane (CIS, p279, 153 mg, y=62%) as yellow oil that was used as such in the next step. MS (m/z): 346.4 [MH]⁺.

Preparation 280: (1S,3S/1R,3R)-1-[4-(trifluoromethyl)phenyl]-5-azaspiro[2.5]octane (CIS)

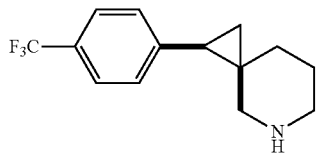

(1S,3S/1R,3R)-5-benzyl-1-[4-(trifluoromethyl)phenyl]-5-azaspiro[2.5]octane (CIS, p279, 153 mg, 0.44 mmol) was dissolved in MeOH (2 mL) under N₂ and ammonium formate (138 mg, 2.2 mmol) was added followed by Pd/C (15 mg). The resulting mixture was stirred at reflux for 1.5 h.

After cooling, it was filtered over a pad of Celite, the solvent was evaporated and the residue was partitioned between DCM and NaHCO₃ (aqueous phase with pH~7) and washed three times with DCM. Organic layers were combined, dried and concentrated. Crude material was purified with C18 cartridge (eluent from Water to ACN 30%) then further purified by FC on silica cartridge (eluent from DCM to MeOH) to obtain (1S,3S/1R,3R)-1-[4-(trifluoromethyl)phenyl]-5-azaspiro[2.5]octane (CIS, p280, 47 mg, y=36%) as white solid. MS (m/z): 256.1 [MH]⁺.

Example 310: (1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS, E310)

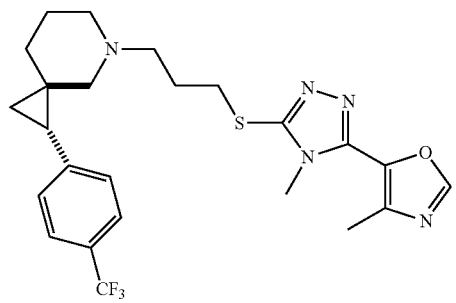 [SMILES: Cc1ncoc1-c1nnc(SCCCN2CCC[C@]3(C[C@H]3c3ccc(C(F)(F)F)cc3)C2)n1C]

The compound was prepared as in Example 1, reacting (1R,3S/1S,3R)-1-[4-(trifluoromethyl)phenyl]-5-azaspiro[2.5]octane (TRANS, p278, 49 mg, 0.19 mmol), 3-[(3-chloropropyl)sulfanyl]-4-methyl-5-(4-methyl-1,3-oxazol-5-yl)-4H-1,2,4-triazole (p148, 57 mg, 0.21 mmol), Na₂CO₃ (24 mg, 0.228 mmol) and NaI (34 mg, 0.228 mmol) in DMF (0.2 mL) affording (1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS, E310, 33 mg, y=34%). NMR: ¹H NMR (Acetone-d₆) δ: 8.25-8.29 (m, 1H), 7.59-7.64 (m, 2H), 7.43-7.52 (m, 2H), 3.81 (s, 3H), 3.31-3.47 (m, 2H), 2.44-2.55 (m, 3H), 2.42 (s, 3H), 2.25-2.39 (m, 3H), 2.14-2.22 (m, 1H), 1.95-2.03 (m, 2H), 1.15-1.48 (m, 4H), 0.93-1.14 (m, 3H). MS (m/z): 492.3 [MH]⁺.

Example 311 and Example 312: (1R,3S or 1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS, E311, Enantiomer 1) and (1S,3R or 1R,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS, E312, Enantiomer 2)

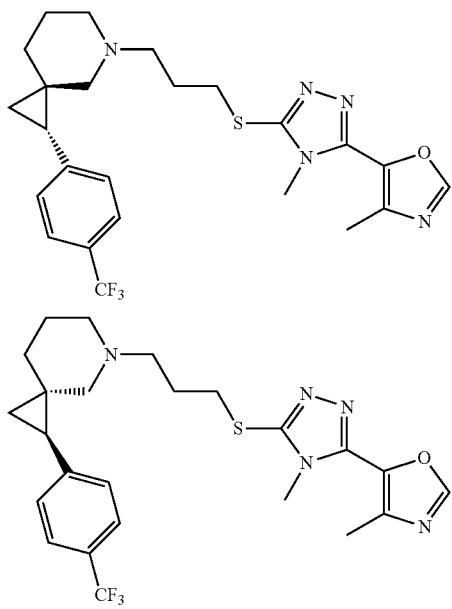

(1R,3S/1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS, E310, 33 mg) was separated into the single enantiomers by preparative chiral HPLC (SFC).

Preparative Chromatography:

| Column | Chiralcel OJ-H (25 × 2.0 cm), 5μ |
|---|---|
| Modifier | (Ethanol + 0.1% isopropylamine) 5% for 25 min -> 8% |
| Flow rate (ml/min) | 45 ml/min |
| Pressure (bar) | 120 |
| Temperature (° C.) | 38 |
| DAD detection | 220 nm |
| Loop | 500 μL |
| Injection | 5 mg/injection | affording (1R,3S or 1S,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS, E311, 10 mg), Enantiomer 1: ret. time 17.7 min, 100% ee. MS (m/z): 492.4 [MH]+ and (1S,3R or 1R,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (TRANS, E312, 10 mg).

Enantiomer 2: ret. time 20.6 min, 100% ee. MS (m/z): 492.5 [MH]+.

Example 313: (1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS, E313)

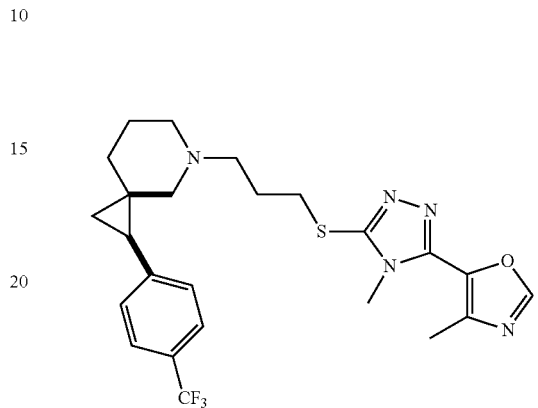

The compound was prepared as in Example 1, reacting (1S,3S/1R,3R)-1-[4-(trifluoromethyl)phenyl]-5-azaspiro[2.5]octane (CIS, p280, 46 mg, 0.18 mmol), 3-[(3-chloropropyl)sulfanyl]-4-methyl-5-(4-methyl-1,3-oxazol-5-yl)-4H-1,2,4-triazole (p148, 54 mg, 0.198 mmol), Na$_2$CO$_3$ (23 mg, 0.216 mmol) and NaI (32 mg, 0.216 mmol) in DMF (0.2 mL) affording (1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS, E313, 23 mg, y=25%). NMR: $^1$H NMR (Acetone-d$_6$) δ: 8.27 (s, 1H), 7.62 (d, 2H), 7.48 (br. s., 2H), 3.81 (s, 3H), 3.40 (br. s., 2H), 2.48 (br. s., 3H), 2.42 (s, 3H), 2.34 (br. s., 3H), 2.21 (br. s., 1H), 1.97 (br. s., 2H), 1.16-1.49 (m, 4H), 0.94-1.15 (m, 3H). MS (m/z): 492.5 [MH]+.

Example 314 and Example 315: (1S,3S or 1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS, E314, Enantiomer 1) and (1R,3R or 1S,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS, E315, Enantiomer 2)

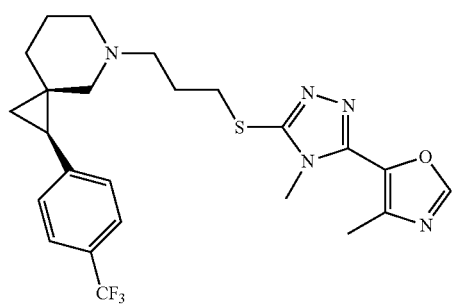 [SMILES: Cc1ncoc1-c1nnc(SCCCN2CCC[C@]3(C[C@@H]3c3ccc(C(F)(F)F)cc3)C2)n1C]

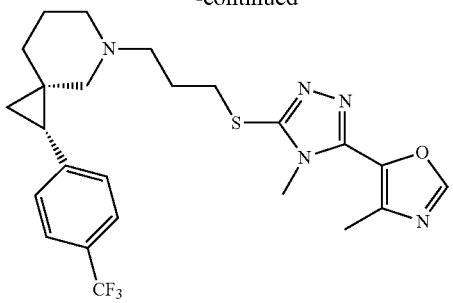

(1S,3S/1R,3R)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS, E313, 23 mg) was separated into the single enantiomers by preparative chiral HPLC.

Preparative Chromatography:

| Column | Chiralcel OJ-H (25 × 2.0 cm), 5μ |
|---|---|
| Mobile phase | n-Hexane/(Ethanol/Methanol 1/1 + 0.1% isopropylamine) 75/25% v/v |
| Flow rate (ml/min) | 17 ml/min |
| DAD detection | 220 nm |
| Loop | 1000 μL |
| Injection | 10.5 mg/injection | affording (1S,3S or 1R,3R)-5-(3-{[4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS, E314, 9.6 mg). Enantiomer 1: ret. time 7.1 min, 100% ee. MS (m/z): 492.5 [MH]$^+$ and (1R,3R or 1S,3S)-5-(3-{[4-methyl-5-(4-methyl-1,3-oxazol-5-yl)-4H-1,2,4-triazol-3-yl]sulfanyl}propyl)-1-[4-(trifluoromethyl)phenyl]-5-azaspiro[2.5]octane (CIS, E315, 7.9 mg). Enantiomer 2: ret. time 8.5 min, 100% ee. MS (m/z): 492.4 [MH]$^+$.

Preparation 281: 3-chloro-1-phenylpropan-1-ol

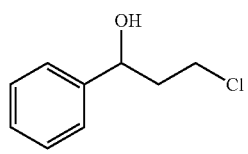 [SMILES: OC(CCCl)c1ccccc1]

To a stirred solution of 3-chloro-1-phenylpropan-1-one (7.80 g, 46.26 mmol) in THF (35 mL) and EtOH (35 mL), at −10° C. and under a nitrogen atmosphere, sodium borohydride (2.20 g, 48.83 mmol) was added portion-wise over 10 min. The reaction mixture was stirred for additional 10 min at −5° C. then cautiously poured into a stirred mixture of saturated ammonium chloride (85 mL) and ice (40 g). The mixture was extracted with ether twice, the organic phase was dried and the solvent removed under reduced pressure. The crude material was purified by FC on silica gel (eluting with Cy/EA from 100/0 to 95/5) to give the title compound 3-chloro-1-phenylpropan-1-ol (p281, 7.50 g, y=95%) as pale yellow oil. NMR: $^1$H NMR (CDCl$_3$) δ: 7.39 (d, 5H), 4.91-5.01 (m, 1H), 3.70-3.83 (m, 1H), 3.59 (s, 1H), 2.20-2.32 (m, 1H), 2.11 (d, 1H)

Preparation 282: (1-bromo-3-chloropropyl)benzene

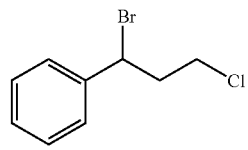 [SMILES: ClCCC(Br)c1ccccc1]

A mixture of 3-chloro-1-phenylpropan-1-ol (p281, 7.50 g, 43.95 mmol) and 48% aqueous hydrobromic acid (98 mL) was stirred at RT for 3 hrs, then cautiously poured into a mixture of potassium carbonate (27 g) and 180 g of ice. Potassium carbonate was cautiously added up to neutral pH. The resulting mixture was extracted twice with ether, the organic phase was dried and the solvent removed under vacuum. The crude material was purified by FC on silica gel (eluting with Cy) affording (1-bromo-3-chloropropyl)benzene (p282, 7.49 g, y=73%) as colourless oil. NMR: $^1$H NMR (CDCl$_3$) δ: 7.32-7.50 (m, 5H), 5.24 (m, 1H), 3.75 (m, 1H), 3.61 (m, 1H), 2.67-2.80 (m, 1H), 2.45-2.58 (m, 1H)

Preparation 283: 1,1-dimethyl 2-phenylcyclobutane-1,1-dicarboxylate

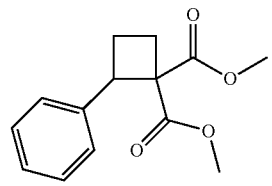 [SMILES: COC(=O)C1(C(=O)OC)CCC1c1ccccc1]

A stirred solution of (1-bromo-3-chloropropyl)benzene (p282, 4.78 g, 20.47 mmol) and dimethyl malonate (2.97 g, 22.52 mmol) in anhydrous dioxane (60 mL) and under a nitrogen atmosphere, was brought to 90° C., then 60% NaH (0.86 g, 21.49 mmol) was cautiously added portion-wise over 10 min and the reaction was heated to reflux. After 1 h, the reaction temperature was allowed to reach about 90° C. and additional 60% NaH (0.86 g, 21.49 mmol) was added portion-wise over 10 min and the reaction mixture was brought to reflux and stirred overnight. After allowing the mixture to reach RT, it was filtered, the solid was washed with ether and the filtrate was concentrated under reduced pressure. The crude material was purified by FC on silica gel (eluting with Cy/EA from 100/0 to 93/7) then further purified inverse FC (C18, eluting with MeCN+0.1% formic acid/water+0.1% formic acid from 0/100 to 70/30) affording 1,1-dimethyl 2-phenylcyclobutane-1,1-dicarboxylate (p283, 2.36 g, y=45%) as colourless oil. NMR: $^1$H NMR (CDCl$_3$) δ: 7.22-7.33 (m, 5H), 4.39 (m, 1H), 3.80 (s, 3H), 3.26 (s, 3H), 2.59-2.76 (m, 2H), 2.16-2.34 (m, 2H)

Preparation 284: methyl 2-phenylcyclobutane-1-carboxylate

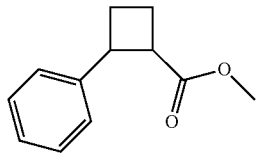

A stirred mixture of 1,1-dimethyl 2-phenylcyclobutane-1,1-dicarboxylate (p283, 2.17 g, 8.74 mmol), LiCl (0.79 g, 18.62 mmol) and water (0.17 mL) in DMSO (12 mL) was brought to reflux and stirred for 1.5 h. After cooling to RT, this mixture was diluted with ether (55 mL) and cyclohexane (23 mL) then was washed sequentially with brine, water (3 times) and brine. The organic phase was dried and the solvent was removed under reduced pressure. The residue was purified by FC on silica gel (eluting with Cy/EA from 100/0 to 97/3) to give methyl 2-phenylcyclobutane-1-carboxylate (p284, 1.07 g, y=64%) as colourless oil. MS (m/z): 191.2 [MH]$^+$.

Preparation 285: methyl 2-phenyl-1-(prop-2-en-1-yl)cyclobutane-1-carboxylate

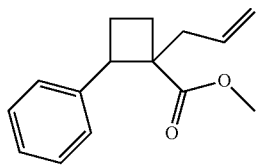 [SMILES: C=CCC1(C(=O)OC)CCC1c1ccccc1]

To a solution of methyl 2-phenylcyclobutane-1-carboxylate (p284, 1.07 g, 5.62 mmol) in THF (14 mL) at −78° C. under N$_2$, 1M/THF LHMDS (7.3 mL, 7.30 mmol) was added dropwise and the reaction was stirred at this temperature for 30'. Then allyl bromide (0.73 mL, 8.44 mmol) was added dropwise and the reaction was allowed to reach RT and stirred overnight. The reaction mixture was treated with aqueous saturated NH$_4$Cl and diluted with EA. The organic phase was washed with water, dried and the solvent removed under reduced pressure. The crude material was purified by FC on silica gel (eluting with Cy/EA from 100/0 to 95/5) affording methyl 2-phenyl-1-(prop-2-en-1-yl)cyclobutane-1-carboxylate (p285, 0.71 g, y=55%) as pale yellow oil. MS (m/z): 232.2 [MH]$^+$.

Preparation 286: methyl 1-(2-oxoethyl)-2-phenylcyclobutane-1-carboxylate

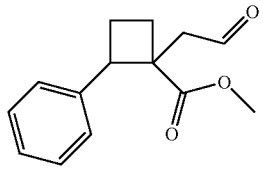 [SMILES: COC(=O)C1(CC=O)CCC1c1ccccc1]

A slow stream of O$_3$ in O$_2$ was passed through a −78° C. cooled solution of methyl 2-phenyl-1-(prop-2-en-1-yl)cyclobutane-1-carboxylate (p285, 0.71 g, 3.08 mmol) in DCM (10 mL) until a pale blue color persisted (30 min). Excess of O$_3$ was purged by nitrogen bubbling, and then a solution of TPP (0.89 g, 3.39 mmol) in DCM (2 mL) was added. The solution was allowed to reach 25° C. and it was stirred for 2 hrs. The solvent was removed in vacuo and the crude material was purified by FC on silica gel (eluting with Cy/EA from 100/0 to 70/30) to give methyl 1-(2-oxoethyl)-2-phenylcyclobutane-1-carboxylate (p286, 0.36 g, y=51%) as colorless oil. MS (m/z): 233.2 [MH]$^+$.

Preparation 287: 6-benzyl-1-phenyl-6-azaspiro[3.4]octan-5-one

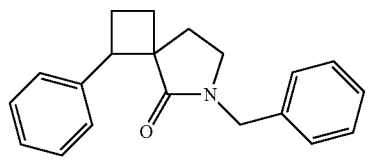 [SMILES: O=C1N(Cc2ccccc2)CCC12CCC2c1ccccc1]

To a solution of methyl 1-(2-oxoethyl)-2-phenylcyclobutane-1-carboxylate (p286, 360 mg, 1.55 mmol) and benzylamine (0.18 mL, 1.63 mmol) in THF (9.0 mL) was added sodium triacetoxyborohydride (493 mg, 2.33 mmol). The reaction mixture was stirred at RT O/N and then quenched with saturated aqueous NaHCO$_3$. The mixture was extracted with DCM twice, the organic phase was dried and the solvent removed under reduced pressure. The residue was dissolved in THF (30 mL) and the resulting solution was refluxed for 8 h. The reaction mixture was concentrated under vacuum and the residue was purified by FC on NH column (eluting with Cy/EA from 100/0 to 70/30) then loaded on a SCX cartridge (washing with MeOH and eluting with 2N NH$_3$/MeOH) affording 6-benzyl-1-phenyl-6-azaspiro[3.4]octan-5-one (p287, 124 mg, y=27%) as white foam. MS (m/z): 292.3 [MH]$^+$.

Preparation 288: 6-benzyl-1-phenyl-6-azaspiro[3.4]octane

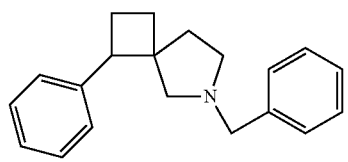 [SMILES: c1ccc(CN2CCC3(CCC3c3ccccc3)C2)cc1]

To a stirred solution of 6-benzyl-1-phenyl-6-azaspiro[3.4]octan-5-one (p287, 124 mg, 0.43 mmol) in THF (4 mL), at 0° C. and under a nitrogen atmosphere, 1M/THF LiAlH$_4$ (0.55 mL, 0.55 mmol) was added drop-wise. The ice-bath was removed and the resulting reaction mixture was allowed to reach RT then refluxed for 1 h. The mixture was then cooled to 0° C. and quenched with Na$_2$SO$_4$*10H$_2$O, diluted with EA, filtered over sodium sulphate and the solvent was removed under vacuum to give 6-benzyl-1-phenyl-6- azaspiro[3.4]octane (p288, 120 mg, y=quant.) that was used as such in the next step. MS (m/z): 278.3 [MH]⁺.

Preparation 289: 1-phenyl-6-azaspiro[3.4]octane

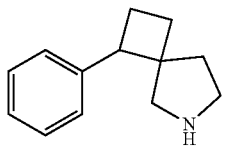 [SMILES: c1ccc(C2CCC23CCNC3)cc1]

To a solution of 6-benzyl-1-phenyl-6-azaspiro[3.4]octane (p288, 120 mg, 0.43 mmol) in MeOH (5 mL), HCOONH₄ (164 mg, 2.60 mmol) and 10% Pd/C (52 mg) were added at RT then the mixture was stirred at reflux for 2 hrs. The reaction mixture was filtered over a pad of celite and the solvent removed under vacuum. The residue was dissolved in DCM, the solution washed with saturated sodium bicarbonate, dried and the solvent removed under vacuum. The residue was dissolved in MeOH and the solution was loaded on a SCX cartridge (washing with MeOH and eluting with 2N/NH₃ in MeOH) affording 1-phenyl-6-azaspiro[3.4]octane (p289, 63 mg, y=78%) as colorless oil. MS (m/z): 188.2 [MH]⁺.

Example 316: 6-(3-{[4-methyl-5-(4-methyl-1,3-oxazol-5-yl)-4H-1,2,4-triazol-3-yl]-sulfanyl}propyl)-1-phenyl-6-azaspiro[3.4]octane (E316)

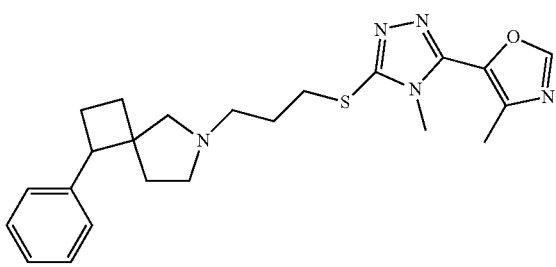 [SMILES: Cc1ncoc1-c1nnc(SCCCN2CCC3(CCC3c3ccccc3)C2)n1C]

The compound was prepared as in Example 1, reacting 1-phenyl-6-azaspiro[3.4]octane (p289, 58 mg, 0.31 mmol), 3-[(3-chloropropyl)sulfanyl]-4-methyl-5-(4-methyl-1,3-oxazol-5-yl)-4H-1,2,4-triazole (p148, 93 mg, 0.34 mmol), Na₂CO₃ (40 mg, 0.37 mmol) and NaI (51 mg, 0.34 mmol) in DMF (0.35 mL) affording the title compound 6-(3-{[4-methyl-5-(4-methyl-1,3-oxazol-5-yl)-4H-1,2,4-triazol-3-yl]sulfanyl}propyl)-1-phenyl-6-azaspiro[3.4]octane (E316, 67 mg, y=51%) as diastereoisomeric mixture. NMR: ¹H NMR (CDCl₃) δ: 7.95 (s, 1H), 7.30-7.38 (m, 2H), 7.18-7.26 (m, 3H), 3.67-3.72 (s, 3H), 3.54 (m, 1H), 3.08-3.20 (m, 2H), 2.65-2.97 (m, 2H), 2.55 (s, 3H), 2.51 (d, 2H), 2.31-2.41 (m, 1H), 2.02-2.30 (m, 7H), 1.94 (d, 2H). MS (m/z): 424.4 [MH]⁺.

Example 317, Example 318, Example 319 and Example 320: (1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane: E317 (Diastereomer 1 Enantiomer 1); E318 (Diastereomer 1 Enantiomer 2); E319 (Diastereomer 2 Enantiomer 1); E320 (Diastereomer 2 Enantiomer 2)

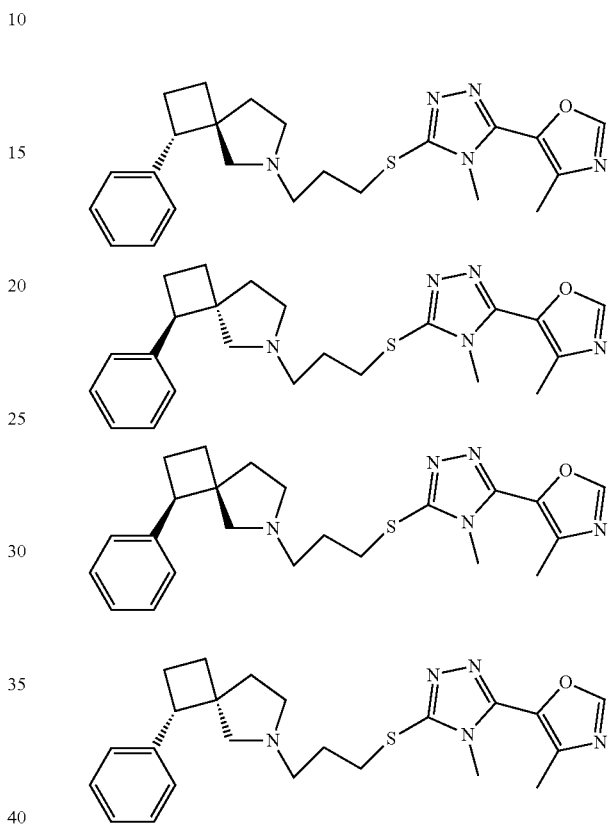

6-(3-{[4-methyl-5-(4-methyl-1,3-oxazol-5-yl)-4H-1,2,4-triazol-3-yl]sulfanyl}propyl)-1-phenyl-6-azaspiro[3.4]octane (E316, 66 mg) was separated into the single enantiomers of each diastereomer by preparative chiral HPLC.

Preparative Chromatography:

| | |
|---|---|
| Column | Chiralpak AD-H (25 × 2.0 cm), 5µ |
| Mobile phase | Ethanol + 0.1% isopropylamine 20% |
| Flow rate (ml/min) | 45 ml/min |
| DAD detection | 220 nm |
| Loop | 500 µL |
| Injection | 11 mg/injection | affording 18 mg E317 (Diastereomer 1 Enantiomer 1): ret. time 10.1 min, 98.2% ee, MS (m/z): 424.4 [MH]⁺ and 23 mg E318 (Diastereomer 1 Enantiomer 2): ret. time 11.9 min, 98.2% ee, MS (m/z): 424.4 [MH]⁺ and 2.3 mg E319 (Diastereomer 2 Enantiomer 1): ret. time 16.7 min, 100% ee, MS (m/z): 424.4 [MH]⁺ and 2 mg E320 (Diastereomer 2 Enantiomer 2): ret. time 21 min, 100% ee, MS (m/z): 424.4 [MH]⁺.

Example 321: (1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane hydrochloride (E321, Diastereomer 1 Enantiomer 2)

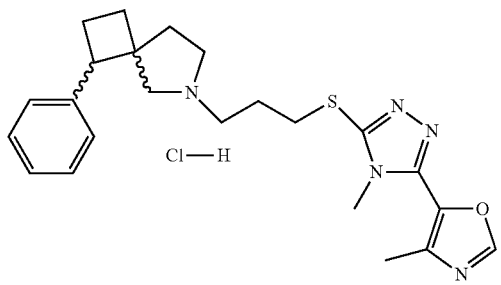

(1R,4S or 1S,4R or 1S,4S or 1R,4R)-6-(3-{[4-methyl-5-(4-methyl-1,3-oxazol-5-yl)-4H-1,2,4-triazol-3-yl]sulfanyl}propyl)-1-phenyl-6-azaspiro[3.4]octane (E318, Diastereomer 1 Enantiomer 2, 23 mg) was treated with 1.1 eq of HCl in Et$_2$O affording the corresponding hydrochloric salt (E321, Diastereomer 1 Enantiomer 2, 24 mg). MS (m/z): 424.4 [MH]$^+$.

Biological Test Methods

[$^3$H]-Spiperone Binding Assay at hD$_3$ and hD$_4$ recombinant receptors. CHO cells transiently transfected with human dopamine type 3 or 4 receptors (CHO-hD$_3$ or CHO-hD$_4$, respectively), were re-suspended in 20 mM HEPES, 2 mM EDTA (pH 7.4), homogenised and centrifuged at 40,000 g (20 min, 4° C.). After re-suspension, homogenization and centrifugation as above, the final pellet was re-suspended in 20 mM HEPES, 100 mM NaCl, 10 mM MgCl$_2$, 1 mM EDTA (pH 7.4) and aliquots were kept at −80° C. [$^3$H]-Spiperone Binding experiments were performed in 96 deep-well polypropylene plates in 50 mM Tris/HCl, 120 mM NaCl, 5 mM KCl, 5 mM MgCl$_2$ (pH 7.4). Compounds of invention were serially diluted in DMSO at 100 fold final concentrations in the assay (1% DMSO final in the assay). Displacement was performed in the presence of 0.3 nM [$^3$H]-Spiperone. The reaction was initiated by the addition of membrane suspension (4 µg and 12 µg of protein for CHO-hD$_3$- and CHO-hD$_4$ membranes, respectively) and lasted for 90 or 100 min (for hD$_3$ or hD$_4$ membranes, respectively) at 23° C. in a final volume of 500 µl. Non specific binding (NSB) was determined in the presence of 1 µM Spiperone. The binding reaction was stopped by rapid filtration through GF/B filterplates pre-soaked in 0.5% polyetylenimmine (PEI) using a Packard cell harvester. After washing with ice-cold 0.9% NaCl, the plate was left to dry before the addition of Microscint 20 (50 µl/well, PerkinElmer). Radioactivity was counted with a TopCount (PerkinElmer).

Data were analysed by non-linear regression analysis using GraphPad Prism 5.0 (GraphPad Software). Saturation binding experiments were performed similar to the competition binding experiments using a radioligand concentrations ranging from 0.015 to 4.0 nM. Ref: Mackenzie R. G. et al. (1994). *Characterization of the human dopamine D3 receptor expressed in transfected cell lines. Eur. J. Pharmacol.*, 266:79-8

[$^{125}$I]-7OH-PIPAT Binding Assay at rat native D$_3$ receptor on membranes from rat ventral striatum. Homogenates from frozen rat brain ventral striatum (nucleus accumbens and olfactory tubercles), were prepared as described by Burris et al. (1994). [$^{125}$I]-7OH-PIPAT binding assay at D$_3$ receptors was performed in 50 mM Tris-HCl (pH 7.0), 50 mM NaCl, 100 µM Gpp(NH)p (Guanosine 5'-[β,γ-imido]triphosphate) and 0.02% BSA, i.e. conditions which inhibit the [$^{125}$I]-7-OH-PIPAT binding to D$_2$ and 5HT$_{1A}$ receptors. Compounds of invention were serially diluted in DMSO at 100 fold final concentrations in the assay (1% DMSO final in the assay). Displacement experiments were performed in the presence of 0.2 nM [$^{125}$I]-7OH-PIPAT. The reaction, carried out in a final volume of 200 µl, was initiated by the addition of membrane suspension (about 20 µg/well protein) and lasted 45 min at 37° C. Non specific binding (NSB) was determined in the presence of 1 µM SB277011A. The binding reaction was stopped by rapid filtration through GF/C filterplates pre-soaked in 0.5% polyetylenimmine (PEI) using a Packard cell harvester. After washing with ice-cold 50 mM Tris (pH 7.4) and addition of Microscint 20 (50 µl/well, PerkinElmer), radioactivity was counted with a TopcCount (PerkinElmer). Data were analyzed by non-linear regression analysis using GraphPad Prism 5.0 (GraphPad Software). Ref: Burris, K. D.; Filtz, T. M; Chumpradit, S.; Kung, M. P.; Foulon, C.; Hensler, J. G.; Kung, H. F.; Molinoff P. B. *Characterization of* [125I](R)-trans-7-hydroxy-2-[N-propyl-N-(3'-iodo-2'-propenyl)amino]tetralin binding to dopamine D3 receptors in rat olfactory tubercle. J. Pharmacol. Exp. Ther. 1994, 268, 935-942.

[$^3$H]-Spiperone Binding Assay at hD$_2$ recombinant receptor. CHO cells stably expressing human dopamine receptor type 2, long variant (hD$_{2L}$), coupled to Gα16 protein (CHO-Gα16-hD$_{2L}$) were re-suspended in 20 mM HEPES, 2 mM EDTA (pH 7.4), homogenised and centrifuged at 40,000 g (20 min, 4° C.). After re-suspension, homogenization and centrifugation as above, the final pellet was re-suspended in 20 mM HEPES, 100 mM NaCl, 10 mM MgCl$_2$, 1 mM EDTA (pH 7.4) and aliquots were kept at −80° C. [$^3$H]-Spiperone Binding experiments were performed in 96 deep-well polypropylene plates in 50 mM Tris/HCl, 120 mM NaCl, 5 mM KCl, 5 mM MgCl$_2$ (pH 7.4). Compounds of invention were serially diluted in DMSO at 100 fold final concentrations in the assay (1% DMSO final in the assay). Displacement was performed in the presence of 0.08 nM [$^3$H]-Spiperone. The reaction was initiated by the addition of membrane suspension (2 µg of protein for CHO-hD$_2$ membranes) and lasted for 120 min at 23° C. in a final volume of 1000 µl. Non specific binding (NSB) was determined in the presence of 0.1 µM Spiperone. The binding reaction was stopped by rapid filtration through GF/B filterplates pre-soaked in 0.5% polyetylenimmine (PEI) using a Packard cell harvester. After washing with ice-cold 0.9% NaCl, the plate was left to dry before the addition of Microscint 20 (50 µl/well, PerkinElmer). Radioactivity was counted with a TopCount (PerkinElmer). Data were analysed by non-linear regression analysis using GraphPad Prism 5.0 (GraphPad Software) or XLfit Version 5.2.0.0 (Copyright © 2006-2009 ID Business Solutions Ltd). Saturation binding experiments were performed similar to the competition binding experiments using a radioligand concentrations ranging from 0.011 to 3.0 nM. Ref: Durcan M. J. et al. (1995). Is Clozapine selective for the dopamine D4 receptor? Life Sciences, 57: 275-283. Petrus J. et al. (2001). Real-time analysis of dopamine: antagonist interactions at recombinant human D2long receptor upon modulation of its activation state. Brit. J. Pharmacol. 134, 88±97.

Functional Calcium Assay at hD$_2$ recombinant receptor. CHO cells stably expressing human dopamine receptor type 2, long variant (hD$_{2L}$), coupled to Gα16 protein (CHO- Gα16-hD$_{2L}$) were seeded into black walled clear-base 384-well plates at a density of 8,000 cells per well and grown overnight at 37° C. After washing with the assay buffer (20 mM HEPES, 145 mM NaCl, 5 mM KCl, 5.5 mM glucose, 1 mM MgCl$_2$ and 2 mM CaCl$_2$, pH 7.4) containing 2.5 mM Probenecid, cells were incubated with the cytoplasmic Ca$^{2+}$ probe Fluo-4 AM at 1 μM (final concentration), 37° C. for 60 min. Plates were washed three times as above and placed into a Fluorometric Imaging Plate Reader (FLIPR Tetra, Molecular Devices) to monitor cell fluorescence (ex=470-495 nm, em=515-575 nm) before and after the addition of different concentrations of test compounds. Compounds of invention were dissolved in DMSO and 200-fold diluted with assay buffer plus 0.01% Pluronic F-127. Cells were exposed first to test compounds for 10 min, then to a submaximal concentration of the hD$_2$ receptor agonist dopamine (EC$_{80}$, 50-140 nM). The fluorescence before compound addition (baseline) and before and after addition of agonist challenge was monitored. The peak of Ca$^{2+}$ stimulation (baseline subtracted) was plotted versus the concentration of test compound and the curve fitted using a four-parameter logistic equation (XLfit) to assess the agonist/antagonist potency and maximal response.

Preparation 290: (1R,3S)-5-(4-methylbenzenesulfonyl)-1-[4-(trifluoromethyl)phenyl]-5-azaspiro[2.4]heptane

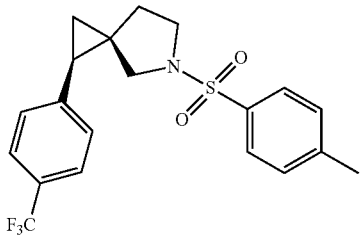 [SMILES: Cc1ccc(S(=O)(=O)N2CC[C@]3(C[C@@H]3c3ccc(C(F)(F)F)cc3)C2)cc1]

(1R,3S)-[4-(trifluoromethyl)phenyl]-5-azaspiro[2.4]heptane (p15, Enantiomer 1, 25 mg, 0.1 mmol) in dichloromethane (3 mL) was stirred at 0° C.; triethylamine (0.022 mL, 0.15 mmol) was added, followed by 4-methylbenzenesulfonyl chloride (21 mg, 0.11 mmol) and then the mixture was slowly warmed to room temperature and stirred at the same temperature for 1 h. DCM was added, washed with water and brine, then dried with Na$_2$SO$_4$, filtered and concentrated. The residue was chromatographed by FC on silica gel (eluent from cHex to 40% Ethyl acetate) affording (1R,3S)-5-(4-methylbenzenesulfonyl)-1-[4-(trifluoromethyl)phenyl]-5-azaspiro[2.4]heptane (p290, 33 mg, y=83%) as white solid.

The latter was suspended in 0.3 mL of EtOH and then heated until dissolution. After slow cooling to RT, crystallization was observed. Crystals were filtered and used for the molecular and crystal structure determination by single crystal high-resolution X-ray diffraction to determine the absolute stereochemistry.

The X-ray data collection was performed on a plate-like crystal of approximate dimensions 0.26×0.22×0.02 mm mounted on a glass capillary. The X-ray intensities were measures on a Bruker Smart system equipped with an APEXII CCD area detector.

The structure was solved by direct methods using the program Sir2011, and was refined with the program SHELXL-2014. Crystal data are reported below:

| | |
|---|---|
| Empirical formula | C$_{80}$H$_{80}$F$_{12}$N$_4$O$_8$S$_4$ |
| Formula weight | 1581.72 |
| Temperature/K | 293 |
| Crystal system | Orthorhombic |
| Space group | P2$_1$2$_1$2$_1$ |
| a/Å | 11.75(5) |
| b/Å | 17.30(7)) |
| c/Å | 41.04(9) |
| α/° | 90 |
| β/° | 90 |
| γ/° | 90 |
| Volume/Å$^3$ | 8342(52) |
| Z, Z' | 16, 4 |
| ρ$_{calc}$g/cm$^3$ | 1.259 |
| μ/mm$^{-1}$ | 0.194 |
| F(000) | 3296 |
| Crystal size/mm$^3$ | 0.26 × 0.22 × 0.02 |
| Radiation | MoKα (λ = 0.71073) |
| 2Θ range for data collection/° | 2.540 to 34.540 |
| Index ranges | −9 ≤ h ≤ 9, −14 ≤ k ≤ 12, −33 ≤ l ≤ 28 |
| Reflections collected | 17849 |
| Independent reflections | 4938 [R$_{int}$ = 0.1815, R$_{sigma}$ = 0.1678] |
| Data/restraints/parameters | 4938/74/686 |
| Goodness-of-fit on F$^2$ | 1.003 |
| Final R indexes [I >= 2σ (I)] | R$_1$ = 0.0786, wR$_2$ = 0.1598 |
| Final R indexes [all data] | R$_1$ = 0.1766, wR$_2$ = 0.2100 |
| Largest diff. peak/hole/e Å$^{-3}$ | 0.20/−0.20 |
| Flack parameter | 0.1(2) |

The compound crystallizes in the chiral orthorhombic space group P2$_1$2$_1$2$_1$. The asymmetric unit comprises four molecules. The Flack parameter for the present structure is 0.094(322) by classical fit to all intensities and 0.064(210) from 639 selected quotients (Parson's method) strongly supporting the present absolute structure determination.

According to the absolute structure determination, the configuration is 1R, 3S. MS (m/z): 396.4 [MH]$^+$.

Preparation 291: (1S,3R)-5-(4-methylbenzenesulfonyl)-1-[4-(trifluoromethyl)phenyl]-5-azaspiro[2.4]heptane

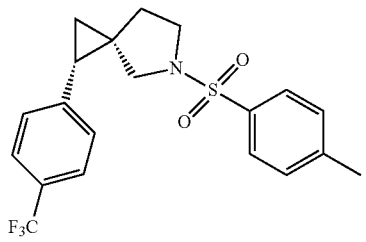 [SMILES: Cc1ccc(S(=O)(=O)N2CC[C@@]3(C[C@H]3c3ccc(C(F)(F)F)cc3)C2)cc1]

(1R,3S/1S,3R)-1-[4-(trifluoromethyl)phenyl]-5-azaspiro[2.4]heptane (CIS, p14, 3 g) was submitted to chiral Prep HPLC (SFC) to separate enantiomers:

Preparative Chromatography:

| | |
|---|---|
| Column | Chiralpak AD-H (25 × 2.1 cm), 5μ |
| Modifier | (Ethanol + 0.1% isopropylamine) 7% |
| Flow rate (ml/min) | 45 ml/min |
| Pressure (bar) | 120 |
| Temperature (° C.) | 38 |
| DAD detection | 220 nm |
| Loop | 900 μL |
| Injection | 53.3 mg/injection | affording: (1R,3S)-1-[4-(trifluoromethyl)phenyl]-5-azaspiro[2.4]heptane (1.1 g), Enantiomer 1: Ret. Time 7.9 min, 100% ee and (1S,3R)-1-[4-(trifluoromethyl)phenyl]-5-azaspiro[2.4]heptane (840 mg), Enantiomer 2: Ret. Time 10.2 min, 100% ee. (1S,3R)-[4-(trifluoromethyl)phenyl]-5-azaspiro[2.4]heptane (Enantiomer 2, 840 mg, 3.48 mmol) in dichloromethane (15 mL) was stirred at 0° C.; triethylamine (0.73 mL, 5.22 mmol) was added, followed by 4-methyl-benzenesulfonyl chloride (730 mg, 3.83 mmol) and then the reaction mixture was slowly warmed to room temperature and stirred at that temperature for 2 hrs. DCM was added, washed with water and brine, then dried with $Na_2SO_4$, filtered and concentrated. The residue was chromatographed by FC on silica gel (eluent from cHex to 40% Ethyl acetate) affording (1S,3R)-5-(4-methylbenzenesulfonyl)-1-[4-(trifluoromethyl)phenyl]-5-azaspiro[2.4]heptane (p291, 1.1 g, y=80%) as white solid.

100 mg of (1S,3R)-5-(4-methylbenzenesulfonyl)-1-[4-(trifluoromethyl)phenyl]-5-azaspiro[2.4]heptane were suspended in 1 mL of EtOH and then heated until dissolution. After slow cooling to RT, the solution was left standing at RT for 3 days after which time crystallization was observed. Crystals were filtered and used for the molecular and crystal structure determination by single crystal high-resolution X-ray diffraction to determine the absolute stereochemistry.

The X-ray data collection was performed on a plate-like crystal of approximate dimensions 0.31×0.24×0.07 mm mounted on a glass capillary. The X-ray intensities were measures on a Bruker Smart system equipped with an APEXII CCD area detector.

The structure was solved by direct methods using the program Sir2011, and was refined with the program SHELXL-2014. Crystal data are reported below.

| | |
|---|---|
| Empirical formula | $C_{80}H_{80}F_{12}N_4O_8S_4$ |
| Formula weight | 1581.72 |
| Temperature/K | 293 |
| Crystal system | Orthorhombic |
| Space group | $P2_12_12_1$ |
| a/Å | 11.567(7) |
| b/Å | 17.155(9) |
| c/Å | 40.16(2) |
| α/° | 90 |
| β/° | 90 |
| γ/° | 90 |
| Volume/Å$^3$ | 7970(8) |
| Z, Z' | 16, 4 |
| $\rho_{calc}$g/cm$^3$ | 1.318 |
| μ/mm$^{-1}$ | 0.203 |
| F(000) | 760.0 |
| Crystal size/mm$^3$ | 0.31 × 0.24 × 0.07 |
| Radiation | MoKα (λ = 0.71073) |
| 2Θ range for data collection/° | 1.291 to 38.640 |
| Index ranges | −10 ≤ h ≤ 10, −15 ≤ k ≤ 15, −37 ≤ l ≤ 37 |
| Reflections collected | 47185 |
| Independent reflections | 6706 [$R_{int}$ = 0.0941, $R_{sigma}$ = 0.0494] |
| Data/restraints/parameters | 6706/56/926 |
| Goodness-of-fit on F$^2$ | 1.013 |
| Final R indexes [I >= 2σ (I)] | $R_1$ = 0.0623, $wR_2$ = 0.1419 |
| Final R indexes [all data] | $R_1$ = 0.0993, $wR_2$ = 0.1665 |
| Largest diff. peak/hole/e Å$^{-3}$ | 0.26/−0.24 |
| Flack parameter | −0.01(6) |

The compound crystallizes in the chiral orthorhombic space group $P2_12_12_1$. The asymmetric unit comprises four molecules. The Flack parameter for the present structure is 0.000(199) by classical fit to all intensities and −0.005(57) from 1566 selected quotients (Parson's method) strongly supporting the present absolute structure determination. According to the absolute structure determination, the configuration is 1S, 3R. MS (m/z): 396.4 [MH]$^+$.

The compounds of the invention listed above have pKi values within the range of 7.0-10.5 at the dopamine D3 receptor. pKi results are only estimated to be accurate to about ±0.3-0.5.

The compounds of the invention listed above have selectivity over D2 preferably greater than 10 fold.

The following Table reports the values of some of the Examples:

| EX | $D_3$ pKi | $D_2$ fpKi | $D_2$ pKi |
|---|---|---|---|
| 2 | 7.11 | 7.02 | |
| 3 | 7.65 | 6.88 | |
| 5 | 7.02 | 6.28 | |
| 7 | 7.34 | 5.87 | |
| 9 | 8.40 | 6.41 | |
| 10 | 7.91 | 6.73 | |
| 11 | 8.78 | 6.46 | |
| 12 | 9.2 | 7.13 | 6.67 |
| 14 | 7.6 | 5.75 | |
| 15 | 7.55 | 5.38 | |
| 16 | 7.38 | 5.84 | |
| 17 | 7.75 | 5.84 | |
| 19 | 8.26 | 6.17 | 6.10 |
| 20 | 8.13 | 6.14 | |
| 21 | 8.03 | 6.42 | |
| 24 | 8.48 | 6.79 | |
| 25 | 8.21 | 6.1 | |
| 26 | 8.98 | 7.15 | |
| 29 | 7.13 | <5 | |
| 30 | 9.38 | 7.59 | 6.65 |
| 31 | 7.6 | 5.96 | |
| 34 | 7.46 | 6.02 | |
| 35 | 7.7 | 5.85 | |
| 36 | 8.7 | 7.02 | |
| 39 | 9.09 | 7.18 | 6.62 |
| 40 | 7.6 | 5.82 | |
| 43 | 7.38 | 5.94 | |
| 44 | 7.54 | 5.89 | |
| 45 | 8.49 | 6.93 | |
| 48 | 9.04 | 7.24 | 6.62 |
| 49 | 8.82 | | 6.91 |
| 52 | 7.05 | | 6.03 |
| 53 | 9.26 | | 7.20 |
| 54 | 7.58 | | 5.80 |
| 55 | 7.05 | | 5.42 |
| 56 | 8.17 | | 5.89 |
| 57 | 8.98 | | 6.78 |
| 58 | 7.12 | | 5.66 |
| 59 | 9.38 | | 7.18 |
| 60 | 9.01 | | 7.21 |
| 61 | 7.49 | | 5.63 |
| 62 | 8.04 | nt | nt |
| 65 | 8.15 | 5.93 | |
| 66 | 8.11 | <5 | |
| 67 | 8.59 | 5.89 | |
| 70 | 8.78 | 6.16 | 6.09 |
| 71 | 8.03 | <5 | |
| 74 | 8.04 | 5.9 | |
| 75 | 7.87 | <5 | |
| 76 | 8.80 | 6.15 | |
| 79 | 9.02 | 6.44 | |
| 80 | 7.65 | <5 | |
| 83 | 7.93 | <5 | |
| 84 | 7.19 | <5 | |
| 85 | 8.40 | 6.08 | |
| 88 | 8.49 | 6.27 | |
| 89 | 9.08 | nt | nt |
| 92 | 9.11 | 6.38 | |
| 93 | 9.06 | 6.89 | |
| 94 | 9.73 | nt | nt |
| 97 | 9.56 | 6.91 | |
| 98 | 7.5 | nt | nt |
| 99 | 8.05 | 5.65 | |
| 100 | 8.13 | 5.93 | |
| 101 | 8.31 | | 5.99 |
| 102 | 8.35 | | 6.00 |
| 104 | 8.00 | | 5.80 |
| 106 | 8.50 | | 6.05 |

| EX | D₃ pKi | D₂ fpKi | D₂ pKi |
|---|---|---|---|
| 107 | 7.18 | | 5.56 |
| 108 | 7.56 | | 6.72 |
| 109 | 8.17 | | 6.14 |
| 112 | 8.56 | | 6.08 |
| 114 | 7.75 | 5.79 | |
| 115 | 8.72 | 7.01 | |
| 118 | 9.07 | 7.38 | 6.60 |
| 119 | 8.06 | | 5.73 |
| 120 | 7.94 | | 5.77 |
| 121 | 8.07 | | 5.92 |
| 122 | 8.59 | | 6.34 |
| 123 | 7.77 | | 6.00 |
| 124 | 7.26 | | 5.32 |
| 125 | 7.51 | | 5.48 |
| 126 | 7.69 | | 5.94 |
| 127 | 8.28 | 6.19 | 6.12 |
| 128 | 8.64 | | 6.47 |
| 129 | 8.50 | | 6.35 |
| 130 | 8.18 | | 6.16 |
| 131 | 8.01 | | 6.16 |
| 132 | 8.23 | | 6.87 |
| 133 | 8.76 | | 6.06 |
| 134 | 8.32 | | 5.84 |
| 135 | 8.09 | | 6.54 |
| 137 | 8.23 | | 5.70 |
| 139 | 8.40 | | 5.83 |
| 140 | 8.11 | | 6.20 |
| 141 | 9.10 | 6.97 | 6.28 |
| 142 | 7.69 | | 5.87 |
| 143 | 8.74 | 6.21 | 6.05 |
| 146 | 8.81 | | 6.07 |
| 147 | 8.55 | | 6.02 |
| 150 | 7.55 | | 5.46 |
| 151 | 8.95 | | 6.19 |
| 152 | 8.39 | | 5.90 |
| 155 | 7.08 | | 4.96 |
| 156 | 8.91 | | 6.18 |
| 157 | 8.22 | | 5.77 |
| 160 | 8.73 | | 6.18 |
| 161 | 7.51 | | 5.48 |
| 162 | 8.08 | | 6.06 |
| 163 | 9.02 | 6.87 | 6.21 |
| 164 | 8.20 | | 6.23 |
| 165 | 8.48 | | 5.77 |
| 166 | 8.57 | | 5.73 |
| 168 | 8.28 | | 6.44 |
| 169 | 8.80 | | 6.01 |
| 170 | 8.69 | | 5.85 |
| 172 | 8.46 | | 5.92 |
| 173 | 8.42 | | 5.75 |
| 174 | 8.15 | | 6.02 |
| 175 | 8.56 | | 6.15 |
| 176 | 8.59 | | 5.95 |
| 177 | 8.84 | | 6.10 |
| 178 | 8.84 | | 6.10 |
| 179 | 8.85 | | 6.10 |
| 180 | 8.58 | | 5.96 |
| 181 | 8.55 | | 5.77 |
| 182 | 9.14 | | 5.83 |
| 184 | 9.47 | | 6.26 |
| 185 | 9.38 | | 5.91 |
| 186 | 7.89 | | 5.31 |
| 187 | 8.90 | | 5.96 |
| 188 | 7.44 | | 5.03 |
| 189 | 9.47 | | 6.36 |
| 190 | 9.55 | | 6.56 |
| 191 | 9.14 | | 6.29 |
| 192 | 8.30 | | 6.36 |
| 193 | 8.48 | | 6.36 |
| 195 | 8.29 | | 5.84 |
| 197 | 7.65 | | 5.66 |
| 199 | 7.77 | | 5.81 |
| 200 | 7.45 | <5 | |
| 201 | 8.40 | | 5.88 |
| 204 | 8.52 | | 5.99 |
| 205 | 7.01 | | 5.75 |
| 206 | 7.78 | | 5.86 |

| EX | D₃ pKi | D₂ fpKi | D₂ pKi |
|---|---|---|---|
| 207 | 8.29 | 6.54 | |
| 210 | 8.25 | 6.28 | |
| 211 | 8.15 | 6.97 | |
| 212 | 8.99 | 6.93 | |
| 213 | 8.98 | 7.09 | 6.53 |
| 214 | 7.97 | 6.03 | |
| 215 | 8.38 | 6.07 | |
| 216 | 8.10 | 6.01 | |
| 217 | 8.90 | 6.62 | |
| 220 | 9.24 | 6.92 | 6.32 |
| 221 | 9.08 | 7.06 | 6.37 |
| 222 | 8.31 | | 5.91 |
| 223 | 8.72 | | 6.00 |
| 224 | 8.70 | | 5.85 |
| 227 | 9.07 | | 6.24 |
| 228 | 9.45 | | 6.33 |
| 229 | 7.28 | 5.63 | |
| 230 | 7.81 | | 6.17 |
| 231 | 8.57 | 6.68 | |
| 234 | 8.82 | 7.01 | 6.42 |
| 235 | 7.82 | | 5.91 |
| 236 | 8.44 | 6.12 | 5.79 |
| 239 | 8.62 | | 6.04 |
| 240 | 7.99 | | 6.33 |
| 241 | 8.86 | 6.74 | 6.37 |
| 244 | 9.01 | | 6.60 |
| 245 | 7.96 | | 6.12 |
| 246 | 8.62 | 6.68 | 6.27 |
| 249 | 8.86 | | 6.57 |
| 250 | 8.76 | | 6.07 |
| 253 | 9.20 | | 6.10 |
| 254 | 8.84 | | 6.32 |
| 255 | 8.76 | | 6.30 |
| 256 | 9.22 | | 6.48 |
| 257 | 9.24 | | 6.46 |
| 258 | 9.38 | | 6.26 |
| 259 | 8.27 | | 6.95 |
| 260 | 8.55 | | 6.89 |
| 261 | 8.65 | | 6.40 |
| 262 | 9.12 | | 6.18 |
| 263 | 9.26 | | 6.23 |
| 265 | 8.86 | | 6.23 |
| 267 | 7.78 | | 5.38 |
| 268 | 8.42 | | 5.80 |
| 269 | 8.59 | | 6.00 |
| 270 | 8.56 | | 6.04 |
| 271 | 8.63 | | 5.91 |
| 272 | 9.63 | | 7.02 |
| 273 | 9.11 | | 5.50 |
| 274 | 9.79 | | 6.52 |
| 275 | 9.93 | | 6.32 |
| 276 | 9.44 | | 6.78 |
| 278 | 10.2 | | 6.41 |
| 279 | 9.74 | | 6.30 |
| 281 | 9.80 | | 6.45 |
| 283 | 9.58 | | 6.46 |
| 284 | 9.61 | | 6.46 |
| 285 | 9.50 | | 6.66 |
| 286 | 9.28 | | 6.33 |
| 287 | 9.07 | | 6.33 |
| 289 | 9.33 | | 6.26 |
| 290 | 7.82 | | 7.40 |
| 291 | 7.70 | 5.96 | |
| 295 | 8.54 | 6.06 | |
| 296 | 7.55 | <5 | |
| 299 | 7.47 | <5 | |
| 300 | 7.35 | <5 | |
| 301 | 7.73 | 5.84 | |
| 302 | 8.19 | | 5.94 |
| 303 | 7.48 | <5 | |
| 304 | 7.44 | <5 | |
| 305 | 7.86 | <5 | |
| 309 | 7.52 | 5.95 | |
| 310 | 8.32 | 7.72 | |
| 312 | 8.40 | 8.26 | |
| 313 | 7.3 | <5 | |
| 314 | 7.14 | <5 | |

-continued

| EX | D$_3$ pKi | D$_2$ fpKi | D$_2$ pKi |
|---|---|---|---|
| 318 | 7.34 | <5 | |
| 321 | 7.62 | 5.65 | |

All publications, including but not limited to patents and patent applications, cited in this specification are herein incorporated by reference as if each individual publication were specifically and individually indicated to be incorporated by reference herein as though fully set forth.

It is to be understood that the present invention covers all combinations of particular groups described herein above.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the following claims:

What is claimed is:

1. A compound or a pharmaceutically acceptable salt thereof, wherein the compound is:

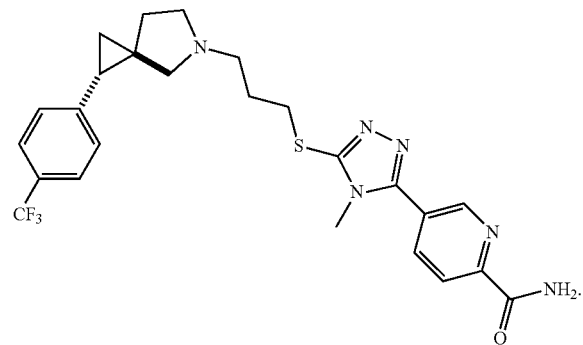

2. A pharmaceutical composition comprising the compound of claim 1 and a pharmaceutically acceptable carrier.

3. A method of modulating dopamine D$_3$ receptors in a mammal in need thereof, the method comprising administering to the mammal an effective amount of the compound of claim 1 to modulate the dopamine D$_3$ receptors.

4. The method of claim 3, wherein the method of modulating dopamine D$_3$ receptors is a method for treating Parkinson's disease; neuroleptic-induced parkinsonism; tardive dyskinesia; depression; anxiety; a cognitive impairment; Alzheimer's disease; an eating disorder; a sexual dysfunction; a sleep disorder; emesis; a movement disorder; obsessive-compulsive disorder; amnesia; aggression; autism; vertigo; dementia; a circadian rhythm disorder; a gastric motility disorder, or a gambling disorder.

5. A method for treating a psychotic condition in a mammal in need thereof, the method comprising administering to the mammal an effective amount of the compound of claim 1 to treat the psychotic condition.

6. A method for treating opioid use disorder in a mammal in need thereof, the method comprising administering to the mammal an effective amount of the compound of claim 1 to treat the opioid use disorder.

7. A method for treating schizophrenia in a mammal in need thereof, the method comprising administering to the mammal an effective amount of the compound of claim 1 to treat the schizophrenia.

8. A method of treating a substance-related disorder in a mammal in need thereof, the method comprising administering to the mammal an effective amount of the compound of claim 1 to treat the substance-related disorder.

9. A compound or a pharmaceutically acceptable salt thereof, wherein the compound is:

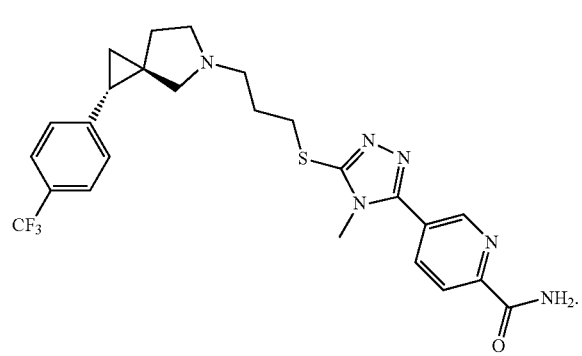 [SMILES: Cn1c(SCCCN2CC[C@]3(C[C@H]3c3ccc(C(F)(F)F)cc3)C2)nnc1-c1ccc(C(N)=O)nc1]

10. A pharmaceutical composition comprising the compound of claim 9 and a pharmaceutically acceptable carrier.

11. A method of modulating dopamine D$_3$ receptors in a mammal in need thereof, the method comprising administering to the mammal an effective amount of the compound of claim 9 to modulate the dopamine D$_3$ receptors.

12. The method of claim 11, wherein the method of modulating dopamine D$_3$ receptors is a method for treating Parkinson's disease; neuroleptic-induced parkinsonism; tardive dyskinesia; depression; anxiety; a cognitive impairment; Alzheimer's disease; an eating disorder; a sexual dysfunction; a sleep disorder; emesis; a movement disorder; obsessive-compulsive disorder; amnesia; aggression; autism; vertigo; dementia; a circadian rhythm disorder; a gastric motility disorder, or a gambling disorder.

13. A method for treating a psychotic condition in a mammal in need thereof, the method comprising administering to the mammal an effective amount of the compound of claim 9 to treat the psychotic condition.

14. A method for treating opioid use disorder in a mammal in need thereof, the method comprising administering to the mammal an effective amount of the compound of claim 9 to treat the opioid use disorder.

15. A method for treating schizophrenia in a mammal in need thereof, the method comprising administering to the mammal an effective amount of the compound of claim 9 to treat the schizophrenia.

16. A method of treating a substance-related disorder in a mammal in need thereof, the method comprising administering to the mammal an effective amount of the compound of claim 9 to treat the substance-related disorder.

17. A compound or a pharmaceutically acceptable salt thereof, wherein the compound is:

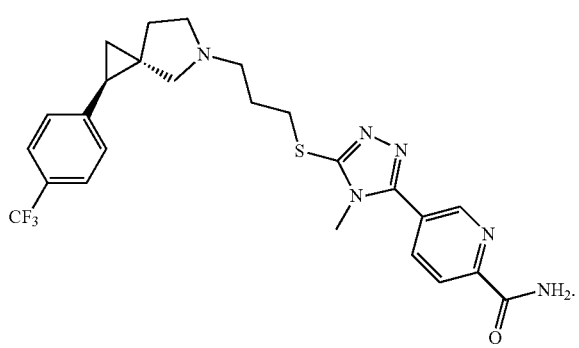 [SMILES: Cn1c(SCCCN2CC[C@@]3(C[C@@H]3c3ccc(C(F)(F)F)cc3)C2)nnc1-c1ccc(C(N)=O)nc1]

18. A pharmaceutical composition comprising the compound of claim 17 and a pharmaceutically acceptable carrier.

19. A method of modulating dopamine $D_3$ receptors in a mammal in need thereof, the method comprising administering to the mammal an effective amount of the compound of claim 17 to modulate the dopamine $D_3$ receptors.

20. The method of claim 19, wherein the method of modulating dopamine $D_3$ receptors is a method for treating Parkinson's disease; neuroleptic-induced parkinsonism; tardive dyskinesia; depression; anxiety; a cognitive impairment; Alzheimer's disease; an eating disorder; a sexual dysfunction; a sleep disorder; emesis; a movement disorder; obsessive-compulsive disorder; amnesia; aggression; autism; vertigo; dementia; a circadian rhythm disorder; a gastric motility disorder, or a gambling disorder.

21. A method for treating a psychotic condition in a mammal in need thereof, the method comprising administering to the mammal an effective amount of the compound of claim 19 to treat the psychotic condition.

22. A method for treating opioid use disorder in a mammal in need thereof, the method comprising administering to the mammal an effective amount of the compound of claim 19 to treat the opioid use disorder.

23. A method for treating schizophrenia in a mammal in need thereof, the method comprising administering to the mammal an effective amount of the compound of claim 19 to treat the schizophrenia.

24. A method of treating a substance-related disorder in a mammal in need thereof, the method comprising administering to the mammal an effective amount of the compound of claim 19 to treat the substance-related disorder.

25. A compound or a pharmaceutically acceptable salt thereof, wherein the compound is:

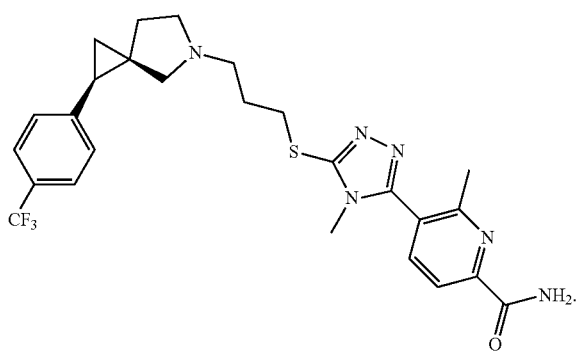 [SMILES: Cc1nc(C(N)=O)ccc1-c1nnc(SCCCN2CC[C@]3(C[C@@H]3c3ccc(C(F)(F)F)cc3)C2)n1C]

26. A pharmaceutical composition comprising the compound of claim 25 and a pharmaceutically acceptable carrier.

27. A method of modulating dopamine $D_3$ receptors in a mammal in need thereof, the method comprising administering to the mammal an effective amount of the compound of claim 25 to modulate the dopamine $D_3$ receptors.

28. The method of claim 27, wherein the method of modulating dopamine $D_3$ receptors is a method for treating Parkinson's disease; neuroleptic-induced parkinsonism; tardive dyskinesia; depression; anxiety; a cognitive impairment; Alzheimer's disease; an eating disorder; a sexual dysfunction; a sleep disorder; emesis; a movement disorder; obsessive-compulsive disorder; amnesia; aggression; autism; vertigo; dementia; a circadian rhythm disorder; a gastric motility disorder, or a gambling disorder.

29. A method for treating a psychotic condition in a mammal in need thereof, the method comprising administering to the mammal an effective amount of the compound of claim 25 to treat the psychotic condition.

30. A method for treating opioid use disorder in a mammal in need thereof, the method comprising administering to the mammal an effective amount of the compound of claim 25 to treat the opioid use disorder.

31. A method for treating schizophrenia in a mammal in need thereof, the method comprising administering to the mammal an effective amount of the compound of claim 25 to treat the schizophrenia.

32. A method of treating a substance-related disorder in a mammal in need thereof, the method comprising administering to the mammal an effective amount of the compound of claim 25 to treat the substance-related disorder.

33. A compound or a pharmaceutically acceptable salt thereof, wherein the compound is:

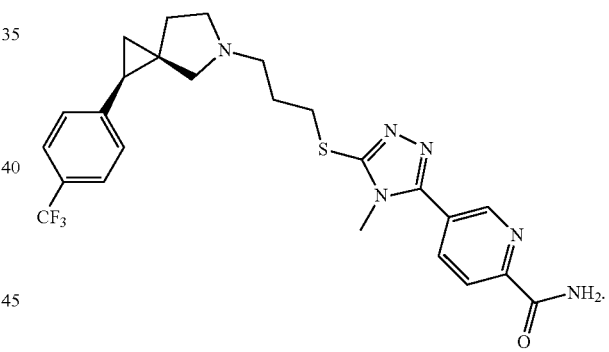

34. A pharmaceutical composition comprising the compound of claim 33 and a pharmaceutically acceptable carrier.

35. A method of modulating dopamine $D_3$ receptors in a mammal in need thereof, the method comprising administering to the mammal an effective amount of the compound of claim 33 to modulate the dopamine $D_3$ receptors.

36. The method of claim 35, wherein the method of modulating dopamine $D_3$ receptors is a method for treating Parkinson's disease; neuroleptic-induced parkinsonism; tardive dyskinesia; depression; anxiety; a cognitive impairment; Alzheimer's disease; an eating disorder; a sexual dysfunction; a sleep disorder; emesis; a movement disorder; obsessive-compulsive disorder; amnesia; aggression; autism; vertigo; dementia; a circadian rhythm disorder; a gastric motility disorder, or a gambling disorder.

37. A method for treating a psychotic condition in a mammal in need thereof, the method comprising administering to the mammal an effective amount of the compound of claim 33 to treat the psychotic condition.

38. A method for treating opioid use disorder in a mammal in need thereof, the method comprising administering to the mammal an effective amount of the compound of claim 33 to treat the opioid use disorder.

39. A method for treating schizophrenia in a mammal in need thereof, the method comprising administering to the mammal an effective amount of the compound of claim 33 to treat the schizophrenia.

40. A method of treating a substance-related disorder in a mammal in need thereof, the method comprising administering to the mammal an effective amount of the compound of claim 33 to treat the substance-related disorder.

\* \* \* \* \*